US012404237B2

(12) United States Patent
Hattori et al.

(10) Patent No.: US 12,404,237 B2
(45) Date of Patent: *Sep. 2, 2025

(54) METHOD OF TREATING EXCESSIVE SLEEPINESS AND/OR CATAPLEXY USING N-{2-(([1,1'-BIPHENYL]-3-YL)METHYL) PYRROLIDIN-3-YL}SULFONAMIDE DERIVATIVES

(71) Applicant: TAKEDA PHARMACEUTICAL COMPANY LIMITED, Osaka (JP)

(72) Inventors: Yasushi Hattori, Kanagawa (JP); Yuhei Miyanohana, Kanagawa (JP); Yuichi Kajita, Kanagawa (JP); Tatsuki Koike, Kanagawa (JP); Yasutaka Hoashi, Kanagawa (JP); Norihito Tokunaga, Kanagawa (JP); Alexander Martin Pawliczek, Kanagawa (JP); Tsuneo Oda, Kanagawa (JP); Tohru Miyazaki, Kanagawa (JP); Yoshiteru Ito, Kanagawa (JP); Kohei Takeuchi, Kanagawa (JP); Keisuke Imamura, Kanagawa (JP); Takahiro Sugimoto, Kanagawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 19/079,199

(22) Filed: Mar. 13, 2025

(65) Prior Publication Data

US 2025/0243157 A1 Jul. 31, 2025

Related U.S. Application Data

(63) Continuation of application No. 18/520,037, filed on Nov. 27, 2023, now abandoned, which is a continuation of application No. 18/175,215, filed on Feb. 27, 2023, now abandoned, which is a continuation of application No. 17/239,191, filed on Apr. 23, 2021, now abandoned, which is a continuation of application No. 16/777,273, filed on Jan. 30, 2020, now Pat. No. 11,028,048.

(30) Foreign Application Priority Data

Jan. 31, 2019 (JP) .................................. 2019-015488

(51) Int. Cl.
| | | |
|---|---|---|
| C07D 207/14 | (2006.01) | |
| C07D 403/06 | (2006.01) | |
| C07D 407/08 | (2006.01) | |
| C07D 417/06 | (2006.01) | |

(52) U.S. Cl.
CPC ......... C07D 207/14 (2013.01); C07D 403/06 (2013.01); C07D 407/08 (2013.01); C07D 417/06 (2013.01)

(58) Field of Classification Search
CPC .................................................. C07D 207/14
See application file for complete search history.

(56) References Cited

U.S. PATENT DOCUMENTS

| | | | |
|---|---|---|---|
| 1,028,305 | A | 6/1912 | Turnbull |
| 6,166,193 | A | 12/2000 | Yanagisawa et al. |
| 6,204,245 | B1 | 3/2001 | Siegel et al. |
| 7,112,566 | B1 | 9/2006 | Siegel et al. |
| 9,527,807 | B2 | 12/2016 | Fukumoto et al. |
| 10,428,023 | B2 | 10/2019 | Kajita et al. |
| 10,584,097 | B2 | 3/2020 | Kajita et al. |
| 11,028,048 | B2 | 6/2021 | Hattori et al. |
| 2003/0083466 | A1 | 5/2003 | Yanagisawa et al. |
| 2005/0048538 | A1 | 3/2005 | Mignot et al. |
| 2006/0035285 | A1 | 2/2006 | Sutton et al. |
| 2006/0134109 | A1 | 6/2006 | Gaitanaris et al. |
| 2007/0010445 | A1 | 1/2007 | Siegel et al. |
| 2008/0260744 | A1 | 10/2008 | Gaitanaris et al. |
| 2009/0143383 | A1 | 6/2009 | Grandel et al. |
| 2009/0178153 | A1 | 7/2009 | Gaitanaris et al. |

(Continued)

FOREIGN PATENT DOCUMENTS

| | | |
|---|---|---|
| AU | 2012200270 A1 | 2/2012 |
| CL | 202101575 A1 | 3/2022 |

(Continued)

OTHER PUBLICATIONS

Boss et al., "Orexin research: patent news from 2016," Expert Opinion on Therapeutic Patents, Jun. 28, 2017, 27(10):1123-1133.

(Continued)

*Primary Examiner* — Valerie Rodriguez-Garcia
(74) *Attorney, Agent, or Firm* — Sterne, Kessler, Goldstein & Fox P.L.L.C.

(57) ABSTRACT

The present invention provides a heterocyclic compound having an orexin type 2 receptor agonist activity.
A compound represented by the formula (I):

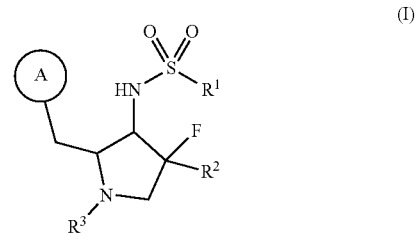

wherein each symbol is as described in the specification, or a salt thereof has an orexin type 2 receptor agonist activity, and is useful as an agent for the prophylaxis or treatment of narcolepsy.

19 Claims, No Drawings

(56) References Cited

U.S. PATENT DOCUMENTS

| | | |
|---|---|---|
| 2009/0253660 A1 | 10/2009 | Johnston |
| 2010/0150840 A1 | 6/2010 | Yanagisawa et al. |
| 2011/0053859 A1 | 3/2011 | Deadwyler et al. |
| 2011/0185439 A1 | 7/2011 | Gaitanaris et al. |
| 2011/0214189 A1 | 9/2011 | Gaitanaris et al. |
| 2013/0247233 A1 | 9/2013 | Gaitanaris et al. |
| 2014/0024650 A1 | 1/2014 | Fukumoto et al. |
| 2015/0252032 A1 | 9/2015 | Bolli et al. |
| 2016/0219845 A1 | 8/2016 | Gaitanaris et al. |
| 2016/0250224 A1 | 9/2016 | Wan |
| 2016/0271214 A1 | 9/2016 | Ashley et al. |
| 2016/0282365 A1 | 9/2016 | Gaitanaris et al. |
| 2016/0362376 A1 | 12/2016 | Nagase et al. |
| 2017/0188555 A1 | 7/2017 | Gaitanaris et al. |
| 2017/0226103 A1 | 8/2017 | Kamenecka et al. |
| 2017/0226137 A1 | 8/2017 | Fujimoto et al. |
| 2018/0179151 A1 | 6/2018 | Nagase et al. |
| 2018/0243245 A1 | 8/2018 | England et al. |
| 2019/0031611 A1 | 1/2019 | Fujimoto et al. |
| 2019/0040010 A1 | 2/2019 | Kajita et al. |
| 2019/0263843 A1 | 8/2019 | Fujimoto et al. |
| 2020/0207715 A1 | 7/2020 | Kajita et al. |
| 2020/0255403 A1 | 8/2020 | Bogen et al. |
| 2020/0392149 A1 | 12/2020 | Mikami et al. |
| 2024/0360080 A1 | 10/2024 | Hattori et al. |

FOREIGN PATENT DOCUMENTS

| | | |
|---|---|---|
| CL | 202101991 A1 | 8/2022 |
| EP | 0 893 498 A2 | 1/1999 |
| EP | 3 029 024 A1 | 6/2016 |
| HU | 0304101 | 3/2004 |
| TW | 201341380 A | 10/2013 |
| WO | WO-01/08720 A2 | 2/2001 |
| WO | WO-01/74162 A1 | 10/2001 |
| WO | WO-2004040000 A2 | 5/2004 |
| WO | WO-2004054510 A2 | 7/2004 |
| WO | WO-2009049215 A1 | 4/2009 |
| WO | WO-2012137982 A2 | 10/2012 |
| WO | WO-2014170343 A1 | 10/2014 |
| WO | WO-2014198880 A1 | 12/2014 |
| WO | WO-2015048091 A1 | 4/2015 |
| WO | WO-2015073707 A1 | 5/2015 |
| WO | WO-2015088000 A1 | 6/2015 |
| WO | WO-2015147240 A1 | 10/2015 |
| WO | WO-2016025669 A1 | 2/2016 |
| WO | WO-2016133160 A1 | 8/2016 |
| WO | WO-2016154332 A1 | 9/2016 |
| WO | WO-2016199906 A1 | 12/2016 |
| WO | WO-2017044889 A1 | 3/2017 |
| WO | WO-2017135306 A1 | 8/2017 |
| WO | WO-2018164191 A1 | 9/2018 |
| WO | WO-2018164192 A1 | 9/2018 |
| WO | WO-2019027003 A1 | 2/2019 |
| WO | WO-2019027058 A1 | 2/2019 |
| WO | WO-2019112007 A1 | 6/2019 |
| WO | WO-2020004536 A1 | 1/2020 |
| WO | WO-2020004537 A1 | 1/2020 |
| WO | WO-2020122092 A1 | 6/2020 |
| WO | WO-2020122093 A1 | 6/2020 |
| WO | WO-2020157652 A2 | 8/2020 |
| WO | WO-2020167701 A1 | 8/2020 |
| WO | WO-2020167706 A1 | 8/2020 |
| WO | WO-2020132269 A1 | 6/2022 |

OTHER PUBLICATIONS

Busquets et al., "Decreased Plasma Levels of Orexin-A in Sleep Apnea," Respiration, 2004, 71:575-579.

Chemelli et al., "Narcolepsy in orexin Knockout Mice: Molecular Genetics of Sleep Regulation," Cell, Aug. 20, 1999, 98:437-451.

Desseilles et al., "Neuroimaging Insights into the Pathophysiology of Sleep Disorders," Sleep, Jun. 1, 2008, 31(6):777-794.

Funato et al., "Enhanced Orexin Receptor-2 Signaling Prevents Diet-Induced Obesity and Improves Leptin Sensitivity," Cell Metabolism, Jan. 7, 2009, 9:64-76.

Jaeger et al., "Effects of orexin-A on memory processing," Peptides, 2002, 23:1683-1688.

Kushikata et al., "Orexinergic Neurons and Barbiturate Anesthesia," Neuroscience, 2003, 121:855-863.

Lin et al., "The Sleep Disorder Canine Narcolepsy Is Caused by a Mutation in the Hypocretin (Orexin) Receptor 2 Gene," Cell, Aug. 6, 1999, 98:365-376.

Mieda et al., "Orexin (Hypocretin) Receptor Agonists and Antagonists for Treatment of Sleep Disorders," CNS Drugs, 2013, 27:83-90.

Mieda et al., "Orexin peptides prevent cataplexy and improve wakefulness in an orexin neuron-ablated model of narcolepsy in mice," PNAS, Mar. 30, 2004, 101(13):4649-4654.

Patani et al., "Bioisoterism: A Rational Approach in Drug Design," Chemical Reviews, 1996, 96:3147-3176.

Perez et al., "Systems Genomics Identifies a Key Role for Hypocretin/Orexin Receptor-2 in Human Heart Failure," Journal of the American College of Cardiology, 2015, 66(22):2522-2533.

Sakurai et al. "Orexins and Orexin Receptors: A Family of Hypothalamic Neuropeptides and G Protein-Coupled Receptors that Regulate Feeding Behavior," Cell, Feb. 20, 1998, 92:573-585.

Thannickal et al., "Hypocretin (orexin) cell loss in Parkinson's disease," Brain, 2007, 130:1586-1595.

Willie et al., "Distinct Narcolepsy Syndromes in Orexin Receptor-2 and Orexin Null Mice: Molecular Genetic Dissection of Non-REM and REM Sleep Regulatory Processes," Neuron, Jun. 5, 2003, 38:715-730.

Co-pending, U.S. Appl. No. 19/079,172, inventors Hattori, Y. et al., filed Mar. 13, 2025 (Not yet Published).

Co-pending, U.S. Appl. No. 19/079,211, inventors Hattori, Y. et al., filed Mar. 13, 2025 (Not yet Published).

Non Final Office Action dated May 21, 2025, in co-pending U.S. Appl. No. 19/079,172, Hattori, Y., et al., filed Mar. 13, 2025, 5 pages.

Non Final Office Action dated Jun. 4, 2025, in co-pending U.S. Appl. No. 19/079,211, Hattori, Y., et al., filed Mar. 13, 2025, 6 pages.

METHOD OF TREATING EXCESSIVE SLEEPINESS AND/OR CATAPLEXY USING N-{2-(([1,1'-BIPHENYL]-3-YL)METHYL)PYRROLIDIN-3-YL}SULFONAMIDE DERIVATIVES

CROSS-REFERENCE TO RELATED APPLICATIONS

This application is a continuation of U.S. application Ser. No. 18/175,215, filed Feb. 27, 2023, which is a continuation of U.S. application Ser. No. 17/239,191, filed Apr. 23, 2021, now abandoned, which is a continuation of U.S. application Ser. No. 16/777,273, filed Jan. 30, 2021, now issued as U.S. Pat. No. 11,028,048, which claims priority from JP 2019-015488, filed Jan. 31, 2019, all of which are incorporated by reference in their entireties.

TECHNICAL FIELD

The present invention relates to a heterocyclic compound, particularly, a heterocyclic compound having an orexin type 2 receptor agonist activity.

BACKGROUND OF THE INVENTION

Orexin is a neuropeptide specifically produced in particular neurons located sparsely in the lateral hypothalamus and its surrounding area, and consists of two subtypes, orexin A and orexin B. Both orexin A and orexin B are endogenous ligands of the orexin receptors, which are G protein-coupled receptors mainly present in the brain, and two types of subtypes, type 1 and type 2, are known for the orexin receptors (non-patent document 1).

Since orexin-producing neurons (orexin neurons) are localized in the vicinity of the feeding center, and intraventricular administration of orexin peptide results in an increase in food intake, orexin initially attracted attention as a neuropeptide having a feeding behavioral regulation. Thereafter, however, it was reported that the cause of dog narcolepsy is genetic variation of orexin type 2 receptor (non-patent document 2), and the role of orexin in controlling sleep and wakefulness has been also attracted.

From the studies using a transgenic mouse having denatured orexin neurons and a double transgenic mouse obtained by crossing this mouse with orexin overexpressing transgenic mouse, it was clarified that narcolepsy-like symptoms that appear by degeneration of orexin neurons disappear due to sustained expression of orexin. Similarly, when orexin peptide was intraventricularly administered to a transgenic mouse having denatured orexin neuron, improvement of narcolepsy-like symptoms was also observed (non-patent document 3). Studies of orexin type 2 receptor knockout mice have suggested that orexin type 2 receptor is important for maintaining arousal (non-patent document 4, non-patent document 5). Such background suggests that orexin type 2 receptor agonists become therapeutic drugs for narcolepsy or therapeutic drugs for other sleep disorders exhibiting excessive sleepiness (non-patent document 6).

In addition, it is suggested that a peptidic agonist that selectively acts on the orexin type 2 receptor improves obesity due to high fat diet load in mice (non-patent document 7).

In addition, it is suggested that intraventricular administration of orexin peptide shortens the systemic anesthetic time of rat (non-patent document 8).

In addition, it is suggested that patients with sleep apnea syndrome show low orexin A concentration levels in plasma (non-patent document 9).

In addition, it is suggested that intraventricular administration of orexin peptide improves memory retention of senescence-accelerated model mouse (SAMP8) with cognitive dysfunction (non-patent document 10).

In addition, it is suggested that Orexin type 2 receptor agonist will be a therapeutic drug for cardiac failure (patent document 1, non-patent document 11).

In addition, it is suggested that the daytime sleepiness of Parkinson's disease patients is caused by orexin nerve fallout (non-patent document 12).

In addition, it is suggested that orexin regulates bone formation and bone loss, and orexin type 2 receptor agonist will be a therapeutic drug for diseases related to bone loss such as osteoporosis, rheumatoid arthritis and the like (patent document 2).

In addition, it is suggested that orexin receptor agonist is useful for the prophylaxis or treatment of sepsis, severe sepsis and septic shock, since the mortality was significantly improved by mere continuous administration of orexin from the periphery in septic shock model mouse (patent document 3).

Therefore, a compound having an orexin type 2 receptor agonist activity is expected to be useful as a novel therapeutic drug for narcolepsy, idiopathic hypersomnia, hypersomnia, sleep apnea syndrome, disturbance of consciousness such as coma and the like, narcolepsy syndrome accompanied by narcolepsy-like symptoms, hypersomnia syndrome accompanied by daytime hypersomnia (e.g., Parkinson's disease, Guillain-Barre syndrome and Kleine Levin syndrome), Alzheimer, obesity, insulin resistance syndrome, cardiac failure, diseases related to bone loss, sepsis and the like, further, anesthetic antagonist, a prophylactic or therapeutic drug for side effects and complications due to anesthesia.

As sulfonamide derivatives, a compound represented by the formula

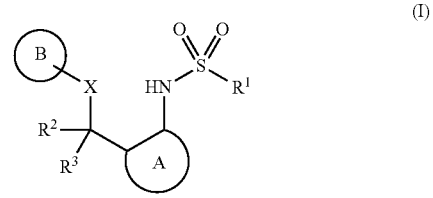

(I)

wherein each symbol is as described in the document (Patent Document 4) has been reported.

In addition, as compounds having an orexin type 2 receptor agonist activity, the following compounds have been reported.

A compound represented by the formula

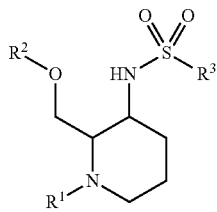

wherein each symbol is as described in the document (Patent Document 5).

A compound represented by the formula

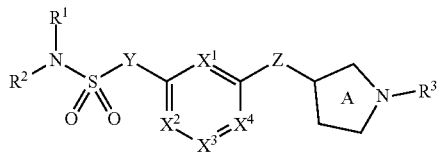

wherein each symbol is as described in the document (Patent Document 6).

A compound represented by the formula

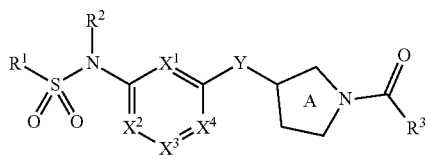

wherein each symbol is as described in the document (Patent Document 7).

A compound represented by the formula

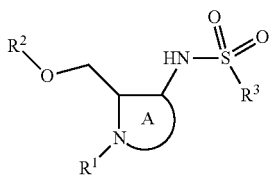

wherein each symbol is as described in the document (Patent Document 8).

A compound represented by the formula

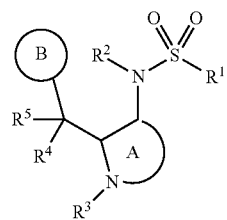

wherein each symbol is as described in the document (Patent Document 9).

A compound represented by the formula

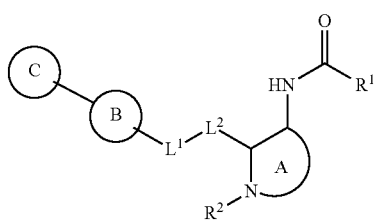

wherein each symbol is as described in the document (Patent Document 10).

A compound represented by the formula

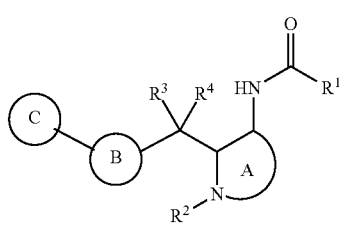

wherein each symbol is as described in the document (Patent Document 11).

Development of a novel compound having an orexin type 2 receptor agonist activity is desired.

DOCUMENT LIST

Patent Document

[Patent Document 1] WO 2015/073707 A1
[Patent Document 2] WO 2015/048091 A1
[Patent Document 3] WO 2015/147240 A1
[Patent Document 4] WO 2012/137982 A9
[Patent Document 5] WO 2017/135306 A1
[Patent Document 6] WO 2018/164191 A1
[Patent Document 7] WO 2018/164192 A1
[Patent Document 8] WO 2019/027003 A1
[Patent Document 9] WO 2019/027058 A1
[Patent Document 10] WO 2020/004536 A1
[Patent Document 11] WO 2020/004537 A1

Non-Patent Document

[Non-Patent Document 1] Cell, Vol. 92, 573-585, 1998
[Non-Patent Document 2] Cell, Vol. 98, 365-376, 1999
[Non-Patent Document 3] Proc. Natl. Acad. Sci. USA, Vol. 101, 4649-4654, 2004
[Non-Patent Document 4] Cell, Vol. 98, 437-451, 1999
[Non-Patent Document 5] Neuron, Vol. 38, 715-730, 2003
[Non-Patent Document 6] CNS Drugs, Vol. 27, 83-90, 2013
[Non-Patent Document 7] Cell Metabolism, Vol. 9, 64-76, 2009
[Non-Patent Document 8] Neuroscience, Vol. 121, 855-863, 2003
[Non-Patent Document 9] Respiration, Vol. 71, 575-579, 2004
[Non-Patent Document 10] Peptides, Vol. 23, 1683-1688, 2002
[Non-Patent Document 11] Journal of the American College of Cardiology. Vol. 66, 2015, Pages 2522-2533
[Non-Patent Document 12] Brain. Vol. 130, 2007, Pages 1586-1595

SUMMARY OF THE INVENTION

Problems to be Solved by the Invention

The present invention aims to provide a heterocyclic compound having an orexin type 2 receptor agonist activity.

Means of Solving the Problems

The present inventors have found that a compound represented by the following formula (I) or a salt thereof (sometimes to be referred to as compound (I) in the present specification) has an orexin type 2 receptor agonist activity. As a result of further studies, they have completed the present invention.

Accordingly, the present invention relates to the followings.

[1]

A compound represented by the formula (I):

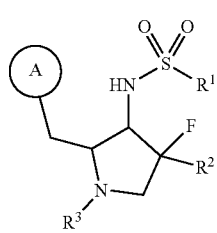

wherein $R^1$ is an optionally substituted $C_{1-6}$ alkyl group, an optionally substituted mono- or di-$C_{1-6}$ alkylamino group, an optionally substituted $C_{3-6}$ cycloalkyl group, or an optionally substituted 3- to 14-membered non-aromatic heterocyclic group;

$R^2$ is a hydrogen atom, a fluorine atom, an optionally substituted $C_{1-6}$ alkyl group, or an optionally substituted $C_{3-6}$ cycloalkyl group;

$R^3$ is an acyl group, an optionally substituted $C_{1-6}$ alkyl group, an optionally substituted $C_{3-6}$ cycloalkyl group, an optionally substituted $C_{6-14}$ aryl group, an optionally substituted 3- to 14-membered non-aromatic heterocyclic group, or an optionally substituted 5- to 14-membered aromatic heterocyclic group; and Ring A is an optionally further substituted $C_{6-14}$ aromatic hydrocarbon ring, or an optionally further substituted 5- to 14-membered aromatic heterocycle, or a salt thereof.

[2]

The compound or salt of the above-mentioned [1], wherein $R^1$ is
  (1) a $C_{1-6}$ alkyl group,
  (2) a mono- or di-$C_{1-6}$ alkylamino group, or
  (3) a $C_{3-6}$ cycloalkyl group;

$R^2$ is
  (1) a hydrogen atom,
  (2) a fluorine atom, or
  (3) a $C_{1-6}$ alkyl group;

$R^3$ is
  (1) a $C_{1-6}$ alkyl-carbonyl group optionally substituted by 1 to 3 substituents selected from
    (a) a halogen atom,
    (b) a hydroxy group, and
    (c) a cyano group,
  (2) a $C_{1-6}$ alkoxy-carbonyl group,
  (3) a $C_{3-10}$ cycloalkyl-carbonyl group (the $C_{3-10}$ cycloalkyl moiety of the $C_{3-10}$ cycloalkyl-carbonyl group is optionally bridged) optionally substituted by 1 to 3 substituents selected from
    (a) a halogen atom,
    (b) a hydroxy group,
    (c) a cyano group, and
    (d) a $C_{1-6}$ alkyl group,
  (4) a 3- to 14-membered non-aromatic heterocyclylcarbonyl group optionally substituted by 1 to 3 substituents selected from
    (a) a halogen atom,
    (b) a hydroxy group, and
    (c) a $C_{1-6}$ alkyl group,
  (5) a mono- or di-$C_{1-6}$ alkyl-carbamoyl group,
  (6) a N—$C_{1-6}$ alkyl-N—$C_{1-6}$ alkoxy-carbamoyl group, or
  (7) a N—$C_{1-6}$ alkyl-N',N'-di-$C_{1-6}$ alkylhydrazine-carbonyl group; and Ring A is
  (1) a benzene ring further substituted by one substituent selected from
    (a) a $C_{6-14}$ aryl group optionally substituted by 1 to 3 substituents selected from
      (i) a halogen atom,
      (ii) an optionally halogenated $C_{1-6}$ alkyl group, and
      (iii) an optionally halogenated $C_{1-6}$ alkoxy group, and
    (b) a 5- to 14-membered aromatic heterocyclic group optionally substituted by 1 to 3 substituents selected from
      (i) a $C_{1-6}$ alkyl group optionally substituted by 1 to 3 substituents selected from a halogen atom and a hydroxy group,
      (ii) a $C_{1-6}$ alkoxy group,
      (iii) a halogen atom, and
      (iv) a $C_{1-6}$ alkoxy-carbonyl group, and
    optionally further substituted by 1 to 3 halogen atoms, or
  (2) a 5- or 6-membered aromatic heterocycle further substituted by one $C_{6-14}$ aryl group optionally substituted by 1 to 3 halogen atoms.

[3]

The compound or salt of the above-mentioned [1], wherein $R^1$ is
  (1) a $C_{1-6}$ alkyl group,
  (2) a mono- or di-$C_{1-6}$ alkylamino group, or
  (3) a $C_{3-6}$ cycloalkyl group;

$R^2$ is
  (1) a hydrogen atom, or
  (2) a fluorine atom;

$R^3$ is
  (1) a $C_{1-6}$ alkyl-carbonyl group optionally substituted by 1 to 3 hydroxy groups,
  (2) a $C_{3-10}$ cycloalkyl-carbonyl group (the $C_{3-10}$ cycloalkyl moiety of the $C_{3-10}$ cycloalkyl-carbonyl group is optionally bridged) optionally substituted by 1 to 3 substituents selected from
    (a) a halogen atom, and
    (b) a hydroxy group,
  (3) a 3- to 8-membered monocyclic non-aromatic heterocyclylcarbonyl group, or
  (4) a mono- or di-$C_{1-6}$ alkyl-carbamoyl group; and Ring A is a benzene ring
further substituted by one $C_{6-14}$ aryl group optionally substituted by 1 to 3 substituents selected from
  (i) a halogen atom, and
  (ii) an optionally halogenated $C_{1-6}$ alkyl group, and
optionally further substituted by 1 to 3 halogen atoms.

[4]

The compound or salt of the above-mentioned [1], wherein $R^1$ is
  (1) a $C_{1-6}$ alkyl group, or
  (2) a mono- or di-$C_{1-6}$ alkylamino group;

R² is
- (1) a hydrogen atom, or
- (2) a fluorine atom;

R³ is
- (1) a $C_{1-6}$ alkyl-carbonyl group optionally substituted by 1 to 3 hydroxy groups,
- (2) a 3- to 8-membered monocyclic non-aromatic heterocyclylcarbonyl group, or
- (3) a mono- or di-$C_{1-6}$ alkyl-carbamoyl group; and Ring A is a benzene ring
further substituted by one $C_{6-14}$ aryl group optionally substituted by 1 to 3 substituents selected from
- (i) a halogen atom, and
- (ii) a $C_{1-6}$ alkyl group, and optionally further substituted by 1 to 3 halogen atoms.

[5]
N'-{(2S,3R,4S)-1-(azetidine-1-carbonyl)-4-fluoro-2-[(2-fluoro-3'-methyl[1,1'-biphenyl]-3-yl)methyl]pyrrolidin-3-yl}-N,N-dimethylsulfuric diamide or a salt thereof.

[6]
N-[(2S,3R)-2-[(2,3'-difluoro[1,1'-biphenyl]-3-yl)methyl]-4,4-difluoro-1-(2-methylpropanoyl)pyrrolidin-3-yl]ethanesulfonamide or a salt thereof.

[7]
N-{(2S,3R)-4,4-difluoro-1-(2-hydroxy-2-methylpropanoyl)-2-[(2,3',5'-trifluoro[1,1'-biphenyl]-3-yl)methyl]pyrrolidin-3-yl}ethanesulfonamide or a salt thereof.

[8]
A medicament comprising the compound or salt of any of the above-mentioned [1] to [7].

[9]
The medicament of the above-mentioned [8], which is an orexin type 2 receptor agonist.

[10]
The medicament of the above-mentioned [8], which is an agent for the prophylaxis or treatment of narcolepsy.

[11]
The compound or salt of any of the above-mentioned [1] to [7] for use in the prophylaxis or treatment of narcolepsy.

[12]
A method of activating an orexin type 2 receptor in a mammal, which comprises administering an effective amount of the compound or salt of any of the above-mentioned [1] to [7] to the mammal.

[13]
A method for the prophylaxis or treatment of narcolepsy in a mammal, which comprises administering an effective amount of the compound or salt of any of the above-mentioned [1] to [7] to the mammal.

[14]
Use of the compound or salt of any of the above-mentioned [1] to [7] for the manufacture of an agent for the prophylaxis or treatment of narcolepsy.

Effect of the Invention

The compound of the present invention has an orexin type 2 receptor agonist activity, and is useful as an agent for the prophylaxis or treatment of narcolepsy.

DETAILED DESCRIPTION OF THE INVENTION

The definition of each substituent used in the present specification is described in detail in the following. Unless otherwise specified, each substituent has the following definition.

In the present specification, examples of the "halogen atom" include fluorine, chlorine, bromine and iodine.

In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the present specification, examples of the "optionally halogenated $C_{1-6}$ alkyl group" include a $C_{1-6}$ alkyl group optionally having 1 to 7, preferably 1 to 5, halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.

In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.

In the present specification, examples of the "optionally halogenated $C_{3-10}$ cycloalkyl group" include a $C_{3-10}$ cycloalkyl group optionally having 1 to 7, preferably 1 to 5, halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl.

In the present specification, examples of the "$C_{3-10}$ cycloalkenyl group" include cyclopropenyl, cyclobutenyl, cyclopentenyl, cyclohexenyl, cycloheptenyl and cyclooctenyl.

In the present specification, examples of the "$C_{6-14}$ aryl group" include phenyl, 1-naphthyl, 2-naphthyl, 1-anthryl, 2-anthryl and 9-anthryl.

In the present specification, examples of the "$C_{7-16}$ aralkyl group" include benzyl, phenethyl, naphthylmethyl and phenylpropyl.

In the present specification, examples of the "$C_{1-6}$ alkoxy group" include methoxy, ethoxy, propoxy, isopropoxy, butoxy, isobutoxy, sec-butoxy, tert-butoxy, pentyloxy and hexyloxy.

In the present specification, examples of the "optionally halogenated $C_{1-6}$ alkoxy group" include a $C_{1-6}$ alkoxy group optionally having 1 to 7, preferably 1 to 5, halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, examples of the "$C_{3-10}$ cycloalkyloxy group" include cyclopropyloxy, cyclobutyloxy, cyclopentyloxy, cyclohexyloxy, cycloheptyloxy and cyclooctyloxy.

In the present specification, examples of the "$C_{1-6}$ alkylthio group" include methylthio, ethylthio, propylthio, isopropylthio, butylthio, sec-butylthio, tert-butylthio, pentylthio and hexylthio.

In the present specification, examples of the "optionally halogenated $C_{1-6}$ alkylthio group" include a $C_{1-6}$ alkylthio group optionally having 1 to 7, preferably 1 to 5, halogen atoms. Specific examples thereof include methylthio, difluoromethylthio, trifluoromethylthio, ethylthio, propylthio, isopropylthio, butylthio, 4,4,4-trifluorobutylthio, pentylthio and hexylthio.

In the present specification, examples of the "$C_{1-6}$ alkylcarbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, examples of the "optionally halogenated $C_{1-6}$ alkyl-carbonyl group" include a $C_{1-6}$ alkyl-carbonyl group optionally having 1 to 7, preferably 1 to 5, halogen atoms. Specific examples thereof include acetyl, chloroacetyl, trifluoroacetyl, trichloroacetyl, propanoyl, butanoyl, pentanoyl and hexanoyl.

In the present specification, examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, examples of the "$C_{6-14}$ aryl-carbonyl group" include benzoyl, 1-naphthoyl and 2-naphthoyl.

In the present specification, examples of the "$C_{7-16}$ aralkyl-carbonyl group" include phenylacetyl and phenylpropionyl.

In the present specification, examples of the "5- to 14-membered aromatic heterocyclylcarbonyl group" include nicotinoyl, isonicotinoyl, thenoyl and furoyl.

In the present specification, examples of the "3- to 14-membered non-aromatic heterocyclylcarbonyl group" include morpholinylcarbonyl, piperidinylcarbonyl and pyrrolidinylcarbonyl.

In the present specification, examples of the "mono- or di-$C_{1-6}$ alkyl-carbamoyl group" include methylcarbamoyl, ethylcarbamoyl, dimethylcarbamoyl, diethylcarbamoyl and N-ethyl-N-methylcarbamoyl.

In the present specification, examples of the "mono- or di-$C_{7-16}$ aralkyl-carbamoyl group" include benzylcarbamoyl and phenethylcarbamoyl.

In the present specification, examples of the "$C_{1-6}$ alkylsulfonyl group" include methylsulfonyl, ethylsulfonyl, propylsulfonyl, isopropylsulfonyl, butylsulfonyl, sec-butylsulfonyl and tert-butylsulfonyl.

In the present specification, examples of the "optionally halogenated $C_{1-6}$ alkylsulfonyl group" include a $C_{1-6}$ alkylsulfonyl group optionally having 1 to 7, preferably 1 to 5, halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

In the present specification, examples of the "$C_{6-14}$ arylsulfonyl group" include phenylsulfonyl, 1-naphthylsulfonyl and 2-naphthylsulfonyl.

In the present specification, examples of the "substituent" include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

In the present specification, examples of the "hydrocarbon group" (including "hydrocarbon group" of "optionally substituted hydrocarbon group") include a $C_{1-6}$ alkyl group, a $C_{2-6}$ alkenyl group, a $C_{2-6}$ alkynyl group, a $C_{3-10}$ cycloalkyl group, a $C_{3-10}$ cycloalkenyl group, a $C_{6-14}$ aryl group and a $C_{7-16}$ aralkyl group.

In the present specification, examples of the "optionally substituted hydrocarbon group" include a hydrocarbon group optionally having substituent(s) selected from the following Substituent group A.

[Substituent Group A]
(1) a halogen atom,
(2) a nitro group,
(3) a cyano group,
(4) an oxo group,
(5) a hydroxy group,
(6) an optionally halogenated $C_{1-6}$ alkoxy group,
(7) a $C_{6-14}$ aryloxy group (e.g., phenoxy, naphthoxy),
(8) a $C_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),
(12) a $C_{6-14}$ aryl-carbonyloxy group (e.g., benzoyloxy, 1-naphthoyloxy, 2-naphthoyloxy),
(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(15) a $C_{6-14}$ aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(19) a $C_{6-14}$ arylsulfonyloxy group optionally substituted by a $C_{1-6}$ alkyl group (e.g., phenylsulfonyloxy, toluenesulfonyloxy),
(20) an optionally halogenated $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(26) a $C_{6-14}$ aryl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(30) a $C_{6-14}$ aryloxy-carbonyl group (e.g., phenyloxycarbonyl, 1-naphthyloxycarbonyl, 2-naphthyloxycarbonyl),

(31) a $C_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-$C_{1-6}$ alkyl-carbamoyl group,
(35) a $C_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(39) a $C_{6-14}$ arylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(42) a $C_{6-14}$ arylsulfinyl group (e.g., phenylsulfinyl, 1-naphthylsulfinyl, 2-naphthylsulfinyl),
(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-$C_{6-14}$ arylamino group (e.g., phenylamino),
(47) a 5- to 14-membered aromatic heterocyclylamino group (e.g., pyridylamino),
(48) a $C_{7-16}$ aralkylamino group (e.g., benzylamino),
(49) a formylamino group,
(50) a $C_{1-6}$ alkyl-carbonylamino group (e.g., acetylamino, propanoylamino, butanoylamino),
(51) a ($C_{1-6}$ alkyl) ($C_{1-6}$ alkyl-carbonyl) amino group (e.g., N-acetyl-N-methylamino),
(52) a $C_{6-14}$ aryl-carbonylamino group (e.g., phenylcarbonylamino, naphthylcarbonylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(54) a $C_{7-16}$ aralkyloxy-carbonylamino group (e.g., benzyloxycarbonylamino),
(55) a $C_{1-6}$ alkylsulfonylamino group (e.g., methylsulfonylamino, ethylsulfonylamino),
(56) a $C_{6-14}$ arylsulfonylamino group optionally substituted by a $C_{1-6}$ alkyl group (e.g., phenylsulfonylamino, toluenesulfonylamino),
(57) an optionally halogenated $C_{1-6}$ alkyl group,
(58) a $C_{2-6}$ alkenyl group,
(59) a $C_{2-6}$ alkynyl group,
(60) a $C_{3-10}$ cycloalkyl group,
(61) a $C_{3-10}$ cycloalkenyl group, and
(62) a $C_{6-14}$ aryl group.

The number of the above-mentioned substituents in the "optionally substituted hydrocarbon group" is, for example, 1 to 5, preferably 1 to 3. When the number of the substituents is two or more, the respective substituents may be the same or different.

In the present specification, examples of the "heterocyclic group" (including "heterocyclic group" of "optionally substituted heterocyclic group") include (i) an aromatic heterocyclic group, (ii) a non-aromatic heterocyclic group and (iii) a 7- to 10-membered bridged heterocyclic group, each containing, as a ring-constituting atom besides carbon atom, 1 to 4 heteroatoms selected from a nitrogen atom, a sulfur atom and an oxygen atom.

In the present specification, examples of the "aromatic heterocyclic group" (including "5- to 14-membered aromatic heterocyclic group") include a 5- to 14-membered (preferably 5- to 10-membered) aromatic heterocyclic group containing, as a ring-constituting atom besides carbon atom, 1 to 4 heteroatoms selected from a nitrogen atom, a sulfur atom and an oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and 8- to 14-membered fused polycyclic (preferably bi- or tricyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, phenoxazinyl and the like.

In the present specification, examples of the "non-aromatic heterocyclic group" (including "3- to 14-membered non-aromatic heterocyclic group") include a 3- to 14-membered (preferably 4- to 10-membered) non-aromatic heterocyclic group containing, as a ring-constituting atom besides carbon atom, 1 to 4 heteroatoms selected from a nitrogen atom, a sulfur atom and an oxygen atom.

Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisoxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and 9- to 14-membered fused polycyclic (preferably bi- or tricyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacrydinyl, tetrahydrophenazinyl, tetrahydrothioxanthenyl, octahydroisoquinolyl and the like.

In the present specification, preferable examples of the "7- to 10-membered bridged heterocyclic group" include quinuclidinyl and 7-azabicyclo[2.2.1]heptanyl.

In the present specification, examples of the "nitrogen-containing heterocyclic group" include a "heterocyclic group" containing at least one nitrogen atom as a ring-constituting atom.

In the present specification, examples of the "optionally substituted heterocyclic group" include a heterocyclic group optionally having substituent(s) selected from the above-mentioned Substituent group A.

The number of the substituents in the "optionally substituted heterocyclic group" is, for example, 1 to 3. When the number of the substituents is two or more, the respective substituents may be the same or different.

In the present specification, examples of the "acyl group" include a formyl group, a carboxy group, a carbamoyl group, a thiocarbamoyl group, a sulfino group, a sulfo group, a sulfamoyl group and a phosphono group, each optionally having "1 or 2 substituents selected from a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-16}$ aralkyl group, a 5- to 14-membered aromatic heterocyclic group, a 3- to 14-membered non-aromatic heterocyclic group, an amino group and a mono- or di-$C_{1-6}$ alkyl-amino group, each of which optionally has 1 to 3 substituents selected from a halogen atom, an optionally halogenated $C_{1-6}$ alkoxy group, a hydroxy group, a nitro group, a cyano group, an amino group and a carbamoyl group".

Examples of the "acyl group" also include a hydrocarbon-sulfonyl group, a heterocyclylsulfonyl group, a hydrocarbon-sulfinyl group and a heterocyclylsulfinyl group.

Here, the hydrocarbon-sulfonyl group means a hydrocarbon group-bonded sulfonyl group, the heterocyclylsulfonyl group means a heterocyclic group-bonded sulfonyl group, the hydrocarbon-sulfinyl group means a hydrocarbon group-bonded sulfinyl group and the heterocyclylsulfinyl group means a heterocyclic group-bonded sulfinyl group.

Preferable examples of the "acyl group" include a formyl group, a carboxy group, a $C_{1-6}$ alkyl-carbonyl group, a $C_{2-6}$ alkenyl-carbonyl group (e.g., crotonoyl), a $C_{3-10}$ cycloalkyl-carbonyl group (e.g., cyclobutanecarbonyl, cyclopentanecarbonyl, cyclohexanecarbonyl, cycloheptanecarbonyl), a $C_{3-10}$ cycloalkenyl-carbonyl group (e.g., 2-cyclohexenecarbonyl), a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a $C_{6-14}$ aryloxy-carbonyl group (e.g., phenyloxycarbonyl, naphthyloxycarbonyl), a $C_{7-16}$ aralkyloxy-carbonyl group (e.g., benzyloxycarbonyl, phenethyloxycarbonyl), a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl), a mono- or di-$C_{6-14}$ aryl-carbamoyl group (e.g., phenylcarbamoyl), a mono- or di-$C_{7-16}$ aralkyl-carbamoyl group, a 5- to 14-membered aromatic heterocyclylcarbamoyl group (e.g., pyridylcarbamoyl), N—$C_{1-6}$ alkyl-N',N'-di-$C_{1-6}$ alkylhydrazine-carbonyl group, a thiocarbamoyl group, a mono- or di-$C_{1-6}$ alkyl-thiocarbamoyl group (e.g., methylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a 5- to 14-membered aromatic heterocyclylthiocarbamoyl group (e.g., pyridylthiocarbamoyl), a sulfino group, a $C_{1-6}$ alkylsulfinyl group (e.g., methylsulfinyl, ethylsulfinyl), a sulfo group, a $C_{1-6}$ alkylsulfonyl group, a $C_{6-14}$ arylsulfonyl group, a phosphono group and a mono- or di-$C_{1-6}$ alkylphosphono group (e.g., dimethylphosphono, diethylphosphono, diisopropylphosphono, dibutylphosphono).

In the present specification, examples of the "optionally substituted amino group" include an amino group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from Substituent group A".

Preferable examples of the optionally substituted amino group include an amino group, a mono- or di-(optionally halogenated $C_{1-6}$ alkyl) amino group (e.g., methylamino, trifluoromethylamino, dimethylamino, ethylamino, diethylamino, propylamino, dibutylamino), a mono- or di-$C_{2-6}$ alkenylamino group (e.g., diallylamino), a mono- or di-$C_{3-10}$ cycloalkylamino group (e.g., cyclopropylamino, cyclohexylamino), a mono- or di-$C_{6-14}$ arylamino group (e.g., phenylamino), a mono- or di-$C_{7-16}$ aralkylamino group (e.g., benzylamino, dibenzylamino), a mono- or di-(optionally halogenated $C_{1-6}$ alkyl)-carbonylamino group (e.g., acetylamino, propionylamino), a mono- or di-$C_{6-14}$ aryl-carbonylamino group (e.g., benzoylamino), a mono- or di-$C_{7-16}$ aralkyl-carbonylamino group (e.g., benzylcarbonylamino), a mono- or di-5- to 14-membered aromatic heterocyclylcarbonylamino group (e.g., nicotinoylamino, isonicotinoylamino), a mono- or di-3- to 14-membered non-aromatic heterocyclylcarbonylamino group (e.g., piperidinylcarbonylamino), a mono- or di-$C_{1-6}$ alkoxy-carbonylamino group (e.g., tert-butoxycarbonylamino), a 5- to 14-membered aromatic heterocyclylamino group (e.g., pyridylamino), a carbamoylamino group, a (mono- or di-$C_{1-6}$ alkyl-carbamoyl) amino group (e.g., methylcarbamoylamino), a (mono- or di-$C_{7-16}$ aralkyl-carbamoyl) amino group (e.g., benzylcarbamoylamino), a $C_{1-6}$ alkylsulfonylamino group (e.g., methylsulfonylamino, ethylsulfonylamino), a $C_{6-14}$ arylsulfonylamino group (e.g., phenylsulfonylamino), a ($C_{1-6}$ alkyl) ($C_{1-6}$ alkyl-carbonyl) amino group (e.g., N-acetyl-N-methylamino) and a ($C_{1-6}$ alkyl) ($C_{6-14}$ aryl-carbonyl) amino group (e.g., N-benzoyl-N-methylamino).

In the present specification, examples of the "optionally substituted carbamoyl group" include a carbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent group A".

Preferable examples of the optionally substituted carbamoyl group include a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{7-16}$ aralkyl-carbamoyl group, a mono- or di-$C_{1-6}$ alkyl-carbonyl-carbamoyl group (e.g., acetylcarbamoyl, propionylcarbamoyl), a mono- or di-$C_{6-14}$ aryl-carbonyl-carbamoyl group (e.g., benzoylcarbamoyl) and a 5- to 14-membered aromatic heterocyclylcarbamoyl group (e.g., pyridylcarbamoyl).

In the present specification, examples of the "optionally substituted thiocarbamoyl group" include a thiocarbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent group A".

Preferable examples of the optionally substituted thiocarbamoyl group include a thiocarbamoyl group, a mono- or di-$C_{1-6}$ alkyl-thiocarbamoyl group (e.g., methylthiocarbamoyl, ethylthiocarbamoyl, dimethylthiocarbamoyl, diethylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a mono- or di-$C_{1-6}$ alkyl-carbonyl-thiocarbamoyl group (e.g., acetylthiocarbamoyl, propionylthiocarbamoyl), a mono- or di-$C_{6-14}$ aryl-carbonyl-thiocarbamoyl group (e.g., benzoylthiocarbamoyl) and a 5- to 14-membered aromatic heterocyclylthiocarbamoyl group (e.g., pyridylthiocarbamoyl).

In the present specification, examples of the "optionally substituted sulfamoyl group" include a sulfamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent group A".

Preferable examples of the optionally substituted sulfamoyl group include a sulfamoyl group, a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl), a mono- or di-$C_{2-6}$ alkenyl-sulfamoyl group (e.g., diallylsulfamoyl), a mono- or di-$C_{3-10}$ cycloalkyl-sulfamoyl group (e.g., cyclopropylsulfamoyl, cyclohexylsulfamoyl), a mono- or di-$C_{6-14}$ aryl-sulfamoyl group (e.g., phenylsulfamoyl), a mono- or di-$C_{7-16}$ aralkyl-sulfamoyl group (e.g., benzylsulfamoyl, phenethylsulfamoyl), a mono- or di-$C_{1-6}$ alkyl-carbonyl-sulfamoyl group (e.g., acetylsulfamoyl, propionylsulfamoyl), a mono- or di-$C_{6-14}$ aryl-carbonyl-sulfamoyl group (e.g., benzoylsulfamoyl) and a 5- to 14-membered aromatic heterocyclylsulfamoyl group (e.g., pyridylsulfamoyl).

In the present specification, examples of the "optionally substituted hydroxy group" include a hydroxy group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from Substituent group A".

Preferable examples of the optionally substituted hydroxy group include a hydroxy group, a $C_{1-6}$ alkoxy group, a $C_{2-6}$ alkenyloxy group (e.g., allyloxy, 2-butenyloxy, 2-pentenyloxy, 3-hexenyloxy), a $C_{3-10}$ cycloalkyloxy group (e.g., cyclohexyloxy), a $C_{6-14}$ aryloxy group (e.g., phenoxy, naphthyloxy), a $C_{7-16}$ aralkyloxy group (e.g., benzyloxy, phenethyloxy), a $C_{1-6}$ alkyl-carbonyloxy group (e.g., acetyloxy, propionyloxy, butyryloxy, isobutyryloxy, pivaloyloxy), a $C_{6-14}$ aryl-carbonyloxy group (e.g., benzoyloxy), a $C_{7-16}$ aralkyl-carbonyloxy group (e.g., benzylcarbonyloxy), a 5- to 14-membered aromatic heterocyclylcarbonyloxy group (e.g., nicotinoyloxy), a 3- to 14-membered non-aromatic heterocyclylcarbonyloxy group (e.g., piperidinylcarbonyloxy), a $C_{1-6}$ alkoxy-carbonyloxy group (e.g., tert-butoxycarbonyloxy), a 5- to 14-membered aromatic heterocyclyloxy group (e.g., pyridyloxy), a carbamoyloxy group, a $C_{1-6}$ alkyl-carbamoyloxy group (e.g., methylcarbamoyloxy), a $C_{7-16}$ aralkyl-carbamoyloxy group (e.g., benzylcarbamoyloxy), a $C_{1-6}$ alkylsulfonyloxy group (e.g., methylsulfonyloxy, ethylsulfonyloxy) and a $C_{6-14}$ arylsulfonyloxy group (e.g., phenylsulfonyloxy).

In the present specification, examples of the "optionally substituted sulfanyl group" include a sulfanyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group and a 5- to 14-membered aromatic heterocyclic group, each of which optionally has 1 to 3 substituents selected from Substituent group A" and a halogenated sulfanyl group.

Preferable examples of the optionally substituted sulfanyl group include a sulfanyl (—SH) group, a $C_{1-6}$ alkylthio group, a $C_{2-6}$ alkenylthio group (e.g., allylthio, 2-butenylthio, 2-pentenylthio, 3-hexenylthio), a $C_{3-10}$ cycloalkylthio group (e.g., cyclohexylthio), a $C_{6-14}$ arylthio group (e.g., phenylthio, naphthylthio), a $C_{7-16}$ aralkylthio group (e.g., benzylthio, phenethylthio), a $C_{1-6}$ alkyl-carbonylthio group (e.g., acetylthio, propionylthio, butyrylthio, isobutyrylthio, pivaloylthio), a $C_{6-14}$ aryl-carbonylthio group (e.g., benzoylthio), a 5- to 14-membered aromatic heterocyclylthio group (e.g., pyridylthio) and a halogenated thio group (e.g., pentafluorothio).

In the present specification, examples of the "optionally substituted silyl group" include a silyl group optionally having "1 to 3 substituents selected from a $C_{1-6}$ alkyl group, a $C_{2-6}$ alkenyl group, a $C_{3-10}$ cycloalkyl group, a $C_{6-14}$ aryl group and a $C_{7-16}$ aralkyl group, each of which optionally has 1 to 3 substituents selected from Substituent group A".

Preferable examples of the optionally substituted silyl group include a tri-$C_{1-6}$ alkylsilyl group (e.g., trimethylsilyl, tert-butyl(dimethyl) silyl).

In the present specification, examples of the "hydrocarbon ring" include a $C_{6-14}$ aromatic hydrocarbon ring, $C_{3-10}$ cycloalkane and $C_{3-10}$ cycloalkene.

In the present specification, examples of the "$C_{6-14}$ aromatic hydrocarbon ring" include benzene and naphthalene.

In the present specification, examples of the "$C_{3-10}$ cycloalkane" include cyclopropane, cyclobutane, cyclopentane, cyclohexane, cycloheptane and cyclooctane.

In the present specification, examples of the "$C_{3-10}$ cycloalkene" include cyclopropene, cyclobutene, cyclopentene, cyclohexene, cycloheptene and cyclooctene.

In the present specification, examples of the "heterocycle" include an aromatic heterocycle and a non-aromatic heterocycle, each containing, as a ring-constituting atom besides carbon atom, 1 to 4 hetero atoms selected from a nitrogen atom, a sulfur atom and an oxygen atom.

In the present specification, examples of the "aromatic heterocycle" include a 5- to 14-membered (preferably 5- to 10-membered) aromatic heterocycle containing, as a ring-constituting atom besides carbon atom, 1 to 4 hetero atoms selected from a nitrogen atom, a sulfur atom and an oxygen atom. Preferable examples of the "aromatic heterocycle" include 5- or 6-membered monocyclic aromatic heterocycles such as thiophene, furan, pyrrole, imidazole, pyrazole, thiazole, isothiazole, oxazole, isoxazole, pyridine, pyrazine, pyrimidine, pyridazine, 1,2,4-oxadiazole, 1,3,4-oxadiazole, 1,2,4-thiadiazole, 1,3,4-thiadiazole, triazole, tetrazole, triazine and the like; and 8- to 14-membered fused polycyclic (preferably bi- or tricyclic) aromatic heterocycles such as benzothiophene, benzofuran, benzimidazole, benzoxazole, benzisoxazole, benzothiazole, benzisothiazole, benzotriazole, imidazopyridine, thienopyridine, furopyridine, pyrrolopyridine, pyrazolopyridine, oxazolopyridine, thiazolopyridine, imidazopyrazine, imidazopyrimidine, thienopyrimidine, furopyrimidine, pyrrolopyrimidine, pyrazolopyrimidine, oxazolopyrimidine, thiazolopyrimidine, pyrazolopyrimidine, pyrazolotriazine, naphtho[2,3-b]thiophene, phenoxathiin, indole, isoindole, 1H-indazole, purine, isoquinoline, quinoline, phthalazine, naphthyridine, quinoxaline, quinazoline, cinnoline, carbazole, β-carboline, phenanthridine, acridine, phenazine, phenothiazine, phenoxazine and the like.

In the present specification, examples of the "non-aromatic heterocycle" include a 3- to 14-membered (preferably 4- to 10-membered) non-aromatic heterocycle containing, as a ring-constituting atom besides carbon atom, 1 to 4 hetero atoms selected from a nitrogen atom, a sulfur atom and an oxygen atom. Preferable examples of the "non-aromatic heterocycle" include 3- to 8-membered monocyclic non-aromatic heterocycles such as aziridine, oxirane, thiirane, azetidine, oxetane, thietane, tetrahydrothiophene, tetrahydrofuran, pyrroline, pyrrolidine, imidazoline, imidazolidine, oxazoline, oxazolidine, pyrazoline, pyrazolidine, thiazoline, thiazolidine, tetrahydroisothiazole, tetrahydrooxazole, tetrahydroisoxazole, piperidine, piperazine, tetrahydropyridine, dihydropyridine, dihydrothiopyran, tetrahydropyrimidine, tetrahydropyridazine, dihydropyran, tetrahydropyran, tetrahydrothiopyran, morpholine, thiomorpholine, azepane, diazepane, azepine, azocane, diazocane, oxepane and the like; and 9- to 14-membered fused polycyclic (preferably bi- or tricyclic) non-aromatic heterocycles such as dihydrobenzofuran, dihydrobenzimidazole, dihydrobenzoxazole, dihydrobenzothiazole, dihydrobenzisothiazole, dihydronaphtho[2,3-b]thiophene, tetrahydroisoquinoline, tetrahydroquinoline, 4H-quinolizine, indoline, isoindoline, tetrahydrothieno[2,3-c]pyridine, tetrahydrobenzazepine, tetrahydroquinoxaline, tetrahydrophenanthridine, hexahydrophenothiazine, hexahydrophenoxazine, tetrahydrophthalazine, tetrahydronaphthyridine, tetrahydroquinazoline, tetrahydrocinnoline, tetrahydrocarbazole, tetrahydro-β-carboline, tetrahydroacridine, tetrahydrophenazine, tetrahydrothioxanthene, octahydroisoquinoline and the like.

In the present specification, examples of the "nitrogen-containing heterocycle" include a heterocycle containing at least one nitrogen atom as a ring-constituting atom, from among the "heterocycle".

In the present specification, examples of the "$C_{3-6}$ cycloalkyl group" include cyclopropyl, cyclobutyl, cyclopentyl and cyclohexyl.

In the present specification, examples of the "mono- or di-$C_{1-6}$ alkylamino group" include methylamino, dimethylamino, ethylamino, diethylamino, propylamino, isopropylamino, butylamino, isobutylamino, sec-butylamino, tert-butylamino, pentylamino, isopentylamino, neopentylamino, 1-ethylpropylamino, hexylamino, isohexylamino, 1,1-dimethylbutylamino, 2,2-dimethylbutylamino, 3,3-dimethylbutylamino, 2-ethylbutylamino and the like.

The definition of each symbol in the formula (I) is explained in detail in the following.

$R^1$ is an optionally substituted $C_{1-6}$ alkyl group, an optionally substituted mono- or di-$C_{1-6}$ alkylamino group, an optionally substituted $C_{3-6}$ cycloalkyl group, or an optionally substituted 3- to 14-membered non-aromatic heterocyclic group.

Examples of the substituent of the above-mentioned "optionally substituted $C_{1-6}$ alkyl group", "optionally substituted mono- or di-$C_{1-6}$ alkylamino group", "optionally substituted $C_{3-6}$ cycloalkyl group" and "optionally substituted 3- to 14-membered non-aromatic heterocyclic group" include substituents selected from Substituent group A. The number of the substituents is preferably 1 to 3. When the number of the substituents is 2 or more, the respective substituents may be the same or different.

$R^1$ is preferably
(1) an optionally substituted $C_{1-6}$ alkyl group (e.g., methyl, ethyl),
(2) an optionally substituted mono- or di-$C_{1-6}$ alkylamino group (e.g., dimethylamino), or
(3) an optionally substituted $C_{3-6}$ cycloalkyl group (e.g., cyclopropyl).

$R^1$ is more preferably
(1) a $C_{1-6}$ alkyl group (e.g., methyl, ethyl),
(2) a mono- or di-$C_{1-6}$ alkylamino group (e.g., dimethylamino), or
(3) a $C_{3-6}$ cycloalkyl group (e.g., cyclopropyl).

$R^1$ is further more preferably
(1) a $C_{1-6}$ alkyl group (e.g., methyl, ethyl), or
(2) a mono- or di-$C_{1-6}$ alkylamino group (e.g., dimethylamino).

$R^2$ is a hydrogen atom, a fluorine atom, an optionally substituted $C_{1-6}$ alkyl group, or an optionally substituted $C_{3-6}$ cycloalkyl group.

Examples of the substituent of the above-mentioned "optionally substituted $C_{1-6}$ alkyl group" and "optionally substituted $C_{3-6}$ cycloalkyl group" include substituents selected from Substituent group A. The number of the substituents is preferably 1 to 3. When the number of the substituents is 2 or more, the respective substituents may be the same or different.

$R^2$ is preferably
(1) a hydrogen atom,
(2) a fluorine atom, or
(3) an optionally substituted $C_{1-6}$ alkyl group (e.g., methyl).

$R^2$ is more preferably
(1) a hydrogen atom,
(2) a fluorine atom, or
(3) a $C_{1-6}$ alkyl group (e.g., methyl).

$R^2$ is further more preferably
(1) a hydrogen atom, or
(2) a fluorine atom.

$R^3$ is an acyl group, an optionally substituted $C_{1-6}$ alkyl group, an optionally substituted $C_{3-6}$ cycloalkyl group, an optionally substituted $C_{6-14}$ aryl group, an optionally substituted 3- to 14-membered non-aromatic heterocyclic group, or an optionally substituted 5- to 14-membered aromatic heterocyclic group.

Examples of the substituent of the above-mentioned "optionally substituted $C_{1-6}$ alkyl group", "optionally substituted $C_{3-6}$ cycloalkyl group", "optionally substituted $C_{6-14}$ aryl group", "optionally substituted 3- to 14-membered non-aromatic heterocyclic group" and "optionally substituted 5- to 14-membered aromatic heterocyclic group" include substituents selected from Substituent group A. The number of the substituents is preferably 1 to 3. When the number of the substituents is 2 or more, the respective substituents may be the same or different.

$R^3$ is preferably an acyl group.

$R^3$ is more preferably
(1) an optionally substituted $C_{1-6}$ alkyl-carbonyl group (e.g., 2-methylpropanoyl, 2,2-dimethylpropanoyl, butanoyl, 2-methylbutanoyl),
(2) an optionally substituted $C_{1-6}$ alkoxy-carbonyl group (e.g., ethoxycarbonyl, tert-butoxycarbonyl),
(3) an optionally substituted $C_{3-10}$ cycloalkyl-carbonyl group (the $C_{3-10}$ cycloalkyl moiety of the $C_{3-10}$ cycloalkyl-carbonyl group is optionally bridged (e.g., cyclopropylcarbonyl, cyclobutylcarbonyl, bicyclo[1.1.1]pentan-1-ylcarbonyl)),
(4) an optionally substituted 3- to 14-membered non-aromatic heterocyclylcarbonyl group (preferably a 3- to 8-membered monocyclic non-aromatic heterocyclylcarbonyl group (e.g., oxetanylcarbonyl, tetrahydrofurylcarbonyl, azetidinylcarbonyl)),
(5) an optionally substituted mono- or di-$C_{1-6}$ alkyl-carbamoyl group (e.g., dimethylcarbamoyl),
(6) an optionally substituted N—$C_{1-6}$ alkyl-N—$C_{1-6}$ alkoxy-carbamoyl group (e.g., N-methyl-N-methoxycarbamoyl), or
(7) a N—$C_{1-6}$ alkyl-N',N'-di-$C_{1-6}$ alkylhydrazine-carbonyl group (e.g., N-methyl-N',N'-dimethylhydrazinecarbonyl).

$R^3$ is further more preferably
(1) a $C_{1-6}$ alkyl-carbonyl group (e.g., 2-methylpropanoyl, 2,2-dimethylpropanoyl, butanoyl, 2-methylbutanoyl) optionally substituted by 1 to 3 substituents selected from
  (a) a halogen atom (e.g., a fluorine atom),
  (b) a hydroxy group, and
  (c) a cyano group,
(2) a $C_{1-6}$ alkoxy-carbonyl group (e.g., ethoxycarbonyl, tert-butoxycarbonyl),
(3) a $C_{3-10}$ cycloalkyl-carbonyl group (the $C_{3-10}$ cycloalkyl moiety of the $C_{3-10}$ cycloalkyl-carbonyl group is optionally bridged (e.g., cyclopropylcarbonyl, cyclobutylcarbonyl, bicyclo[1.1.1]pentan-1-ylcarbonyl)) optionally substituted by 1 to 3 substituents selected from
  (a) a halogen atom (e.g., a fluorine atom),
  (b) a hydroxy group,
  (c) a cyano group, and
  (d) a $C_{1-6}$ alkyl group (e.g., methyl),
(4) a 3- to 14-membered non-aromatic heterocyclylcarbonyl group (preferably a 3- to 8-membered monocyclic non-aromatic heterocyclylcarbonyl group (e.g., oxetanylcarbonyl, tetrahydrofurylcarbonyl, azetidinylcarbonyl)) optionally substituted by 1 to 3 substituents selected from
  (a) a halogen atom (e.g., a fluorine atom),
  (b) a hydroxy group, and
  (c) a $C_{1-6}$ alkyl group (e.g., methyl),
(5) a mono- or di-$C_{1-6}$ alkyl-carbamoyl group (e.g., dimethylcarbamoyl),
(6) a N—$C_{1-6}$ alkyl-N—$C_{1-6}$ alkoxy-carbamoyl group (e.g., N-methyl-N-methoxycarbamoyl), or
(7) a N—$C_{1-6}$ alkyl-N',N'-di-$C_{1-6}$ alkylhydrazine-carbonyl group (e.g., N-methyl-N',N'-dimethylhydrazinecarbonyl).

$R^3$ is still more preferably
(1) a $C_{1-6}$ alkyl-carbonyl group (e.g., 2-methylpropanoyl, butanoyl) optionally substituted by 1 to 3 hydroxy groups,
(2) a $C_{3-10}$ cycloalkyl-carbonyl group (the $C_{3-10}$ cycloalkyl moiety of the $C_{3-10}$ cycloalkyl-carbonyl group is optionally bridged (e.g., cyclopropylcarbonyl, cyclobutylcarbonyl, bicyclo[1.1.1]pentan-1-ylcarbonyl)) optionally substituted by 1 to 3 substituents selected from
  (a) a halogen atom (e.g., a fluorine atom), and
  (b) a hydroxy group,
(3) a 3- to 8-membered monocyclic non-aromatic heterocyclylcarbonyl group (e.g., oxetanylcarbonyl, tetrahydrofurylcarbonyl, azetidinylcarbonyl), or
(4) a mono- or di-$C_{1-6}$ alkyl-carbamoyl group (e.g., dimethylcarbamoyl).

$R^3$ is even more preferably
(1) a $C_{1-6}$ alkyl-carbonyl group (e.g., 2-methylpropanoyl) optionally substituted by 1 to 3 hydroxy groups,
(2) a $C_{3-10}$ cycloalkyl-carbonyl group (the $C_{3-10}$ cycloalkyl moiety of the $C_{3-10}$ cycloalkyl-carbonyl group is optionally bridged (e.g., cyclopropylcarbonyl, cyclobutylcarbonyl, bicyclo[1.1.1]pentan-1-ylcarbonyl)) optionally substituted by 1 to 3 substituents selected from
  (a) a halogen atom (e.g., a fluorine atom), and
  (b) a hydroxy group,
(3) a 3- to 8-membered monocyclic non-aromatic heterocyclylcarbonyl group (e.g., oxetanylcarbonyl, azetidinylcarbonyl), or
(4) a mono- or di-$C_{1-6}$ alkyl-carbamoyl group (e.g., dimethylcarbamoyl).

$R^3$ is particularly preferably
(1) a $C_{1-6}$ alkyl-carbonyl group (e.g., 2-methylpropanoyl) optionally substituted by 1 to 3 hydroxy groups,
(2) a 3- to 8-membered monocyclic non-aromatic heterocyclylcarbonyl group (e.g., oxetanylcarbonyl, azetidinylcarbonyl), or
(3) a mono- or di-$C_{1-6}$ alkyl-carbamoyl group (e.g., dimethylcarbamoyl).

Ring A is an optionally further substituted $C_{6-14}$ aromatic hydrocarbon ring, or an optionally further substituted 5- to 14-membered aromatic heterocycle.

Ring A optionally has substituent(s) in addition to —CH$_2$-pyrrolidine ring in the formula (I). Examples of the substituent include the above-mentioned "substituent". The number of the substituents is preferably 1 to 3. When the number of the substituents is 2 or more, the respective substituents may be the same or different.

Ring A is preferably
(1) an optionally further substituted benzene ring, or
(2) an optionally further substituted 5- or 6-membered aromatic heterocycle (e.g., thiazole, pyridine).

Ring A is more preferably
(1) a benzene ring further substituted by one substituent selected from
  (a) a C$_{6-14}$ aryl group (e.g., phenyl) optionally substituted by 1 to 3 substituents selected from
    (i) a halogen atom (e.g., a fluorine atom, a chlorine atom, a bromine atom),
    (ii) an optionally halogenated C$_{1-6}$ alkyl group (e.g., methyl, difluoromethyl), and
    (iii) an optionally halogenated C$_{1-6}$ alkoxy group (e.g., methoxy, difluoromethoxy), and
  (b) a 5- to 14-membered aromatic heterocyclic group (preferably a 5- or 6-membered aromatic heterocyclic group (e.g., pyridyl, pyrimidinyl, pyridazinyl, thiazolyl, oxazolyl)) optionally substituted by 1 to 3 substituents selected from
    (i) a C$_{1-6}$ alkyl group (e.g., methyl, ethyl) optionally substituted by 1 to 3 substituents selected from a halogen atom (e.g., a fluorine atom) and a hydroxy group,
    (ii) a C$_{1-6}$ alkoxy group (e.g., methoxy),
    (iii) a halogen atom (e.g., a fluorine atom, a chlorine atom), and
    (iv) a C$_{1-6}$ alkoxy-carbonyl group (e.g., ethoxycarbonyl), and
optionally further substituted by 1 to 3 halogen atoms (e.g., a fluorine atom), or
(2) a 5- or 6-membered aromatic heterocycle (e.g., thiazole, pyridine) further substituted by one C$_{6-14}$ aryl group (e.g., phenyl) optionally substituted by 1 to 3 halogen atoms (e.g., a fluorine atom).

Ring A is further more preferably a benzene ring further substituted by one C$_{6-14}$ aryl group (e.g., phenyl) optionally substituted by 1 to 3 substituents selected from
  (i) a halogen atom (e.g., a fluorine atom, a chlorine atom), and
  (ii) an optionally halogenated C$_{1-6}$ alkyl group (e.g., methyl, difluoromethyl), and
optionally further substituted by 1 to 3 halogen atoms (e.g., a fluorine atom).

Ring A is particularly preferably a benzene ring further substituted by one C$_{6-14}$ aryl group (e.g., phenyl) optionally substituted by 1 to 3 substituents selected from
  (i) a halogen atom (e.g., a fluorine atom), and
  (ii) a C$_{1-6}$ alkyl group (e.g., methyl), and
optionally further substituted by 1 to 3 halogen atoms (e.g., a fluorine atom).

Regarding the pyrrolidine ring of compound (I), the configuration based on the carbon atom that —NHSO$_2$R$^1$ is bonded to and the carbon atom that —CH$_2$-Ring A is bonded to is preferably cis-form. That is, compound (I) is preferably represented by the formula (IA) or (IB):

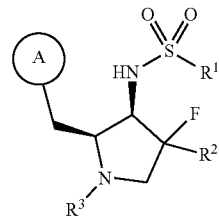

(IA)

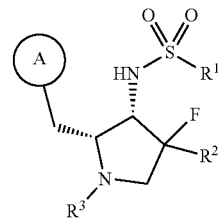

(IB)

wherein each symbol is as defined above,
more preferably represented by the formula (IA):

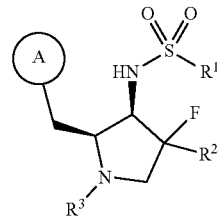

(IA)

wherein each symbol is as defined above.

Preferable examples of compound (I) include the following compounds. These compounds are preferably represented by the above formula (IA) or (IB), more preferably represented by the formula (IA).

[Compound A]
Compound (I) wherein
R$^1$ is
(1) an optionally substituted C$_{1-6}$ alkyl group (e.g., methyl, ethyl),
(2) an optionally substituted mono- or di-C$_{1-6}$ alkylamino group (e.g., dimethylamino), or
(3) an optionally substituted C$_{3-6}$ cycloalkyl group (e.g., cyclopropyl);
R$^2$ is
(1) a hydrogen atom,
(2) a fluorine atom, or
(3) an optionally substituted C$_{1-6}$ alkyl group (e.g., methyl);
R$^3$ is
(1) an optionally substituted C$_{1-6}$ alkyl-carbonyl group (e.g., 2-methylpropanoyl, 2,2-dimethylpropanoyl, butanoyl, 2-methylbutanoyl),
(2) an optionally substituted C$_{1-6}$ alkoxy-carbonyl group (e.g., ethoxycarbonyl, tert-butoxycarbonyl),
(3) an optionally substituted C$_{3-10}$ cycloalkyl-carbonyl group (the C$_{3-10}$ cycloalkyl moiety of the C$_{3-10}$ cycloalkyl-carbonyl group is optionally bridged (e.g., cyclopropylcarbonyl, cyclobutylcarbonyl, bicyclo[1.1.1]pentan-1-ylcarbonyl)),
(4) an optionally substituted 3- to 14-membered non-aromatic heterocyclylcarbonyl group (preferably a 3- to 8-membered monocyclic non-aromatic heterocyclyl-carbonyl group (e.g., oxetanylcarbonyl, tetrahydrofurylcarbonyl, azetidinylcarbonyl)),
(5) an optionally substituted mono- or di-$C_{1-6}$ alkyl-carbamoyl group (e.g., dimethylcarbamoyl),
(6) an optionally substituted N—$C_{1-6}$ alkyl-N—$C_{1-6}$ alkoxy-carbamoyl group (e.g., N-methyl-N-methoxycarbamoyl), or
(7) a N—$C_{1-6}$ alkyl-N',N'-di-$C_{1-6}$ alkylhydrazine-carbonyl group (e.g., N-methyl-N',N'-dimethylhydrazinecarbonyl); and Ring A is
(1) an optionally further substituted benzene ring, or
(2) an optionally further substituted 5- or 6-membered aromatic heterocycle (e.g., thiazole, pyridine).

[Compound B]
Compound (I) wherein
$R^1$ is
(1) a $C_{1-6}$ alkyl group (e.g., methyl, ethyl),
(2) a mono- or di-$C_{1-6}$ alkylamino group (e.g., dimethylamino), or
(3) a $C_{3-6}$ cycloalkyl group (e.g., cyclopropyl);
$R^2$ is
(1) a hydrogen atom,
(2) a fluorine atom, or
(3) a $C_{1-6}$ alkyl group (e.g., methyl);
$R^3$ is
(1) a $C_{1-6}$ alkyl-carbonyl group (e.g., 2-methylpropanoyl, 2,2-dimethylpropanoyl, butanoyl, 2-methylbutanoyl) optionally substituted by 1 to 3 substituents selected from
  (a) a halogen atom (e.g., a fluorine atom),
  (b) a hydroxy group, and
  (c) a cyano group,
(2) a $C_{1-6}$ alkoxy-carbonyl group (e.g., ethoxycarbonyl, tert-butoxycarbonyl),
(3) a $C_{3-10}$ cycloalkyl-carbonyl group (the $C_{3-10}$ cycloalkyl moiety of the $C_{3-10}$ cycloalkyl-carbonyl group is optionally bridged (e.g., cyclopropylcarbonyl, cyclobutylcarbonyl, bicyclo[1.1.1]pentan-1-ylcarbonyl)) optionally substituted by 1 to 3 substituents selected from
  (a) a halogen atom (e.g., a fluorine atom),
  (b) a hydroxy group,
  (c) a cyano group, and
  (d) a $C_{1-6}$ alkyl group (e.g., methyl),
(4) a 3- to 14-membered non-aromatic heterocyclylcarbonyl group (preferably a 3- to 8-membered monocyclic non-aromatic heterocyclylcarbonyl group (e.g., oxetanylcarbonyl, tetrahydrofurylcarbonyl, azetidinylcarbonyl)) optionally substituted by 1 to 3 substituents selected from
  (a) a halogen atom (e.g., a fluorine atom),
  (b) a hydroxy group, and
  (c) a $C_{1-6}$ alkyl group (e.g., methyl),
(5) a mono- or di-$C_{1-6}$ alkyl-carbamoyl group (e.g., dimethylcarbamoyl),
(6) a N—$C_{1-6}$ alkyl-N—$C_{1-6}$ alkoxy-carbamoyl group (e.g., N-methyl-N-methoxycarbamoyl), or
(7) a N—$C_{1-6}$ alkyl-N',N'-di-$C_{1-6}$ alkylhydrazine-carbonyl group (e.g., N-methyl-N',N'-dimethylhydrazinecarbonyl); and Ring A is
(1) a benzene ring
further substituted by one substituent selected from
  (a) a $C_{6-14}$ aryl group (e.g., phenyl) optionally substituted by 1 to 3 substituents selected from
    (i) a halogen atom (e.g., a fluorine atom, a chlorine atom, a bromine atom),
    (ii) an optionally halogenated $C_{1-6}$ alkyl group (e.g., methyl, difluoromethyl), and
    (iii) an optionally halogenated $C_{1-6}$ alkoxy group (e.g., methoxy, difluoromethoxy), and
  (b) a 5- to 14-membered aromatic heterocyclic group (preferably a 5- or 6-membered aromatic heterocyclic group (e.g., pyridyl, pyrimidinyl, pyridazinyl, thiazolyl, oxazolyl)) optionally substituted by 1 to 3 substituents selected from
    (i) a $C_{1-6}$ alkyl group (e.g., methyl, ethyl) optionally substituted by 1 to 3 substituents selected from a halogen atom (e.g., a fluorine atom) and a hydroxy group,
    (ii) a $C_{1-6}$ alkoxy group (e.g., methoxy),
    (iii) a halogen atom (e.g., a fluorine atom, a chlorine atom), and
    (iv) a $C_{1-6}$ alkoxy-carbonyl group (e.g., ethoxycarbonyl), and
optionally further substituted by 1 to 3 halogen atoms (e.g., a fluorine atom), or
(2) a 5- or 6-membered aromatic heterocycle (e.g., thiazole, pyridine) further substituted by one $C_{6-14}$ aryl group (e.g., phenyl) optionally substituted by 1 to 3 halogen atoms (e.g., a fluorine atom).

[Compound C]
Compound (I) wherein
$R^1$ is
(1) a $C_{1-6}$ alkyl group (e.g., methyl, ethyl),
(2) a mono- or di-$C_{1-6}$ alkylamino group (e.g., dimethylamino), or
(3) a $C_{3-6}$ cycloalkyl group (e.g., cyclopropyl);
$R^2$ is
(1) a hydrogen atom, or
(2) a fluorine atom;
$R^3$ is
(1) a $C_{1-6}$ alkyl-carbonyl group (e.g., 2-methylpropanoyl, butanoyl) optionally substituted by 1 to 3 hydroxy groups,
(2) a $C_{3-10}$ cycloalkyl-carbonyl group (the $C_{3-10}$ cycloalkyl moiety of the $C_{3-10}$ cycloalkyl-carbonyl group is optionally bridged (e.g., cyclopropylcarbonyl, cyclobutylcarbonyl, bicyclo[1.1.1]pentan-1-ylcarbonyl)) optionally substituted by 1 to 3 substituents selected from
  (a) a halogen atom (e.g., a fluorine atom), and
  (b) a hydroxy group,
(3) a 3- to 8-membered monocyclic non-aromatic heterocyclylcarbonyl group (e.g., oxetanylcarbonyl, tetrahydrofurylcarbonyl, azetidinylcarbonyl), or
(4) a mono- or di-$C_{1-6}$ alkyl-carbamoyl group (e.g., dimethylcarbamoyl); and
Ring A is a benzene ring
further substituted by one $C_{6-14}$ aryl group (e.g., phenyl) optionally substituted by 1 to 3 substituents selected from
  (i) a halogen atom (e.g., a fluorine atom, a chlorine atom), and
  (ii) an optionally halogenated $C_{1-6}$ alkyl group (e.g., methyl, difluoromethyl), and
optionally further substituted by 1 to 3 halogen atoms (e.g., a fluorine atom).

[Compound D]
Compound (I) wherein
$R^1$ is
(1) a $C_{1-6}$ alkyl group (e.g., methyl, ethyl), or
(2) a mono- or di-$C_{1-6}$ alkylamino group (e.g., dimethylamino);

R² is
(1) a hydrogen atom, or
(2) a fluorine atom;
R³ is
(1) a $C_{1-6}$ alkyl-carbonyl group (e.g., 2-methylpropanoyl) optionally substituted by 1 to 3 hydroxy groups,
(2) a $C_{3-10}$ cycloalkyl-carbonyl group (the $C_{3-10}$ cycloalkyl moiety of the $C_{3-10}$ cycloalkyl-carbonyl group is optionally bridged (e.g., cyclopropylcarbonyl, cyclobutylcarbonyl, bicyclo[1.1.1]pentan-1-ylcarbonyl)) optionally substituted by 1 to 3 substituents selected from
(a) a halogen atom (e.g., a fluorine atom), and
(b) a hydroxy group,
(3) a 3- to 8-membered monocyclic non-aromatic heterocyclylcarbonyl group (e.g., oxetanylcarbonyl, azetidinylcarbonyl), or
(4) a mono- or di-$C_{1-6}$ alkyl-carbamoyl group (e.g., dimethylcarbamoyl); and
Ring A is a benzene ring
further substituted by one $C_{6-14}$ aryl group (e.g., phenyl) optionally substituted by 1 to 3 substituents selected from
(i) a halogen atom (e.g., a fluorine atom), and
(ii) a $C_{1-6}$ alkyl group (e.g., methyl), and
optionally further substituted by 1 to 3 halogen atoms (e.g., a fluorine atom).

[Compound E]
Compound (I) wherein
R¹ is
(1) a $C_{1-6}$ alkyl group (e.g., ethyl), or
(2) a mono- or di-$C_{1-6}$ alkylamino group (e.g., dimethylamino);
R² is
(1) a hydrogen atom, or
(2) a fluorine atom;
R³ is
(1) a $C_{1-6}$ alkyl-carbonyl group (e.g., 2-methylpropanoyl) optionally substituted by 1 to 3 hydroxy groups,
(2) a 3- to 8-membered monocyclic non-aromatic heterocyclylcarbonyl group (e.g., oxetanylcarbonyl, azetidinylcarbonyl), or
(3) a mono- or di-$C_{1-6}$ alkyl-carbamoyl group (e.g., dimethylcarbamoyl); and
Ring A is a benzene ring
further substituted by one $C_{6-14}$ aryl group (e.g., phenyl) optionally substituted by 1 to 3 substituents selected from
(i) a halogen atom (e.g., a fluorine atom), and
(ii) a $C_{1-6}$ alkyl group (e.g., methyl), and
optionally further substituted by 1 to 3 halogen atoms (e.g., a fluorine atom).

Specific examples of compound (I) include the compounds of the below-mentioned Examples 1 to 616.
Specifically, compound (I) is preferably
N-[(2S,3R)-2-[(2,3'-difluoro[1,1'-biphenyl]-3-yl)methyl]-4,4-difluoro-1-((2R)-oxetane-2-carbonyl)pyrrolidin-3-yl]ethanesulfonamide or a salt thereof (Example 1);
N-{(2S,3R)-4,4-difluoro-1-(2-hydroxy-2-methylpropanoyl)-2-[(2,3',5'-trifluoro[1,1'-biphenyl]-3-yl)methyl]pyrrolidin-3-yl}methanesulfonamide or a salt thereof (Example 2);
N-{(2S,3R)-4,4-difluoro-1-(2-hydroxy-2-methylpropanoyl)-2-[(2,3',5'-trifluoro[1,1'-biphenyl]-3-yl)methyl]pyrrolidin-3-yl}ethanesulfonamide or a salt thereof (Example 3);
N-[(2S,3R)-4,4-difluoro-2-[(2-fluoro[1,1'-biphenyl]-3-yl)methyl]-1-(2-hydroxy-2-methylpropanoyl)pyrrolidin-3-yl]ethanesulfonamide or a salt thereof (Example 5);
N-{(2S,3R)-4,4-difluoro-1-((2R)-oxetane-2-carbonyl)-2-[(2,3',5'-trifluoro[1,1'-biphenyl]-3-yl)methyl]pyrrolidin-3-yl}ethanesulfonamide or a salt thereof (Example 56);
N-{(2S,3R)-4,4-difluoro-1-(2-hydroxy-2-methylpropanoyl)-2-[(2,2',3'-trifluoro[1,1'-biphenyl]-3-yl)methyl]pyrrolidin-3-yl}ethanesulfonamide or a salt thereof (Example 66);
N-{(2S,3R)-4,4-difluoro-1-(2-hydroxy-2-methylpropanoyl)-2-[(2,2',5'-trifluoro[1,1'-biphenyl]-3-yl)methyl]pyrrolidin-3-yl}ethanesulfonamide or a salt thereof (Example 67);
N-{(2S,3R)-1-(bicyclo[1.1.1]pentane-1-carbonyl)-4,4-difluoro-2-[(2,3',5'-trifluoro[1,1'-biphenyl]-3-yl)methyl]pyrrolidin-3-yl}methanesulfonamide or a salt thereof (Example 87);
N-{(2S,3R)-4,4-difluoro-1-((2R)-oxetane-2-carbonyl)-2-[(2,3',5'-trifluoro[1,1'-biphenyl]-3-yl)methyl]pyrrolidin-3-yl}methanesulfonamide or a salt thereof (Example 91);
N-[(2S,3R)-2-[(2,3'-difluoro[1,1'-biphenyl]-3-yl)methyl]-4,4-difluoro-1-(2-methylpropanoyl)pyrrolidin-3-yl]ethanesulfonamide or a salt thereof (Example 94);
N-{(2S,3R)-1-(cyclopropanecarbonyl)-4,4-difluoro-2-[(2,3',5'-trifluoro[1,1'-biphenyl]-3-yl)methyl]pyrrolidin-3-yl}ethanesulfonamide or a salt thereof (Example 144);
N-{(2S,3R)-4,4-difluoro-1-(2-methylpropanoyl)-2-[(2,3',5'-trifluoro[1,1'-biphenyl]-3-yl)methyl]pyrrolidin-3-yl}ethanesulfonamide or a salt thereof (Example 146);
N-[(2S,3R)-2-[(2,3'-difluoro[1,1'-biphenyl]-3-yl)methyl]-4,4-difluoro-1-((1r,3S)-3-fluorocyclobutane-1-carbonyl)pyrrolidin-3-yl]ethanesulfonamide or a salt thereof (Example 225);
N-{(2S,3R,4S)-1-(cyclopropanecarbonyl)-4-fluoro-2-[(2,3',5'-trifluoro[1,1'-biphenyl]-3-yl)methyl]pyrrolidin-3-yl}ethanesulfonamide or a salt thereof (Example 236);
N-[(2S,3R,4S)-4-fluoro-2-[(2-fluoro[1,1'-biphenyl]-3-yl)methyl]-1-((2R)-oxetane-2-carbonyl)pyrrolidin-3-yl]ethanesulfonamide or a salt thereof (Example 302);
N-{(2S,3R)-4,4-difluoro-1-((1r,3S)-3-fluorocyclobutane-1-carbonyl)-2-[(2,3',5'-trifluoro[1,1'-biphenyl]-3-yl)methyl]pyrrolidin-3-yl}ethanesulfonamide or a salt thereof (Example 375);
N-{(2S,3R)-4,4-difluoro-1-((1s,3R)-3-fluorocyclobutane-1-carbonyl)-2-[(2,3',5'-trifluoro[1,1'-biphenyl]-3-yl)methyl]pyrrolidin-3-yl}ethanesulfonamide or a salt thereof (Example 380);
N-{(2S,3R)-4,4-difluoro-1-(3-fluorocyclobutane-1-carbonyl)-2-[(2,3',5'-trifluoro[1,1'-biphenyl]-3-yl)methyl]pyrrolidin-3-yl}methanesulfonamide or a salt thereof (Example 433);
N'-{(2S,3R)-1-(azetidine-1-carbonyl)-4,4-difluoro-2-[(2-fluoro-3'-methyl[1,1'-biphenyl]-3-yl)methyl]pyrrolidin-3-yl}-N,N-dimethylsulfuric diamide or a salt thereof (Example 443);
N-{(2S,3R,4S)-1-(azetidine-1-carbonyl)-4-fluoro-2-[(2,3',5'-trifluoro[1,1'-biphenyl]-3-yl)methyl]pyrrolidin-3-yl}ethanesulfonamide or a salt thereof (Example 450);
N-{(2S,3R,4S)-1-(azetidine-1-carbonyl)-4-fluoro-2-[(2-fluoro-3'-methyl[1,1'-biphenyl]-3-yl)methyl]pyrrolidin-3-yl}ethanesulfonamide or a salt thereof (Example 451);
(2S,3R,4S)-3-[(dimethylsulfamoyl)amino]-4-fluoro-2-[(2-fluoro-3'-methyl[1,1'-biphenyl]-3-yl)methyl]-N,N-dimethylpyrrolidine-1-carboxamide or a salt thereof (Example 459);

N'-[(2S,3R,4S)-4-fluoro-2-[(2-fluoro-3'-methyl[1,1'-biphenyl]-3-yl)methyl]-1-(1-hydroxycyclobutane-1-carbonyl)pyrrolidin-3-yl]-N,N-dimethylsulfuric diamide or a salt thereof (Example 462);

N'-{(2S,3R,4S)-1-(azetidine-1-carbonyl)-4-fluoro-2-[(2-fluoro-3'-methyl[1,1'-biphenyl]-3-yl)methyl]pyrrolidin-3-yl}-N,N-dimethylsulfuric diamide or a salt thereof (Example 463); or N'-{(2S,3R)-4,4-difluoro-1-[(2R)-oxetane-2-carbonyl]-2-[(2,3',5'-trifluoro[1,1'-biphenyl]-3-yl)methyl]pyrrolidin-3-yl}-N,N-dimethylsulfuric diamide or a salt thereof (Example 542).

Compound (I) is particularly preferably
N-[(2S,3R)-2-[(2,3'-difluoro[1,1'-biphenyl]-3-yl)methyl]-4,4-difluoro-1-((2R)-oxetane-2-carbonyl)pyrrolidin-3-yl]ethanesulfonamide or a salt thereof (Example 1);

N-{(2S,3R)-4,4-difluoro-1-(2-hydroxy-2-methylpropanoyl)-2-[(2,3',5'-trifluoro[1,1'-biphenyl]-3-yl)methyl]pyrrolidin-3-yl}ethanesulfonamide or a salt thereof (Example 3);

N-[(2S,3R)-2-[(2,3'-difluoro[1,1'-biphenyl]-3-yl)methyl]-4,4-difluoro-1-(2-methylpropanoyl)pyrrolidin-3-yl]ethanesulfonamide or a salt thereof (Example 94);

N'-{(2S,3R)-1-(azetidine-1-carbonyl)-4,4-difluoro-2-[(2-fluoro-3'-methyl[1,1'-biphenyl]-3-yl)methyl]pyrrolidin-3-yl}-N,N-dimethylsulfuric diamide or a salt thereof (Example 443);

N-{(2S,3R,4S)-1-(azetidine-1-carbonyl)-4-fluoro-2-[(2-fluoro-3'-methyl[1,1'-biphenyl]-3-yl)methyl]pyrrolidin-3-yl}ethanesulfonamide or a salt thereof (Example 451);

(2S,3R,4S)-3-[(dimethylsulfamoyl)amino]-4-fluoro-2-[(2-fluoro-3'-methyl[1,1'-biphenyl]-3-yl)methyl]-N,N-dimethylpyrrolidine-1-carboxamide or a salt thereof (Example 459);

N'-{(2S,3R,4S)-1-(azetidine-1-carbonyl)-4-fluoro-2-[(2-fluoro-3'-methyl[1,1'-biphenyl]-3-yl)methyl]pyrrolidin-3-yl}-N,N-dimethylsulfuric diamide or a salt thereof (Example 463); or N'-{(2S,3R)-4,4-difluoro-1-[(2R)-oxetane-2-carbonyl]-2-[(2,3',5'-trifluoro[1,1'-biphenyl]-3-yl)methyl]pyrrolidin-3-yl}-N,N-dimethylsulfuric diamide or a salt thereof (Example 542).

As a salt of a compound represented by the formula (I), a pharmacologically acceptable salt is preferable, and examples of such salt include a salt with inorganic base, a salt with organic base, a salt with inorganic acid, a salt with organic acid, a salt with basic or acidic amino acid and the like.

Preferable examples of the salt with inorganic base include alkali metal salts such as sodium salt, potassium salt and the like, alkaline earth metal salts such as calcium salt, magnesium salt and the like, aluminum salt, ammonium salt and the like.

Preferable examples of the salt with organic base include salts with trimethylamine, triethylamine, pyridine, picoline, ethanolamine, diethanolamine, triethanolamine, tromethamine[tris(hydroxymethyl)methylamine], tert-butylamine, cyclohexylamine, benzylamine, dicyclohexylamine, N,N-dibenzylethylenediamine and the like.

Preferable examples of the salt with inorganic acid include salts with hydrochloric acid, hydrobromic acid, nitric acid, sulfuric acid, phosphoric acid and the like.

Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salt with basic amino acid include salts with arginine, lysine, ornithine and the like. Preferable examples of the salt with acidic amino acid include salts with aspartic acid, glutamic acid and the like.

The production method of the compound of the present invention is explained below.

The raw material compound and reagent used and the compound obtained in each step in the following production method may be each in a form of a salt, and examples of such salt include those similar to the salts of the compound represented by the formula (I), and the like.

When the compound obtained in each step is a free form, it can be converted to the objective salt according to a method known per se. When the compound obtained in each step is a salt, it can be converted to the objective free form or the other salt according to a method known per se.

The compound obtained in each step can be used directly as the reaction mixture or as a crude product for the next reaction. Alternatively, the compound obtained in each step can be isolated and purified from a reaction mixture according to a method known per se, for example, a separation means such as concentration, crystallization, recrystallization, distillation, solvent extraction, fractional distillation, column chromatography and the like.

When the raw material compound and reagent used in each step are commercially available, the commercially available product can also be used directly.

In the reaction in each step, while the reaction time varies depending on the kind of the reagent and solvent to be used, it is generally 1 min-48 hr, preferably 10 min-8 hr, unless otherwise specified.

In the reaction in each step, while the reaction temperature varies depending on the kind of the reagent and solvent to be used, it is generally $-78°$ C.-300° C., preferably $-78°$ C.-150° C., unless otherwise specified.

In the reaction in each step, while the pressure varies depending on the kind of the reagent and solvent to be used, it is generally 1 atm-20 atm, preferably 1 atm-3 atm, unless otherwise specified.

Microwave synthesizer such as Initiator manufactured by Biotage and the like may be used for the reaction in each step. While the reaction temperature varies depending on the kind of the reagent and solvent to be used, it is generally room temperature $-300°$ C., preferably 50° C.-250° C., unless otherwise specified. While the reaction time varies depending on the kind of the reagent and solvent to be used, it is generally 1 min-48 hr, preferably 1 min-8 hr, unless otherwise specified.

In the reaction in each step, the reagent is used in an amount of 0.5 equivalents-20 equivalents, preferably 0.8 equivalents-5 equivalents, relative to the substrate, unless otherwise specified. When the reagent is used as a catalyst, the reagent is used in an amount of 0.001 equivalent-1 equivalent, preferably 0.01 equivalent-0.2 equivalent, relative to the substrate. When the reagent is used as a reaction solvent, the reagent is used in a solvent amount.

Unless otherwise specified, the reaction in each step is carried out without solvent, or by dissolving or suspending the raw material compound in a suitable solvent. Examples of the solvent include those described in Examples and the following solvents.

alcohols: methanol, ethanol, tert-butyl alcohol, 2-methoxyethanol and the like;

ethers: diethyl ether, diphenyl ether, tetrahydrofuran, 1,2-dimethoxyethane and the like;

aromatic hydrocarbons: chlorobenzene, toluene, xylene and the like;

saturated hydrocarbons: cyclohexane, hexane and the like;

amides: N,N-dimethylformamide, N-methylpyrrolidone and the like;

halogenated hydrocarbons: dichloromethane, carbon tetrachloride and the like;

nitriles: acetonitrile and the like;

sulfoxides: dimethyl sulfoxide and the like;

aromatic organic bases: pyridine and the like;

anhydrides: acetic anhydride and the like;

organic acids: formic acid, acetic acid, trifluoroacetic acid and the like;

inorganic acids: hydrochloric acid, sulfuric acid and the like;

esters: ethyl acetate and the like;

ketones: acetone, methyl ethyl ketone and the like;

water.

The above-mentioned solvent can be used in a mixture of two or more kinds thereof in an appropriate ratio.

When a base is used for the reaction in each step, examples thereof include those described in Examples and the following bases.

inorganic bases: sodium hydroxide, magnesium hydroxide, sodium carbonate, calcium carbonate, sodium hydrogen carbonate and the like;

organic bases: triethylamine, diethylamine, pyridine, 4-dimethylaminopyridine, N,N-dimethylaniline, 1,4-diazabicyclo[2.2.2]octane, 1,8-diazabicyclo[5.4.0]-7-undecene, imidazole, piperidine and the like;

metal alkoxides: sodium ethoxide, potassium tert-butoxide and the like;

alkali metal hydrides: sodium hydride and the like;

metal amides: sodium amide, lithium diisopropylamide, lithium hexamethyldisilazide and the like;

organic lithiums: n-butyllithium and the like.

When an acid or an acid catalyst is used for the reaction in each step, examples thereof include those described in Examples and the following acids and acid catalysts.

inorganic acids: hydrochloric acid, sulfuric acid, nitric acid, hydrobromic acid, phosphoric acid and the like;

organic acids: acetic acid, trifluoroacetic acid, citric acid, p-toluenesulfonic acid, 10-camphorsulfonic acid and the like;

Lewis acid: boron trifluoride diethyl ether complex, zinc iodide, anhydrous aluminum chloride, anhydrous zinc chloride, anhydrous iron chloride and the like.

Unless otherwise specified, the reaction in each step is carried out according to a method known per se, for example, the method described in Jikken Kagaku Kouza, 5th Edition, vol. 13-19 (the Chemical Society of Japan ed.); Shin Jikken Kagaku Kouza, vol. 14-15 (the Chemical Society of Japan ed.); Fine Organic Chemistry, Revised 2nd Edition (L. F. Tietze, Th. Eicher, Nankodo); Organic Name Reactions, the Reaction Mechanism and Essence, Revised Edition (Hideo Togo, Kodansha); ORGANIC SYNTHESES Collective Volume I-VII (John Wiley & Sons Inc.); Modern Organic Synthesis in the Laboratory A Collection of Standard Experimental Procedures (Jie Jack Li, OXFORD UNIVERSITY); Comprehensive Heterocyclic Chemistry III, Vol. 1-Vol. 14 (Elsevier Japan); Strategic Applications of Named Reactions in Organic Synthesis (translated by Kiyoshi Tomioka, Kagakudojin); Comprehensive Organic Transformations (VCH Publishers Inc.), 1989, or the like, or the method described in Examples.

In each step, the protection or deprotection reaction of an functional group is carried out according to a method known per se, for example, the method described in "Protective Groups in Organic Synthesis, 4th Ed", Wiley-Interscience, Inc., 2007 (Theodora W. Greene, Peter G. M. Wuts); "Protecting Groups 3rd Ed." Thieme, 2004 (P. J. Kocienski), or the like, or the method described in Examples.

Examples of the protecting group for a hydroxy group of an alcohol and the like and a phenolic hydroxy group include ether-type protecting groups such as methoxymethyl ether, benzyl ether, tert-butyldimethylsilyl ether, tetrahydropyranyl ether and the like; carboxylate ester-type protecting groups such as acetate ester and the like; sulfonate ester-type protecting groups such as methanesulfonate ester and the like; carbonate ester-type protecting groups such as tert-butylcarbonate and the like, and the like.

Examples of the protecting group for a carbonyl group of an aldehyde include acetal-type protecting groups such as dimethylacetal and the like; cyclic acetal-type protecting groups such as 1,3-dioxane and the like, and the like.

Examples of the protecting group for a carbonyl group of a ketone include ketal-type protecting groups such as dimethylketal and the like; cyclic ketal-type protecting groups such as 1,3-dioxane and the like; oxime-type protecting groups such as O-methyloxime and the like; hydrazone-type protecting groups such as N,N-dimethylhydrazone and the like, and the like.

Examples of the protecting group for a carboxyl group include ester-type protecting groups such as methyl ester and the like; amide-type protecting groups such as N,N-dimethylamide and the like, and the like.

Examples of the protecting group for a thiol include ether-type protecting groups such as benzyl thioether and the like; ester-type protecting groups such as thioacetate ester, thiocarbonate, thiocarbamate and the like, and the like.

Examples of the protecting group for an amino group and an aromatic heterocycle such as imidazole, pyrrole, indole and the like include carbamate-type protecting groups such as benzyl carbamate and the like; amide-type protecting groups such as acetamide and the like; alkyl amine-type protecting groups such as N-triphenylmethylamine and the like; sulfonamide-type protecting groups such as methanesulfonamide and the like, and the like.

The protecting groups can be removed according to a method known per se, for example, by employing a method using acid, base, ultraviolet rays, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide) and the like, a reduction method, and the like.

When reduction reaction is carried out in each step, examples of the reducing agent to be used include metal hydrides such as lithium aluminum hydride, sodium triacetoxyborohydride, sodium cyanoborohydride, diisobutylaluminum hydride (DIBAL-H), sodium borohydride, tetramethylammonium triacetoxyborohydride and the like; boranes such as borane tetrahydrofuran complex and the like; Raney nickel; Raney cobalt; hydrogen; formic acid; triethylsilane and the like. When carbon-carbon double bond or triple bond is reduced, a method using a catalyst such as palladium-carbon, Lindlar's catalyst and the like may be employed.

When oxidation reaction is carried out in each step, examples of the oxidizing agent to be used include peroxides such as m-chloroperbenzoic acid (mCPBA), hydrogen peroxide, tert-butylhydroperoxide and the like; perchlorates such as tetrabutylammonium perchlorate and the like; chlorates such as sodium chlorate and the like; chlorites such as sodium chlorite and the like; periodates such as sodium periodate and the like; hypervalent iodine reagents such as iodosylbenzene and the like; reagents containing manganese such as manganese dioxide, potassium permanganate and the like; leads such as lead tetraacetate and the like; reagents containing chromium such as pyridinium chlorochromate (PCC), pyridinium dichromate (PDC), Jones reagent and the like; halogen compounds such as N-bromosuccinimide (NBS) and the like; oxygen; ozone; sulfur trioxide-pyridine complex; osmium tetroxide; selenium dioxide; 2,3-dichloro-5,6-dicyano-1,4-benzoquinone (DDQ) and the like.

When radical cyclization reaction is carried out in each step, examples of the radical initiator to be used include azo compounds such as azobisisobutyronitrile (AIBN) and the like; water-soluble radical initiators such as 4-4'-azobis-4-cyanopentanoic acid (ACPA) and the like; triethylboron in the presence of air or oxygen; benzoyl peroxide and the like. Examples of the radical reagent to be used include tributylstannane, tristrimethylsilylsilane, 1,1,2,2-tetraphenyldisilane, diphenylsilane, samarium iodide and the like.

When Wittig reaction is carried out in each step, examples of the Wittig reagent to be used include alkylidene phosphoranes and the like. The alkylidene phosphoranes can be prepared according to a method known per se, for example, by reacting a phosphonium salt with a strong base.

When Horner-Emmons reaction is carried out in each step, examples of the reagent to be used include phosphonoacetates such as methyl dimethylphosphonoacetate, ethyl diethylphosphonoacetate and the like; and bases such as alkali metal hydrides, organic lithiums and the like.

When Friedel-Crafts reaction is carried out in each step, a combination of a Lewis acid and an acid chloride or a combination of a Lewis acid and an alkylating agent (e.g., an alkyl halide, an alcohol, an olefin etc.) is used as a reagent. Alternatively, an organic acid or an inorganic acid can also be used instead of a Lewis acid, and an anhydride such as acetic anhydride and the like can also be used instead of an acid chloride.

When aromatic nucleophilic substitution reaction is carried out in each step, a nucleophile (e.g., an amine, imidazole etc.) and a base (e.g., an organic base etc.) are used as a reagent.

When nucleophilic addition reaction by a carbo anion, nucleophilic 1,4-addition reaction (Michael addition reaction) by a carbo anion or nucleophilic substitution reaction by a carbo anion is carried out in each step, and examples of the base to be used for generation of the carbo anion include organic lithiums, metal alkoxides, inorganic bases, organic bases and the like.

When Grignard reaction is carried out in each step, examples of the Grignard reagent to be used include arylmagnesium halides such as phenylmagnesium bromide and the like; and alkylmagnesium halides such as methylmagnesium bromide and the like. The Grignard reagent can be prepared according to a method known per se, for example, by reacting an alkyl halide or an aryl halide with a metal magnesium in an ether or tetrahydrofuran as a solvent.

When Knoevenagel condensation reaction is carried out in each step, a compound having an activated methylene group with two electron withdrawing groups (e.g., malonic acid, diethyl malonate, malononitrile etc.) and a base (e.g., an organic base, a metal alkoxide, an inorganic base) are used as a reagent.

When Vilsmeier-Haack reaction is carried out in each step, phosphoryl chloride and an amide derivative (e.g., N,N-dimethylformamide etc.) are used as a reagent.

When azidation reaction of an alcohol, an alkyl halide or a sulfonate is carried out in each step, examples of the azidating agent to be used include diphenylphosphorylazide (DPPA), trimethylsilylazide, sodium azide and the like. For example, for the azidation reaction of an alcohol, a method using diphenylphosphorylazide and 1,8-diazabicyclo[5.4.0]undec-7-ene (DBU), a method using trimethylsilylazide and a Lewis acid, and the like are employed.

When reductive amination reaction is carried out in each step, examples of the reducing agent to be used include sodium triacetoxyborohydride, sodium cyanoborohydride, hydrogen, formic acid and the like. When the substrate is an amine compound, examples of the carbonyl compound to be used include paraformaldehyde, aldehydes such as acetaldehyde and the like, and ketones such as cyclohexanone and the like. When the substrate is a carbonyl compound, examples of the amine to be used include ammonia, primary amines such as methylamine and the like; secondary amines such as dimethylamine and the like, and the like.

When Mitsunobu reaction is carried out in each step, an azodicarboxylate (e.g., diethyl azodicarboxylate (DEAD), diisopropyl azodicarboxylate (DIAD) etc.) and triphenylphosphine are used as a reagent.

When esterification reaction, amidation reaction or urea formation reaction is carried out in each step, examples of the reagent to be used include acyl halides such as acid chlorides, acid bromides and the like; activated carboxylic acids such as acid anhydrides, activated esters, sulfates and the like. Examples of the activating agent of the carboxylic acid include carbodiimide condensing agents such as 1-ethyl-3-(3-dimethylaminopropyl) carbodiimide hydrochloride (WSCD) and the like; triazine condensing agents such as 4-(4,6-dimethoxy-1,3,5-triazin-2-yl)-4-methylmorpholinium chloride n-hydrate (DMT-MM) and the like; carbonate condensing agents such as 1,1-carbonyldiimidazole (CDI) and the like; diphenylphosphoryl azide (DPPA); benzotriazol-1-yloxy-trisdimethylaminophosphonium salt (BOP reagent); 2-chloro-1-methyl-pyridinium iodide (Mukaiyama reagent); thionyl chloride; lower alkyl haloformates such as ethyl chloroformate and the like; O-(7-azabenzotriazol-1-yl)-N,N,N',N'-tetramethyluronium hexafluorophosphorate (HATU); sulfuric acid; combinations thereof and the like. When carbodiimide condensing agent is used, an additive such as 1-hydroxybenzotriazole (HOBt), N-hydroxysuccinimide (HOSu), dimethylaminopyridine (DMAP) and the like may be added to the reaction system.

When coupling reaction is carried out in each step, examples of the metal catalyst to be used include palladium compounds such as palladium(II) acetate, tetrakis(triphenylphosphine)palladium(0), dichlorobis(triphenylphosphine)palladium(II), dichlorobis(triethylphosphine)palladium(II), tris(dibenzylideneacetone)dipalladium (0), 1,1'-bis(diphenylphosphino)ferrocene palladium(II) chloride and the like; nickel compounds such as tetrakis(triphenylphosphine)nickel(0) and the like; rhodium compounds such as tris(triphenylphosphine)rhodium(III) chloride and the like; cobalt compounds; copper compounds such as copper oxide, copper(I) iodide and the like; platinum compounds and the like. In addition, a base can be added to the reaction system, and examples thereof include inorganic bases and the like.

When thiocarbonylation reaction is carried out in each step, phosphorus pentasulfide is typically used as the thiocarbonylating agent. Alternatively, a reagent having a 1,3,2,4-dithiadiphosphetane-2,4-disulfide structure (e.g., 2,4-bis (4-methoxyphenyl)-1,3,2,4-dithiadiphosphetane-2,4-disulfide (Lawesson reagent) etc.) can also be used instead of phosphorus pentasulfide.

When Wohl-Ziegler reaction is carried out in each step, examples of the halogenating agent to be used include N-iodosuccinimide, N-bromosuccinimide (NBS), N-chlorosuccinimide (NCS), bromine, sulfuryl chloride and the like. In addition, the reaction can be accelerated by subjecting a radical initiator such as heat, light, benzoyl peroxide, azobisisobutyronitrile and the like to the reaction system reaction.

When halogenation reaction of a hydroxy group is carried out in each step, examples of the halogenating agent to be used include hydrohalic acids and acid halides of inorganic acids, specifically, hydrochloric acid, thionyl chloride, phosphorus oxychloride and the like for chlorination, 48% hydrobromic acid and the like for bromination. In addition, a method of producing an alkyl halide by reacting an alcohol with triphenylphosphine and carbon tetrachloride or carbon tetrabromide or the like can be employed. Alternatively, a method of producing an alkyl halide via two steps comprising converting an alcohol to the corresponding sulfonate, and then reacting the sulfonate with lithium bromide, lithium chloride or sodium iodide can also be employed.

When Arbuzov reaction is carried out in each step, examples of the reagent to be used include alkyl halides such as ethyl bromoacetate and the like; and phosphites such as triethyl phosphite, tri (isopropyl) phosphite and the like.

When sulfonate esterification reaction is carried out in each step, examples of the sulfonating agent to be used include methanesulfonyl chloride, p-toluenesulfonyl chloride, methanesulfonic anhydride, p-toluenesulfonic anhydride and the like.

When hydrolysis reaction is carried out in each step, an acid or a base is used as a reagent. For acid hydrolysis reaction of tert-butyl ester, formic acid, triethylsilane and the like may be added to reductively-trap tert-butyl cation which is by-produced.

When dehydration reaction is carried out in each step, examples of the dehydrating agent to be used include sulfuric acid, diphosphorus pentaoxide, phosphorus oxychloride, N,N'-dicyclohexylcarbodiimide, alumina, polyphosphoric acid and the like.

Compound (I) can be produced from compound (1) according to the method shown in the following Reaction Scheme 1. In the reaction scheme, $LG^1$ and $LG^2$ are each independently a leaving group, $R^4$ and $R^5$ are each independently an optionally substituted $C_{1-6}$ alkyl group or an optionally substituted $C_{6-14}$ aryl group, $P^1$ and $P^2$ are each independently a protecting group, and the other symbols are as defined above.

Reaction Scheme 1

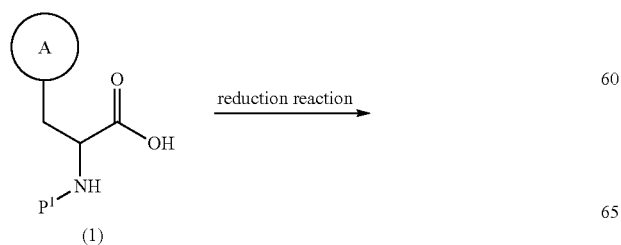

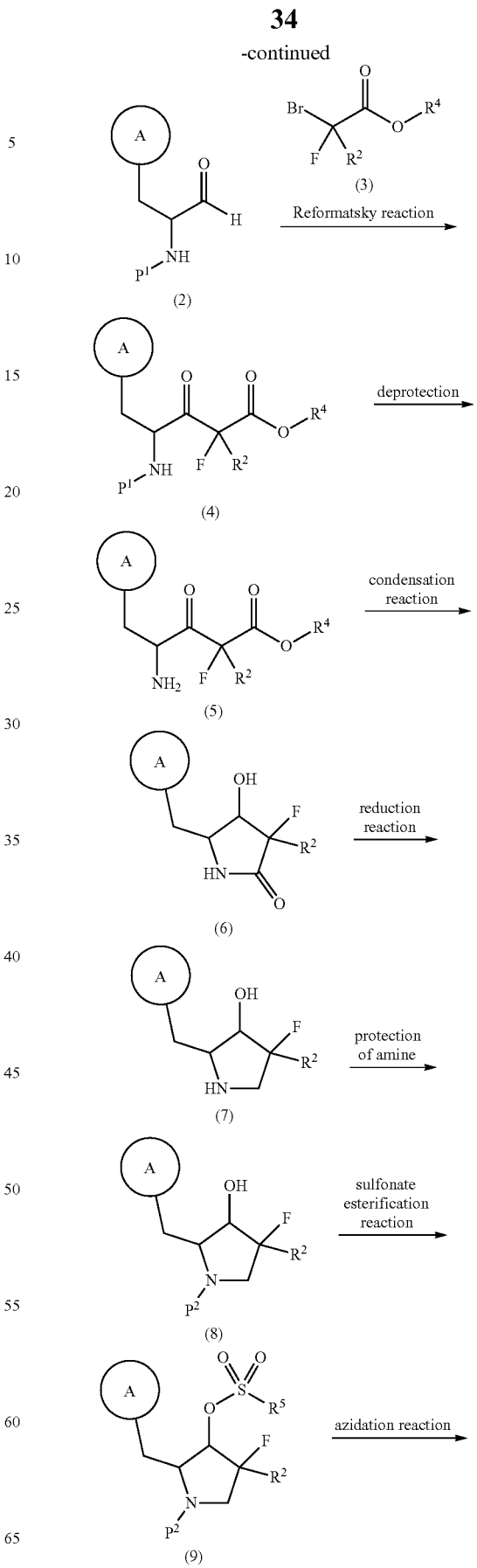

-continued

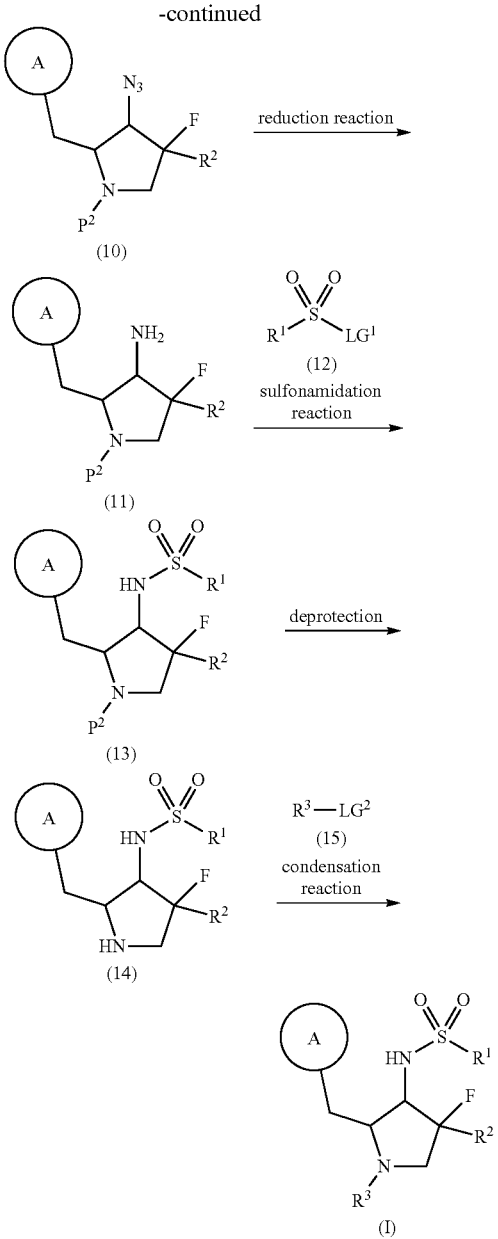

Examples of the "leaving group" represented by $LG^1$ or $LG^2$ include halogen atoms, optionally halogenated $C_{1-6}$ alkylsulfonyloxy groups (e.g., methanesulfonyloxy, ethanesulfonyloxy, trifluoromethanesulfonyloxy), and $C_{6-14}$ arylsulfonyloxy groups optionally substituted by $C_{1-6}$ alkyl group(s) (e.g., benzenesulfonyloxy, toluenesulfonyloxy) and the like.

Examples of the substituent of the "optionally substituted $C_{1-6}$ alkyl group" and "optionally substituted $C_{6-14}$ aryl group" represented by $R^4$ or $R^5$ include substituents selected from Substituent group A. The number of the substituents is preferably 1 to 3. When the number of the substituents is 2 or more, the respective substituents may be the same or different.

Examples of the "protecting group" represented by $P^1$ or $P^2$ include those exemplified as the above-mentioned "protecting group for an amino group and an aromatic heterocycle such as imidazole, pyrrole, indole and the like".

Compound (1) may be commercially available, or can be produced according to a method known per se or a method analogous thereto.

Compound (4) can be produced by subjecting compound (2) to the Reformatsky reaction with compound (3) in the presence of a metal. Examples of the metal to be used include zinc, samarium iodide, indium and the like. Compound (3) may be commercially available, or can be produced according to a method known per se or a method analogous thereto.

Compound (6) can be produced by subjecting compound (5) to a condensation reaction in the presence of a base. Examples of the base to be used include inorganic bases, organic bases, alkali metal hydrides and the like.

Compound (9) can be produced by subjecting compound (8) to a sulfonate esterification reaction. Examples of the sulfonating agent to be used include methanesulfonyl chloride, p-toluenesulfonyl chloride, methanesulfonic anhydride, p-toluenesulfonic anhydride, trifluoromethanesulfonic anhydride and the like.

Compound (10) can be produced by subjecting compound (9) to an azidation reaction. Examples of the azidating agent to be used include tetra-n-butylammonium azide, trimethylsilylazide, sodium azide and the like.

Compound (13) can be produced by subjecting compound (11) to a sulfonamidation reaction with compound (12). Examples of compound (12) to be used include sulfonyl chlorides, sulfamoyl chlorides and the like. Compound (12) may be commercially available, or can be produced according to a method known per se or a method analogous thereto.

Compound (I) can be produced by subjecting compound (14) to a condensation reaction with compound (15). Examples of compound (15) to be used include acyl halides such as acid chlorides, acid bromides, alkyl chloroformates, carbamoyl chlorides and the like; and activated carboxylic acids such as acid anhydrides, activated esters, sulfates and the like. Examples of the activating agent of the carboxylic acid include carbodiimide condensing agents such as 1-ethyl-3-(3-dimethylaminopropyl) carbodiimide hydrochloride (WSCD) and the like; triazine condensing agents such as 4-(4,6-dimethoxy-1,3,5-triazin-2-yl)-4-methylmorpholinium chloride-n-hydrate (DMT-MM) and the like; carbonate ester condensing agents such as 1,1-carbonyldiimidazole (CDI) and the like; diphenylphosphoryl azide (DPPA); benzotriazol-1-yloxy-trisdimethylaminophosphonium salt (BOP reagent); 2-chloro-1-methyl-pyridinium iodide (Mukaiyama reagent); thionyl chloride; lower alkyl haloformates such as chloroethyl formate and the like; O-(7-azabenzotriazol-1-yl)-N,N,N',N'-tetramethyluronium hexafluorophosphorate (HATU); sulfuric acid; combinations thereof, and the like. In addition, a base may be added to the reaction system. Examples of the base include inorganic bases, organic bases and the like. When a carbodiimide condensing agent is used, an additive such as 1-hydroxybenzotriazole (HOBt), N-hydroxysuccinimide (HOSu), dimethylaminopyridine (DMAP) and the like may be further added to the reaction system.

In the thus-obtained compound (I), an intramolecular functional group can also be converted to an object functional group by a combination of chemical reactions known per se. Examples of the chemical reaction include oxidation reaction, reduction reaction, alkylation reaction, acylation reaction, ureation reaction, hydrolysis reaction, amination reaction, esterification reaction, aryl coupling reaction, deprotection reaction and the like.

In the above-mentioned production method, when a starting compound has an amino group, a carboxyl group, a hydroxy group, a carbonyl group or a mercapto group as a substituent, a protecting group generally used in the peptide chemistry may be introduced into these groups, and the object compound can be obtained by removing the protecting group as necessary after the reaction.

Compound (I) obtained by the above-mentioned production method can be isolated and purified by a known means, such as solvent extraction, liquid conversion, phase transfer, crystallization, recrystallization, chromatography and the like.

When compound (I) contains optical isomer, stereoisomer, regio isomer and rotamer, these compounds are also included in compound (I), and each can be obtained as a single product by a synthesis method or a separation method known per se. For example, when an optical isomer exists in compound (I), an optical isomer resolved from the compound is also encompassed in compound (I).

Here, an optical isomer can be produced by a method known per se.

Compound (I) may be a crystal.

A crystal of compound (I) (hereinafter sometimes to be abbreviated as the crystal of the present invention) can be produced by crystallizing compound (I), by applying a crystallization method known per se.

In the present specification, the melting point means a melting point measured, for example, by micro melting point apparatus (Yanako, MP-500D or Buchi, B-545), DSC (differential scanning calorimetry analysis) apparatus (METTLER TOLEDO, DSC1) and the like.

Generally, the melting point sometimes varies depending on the measurement device, measurement condition and the like. The crystal in the present specification may be a crystal showing a melting point different from the values described in the present specification as long as the difference is within a general error range.

The crystal of the present invention is superior in the physicochemical properties (e.g., melting point, solubility, stability) and biological properties (e.g., pharmacokinetics (absorbability, distribution, metabolism, excretion), efficacy expression), and is extremely useful as a medicament.

Compound (I) may be used as a prodrug. A prodrug of the compound (I) means a compound which is converted to the compound (I) of the present invention with a reaction due to an enzyme, an gastric acid, etc. under the physiological condition in the living body, that is, a compound which is converted to the compound (I) of the present invention with oxidation, reduction, hydrolysis, etc. according to an enzyme; a compound which is converted to the compound (I) of the present invention by hydrolysis etc. due to gastric acid, etc.

A prodrug of compound (I) may be a compound obtained by subjecting an amino group in compound (I) to an acylation, alkylation or phosphorylation (e.g., a compound obtained by subjecting an amino group in compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation and tert-butylation, etc.);

a compound obtained by subjecting a hydroxy group in compound (I) to an acylation, alkylation, phosphorylation or boration (e.g., a compound obtained by subjecting an hydroxy group in compound (I) to an acetylation, palmitoylation, propanoylation, pivaloylation, succinylation, fumarylation, alanylation, dimethylaminomethylcarbonylation, etc.);

a compound obtained by subjecting a carboxyl group in compound (I) to an esterification or amidation (e.g., a compound obtained by subjecting a carboxyl group in compound (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification and methylamidation, etc.)

and the like. Any of these compounds can be produced from compound (I) by a method known per se.

A prodrug for compound (I) may also be one which is converted into compound (I) under a physiological condition, such as those described in *IYAKUHIN no KAIHATSU* (Development of Pharmaceuticals), Vol. 7, Design of Molecules, p. 163-198, Published by HIROKAWA SHOTEN (1990).

In the present specification, a prodrug may form a salt, and as such salt, those exemplified as a salt of the compound represented by the above-mentioned formula (I) can be mentioned.

Compound (I) may be labeled with an isotope (e.g., $^{3}$H, $^{13}$C, $^{14}$C, $^{18}$F, $^{35}$S, $^{125}$I) and the like.

Compound (I) labeled with or substituted by an isotope can be used, for example, as a tracer used for Positron Emission Tomography (PET) (PET tracer), and is useful in the field of medical diagnosis and the like.

Furthermore, compound (I) may be a hydrate or a non-hydrate, or a non-solvate (e.g., anhydride), or a solvate (e.g., hydrate).

Compound (I) also encompasses a deuterium conversion form wherein $^{1}$H is converted to $^{2}$H(D).

Furthermore, compound (I) may be a pharmaceutically acceptable cocrystal or cocrystal salt. The cocrystal or cocrystal salt means a crystalline substance constituted with two or more special solids at room temperature, each having different physical properties (e.g., structure, melting point, melting heat, hygroscopicity, solubility and stability). The cocrystal or cocrystal salt can be produced by a cocrystallization method known per se.

Compound (I) or a prodrug thereof (hereinafter sometimes to be simply abbreviated as the compound of the present invention) can be used as it is or in the form of a pharmaceutical composition (also referred to as a medicament) by mixing with a pharmacologically acceptable carrier etc. to mammals (e.g., human, mouse, rat, rabbit, dog, cat, bovine, horse, swine, monkey) as an agent for the prophylaxis or treatment of various diseases mentioned below.

As pharmacologically acceptable carriers, various organic or inorganic carrier substances conventionally used as preparation materials can be used. These are incorporated as excipient, lubricant, binder and disintegrant for solid preparations; or solvent, solubilizing agent, suspending agent, isotonicity agent, buffer and soothing agent for liquid preparations; and the like; and preparation additives such as preservative, antioxidant, colorant, sweetening agent and the like can be added as necessary.

Preferable examples of the excipient include lactose, sucrose, D-mannitol, D-sorbitol, starch, gelatinated starch, dextrin, crystalline cellulose, low-substituted hydroxypropylcellulose, sodium carboxymethylcellulose, gum arabic, pullulan, light anhydrous silicic acid, synthetic aluminum silicate and magnesium alumino metasilicate.

Preferable examples of the lubricant include magnesium stearate, calcium stearate, talc and colloidal silica.

Preferable examples of the binder include gelatinated starch, sucrose, gelatin, gum arabic, methylcellulose, carboxymethylcellulose, sodium carboxymethylcellulose, crystalline cellulose, sucrose, D-mannitol, trehalose, dextrin, pullulan, hydroxypropylcellulose, hydroxypropylmethylcellulose and polyvinylpyrrolidone.

Preferable examples of the disintegrant include lactose, sucrose, starch, carboxymethylcellulose, calcium carboxymethylcellulose, croscarmellose sodium, sodium carboxymethyl starch, light anhydrous silicic acid and low-substituted hydroxypropylcellulose.

Preferable examples of the solvent include water for injection, physiological brine, Ringer's solution, alcohol, propylene glycol, polyethylene glycol, sesame oil, corn oil, olive oil and cottonseed oil.

Preferable examples of the solubilizing agent include polyethylene glycol, propylene glycol, D-mannitol, trehalose, benzyl benzoate, ethanol, trisaminomethane, cholesterol, triethanolamine, sodium carbonate, sodium citrate, sodium salicylate and sodium acetate.

Preferable examples of the suspending agent include surfactants such as stearyltriethanolamine, sodium lauryl sulfate, lauryl aminopropionate, lecithin, benzalkonium chloride, benzethonium chloride, glycerol monostearate and the like; hydrophilic polymers such as poly(vinyl alcohol), polyvinylpyrrolidone, carboxymethylcellulose sodium, methylcellulose, hydroxymethylcellulose, hydroxyethylcellulose, hydroxypropylcellulose and the like, polysorbates; and polyoxyethylene hydrogenated castor oil.

Preferable examples of the isotonicity agent include sodium chloride, glycerol, D-mannitol, D-sorbitol and glucose.

Preferable examples of the buffer include buffers of phosphate, acetate, carbonate, citrate etc.

Preferable examples of the soothing agent include benzyl alcohol.

Preferable examples of the preservative include p-oxybenzoate esters, chlorobutanol, benzyl alcohol, phenethyl alcohol, dehydroacetic acid and sorbic acid.

Preferable examples of the antioxidant include sulfite salts and ascorbate salts.

Preferable examples of the colorant include aqueous food tar colors (e.g., food colors such as Food Color Red Nos. 2 and 3, Food Color Yellow Nos. 4 and 5, Food Color Blue Nos. 1 and 2 and the like food colors), water insoluble lake dyes (e.g., aluminum salt of the above-mentioned aqueous food tar color), natural dyes (e.g., β-carotene, chlorophyll, red iron oxide) and the like.

Preferable examples of the sweetening agent include saccharin sodium, dipotassium glycyrrhizinate, aspartame and stevia.

Examples of the dosage form of the above-mentioned pharmaceutical composition include oral preparations such as tablet (including sugar-coated tablet, film-coated tablet, sublingual tablet, orally disintegrating tablet, buccal tablet), capsule (including soft capsule, microcapsule), pill, granule, powder, troche, syrup, liquid, emulsion, suspension, aerosol, films (e.g., orally disintegrable films, oral mucosa-adhesive film) and the like; and parenteral agents such as injection (e.g., subcutaneous injection, intravenous injection, intramuscular injection, intraperitoneal injection, drip infusion), external preparation (e.g., transdermal absorption type preparation, ointment, lotion, adhesive preparation), suppository (e.g., rectal suppository, vaginal suppository), pellet, nasal preparation, pulmonary preparation (inhalant), eye drop and the like. The compound and medicament of the present invention can be respectively safely administered orally or parenterally (e.g., intrarectal, intravenous, intraarterial, intramuscular, subcutaneous, intraorgan, intranasal, intradermal, instillation, intracerebral, intravaginal, intraperitoneal, intratumoral, proximal tumor administrations, and administration to the lesion).

These preparations may be a release control preparation (e.g., sustained-release microcapsule) such as an immediate-release preparation, a sustained-release preparation and the like.

The pharmaceutical composition can be produced according to a method conventionally used in the field of pharmaceutical formulation, for example, the method described in the Japanese Pharmacopoeia, and the like.

While the content of the compound of the present invention in the pharmaceutical composition of the present invention varies depending on the dosage form, dose of the compound of the present invention and the like, it is, for example, about 0.1 to 100 wt %.

When an oral preparation is produced, coating may be applied where necessary for the purpose of taste masking, enteric solubility or sustainability.

Examples of the coating base used for coating include sugar coating base, water-soluble film coating base, enteric film coating base, and sustained-release film coating base.

As the sugar coating base, sucrose is used, and one or more kinds selected from talc, and the precipitated calcium carbonate, gelatin, gum arabic, pullulan, carnauba wax and the like may be further used in combination.

Examples of the water-soluble film coating base include cellulose polymers such as hydroxypropylcellulose, hydroxypropylmethylcellulose, hydroxyethylcellulose, methylhydroxyethylcellulose and the like; synthetic polymers such as polyvinyl acetal diethylaminoacetate, aminoalkylmethacrylate copolymer E [Eudragit E (trade name)], polyvinylpyrrolidone and the like; and polysaccharides such as pullulan and the like.

Examples of the enteric film coating base include cellulose polymers such as hydroxypropylmethylcellulose phthalate, hydroxypropylmethylcellulose acetate succinate, carboxymethylethylcellulose, cellulose acetate phthalate and the like; acrylic acid polymers such as methacrylic acid copolymer L [Eudragit L (trade name)], methacrylic acid copolymer LD [Eudragit L-30D-55 (trade name)], methacrylic acid copolymer S [Eudragit S (trade name)] and the like; and naturally-occurring substances such as shellac and the like.

Examples of the sustained-release film coating base include cellulose polymers such as ethylcellulose and the like; and acrylic acid polymers such as aminoalkylmethacrylate copolymer RS [Eudragit RS (trade name)], ethyl acrylate-methyl methacrylate copolymer suspension [Eudragit NE (trade name)] and the like.

Two or more kinds of the above-mentioned coating bases may be used in a mixture at an appropriate ratio. In addition, for example, light shielding agents such as titanium oxide, red ferric oxide and the like may also be used during coating.

Since the compound of the present invention shows low toxicity (e.g., acute toxicity, chronic toxicity, genetic toxicity, reproductive toxicity, cardiotoxicity, carcinogenicity) and less side effects, it can be used as a prophylactic or therapeutic agent, or diagnostic agent for various diseases in mammals (e.g., human, bovine, horse, dog, cat, monkey, mouse, rat).

Moreover, the compound of the present invention is expected to be superior in central migration.

The compound of the present invention has an excellent an orexin type 2 receptor agonist activity, and may treat, prevent or ameliorate the risk of various neurological and psychiatric diseases associated with an orexin type 2 receptor. The compound of the present invention is useful as an agent for the prophylaxis or treatment of various diseases such as narcolepsy, idiopathic hypersomnia, hypersomnia, sleep apnea syndrome, narcolepsy syndrome accompanied by narcolepsy-like symptoms, hypersomnia syndrome accompanied by daytime hypersomnia (e.g., Kleine Levin syndrome, major depression with hypersomnia, Lewy body dementia, Parkinson's disease, progressive supranuclear paralysis, Prader-Willi syndrome, Moebius syndrome, hypoventilation syndrome, Niemann-Pick disease type C, brain contusion, cerebral infarction, brain tumor, muscular dystrophy, multiple sclerosis, acute disseminated encephalomyelitis, Guillain-Barre syndrome, Rasmussen's encephalitis, Wernicke's encephalitis, limbic encephalitis, Hashimoto's encephalopathy), coma, loss of consciousness, obesity (e.g., malignant mastocytosis, exogenous obesity, hyperinsulinar obesity, hyperplasmic obesity, hypop hyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity), insulin resistance syndrome, Alzheimer's disease, disturbance of consciousness such as coma and the like, side effects and complications due to anesthesia, sleep disturbance, sleep problem, insomnia, Intermittent sleep, nocturnal myoclonus, REM sleep interruption, jet lag, jet lag syndrome, sleep disorder of alternating worker, sleep disorder, night terror, depression, major depression, sleepwalking disease, enuresis, sleep disorder, Alzheimer's dusk, diseases associated with circadian rhythm, fibromyalgia, condition arising from decline in the quality of sleep, overeating, obsessive compulsive eating disorder, obesity-related disease, hypertension, diabetes, elevated plasma insulin concentration and insulin resistance, hyperlipidemia, hyperlipemia, endometrial cancer, breast cancer, prostate cancer, colorectal cancer, cancer, osteoarthritis, obstructive sleep apnea, cholelithiasis, gallstones, cardiac disease, abnormal heartbeat, arrhythmia, myocardial infarction, congestive cardiac failure, cardiac failure, coronary heart disease, cardiovascular disorder, sudden death, polycysticovarian disease, craniopharingioma, Froelich's syndrome, growth hormone deficient, normal mutant short stature, Turner's syndrome, children suffering from acute lymphoblastic leukemia, syndrome X, reproductive hormone abnormality, declining fertility, infertility, male gonadal function decline, sexual and reproductive dysfunction such as female male hirsutism, fetal defects associated with pregnant women obesity, gastrointestinal motility disorders such as obesity-related gastroesophageal reflux, obesity hypoventilation syndrome (Pickwick syndrome), respiratory diseases such as dyspnea, inflammation such as systemic inflammation of the vascular system, arteriosclerosis, hypercholesterolemia, hyperuricemia, lower back pain, gall bladder disease, gout, kidney cancer, risk of secondary outcomes of obesity such as lowering the risk of left ventricular hypertrophy, migraine pain, headache, neuropathic pain, Parkinson's disease, psychosis, schizophrenia, facial flushing, night sweats, diseases of the genital/urinary system, diseases related to sexual function or fertility, dysthymic disorder, bipolar disorder, bipolar I disorder, bipolar II disorder, cyclothymic disorder, acute stress disorder, agoraphobia, generalized anxiety disorder, obsessive disorder, panic attack, panic disorder, posttraumatic stress disorder, separation anxiety disorder, social phobia, anxiety disorder, acute neurological and psychiatric disorders such as cardiac bypass surgery and post-transplant cerebral deficit, stroke, ischemic stroke, cerebral ischemia, spinal cord trauma, head trauma, perinatal hypoxia, cardiac arrest, hypoglycemic nerve injury, Huntington's disease, amyotrophic lateral sclerosis, multiple sclerosis, eye damage, retinopathy, cognitive impairment, muscle spasm, tremor, epilepsy, disorders associated with muscle spasticity, delirium, amnestic disorder, age-related cognitive decline, schizoaffective disorder, delusional disorder, drug addiction, dyskinesia, chronic fatigue syndrome, fatigue, medication-induced Parkinsonism syndrome, Jill-do La Tourette's syndrome, chorea, myoclonus, tic, restless legs syndrome, dystonia, dyskinesia, attention deficit hyperactivity disorder (ADHD), behavior disorder, urinary incontinence, withdrawal symptoms, trigeminal neuralgia, hearing loss, tinnitus, nerve damage, retinopathy, macular degeneration, vomiting, cerebral edema, pain, bone pain, arthralgia, toothache, cataplexy, and traumatic brain injury (TBI).

Particularly, the compound of the present invention is useful as an agent for the prophylaxis or treatment of narcolepsy, idiopathic hypersomnia, hypersomnia, sleep apnea syndrome, narcolepsy syndrome accompanied by narcolepsy-like symptoms, hypersomnia syndrome accompanied by daytime hypersomnia (e.g., Parkinson's disease, Guillain-Barre syndrome and Kleine Levin syndrome), Alzheimer's disease, obesity, insulin resistance syndrome, cardiac failure, diseases related to bone loss, sepsis, disturbance of consciousness such as coma and the like, side effects and complications due to anesthesia, and the like, or anesthetic antagonist.

While the dose of the compound of the present invention varies depending on the subject of administration, administration route, target disease, symptom and the like, for example, when the compound of the present invention is administered orally or parenterally to an adult patient, its dose is for example, about 0.01 to 100 mg/kg body weight per dose, preferably 0.1 to 50 mg/kg body weight per dose and more preferably 0.5 to 20 mg/kg body weight per dose. This amount is desirably administered in one to 3 portions daily.

The compound of the present invention can be used in combination with other drugs (hereinafter to be abbreviated as concomitant drug).

By combining the compound of the present invention and a concomitant drug, a superior effect, for example, (1) the dose can be reduced as compared to single administration of the compound of the present invention or a concomitant drug, (2) the drug to be combined with the compound of the present invention can be selected according to the condition of patients (mild case, severe case and the like), (3) the period of treatment can be set longer by selecting a concomitant drug having different action and mechanism from the compound of the present invention, (4) a sustained treatment effect can be designed by selecting a concomitant drug having different action and mechanism from the compound of the present invention, (5) a synergistic effect can be afforded by a combined use of the compound of the present invention and a concomitant drug, and the like, can be achieved.

In the present specification, the compound of the present invention and a concomitant drug used in combination are referred to as the "combination agent of the present invention".

When using the combination agent of the present invention, the administration time of the compound of the present invention and the concomitant drug is not restricted, and the compound of the present invention or a pharmaceutical composition thereof, or the concomitant drug or a pharmaceutical composition thereof can be administered to an administration subject simultaneously, or may be administered at different times. The dosage of the concomitant drug may be determined according to the dose clinically used, and can be appropriately selected depending on an administration subject, administration route, disease, combination and the like.

The administration mode of the combination agent of the present invention and the concomitant drug is not particularly limited, and the compound of the present invention and the concomitant drug only need to be combined on administration. Examples of such administration mode include the following: (1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (e.g., administration in the order of the compound of the present invention and the concomitant drug, or in the reverse order) and the like.

The dose of the concomitant drug can be appropriately determined based on the dose employed in clinical situations. The mixing ratio of the compound of the present invention and a concomitant drug can be appropriately determined depending on the administration subject, administration route, target disease, symptom, combination and the like.

For example, the content of the compound of the present invention in the combination agent of the present invention differs depending on the form of a preparation, and usually from about 0.01 to about 100 wt %, preferably from about 0.1 to about 50 wt %, further preferably from about 0.5 to about 20 wt %, based on the whole preparation.

The content of the concomitant drug in the combination agent of the present invention differs depending on the form of a preparation, and usually from about 0.01 to about 100 wt %, preferably from about 0.1 to about 50 wt %, further preferably from about 0.5 to about 20 wt %, based on the whole preparation.

The content of additives such as a carrier and the like in the combination agent of the present invention differs depending on the form of a preparation, and usually from about 1 to about 99.99 wt %, preferably from about 10 to about 90 wt %, based on the preparation.

Similar contents may be employed even when the compound of the present invention and a concomitant drug are separately formulated into preparations.

Examples of the concomitant drug include the followings. A therapeutic drug for narcolepsy (e.g., methylphenidate, amphetamine, pemoline, phenelzine, protriptyline, sodium oxybate, modafinil, caffeine), antiobesity drug (amphetamine, benzfetamine, bromocriptine, bupropion, diethylpropion, exenatide, fenfluramine, liothyronine, liraglutide, mazindol, methamphetamine, octreotide, octreotide, orlistat, phendimetrazine, phendimetrazine, phenmetrazine, phentermine, Qnexa (registered trade mark), phenylpropanolamine, pramlintide, propylhexedrine, recombinant leptin, sibutramine, topiramate, zimelidine, zonisamide, Lorcaserin, metformin), acetylcholine esterase inhibitor (e.g., donepezil, rivastigmine, galanthamine, zanapezil, idebenone, tacrine), antidementia agent (e.g., memantine), inhibitor of β amyloid protein production, secretion, accumulation, aggregation and/or deposition, β secretase inhibitor (e.g., 6-(4-biphenylyl)methoxy-2-[2-(N,N-dimethylamino)ethyl]tetralin, 6-(4-biphenylyl)methoxy-2-(N,N-dimethylamino)methyltetralin, 6-(4-biphenylyl)methoxy-2-(N,N-dipropylamino)methyltetralin, 2-(N,N-dimethylamino)methyl-6-(4'-methoxybiphenyl-4-yl) methoxytetralin, 6-(4-biphenylyl)methoxy-2-[2-(N,N-diethylamino)ethyl]tetralin, 2-[2-(N,N-dimethylamino) ethyl]-6-(4'-methylbiphenyl-4-yl)methoxytetralin, 2-[2-(N, N-dimethylamino)ethyl]-6-(4'-methoxybiphenyl-4-yl) methoxytetralin, 6-(2',4'-dimethoxybiphenyl-4-yl)methoxy-2-[2-(N,N-dimethylamino)ethyl]tetralin, 6-[4-(1,3-benzodioxol-5-yl)phenyl]methoxy-2-[2-(N,N-dimethylamino)ethyl]tetralin, 6-(3',4'-dimethoxybiphenyl-4-yl)methoxy-2-[2-(N,N-dimethylamino)ethyl]tetralin, an optically active form thereof, a salt thereof and a hydrate thereof, OM99-2 (WO01/00663)), γ secretase inhibitor, β amyloid protein aggregation inhibitor (e.g., PTI-00703, ALZHEMED (NC-531), PPI-368 (National Publication of International Patent Application No. 11-514333), PPI-558 (National Publication of International Patent Application No. 2001-500852), SKF-74652 (Biochem. J. (1999), 340(1), 283-289)), β amyloid vaccine, β amyloid-degrading enzyme and the like, brain function enhancer (e.g., aniracetam, nicergoline), therapeutic drug for Parkinson's disease [(e.g., dopamine receptor agonist (e.g., L-DOPA, bromocriptine, pergolide, talipexole, pramipexole, cabergoline, amantadine), monoamine oxidase enzyme (MAO) inhibitor (e.g., deprenyl, selegiline, remacemide, riluzole), anticholinergic agent (e.g., trihexyphenidyl, biperiden), COMT inhibitor (e.g., entacapone)], therapeutic drug for amyotrophic lateral sclerosis (e.g., riluzole etc., neurotrophic factor), therapeutic drug for abnormal behavior accompanying progress of dementia, wandering and the like (e.g., sedative, anti-anxiety drug), apoptosis inhibitor (e.g., CPI-1189, IDN-6556, CEP-1347), neuronal differentiation-regenerate promoter (e.g., leteprinim, xaliproden; SR-57746-A), SB-216763, Y-128, VX-853, prosaptide, 5,6-dimethoxy-2-[2,2,4,6,7-pentamethyl-3-(4-methylphenyl)-2,3-dihydro-1-benzofuran-5-yl]isoindoline, 5,6-dimethoxy-2-[3-(4-isopropylphenyl)-2,2,4,6,7-pentamethyl-2,3-dihydro-1-benzofuran-5-yl]isoindoline, 6-[3-(4-isopropylphenyl)-2,2,4,6,7-pentamethyl-2,3-dihydro-1-benzofuran-5-yl]-6,7-dihydro-5H-[1,3]dioxolo[4,5-f]isoindole and an optically active form, salt or hydrate thereof), non-steroidal antiinflammatory agents (meloxicam, tenoxicam, indomethacin, ibuprofen, celecoxib, rofecoxib, aspirin, indomethacin etc.), steroid drug (dexamethasone, hexestrol, cortisone acetate etc.), disease-modifying anti-rheumatic drug (DMARDs), anti-cytokine drug (e.g., TNF inhibitor, MAP kinase inhibitor), therapeutic agent for incontinence, frequent urination (e.g., flavoxate hydrochloride, oxybutynin hydrochloride, propiverine hydrochloride), phosphodiesterase inhibitor (e.g., sildenafil (citrate)), dopamine agonist (e.g., apomorphine), antiarrhythmic drugs (e.g., mexiletine), sex hormone or a derivative thereof (e.g., progesterone, estradiol, estradiol benzoate), therapeutic agent for osteoporosis (e.g., alfacalcidol, calcitriol, elcatonin, calcitonin salmon, estriol, ipriflavone, pamidronate disodium, alendronate sodium hydrate, incadronate disodium), parathyroid hormone (PTH), calcium receptor antagonists, therapeutic drug for insomnia (e.g., benzodiazepines medicament, non-benzodiazepines medicament, melatonin agonist, orexin receptor antagonists), therapeutic drug for schizophrenia (e.g., typical antipsychotic agents such as haloperidol and the like; atypical antipsychotic agents such as clozapine, olanzapine, risperidone, aripiprazole and the like; medicament acting on metabotropic glutamate receptor or ion channel conjugated-type glutamate receptor; phosphodiesterase inhibitor), benzodiazepines medicament (chlordiazepoxide, diazepam, potassium clorazepate, lorazepam, clonazepam, alprazolam etc.), L-type calcium channel inhibitor (pregabalin etc.), tricyclic or tetracyclic antidepressant (imipramine hydrochloride, amitriptyline hydrochloride, desipramine hydrochloride, clomipramine hydrochloride etc.), selective serotonin reuptake inhibitor (fluvoxamine maleate, fluoxetine hydrochloride, citalopram hydrobromide, sertraline hydrochloride, paroxetine hydrochloride, escitalopram oxalate etc.), serotonin-noradrenaline reuptake inhibitor (venlafaxine hydrochloride, duloxetine hydrochloride, desvenlafaxine hydrochloride etc.), noradrenaline reuptake inhibitor (reboxetine mesylate etc.), mirtazapine, trazodone hydrochloride, nefazodone hydrochloride, bupropion hydrochloride, setiptiline maleate, 5-$HT_{1A}$ agonist, (buspirone hydrochloride, tandospirone citrate, osemozotan hydrochloride etc.), 5-$HT_{2A}$ antagonist, 5-$HT_{2A}$ inverse agonist, 5-$HT_3$ antagonist (cyamemazine etc.), heart non-selective β inhibitor (propranolol hydrochloride, oxprenolol hydrochloride etc.), histamine $H_1$ antagonist (hydroxyzine hydrochloride etc.), CRF antagonist, other antianxiety drug (meprobamate etc.), tachykinin antagonist (MK-869, saredutant etc.), medicament that acts on metabotropic glutamate receptor, CCK antagonist, $β_3$ adrenaline antagonist (amibegron hydrochloride etc.), GAT-1 inhibitor (tiagabine hydrochloride etc.), N-type calcium channel inhibitor, carbonic anhydrase II inhibitor, NMDA glycine moiety agonist, NMDA antagonist (memantine etc.), peripheral benzodiazepine receptor agonist, vasopressin antagonist, vasopressin V1b antagonist, vasopressin V1a antagonist, phosphodiesterase inhibitor, opioid antagonist, opioid agonist, uridine, nicotinic acid receptor agonist, thyroid hormone (T3, T4), TSH, TRH, MAO inhibitor (phenelzine sulfate, tranylcypromine sulfate, moclobemide etc.), therapeutic drug for bipolar disorder (lithium carbonate, sodium valproate, lamotrigine, riluzole, felbamate etc.), cannabinoid CB1 antagonist (rimonabant etc.), FAAH inhibitor, sodium channel inhibitor, anti-ADHD drug (methylphenidate hydrochloride, methamphetamine hydrochloride etc.), therapeutic drug for alcoholism, therapeutic drug for autism, therapeutic drug for chronic fatigue syndrome, therapeutic drug for spasm, therapeutic drug for fibromyalgia syndrome, therapeutic drug for headache, therapeutic drug for quitting smoking, therapeutic drug for myasthenia gravis, therapeutic drug for cerebral infarction, therapeutic drug for mania, therapeutic drug for hypersomnia, therapeutic drug for pain, therapeutic drug for dysthymia, therapeutic drug for autonomic ataxia, therapeutic drug for male and female sexual dysfunction, therapeutic drug for migraine, therapeutic drug for pathological gambler, therapeutic drug for restless legs syndrome, therapeutic drug for substance addiction, therapeutic drug for alcohol-related syndrome, therapeutic drug for irritable bowel syndrome, therapeutic drug for lipid abnormality such as cholesterol-lowering drug (statin series (pravastatin sodium, atorvastatin, simvastatin, rosuvastatin etc.), fibrate (clofibrate etc.), squalene synthetase inhibitor), therapeutic drug for abnormal behavior or suppressant of dromomania due to dementia (sedatives, antianxiety drug etc.), therapeutic drug for diabetes, therapeutic agent for diabetic complications, therapeutic drug for hypertension, therapeutic drug for hypotension, diuretic, chemotherapeutic agent, immunotherapeutic agent, antithrombotic agent, anti-cancer agent and the like.

Two or more kinds of the above-mentioned concomitant drug may be used in a mixture at an appropriate ratio.

When the compound of the present invention is applied to each of the above-mentioned diseases, it can also be used in combination with biologics (e.g., antibody drug, nucleic acid or nucleic acid derivative, aptamer drug, vaccine preparation), or can be used in combination with a gene therapy method and the like, or can also be used in combination with a treatment in psychiatric field without using drugs.

Examples of the antibody drug and vaccine preparation include vaccine preparation against angiotensin II, vaccine preparation against CETP, CETP antibody, antibody against TNFα antibody and other cytokines, amyloid β vaccine preparation, vaccine for type 1 diabetes (e.g., DIAPEP-277 of Peptor), anti-HIV antibody and HIV vaccine preparation, as well as antibodies or vaccine preparations against cytokines, renin-angiotensin type enzymes and products thereof, antibodies or vaccine preparations against enzymes or proteins involved in blood lipid metabolism, antibodies or vaccines relating to enzymes and proteins involved in blood coagulation or fibrinolysis system, antibodies or vaccine preparations against proteins involved in sugar metabolism and insulin resistance, and the like. In addition, it can be used in combination with biologics relating to growth factors such as GH, IGF and the like.

Examples of the gene therapy method include a treatment method using gene relating to cytokine, renin-angiotensin type enzyme and product thereof, G protein, G protein conjugated receptor and phosphorylating enzyme thereof, a treatment method using a DNA decoy such as NFκB decoy and the like, a treatment method using antisense, a treatment method using a gene relating to an enzyme or protein involved in blood lipid metabolism (e.g., a gene relating to metabolism, excretion and absorption of cholesterol or triglyceride or HDL-cholesterol or blood phospholipid), a treatment method using a gene relating to an enzyme or protein involved in angiogenesis therapy for peripheral vascular obstruction and the like (e.g., growth factors such as HGF, VEGF etc.), a treatment method using a gene relating to a protein involved in glucose metabolism and insulin resistance, antisense against cytokines such as TNF etc., and the like.

Examples of the treatment method in the psychiatric field without using drug include modified electroconvulsive therapy, deep brain stimulation therapy, repetitive transcranial magnetic stimulation therapy, psychotherapy including cognitive behavioral therapy and the like.

The compound of the present invention can also be used in combination with various organ regeneration methods such as cardiac regeneration, renal regeneration, pancreatic regeneration, revascularization and the like, cell transplantation therapy utilizing bone marrow cells (bone marrow-derived mononuclear cell, myelogenic stem cell), or artificial organ utilizing tissue engineering (e.g., artificial blood vessel, cardiomyocyte sheet).

EXAMPLES

The present invention is explained in detail in the following by referring to Examples, Experimental Examples and Formulation Examples. However, the examples do not limit the present invention and the examples can be modified within the scope of the present invention.

The "room temperature" in the following Examples is generally about 10° C. to about 35° C. The ratio for mixed solvent is, unless otherwise specified, a volume mixing ratio and % means wt % unless otherwise specified.

The elution by column chromatography in the Examples was performed under the observation by TLC (Thin Layer Chromatography) unless otherwise specified. In the observation by TLC, 60 $F_{254}$ manufactured by Merck was used as a TLC plate, the solvent used as an elution solvent in column chromatography was used as an eluent, and UV detector was used for the detection. In silica gel column chromatography, the indication of NH means use of aminopropylsilane-bonded silica gel and the indication of Diol means use of 3-(2,3-dihydroxypropoxy)propylsilane-bonded silica gel. In preparative HPLC (high performance liquid chromatography), the indication of C18 means use of octadecyl-bonded silica gel. The ratio for elution solvent is, unless otherwise specified, a volume mixing ratio.

For the analysis of $^1$H NMR, ACD/SpecManager (trade name) software and the like were used. Peaks of a hydroxyl group, an amino group and the like, having very mild proton peak, are not sometimes described.

MS was measured by LC/MS. As the ionization method, ESI method, or APCI method was used. The data indicates actual measured value (found). While molecular ion peak is generally observed, a fragment ion is sometimes observed. In the case of a salt, a molecular ion peak or fragment ion peak of free form is generally observed.

The unit of sample concentration (c) for optical rotation ($[\alpha]_D$) is g/100 mL.

Elemental analysis value (Anal.) is described as calculated value (Calcd) and actual measured value (Found).

The retention time in the Examples was measured by liquid chromatograph method. The measurement conditions are as follows, unless otherwise specified.

column: YMC PackPro C18 2.0 mm i.d.×75 mm (3 μm)
mobile phase: the solution prepared by adding 0.04 M Britton-Robinson buffer solution (pH 6.5) to methanol (5:2), and mixing them well, and adjusting the pH to 7.4 with 0.2 M sodium hydroxide solution.

Peaks by powder X-ray diffraction in the Examples mean peaks measured at room temperature by Ultima IV (Rigaku Corporation, Japan) using Cu Kα radiation as a radiation source. The measurement conditions are as follows.

Electric pressure/Electric current: 40 kV/50 mA
Scan speed: 6 degrees/min
Scan range of 2 Theta: 2-35 degrees
The crystallinity by powder X-ray diffraction in the Examples was calculated by the Hermans method.

In the following Examples, the following abbreviations are used.
mp: melting point
MS: mass spectrum
M: mol concentration
N: normality
CDCl$_3$: deuterochloroform
DMSO-d$_6$: deuterodimethyl sulfoxide
$^1$H NMR: proton nuclear magnetic resonance
LC/MS: liquid chromatograph mass spectrometer
ESI: Electrospray Ionization
APCI: Atmospheric Pressure Chemical Ionization
HATU: (dimethylamino)-N,N-dimethyl (3H-[1,2,3]triazolo[4,5-b]pyridin-3-yloxy)methaneiminium hexafluorophosphate
PPh$_3$: triphenylphosphine
TFA: trifluoroacetic acid
DMAP: N,N-dimethyl-4-aminopyridine
CPME: cyclopentyl methyl ether
WSC: N-(3-(dimethylamino)propyl)-N'-ethylcarbodiimide
IPE: 2-isopropoxypropane
DIPEA: N-ethyl-N-isopropylpropan-2-amine
DMF: N,N-dimethylformamide
HOBt: 1H-benzotriazol-1-ol
THF: tetrahydrofuran
DME: 1,2-dimethoxyethane
MeOH: methanol
WSC·HCl: N-(3-(dimethylamino)propyl)-N'-ethylcarbodiimide hydrochloride (1:1)
EtOH: ethanol
Boc$_2$O: di-tert-butyl dicarbonate
TEA: triethylamine
Et$_2$O: ethoxyethane
EtOAc: ethyl acetate
CH$_3$CN: acetonitrile
TMSCl: trimethylsilyl chloride
XPhos Pd G3: methanesulfonato(2-dicyclohexylphosphino-2',4',6'-triisopropyl-1,1'-biphenyl)(2'-amino-1,1'-biphenyl-2-yl)palladium(II)
PdCl$_2$(dppf): [1,1'-bis(diphenylphosphino)ferrocene]palladium(II) dichloride Example 1

N-[(2S,3R)-2-[(2,3'-difluoro[1,1'-biphenyl]-3-yl)methyl]-4,4-difluoro-1-((2R)-oxetane-2-carbonyl)pyrrolidin-3-yl]ethanesulfonamide A) 3-chloro-2-fluorophenylalanine Hydrochloride To a mixture of 1-(bromomethyl)-3-chloro-2-fluorobenzene (55.0 g), diethyl acetamidomalonate (56.1 g) and EtOH (400 mL) was added 20% sodium ethoxide ethanol solution (88 g) at 0° C. The mixture was refluxed for 2 hr 30 min, and cooled to room temperature. The impurity was removed by filtration, the filtrate was concentrated under reduced pressure, and a mixture of the residue and 6 M hydrochloric acid (500 mL) was refluxed for 15 hr. The reaction solution was concentrated under reduced pressure, and the obtained residue was washed with isopropanol/diisopropyl ether to give the title compound (67.1 g).

MS: [M+H]$^+$ 217.8.

B) N-(tert-butoxycarbonyl)-3-chloro-2-fluorophenylalanine

To a mixture of 3-chloro-2-fluorophenylalanine hydrochloride (67.1 g), 1 M aqueous sodium hydroxide solution (528 mL) and DME (480 mL) was added Boc$_2$O (63.4 g) at room temperature. The mixture was stirred at room temperature for 2 hr 30 min, and poured into ice water. The mixture was basified with 1 M aqueous sodium hydroxide solution, and the aqueous layer was washed with diethyl ether. The aqueous layer was acidified with 1 M hydrochloric acid, and extracted with EtOAc. The organic layer was separated, washed with water and saturated brine, dried over anhydrous magnesium sulfate, and concentrated under

C) tert-butyl {3-(3-chloro-2-fluorophenyl)-1-[methoxy(methyl)amino]-1-oxopropan-2-yl}carbamate To a mixture of N-(tert-butoxycarbonyl)-3-chloro-2-fluorophenylalanine (63.8 g), N-methoxymethanamine hydrochloride (21.5 g), HOBt (29.8 g), TEA (44.7 g) and DMF (425 mL) was added WSC·HCl (46.2 g) at 0° C. The mixture was stirred at room temperature for 15 hr, and the reaction mixture was added to aqueous sodium hydrogen carbonate solution, and extracted with EtOAc/THF. The organic layer was separated, washed with water and saturated brine, dried over anhydrous magnesium sulfate, and concentrated under reduced pressure. The obtained solid was washed with diisopropyl ether/hexane to give the title compound (70.0 g).

MS, found: 260.9.

D) tert-butyl {3-(3-chloro-2-fluorophenyl)-1-[methoxy(methyl)amino]-1-oxopropan-2-yl}(4-methoxybenzyl)carbamate To a mixture of tert-butyl {3-(3-chloro-2-fluorophenyl)-1-[methoxy(methyl)amino]-1-oxopropan-2-yl}carbamate (70.0 g) and DMF (390 mL) was added 60% sodium hydride (10.1 g) at 0° C. The mixture was stirred at 0° C. for 5 min, and then at room temperature for 10 min, and to the reaction mixture were added 1-(chloromethyl)-4-methoxybenzene (60.7 g) and tetrabutylammonium iodide (7.16 g) at 0° C. The mixture was stirred at room temperature for 2 hr 30 min, poured into ice water, and extracted with EtOAc. The organic layer was separated, washed with water and saturated brine, dried over anhydrous magnesium sulfate, and concentrated under reduced pressure. The residue was purified by silica gel column chromatography (EtOAc/hexane) to give the title compound (90.7 g).

MS: $[M+H]^+$ 481.1.

E) tert-butyl [1-(3-chloro-2-fluorophenyl)-3-oxopropan-2-yl][(4-methoxyphenyl)methyl]carbamate To a mixture of tert-butyl {3-(3-chloro-2-fluorophenyl)-1-[methoxy(methyl)amino]-1-oxopropan-2-yl}(4-methoxybenzyl)carbamate (90.7 g) and Et$_2$O (500 mL) was added lithium aluminium hydride (9.30 g) by small and small at −78° C. The mixture was stirred at −15° C. for 1 hr 30 min, and to the reaction mixture were added dropwise sequentially EtOAc and 10% aqueous potassium hydrogensulfite solution at −78° C. The mixture was stirred at room temperature for 15 min, and to the mixture was added water. The insoluble substance was removed by filtration through Celite, and the filtrate was extracted with EtOAc. The organic layer was separated, washed with water and saturated brine, dried over anhydrous magnesium sulfate, and concentrated under reduced pressure. The residue was purified by silica gel column chromatography (EtOAc/hexane) to give the title compound (74.7 g).

MS: $[M-H]^-$ 420.0.

F) ethyl 4-{(tert-butoxycarbonyl)[(4-methoxyphenyl)methyl]amino}-5-(3-chloro-2-fluorophenyl)-2,4,5-trideoxy-2,2-difluoropentonate To a mixture of zinc (37.0 g) and THF (500 mL) was added TMSCl (3.85 g) under argon atmosphere at room temperature. The mixture was stirred at room temperature for 15 min, and ethyl bromo (difluoro)acetate (71.9 g) was added dropwise to the mixture with vigorously stirring at room temperature while keeping the internal temperature of about 50° C. The mixture was stirred at room temperature for 15 min, and to the mixture was added dropwise a mixture of tert-butyl [1-(3-chloro-2-fluorophenyl)-3-oxopropan-2-yl][(4-methoxyphenyl)methyl]carbamate (74.7 g) and THF (100 mL), while keeping the internal temperature of about 40° C. The mixture was stirred at room temperature for 2 hr, and added to 5% aqueous potassium hydrogensulfite solution under ice cooling, and extracted with EtOAc. The organic layer was separated, washed with water and saturated brine, dried over anhydrous magnesium sulfate, and concentrated under reduced pressure. The residue was purified by silica gel column chromatography (EtOAc/hexane) to give the title compound (61.6 g).

MS, found: 490.0.

G) 5-[(3-chloro-2-fluorophenyl)methyl]-3,3-difluoro-4-hydroxy-1-[(4-methoxyphenyl)methyl]pyrrolidin-2-one To a mixture of ethyl 4-{(tert-butoxycarbonyl)[(4-methoxyphenyl)methyl]amino}-5-(3-chloro-2-fluorophenyl)-2,4,5-trideoxy-2,2-difluoropentonate (61.6 g) and EtOH (160 mL) was added 4 M hydrogen chloride CPME solution (282 mL) at room temperature. The mixture was stirred at room temperature for 2 hr, and the reaction solution was concentrated. To the obtained residue were added EtOH (360 mL) and DIPEA (43.8 g). The mixture was stirred at 70° C. for 1 hr 30 min, and the reaction mixture was poured into ice water, and extracted with EtOAc. The organic layer was separated, washed with water and saturated brine, dried over anhydrous magnesium sulfate, and concentrated under reduced pressure. The residue was purified by silica gel column chromatography (EtOAc/hexane), and the obtained solid was washed with diisopropyl ether/hexane to give the title compound (36.1 g).

MS: $[M+H]^+$ 399.9.

H) 5-[(3-chloro-2-fluorophenyl)methyl]-3,3-difluoro-4-hydroxypyrrolidin-2-one To a mixture of 5-[(3-chloro-2-fluorophenyl)methyl]-3,3-difluoro-4-hydroxy-1-[(4-methoxyphenyl)methyl]pyrrolidin-2-one (36.1 g), CH$_3$CN (315 mL) and water (105 mL) was added ammonium hexanitratocerate (IV) (99 g) at room temperature. The mixture was stirred at room temperature for 4 hr, poured into ice water, and extracted with EtOAc. The organic layer was separated, washed with water and saturated brine, dried over anhydrous magnesium sulfate, and concentrated under reduced pressure. The residue was purified by silica gel column chromatography (EtOAc/hexane), and then silica gel column chromatography (NH, methanol/EtOAc) to give the title compound (22.7 g).

MS: $[M-H]^-$ 278.0.

I) tert-butyl 2-[(3-chloro-2-fluorophenyl)methyl]-4,4-difluoro-3-hydroxypyrrolidine-1-carboxylate To a mixture of 5-[(3-chloro-2-fluorophenyl)methyl]-3,3-difluoro-4-hydroxypyrrolidin-2-one (22.7 g) and THF (350 mL) was added dropwise 1 M borane-THF complex THF solution (284 mL) at room temperature. The mixture was slowly warmed to 60° C., and stirred for 4 hr. Water was added dropwise to the mixture at 0° C., and the mixture was stirred at room temperature for 10 min, and concentrated under reduced pressure. To the residue was added 1 M hydrochloric acid (500 mL), and the mixture was vigorously stirred at 60° C. for 1 hr 30 min. The mixture was slowly added to 1 M aqueous sodium hydroxide solution under ice cooling, basified with potassium carbonate, saturated with salt, and extracted with EtOAc/THF. The organic layer was separated, washed with water and saturated brine, dried over anhydrous magnesium sulfate, and concentrated under reduced pressure. To a mixture of the obtained residue, sodium hydrogen carbonate (6.83 g) and THF (190 mL)/water (210 mL) was added a solution of $Boc_2O$ (19.5 g) in THF (20 mL) at room temperature. The mixture was vigorously stirred at room temperature for 15 hr, poured into water, and extracted with EtOAc. The organic layer was separated, washed with water and saturated brine, dried over anhydrous magnesium sulfate, and concentrated under reduced pressure. The residue was purified by silica gel column chromatography (EtOAc/hexane) to give the title compound (22.2 g).

MS, found: 265.9.

J) rac-tert-butyl (2S,3S)-2-[(3-chloro-2-fluorophenyl)methyl]-4,4-difluoro-3-[(trifluoromethanesulfonyl)oxy]pyrrolidine-1-carboxylate To a mixture of tert-butyl 2-[(3-chloro-2-fluorophenyl)methyl]-4,4-difluoro-3-hydroxypyrrolidine-1-carboxylate (22.1 g), pyridine (96 g) and $Et_2O$ (355 mL) was added dropwise trifluoromethanesulfonic anhydride (51.2 g) under argon atmosphere at 0° C. The mixture was stirred at room temperature for 2 hr 30 min, poured into ice water, and extracted with EtOAc/hexane. The organic layer was separated, washed with 10% aqueous citric acid solution, aqueous sodium hydrogen carbonate solution, water and saturated brine, dried over anhydrous magnesium sulfate, and concentrated under reduced pressure. The residue was purified by silica gel column chromatography (EtOAc/hexane) to give the title compound (22.4 g).

MS, found: 397.9.

K) rac-tert-butyl (2S,3R)-3-azido-2-[(3-chloro-2-fluorophenyl)methyl]-4,4-difluoropyrrolidine-1-carboxylate To a mixture of rac-tert-butyl (2S,3S)-2-[(3-chloro-2-fluorophenyl)methyl]-4,4-difluoro-3-[(trifluoromethanesulfonyl)oxy]pyrrolidine-1-carboxylate (22.4 g) and $CH_3CN$ (265 mL) was added tetra-n-butylammonium azide (38.3 g) at room temperature. The mixture was slowly warmed to 80° C., stirred for 1 hr, poured into ice water, and extracted with EtOAc. The organic layer was separated, washed with water and saturated brine, dried over anhydrous magnesium sulfate, and concentrated under reduced pressure. The residue was purified by silica gel column chromatography (EtOAc/hexane) to give the title compound (16.2 g).

MS, found: 290.9.

L) rac-tert-butyl (2S,3R)-3-amino-2-[(3-chloro-2-fluorophenyl)methyl]-4,4-difluoropyrrolidine-1-carboxylate To a mixture of rac-tert-butyl (2S,3R)-3-azido-2-[(3-chloro-2-fluorophenyl)methyl]-4,4-difluoropyrrolidine-1-carboxylate (16.2 g) and THF (200 mL)/water (5 mL) was added $PPh_3$ (13.1 g) under argon atmosphere at room temperature. The mixture was stirred at 55° C. for 18 hr, added to aqueous sodium hydrogen carbonate solution under ice cooling, and extracted with EtOAc/THF. The organic layer was separated, washed with water and saturated brine, dried over anhydrous magnesium sulfate, and concentrated under reduced pressure. The residue was purified by silica gel column chromatography (NH, EtOAc/hexane) to give the title compound and by-product, respectively. To a mixture of the obtained by-product and THF (100 mL)/water (10 mL) was added 40% aqueous methanamine solution (3.22 g) at room temperature. The mixture was stirred at 70° C. for 15 hr, poured into water, and extracted with EtOAc. The organic layer was separated, washed with water and saturated brine, dried over anhydrous magnesium sulfate, and concentrated under reduced pressure. The residue was purified by silica gel column chromatography (NH, EtOAc/hexane) to give the title compound (14.6 g), combined with the title compound obtained above.

MS, found: 308.9.

M) tert-butyl (2S,3R)-3-amino-2-[(3-chloro-2-fluorophenyl)methyl]-4,4-difluoropyrrolidine-1-carboxylate rac-tert-Butyl (2S,3R)-3-amino-2-[(3-chloro-2-fluorophenyl)methyl]-4,4-difluoropyrrolidine-1-carboxylate (14.6 g) was resolved by HPLC (column: CHIRALPAK IA, 50 mmID×500 mmL, 20 μm, mobile phase: hexane/ethanol/diethylamine=800/200/1) to give the title compound (6.84 g) with shorter retention time (column: CHIRALPAK IA, 4.6 mmID×250 mmL, 5 μm, mobile phase: hexane/ethanol/diethylamine=800/200/1).

MS, found: 309.1.

N) tert-butyl (2S,3R)-2-[(3-chloro-2-fluorophenyl)methyl]-3-[(ethanesulfonyl)amino]-4,4-difluoropyrrolidine-1-carboxylate To a mixture of tert-butyl (2S,3R)-3-amino-2-[(3-chloro-2-fluorophenyl)methyl]-4,4-difluoropyrrolidine-1-carboxylate (1.04 g), TEA (0.577 g), DMAP (0.174 g) and THF (30 mL) was added ethanesulfonyl chloride (0.550 g) at 0° C. The mixture was stirred at room temperature for 5 hr, water was added to mixture at room temperature, and the mixture was extracted with EtOAc. The organic layer was separated, washed with water and saturated brine, dried over anhydrous sodium sulfate, and concentrated under reduced pressure. The residue was purified by silica gel column chromatography (NH, EtOAc/hexane) to give the title compound (1.25 g).

MS: [M−H]⁻ 455.1.

O) N-{(2S,3R)-2-[(2,3'-difluoro[1,1'-biphenyl]-3-yl)methyl]-4,4-difluoropyrrolidin-3-yl}ethanesulfonamide Hydrochloride A mixture of tert-butyl (2S,3R)-2-[(3-chloro-2-fluorophenyl)methyl]-3-[(ethanesulfonyl)amino]-4,4-difluoropyrrolidine-1-carboxylate (24.9 mg), (3-fluorophenyl)boronic acid (15.3 mg), XPhos Pd G3 (4.61 mg), 1 M aqueous potassium phosphate solution (0.163 mL) and DME (0.6 mL) was stirred at 80° C. for 2 hr. The reaction solution was concentrated, and the residue was purified by silica gel column chromatography (NH, EtOAc/hexane). A mixture of the obtained residue (27 mg) and 4 M hydrogen chloride CPME solution (2 mL) was stirred at room temperature for 4 hr. The insoluble substance was collected by filtration to give the title compound (17 mg).
MS: [M+H]⁺ 417.1.

P) N-[(2S,3R)-2-[(2,3'-difluoro[1,1'-biphenyl]-3-yl)methyl]-4,4-difluoro-1-((2R)-oxetane-2-carbonyl)pyrrolidin-3-yl]ethanesulfonamide To a mixture of N-{(2S,3R)-2-[(2,3'-difluoro[1,1'-biphenyl]-3-yl)methyl]-4,4-difluoropyrrolidin-3-yl}ethanesulfonamide hydrochloride (250 mg), oxetane-2-carboxylic acid (67.6 mg) and DMF (2 mL) were added HATU (315 mg) and DIPEA (357 mg) at room temperature. The mixture was stirred overnight at room temperature, to the mixture was added saturated aqueous ammonium chloride solution, and the mixture was extracted with EtOAc. The organic layer was separated, washed with water and saturated brine, dried over anhydrous sodium sulfate, and concentrated under reduced pressure. The residue was purified by silica gel column chromatography (NH, EtOAc/hexane), and the obtained solid was crystallized from EtOAc/hexane to give the title compound (66 mg) with shorter retention time.
¹H NMR (400 MHz, CDCl₃) δ 1.27-1.47 (3H, m), 2.68-5.20 (14H, m), 7.03-7.13 (1H, m), 7.16-7.45 (6H, m).

Example 2

N-{(2S,3R)-4,4-difluoro-1-(2-hydroxy-2-methylpropanoyl)-2-[(2,3',5'-trifluoro[1,1'-biphenyl]-3-yl)methyl]pyrrolidin-3-yl}methanesulfonamide A) tert-butyl (2S,3R)-2-(3-chloro-2-fluorobenzyl)-4,4-difluoro-3-(methylsulfonamido)pyrrolidine-1-carboxylate Methanesulfonic anhydride (143 mg) was added to a mixture of tert-butyl (2S,3R)-3-amino-2-(3-chloro-2-fluorobenzyl)-4,4-difluoropyrrolidine-1-carboxylate (200 mg), TEA (0.229 mL) and THF (5 mL) at room temperature. The mixture was stirred overnight at room temperature. The mixture was concentrated under reduced pressure. The residue was purified by column chromatography (silica gel, EtOAc/hexane) to give the title compound (244 mg).
MS: [M–H]⁻ 441.1.

B) tert-butyl (2S,3R)-4,4-difluoro-3-(methylsulfonamido)-2-((2,3',5'-trifluoro-[1,1'-biphenyl]-3-yl)methyl)pyrrolidine-1-carboxylate A mixture of tert-butyl (2S,3R)-2-(3-chloro-2-fluorobenzyl)-4,4-difluoro-3-(methylsulfonamido)pyrrolidine-1-carboxylate (4.52 g), (3,5-difluorophenyl)boronic acid (3.22 g), XPhos Pd G3 (0.432 g) and 1 M aqueous potassium phosphate solution (30.6 mL) in DME (100 mL) was stirred at 80° C. for 3 h under nitrogen atmosphere. The mixture was purified by column chromatography (silica gel, EtOAc/hexane, then NH silica gel, EtOAc/hexane) to give the title compound (5.30 g).
MS: [M–H]⁻ 519.1.

C) N-{(2S,3R)-4,4-difluoro-2-[(2,3',5'-trifluoro[1,1'-biphenyl]-3-yl)methyl]pyrrolidin-3-yl}methanesulfonamide Hydrochloride A mixture of tert-butyl (2S,3R)-4,4-difluoro-3-(methylsulfonamido)-2-((2,3',5'-trifluoro-[1,1'-biphenyl]-3-yl)methyl)pyrrolidine-1-carboxylate (73 mg) and 4 M HCl/CPME solution (1 mL) was stirred overnight at room temperature. The mixture was diluted with EtOAc and precipitate was collected by filtration to give the title compound (50.0 mg).
MS: [M+H]⁺ 421.0.

D) N-{(2S,3R)-4,4-difluoro-1-(2-hydroxy-2-methylpropanoyl)-2-[(2,3',5'-trifluoro[1,1'-biphenyl]-3-yl)methyl]pyrrolidin-3-yl}methanesulfonamide To a mixture of N-{(2S,3R)-4,4-difluoro-2-[(2,3',5'-trifluoro[1,1'-biphenyl]-3-yl)methyl]pyrrolidin-3-yl}methanesulfonamide hydrochloride (4.3 g) and DIPEA (8.14 mL) in THF (60 mL) was added alpha-acetoxyisobutyryl chloride (1.64 mL) at 0° C., and the mixture was stirred at same temperature for 10 min. To the mixture were added water (20 mL) and 4 M lithium hydroxide solution (23.5 mL), and the mixture was stirred overnight at room temperature. The mixture was diluted with saturated brine and extracted with EtOAc. The extract was dried over magnesium sulfate and concentrated under reduced pressure. The residue was purified by column chromatography (silica gel, EtOAc/hexane) to give the title compound (4.40 g).
¹H NMR (400 MHz, CDCl₃) δ 1.31-1.47 (6H, m), 2.25-2.60 (1H, m), 2.88-3.02 (4H, m), 3.10 (1H, dd, J=14.2, 7.5 Hz), 4.01-4.49 (3H, m), 4.92-5.17 (2H, m), 6.75-6.87 (1H, m), 7.01-7.11 (2H, m), 7.16-7.23 (1H, m), 7.26-7.32 (1H, m), 7.36-7.46 (1H, m).

Example 3

N-{(2S,3R)-4,4-difluoro-1-(2-hydroxy-2-methylpropanoyl)-2-[(2,3',5'-trifluoro[1,1'-biphenyl]-3-yl)methyl]pyrrolidin-3-yl}ethanesulfonamide A) tert-butyl (2S,3R)-3-(ethylsulfonamido)-4,4-difluoro-2-((2,3',5'-trifluoro-[1,1'-biphenyl]-3-yl)methyl)pyrrolidine-1-carboxylate To a mixture of tert-butyl (2S,3R)-2-(3-chloro-2-fluorobenzyl)-3-(ethylsulfonamido)-4,4-difluoropyrrolidine-1-carboxylate (3.70 g), (3,5-difluorophenyl)boronic acid (2.56 g) and 1 M aqueous potassium phosphate solution (24.3 mL) in DME (50 mL) was added XPhos Pd G3 (0.343 g) at room temperature. The mixture was stirred at 90° C. under nitrogen atmosphere for 15 h. The reaction mixture was poured into water and extracted with EtOAc. The organic layer was washed with saturated brine, dried over magnesium sulfate and concentrated under reduced pressure. The residue was purified by column chromatography (silica gel, EOAc/hexane) to give the title compound (3.30 g).
MS: [M–H]⁻ 533.2.

B) N-((2S,3R)-4,4-difluoro-2-((2,3',5'-trifluoro-[1,1'-biphenyl]-3-yl)methyl)pyrrolidin-3-yl)ethanesulfonamide Hydrochloride A mixture of tert-butyl (2S,3R)-3-(ethylsulfonamido)-4,4-difluoro-2-((2,3',5'-trifluoro-[1,1'-biphenyl]-3-yl)methyl)pyrrolidine-1-carboxylate (3.30 g) and 4 M HCl/CPME solution (30 mL) was stirred overnight at room temperature. By filtration, the title compound (2.86 g) was obtained.
MS: [M+H]⁺ 435.1.

C) N-{(2S,3R)-4,4-difluoro-1-(2-hydroxy-2-methyl-propanoyl)-2-[(2,3',5'-trifluoro[1,1'-biphenyl]-3-yl)methyl]pyrrolidin-3-yl}ethanesulfonamide To a mixture of N-((2S,3R)-4,4-difluoro-2-((2,3',5'-trifluoro-[1,1'-biphenyl]-3-yl)methyl)pyrrolidin-3-yl)ethanesulfonamide hydrochloride (200 mg) and DIPEA (0.367 mL) in THF (3 mL) was added alpha-acetoxy-isobutyryl chloride (0.074 mL) at 0° C., and the mixture was stirred at same temperature for 10 min. To the mixture were added water (1 mL) and 4 M lithium hydroxide solution (1.06 mL), and the mixture was stirred overnight at room temperature. The mixture was diluted with saturated brine and extracted with EtOAc. The extract was dried over magnesium sulfate and concentrated under reduced pressure. The residue was purified by column chromatography (silica gel, EtOAc/hexane) and recrystallized from EtOAc/hexane to give the title compound (154 mg).

$^1$H NMR (400 MHz, CDCl$_3$) δ 1.32-1.40 (9H, m), 2.27-2.54 (1H, m), 2.88-3.16 (4H, m), 4.02-4.49 (3H, m), 4.86-5.20 (2H, m), 6.78-6.86 (1H, m), 7.02-7.10 (2H, m), 7.16-7.22 (1H, m), 7.27-7.31 (1H, m), 7.35-7.43 (1H, m).

Example 4

N-[(2S,3R)-4,4-difluoro-2-[(2-fluoro[1,1'-biphenyl]-3-yl)methyl]-1-(2-hydroxy-2-methylpropanoyl)pyrrolidin-3-yl]methanesulfonamide A) 2-amino-3-(3-bromo-2-fluorophenyl)propanoic Acid Hydrochloride Sodium ethoxide (121 g) was added to a solution of 1-bromo-3-(bromomethyl)-2-fluorobenzene (91 g) and diethyl 2-acetamidomalonate (77 g) in EtOH (566 ml) at room temperature. After being refluxed for 2 h, the reaction mixture was cooled to room temperature, and the insoluble substance was filtered off. The filtrate was concentrated under reduced pressure, and the residue was diluted with 8 M hydrochloric acid (849 ml), and the mixture was refluxed for 17 h. The reaction mixture was concentrated under reduced pressure to give crystals, which were collected by filtration and washed with 2-propanol/IPE to give the title compound (100 g).

MS: [M+H]$^+$ 261.9.

B) 3-(3-bromo-2-fluorophenyl)-2-((tert-butoxycarbonyl)amino)propanoic Acid

Boc$_2$O (92 ml) was added to a solution of 2-amino-3-(3-bromo-2-fluorophenyl)propanoic acid hydrochloride (100 g) and 0.75 M sodium hydroxide solution (893 ml) in DME (918 ml) at 0° C. After being vigorously stirred at room temperature for 16 h, the reaction mixture was poured into ice water, basified with 1 M NaOH aqueous solution and washed with Et$_2$O. The aqueous layer was acidified to pH 3 with 1 M hydrochloric acid and extracted with EtOAc. The organic layer was dried over magnesium sulfate and concentrated under reduced pressure to give the title compound (105 g).

MS, found: 261.8.

C) tert-butyl (3-(2-fluoro-[1,1'-biphenyl]-3-yl)-1-(methoxy(methyl)amino)-1-oxopropan-2-yl)carbamate To a mixture of 3-(3-bromo-2-fluorophenyl)-2-((tert-butoxycarbonyl)amino)propanoic acid (250 g) in 1,4-dioxane (1.2 L) were added phenylboronic acid (101 g) and Pd(dppf)Cl$_2$·CH$_2$Cl$_2$ (28.2 g) at 15° C. under nitrogen atmosphere. After stirring for 15 min, a solution of K$_2$CO$_3$ (191 g) in H$_2$O (600 mL) was added thereto. The reaction mixture was stirred at 100° C. for 16 h. The reaction mixture was poured into water and it was adjusted to pH 2 with 2 M hydrochloric acid and then it was extracted with EtOAc. The combined organic layer was washed with saturated brine, dried over anhydrous sodium sulfate and concentrated under reduced pressure. To a stirred solution of the obtained residue (250 g) and N,O-dimethylhydroxylamine (71.3 g) in DMF (2 L) was added HATU (250 g) and then DIPEA (331 g) was added thereto at 0° C. The reaction mixture was stirred at 15° C. under nitrogen atmosphere for 16 h. The reaction mixture was poured into water and the organic layer was separated. The water layer was extracted with EtOAc. The combined organic layer was washed with saturated brine, dried over anhydrous sodium sulfate and concentrated under reduced pressure. The residue was collected by filtration and washed with petroleum ether/EtOAc to give the title compound (180 g).

$^1$H NMR (400 MHz, CDCl$_3$) δ 1.38 (9H, s), 3.00-3.18 (2H, m), 3.20 (3H, s), 3.77 (3H, s), 4.91-5.09 (1H, m), 5.17-5.30 (1H, m), 7.09-7.19 (2H, m), 7.28-7.48 (4H, m), 7.50-7.57 (2H, m).

D) ethyl 4-((tert-butoxycarbonyl)amino)-2,2-difluoro-5-(2-fluoro-[1,1'-biphenyl]-3-yl)-3-hydroxypentanoate To a stirred solution of tert-butyl (3-(2-fluoro-[1,1'-biphenyl]-3-yl)-1-(methoxy(methyl)amino)-1-oxopropan-2-yl)carbamate (40.0 g) in THF (1.2 L) was added lithium aluminium hydride (4.53 g) in portions at −78° C., and the reaction mixture was stirred at −10° C. under nitrogen atmosphere for 3 h. The reaction mixture was poured into cooled aqueous saturated ammonium chloride solution, and the mixture was filtered. The filter cake was washed with EtOAc and the filtrate was extracted with EtOAc. The combined organic layer was washed with 1 M hydrochloric acid, saturated aqueous sodium hydrogen carbonate solution and saturated brine, dried over anhydrous sodium sulfate and concentrated under reduced pressure to give the tert-butyl (1-(2-fluoro-[1,1'-biphenyl]-3-yl)-3-oxopropan-2-yl)carbamate (40.0 g). To the mixture of activated zinc (56.8 g) in THF (300 mL) was added TMSCl (4.43 g) at 20° C., and the resulting mixture was stirred at 20° C. for min under nitrogen atmosphere. Then a solution of ethyl 2-bromo-2,2-difluoroacetate (82.8 g) in THF (500 mL) was added dropwise to the above mixture at 40° C., and it was stirred at 40° C. for another 1.5 h under nitrogen atmosphere to give 0.51 M (2-ethoxy-1,1-difluoro-2-oxoethyl)zinc(II) bromide/THF solution (800 mL). To a stirred solution of tert-butyl (1-(2-fluoro-[1,1'-biphenyl]-3-yl)-3-oxopropan-2-yl)carbamate (27.0 g) in THF (150 mL) was added 0.51 M (2-ethoxy-1,1-difluoro-2-oxoethyl)zinc(II) bromide/THF solution (385 mL) at 15° C., and the reaction mixture was stirred at 15° C. under nitrogen atmosphere for 20 min. Then it was stirred at 55° C. for another 20 min. The reaction mixture was poured into aqueous ammonium chloride solution and it was extracted with EtOAc. The combined organic layer was washed with saturated brine, dried over anhydrous sodium sulfate and concentrated under reduced pressure. The residue was purified by column chromatography (silica gel, EtOAc/petroleum ether) to give the title compound (12.0 g).

¹H NMR (400 MHz, CDCl₃) δ 1.30-1.54 (12H, m), 3.00-3.35 (2H, m), 3.70-4.55 (3H, m), 4.74-5.19 (1H, m), 7.08-7.25 (2H, m), 7.35-7.57 (7H, m).

E) ethyl 4-amino-2,2-difluoro-5-(2-fluoro-[1,1'-biphenyl]-3-yl)-3-hydroxypentanoate Hydrochloride To a stirred solution of ethyl 4-((tert-butoxycarbonyl)amino)-2,2-difluoro-5-(2-fluoro-[1,1'-biphenyl]-3-yl)-3-hydroxypentanoate (39.0 g) in 1,4-dioxane (80 mL) was added 4 M HCl/1,4-dioxane solution (250 mL), and the reaction mixture was stirred at 15° C. for 3 h. The mixture was concentrated under reduced pressure to give the title compound (34.0 g).
MS: [M+H]⁺ 368.1.

F) 3,3-difluoro-5-((2-fluoro-[1,1'-biphenyl]-3-yl)methyl)-4-hydroxypyrrolidin-2-one To a stirred solution of ethyl 4-amino-2,2-difluoro-5-(2-fluoro-[1,1'-biphenyl]-3-yl)-3-hydroxypentanoate hydrochloride (66.0 g) in EtOH (850 mL) was added DIPEA (66.0 g), and the reaction mixture was stirred at 80° C. under nitrogen atmosphere for 0.5 h. The reaction mixture was concentrated under reduced pressure. The residue was purified by column chromatography (silica gel, EtOAc/petroleum ether) to give the title compound (35.0 g).
MS: [M+H]⁺ 322.0.

G) 4,4-difluoro-2-((2-fluoro-[1,1'-biphenyl]-3-yl)methyl)pyrrolidin-3-ol

To a stirred solution of 3,3-difluoro-5-((2-fluoro-[1,1'-biphenyl]-3-yl)methyl)-4-hydroxypyrrolidin-2-one (36.0 g) in THF (400 mL) was added 1 M BH₃-THF complex/THF solution (336 mL) at 15° C., and the reaction mixture was stirred at 70° C. for 16 h under nitrogen atmosphere. Then the reaction mixture was quenched with water dropwise at 0° C., and then 1 M hydrochloric acid was added thereto, and it was stirred at 66° C. for 2 h. The reaction mixture was adjusted to pH 8 with saturated aqueous sodium hydrogen carbonate solution and extracted with EtOAc. The combined organic layer was washed with water, dried over anhydrous sodium sulfate and concentrated under reduced pressure to give the title compound (35.0 g).
MS: [M+H]⁺ 308.1.

H) rac-tert-butyl (2S,3S)-4,4-difluoro-2-((2-fluoro-[1,1'-biphenyl]-3-yl)methyl)-3-hydroxypyrrolidine-1-carboxylate To 4,4-difluoro-2-((2-fluoro-[1,1'-biphenyl]-3-yl)methyl)pyrrolidin-3-ol (37.0 g) was added tert-butoxycarbonyl tert-butyl carbonate (26.3 g) in THF (300 mL), and the mixture was basified to pH 8 with saturated aqueous sodium hydrogen carbonate solution, and the reaction mixture was stirred at 15° C. for 2 h. The reaction mixture was poured into water and extracted with EtOAc. The combined organic layer was washed with saturated brine, dried over anhydrous sodium sulfate and concentrated under reduced pressure. The residue was purified by column chromatography (silica gel, EtOAc/petroleum ether), and then purified by preparative HPLC (column: C18, mobile phase: CH₃CN/water (containing 10 mM ammonium bicarbonate)) to give the title compound (9 g).
¹H NMR (400 MHz, CDCl₃) δ 1.48 (9H, s), 2.14-2.28 (1H, m), 2.78-3.00 (1H, m), 3.24-3.40 (1H, m), 3.69-4.00 (2H, m), 4.00-4.08 (1H, m), 4.14-4.20 (1H, m), 7.13-7.24 (2H, m), 7.32-7.50 (4H, m), 7.52-7.59 (2H, m).

I) rac-tert-butyl (2S,3S)-4,4-difluoro-2-((2-fluoro-[1,1'-biphenyl]-3-yl)methyl)-3-(((trifluoromethyl)sulfonyl)oxy)pyrrolidine-1-carboxylate To a stirred solution of rac-tert-butyl (2S,3S)-4,4-difluoro-2-((2-fluoro-[1,1'-biphenyl]-3-yl)methyl)-3-hydroxypyrrolidine-1-carboxylate (9.00 g) in dichloromethane (150 mL) was added pyridine (8.74 g), and then a solution of trifluoromethanesulfonic anhydride (15.6 g) in dichloromethane (50 mL) was added dropwise thereto at −10° C., and the reaction mixture was stirred at −10° C. under nitrogen atmosphere for 1 h. The reaction mixture was poured into water and it was extracted with dichloromethane. The combined organic layer was washed with 5% aqueous citric acid solution and saturated brine, dried over anhydrous sodium sulfate and concentrated under reduced pressure to give the title compound (11.0 g).
¹H NMR (400 MHz, CDCl₃) δ 1.51 (9H, s), 2.76-2.97 (1H, m), 3.34-3.52 (1H, m), 3.84-3.99 (2H, m), 4.32-4.51 (1H, m), 4.89-5.05 (1H, m), 7.10-7.25 (2H, m), 7.34-7.56 (6H, m).

J) rac-tert-butyl (2S,3R)-3-amino-4,4-difluoro-2-((2-fluoro-[1,1'-biphenyl]-3-yl)methyl)pyrrolidine-1-carboxylate To a stirred solution of rac-tert-butyl (2S,3S)-4,4-difluoro-2-((2-fluoro-[1,1'-biphenyl]-3-yl)methyl)-3-(((trifluoromethyl)sulfonyl)oxy)pyrrolidine-1-carboxylate (11.0 g) in N,N-Dimethylacetamide (450 mL) was added sodium azide (5.30 g), and the reaction mixture was stirred at 130° C. for 3 h. The mixture was diluted with water and it was adjusted to pH 9-10 with aqueous sodium hydrogen carbonate solution and extracted with EtOAc. The combined organic layers were washed with water, dried over anhydrous sodium sulfate and concentrated reduced pressure to give rac-tert-butyl (2S,3R)-3-azido-4,4-difluoro-2-((2-fluoro-[1,1'-biphenyl]-3-yl)methyl)pyrrolidine-1-carboxylate (9.00 g). To a stirred solution of rac-tert-butyl (2S,3R)-3-azido-4,4-difluoro-2-((2-fluoro-[1,1'-biphenyl]-3-yl)methyl)pyrrolidine-1-carboxylate (1.00 g) in MeOH (30 mL) was added 10% Pd on carbon (100 mg), and the mixture was degassed under reduced pressure and purged with hydrogen several times and then stirred at 25° C. under hydrogen atmosphere (15 psi) for 16 h. The reaction mixture was filtered through a pad of celite and the filter cake was washed with MeOH and the combined filtrate was concentrated under reduced pressure to give crude product as 1ˢᵗ batch. To a stirred solution of rac-tert-butyl (2S,3S)-4,4-difluoro-2-((2-fluoro-1,1'-biphenyl]-3-yl)methyl)-3-(((trifluoromethyl)sulfonyl)oxy)pyrrolidine-1-carboxylate (8.00 g) in MeOH (200 mL) was added 10% Pd on carbon (800 mg), and the mixture was degassed under reduced pressure and purged with hydrogen several times and then stirred at 25° C. under hydrogen atmosphere (15 psi) for 3 h. The reaction mixture was filtered through a pad of celite and the filter cake was washed with MeOH. The combined filtrate was concentrated under reduced pressure. The residue and crude product of 1st batch were purified by column chromatography (silica gel, EtOAc/petroleum ether) to give the title compound (6.04 g).
¹H NMR (400 MHz, DMSO-d₆) δ 0.89-1.32 (9H, m), 1.86-2.01 (2H, m), 2.53-2.78 (1H, m), 2.94-3.13 (1H, m), 3.63-3.95 (3H, m), 4.11-4.36 (1H, m), 7.13-7.55 (8H, m).

K) tert-butyl (2S,3R)-3-amino-4,4-difluoro-2-((2-fluoro-[1,1'-biphenyl]-3-yl)methyl)pyrrolidine-1-carboxylate Optical resolution of rac-tert-butyl (2S,3R)-3-amino-4,4-difluoro-2-((2-fluoro-[1,1'-biphenyl]-3-yl)methyl)pyrrolidine-1-carboxylate (6.03 g) was performed using preparative HPLC (Column: CHIRALPAK AD, mobile phase: hexane/EtOH=900/100 (v/v)) to afford the title compound (3.09 g) with shorter retention time (Column: CHIRALPAK AD-H, eluted with hexane/EtOH=900/100 (v/v)).

MS, found: 351.1.

L) tert-butyl (2S,3R)-4,4-difluoro-2-((2-fluoro-[1,1'-biphenyl]-3-yl)methyl)-3-(methylsulfonamido)pyrrolidine-1-carboxylate Methanesulfonic anhydride (292 mg) was added to a stirred solution of tert-butyl (2S,3R)-3-amino-4,4-difluoro-2-((2-fluoro-[1,1'-biphenyl]-3-yl)methyl)pyrrolidine-1-carboxylate (355 mg) and TEA (0.365 mL) in THF (8 mL) at room temperature. After 0.5 h, the reaction mixture was concentrated under reduced pressure, and the residue was purified by column chromatography (silica gel, eluted with EtOAc/hexane) to give the title compound (427 mg).

MS, found: 385.0.

M) N-((2S,3R)-4,4-difluoro-2-((2-fluoro-[1,1'-biphenyl]-3-yl)methyl)pyrrolidin-3-yl)methanesulfonamide Hydrochloride A mixture of tert-butyl (2S,3R)-4,4-difluoro-2-((2-fluoro-[1,1'-biphenyl]-3-yl)methyl)-3-(methylsulfonamido)pyrrolidine-1-carboxylate (427 mg) in 4 M HCl/CPME solution (12 mL) was stirred at room temperature for 2 h. The solid was collected by filtration to give the title compound (340 mg).

MS: [M+H]$^+$ 385.0.

N) N-[(2S,3R)-4,4-difluoro-2-[(2-fluoro[1,1'-biphenyl]-3-yl)methyl]-1-(2-hydroxy-2-methylpropanoyl)pyrrolidin-3-yl]methanesulfonamide A mixture of N-((2S,3R)-4,4-difluoro-2-((2-fluoro-[1,1'-biphenyl]-3-yl)methyl)pyrrolidin-3-yl)methanesulfonamide hydrochloride (45 mg) and DIPEA (0.092 mL) in THF (1.28 mL) was stirred at room temperature for 30 min. To the suspension was added dropwise alpha-acetoxy-isobutyryl chloride (0.0186 mL) at 0° C., and the mixture was stirred overnight at same temperature. To the mixture were added water (0.855 mL) and 4M lithium hydroxide solution (0.267 mL), and the mixture was stirred overnight at room temperature. The mixture was quenched with saturated aqueous sodium hydrogen carbonate solution and extracted with EtOAc. The extract was washed with saturated brine, dried over magnesium sulfate and concentrated under reduced pressure. The residue was purified by column chromatography (silica gel, EtOAc/hexane) to give the title compound (45 mg).

$^1$H NMR (400 MHz, DMSO-d$_6$) δ 0.91-1.26 (6H, m), 2.62-2.72 (1H, m), 2.97-3.07 (4H, m), 4.09-4.44 (2H, m), 4.59-4.81 (1H, m), 4.82-5.02 (1H, m), 5.27 (1H, s), 7.07-7.17 (1H, m), 7.25-7.34 (2H, m), 7.34-7.41 (1H, m), 7.42-7.49 (2H, m), 7.49-7.56 (2H, m), 8.09-8.19 (1H, m).

Example 5

N-[(2S,3R)-4,4-difluoro-2-[(2-fluoro[1,1'-biphenyl]-3-yl)methyl]-1-(2-hydroxy-2-methylpropanoyl)pyrrolidin-3-yl]ethanesulfonamide A) tert-butyl (2S,3R)-3-(ethylsulfonamido)-4,4-difluoro-2-((2-fluoro-[1,1'-biphenyl]-3-yl)methyl)pyrrolidine-1-carboxylate Ethanesulfonyl chloride (0.233 mL) was added to a solution of tert-butyl (2S,3R)-3-amino-4,4-difluoro-2-((2-fluoro-[1,1'-biphenyl]-3-yl)methyl)pyrrolidine-1-carboxylate (500 mg), TEA (0.514 mL) and DMAP (75 mg) in THF (5 mL) at room temperature. After being stirred at room temperature for 2 h, the reaction mixture was poured into water and extracted with EtOAc. The organic layer was washed with saturated brine, dried over magnesium sulfate and concentrated under reduced pressure. The residual oil was purified by column chromatography (silica gel, eluted with EtOAc/hexane) to give the title compound (441 mg).

MS, found: 399.1.

B) N-((2S,3R)-4,4-difluoro-2-((2-fluoro-[1,1'-biphenyl]-3-yl)methyl)pyrrolidin-3-yl)ethanesulfonamide Hydrochloride A mixture of tert-butyl (2S,3R)-3-(ethylsulfonamido)-4,4-difluoro-2-((2-fluoro-[1,1'-biphenyl]-3-yl)methyl)pyrrolidine-1-carboxylate (441 mg) and 4 M HCl/CPME (5 mL) was stirred at room temperature for 2 h. The mixture was concentrated under reduced pressure to give the title compound (360 mg).

MS: [M+H]$^+$ 399.1.

C) N-[(2S,3R)-4,4-difluoro-2-[(2-fluoro[1,1'-biphenyl]-3-yl)methyl]-1-(2-hydroxy-2-methylpropanoyl)pyrrolidin-3-yl]ethanesulfonamide A mixture of N-((2S,3R)-4,4-difluoro-2-((2-fluoro-[1,1'-biphenyl]-3-yl)methyl)pyrrolidin-3-yl)ethanesulfonamide hydrochloride (60 mg) and DIPEA (0.119 mL) in THF (1.66 mL) was stirred at room temperature for 30 min. To the suspension was added dropwise alpha-acetoxy-isobutyryl chloride (0.024 mL) at 0° C., and the mixture was stirred overnight at same temperature. To the mixture were added water (1.10 mL) and 4 M lithium hydroxide solution (0.345 mL), and the mixture was stirred overnight at room temperature. The mixture was quenched with saturated aqueous sodium hydrogen carbonate solution and extracted with EtOAc. The extract was washed with saturated brine, dried over magnesium sulfate and concentrated under reduced pressure. The residue was purified by column chromatography (silica gel, eluted with EtOAc/hexane) to give the title compound (42.0 mg).

$^1$H NMR (400 MHz, DMSO-d$_6$) δ 0.95-1.36 (9H, m), 2.60-2.73 (1H, m), 2.99-3.15 (3H, m), 4.09-4.51 (2H, m), 4.58-4.98 (2H, m), 5.26 (1H, s), 7.07-7.18 (1H, m), 7.24-7.33 (2H, m), 7.34-7.42 (1H, m), 7.42-7.56 (4H, m), 8.13 (1H, brs).

Example 7

N-[(2S,3R)-2-[(2,3'-difluoro[1,1'-biphenyl]-3-yl)methyl]-4,4-difluoro-1-(2-hydroxy-2-methylpropanoyl)pyrrolidin-3-yl]methanesulfonamide

A) tert-butyl (3-(2,3'-difluoro-[1,1'-biphenyl]-3-yl)-1-(methoxy(methyl)amino)-1-oxopropan-2-yl)carbamate WSC (63.7 mL) was added to a mixture of 3-(3-bromo-2-fluorophenyl)-2-((tert-butoxycarbonyl)amino)propanoic acid (105 g), N, O-dimethylhydroxylamine hydrochloride (31.1 g), HOBt (43.1 g), TEA (48.5 mL) and DMF (580 mL) at 0° C. After being stirred at room temperature for 15 h, the reaction mixture was poured into half-saturated aqueous sodium hydrogen carbonate solution and stirred at room temperature for 20 min to give crystals, which were collected by filtration and washed successively with water, 2-propanol and IPE. A mixture of the obtained solid, (3-fluorophenyl)boronic acid (48.7 g), XPhos Pd G3 (2.45 g), 2 M aqueous potassium phosphate solution (435 mL) and THF (537 mL) was stirred at 70° C. for 1 h under argon atmosphere. The reaction mixture was poured into half-saturated aqueous sodium hydrogen carbonate solution and extracted with EtOAc. The organic layer was washed with water and saturated brine, dried over magnesium sulfate, passed through NH silica gel pad (eluted with EtOAc) and concentrated under reduced pressure to give crystals, which were collected by filtration and washed with IPE to give the title compound (92.8 g).

MS, found: 321.0.

B) tert-butyl {3-(2,3'-difluoro[1,1'-biphenyl]-3-yl)-1-[methoxy(methyl)amino]-1-oxopropan-2-yl}[(4-methoxyphenyl)methyl]carbamate To a stirred suspension of tert-butyl (3-(2,3'-difluoro-[1,1'-biphenyl]-3-yl)-1-(methoxy(methyl)amino)-1-oxopropan-2-yl)carbamate (77.0 g) in DMF (366 mL) was added NaH (60% in oil) (9.52 g) at 0° C. After being stirred for 10 min at room temperature, alpha-chloro-4-methoxytoluene (49.7 mL) and tetrabutylaminium iodide (6.76 g) were added thereto at 0° C. After 1.5 h at room temperature, the reaction mixture was poured into a stirred mixture of EtOAc and 5% KHSO$_4$ aqueous solution at 0° C., and the organic layer was separated. The organic layer was washed with saturated brine, dried over sodium sulfate, filtrated and concentrated under reduced pressure. The residue was purified by column chromatography (silica gel, eluted with EtOAc/hexane) to give the title compound (83 g).

MS, found: 441.2.

C) tert-butyl [1-(2,3'-difluoro[1,1'-biphenyl]-3-yl)-3-oxopropan-2-yl][(4-methoxyphenyl)methyl]carbamate Lithium aluminium hydride (0.983 g) was added to a stirred solution of tert-butyl {3-(2,3'-difluoro[1,1'-biphenyl]-3-yl)-1-[methoxy(methyl)amino]-1-oxopropan-2-yl}[(4-methoxyphenyl)methyl]carbamate (10 g) in Et$_2$O (83 mL) at −78° C. The mixture was warmed up to 0° C. After 0.5 h, the reaction mixture was quenched with EtOAc (3.61 mL) with keeping temperature of the reaction mixture under 10° C., and a solution of potassium bisulfate (6.30 g) in water (83 mL) was added to the mixture. The mixture was extracted with Et$_2$O. The organic layer was separated, washed with water and a mixture of saturated brine and aqueous sodium hydrogen carbonate solution, and through silica gel pad (eluted with EtOAc/hexane) to give the title compound (8.43 g).

MS, found: 426.0.

D) ethyl 4-{(tert-butoxycarbonyl)[(4-methoxyphenyl)methyl]amino}-2,4,5-trideoxy-5-(2,3'-difluoro[1,1'-biphenyl]-3-yl)-2,2-difluoropentonate Chlorotrimethylsilane (0.305 mL) was added to a stirred suspension of zinc (2.75 g) in THF (24 mL) at room temperature. After 10 min, ethyl 2-bromo-2,2-difluoroacetate (3.08 mL) was added to the mixture under water bath cooling with keeping temperature of the reaction mixture under 40° C. After 10 min, a solution of tert-butyl [1-(2,3'-difluoro[1,1'-biphenyl]-3-yl)-3-oxopropan-2-yl][(4-methoxyphenyl)methyl]carbamate (5.78 g) in THF (6 mL) was added to the mixture at room temperature. After 1.5 h, the reaction mixture was poured into a stirred mixture of 10% KHSO$_4$ aqueous solution (60 mL) and EtOAc (120 mL). The organic layer was separated, washed with saturated brine, dried over sodium sulfate, filtrated, and concentrated under reduced pressure. The residue was purified by column chromatography (silica gel, eluted with EtOAc/hexane) to give the title compound (6.71 g).

MS, found: 550.1

E) 5-[(2,3'-difluoro[1,1'-biphenyl]-3-yl)methyl]-3,3-difluoro-4-hydroxy-1-[(4-methoxyphenyl)methyl]pyrrolidin-2-one 4 M HCl/CPME (30.1 mL) was added to a solution of ethyl 4-{(tert-butoxycarbonyl)[(4-methoxyphenyl)methyl]amino}-2,4,5-trideoxy-5-(2,3'-difluoro[1,1'-biphenyl]-3-yl)-2,2-difluoropentonate (7.28 g) in EtOH (3.8 mL) at room temperature. After being stirred at room temperature for 1 h, the reaction mixture was concentrated under reduced pressure. The residual oil was dissolved in EtOH (38 mL), and DIPEA (6.28 mL) was added thereto at room temperature. After being stirred at 80° C. for 0.5 h, the reaction mixture was concentrated under reduced pressure. The residue was poured into water, and the mixture was extracted with EtOAc. The organic layer was concentrated under reduced pressure, and the residue was purified by column chromatography (silica gel, eluted with EtOAc/hexane) to give the title compound (5.00 g).

MS: [M+H]$^+$ 460.2.

F) 5-[(2,3'-difluoro[1,1'-biphenyl]-3-yl)methyl]-3,3-difluoro-4-hydroxypyrrolidin-2-one Ceric ammonium nitrate (14.0 g) in water (15.9 mL) was added to a solution of 5-[(2,3'-difluoro[1,1'-biphenyl]-3-yl)methyl]-3,3-difluoro-4-hydroxy-1-[(4-methoxyphenyl)methyl]pyrrolidin-2-one (5.85 g) in CH$_3$CN (47.7 mL) at room temperature. The mixture was stirred at room temperature for 2 h. The mixture was neutralized with saturated aqueous sodium hydrogen carbonate solution and diluted with EtOAc. The insoluble material was removed by filtration, and the filtrate was extracted with EtOAc. The organic layer was separated, washed with saturated brine, dried over magnesium sulfate and concentrated under reduced pressure. The residue was purified by column chromatography (silica gel, eluted with EtOAc/hexane) to give the title compound (3.80 g).

MS: [M−H]⁻ 338.2.

G) tert-butyl 2-[(2,3'-difluoro[1,1'-biphenyl]-3-yl)methyl]-4,4-difluoro-3-hydroxypyrrolidine-1-carboxylate 0.9 M Borane-THF complex (37.3 mL) was added dropwise to a solution of 5-[(2,3'-difluoro[1,1'-biphenyl]-3-yl)methyl]-3,3-difluoro-4-hydroxypyrrolidin-2-one (3.80 g) in THF (37.3 mL) at room temperature. After being stirred at 60° C. for 3 h, the reaction mixture was quenched by dropwise addition of water at 0° C. The mixture was stirred at room temperature for 10 min and concentrated under reduced pressure. The residue was diluted with EtOH (25 mL) and 1 M hydrochloric acid (125 mL), and the mixture was stirred at 60° C. for 1 h. The reaction mixture was poured carefully into iced saturated aqueous sodium hydrogen carbonate solution (250 mL) and extracted with EtOAc. The organic layer was washed with water and saturated brine, dried over magnesium sulfate and concentrated under reduced pressure. The residue was mixed with sodium hydrogen carbonate (0.941 g), THF (28.0 mL) and water (28.0 mL), and Boc₂O (2.83 mL) was added to the mixture at room temperature. The mixture was stirred at room temperature under nitrogen atmosphere for 3 h. The mixture was poured into water at room temperature and extracted with EtOAc. The organic layer was separated, washed with saturated brine, dried over magnesium sulfate and concentrated under reduced pressure. The residual oil was purified by column chromatography (silica gel, eluted with EtOAc/hexane) to give the title compound (4.00 g).

MS, found: 326.2.

H) rac-tert-butyl (2S,3S)-2-[(2,3'-difluoro[1,1'-biphenyl]-3-yl)methyl]-4,4-difluoro-3-[(trifluoromethanesulfonyl)oxy]pyrrolidine-1-carboxylate Trifluoromethanesulfonic anhydride (3.16 mL) was added to a solution of tert-butyl 2-[(2,3'-difluoro[1,1'-biphenyl]-3-yl)methyl]-4,4-difluoro-3-hydroxypyrrolidine-1-carboxylate (4.0 g) and pyridine (3.80 mL) in Et₂O (47.0 mL) at 0° C. After being stirred at room temperature for 20 h, the mixture was quenched with water at room temperature and extracted with EtOAc. The organic layer was separated, washed with saturated brine, dried over magnesium sulfate and concentrated under reduced pressure. The organic layer was purified by column chromatography (silica gel, eluted with EtOAc/hexane) to give the title compound (3.22 g).

¹H NMR (400 MHz, CDCl₃) δ 1.50 (9H, s), 2.74-2.99 (1H, m), 3.33-3.51 (1H, m), 3.72-4.02 (2H, m), 4.33-4.49 (1H, m), 4.86-5.02 (1H, m), 7.03-7.13 (1H, m), 7.17-7.32 (4H, m), 7.33-7.47 (2H, m).

I) rac-tert-butyl (2S,3R)-3-azido-2-[(2,3'-difluoro[1,1'-biphenyl]-3-yl)methyl]-4,4-difluoropyrrolidine-1-carboxylate Tetra-n-butylammonium azide (24.9 g) was added to a solution of rac-tert-butyl (2S,3S)-2-[(2,3'-difluoro[1,1'-biphenyl]-3-yl)methyl]-4,4-difluoro-3-[(trifluoromethanesulfonyl)oxy]pyrrolidine-1-carboxylate (24.4 g) in CH₃CN (292 mL) at room temperature. After being stirred at 80° C. for 1 h, the reaction mixture was poured into iced water and extracted with EtOAc. The organic layer was washed with water and saturated brine, dried over magnesium sulfate and concentrated under reduced pressure. The residual oil was purified by column chromatography (silica gel, eluted with EtOAc/hexane) to give the title compound (19.5 g).

MS, found: 351.0.

J) rac-tert-butyl (2S,3R)-3-amino-2-[(2,3'-difluoro[1,1'-biphenyl]-3-yl)methyl]-4,4-difluoropyrrolidine-1-carboxylate A solution of rac-tert-butyl (2S,3R)-3-azido-2-[(2,3'-difluoro[1,1'-biphenyl]-3-yl)methyl]-4,4-difluoropyrrolidine-1-carboxylate (19.5 g) in MeOH (433 mL) was hydrogenated in the presence of 20% Pd(OH)₂ on carbon (50% wet) (1.95 g) at room temperature under ordinary pressure for 1 h. After removal of the catalyst by filtration, the filtrate was concentrated under reduced pressure. The residual oil was purified by column chromatography (silica gel, eluted with EtOAc/hexane) to give the title compound (16.5 g).

MS, found: 369.0.

K) tert-butyl (2S,3R)-3-amino-2-[(2,3'-difluoro[1,1'-biphenyl]-3-yl)methyl]-4,4-difluoropyrrolidine-1-carboxylate Optical resolution of rac-tert-butyl (2S,3R)-3-amino-2-[(2,3'-difluoro[1,1'-biphenyl]-3-yl)methyl]-4,4-difluoropyrrolidine-1-carboxylate (16.5 g) was performed using preparative HPLC (Column: CHIRALPAK AD, mobile phase: hexane/EtOH/diethylamine=900/100/1 (v/v/v)) to afford the title compound (7.32 g) with shorter retention time (Column: CHIRALPAK AD-H, mobile phase: hexane/EtOH/diethylamine=900/100/1 (v/v/v)).

MS, found: 369.1.

L) tert-butyl (2S,3R)-2-[(2,3'-difluoro[1,1'-biphenyl]-3-yl)methyl]-4,4-difluoro-3-[(methanesulfonyl)amino]pyrrolidine-1-carboxylate Methanesulfonic anhydride (185 mg) was added to a stirred mixture of tert-butyl (2S,3R)-3-amino-2-[(2,3'-difluoro[1,1'-biphenyl]-3-yl)methyl]-4,4-difluoropyrrolidine-1-carboxylate (300 mg) and TEA (0.296 mL) in THF (5 mL) at room temperature and the mixture was stirred overnight. The reaction mixture was directly purified by column chromatography (silica gel, eluted with EtOAc/hexane) to give the title compound (309 mg).

MS: [M−H]⁻ 501.1.

M) N-{(2S,3R)-2-[(2,3'-difluoro[1,1'-biphenyl]-3-yl)methyl]-4,4-difluoropyrrolidin-3-yl}methanesulfonamide Hydrochloride A mixture of tert-butyl (2S,3R)-2-[(2,3'-difluoro[1,1'-biphenyl]-3-yl)methyl]-4,4-difluoro-3-[(methanesulfonyl)amino]pyrrolidine-1-carboxylate (309 mg) and 4 M HCl/EtOAc (3 mL) was stirred at room temperature for 1 h. The mixture was diluted with EtOAc. The resulting solid was collected by filtration to give the title compound (230 mg).

MS: [M−H]⁻ 401.0.

N) N-[(2S,3R)-2-[(2,3'-difluoro[1,1'-biphenyl]-3-yl)methyl]-4,4-difluoro-1-(2-hydroxy-2-methylpropanoyl)pyrrolidin-3-yl]methanesulfonamide A mixture of N-{(2S,3R)-2-[(2,3'-difluoro[1,1'-biphenyl]-3-yl)methyl]-4,4-difluoropyrrolidin-3-yl}methanesulfonamide hydrochloride (40 mg) and DIPEA (0.079 mL) in THF (1.09 mL) was stirred at room temperature for 30 min. To the suspension was added dropwise alpha-acetoxy-isobutyryl chloride (0.159 mL) at 0° C., and the mixture was stirred overnight at same temperature. To the mixture were added water (0.729 mL) and 4 M aqueous lithium hydroxide solution (0.228 mL), and the mixture was stirred overnight at room temperature. The mixture was quenched with saturated aqueous sodium hydrogen carbonate solution and extracted with EtOAc. The extract was washed with saturated brine, dried over magnesium sulfate and concentrated under reduced pressure. The residue was purified by column chromatography (silica gel, eluted with EtOAc/hexane) to give the title compound (41 mg).

$^1$H NMR (400 MHz, DMSO-d$_6$) δ 0.95-1.34 (6H, m), 2.61-2.75 (1H, m), 2.96-3.10 (4H, m), 4.10-4.47 (2H, m), 4.60-4.81 (1H, m), 4.84-5.01 (1H, m), 5.28 (1H, s), 7.08-7.18 (1H, m), 7.20-7.28 (1H, m), 7.31-7.41 (4H, m), 7.47-7.56 (1H, m), 8.14 (1H, brs).

Example 8

N-[(2S,3R)-2-[(2,3'-difluoro[1,1'-biphenyl]-3-yl)methyl]-4,4-difluoro-1-(2-hydroxy-2-methylpropanoyl)pyrrolidin-3-yl]ethanesulfonamide To a mixture of N-((2S,3R)-2-((2,3'-difluoro-[1,1'-biphenyl]-3-yl)methyl)-4,4-difluoropyrrolidin-3-yl)ethanesulfonamide hydrochloride (57 mg) and DIPEA (81 mg) in THF (2 mL) was added 1-chloro-2-methyl-1-oxopropan-2-yl acetate (31.1 mg) at room temperature. The mixture was stirred at room temperature for 1 h. To the mixture were added water (1 mL) and 4 M aqueous lithium hydroxide solution (0.314 mL) at room temperature. The mixture was stirred at room temperature for 1 h. After azeotropic evaporation with toluene, the residue was purified by column chromatography (silica gel, eluted with EtOAc/hexane) to give the title compound (17.0 mg).

$^1$H NMR (300 MHz, DMSO-d$_6$) δ 0.87-1.43 (9H, m), 2.60-2.77 (1H, m), 2.97-3.17 (3H, m), 4.07-5.01 (3H, m), 5.27 (1H, s), 7.03-7.62 (8H, m), 8.14 (1H, brs).

Example 13

N-[(2S,3R)-2-[(2,3'-difluoro[1,1'-biphenyl]-3-yl)methyl]-4,4-difluoro-1-(1-hydroxycyclobutane-1-carbonyl)pyrrolidin-3-yl]methanesulfonamide To a solution of N-{(2S,3R)-2-[(2,3'-difluoro[1,1'-biphenyl]-3-yl)methyl]-4,4-difluoropyrrolidin-3-yl}methanesulfonamide hydrochloride (29 mg), DIPEA (42.7 mg) and 1-hydroxycyclobutane-1-carboxylic acid (9.21 mg) in THF (4 mL) was added HATU (37.7 mg) at room temperature. The mixture was stirred at room temperature for 15 h. The mixture was quenched with saturated aqueous sodium hydrogen carbonate solution and extracted with EtOAc. The organic layer was separated, washed with saturated brine (5 mL), dried over magnesium sulfate and concentrated under reduced pressure. The residue was purified by column chromatography (silica gel, eluted with EtOAc/hexane) to give the title compound (29.0 mg).

$^1$H NMR (300 MHz, DMSO-d$_6$) δ 1.02-1.17 (1H, m), 1.44-1.66 (1H, m), 1.79-2.04 (2H, m), 2.16-2.42 (2H, m), 2.65-2.84 (1H, m), 2.95-3.10 (4H, m), 3.91-4.11 (1H, m), 4.25-4.53 (2H, m), 4.82-4.96 (1H, m), 5.95 (1H, s), 7.09-7.42 (6H, m), 7.45-7.59 (1H, m), 8.19 (1H, brs).

Example 21

N-{(2S,3R)-1-(bicyclo[1.1.1]pentane-1-carbonyl)-4,4-difluoro-2-[(3'-fluoro[1,1'-biphenyl]-3-yl)methyl]pyrrolidin-3-yl}methanesulfonamide A) tert-butyl(S)-(3-(3-chlorophenyl)-1-(methoxy(methyl)amino)-1-oxopropan-2-yl)carbamate To a mixture of (S)-2-((tert-butoxycarbonyl)amino)-3-(3-chlorophenyl)propanoic acid (25.3 g), DIPEA (27.3 g) and HATU (35.3 g) in THF (250 mL) was added N,O-dimethylhydroxylamine hydrochloride (12.4 g) at room temperature. The mixture was stirred at room temperature for 15 h. The mixture was diluted with EtOAc (250 mL). The mixture was quenched with saturated aqueous sodium hydrogen carbonate solution (200 mL) at room temperature. The organic layer was separated, washed with saturated brine (100 mL), dried over magnesium sulfate and concentrated under reduced pressure. The residue was purified by column chromatography (silica gel, eluted with EtOAc/hexane) to give the title compound (28.5 g).

MS, found: 243.0.

B) tert-butyl(S)-(3-(3-chlorophenyl)-1-(methoxy(methyl)amino)-1-oxopropan-2-yl)(4-methoxybenzyl)carbamate To a mixture of tert-butyl(S)-(3-(3-chlorophenyl)-1-(methoxy(methyl)amino)-1-oxopropan-2-yl)carbamate (13.7 g) in DMF (80 mL) was added sodium hydride (2.08 g) at 0° C. After being stirred for 10 min at room temperature, 1-(chloromethyl)-4-methoxybenzene (12.5 g) and tetrabutylammonium iodide (1.48 g) were added thereto at 0° C. After being stirred 1.5 h at room temperature, the reaction mixture was poured into a stirred mixture of EtOAc (200 mL) and 5% KHSO$_4$ aqueous solution (100 mL) at 0° C., and the organic layer was separated. The organic layer was washed with water and saturated brine, dried over magnesium sulfate, filtrated and concentrated under reduced pressure. The residue was purified by column chromatography (silica gel, eluted with EtOAc/hexane) to give the title compound (18.3 g).

MS: [M+H]$^+$ 463.1.

C) tert-butyl [(2)-1-(3-chlorophenyl)-3-oxopropan-2-yl][(4-methoxyphenyl)methyl]carbamate Aluminum(III) lithium hydride (2.10 g) was added to a stirred solution of tert-butyl(S)-(3-(3-chlorophenyl)-1-(methoxy(methyl)amino)-1-oxopropan-2-yl)(4-methoxybenzyl)carbamate (18.3 g) in Et$_2$O (150 mL) at −78° C. The mixture was warmed up to 0° C. After 0.5 h, the reaction mixture was quenched with EtOAc (6.97 g) and a solution of potassium hydrogen sulfate (13.5 g) in water (150 mL). And then, EtOAc and water were added thereto. The organic layer was separated, washed with water and a mixture of saturated brine and aqueous sodium hydrogen carbonate solution, dried over magnesium sulfate, filtrated and concentrated under reduced pressure. The residue was purified by column chromatography (silica gel, eluted with EtOAc/hexane) to give the title compound (12.8 g).

MS: [M−H]$^-$ 402.1.

D) ethyl (4S)-4-((tert-butoxycarbonyl)(4-methoxybenzyl)amino)-5-(3-chlorophenyl)-2,2-difluoro-3-hydroxypentanoate To a stirred mixture of zinc (0.456 g) in THF (6 mL) was added chlorotrimethylsilane (0.051 g) at room temperature.

After 5 min, ethyl 2-bromo-2,2-difluoroacetate (0.945 g) was added to the mixture under water bath cooling. After 10 min, a solution of tert-butyl [(2S)-1-(3-chlorophenyl)-3-oxopropan-2-yl][(4-methoxyphenyl)methyl]carbamate (0.94 g) in THF (2 mL) was added to the mixture at room temperature. The mixture was stirred at room temperature under nitrogen atmosphere for 2 h. The reaction mixture was poured into a stirred mixture of 10% aqueous citric acid solution and EtOAc. The organic layer was separated, washed with saturated brine, dried over magnesium sulfate, filtrated, and concentrated under reduced pressure. The residue was purified by column chromatography (silica gel, eluted with EtOAc/hexane) to give the title compound (1.11 g).
MS, found: 472.1.

E) ethyl (4S)-5-(3-chlorophenyl)-2,2-difluoro-3-hydroxy-4-((4-methoxybenzyl)amino)pentanoate Hydrochloride To a mixture of ethyl (4S)-4-((tert-butoxycarbonyl)(4-methoxybenzyl)amino)-5-(3-chlorophenyl)-2,2-difluoro-3-hydroxypentanoate (1.11 g) in EtOH (3 mL) was added 4 M HCl/CPME solution (5.26 mL) at room temperature. The mixture was stirred at room temperature for 2 h. Evaporation gave the title compound (0.976 g).
MS: [M+H]$^+$ 428.0.

F) (5S)-5-[(3-chlorophenyl methyl]-3,3-difluoro-4-hydroxy-1-[(4-methoxyphenyl)methyl]pyrrolidin-2-one To a mixture of ethyl (4S)-5-(3-chlorophenyl)-2,2-difluoro-3-hydroxy-4-((4-methoxybenzyl)amino)pentanoate hydrochloride (0.976 g) in EtOH (5 mL) was added DIPEA (2.72 g) at room temperature. The mixture was stirred at room temperature for 2 h. After evaporation of the solvent, the residue was poured into water, and the mixture was extracted with EtOAc. The organic layer was separated, washed with saturated brine, dried over magnesium sulfate and concentrated under reduced pressure. The residue was purified by column chromatography (silica gel, eluted with EtOAc/hexane) to give the title compound (0.770 g).
MS: [M−H]$^-$ 380.1.

G) (5S)-5-[(3-chlorophenyl)methyl]-3,3-difluoro-4-hydroxypyrrolidin-2-one

To a mixture of (5S)-5-[(3-chlorophenyl)methyl]-3,3-difluoro-4-hydroxy-1-[(4-methoxyphenyl)methyl]pyrrolidin-2-one (0.77 g) in CH$_3$CN (7 mL) and water (2.33 mL) was added ammonium cerium (IV) nitrate (2.21 g) at room temperature. The mixture was stirred at room temperature for 2 h. The mixture was quenched with saturated aqueous sodium carbonate solution and extracted with EtOAc. The organic layer was separated, washed with saturated brine, dried over magnesium sulfate and concentrated under reduced pressure. The residue was purified by column chromatography (silica gel, eluted with EtOAc/hexane) to give the title compound (0.460 g).
MS: [M−H]$^-$ 260.0.

H) (2S)-2-[(3-chlorophenyl)methyl]-4,4-difluoropyrrolidin-3-ol

To a mixture of (5S)-5-[(3-chlorophenyl)methyl]-3,3-difluoro-4-hydroxypyrrolidin-2-one (3.45 g) in THF (40 mL) was added 0.9 M borane-THF complex/THF solution (44.0 mL) at room temperature. The mixture was stirred at 60° C. under nitrogen atmosphere for 3 h. The mixture was quenched with water at 0° C. The mixture was stirred at room temperature for 10 min and concentrated under reduced pressure. The residue was diluted with EtOH (10 mL) and 1 M hydrochloric acid (50 mL), and the mixture was stirred at 60° C. for 1 h. Sodium hydrogen carbonate was carefully added to the reaction mixture in the iced bath to bring the pH of the solution to 8. Evaporation gave the title compound (3.27 g).
MS, found: 247.9.

I) tert-butyl (2S)-2-[(3-chlorophenyl)methyl]-4,4-difluoro-3-hydroxypyrrolidine-1-carboxylate To a crude mixture of (2S)-2-[(3-chlorophenyl)methyl]-4,4-difluoropyrrolidin-3-ol (2.27 g) and TEA (1.86 g) in THF (30 mL) was added Boc$_2$O (3.00 g) at room temperature. The mixture was stirred at room temperature under nitrogen atmosphere for 3 h. After evaporation, the mixture was diluted with water and extracted with EtOAc. The organic layer was separated, washed with saturated brine, dried over magnesium sulfate and concentrated under reduced pressure. The residue was purified by column chromatography (silica gel, eluted with EtOAc/hexane) to give the title compound (2.84 g).
MS, found: 247.9.

J) tert-butyl (2S,3S)-2-[(3-chlorophenyl)methyl]-4,4-difluoro-3-[(trifluoromethanesulfonyl)oxy]pyrrolidine-1-carboxylate Trifluoromethanesulfonic anhydride (406 μL) was added to a solution of tert-butyl (2S)-2-[(3-chlorophenyl)methyl]-4,4-difluoro-3-hydroxypyrrolidine-1-carboxylate (420 mg) and pyridine (488 μL) in Et$_2$O (6.04 mL) at 0° C. After being stirred at room temperature for 2 h and then at 40° C. for 2 h, the mixture was quenched with water at room temperature and extracted with EtOAc. The organic layer was separated, washed with saturated brine, dried over magnesium sulfate and concentrated under reduced pressure. The organic layer was purified by column chromatography (silica gel, eluted with EtOAc/hexane) to give the title compound (410 mg).
MS, found: 379.9.

K) tert-butyl (2S,3R)-3-azido-2-[(3-chlorophenyl)methyl]-4,4-difluoropyrrolidine-1-carboxylate To a mixture of tert-butyl (2S,3S)-2-[(3-chlorophenyl)methyl]-4,4-difluoro-3-[(trifluoromethanesulfonyl)oxy]pyrrolidine-1-carboxylate (2.43 g) in CH$_3$CN (20 mL) was added tetrabutylammonium azide (2.16 g) at room temperature. The mixture was stirred at 80° C. for 1 h. The mixture was quenched with water at 0° C. and extracted with EtOAc. The organic layer was separated, washed with water and saturated brine, dried over magnesium sulfate and concentrated under reduced pressure. The residue was purified by column chromatography (silica gel, eluted with EtOAc/hexane) to give the title compound (1.85 g).
MS, found: 272.9.

L) tert-butyl (2S,3R)-3-amino-2-[(3-chlorophenyl)methyl]-4,4-difluoropyrrolidine-1-carboxylate To a mixture of tert-butyl (2S,3R)-3-azido-2-[(3-chlorophenyl)methyl]-4,4-difluoropyrrolidine-1-carboxylate (1.57 g) in THF (20 mL) was added PPh₃ (1.33 g) at room temperature. The mixture was stirred at 50° C. for 15 h. After evaporation, the residue was purified by column chromatography (silica gel, eluted with EtOAc/hexane). The residue was further purified by preparative HPLC (Column: CHIRALPAK IA, mobile phase: hexane/EtOH/diethylamine=650/350/1 (v/v/v)) to afford the title compound (1.13 g) with shorter retention time (Column: CHIRALPAK IA, mobile phase: hexane/EtOH/diethylamine=650/350/1 (v/v/v)).

MS, found: 291.1.

M) tert-butyl (2S,3R)-2-[(3-chlorophenyl)methyl]-4,4-difluoro-3-[(methanesulfonyl)amino]pyrrolidine-1-carboxylate Methanesulfonic anhydride (166 mg) was added to a stirred solution of tert-butyl (2S,3R)-3-amino-2-[(3-chlorophenyl)methyl]-4,4-difluoropyrrolidine-1-carboxylate (165 mg) and TEA (0.199 mL) in THF (3 mL) at room temperature. After 0.5 h, the reaction mixture was concentrated under reduced pressure, and the residue was purified by column chromatography (silica gel, eluted with EtOAc/hexane) to give the title compound (186 mg).

MS: [M−H]⁻ 423.1.

N) tert-butyl (2S,3R)-4,4-difluoro-2-[(3'-fluoro[1,1'-biphenyl]-3-yl)methyl]-3-[(methanesulfonyl)amino]pyrrolidine-1-carboxylate A mixture of tert-butyl (2S,3R)-2-[(3-chlorophenyl)methyl]-4,4-difluoro-3-[(methanesulfonyl)amino]pyrrolidine-1-carboxylate (186 mg), (3-fluorophenyl)boronic acid (92 mg), XPhos Pd G3 (37.1 mg) and 1 M aqueous potassium phosphate solution (1.31 mL) in DME (1.46 mL) was stirred overnight at 90° C. The mixture was purified by column chromatography (NH silica gel, EtOAc/hexane) to give the title compound (205 mg).

MS: [M−H]⁻ 483.2.

O) N-{(2S,3R)-4,4-difluoro-2-[(3'-fluoro[1,1'-biphenyl]-3-yl)methyl]pyrrolidin-3-yl}methanesulfonamide Hydrochloride A mixture of tert-butyl (2S,3R)-4,4-difluoro-2-[(3'-fluoro[1,1'-biphenyl]-3-yl)methyl]-3-[(methanesulfonyl)amino]pyrrolidine-1-carboxylate (205 mg) and 4 M HCl/CPME solution (5 mL) was stirred at room temperature for 2 h. The solid was collected by filtration to give the title compound (175 mg).

MS: [M+H]⁺ 385.0.

P) N-{(2S,3R)-1-(bicyclo[1.1.1]pentane-1-carbonyl)-4,4-difluoro-2-[(3'-fluoro[1,1'-biphenyl]-3-yl)methyl]pyrrolidin-3-yl}methanesulfonamide HATU (43.4 mg) was added to a solution of N-{(2S,3R)-4,4-difluoro-2-[(3'-fluoro[1,1'-biphenyl]-3-yl)methyl]pyrrolidin-3-yl}methanesulfonamide hydrochloride (40 mg), bicyclo[1.1.1]pentane-1-carboxylic acid (12.8 mg) and TEA (0.066 mL) in DMF (1 mL) at room temperature. The mixture was stirred at room temperature under a dry atmosphere for 30 min. The mixture was quenched with saturated aqueous sodium hydrogen carbonate solution at room temperature and extracted with EtOAc. The organic layer was separated, washed with saturated brine, dried over magnesium sulfate and concentrated under reduced pressure. The residue was purified by column chromatography (NH silica gel, eluted with EtOAc/hexane) to give the title compound (32.0 mg).

¹H NMR (400 MHz, CDCl₃) δ 1.21-1.76 (3H, m), 1.98-3.18 (9H, m), 3.70-5.01 (5H, m), 6.97-7.53 (8H, m).

Example 25

N-[(2S,3R)-4,4-difluoro-2-[(2-fluoro-3'-methyl[1,1'-biphenyl]-3-yl)methyl]-1-(2-hydroxy-2-methylpropanoyl)pyrrolidin-3-yl]methanesulfonamide A mixture of N-[(2S,3R)-2-[(3-chloro-2-fluorophenyl)methyl]-4,4-difluoro-1-(2-hydroxy-2-methylpropanoyl)pyrrolidin-3-yl]methanesulfonamide (35 mg), m-tolylboronic acid (16.6 mg), XPhos Pd G3 (6.91 mg) and 1 M aqueous potassium phosphate solution (245 μL) in THF (408 μL) was stirred at 90° C. for 1 h. The mixture was purified by column chromatography (NH silica gel, eluted with EtOAc/hexane) to give the title compound (33.0 mg).

¹H NMR (400 MHz, DMSO-d₆) δ 0.97-1.23 (6H, m), 2.36 (3H, s), 2.61-2.71 (1H, m), 2.99 (3H, s), 3.00-3.08 (1H, m), 4.08-4.45 (2H, m), 4.58-5.02 (2H, m), 5.28 (1H, s), 7.05-7.15 (1H, m), 7.17-7.22 (1H, m), 7.24-7.39 (5H, m), 8.05-8.23 (1H, m).

Example 26

N-{(2S,3R)-4,4-difluoro-2-[(3'-fluoro[1,1'-biphenyl]-3-yl)methyl]-1-[(2R)-oxolane-2-carbonyl]pyrrolidin-3-yl}methanesulfonamide HATU (43.4 mg) was added to a solution of N-{(2S,3R)-4,4-difluoro-2-[(3'-fluoro[1,1'-biphenyl]-3-yl)methyl]pyrrolidin-3-yl}methanesulfonamide hydrochloride (40 mg), (R)-tetrahydrofuran-2-carboxylic acid (13.2 mg) and TEA (0.066 mL) in DMF (0.5 mL) at room temperature. The mixture was stirred at room temperature under a dry atmosphere for 30 min. The mixture was quenched with saturated aqueous sodium hydrogen carbonate solution at room temperature and extracted with EtOAc. The organic layer was separated, washed with saturated brine, dried over magnesium sulfate and concentrated under reduced pressure. The residue was purified by column chromatography (silica gel, eluted with EtOAc then, NH silica gel, eluted with EtOAc/hexane) to give the title compound (39.0 mg).

¹H NMR (400 MHz, DMSO-d₆) δ 1.54-1.81 (3H, m), 1.88-2.06 (1H, m), 2.62-3.14 (5H, m), 3.41-4.76 (7H, m), 7.12-7.23 (1H, m), 7.29-7.44 (2H, m), 7.45-7.57 (4H, m), 7.59-7.76 (1H, m), 8.14-8.30 (1H, m).

Example 35

N-[(2S,3R)-2-[(3',5'-difluoro[1,1'-biphenyl]-3-yl)methyl]-4,4-difluoro-1-(2-methylpropanoyl)pyrrolidin-3-yl]methanesulfonamide A) tert-butyl (2S,3R)-2-[(3',5'-difluoro[1,1'-biphenyl]-3-yl)methyl]-4,4-difluoro-3-[(methanesulfonyl)amino]pyrrolidine-1-carboxylate A mixture of tert-butyl (2S,3R)-2-[(3-chlorophenyl)methyl]-4,4-difluoro-3-[(methanesulfonyl)amino]pyrrolidine-1-carboxylate (90 mg), (3,5-difluorophenyl)boronic acid (50.2 mg), XPhos Pd G3 (17.9 mg) and 1 M aqueous potassium phosphate solution (635 μL) in DME (1.06 mL) was stirred overnight at 90° C. The mixture was quenched with saturated aqueous sodium hydrogen carbonate solution and extracted with EtOAc. The organic layer was separated, washed with saturated brine, dried over magnesium sulfate and concentrated under reduced pressure. The residue was purified by column chromatography (silica gel, eluted with EtOAc/hexane) to give the title compound (104 mg).
MS, found: 403.0.

B) N-{(2S,3R)-2-[(3',5'-difluoro[1,1'-biphenyl]-3-yl)methyl]-4,4-difluoropyrrolidin-3-yl}methanesulfonamide Hydrochloride A mixture of tert-butyl (2S,3R)-2-[(3',5'-difluoro[1,1'-biphenyl]-3-yl)methyl]-4,4-difluoro-3-[(methanesulfonyl)amino]pyrrolidine-1-carboxylate (104 mg) and 4 M HCl/CPME solution (2 mL) was stirred at room temperature for 2 h. The solid was collected by filtration to give the title compound (85 mg).
MS: [M+H]$^+$ 403.0.

C) N-[(2S,3R)-2-[(3',5'-difluoro[1,1'-biphenyl]-3-yl)methyl]-4,4-difluoro-1-(2-methylpropanoyl)pyrrolidin-3-yl]methanesulfonamide To a solution of N-{(2S,3R)-2-[(3',5'-difluoro[1,1'-biphenyl]-3-yl)methyl]-4,4-difluoropyrrolidin-3-yl}methanesulfonamide hydrochloride (20.0 mg) and isobutyric acid (5.09 µL) in DMF (1.5 mL) were added HATU (26.0 mg) and DIPEA (0.032 mL) at room temperature. The mixture was stirred overnight at room temperature. The mixture was quenched with saturated aqueous sodium hydrogen carbonate solution and extracted with EtOAc. The organic layer was separated, washed with water and saturated brine, dried over magnesium sulfate and concentrated under reduced pressure. The residue was purified by column chromatography (NH silica gel, eluted with EtOAc/hexane) to give the title compound (19.7 mg).
$^1$H NMR (400 MHz, DMSO-d$_6$) δ 0.11-0.98 (6H, m), 1.82-1.91 (1H, m), 2.54-3.15 (5H, m), 3.81-4.25 (2H, m), 4.37-4.70 (2H, m), 7.16-7.84 (7H, m), 8.23 (1H, brs).

Example 44

N-[(2S,3R)-2-[(3'-chloro-2-fluoro[1,1'-biphenyl]-3-yl)methyl]-4,4-difluoro-1-(2-hydroxy-2-methylpropanoyl)pyrrolidin-3-yl]methanesulfonamide A) N-[(2S,3R)-2-[(3-chloro-2-fluorophenyl)methyl]-4,4-difluoro-1-(2-hydroxy-2-methylpropanoyl)pyrrolidin-3-yl]methanesulfonamide A mixture of N-((2S,3R)-2-(3-chloro-2-fluorobenzyl)-4,4-difluoropyrrolidin-3-yl)methanesulfonamide hydrochloride (200 mg) and DIPEA (456 µL) in THF (3.16 mL) was stirred at room temperature for 30 min. To the suspension was added dropwise alpha-acetoxy-isobutyryl chloride (92 µL) at 0° C., and the mixture was stirred overnight at same temperature. To the mixture were added water (2.11 mL) and 4 M aqueous lithium hydroxide solution (1.32 mL), and the mixture was stirred overnight at room temperature. The mixture was quenched with saturated aqueous sodium hydrogen carbonate solution and extracted with EtOAc. The extract was washed with saturated brine, dried over magnesium sulfate and concentrated under reduced pressure. The residue was purified by column chromatography (silica gel, eluted with EtOAc/hexane) to give the title compound (184 mg).
MS: [M+H]$^+$ 429.0.

B) N-[(2S,3R)-2-[(3'-chloro-2-fluoro[1,1'-biphenyl]-3-yl)methyl]-4,4-difluoro-1-(2-hydroxy-2-methylpropanoyl)pyrrolidin-3-yl]methanesulfonamide The mixture of N-[(2S,3R)-2-[(3-chloro-2-fluorophenyl)methyl]-4,4-difluoro-1-(2-hydroxy-2-methylpropanoyl)pyrrolidin-3-yl]methanesulfonamide (24 mg), 4,4,4',4',5,5,5',5'-octamethyl-2,2'-bi(1,3,2-dioxaborolane) (17.1 mg), XPhos Pd G3 (9.47 mg), potassium acetate (11.0 mg) and toluene (1 mL) was stirred at 80° C. under nitrogen atmosphere for 4 h. The mixture was quenched with water at room temperature and extracted with EtOAc. The organic layer was separated, washed with saturated brine, dried over magnesium sulfate and concentrated under reduced pressure. The mixture of the obtained residue, cesium carbonate (58.6 mg), 1-chloro-3-iodobenzene (0.011 mL), PdCl$_2$ (dppf) (8.78 mg) and DME (1 mL)/water (0.300 mL) was stirred at 80° C. under nitrogen atmosphere for 1 h. The residue was purified by column chromatography (silica gel, eluted with EtOAc/hexane). The obtained solid was purified by preparative HPLC to give the title compound (7.50 mg).
$^1$H NMR (300 MHz, DMSO-d$_6$) δ 0.93-1.28 (6H, m), 2.61-2.74 (1H, m), 2.93-3.12 (4H, m), 4.10-4.48 (2H, m), 4.57-4.81 (1H, m), 4.84-5.02 (1H, m), 5.29 (1H, s), 7.10-7.18 (1H, m), 7.29-7.39 (2H, m), 7.42-7.53 (3H, m), 7.57 (1H, s), 8.16 (1H, brs).

Example 45

N-[(2S,3R)-4,4-difluoro-2-[(2-fluoro[1,1'-biphenyl]-3-yl)methyl]-1-(oxetane-2-carbonyl)pyrrolidin-3-yl]ethanesulfonamide with Shorter Retention Time To a solution of N-((2S,3R)-4,4-difluoro-2-((2-fluoro-[1,1'-biphenyl]-3-yl)methyl)pyrrolidin-3-yl)ethanesulfonamide hydrochloride (40.4 mg) and oxetane-2-carboxylic acid (9.33 µL) in DMF (3 mL) were added HATU (53.0 mg) and DIPEA (0.065 mL) at room temperature. The mixture was stirred overnight at room temperature. The mixture was quenched with saturated aqueous sodium hydrogen carbonate solution and extracted with EtOAc. The organic layer was separated, washed with water and saturated brine, dried over magnesium sulfate and concentrated under reduced pressure. The residue was purified by column chromatography (NH silica gel, eluted with EtOAc/hexane) to give the title compound (12.1 mg).
$^1$H NMR (300 MHz, DMSO-d$_6$) δ 1.19-1.33 (3H, m), 2.20-2.44 (1H, m), 2.60-3.15 (5H, m), 3.80-5.22 (7H, m), 7.11-7.57 (8H, m), 8.09-8.29 (1H, m).

Example 46

N-[(2S,3R)-4,4-difluoro-2-[(2-fluoro[1,1'-biphenyl]-3-yl)methyl]-1-(oxetane-2-carbonyl)pyrrolidin-3-yl]ethanesulfonamide with Longer Retention Time To a solution of N-((2S,3R)-4,4-difluoro-2-((2-fluoro-[1,1'-biphenyl]-3-yl)methyl)pyrrolidin-3-yl)ethanesulfonamide hydrochloride (40.4 mg) and oxetane-2-carboxylic acid (9.33 µL) in DMF (3 mL) were added HATU (53.0 mg) and DIPEA (0.065 mL) at room temperature. The mixture was stirred overnight at room temperature. The mixture was quenched with saturated aqueous sodium hydrogen carbonate solution and extracted with EtOAc. The organic layer was separated, washed with water and saturated brine, dried over magnesium sulfate and concentrated under reduced pressure. The residue was purified by column chromatography (NH silica gel, eluted with EtOAc/hexane) to give the title compound (13.3 mg).

$^1$H NMR (300 MHz, DMSO-d$_6$) δ 1.15-1.43 (3H, m), 1.95-2.41 (1H, m), 2.61-3.22 (5H, m), 3.76-5.13 (7H, m), 7.11-7.61 (8H, m), 8.13-8.38 (1H, m).

Example 50

N-[(2S,3R)-2-[([1,1'-biphenyl]-3-yl)methyl]-4,4-difluoro-1-(oxetane-2-carbonyl)pyrrolidin-3-yl]ethanesulfonamide with Shorter Retention Time A) tert-butyl (2S,3R)-2-[(3-chlorophenyl)methyl]-3-[(ethanesulfonyl)amino]-4,4-difluoropyrrolidine-1-carboxylate Ethanesulfonyl chloride (0.065 mL) was added to a mixture of tert-butyl (2S,3R)-3-amino-2-[(3-chlorophenyl)methyl]-4,4-difluoropyrrolidine-1-carboxylate (158 mg), TEA (0.127 mL), DMAP (11.2 mg) and THF (5 mL) at room temperature. After being stirred at room temperature for 2 h, the reaction mixture was quenched with saturated brine and concentrated under reduced pressure. The residual oil was purified by column chromatography (silica gel, eluted with EtOAc/hexane) to give the title compound (198 mg).

MS, found: 338.9.

B) N-{(2S,3R)-2-[(3-chlorophenyl)methyl]-4,4-difluoropyrrolidin-3-yl}ethanesulfonamide Hydrochloride A mixture of tert-butyl (2S,3R)-2-[(3-chlorophenyl)methyl]-3-[(ethanesulfonyl)amino]-4,4-difluoropyrrolidine-1-carboxylate (191 mg) and 4 M HCl/CPME solution (4 mL) was stirred at room temperature for 2 h. The solid was collected by filtration to give the title compound (149 mg).

MS: [M+H]$^+$ 338.9.

C) N-[(2S,3R)-2-[(3-chlorophenyl)methyl]-4,4-difluoro-1-(oxetane-2-carbonyl)pyrrolidin-3-yl]ethanesulfonamide To a solution of N-{(2S,3R)-2-[(3-chlorophenyl)methyl]-4,4-difluoropyrrolidin-3-yl}ethanesulfonamide hydrochloride (145 mg) and oxetane-2-carboxylic acid (0.049 mL) in DMF (5 mL) were added HATU (220 mg) and DIPEA (0.270 mL) at room temperature. The mixture was stirred overnight at room temperature. The mixture was quenched with aqueous saturated ammonium chloride solution and extracted with EtOAc. The organic layer was separated, washed with water and saturated brine, dried over sodium sulfate and concentrated under reduced pressure. The residue was purified by column chromatography (NH silica gel, eluted with EtOAc/hexane) to give the title compound (125 mg).

MS: [M+H]$^+$ 423.0.

D) N-[(2S,3R)-2-[([1,1'-biphenyl]-3-yl)methyl]-4,4-difluoro-1-(oxetane-2-carbonyl)pyrrolidin-3-yl]ethanesulfonamide with Shorter Retention Time A mixture of N-[(2S,3R)-2-[(3-chlorophenyl)methyl]-4,4-difluoro-1-(oxetane-2-carbonyl)pyrrolidin-3-yl]ethanesulfonamide (52.7 mg), phenylboronic acid (30.4 mg), XPhos Pd G3 (10.6 mg) and 1 M aqueous potassium phosphate solution (0.374 mL) in DME (1 mL) was stirred overnight at 90° C. After cooling back to room temperature, the solution was diluted with EtOAc and dried over sodium sulfate. After removal of the solvent under reduced pressure, the residue was purified by column chromatography (silica gel, eluted with EtOAc/hexane), and then by preparative HPLC to give the title compound (8.7 mg).

$^1$H NMR (300 MHz, DMSO-d$_6$) δ 1.01-1.29 (3H, m), 2.53-3.18 (6H, m), 3.75-5.29 (7H, m), 7.20-7.76 (9H, m), 8.18 (1H, d, J=9.8 Hz).

Example 51

N-[(2S,3R)-2-[([1,1'-biphenyl]-3-yl)methyl]-4,4-difluoro-1-(oxetane-2-carbonyl)pyrrolidin-3-yl]ethanesulfonamide with Longer Retention Time A mixture of N-[(2S,3R)-2-[(3-chlorophenyl)methyl]-4,4-difluoro-1-(oxetane-2-carbonyl)pyrrolidin-3-yl]ethanesulfonamide (52.7 mg), phenylboronic acid (30.4 mg), XPhos Pd G3 (10.6 mg) and 1 M aqueous potassium phosphate solution (0.374 mL) in DME (1 mL) was stirred overnight at 90° C. After cooling back to room temperature, the solution was diluted with EtOAc and dried over sodium sulfate. After removal of the solvent under reduced pressure, the residue was purified by column chromatography (silica gel, eluted with EtOAc/hexane), and then by preparative HPLC to give the title compound (11.4 mg).

$^1$H NMR (300 MHz, DMSO-d$_6$) δ 1.01-1.32 (3H, m), 1.75-2.28 (1H, m), 2.52-3.23 (5H, m), 3.73-5.22 (7H, m), 7.18-7.71 (9H, m), 8.07-8.36 (1H, m).

Example 52

N-[(2S,3R)-4,4-difluoro-2-[(3'-fluoro[1,1'-biphenyl]-3-yl)methyl]-1-(oxetane-2-carbonyl)pyrrolidin-3-yl]ethanesulfonamide with Shorter Retention Time A mixture of N-[(2S,3R)-2-[(3-chlorophenyl)methyl]-4,4-difluoro-1-(oxetane-2-carbonyl)pyrrolidin-3-yl]ethanesulfonamide (50.9 mg), (3-fluorophenyl)boronic acid (33.7 mg), XPhos Pd G3 (10.2 mg) and 1 M aqueous potassium phosphate solution (0.361 mL) in DME (1 mL) was stirred overnight at 90° C. After cooling back to room temperature, the solution was diluted with EtOAc and dried over sodium sulfate. After removal of the solvent under reduced pressure, the residue was purified by column chromatography (silica gel, eluted with EtOAc/hexane), and then by preparative HPLC to give the title compound (9.6 mg).

$^1$H NMR (300 MHz, DMSO-d$_6$) δ 1.03-1.25 (3H, m), 2.52-3.19 (6H, m), 3.84-5.25 (7H, m), 7.11-7.82 (8H, m), 8.07-8.30 (1H, m).

Example 56

N-{(2S,3R)-4,4-difluoro-1-((2R)-oxetane-2-carbonyl)-2-[(2,3',5'-trifluoro[1,1'-biphenyl]-3-yl)methyl]pyrrolidin-3-yl}ethanesulfonamide A) N-{(2S,3R)-2-[(3-chloro-2-fluorophenyl)methyl]-4,4-difluoropyrrolidin-3-yl}ethanesulfonamide Hydrochloride A mixture of tert-butyl (2S,3R)-2-[(3-chloro-2-fluorophenyl)methyl]-3-[(ethanesulfonyl)amino]-4,4-difluoropyrrolidine-1-carboxylate (580 mg) and 4 M hydrogen chloride CPME solution (10 mL) was stirred overnight at room temperature. The insoluble substance was collected by filtration to give the title compound (464 mg).

MS, found: 356.9.

B) N-[(2S,3R)-2-[(3-chloro-2-fluorophenyl)methyl]-4,4-difluoro-1-(oxetane-2-carbonyl)pyrrolidin-3-yl]ethanesulfonamide To a mixture of N-{(2S,3R)-2-[(3-chloro-2-fluorophenyl)methyl]-4,4-difluoropyrrolidin-3-yl}ethanesulfonamide hydrochloride (200 mg), oxetane-2-carboxylic acid (78 mg) and DMF (3 mL) were added HATU (290 mg) and DIPEA (263 mg) at room temperature. The mixture was stirred overnight at room temperature, to the mixture was added saturated aqueous ammonium chloride solution, and the mixture was extracted with EtOAc. The organic layer was separated, washed with water and saturated brine, dried over anhydrous sodium sulfate, and concentrated under reduced pressure. The residue was purified by silica gel column chromatography (NH, EtOAc/hexane) to give the title compound (147 mg).

MS: [M+H]$^+$ 441.0.

C) N-{(2S,3R)-4,4-difluoro-1-((2R)-oxetane-2-carbonyl)-2-[(2,3',5'-trifluoro[1,1'-biphenyl]-3-yl)methyl]pyrrolidin-3-yl}ethanesulfonamide A mixture of N-[(2S,3R)-2-[(3-chloro-2-fluorophenyl)methyl]-4,4-difluoro-1-(oxetane-2-carbonyl)pyrrolidin-3-yl]ethanesulfonamide (147 mg), (3,5-difluorophenyl)boronic acid (105 mg), XPhos Pd G3 (28.2 mg), 1 M aqueous potassium phosphate solution (1.00 mL) and DME (2 mL) was stirred at 70° C. for 1 hr. The mixture was cooled to room temperature, and purified by silica gel column chromatography (EtOAc/hexane). The obtained solid was crystallized from EtOAc/hexane to give the title compound (101 mg) with shorter retention time.

$^1$H NMR (400 MHz, DMSO-d$_6$) δ1.18-1.33 (3H, m), 2.26-2.45 (1H, m), 2.58-2.83 (2H, m), 2.95-3.22 (3H, m), 3.74-5.20 (7H, m), 7.14-7.52 (6H, m), 8.21 (1H, brs).

Example 66

N-{(2S,3R)-4,4-difluoro-1-(2-hydroxy-2-methylpropanoyl)-2-[(2,2',3'-trifluoro[1,1'-biphenyl]-3-yl)methyl]pyrrolidin-3-yl}ethanesulfonamide A) N-[(2S,3R)-2-[(3-chloro-2-fluorophenyl)methyl]-4,4-difluoro-1-(2-hydroxy-2-methylpropanoyl)pyrrolidin-3-yl]ethanesulfonamide To a mixture of N-{(2S,3R)-2-[(3-chloro-2-fluorophenyl)methyl]-4,4-difluoropyrrolidin-3-yl}ethanesulfonamide hydrochloride (160 mg) and DIPEA (0.352 mL) in THF (2 mL) was added alpha-acetoxy-isobutyryl chloride (0.071 mL) at 0° C. and the mixture was stirred at same temperature for 10 min. To the mixture were added water (1 mL) and 4 M aqueous lithium hydroxide solution (1.02 mL) and the mixture was stirred overnight at room temperature. The mixture was quenched with saturated aqueous sodium hydrogen carbonate solution and extracted with EtOAc. The extract was washed with saturated brine, dried over magnesium sulfate and concentrated under reduced pressure. The residue was purified by column chromatography (silica gel, eluted with EtOAc/hexane) to give the title compound (172 mg).

MS: [M+H]$^+$ 443.0.

B) N-{(2S,3R)-4,4-difluoro-1-(2-hydroxy-2-methylpropanoyl)-2-[(2,2',3'-trifluoro[1,1'-biphenyl]-3-yl)methyl]pyrrolidin-3-yl}ethanesulfonamide A mixture of N-[(2S,3R)-2-[(3-chloro-2-fluorophenyl)methyl]-4,4-difluoro-1-(2-hydroxy-2-methylpropanoyl)pyrrolidin-3-yl]ethanesulfonamide (20 mg), (2,3-difluorophenyl)boronic acid (14.3 mg), XPhos Pd G3 (7.64 mg) and 1 M aqueous potassium phosphate solution (0.135 mL) in THF (0.5 mL) was stirred at 90° C. in sealed tube for 6 h. The mixture was purified by column chromatography (NH silica gel, eluted with EtOAc/hexane) to give the title compound (19.2 mg).

$^1$H NMR (300 MHz, CDCl$_3$) δ 1.30-1.43 (9H, m), 2.05-3.25 (5H, m), 3.99-4.53 (3H, m), 4.87 (1H, d, J=9.1 Hz), 4.99-5.33 (1H, m), 7.07-7.30 (5H, m), 7.35-7.48 (1H, m).

Example 67

N-{(2S,3R)-4,4-difluoro-1-(2-hydroxy-2-methylpropanoyl)-2-[(2,2',5'-trifluoro[1,1'-biphenyl]-3-yl)methyl]pyrrolidin-3-yl}ethanesulfonamide A mixture of N-[(2S,3R)-2-[(3-chloro-2-fluorophenyl)methyl]-4,4-difluoro-1-(2-hydroxy-2-methylpropanoyl)pyrrolidin-3-yl]ethanesulfonamide (20 mg), (2,5-difluorophenyl)boronic acid (14.3 mg), XPhos Pd G3 (7.64 mg) and 1 M aqueous potassium phosphate solution (0.135 mL) in THF (0.5 mL) was stirred at 90° C. in sealed tube for 6 h. The mixture was purified by column chromatography (silica gel, eluted with EtOAc/hexane) to give the title compound (17.4 mg).

$^1$H NMR (300 MHz, CDCl$_3$) δ 1.28-2.66 (10H, m), 2.87-3.22 (4H, m), 3.94-4.57 (3H, m), 4.86 (1H, d, J=10.6 Hz), 4.99-5.30 (1H, m), 6.99-7.24 (5H, m), 7.35-7.48 (1H, m).

Example 68

N-[(2S,3R)-2-[(3'-chloro-2-fluoro[1,1'-biphenyl]-3-yl)methyl]-4,4-difluoro-1-(2-hydroxy-2-methylpropanoyl)pyrrolidin-3-yl]ethanesulfonamide A) N-[(2S,3R)-4,4-difluoro-2-{[2-fluoro-3-(4,4,5,5-tetramethyl-1,3,2-dioxaborolan-2-yl)phenyl]methyl}-1-(2-hydroxy-2-methylpropanoyl)pyrrolidin-3-yl]ethanesulfonamide A mixture of N-[(2S,3R)-2-[(3-chloro-2-fluorophenyl)methyl]-4,4-difluoro-1-(2-hydroxy-2-methylpropanoyl)pyrrolidin-3-yl]ethanesulfonamide (75 mg), 4,4,4',4',5,5,5',5'-octamethyl-2,2'-bi(1,3,2-dioxaborolane) (51.6 mg), XPhos Pd G3 (28.7 mg) and potassium acetate (33.2 mg) in toluene (1 mL) was stirred at 80° C. under nitrogen atmosphere for 5 h. The reaction mixture was diluted with water and extracted with EtOAc. The extract was washed with saturated brine, dried over magnesium sulfate, filtered and concentrated under reduced pressure to give the title compound (151 mg).

MS: [M+H]$^+$ 535.2.

B) N-[(2S,3R)-2-[(3'-chloro-2-fluoro[1,1'-biphenyl]-3-yl)methyl]-4,4-difluoro-1-(2-hydroxy-2-methylpropanoyl)pyrrolidin-3-yl]ethanesulfonamide A mixture of N-[(2S,3R)-4,4-difluoro-2-{[2-fluoro-3-(4,4,5,5-tetramethyl-1,3,2-dioxaborolan-2-yl)phenyl]methyl}-

1-(2-hydroxy-2-methylpropanoyl)pyrrolidin-3-yl]ethanesulfonamide (0.022 g), cesium carbonate (0.040 g), 1-chloro-3-iodobenzene (7.65 µL), PdCl$_2$(dppf) (6.02 mg) and DME (0.5 mL)/water (0.150 mL) was stirred overnight at 80° C. under nitrogen atmosphere. The mixture was purified by column chromatography (NH silica gel, eluted with EtOAc/hexane) to give the title compound (0.017 g).

$^1$H NMR (300 MHz, CDCl$_3$) δ 1.31-1.42 (9H, m), 2.21-2.58 (1H, m), 2.86-3.18 (4H, m), 3.99-4.53 (3H, m), 4.90 (1H, d, J=8.3 Hz), 5.01-5.29 (1H, m), 7.14-7.22 (1H, m), 7.27-7.44 (5H, m), 7.47-7.56 (1H, m).

Example 73

N-{(2S,3R)-4,4-difluoro-2-[(2-fluoro[1,1'-biphenyl]-3-yl)methyl]-1-[(2R)-oxolane-2-carbonyl]pyrrolidin-3-yl}methanesulfonamide A) tert-butyl (2S,3R)-2-[(3-chloro-2-fluorophenyl)methyl]-4,4-difluoro-3-[(methanesulfonyl)amino]pyrrolidine-1-carboxylate To a mixture of tert-butyl (2S,3R)-3-amino-2-[(3-chloro-2-fluorophenyl)methyl]-4,4-difluoropyrrolidine-1-carboxylate (200 mg), TEA (166 mg) and THF (5 mL) was added methanesulfonic anhydride (143 mg) at room temperature. The reaction mixture was stirred overnight at room temperature, and concentrated under reduced pressure. The residue was purified by silica gel column chromatography (EtOAc/hexane) to give the title compound (244 mg).

MS: [M−H]$^-$ 441.1.

B) N-{(2S,3R)-2-[(3-chloro-2-fluorophenyl)methyl]-4,4-difluoropyrrolidin-3-yl}methanesulfonamide Hydrochloride A mixture of tert-butyl (2S,3R)-2-[(3-chloro-2-fluorophenyl)methyl]-4,4-difluoro-3-[(methanesulfonyl)amino]pyrrolidine-1-carboxylate (360 mg) and 4 M hydrogen chloride CPME solution (5 mL) was stirred at room temperature for 2 hr. The reaction solution was concentrated to give the title compound (300 mg).

MS, found: 342.9.

C) N-{(2S,3R)-2-[(3-chloro-2-fluorophenyl)methyl]-4,4-difluoro-1-[(2R)-oxolan-2-carbonyl]pyrrolidin-3-yl}methanesulfonamide To a mixture of N-{(2S,3R)-2-[(3-chloro-2-fluorophenyl)methyl]-4,4-difluoropyrrolidin-3-yl}methanesulfonamide hydrochloride (300 mg), TEA (400 mg), (2R)-tetrahydrofuran-2-carboxylic acid (110 mg) and DMF (5 mL) was added HATU (361 mg) at room temperature. The mixture was stirred at room temperature for 30 min, to the mixture was added saturated aqueous sodium hydrogen carbonate solution at room temperature, and the mixture was extracted with EtOAc. The organic layer was separated, washed with saturated brine, dried over anhydrous magnesium sulfate, and concentrated under reduced pressure. The residue was purified by silica gel column chromatography (EtOAc/hexane). The obtained solid was washed with IPE to give the title compound (350 mg).

MS: [M+H]$^+$ 441.0.

D) N-{(2S,3R)-4,4-difluoro-2-[(2-fluoro[1,1'-biphenyl]-3-yl)methyl]-1-[(2R)-oxolan-2-carbonyl]pyrrolidin-3-yl}methanesulfonamide A mixture of N-{(2S,3R)-2-[(3-chloro-2-fluorophenyl)methyl]-4,4-difluoro-1-[(2R)-oxolan-2-carbonyl]pyrrolidin-3-yl}methanesulfonamide (30 mg), phenylboronic acid (12.5 mg), 1 M aqueous potassium phosphate solution (0.204 mL), XPhos Pd G3 (5.76 mg) and THF (0.340 mL) was stirred at 90° C. for 1 hr. The residue was purified by silica gel column chromatography (NH, EtOAc/hexane) to give the title compound (22 mg).

$^1$H NMR (400 MHz, DMSO-d$_6$) δ1.37-2.08 (4H, m), 2.60-3.12 (5H, m), 3.31-4.95 (7H, m), 7.08-7.55 (8H, m), 8.14-8.29 (1H, m).

Example 76

N-[(2S,3R)-4,4-difluoro-2-[(2-fluoro[1,1'-biphenyl]-3-yl)methyl]-1-(1-hydroxycyclobutane-1-carbonyl)pyrrolidin-3-yl]methanesulfonamide To a solution of N-((2S,3R)-4,4-difluoro-2-((2-fluoro-[1,1'-biphenyl]-3-yl)methyl)pyrrolidin-3-yl)methanesulfonamide hydrochloride (35.0 mg) and 1-hydroxycyclobutane-1-carboxylic acid (9.50 µL) in DMF (1.5 mL) were added HATU (47.4 mg) and DIPEA (0.058 mL) at room temperature. The mixture was stirred overnight at room temperature. The mixture was quenched with saturated aqueous sodium hydrogen carbonate solution and extracted with EtOAc. The organic layer was separated, washed with water and saturated brine, dried over magnesium sulfate and concentrated under reduced pressure. The residue was purified by column chromatography (NH silica gel, eluted with EtOAc/hexane) to give the title compound (23.5 mg).

$^1$H NMR (400 MHz, CDCl$_3$) δ 1.79-2.12 (4H, m), 2.51-2.62 (2H, m), 2.87 (3H, s), 2.92-3.14 (2H, m), 3.93-4.13 (1H, m), 4.19-4.41 (2H, m), 4.97-5.13 (2H, m), 7.16-7.21 (1H, m), 7.27-7.54 (8H, m).

Example 77

N-[(2S,3R)-4,4-difluoro-2-[(2-fluoro[1,1'-biphenyl]-3-yl)methyl]-1-(2-methylpropanoyl)pyrrolidin-3-yl]methanesulfonamide To a solution of N-((2S,3R)-4,4-difluoro-2-((2-fluoro-[1,1'-biphenyl]-3-yl)methyl)pyrrolidin-3-yl)methanesulfonamide hydrochloride (35.0 mg) and isobutyric acid (0.012 mL) in DMF (1.5 mL) were added HATU (47.4 mg) and DIPEA (0.058 mL) at room temperature. The mixture was stirred overnight at room temperature. The mixture was quenched with aqueous saturated ammonium chloride solution and extracted with EtOAc. The organic layer was separated, washed with water and saturated brine, dried over magnesium sulfate and concentrated under reduced pressure. The residue was purified by column chromatography (NH silica gel, eluted with EtOAc/hexane) to give the title compound (33.0 mg).

$^1$H NMR (400 MHz, CDCl$_3$) δ 0.45-1.15 (6H, m), 1.94-2.49 (1H, m), 2.74-3.17 (5H, m), 3.72-4.02 (1H, m), 4.28-4.60 (2H, m), 4.87-5.19 (1H, m), 7.09-7.24 (2H, m), 7.29-7.54 (6H, m).

Example 78

N-{(2S,3R)-1-(bicyclo[1.1.1]pentane-1-carbonyl)-4,4-difluoro-2-[(2-fluoro[1,1'-biphenyl]-3-yl)methyl]pyrrolidin-3-yl}methanesulfonamide To a solution of N-((2S,3R)-4,4-difluoro-2-((2-fluoro-[1,1'-biphenyl]-3-yl)methyl)pyrrolidin-3-yl)methanesulfonamide hydrochloride (35.0 mg) and bicyclo[1.1.1]pentane-1- carboxylic acid (9.17 µL) in DMF (1.5 mL) were added HATU (47.4 mg) and DIPEA (0.058 mL) at room temperature. The mixture was stirred overnight at room temperature. The mixture was quenched with aqueous saturated ammonium chloride solution and extracted with EtOAc. The organic layer was separated, washed with water and saturated brine, dried over magnesium sulfate and concentrated under reduced pressure. The residue was purified by column chromatography (NH silica gel, eluted with EtOAc/hexane) to give the title compound (33.2 mg).

$^1$H NMR (400 MHz, CDCl$_3$) δ 1.78-1.91 (2H, m), 2.10 (4H, s), 2.26-2.51 (1H, m), 2.77-3.12 (5H, m), 3.92-4.08 (1H, m), 4.17-4.44 (1H, m), 4.71-5.20 (2H, m), 7.11-7.24 (2H, m), 7.27-7.55 (7H, m).

Example 79

N-[(2S,3R)-4,4-difluoro-2-[(2-fluoro[1,1'-biphenyl]-3-yl)methyl]-1-(oxetane-2-carbonyl)pyrrolidin-3-yl]methanesulfonamide with Shorter Retention Time To a solution of N-((2S,3R)-4,4-difluoro-2-((2-fluoro-[1,1'-biphenyl]-3-yl)methyl)pyrrolidin-3-yl)methanesulfonamide hydrochloride (110 mg) and oxetane-2-carboxylic acid (0.026 mL) in DMF (5 mL) were added HATU (149 mg) and DIPEA (0.183 mL) at room temperature. The mixture was stirred overnight at room temperature. The mixture was quenched with saturated aqueous sodium hydrogen carbonate solution and extracted with EtOAc. The organic layer was separated, washed with water and saturated brine, dried over magnesium sulfate and concentrated under reduced pressure. The residue was purified by column chromatography (NH silica gel, eluted with EtOAc/hexane), and then by preparative HPLC to give the title compound (33.2 mg).

$^1$H NMR (300 MHz, DMSO-d$_6$) δ 2.23-2.47 (1H, m), 2.61-3.09 (6H, m), 3.72-5.19 (7H, m), 7.11-7.56 (8H, m), 8.23 (1H, brs).

Example 81

N-[(2S,3R)-2-[(2,3'-difluoro[1,1'-biphenyl]-3-yl)methyl]-4,4-difluoro-1-((2R)-oxetane-2-carbonyl)pyrrolidin-3-yl]methanesulfonamide To a solution of N-{(2S,3R)-2-[(2,3'-difluoro[1,1'-biphenyl]-3-yl)methyl]-4,4-difluoropyrrolidin-3-yl}methanesulfonamide hydrochloride (100 mg) and oxetane-2-carboxylic acid (0.023 mL) in DMF (2 mL) were added HATU (130 mg) and DIPEA (0.159 mL) at room temperature. The mixture was stirred at room temperature for 1 h. The mixture was quenched with saturated aqueous sodium hydrogen carbonate solution and extracted with EtOAc. The organic layer was separated, washed with water and saturated brine, dried over magnesium sulfate and concentrated under reduced pressure. The residue was purified by column chromatography (NH silica gel, eluted with EtOAc/hexane) to give the title compound (41 mg).

$^1$H NMR (400 MHz, DMSO-d$_6$) δ 2.30-2.47 (1H, m), 2.64-2.78 (2H, m), 2.96-3.10 (4H, m), 3.75-5.19 (7H, m), 7.11-7.57 (7H, m), 8.14-8.32 (1H, m).

Example 87

N-{(2S,3R)-1-(bicyclo[1.1.1]pentane-1-carbonyl)-4,4-difluoro-2-[(2,3',5'-trifluoro[1,1'-biphenyl]-3-yl)methyl]pyrrolidin-3-yl}methanesulfonamide A) N-{(2S,3R)-1-(bicyclo[1.1.1]pentane-1-carbonyl)-2-[(3-chloro-2-fluorophenyl)methyl]-4,4-difluoropyrrolidin-3-yl}methanesulfonamide To a mixture of N-{(2S,3R)-2-[(3-chloro-2-fluorophenyl)methyl]-4,4-difluoropyrrolidin-3-yl}methanesulfonamide hydrochloride (157 mg), bicyclo[1.1.1]pentane-1-carboxylic acid (55.7 mg), TEA (209 mg) and DMF (4 mL) was added HATU (236 mg) at room temperature. The mixture was stirred at room temperature for 1 hr, to the mixture was added water, and the insoluble substance was collected by filtration to give the title compound (180 mg).

MS: [M+H]$^+$ 437.0.

B) N-{(2S,3R)-1-(bicyclo[1.1.1]pentane-1-carbonyl)-4,4-difluoro-2-[(2,3',5'-trifluoro[1,1'-biphenyl]-3-yl)methyl]pyrrolidin-3-yl}methanesulfonamide A mixture of N-{(2S,3R)-1-(bicyclo[1.1.1]pentane-1-carbonyl)-2-[(3-chloro-2-fluorophenyl)methyl]-4,4-difluoropyrrolidin-3-yl}methanesulfonamide (180 mg), (3,5-difluorophenyl)boronic acid (130 mg), XPhos Pd G3 (69.8 mg), 1 M aqueous potassium phosphate solution (1.24 mL) and DME (3 mL) was stirred at 90° C. for 2 hr. The residue was purified by silica gel column chromatography (NH, EtOAc/hexane), and then silica gel column chromatography (EtOAc/hexane). The obtained residue was crystallized from ethanol/water to give the title compound (121 mg).

$^1$H NMR (400 MHz, DMSO-d$_6$) δ 1.20-1.68 (2H, m), 1.90 (4H, s), 2.08-2.40 (1H, m), 2.61-2.77 (1H, m), 2.90-3.16 (4H, m), 3.70-4.31 (2H, m), 4.37-4.86 (2H, m), 7.08-7.57 (6H, m), 8.02-8.30 (1H, m).

Example 88

N-{(2S,3R)-4,4-difluoro-2-[(3'-fluoro[1,1'-biphenyl]-3-yl)methyl]-1-[(2R)-oxolane-2-carbonyl]pyrrolidin-3-yl}ethanesulfonamide A) tert-butyl (2S,3R)-3-[(ethanesulfonyl)amino]-4,4-difluoro-2-[(3'-fluoro[1,1'-biphenyl]-3-yl)methyl]pyrrolidine-1-carboxylate A mixture of tert-butyl (2S,3R)-2-[(3-chlorophenyl)methyl]-3-[(ethanesulfonyl)amino]-4,4-difluoropyrrolidine-1-carboxylate (97 mg), (3-fluorophenyl)boronic acid (46.4 mg), XPhos Pd G3 (18.7 mg) and 1 M aqueous potassium phosphate solution (0.663 mL) in THF (1 mL) was heated at 80° C. under nitrogen atmosphere for 3 h. The mixture was purified by column chromatography (NH silica gel, eluted with EtOAc/hexane) to give the title compound (100 mg).

MS: [M−H]$^-$ 497.2.

B) N-{(2S,3R)-4,4-difluoro-2-[(3'-fluoro[1,1'-biphenyl]-3-yl)methyl]pyrrolidin-3-yl}ethanesulfonamide Hydrochloride A mixture of tert-butyl (2S,3R)-3-[(ethanesulfonyl)amino]-4,4-difluoro-2-[(3'-fluoro[1,1'-biphenyl]-3-yl)methyl]pyrrolidine-1-carboxylate (100 mg) and 4 M HCl/CPME solution (5 mL) was stirred overnight at room temperature. The mixture was concentrated under reduced pressure to give the title compound (86 mg).
MS: [M+H]⁺ 399.0.

C) N-{(2S,3R)-4,4-difluoro-2-[(3'-fluoro[1,1'-biphenyl]-3-yl)methyl]-1-[(2R)-oxolane-2-carbonyl]pyrrolidin-3-yl}ethanesulfonamide HATU (22.7 mg) was added to a solution of N-{(2S,3R)-4,4-difluoro-2-[(3'-fluoro[1,1'-biphenyl]-3-yl)methyl]pyrrolidin-3-yl}ethanesulfonamide hydrochloride (20 mg), (R)-tetrahydrofuran-2-carboxylic acid (6.94 mg) and TEA (0.032 mL) in DMF (1 mL) at room temperature. The mixture was stirred at room temperature under a dry atmosphere for 30 min. The mixture was quenched with saturated aqueous sodium hydrogen carbonate solution at room temperature and extracted with EtOAc. The organic layer was separated, washed with saturated brine, dried over magnesium sulfate and concentrated under reduced pressure. The residue was purified by column chromatography (NH silica gel, eluted with EtOAc/hexane) to give the title compound (18.0 mg).
$^1$H NMR (400 MHz, DMSO-$d_6$) δ 1.03-2.06 (7H, m), 2.66-3.14 (4H, m), 3.41-4.74 (7H, m), 7.10-7.74 (8H, m), 8.07-8.31 (1H, m).

Example 91

N-{(2S,3R)-4,4-difluoro-1-((2R)-oxetane-2-carbonyl)-2-[(2,3',5'-trifluoro[1,1'-biphenyl]-3-yl)methyl]pyrrolidin-3-yl}methanesulfonamide A) N-[(2S,3R)-2-[(3-chloro-2-fluorophenyl)methyl]-4,4-difluoro-1-((2R)-oxetane-2-carbonyl)pyrrolidin-3-yl]methanesulfonamide To a mixture of N-{(2S,3R)-2-[(3-chloro-2-fluorophenyl)methyl]-4,4-difluoropyrrolidin-3-yl}methanesulfonamide hydrochloride (188 mg), oxetane-2-carboxylic acid (60.7 mg), TEA (251 mg) and DMF (4 mL) was added HATU (283 mg) at room temperature. The mixture was stirred at room temperature for 6 hr, to the mixture was added water, and the mixture was extracted with EtOAc. The organic layer was separated, washed with saturated aqueous sodium hydrogen carbonate solution, water and saturated brine, dried over anhydrous magnesium sulfate, and concentrated under reduced pressure. The residue was purified by silica gel column chromatography (EtOAc/hexane), and then silica gel column chromatography (NH, EtOAc/hexane), and then HPLC (column: L-Column2 ODS (3.0 mmI.D.×50 mm, 3 μm), mobile phase: water/CH₃CN (containing 5 mM ammonium acetate)) to give the title compound (65.2 mg) with shorter retention time.
MS: [M+H]⁺ 426.9.

B) N-{(2S,3R)-4,4-difluoro-1-((2R)-oxetane-2-carbonyl)-2-[(2,3',5'-trifluoro[1,1'-biphenyl]-3-yl)methyl]pyrrolidin-3-yl}methanesulfonamide A mixture of N-[(2S,3R)-2-[(3-chloro-2-fluorophenyl)methyl]-4,4-difluoro-1-((2R)-oxetane-2-carbonyl)pyrrolidin-3-yl]methanesulfonamide (30 mg), (3,5-difluorophenyl)boronic acid (22.2 mg), XPhos Pd G3 (11.9 mg), 1 M aqueous potassium phosphate solution (0.211 mL) and THF (0.5 mL) was stirred at 90° C. for 4 hr. The mixture was purified by silica gel column chromatography (NH, EtOAc/hexane), and recrystallized from EtOAc/hexane to give the title compound (27.6 mg).
$^1$H NMR (400 MHz, CDCl₃) δ 2.77-3.25 (7H, m), 3.68-3.92 (1H, m), 4.16-4.98 (5H, m), 5.01-5.21 (2H, m), 6.76-6.87 (1H, m), 7.01-7.10 (2H, m), 7.16-7.50 (3H, m).

Example 92

N-{(2S,3R)-4,4-difluoro-1-((2S)-oxetane-2-carbonyl)-2-[(2,3',5'-trifluoro[1,1'-biphenyl]-3-yl)methyl]pyrrolidin-3-yl}methanesulfonamide HATU (43.7 mg) was added to a solution of N-{(2S,3R)-4,4-difluoro-2-[(2,3',5'-trifluoro[1,1'-biphenyl]-3-yl)methyl]pyrrolidin-3-yl}methanesulfonamide hydrochloride (35 mg), oxetane-2-carboxylic acid (9.39 mg) and TEA (0.053 mL) in DMF (0.5 mL) at room temperature. The mixture was stirred at room temperature for 30 min, and then additional oxetane-2-carboxylic acid (9.39 mg) was added to the mixture. The mixture was stirred at room temperature for 30 min. The mixture was diluted with water and extracted with EtOAc. The extract was washed with saturated aqueous sodium hydrogen carbonate solution, water and saturated brine, dried over magnesium sulfate, filtered and concentrated under reduced pressure. The residue was purified by column chromatography (silica gel, eluted with EtOAc/hexane) to give the title compound (10.4 mg).
$^1$H NMR (300 MHz, CDCl₃) δ 2.31-3.21 (7H, m), 3.77-4.66 (6H, m), 4.96-5.11 (2H, m), 6.75-6.89 (1H, m), 6.99-7.15 (2H, m), 7.17-7.47 (3H, m).

Example 94

N-[(2S,3R)-2-[(2,3'-difluoro[1,1'-biphenyl]-3-yl)methyl]-4,4-difluoro-1-(2-methylpropanoyl)pyrrolidin-3-yl]ethanesulfonamide To a mixture of N-{(2S,3R)-2-[(2,3'-difluoro[1,1'-biphenyl]-3-yl)methyl]-4,4-difluoropyrrolidin-3-yl}ethanesulfonamide hydrochloride (15.2 mg), DIPEA (21.7 mg) and THF (0.5 mL) was added 2-methylpropanoyl chloride (5.36 mg) at room temperature. The mixture was stirred overnight at room temperature, to the mixture was added saturated aqueous sodium hydrogen carbonate solution, and the mixture was extracted with EtOAc. The organic layer was separated, washed with saturated brine, dried over anhydrous magnesium sulfate, and concentrated under reduced pressure. The residue was purified by silica gel column chromatography (EtOAc/hexane) to give the title compound (13.6 mg).
$^1$H NMR (400 MHz, DMSO-$d_6$) δ 0.17-0.92 (6H, m), 1.22-1.35 (3H, m), 1.79-2.48 (1H, m), 2.60-2.77 (1H, m), 2.97-3.24 (3H, m), 3.70-4.22 (2H, m), 4.35-4.93 (2H, m), 7.03-7.65 (7H, m), 8.01-8.45 (1H, m).

Example 97

N-[(2S,3R)-4,4-difluoro-2-[(3'-fluoro[1,1'-biphenyl]-3-yl)methyl]-1-(2-methylpropanoyl)pyrrolidin-3-yl]ethanesulfonamide HATU (20.46 mg) was added to a solution of N-{(2S,3R)-4,4-difluoro-2-[(3'-fluoro[1,1'-biphenyl]-3-yl)methyl]pyrrolidin-3-yl}ethanesulfonamide hydrochloride (18 mg), isobutyric acid (5.47 mg) and TEA (0.029 mL) in DMF (0.5 mL) at room temperature. The mixture was stirred at room temperature under a dry atmosphere for 30 min. The mixture was quenched with saturated aqueous sodium hydrogen carbonate solution at room temperature and extracted with EtOAc. The organic layer was separated, washed with saturated brine, dried over magnesium sulfate and concentrated under reduced pressure. The residue was purified by column chromatography (NH silica gel, eluted with EtOAc/hexane) to give the title compound (12.0 mg).

$^1$H NMR (400 MHz, DMSO-$d_6$) δ 0.11-1.38 (9H, m), 1.75-2.04 (1H, m), 2.52-2.92 (2H, m), 2.96-3.12 (1H, m), 3.15-3.24 (1H, m), 3.81-4.22 (2H, m), 4.35-4.65 (2H, m), 7.12-7.79 (8H, m), 8.10-8.30 (1H, m).

Example 98

N-[(2S,3R)-2-[(2,3'-difluoro[1,1'-biphenyl]-3-yl)methyl]-4,4-difluoro-1-(2-methylpropanoyl)pyrrolidin-3-yl]methanesulfonamide To a solution of N-{(2S,3R)-2-[(2,3'-difluoro[1,1'-biphenyl]-3-yl)methyl]-4,4-difluoropyrrolidin-3-yl}methanesulfonamide hydrochloride (20 mg) and isobutyric acid (3.95 µL) in DMF (0.5 mL) were added HATU (26.0 mg) and DIPEA (0.032 mL) at room temperature. The mixture was stirred at room temperature for 1 h. The mixture was quenched with saturated aqueous sodium hydrogen carbonate solution and extracted with EtOAc. The organic layer was separated, washed with water and saturated brine, dried over magnesium sulfate and concentrated under reduced pressure. The residue was purified by column chromatography (NH silica gel, eluted with EtOAc/hexane) to give the title compound (16 mg).

$^1$H NMR (400 MHz, DMSO-$d_6$) δ 0.17-0.92 (6H, m), 1.11-1.94 (1H, m), 2.58-3.22 (5H, m), 3.65-4.26 (2H, m), 4.36-4.89 (2H, m), 7.06-7.57 (7H, m), 8.13-8.34 (1H, m).

Example 106

N-[(2S,3R)-4,4-difluoro-2-[(2-fluoro[1,1'-biphenyl]-3-yl)methyl]-1-(2-methylpropanoyl)pyrrolidin-3-yl]ethanesulfonamide To a solution of N-((2S,3R)-4,4-difluoro-2-((2-fluoro-[1,1'-biphenyl]-3-yl)methyl)pyrrolidin-3-yl)ethanesulfonamide hydrochloride (30 mg) and isobutyric acid (7.29 mg) in DMF (0.5 mL) were added HATU (39.3 mg) and DIPEA (0.048 mL) at room temperature. The mixture was stirred at room temperature for 1 h. The mixture was quenched with saturated aqueous sodium hydrogen carbonate solution and extracted with EtOAc. The organic layer was separated, washed with water and saturated brine, dried over magnesium sulfate and concentrated under reduced pressure. The residue was purified by column chromatography (NH silica gel, eluted with EtOAc/hexane) to give the title compound (29.0 mg).

$^1$H NMR (400 MHz, DMSO-$d_6$) δ 0.16-0.94 (6H, m), 1.19-1.95 (4H, m), 2.59-2.80 (1H, m), 2.97-3.25 (3H, m), 3.65-4.21 (2H, m), 4.33-4.89 (2H, m), 7.05-7.55 (8H, m), 8.03-8.43 (1H, m).

Example 116

N-[(2S,3R)-2-[(3',5'-difluoro[1,1'-biphenyl]-3-yl)methyl]-4,4-difluoro-1-(2-methylpropanoyl)pyrrolidin-3-yl]ethanesulfonamide A) N-[(2S,3R)-2-[(3-chlorophenyl)methyl]-4,4-difluoro-1-(2-methylpropanoyl)pyrrolidin-3-yl]ethanesulfonamide To a solution of N-{(2S,3R)-2-[(3-chlorophenyl)methyl]-4,4-difluoropyrrolidin-3-yl}ethanesulfonamide hydrochloride (128 mg) and isobutyric acid (0.038 mL) in DMF (5 mL) were added HATU (195 mg) and DIPEA (0.238 mL) at room temperature. The mixture was stirred overnight at room temperature. The mixture was quenched with aqueous saturated ammonium chloride solution and extracted with EtOAc. The organic layer was separated, washed with water and saturated brine, dried over sodium sulfate and concentrated under reduced pressure. The residue was purified by column chromatography (NH silica gel, eluted with EtOAc/hexane) to give the title compound (108 mg).

MS: [M+H]$^+$ 409.0.

B) N-[(2S,3R)-2-[(3',5'-difluoro[1,1'-biphenyl]-3-yl)methyl]-4,4-difluoro-1-(2-methylpropanoyl)pyrrolidin-3-yl]ethanesulfonamide A mixture of N-[(2S,3R)-2-[(3-chlorophenyl)methyl]-4,4-difluoro-1-(2-methylpropanoyl)pyrrolidin-3-yl]ethanesulfonamide (17 mg), (3,5-difluorophenyl)boronic acid (13.1 mg), XPhos Pd G3 (3.52 mg) and 1 M aqueous potassium phosphate solution (0.125 mL) in DME (1 mL) was stirred overnight at 80° C. After cooling back to room temperature, the solution was diluted with EtOAc and dried over sodium sulfate. After removal of the solvent under reduced pressure, the residue was purified by column chromatography (silica gel, eluted with EtOAc/hexane) to give the title compound (18.2 mg).

$^1$H NMR (400 MHz, DMSO-$d_6$) δ 0.12-0.98 (6H, m), 1.03-1.88 (4H, m), 2.53-3.24 (4H, m), 3.81-4.23 (2H, m), 4.36-4.63 (2H, m), 7.16-7.78 (7H, m), 8.12-8.32 (1H, m).

Example 121

N-{(2S,3R)-4,4-difluoro-1-((2R)-oxetane-2-carbonyl)-2-[(2,2',3'-trifluoro[1,1'-biphenyl]-3-yl)methyl]pyrrolidin-3-yl}methanesulfonamide A mixture of N-[(2S,3R)-2-[(3-chloro-2-fluorophenyl)methyl]-4,4-difluoro-1-((2R)-oxetane-2-carbonyl)pyrrolidin-3-yl]methanesulfonamide (17 mg), (2,3-difluorophenyl)boronic acid (12.6 mg), XPhos Pd G3 (6.74 mg) and 1 M aqueous potassium phosphate solution (0.119 mL) in THF (0.5 mL) was stirred at 90° C. in sealed tube for 1 h. The mixture was purified by column chromatography (NH silica gel, eluted with EtOAc/hexane) to give the title compound (15.3 mg).

$^1$H NMR (400 MHz, CDCl$_3$) δ 2.67-3.30 (7H, m), 3.67-3.93 (1H, m), 4.18-5.20 (7H, m), 7.06-7.49 (6H, m).

Example 122

N-{(2S,3R)-4,4-difluoro-1-((2R)-oxetane-2-carbonyl)-2-[(2,2',5'-trifluoro[1,1'-biphenyl]-3-yl)methyl]pyrrolidin-3-yl}methanesulfonamide A mixture of N-[(2S,3R)-2-[(3-chloro-2-fluorophenyl)methyl]-4,4-difluoro-1-((2R)-oxetane-2-carbonyl)pyrrolidin-3-yl]methanesulfonamide (17 mg), (2,5-difluorophenyl)boronic acid (12.6 mg), XPhos Pd G3 (6.74 mg) and 1 M aqueous potassium phosphate solution (0.119 mL) in THF (0.5 mL) was stirred at 90° C. in sealed tube for 1 h. The mixture was directly purified by column chromatography (NH silica gel, eluted with EtOAc/hexane) to give the title compound (10.9 mg).

$^1$H NMR (400 MHz, CDCl$_3$) δ 2.66-3.32 (7H, m), 3.64-3.91 (1H, m), 4.17-5.21 (7H, m), 6.99-7.17 (3H, m), 7.17-7.30 (2H, m), 7.32-7.49 (1H, m).

Example 124

N-[(2S,3R)-4,4-difluoro-2-[(2-fluoro[1,1'-biphenyl]-3-yl)methyl]-1-(oxetane-2-carbonyl)pyrrolidin-3-yl]cyclopropanesulfonamide with Shorter Retention Time

A) tert-butyl (2S,3R)-3-[(cyclopropanesulfonyl)amino]-4,4-difluoro-2-[(2-fluoro[1,1'-biphenyl]-3-yl)methyl]pyrrolidine-1-carboxylate Cyclopropanesulfonyl chloride (0.081 mL) was added to a stirred solution of tert-butyl (2S,3R)-3-amino-4,4-difluoro-2-((2-fluoro-[1,1'-biphenyl]-3-yl)methyl)pyrrolidine-1-carboxylate (130 mg) and TEA (0.178 mL) in THF (2 mL) at room temperature. The mixture was stirred at the same temperature overnight, heated up to at 70° C. and stirred for 1 h. Additional cyclopropanesulfonyl chloride (0.081 mL) and TEA (0.178 mL) were added to the mixture, and the mixture was stirred overnight at 70° C. The reaction mixture was purified by column chromatography on silica gel (eluted with EtOAc/hexane) to give the title compound (130 mg).

MS, found: 411.1.

B) N-{(2S,3R)-4,4-difluoro-2-[(2-fluoro[1,1'-biphenyl]-3-yl)methyl]pyrrolidin-3-yl}cyclopropanesulfonamide Hydrochloride A mixture of tert-butyl (2S,3R)-3-[(cyclopropanesulfonyl)amino]-4,4-difluoro-2-[(2-fluoro[1,1'-biphenyl]-3-yl)methyl]pyrrolidine-1-carboxylate (186 mg) and 4 M HCl/CPME solution (4.0 mL) was stirred overnight at room temperature, and concentrated under reduced pressure to give the title compound (150 mg).

MS: [M+H]$^+$ 411.1.

C) N-[(2S,3R)-4,4-difluoro-2-[(2-fluoro[1,1'-biphenyl]-3-yl)methyl]-1-(oxetane-2-carbonyl)pyrrolidin-3-yl]cyclopropanesulfonamide with Shorter Retention Time To a mixture of N-{(2S,3R)-4,4-difluoro-2-[(2-fluoro[1,1'-biphenyl]-3-yl)methyl]pyrrolidin-3-yl}cyclopropanesulfonamide hydrochloride (80.0 mg), oxetane-2-carboxylic acid (29.3 mg), HATU (117 mg) and DMF (2.0 mL) was added DIPEA (0.200 mL) at room temperature. The mixture was stirred at room temperature for 1 h. To the mixture was added saturated aqueous sodium hydrogen carbonate solution, and the mixture was extracted with EtOAc/hexane. The organic layer was separated, washed with water and saturated brine, dried over sodium sulfate and concentrated under reduced pressure. The residue was purified by column chromatography (silica gel, eluted with EtOAc/hexane, then NH silica gel, eluted with EtOAc/hexane) to give the title compound (21.2 mg).

$^1$H NMR (400 MHz, DMSO-d$_6$) δ 0.90-1.08 (3H, m), 1.21-1.33 (1H, m), 2.24-2.38 (1H, m), 2.54-2.81 (3H, m), 3.01-3.15 (1H, m), 3.70-5.22 (7H, m), 7.07-7.58 (8H, m), 8.05-8.42 (1H, m).

Example 129

N-[(2S,3R)-2-[(2,3'-difluoro[1,1'-biphenyl]-3-yl)methyl]-4,4-difluoro-1-(oxetane-2-carbonyl)pyrrolidin-3-yl]cyclopropanesulfonamide with Shorter Retention Time

A) tert-butyl (2S,3R)-2-[(3-chloro-2-fluorophenyl)methyl]-3-[(cyclopropanesulfonyl)amino]-4,4-difluoropyrrolidine-1-carboxylate To a mixture of tert-butyl (2S,3R)-3-amino-2-[(3-chloro-2-fluorophenyl)methyl]-4,4-difluoropyrrolidine-1-carboxylate (100 mg), TEA (83 mg) and THF (3 mL) was added cyclopropanesulfonyl chloride (96 mg) at room temperature. The mixture was stirred overnight at 70° C., and purified by silica gel column chromatography (EtOAc/hexane) to give the title compound (75 mg).

MS: [M−H]$^-$ 467.0.

B) N-{(2S,3R)-2-[(3-chloro-2-fluorophenyl)methyl]-4,4-difluoropyrrolidin-3-yl}cyclopropanesulfonamide Hydrochloride A mixture of tert-butyl (2S,3R)-2-[(3-chloro-2-fluorophenyl)methyl]-3-[(cyclopropanesulfonyl)amino]-4,4-difluoropyrrolidine-1-carboxylate (328 mg) and 4 M hydrogen chloride CPME solution (6 mL) was stirred at room temperature for 4 hr. The insoluble substance was collected by filtration to give the title compound (240 mg).

MS, found: 369.0.

C) N-[(2S,3R)-2-[(3-chloro-2-fluorophenyl)methyl]-4,4-difluoro-1-(oxetane-2-carbonyl)pyrrolidin-3-yl]cyclopropanesulfonamide with Shorter Retention Time (Obtained by HPLC (Column: L-Column2 ODS (3.0 mmI.D.×50 mm, 3 Um), Mobile Phase: Water/CH$_3$CN (Containing 5 mM Ammonium Acetate)))

To a mixture of N-{(2S,3R)-2-[(3-chloro-2-fluorophenyl)methyl]-4,4-difluoropyrrolidin-3-yl}cyclopropanesulfonamide hydrochloride (35 mg), oxetane-2-carboxylic acid (13.2 mg) and DMF (1.5 mL) were added HATU (49.3 mg) and DIPEA (44.6 mg) at room temperature. The mixture was stirred overnight at room temperature, to the mixture was added saturated aqueous ammonium chloride solution, and the mixture was extracted with EtOAc. The organic layer was separated, washed with water and saturated brine, dried over anhydrous sodium sulfate, and concentrated under reduced pressure. The residue was purified by silica gel column chromatography (EtOAc/hexane) to give the title compound (11 mg).

MS: [M+H]$^+$ 453.1.

D) N-[(2S,3R)-2-[(2,3'-difluoro[1,1'-biphenyl]-3-yl)methyl]-4,4-difluoro-1-(oxetane-2-carbonyl)pyrrolidin-3-yl]cyclopropanesulfonamide with Shorter Retention Time A mixture of N-[(2S,3R)-2-[(3-chloro-2-fluorophenyl)methyl]-4,4-difluoro-1-(oxetane-2-carbonyl)pyrrolidin-3-yl]cyclopropanesulfonamide (10 mg) with shorter retention time (obtained by HPLC (column: L-Column2 ODS (3.0 mmI.D.×50 mm, 3 μm), mobile phase: water/CH$_3$CN (containing 5 mM ammonium acetate))), (3-fluorophenyl)boronic acid (6.18 mg), Xphos Pd G3 (1.87 mg), 1 M aqueous potassium phosphate solution (0.066 mL) and DME (0.5 mL) was stirred overnight at 80° C. The mixture was cooled to room temperature, and EtOAc was added thereto. The mixture was dried over anhydrous sodium sulfate, and concentrated under reduced pressure. The residue was purified by silica gel column chromatography (NH, EtOAc/hexane) to give the title compound (3.6 mg).

$^1$H NMR (400 MHz, CDCl$_3$) δ 0.91-1.21 (4H, m), 2.15-2.43 (1H, m), 2.71-3.04 (3H, m), 3.08-3.26 (1H, m), 3.68-3.88 (1H, m), 4.16-5.18 (7H, m), 7.03-7.25 (3H, m), 7.27-7.44 (4H, m).

Example 131

N-[(2S,3R)-2-[(2',3'-difluoro[1,1'-biphenyl]-3-yl)methyl]-4,4-difluoro-1-(2-methylpropanoyl)pyrrolidin-3-yl]methanesulfonamide A) N-{(2S,3R)-2-[(3-chlorophenyl)methyl]-4,4-difluoropyrrolidin-3-yl}methanesulfonamide Hydrochloride A mixture of tert-butyl (2S,3R)-2-[(3-chlorophenyl)methyl]-4,4-difluoro-3-[(methanesulfonyl)amino]pyrrolidine-1-carboxylate (187 mg) and 4 M HCl/CPME solution (5 mL) was stirred at room temperature for 2 h. The solid was collected by filtration to give the title compound (145 mg).

MS: [M+H]$^+$ 325.0.

B) N-[(2S,3R)-2-[(3-chlorophenyl)methyl]-4,4-difluoro-1-(2-methylpropanoyl)pyrrolidin-3-yl]methanesulfonamide To a solution of N-{(2S,3R)-2-[(3-chlorophenyl)methyl]-4,4-difluoropyrrolidin-3-yl}methanesulfonamide hydrochloride (51.1 mg) and isobutyric acid (0.020 mL) in DMF (2 mL) were added HATU (81 mg) and DIPEA (0.099 mL) at room temperature. The mixture was stirred overnight at room temperature. The mixture was quenched with aqueous saturated ammonium chloride solution and extracted with EtOAc. The organic layer was separated, washed with water and saturated brine, dried over sodium sulfate and concentrated under reduced pressure. The residue was purified by column chromatography (silica gel, eluted with EtOAc/hexane) to give the title compound (53.0 mg).

MS: [M+H]$^+$ 395.0.

C) N-[(2S,3R)-2-[(2',3'-difluoro[1,1'-biphenyl]-3-yl)methyl]-4,4-difluoro-1-(2-methylpropanoyl)pyrrolidin-3-yl]methanesulfonamide A mixture of N-[(2S,3R)-2-[(3-chlorophenyl)methyl]-4,4-difluoro-1-(2-methylpropanoyl)pyrrolidin-3-yl]methanesulfonamide (14.5 mg), (2,3-difluorophenyl)boronic acid (11.6 mg), XPhos Pd G3 (3.11 mg) and 1 M aqueous potassium phosphate solution (0.110 mL) in DME (0.5 mL) was stirred at 80° C. for 2 h. After cooling back to room temperature, the solvent was removed under reduced pressure, and the residue was purified by column chromatography (NH silica gel, eluted with EtOAc/hexane) to give the title compound (17.1 mg).

$^1$H NMR (400 MHz, DMSO-d$_6$) δ 0.16-0.98 (6H, m), 1.78-2.36 (1H, m), 2.54-3.13 (5H, m), 3.75-4.72 (4H, m), 7.26-7.64 (7H, m), 8.10-8.36 (1H, m).

Example 133

N-{(2S,3R)-4,4-difluoro-1-((2S)-oxetane-2-carbonyl)-2-[(2,2',3'-trifluoro[1,1'-biphenyl]-3-yl)methyl]pyrrolidin-3-yl}methanesulfonamide A) N-((2S,3R)-2-(3-chloro-2-fluorobenzyl)-4,4-difluoro-1-((2S)-oxetane-2-carbonyl)pyrrolidin-3-yl)methanesulfonamide HATU (283 mg) was added to a solution of N-((2S,3R)-2-(3-chloro-2-fluorobenzyl)-4,4-difluoropyrrolidin-3-yl)methanesulfonamide hydrochloride (188 mg), oxetane-2-carboxylic acid (60.7 mg) and TEA (0.345 mL) in DMF (4 mL) at room temperature. The mixture was stirred at room temperature for 6 h. The mixture was diluted with water and extracted with EtOAc. The extract was washed with saturated aqueous sodium hydrogen carbonate solution, water and saturated brine, dried over magnesium sulfate, filtered and concentrated under reduced pressure. The residue was purified by column chromatography (silica gel, eluted with EtOAc/hexane, then NH silica gel, eluted with EtOAc/hexane) to give the title compound (84.5 mg).

MS: [M+H]$^+$ 426.9

B) N-{(2S,3R)-4,4-difluoro-1-((2S)-oxetane-2-carbonyl)-2-[(2,2',3'-trifluoro[1,1'-biphenyl]-3-yl)methyl]pyrrolidin-3-yl}methanesulfonamide A mixture of N-((2S,3R)-2-(3-chloro-2-fluorobenzyl)-4,4-difluoro-1-((2S)-oxetane-2-carbonyl)pyrrolidin-3-yl)methanesulfonamide (20 mg), (2,3-difluorophenyl)boronic acid (14.8 mg), XPhos Pd G3 (7.93 mg) and 1 M aqueous potassium phosphate solution (0.141 mL) in THF (0.5 mL) was stirred at 90° C. in sealed tube for 1 h. The mixture was purified by column chromatography (NH silica gel, eluted with EtOAc/hexane) to give the title compound (10.1 mg).

$^1$H NMR (400 MHz, CDCl$_3$) δ 2.31-3.22 (7H, m), 3.77-3.94 (1H, m), 4.01-4.20 (1H, m), 4.24-5.17 (6H, m), 7.06-7.48 (6H, m).

Example 144

N-{(2S,3R)-1-(cyclopropanecarbonyl)-4,4-difluoro-2-[(2,3',5'-trifluoro[1,1'-biphenyl]-3-yl)methyl]pyrrolidin-3-yl}ethanesulfonamide A) N-[(2S,3R)-2-[(3-chloro-2-fluorophenyl)methyl]-1-(cyclopropanecarbonyl)-4,4-difluoropyrrolidin-3-yl]ethanesulfonamide To a mixture of N-{(2S,3R)-2-[(3-chloro-2-fluorophenyl)methyl]-4,4-difluoropyrrolidin-3-yl}ethanesulfonamide hydrochloride (146 mg), cyclopropanecarboxylic acid (47.8 mg) and DMF (4 mL) were added HATU (211 mg) and DIPEA (191 mg) at room temperature. The mixture was stirred overnight at room temperature, to the mixture was added saturated aqueous ammonium chloride solution, and the mixture was extracted with EtOAc. The organic layer was separated, washed with water and saturated brine, dried over anhydrous sodium sulfate, and concentrated under reduced pressure. The residue was purified by silica gel column chromatography (NH, EtOAc/hexane) to give the title compound (144 mg).

MS: [M−H]$^-$ 423.0.

B) N-{(2S,3R)-1-(cyclopropanecarbonyl)-4,4-difluoro-2-[(2,3',5'-trifluoro[1,1'-biphenyl]-3-yl)methyl]pyrrolidin-3-yl}ethanesulfonamide To a mixture of N-[(2S,3R)-2-[(3-chloro-2-fluorophenyl)methyl]-1-(cyclopropanecarbonyl)-4,4-difluoropyrrolidin-3-yl]ethanesulfonamide (16.0 mg), (3,5-difluorophenyl)boronic acid (12.0 mg), 1 M aqueous potassium phosphate solution (0.116 mL) and DME (0.500 mL) was added XPhos Pd G3 (3.2 mg) at room temperature. The mixture was stirred overnight under nitrogen atmosphere at 90° C., and purified by silica gel column chromatography (NH, EtOAc/hexane) to give the title compound (15.0 mg).
$^1$H NMR (400 MHz, CDCl$_3$) δ 0.43-1.49 (8H, m), 2.85-5.03 (9H, m), 6.72-7.61 (6H, m).

Example 145

N'-[(2S,3R)-4,4-difluoro-2-[(2-fluoro[1,1'-biphenyl]-3-yl)methyl]-1-(1-hydroxycyclobutane-1-carbonyl)pyrrolidin-3-yl]-N,N-dimethylsulfuric Diamide A) tert-butyl (2S,3R)-3-[(dimethylsulfamoyl)amino]-4,4-difluoro-2-[(2-fluoro[1,1'-biphenyl]-3-yl)methyl]pyrrolidine-1-carboxylate A mixture of dimethylsulfamoyl chloride (3 mL), tert-butyl (2S,3R)-3-amino-4,4-difluoro-2-((2-fluoro-[1,1'-biphenyl]-3-yl)methyl)pyrrolidine-1-carboxylate (400 mg) and DMAP (240 mg) was stirred overnight at 50° C. under nitrogen atmosphere. The reaction mixture was purified by column chromatography (NH silica gel, eluted with EtOAc/hexane) to give the title compound (500 mg).
MS: [M−H]$^-$ 512.1.

B) N'-{(2S,3R)-4,4-difluoro-2-[(2-fluoro[1,1'-biphenyl]-3-yl)methyl]pyrrolidin-3-yl}-N,N-dimethylsulfuric Diamide Hydrochloride A mixture of 4 M HCl/CPME solution (12.2 mL) and tert-butyl (2S,3R)-3-[(dimethylsulfamoyl)amino]-4,4-difluoro-2-[(2-fluoro[1,1'-biphenyl]-3-yl)methyl]pyrrolidine-1-carboxylate (500 mg) was stirred overnight at 45° C. under nitrogen atmosphere. The reaction mixture was concentrated, and the solids were washed with EtOAc and filtered to afford the title compound (435 mg).
MS: [M+H]$^+$ 414.0.

C) N'-[(2S,3R)-4,4-difluoro-2-[(2-fluoro[1,1'-biphenyl]-3-yl)methyl]-1-(1-hydroxycyclobutane-1-carbonyl)pyrrolidin-3-yl]-N,N-dimethylsulfuric Diamide To a solution of N'-{(2S,3R)-4,4-difluoro-2-[(2-fluoro[1,1'-biphenyl]-3-yl)methyl]pyrrolidin-3-yl}-N,N-dimethylsulfuric diamide hydrochloride (20 mg), 1-hydroxy-cyclobutanecarboxylic acid (5.16 mg) and DIPEA (7.76 μL) in DMF (1 mL) was added HATU (16.9 mg) at room temperature. The mixture was stirred overnight at room temperature. The mixture was quenched with saturated aqueous sodium hydrogen carbonate solution and extracted with EtOAc. The organic layer was separated, washed with water and saturated brine, dried over magnesium sulfate and concentrated under reduced pressure. The residue was purified by column chromatography (NH silica gel, eluted with EtOAc/hexane) to give the title compound (12.7 mg).
$^1$H NMR (400 MHz, CDCl$_3$) δ 1.40-1.59 (1H, m), 1.74-1.91 (1H, m), 1.92-2.08 (2H, m), 2.47-2.60 (2H, m), 2.69-2.75 (6H, m), 2.89-3.02 (2H, m), 3.06-3.22 (1H, m), 3.90-4.07 (1H, m), 4.08-4.22 (1H, m), 4.22-4.43 (1H, m), 5.04 (2H, brs), 7.10-7.19 (1H, m), 7.24-7.38 (3H, m), 7.39-7.45 (2H, m), 7.48-7.53 (2H, m).

Example 146

N-{(2S,3R)-4,4-difluoro-1-(2-methylpropanoyl)-2-[(2,3',5'-trifluoro[1,1'-biphenyl]-3-yl)methyl]pyrrolidin-3-yl}ethanesulfonamide A) N-[(2S,3R)-2-[(3-chloro-2-fluorophenyl)methyl]-4,4-difluoro-1-(2-methylpropanoyl)pyrrolidin-3-yl]ethanesulfonamide To a mixture of N-{(2S,3R)-2-[(3-chloro-2-fluorophenyl)methyl]-4,4-difluoropyrrolidin-3-yl}ethanesulfonamide hydrochloride (47.9 mg), isobutyric acid (20.2 mg), DIPEA (0.080 mL) and DMF (0.80 mL) was added HATU (96.2 mg) at room temperature. The mixture was stirred overnight at room temperature. The mixture was diluted with saturated aqueous sodium hydrogen carbonate solution and extracted with EtOAc. The organic layer was separated, washed with water and saturated brine, dried over sodium sulfate and concentrated under reduced pressure. The residue was purified by column chromatography (NH silica gel, eluted with EtOAc/hexane) to give the title compound (44.6 mg).
MS: [M+H]$^+$ 427.0.

B) N-{(2S,3R)-4,4-difluoro-1-(2-methylpropanoyl)-2-[(2,3',5'-trifluoro[1,1'-biphenyl]-3-yl)methyl]pyrrolidin-3-yl}ethanesulfonamide To a mixture of N-[(2S,3R)-2-[(3-chloro-2-fluorophenyl)methyl]-4,4-difluoro-1-(2-methylpropanoyl)pyrrolidin-3-yl]ethanesulfonamide (15.9 mg), (3,5-difluorophenyl)boronic acid (12.0 mg), 1 M aqueous potassium phosphate solution (0.100 mL) and DME (0.300 mL) was added XPhos Pd G3 (3.0 mg) at room temperature. The mixture was stirred overnight at 90° C. under nitrogen atmosphere. The mixture was purified by column chromatography (NH silica gel, eluted with EtOAc/hexane) to give the title compound (13.4 mg).
$^1$H NMR (400 MHz, CDCl$_3$) δ 0.52 (1H, d, J=6.4 Hz), 0.85-1.49 (8H, m), 1.82-5.09 (10H, m), 6.75-7.55 (6H, m).

Example 147

N-{(2S,3R)-4,4-difluoro-1-(2-methylpropanoyl)-2-[(2,2',5'-trifluoro[1,1'-biphenyl]-3-yl)methyl]pyrrolidin-3-yl}ethanesulfonamide To a mixture of N-[(2S,3R)-2-[(3-chloro-2-fluorophenyl)methyl]-4,4-difluoro-1-(2-methylpropanoyl)pyrrolidin-3-yl]ethanesulfonamide (14.5 mg), (2,5-difluorophenyl)boronic acid (10.0 mg), 1 M aqueous potassium phosphate solution (0.100 mL) and DME (0.300 mL) was added XPhos Pd G3 (3.0 mg) at room temperature. The mixture was stirred overnight under nitrogen atmosphere at 90° C. Additionally, to the mixture were added (2,5-difluorophenyl)boronic acid (10.0 mg) and XPhos Pd G3 (3.0 mg) at room temperature. The mixture was stirred at 120° C. for 20 min under microwave irradiation. The mixture was purified by column chromatography (NH silica gel, eluted with EtOAc/hexane) to give the title compound (9.70 mg).

$^1$H NMR (400 MHz, CDCl$_3$) δ 0.53 (1H, d, J=6.5 Hz), 0.83-1.48 (8H, m), 1.90-5.01 (10H, m), 6.98-7.55 (6H, m).

Example 171

N-[(2S,3R)-4,4-difluoro-2-[(2-fluoro[1,1'-biphenyl]-3-yl)methyl]-1-(2-methylpropanoyl)pyrrolidin-3-yl]cyclopropanesulfonamide To a mixture of N-{(2S,3R)-4,4-difluoro-2-[(2-fluoro[1,1'-biphenyl]-3-yl)methyl]pyrrolidin-3-yl}cyclopropanesulfonamide hydrochloride (44.3 mg), isobutyric acid (15 μL), DIPEA (50 μL) and DMF (0.80 mL) was added HATU (60.0 mg) at room temperature. The mixture was stirred at room temperature for 3 days. To the mixture was added saturated aqueous sodium hydrogen carbonate solution, and the mixture was extracted with EtOAc. The organic layer was separated, washed with water and saturated brine, dried over sodium sulfate and concentrated under reduced pressure. The residue was purified by column chromatography (NH silica gel, eluted with EtOAc/hexane) to give the title compound (30.6 mg).

$^1$H NMR (400 MHz, CDCl$_3$) δ 0.52 (1H, d, J=6.5 Hz), 0.76-1.39 (9H, m), 1.84-5.16 (9H, m), 6.98-7.54 (8H, m).

Example 202

N-{(2S,3R)-1-(cyclopropanecarbonyl)-2-[(2,3'-difluoro[1,1'-biphenyl]-3-yl)methyl]-4,4-difluoropyrrolidin-3-yl}ethanesulfonamide A mixture of N-[(2S,3R)-2-[(3-chloro-2-fluorophenyl)methyl]-1-(cyclopropanecarbonyl)-4,4-difluoropyrrolidin-3-yl]ethanesulfonamide (15 mg), (3-fluorophenyl)boronic acid (9.88 mg), XPhos Pd G3 (2.99 mg) and 1 M aqueous potassium phosphate solution (0.106 mL) in DME (1 mL) was stirred at 80° C. for 2 h. After cooling back to room temperature, the solvent was removed under reduced pressure, and the residue was purified by column chromatography (NH silica gel, eluted with EtOAc/hexane) to give the title compound (17.1 mg).

$^1$H NMR (400 MHz, CDCl$_3$) δ 0.05-1.49 (8H, m), 2.86-5.01 (9H, m), 7.04-7.44 (7H, m).

Example 205

N-{(2S,3R)-1-(cyclopropanecarbonyl)-4,4-difluoro-2-[(2-fluoro[1,1'-biphenyl]-3-yl)methyl]pyrrolidin-3-yl}ethanesulfonamide A mixture of N-[(2S,3R)-2-[(3-chloro-2-fluorophenyl)methyl]-1-(cyclopropanecarbonyl)-4,4-difluoropyrrolidin-3-yl]ethanesulfonamide (13 mg), phenylboronic acid (7.46 mg), XPhos Pd G3 (2.59 mg) and 1 M aqueous potassium phosphate solution (0.092 mL) in DME (1 mL) was stirred at 80° C. for 2 h. After cooling back to room temperature, the solvent was removed under reduced pressure, and the residue was purified by column chromatography (NH silica gel, eluted with EtOAc/hexane) to give the title compound (4.90 mg).

$^1$H NMR (400 MHz, CDCl$_3$) δ −0.13-0.18 (2H, m), 0.49-1.48 (6H, m), 2.83-4.97 (9H, m), 7.15-7.54 (8H, m).

Example 210

(2S,3R,4S)-2-[(2,3'-difluoro[1,1'-biphenyl]-3-yl)methyl]-3-[(ethanesulfonyl)amino]-4-fluoro-N,N-dimethylpyrrolidine-1-carboxamide A) tert-butyl 2-[(3-chloro-2-fluorophenyl)methyl]-1H-pyrrole-1-carboxylate To a mixture of 1-(bromomethyl)-3-chloro-2-fluorobenzene (40.0 g), (1-(tert-butoxycarbonyl)-1H-pyrrol-2-yl)boronic acid (49.1 g), 1 M aqueous potassium phosphate solution (537 mL) and THF (900 mL) was added PdCl$_2$(dppf) (2.62 g) under argon atmosphere at room temperature. The mixture was refluxed for 16 hr, poured into ice water, and extracted with EtOAc. The organic layer was separated, washed with water and saturated brine, dried over anhydrous magnesium sulfate, and concentrated under reduced pressure. The residue was purified by silica gel column chromatography (EtOAc/hexane) to give the title compound (54.7 g).

MS: [M−H]$^−$ 308.0.

B) 2-[(3-chloro-2-fluorophenyl)methyl]-1H-pyrrole

To a mixture of tert-butyl 2-[(3-chloro-2-fluorophenyl)methyl]-1H-pyrrole-1-carboxylate (54.7 g) and MeOH (250 mL) was added 28% sodium methoxide methanol solution (170 g) under argon atmosphere at room temperature. The mixture was stirred at room temperature for 5 hr, and the reaction mixture was added to aqueous ammonium chloride solution under ice cooling, and extracted with EtOAc. The organic layer was separated, washed with water and saturated brine, dried over anhydrous magnesium sulfate, and concentrated under reduced pressure to give the title compound (35.9 g).

MS: [M+H]$^+$ 209.9.

C) benzyl 2-[(3-chloro-2-fluorophenyl)methyl]-2,5-dihydro-1H-pyrrole-1-carboxylate To a mixture of 2-[(3-chloro-2-fluorophenyl)methyl]-1H-pyrrole (35.9 g), zinc (112 g) and EtOH (500 mL) was added dropwise conc. hydrochloric acid (171 mL) at 85° C. The mixture was stirred at 85° C. for 30 min, and the reaction mixture was poured into ice water, and basified with 8 M aqueous sodium hydroxide solution (pH=8). The insoluble substance was removed by filtration, and the filtrate was extracted with EtOAc/THF. The organic layer was separated, washed with saturated brine, dried over anhydrous magnesium sulfate, and concentrated under reduced pressure. To a mixture of the obtained residue, THF (400 mL) and water (400 mL) were added sodium hydrogen carbonate (21.6 g) and 1-(((benzyloxy)carbonyl)oxy)pyrrolidine-2,5-dione (44.8 g) at room temperature. The mixture was stirred at room temperature for 15 hr, and the reaction mixture was poured into water, and extracted with EtOAc. The organic layer was separated, washed with water and saturated brine, dried over anhydrous magnesium sulfate, and concentrated under reduced pressure. The residue was purified by silica gel column chromatography (EtOAc/hexane), and then silica gel column chromatography (NH, EtOAc/hexane) to give the title compound (25.7 g).

MS: [M+H]$^+$ 346.0.

D) rac-benzyl (1S,2S,5R)-2-[(3-chloro-2-fluorophenyl)methyl]-6-oxa-3-azabicyclo[3.1.0]hexane-3-carboxylate To a mixture of benzyl 2-[(3-chloro-2-fluorophenyl)methyl]-2,5-dihydro-1H-pyrrole-1-carboxylate (25.7 g), 1,1,1-trifluoroacetone (70.3 g), sodium 2,2'-((2-(bis(carboxymethyl)amino)ethyl)imino)diacetate dihydrate (0.055 g) and CH₃CN (180 mL)/water (120 mL) were added potassium peroxymonosulfate (137 g) and sodium hydrogen carbonate (94 g) over 35 min at 0° C. The mixture was vigorously stirred at 0° C. for 2 hr 30 min, poured into ice water, and extracted with EtOAc. The organic layer was separated, washed with water and saturated brine, dried over anhydrous magnesium sulfate, and concentrated under reduced pressure. The residue was purified by silica gel column chromatography (EtOAc/hexane), and then silica gel column chromatography (NH, EtOAc/hexane) to give the title compound (24.6 g).

MS: [M+H]⁺ 362.0.

E) rac-benzyl (2S,3S,4S)-2-[(3-chloro-2-fluorophenyl)methyl]-4-fluoro-3-hydroxypyrrolidine-1-carboxylate A mixture of rac-benzyl (1S,2S,5R)-2-[(3-chloro-2-fluorophenyl)methyl]-6-oxa-3-azabicyclo[3.1.0]hexane-3-carboxylate (24.0 g) and N,N-diethylethanamine trihydrofluoride (64.1 g) was stirred at 120° C. for 17 hr. The mixture was poured into ice water, and extracted with EtOAc. The organic layer was separated, washed with aqueous sodium hydrogen carbonate solution and saturated brine, dried over anhydrous magnesium sulfate, and concentrated under reduced pressure. The residue was purified by silica gel column chromatography (EtOAc/hexane) to give the title compound (24.2 g).

MS: [M+H]⁺ 382.0.

F) rac-benzyl (2S,3S,4S)-2-[(3-chloro-2-fluorophenyl)methyl]-4-fluoro-3-[(trifluoromethanesulfonyl)oxy]pyrrolidine-1-carboxylate To a mixture of rac-benzyl (2S,3S,4S)-2-[(3-chloro-2-fluorophenyl)methyl]-4-fluoro-3-hydroxypyrrolidine-1-carboxylate (24.2 g), pyridine (100 g) and Et₂O (370 mL) was added dropwise trifluoromethanesulfonic anhydride (53.6 g) under argon atmosphere at 0° C. The mixture was stirred at room temperature for 2 hr 30 min, poured into ice water, and extracted with EtOAc. The organic layer was separated, washed successively with 10% aqueous citric acid solution, aqueous sodium hydrogen carbonate solution and saturated brine, dried over anhydrous magnesium sulfate, and concentrated under reduced pressure. The residue was purified by silica gel column chromatography (EtOAc/hexane) to give the title compound (29.0 g).

MS: [M+H]⁺ 514.0.

G) rac-benzyl (2S,3R,4S)-3-azido-2-[(3-chloro-2-fluorophenyl)methyl]-4-fluoropyrrolidine-1-carboxylate To a mixture of rac-benzyl (2S,3S,4S)-2-[(3-chloro-2-fluorophenyl)methyl]-4-fluoro-3-[(trifluoromethanesulfonyl)oxy]pyrrolidine-1-carboxylate (29.0 g) and CH₃CN (335 mL) was added tetra-n-butylammonium azide (48.2 g) at room temperature. The mixture was stirred at 80° C. for 1 hr, poured into ice water, and extracted with EtOAc. The organic layer was separated, washed with water and saturated brine, dried over anhydrous magnesium sulfate, and concentrated under reduced pressure. The residue was purified by silica gel column chromatography (EtOAc/hexane) to give the title compound (22.2 g).

MS: [M+H]⁺ 407.0.

H) rac-benzyl (2S,3R,4S)-3-amino-2-[(3-chloro-2-fluorophenyl)methyl]-4-fluoropyrrolidine-1-carboxylate To a mixture of rac-benzyl (2S,3R,4S)-3-azido-2-[(3-chloro-2-fluorophenyl)methyl]-4-fluoropyrrolidine-1-carboxylate (2.17 g) and THF (42.7 mL)/water (10.7 mL) was added triphenylphosphine (1.68 g) at room temperature. The mixture was stirred at 50° C. for 15 hr, to the mixture was added saturated brine at room temperature, and the mixture was extracted with EtOAc. The organic layer was separated, washed with saturated brine, dried over anhydrous magnesium sulfate, and concentrated under reduced pressure. The residue was purified by silica gel column chromatography (methanol/EtOAc) to give the title compound (1.74 g).

MS: [M+H]⁺ 381.0.

I) benzyl (2S,3R,4S)-3-amino-2-[(3-chloro-2-fluorophenyl)methyl]-4-fluoropyrrolidine-1-carboxylate rac-Benzyl (2S,3R,4S)-3-amino-2-[(3-chloro-2-fluorophenyl)methyl]-4-fluoropyrrolidine-1-carboxylate (668 mg) was resolved by HPLC (column: CHIRALPAK ID, 50 mmID×500 mmL, 20 μm, mobile phase: hexane/2-propanol/diethylamine=600/400/1) to give the title compound (251 mg) with longer retention time.

MS: [M+H]⁺ 381.1.

J) benzyl (2S,3R,4S)-2-[(3-chloro-2-fluorophenyl)methyl]-3-[(ethanesulfonyl)amino]-4-fluoropyrrolidine-1-carboxylate To a mixture of benzyl (2S,3R,4S)-3-amino-2-[(3-chloro-2-fluorophenyl)methyl]-4-fluoropyrrolidine-1-carboxylate (289 mg), TEA (189 mg) and THF (4.0 mL) was added ethanesulfonyl chloride (190 mg) at 0° C. The mixture was stirred at room temperature for 2 hr, to the mixture was added water, and the mixture was extracted with EtOAc. The organic layer was separated, washed with water and saturated brine, dried over anhydrous sodium sulfate, and concentrated under reduced pressure. The residue was purified by silica gel column chromatography (EtOAc/hexane) to give the title compound (295 mg).

MS: [M+H]⁺ 473.0.

K) benzyl (2S,3R,4S)-2-[(2,3'-difluoro[1,1'-biphenyl]-3-yl)methyl]-3-[(ethanesulfonyl)amino]-4-fluoropyrrolidine-1-carboxylate To a mixture of benzyl (2S,3R,4S)-2-[(3-chloro-2-fluorophenyl)methyl]-3-[(ethanesulfonyl)amino]-4-fluoropyrrolidine-1-carboxylate (340 mg), (3-fluorophenyl)boronic acid (150 mg), XPhos Pd G3 (30.9 mg) and DME (4.0 ml) was added 1 M aqueous potassium phosphate solution (1.2 mL) at room temperature, and the mixture was stirred under nitrogen atmosphere at 90° C. for 2 hr. To the reaction mixture were added 1 M aqueous potassium phosphate solution (0.4 mL), (3-fluorophenyl)boronic acid (50.5 mg) and XPhos Pd G3 (15.2 mg) at 90° C. The mixture was stirred under nitrogen atmosphere at 90° C. for 1 hr, to the reaction mixture was added water, and the mixture was extracted with EtOAc. The organic layer was separated, washed with water and saturated brine, dried over anhydrous sodium sulfate, and concentrated under reduced pressure. The residue was purified by silica gel column chromatography (EtOAc/hexane) to give the title compound (250 mg).
MS: [M+H]⁺ 533.2.

L) N-{(2S,3R,4S)-2-[(2,3'-difluoro[1,1'-biphenyl]-3-yl)methyl]-4-fluoropyrrolidin-3-yl}ethanesulfonamide A mixture of benzyl (2S,3R,4S)-2-[(2,3'-difluoro[1,1'-biphenyl]-3-yl)methyl]-3-[(ethanesulfonyl)amino]-4-fluoropyrrolidine-1-carboxylate (240 mg), 10% palladium on carbon (24.0 mg) and MeOH (5.0 mL)/THF (3.0 mL) was stirred overnight under normal pressure of hydrogen atmosphere at room temperature. The catalyst was removed by filtration, and the filtrate was concentrated under reduced pressure to give the title compound (178 mg).
MS: [M+H]⁺ 399.0.

M) (2S,3R,4S)-2-[(2,3'-difluoro[1,1'-biphenyl]-3-yl)methyl]-3-[(ethanesulfonyl)amino]-4-fluoro-N,N-dimethylpyrrolidine-1-carboxamide To a mixture of N-{(2S,3R,4S)-2-[(2,3'-difluoro[1,1'-biphenyl]-3-yl)methyl]-4-fluoropyrrolidin-3-yl}ethanesulfonamide (10.0 mg), DIPEA (22.2 mg) and THF (0.200 mL) was added dimethylcarbamoyl chloride (11.7 mg) at 0° C. The mixture was stirred at room temperature for 3 hr, and the reaction solution was dried by blowing of nitrogen. The residue was purified by silica gel column chromatography (EtOAc/hexane) to give the title compound (6.7 mg).
¹H NMR (400 MHz, CDCl₃) δ 0.81-1.44 (3H, m), 2.59-4.17 (13H, m), 4.73-4.90 (2H, m), 5.06-5.27 (1H, m), 6.98-7.53 (7H, m).

Example 211

N-{(2S,3R,4S)-1-(azetidine-1-carbonyl)-2-[(2,3'-difluoro[1,1'-biphenyl]-3-yl)methyl]-4-fluoropyrrolidin-3-yl}ethanesulfonamide To a mixture of N-{(2S,3R,4S)-2-[(2,3'-difluoro[1,1'-biphenyl]-3-yl)methyl]-4-fluoropyrrolidin-3-yl}ethanesulfonamide (8.9 mg), bis(trichloromethyl) carbonate (4.0 mg) and THF (0.200 mL) was added DIPEA (7.40 mg) at 0° C. The mixture was stirred at 0° C. for 30 min, and the reaction solution was concentrated under reduced pressure. The obtained residue was diluted with THF (0.200 mL), azetidine (3.83 mg) was added thereto at room temperature, and the mixture was stirred at room temperature for 1 hr. The mixture was dried by blowing of nitrogen, and the residue was purified by silica gel column chromatography (EtOAc/hexane) to give the title compound (4.8 mg).
¹H NMR (400 MHz, CDCl₃) δ 0.81-1.35 (3H, m), 2.06-2.16 (2H, m), 2.85-4.23 (11H, m), 4.64-5.29 (3H, m), 6.98-7.54 (7H, m).

Example 212

N-{(2S,3R,4S)-1-(cyclopropanecarbonyl)-2-[(2,3'-difluoro[1,1'-biphenyl]-3-yl)methyl]-4-fluoropyrrolidin-3-yl}ethanesulfonamide To a mixture of N-{(2S,3R,4S)-2-[(2,3'-difluoro[1,1'-biphenyl]-3-yl)methyl]-4-fluoropyrrolidin-3-yl}ethanesulfonamide (11.6 mg), cyclopropanecarboxylic acid (4.6 mg), DIPEA (11.8 mg) and DMF (0.200 mL) was added HATU (20.5 mg) at room temperature. The mixture was stirred overnight at room temperature, to the mixture was added water, and the mixture was extracted with EtOAc. The organic layer was dried by blowing of nitrogen. The residue was purified by silica gel column chromatography (EtOAc/hexane) to give the title compound (8.4 mg).
¹H NMR (400 MHz, CDCl₃) δ 0.05-1.47 (7H, m), 2.64-5.43 (11H, m), 6.98-7.54 (7H, m).

Example 220

N-{(2S,3R,4S)-4-fluoro-1-(2-hydroxy-2-methylpropanoyl)-2-[(2,3',5'-trifluoro[1,1'-biphenyl]-3-yl)methyl]pyrrolidin-3-yl}ethanesulfonamide A) N-{(2S,3R,4S)-2-[(3-chloro-2-fluorophenyl)methyl]-4-fluoropyrrolidin-3-yl}ethanesulfonamide Hydrobromide To benzyl (2S,3R,4S)-2-[(3-chloro-2-fluorophenyl)methyl]-3-[(ethanesulfonyl)amino]-4-fluoropyrrolidine-1-carboxylate (78 mg) was added 30% hydrogen bromide-acetic acid solution (0.8 mL) at room temperature. The mixture was stirred at room temperature for 1 hr, and the reaction solution was concentrated under reduced pressure. The obtained residue was subjected to azeotrope with toluene, and suspended in IPE, and the insoluble substance was collected by filtration to give the title compound (65 mg).
MS, found: 338.9.

B) N-[(2S,3R,4S)-2-[(3-chloro-2-fluorophenyl)methyl]-4-fluoro-1-(2-hydroxy-2-methylpropanoyl)pyrrolidin-3-yl]ethanesulfonamide To a mixture of N-{(2S,3R,4S)-2-[(3-chloro-2-fluorophenyl)methyl]-4-fluoropyrrolidin-3-yl}ethanesulfonamide hydrobromide (65 mg), DIPEA (60.0 mg) and THF (0.8 mL) was added 1-chloro-2-methyl-1-oxopropan-2-yl acetate (30.6 mg) at 0° C. The mixture was stirred at the same temperature for 1 hr, and water (0.4 mL) and 4 M aqueous lithium hydroxide solution (0.387 mL) were added thereto at 0° C. The mixture was stirred at room temperature for 1 hr, to the mixture was added water, and the mixture was extracted with EtOAc. The organic layer was separated, washed with saturated brine, dried over anhydrous magnesium sulfate, and concentrated under reduced pressure to give the title compound (66 mg).
MS: [M+H]⁺ 425.0.

C) N-{(2S,3R,4S)-4-fluoro-1-(2-hydroxy-2-methylpropanoyl)-2-[(2,3',5'-trifluoro[1,1'-biphenyl]-3-yl)methyl]pyrrolidin-3-yl}ethanesulfonamide A mixture of N-[(2S,3R,4S)-2-[(3-chloro-2-fluorophenyl)methyl]-4-fluoro-1-(2-hydroxy-2-methylpropanoyl)pyrrolidin-3-yl]ethanesulfonamide (22 mg), (3,5-difluorophenyl) boronic acid (16.4 mg), XPhos Pd G3 (4.38 mg), 1 M aqueous potassium phosphate solution (0.155 mL) and DME (0.8 mL) was stirred under nitrogen atmosphere at 80° C. for 1 hr. The mixture was purified by silica gel column chromatography (EtOAc/hexane), and then silica gel column chromatography (NH, EtOAc/hexane) to give the title compound (20.2 mg).
¹H NMR (400 MHz, CDCl₃) δ 1.20 (3H, t, J=7.0 Hz), 1.40 (6H, s), 2.85 (2H, q, J=6.9 Hz), 3.02 (2H, dd, J=13.4, 6.1

Hz), 3.22 (1H, dd, J=13.9, 7.8 Hz), 3.96-4.30 (3H, m), 4.75-5.02 (2H, m), 5.10-5.32 (1H, m), 6.82 (1H, t, J=8.9 Hz), 7.02-7.13 (2H, m), 7.16-7.23 (1H, m), 7.27-7.50 (2H, m).

Example 225

N-[(2S,3R)-2-[(2,3'-difluoro[1,1'-biphenyl]-3-yl)methyl]-4,4-difluoro-1-((1r,3S)-3-fluorocyclobutane-1-carbonyl)pyrrolidin-3-yl]ethanesulfonamide A) N-{(2S,3R)-2-[(3-chloro-2-fluorophenyl)methyl]-4,4-difluoro-1-[(1r,3S)-3-fluorocyclobutane-1-carbonyl]pyrrolidin-3-yl}ethanesulfonamide To a solution of N-{(2S,3R)-2-[(3-chloro-2-fluorophenyl)methyl]-4,4-difluoropyrrolidin-3-yl}ethanesulfonamide hydrochloride (0.310 g) and 3-fluorocyclobutane-1-carboxylic acid (0.128 mL) in DMF (10 mL) were added HATU (0.450 g) and DIPEA (0.551 mL) at room temperature. The mixture was stirred overnight at room temperature. The mixture was quenched with aqueous saturated ammonium chloride solution and extracted with EtOAc. The organic layer was separated, washed with water and saturated brine, dried over sodium sulfate and concentrated under reduced pressure. The residue was purified by column chromatography (NH silica gel, eluted with EtOAc/hexane), and then purified by preparative HPLC (Column: CHIRALCEL OD-H, mobile phase: carbon dioxide/(MeOH/diethylamine=1000/3)=850/150 (v/v) to give the title compound (177 mg) with shorter retention time by HPLC (Column: CHIRALCEL OD-H, mobile phase: carbon dioxide/(MeOH/diethylamine=1000/3)=850/150 (v/v)).

MS: [M+H]+ 457.1.

B) N-[(2S,3R)-2-[(2,3'-difluoro[1,1'-biphenyl]-3-yl)methyl]-4,4-difluoro-1-((1r,3S)-3-fluorocyclobutane-1-carbonyl)pyrrolidin-3-yl]ethanesulfonamide To a mixture of N-{(2S,3R)-2-[(3-chloro-2-fluorophenyl)methyl]-4,4-difluoro-1-[(1r,3S)-3-fluorocyclobutane-1-carbonyl]pyrrolidin-3-yl}ethanesulfonamide (50 mg), (3-fluorophenyl)boronic acid (30.6 mg) and XPhos Pd G3 (9.26 mg) were added DME (2 mL) and 1 M aqueous potassium phosphate solution (0.328 mL) at room temperature. The mixture was stirred at 80° C. under nitrogen atmosphere for 1 h. After cooling back to room temperature, the solvent was removed under reduced pressure, and the residue was purified by column chromatography (NH silica gel, eluted with EtOAc/hexane) to give the title compound (54.1 mg).

$^1$H NMR (400 MHz, CDCl$_3$) δ 1.29-1.48 (3H, m), 1.55-2.03 (2H, m), 2.25-3.26 (7H, m), 3.33-4.55 (4H, m), 4.88-5.24 (2H, m), 7.03-7.48 (7H, m).

Example 226

N-[(2S,3R)-2-[(2,3'-difluoro[1,1'-biphenyl]-3-yl)methyl]-4,4-difluoro-1-((1s,3R)-3-fluorocyclobutane-1-carbonyl)pyrrolidin-3-yl]ethanesulfonamide A) N-{(2S,3R)-2-[(3-chloro-2-fluorophenyl)methyl]-4,4-difluoro-1-[(1s,3R)-3-fluorocyclobutane-1-carbonyl]pyrrolidin-3-yl}ethanesulfonamide To a solution of N-{(2S,3R)-2-[(3-chloro-2-fluorophenyl)methyl]-4,4-difluoropyrrolidin-3-yl}ethanesulfonamide hydrochloride (0.310 g) and 3-fluorocyclobutane-1-carboxylic acid (0.128 mL) in DMF (10 mL) were added HATU (0.450 g) and DIPEA (0.551 mL) at room temperature. The mixture was stirred overnight at room temperature. The mixture was quenched with aqueous saturated ammonium chloride solution and extracted with EtOAc. The organic layer was separated, washed with water and saturated brine, dried over sodium sulfate and concentrated under reduced pressure. The residue was purified by column chromatography (NH silica gel, eluted with EtOAc/hexane), and then purified by preparative HPLC (Column: CHIRALCEL OD-H, mobile phase: carbon dioxide/(MeOH/diethylamine=1000/3)=850/150 (v/v) to give the title compound (134 mg) with longer retention time by HPLC (Column: CHIRALCEL OD-H, mobile phase: carbon dioxide/(MeOH/diethylamine=1000/3)=850/150 (v/v)).

MS: [M+H]+ 457.1.

B) N-[(2S,3R)-2-[(2,3'-difluoro[1,1'-biphenyl]-3-yl)methyl]-4,4-difluoro-1-((1s,3R)-3-fluorocyclobutane-1-carbonyl)pyrrolidin-3-yl]ethanesulfonamide A mixture of N-{(2S,3R)-2-[(3-chloro-2-fluorophenyl)methyl]-4,4-difluoro-1-[(1s,3R)-3-fluorocyclobutane-1-carbonyl]pyrrolidin-3-yl}ethanesulfonamide (45 mg), (3-fluorophenyl)boronic acid (17.9 mg), XPhos Pd G3 (8.34 mg) and 1 M aqueous potassium phosphate solution (0.295 mL) in DME (2 mL) was stirred at 80° C. for 2 h. After cooling back to room temperature, the solvent was removed under reduced pressure, and the residue was purified by column chromatography (NH silica gel, eluted with EtOAc/hexane). The residue was crystallized from EtOAc/hexane to give the title compound (19.5 mg).

$^1$H NMR (400 MHz, CDCl$_3$) δ 1.29-1.47 (3H, m), 1.80-3.92 (11H, m), 4.19-5.01 (4H, m), 7.02-7.46 (7H, m).

Example 236

N-{(2S,3R,4S)-1-(cyclopropanecarbonyl)-4-fluoro-2-[(2,3',5'-trifluoro[1,1'-biphenyl]-3-yl)methyl]pyrrolidin-3-yl}ethanesulfonamide A) N-[(2S,3R,4S)-2-[(3-chloro-2-fluorophenyl)methyl]-1-(cyclopropanecarbonyl)-4-fluoropyrrolidin-3-yl]ethanesulfonamide A mixture of benzyl (2S,3R,4S)-2-[(3-chloro-2-fluorophenyl)methyl]-3-[(ethanesulfonyl)amino]-4-fluoropyrrolidine-1-carboxylate (179 mg) and 30% hydrogen bromide/acetic acid solution (2.0 mL) was stirred overnight at room temperature. Toluene (20 mL) was added thereto, and the mixture was concentrated under reduced pressure. The residue was diluted with EtOAc, and the insoluble substance was collected by filtration, and washed with EtOAc to give a solid. To a mixture of the obtained solid, THF (2.0 ml) and 2M aqueous sodium hydroxide solution (0.50 ml) was added cyclopropanecarbonyl chloride (81 mg) at room temperature. The mixture was stirred at room temperature for 30 min. To the mixture was added water, and the mixture was extracted with EtOAc. The organic layer was separated, washed with water and saturated brine, dried over anhydrous sodium sulfate, and concentrated under reduced pressure. The residue was purified by silica gel column chromatography (EtOAc/hexane) to give the title compound (88.2 mg).

MS: [M+H]+ 407.0.

B) N-{(2S,3R,4S)-1-(cyclopropanecarbonyl)-4-fluoro-2-[(2,3',5'-trifluoro[1,1'-biphenyl]-3-yl)methyl]pyrrolidin-3-yl}ethanesulfonamide To a mixture of N-[(2S,3R,4S)-2-[(3-chloro-2-fluorophenyl)methyl]-1-(cyclopropanecarbonyl)-4-fluoropyrrolidin-3-yl]ethanesulfonamide (22.0 mg), (3,5-difluorophenyl)boronic acid (17.3 mg), 1M aqueous potassium phosphate solution (0.130 mL) and DME (0.500 mL) was added XPhos Pd G3 (5.0 mg) at room temperature. The mixture was stirred overnight under nitrogen atmosphere at 90° C. The mixture was purified by silica gel column chromatography (NH, EtOAc/hexane), and recrystallized from EtOAc/hexane to give the title compound (13.5 mg).

$^1$H NMR (400 MHz, CDCl$_3$) δ 0.05-1.48 (7H, m), 2.68-4.30 (8H, m), 4.60-5.41 (3H, m), 6.76-7.54 (6H, m).

Example 239

N-{(2S,3R,4S)-1-(cyclopropanecarbonyl)-4-fluoro-2-[(2-fluoro[1,1'-biphenyl]-3-yl)methyl]pyrrolidin-3-yl}ethanesulfonamide To a mixture of N-[(2S,3R,4S)-2-[(3-chloro-2-fluorophenyl)methyl]-1-(cyclopropanecarbonyl)-4-fluoropyrrolidin-3-yl]ethanesulfonamide (22.0 mg), phenylboronic acid (17.0 mg), 1 M aqueous potassium phosphate solution (0.130 mL) and DME (0.500 mL) was added XPhos Pd G3 (6.0 mg) at room temperature. The mixture was stirred overnight under nitrogen atmosphere at 90° C. The mixture was purified by column chromatography (NH silica gel, eluted with EtOAc/hexane), then recrystallization (EtOAc/heptane) to give the title compound (13.2 mg).

$^1$H NMR (400 MHz, CDCl$_3$) δ 0.09-1.47 (7H, m), 2.60-4.31 (8H, m), 4.60-5.38 (3H, m), 6.98-7.57 (8H, m).

Example 245

N-[(2S,3R)-2-[(3'-chloro-2,5'-difluoro[1,1'-biphenyl]-3-yl)methyl]-1-(cyclopropanecarbonyl)-4,4-difluoropyrrolidin-3-yl]methanesulfonamide A) N-[(2S,3R)-2-[(3-chloro-2-fluorophenyl)methyl]-1-(cyclopropanecarbonyl)-4,4-difluoropyrrolidin-3-yl]methanesulfonamide To a solution of N-{(2S,3R)-2-[(3-chloro-2-fluorophenyl)methyl]-4,4-difluoropyrrolidin-3-yl}methanesulfonamide hydrochloride (141 mg) and cyclopropanecarboxylic acid (0.044 mL) in DMF (4 mL) were added HATU (212 mg) and DIPEA (0.260 mL) at room temperature. The mixture was stirred overnight at room temperature. The mixture was quenched with aqueous saturated ammonium chloride solution and extracted with EtOAc. The organic layer was separated, washed with water and saturated brine, dried over sodium sulfate and concentrated under reduced pressure. The residue was purified by column chromatography (NH silica gel, eluted with EtOAc/hexane) to give the title compound (134 mg).

MS: [M+H]$^+$ 411.0.

B) N-[(2S,3R)-2-[(3'-chloro-2,5'-difluoro[1,1'-biphenyl]-3-yl)methyl]-1-(cyclopropanecarbonyl)-4,4-difluoropyrrolidin-3-yl]methanesulfonamide A mixture of N-[(2S,3R)-2-[(3-chloro-2-fluorophenyl)methyl]-1-(cyclopropanecarbonyl)-4,4-difluoropyrrolidin-3-yl]methanesulfonamide (134 mg), 4,4,4',4',5,5,5',5'-octamethyl-2,2'-bi(1,3,2-dioxaborolane) (124 mg), XPhos Pd G3 (55.2 mg) and potassium acetate (64.0 mg) in toluene (4 mL) was stirred at 80° C. under nitrogen atmosphere for 8 h. The reaction mixture was diluted with water and extracted with EtOAc. The extract was washed with saturated brine, dried over magnesium sulfate, filtered and concentrated under reduced pressure. The mixture of the obtained residue (0.041 g), cesium carbonate (0.080 g), 1-bromo-3-chloro-5-fluorobenzene (0.051 g), PdCl$_2$(dppf) (0.012 g) and DME (1 mL)/water (0.300 mL) was stirred in a sealed flask at 80° C. under nitrogen atmosphere for 1 h. The solvent was removed under reduced pressure, and the residue was purified by preparative HPLC (Column: YMC-Actus Triant C18, mobile phase: H$_2$O 10 mM NH$_4$HCO$_3$/CH$_3$CN) to give the title compound (13.8 mg).

$^1$H NMR (400 MHz, CDCl$_3$) δ 0.05-1.47 (5H, m), 2.83-5.42 (10H, m), 7.07-7.47 (6H, m).

Example 248

N-[(2S,3R)-2-[(3'-chloro-2,5'-difluoro[1,1'-biphenyl]-3-yl)methyl]-1-(cyclopropanecarbonyl)-4,4-difluoropyrrolidin-3-yl]ethanesulfonamide A mixture of N-[(2S,3R)-2-[(3-chloro-2-fluorophenyl)methyl]-1-(cyclopropanecarbonyl)-4,4-difluoropyrrolidin-3-yl]ethanesulfonamide (144 mg), 4,4,4',4',5,5,5',5'-octamethyl-2,2'-bi(1,3,2-dioxaborolane) (129 mg), XPhos Pd G3 (57.4 mg) and potassium acetate (66.5 mg) in toluene (4 mL) was stirred at 80° C. under nitrogen atmosphere for 36 h. The reaction mixture was diluted with water and extracted with EtOAc. The extract was washed with saturated brine, dried over magnesium sulfate, filtered and concentrated under reduced pressure. The mixture of the obtained residue (0.043 g), cesium carbonate (0.081 g), 1-bromo-3-chloro-5-fluorobenzene (0.052 g), PdCl$_2$(dppf) (0.012 g) and DME (1 mL)/water (0.300 mL) was stirred in a sealed flask at 80° C. under nitrogen atmosphere for 1 h. The solvent was removed under reduced pressure, and the residue was purified by preparative HPLC (Column: YMC-Actus Triant C18, mobile phase: H$_2$O 10 mM NH$_4$HCO$_3$/CH$_3$CN) to give the title compound (6.00 mg).

$^1$H NMR (400 MHz, CDCl$_3$) δ 0.06-1.51 (8H, m), 2.84-5.44 (9H, m), 7.05-7.48 (6H, m).

Example 249

N-[(2S,3R)-2-[(3'-chloro-2,2'-difluoro[1,1'-biphenyl]-3-yl)methyl]-1-(cyclopropanecarbonyl)-4,4-difluoropyrrolidin-3-yl]ethanesulfonamide A mixture of N-[(2S,3R)-2-[(3-chloro-2-fluorophenyl)methyl]-1-(cyclopropanecarbonyl)-4,4-difluoropyrrolidin-3-yl]ethanesulfonamide (144 mg), 4,4,4',4',5,5,5',5'-octamethyl-2,2'-bi(1,3,2-dioxaborolane) (129 mg), XPhos Pd G3 (57.4 mg) and potassium acetate (66.5 mg) in toluene (4 mL) was stirred at 80° C. under nitrogen atmosphere for 36 h. The reaction mixture was diluted with water and extracted with EtOAc. The extract was washed with saturated brine, dried over magnesium sulfate, filtered and concentrated under reduced pressure. The mixture of the obtained residue (0.043 g), cesium carbonate (0.081 g), 1-bromo-3-chloro-2-fluorobenzene (0.052 g) and PdCl$_2$(dppf) (0.012 g) in DME (1 mL)/water (0.300 mL) was stirred in a sealed flask at 80° C. under nitrogen atmosphere for 1 h. The solvent was removed under reduced pressure, and the residue was purified by preparative HPLC (Column: YMC-Actus Triant C18, mobile phase: H$_2$O 10 mM NH$_4$HCO$_3$/CH$_3$CN) to give the title compound (9.30 mg).

$^1$H NMR (400 MHz, CDCl$_3$) δ −0.11-0.22 (1H, m), 0.47-1.48 (7H, m), 2.79-4.98 (9H, m), 6.95-7.61 (6H, m).

Example 250

N-[(2S,3R)-2-[(3'-chloro-2-fluoro[1,1'-biphenyl]-3-yl)methyl]-1-(cyclopropanecarbonyl)-4,4-difluoropyrrolidin-3-yl]methanesulfonamide A mixture of N-[(2S,3R)-2-[(3-chloro-2-fluorophenyl)methyl]-1-(cyclopropanecarbonyl)-4,4-difluoropyrrolidin-3-yl]methanesulfonamide (134 mg), 4,4,4',4',5,5,5',5'-octamethyl-2,2'-bi(1,3,2-dioxaborolane) (124 mg), XPhos Pd G3 (55.2 mg) and potassium acetate (64.0 mg) in toluene (4 mL) was stirred at 80° C. under nitrogen atmosphere for 8 h. The reaction mixture was diluted with water and extracted with EtOAc. The extract was washed with saturated brine, dried over magnesium sulfate, filtered and concentrated under reduced pressure. The mixture of the obtained residue (0.041 g), cesium carbonate (0.080 g), 1-chloro-3-iodobenzene (0.058 g) and PdCl$_2$(dppf) (0.012 g) in DME (1 mL)/water (0.300 mL) was stirred in a sealed flask at 80° C. under nitrogen atmosphere for 1 h. The solvent was removed under reduced pressure, and the residue was purified by preparative HPLC (Column: YMC-Actus Triant C18, mobile phase: H$_2$O 10 mM NH$_4$HCO$_3$/CH$_3$CN) to give the title compound (0.013 g).

$^1$H NMR (400 MHz, CDCl$_3$) δ 0.07-1.48 (5H, m), 2.76-5.27 (10H, m), 7.12-7.51 (7H, m).

Example 251

N-[(2S,3R)-2-[(5'-chloro-2,2'-difluoro[1,1'-biphenyl]-3-yl)methyl]-1-(cyclopropanecarbonyl)-4,4-difluoropyrrolidin-3-yl]ethanesulfonamide A mixture of N-[(2S,3R)-2-[(3-chloro-2-fluorophenyl)methyl]-1-(cyclopropanecarbonyl)-4,4-difluoropyrrolidin-3-yl]ethanesulfonamide (144 mg), 4,4,4',4',5,5,5',5'-octamethyl-2,2'-bi(1,3,2-dioxaborolane) (129 mg), XPhos Pd G3 (57.4 mg) and potassium acetate (66.5 mg) in toluene (4 mL) was stirred at 80° C. under nitrogen atmosphere for 36 h. The reaction mixture was diluted with water and extracted with EtOAc. The extract was washed with saturated brine, dried over magnesium sulfate, filtered and concentrated under reduced pressure. The mixture of the obtained residue (0.043 g), cesium carbonate (0.081 g, 2-bromo-4-chloro-1-fluorobenzene (0.052 g), PdCl$_2$(dppf) (0.012 g) and DME (1 mL)/water (0.300 mL) was stirred in a sealed flask at 80° C. under nitrogen atmosphere for 1 h. The solvent was removed under reduced pressure, and the residue was purified by preparative HPLC (Column: YMC-Actus Triant C18, mobile phase: H$_2$O 10 mM NH$_4$HCO$_3$/CH$_3$CN) to give the title compound (10.6 mg).

$^1$H NMR (400 MHz, CDCl$_3$) δ 0.11-1.47 (8H, m), 2.77-5.39 (9H, m), 6.97-7.61 (6H, m).

Example 257

N-{(2S,3R)-1-butanoyl-2-[(2,3'-difluoro[1,1'-biphenyl]-3-yl)methyl]-4,4-difluoropyrrolidin-3-yl}ethanesulfonamide To a solution of N-((2S,3R)-2-((2,3'-difluoro-[1,1'-biphenyl]-3-yl)methyl)-4,4-difluoropyrrolidin-3-yl)ethanesulfonamide hydrochloride (0.020 g) and butyric acid (6.08 µL) in DMF (1 mL) were added HATU (0.025 g) and DIPEA (0.031 mL) at room temperature. The mixture was stirred overnight at room temperature. The mixture was quenched with aqueous saturated ammonium chloride solution and extracted with EtOAc. The organic layer was separated, washed with water and saturated brine, dried over sodium sulfate and concentrated under reduced pressure. The residue was purified by column chromatography (NH silica gel, eluted with EtOAc/hexane), and then purified by preparative HPLC (Column: YMC-Actus Triant C18, mobile phase: H$_2$O 10 mM NH$_4$HCO$_3$/CH$_3$CN) to give the title compound (9.90 mg).

$^1$H NMR (300 MHz, DMSO-d$_6$) δ 0.44-0.69 (3H, m), 0.70-1.33 (6H, m), 1.81-2.31 (1H, m), 2.56-3.24 (4H, m), 3.64-4.82 (4H, m), 7.08-7.58 (7H, m), 8.11-8.41 (1H, m).

Example 267

N-[(2S,3R)-2-[(3'-chloro-2-fluoro[1,1'-biphenyl]-3-yl)methyl]-4,4-difluoro-1-(oxetane-2-carbonyl)pyrrolidin-3-yl]ethanesulfonamide with Shorter Retention Time A) tert-butyl (2S,3R)-2-[(3'-chloro-2-fluoro[1,1'-biphenyl]-3-yl)methyl]-3-[(ethanesulfonyl)amino]-4,4-difluoropyrrolidine-1-carboxylate A mixture of tert-butyl (2S,3R)-2-[(3-chloro-2-fluorophenyl)methyl]-3-[(ethanesulfonyl)amino]-4,4-difluoropyrrolidine-1-carboxylate (51 mg), 4,4,4',4',5,5,5',5'-octamethyl-2,2'-bi-1,3,2-dioxaborolane (42.5 mg), XPhos Pd G3 (18.9 mg), potassium acetate (21.9 mg) and toluene (2 ml) was stirred under nitrogen atmosphere at 80° C. for 36 hr. The reaction mixture was diluted with water, and extracted with EtOAc. The organic layer was separated, washed with saturated brine, dried over anhydrous magnesium sulfate, and concentrated under reduced pressure. A mixture of the obtained residue, cesium carbonate (108 mg), 1-chloro-3-iodobenzene (39.3 mg), PdCl$_2$(dppf) (16.1 mg) and DME (1 ml)/water (0.3 mL) was stirred under sealed condition, under nitrogen atmosphere at 80° C. for 1 hr. The solvent was evaporated under reduced pressure, and the residue was purified by silica gel column chromatography (NH, EtOAc/hexane) to give the title compound (22 mg).

MS: [M−H]⁻ 531.1.

B) N-{(2S,3R)-2-[(3'-chloro-2-fluoro[1,1'-biphenyl]-3-yl)methyl]-4,4-difluoropyrrolidin-3-yl}ethanesulfonamide Hydrochloride A mixture of tert-butyl (2S,3R)-2-[(3'-chloro-2-fluoro[1,1'-biphenyl]-3-yl)methyl]-3-[(ethanesulfonyl)amino]-4,4-difluoropyrrolidine-1-carboxylate (22 mg) and 4M hydrogen chloride/CPME solution (15 mL) was stirred overnight at room temperature. The insoluble substance was collected by filtration to give the title compound (4.5 mg).

MS: [M−H]⁻ 431.0.

C) N-[(2S,3R)-2-[(3'-chloro-2-fluoro[1,1'-biphenyl]-3-yl)methyl]-4,4-difluoro-1-(oxetane-2-carbonyl)pyrrolidin-3-yl]ethanesulfonamide with Shorter Retention Time To a mixture of N-{(2S,3R)-2-[(3'-chloro-2-fluoro[1,1'-biphenyl]-3-yl)methyl]-4,4-difluoropyrrolidin-3-yl}ethanesulfonamide hydrochloride (4.5 mg), oxetane-2- carboxylic acid (1.47 mg) and DMF (1 ml) were added HATU (5.47 mg) and DIPEA (4.96 mg) at room temperature. The mixture was stirred overnight at room temperature, and concentrated under reduced pressure. The residue was purified by HPLC (YMC-Actus Triant C18 mobile phase: water/$CH_3CN$ (containing 10 mM ammonium bicarbonate)) to give the title compound (0.4 mg).
$^1$H NMR (300 MHz, DMSO-$d_6$) δ 1.18-1.32 (3H, m), 2.23-2.40 (1H, m), 2.61-3.16 (5H, m), 3.78-5.11 (7H, m), 7.12-7.61 (7H, m), 8.12-8.42 (1H, m).

Example 272

N-{(2S,3R)-4,4-difluoro-1-(1-hydroxycyclobutane-1-carbonyl)-2-[(2,3',5'-trifluoro[1,1'-biphenyl]-3-yl)methyl]pyrrolidin-3-yl}ethanesulfonamide To a solution of N-((2S,3R)-4,4-difluoro-2-((2,3',5'-trifluoro-[1,1'-biphenyl]-3-yl)methyl)pyrrolidin-3-yl)ethanesulfonamide hydrochloride (0.030 g) and 1-hydroxycyclobutane-1-carboxylic acid (10.2 μL) in DMF (1 mL) were added HATU (0.036 g) and DIPEA (0.045 mL) at room temperature. The mixture was stirred overnight at room temperature. The mixture was quenched with aqueous saturated ammonium chloride solution and extracted with EtOAc. The organic layer was separated, washed with water and saturated brine, dried over sodium sulfate and concentrated under reduced pressure. The residue was purified by column chromatography (silica gel, eluted with EtOAc/hexane) to give the title compound (0.016 g).
$^1$H NMR (400 MHz, $CDCl_3$) δ 1.36 (3H, t, J=7.3 Hz), 1.77-1.92 (1H, m), 1.96-2.11 (3H, m), 2.45-2.62 (2H, m), 2.90-3.19 (4H, m), 3.35-3.67 (1H, m), 3.98-4.39 (3H, m), 4.86-5.08 (2H, m), 6.78-6.86 (1H, m), 7.02-7.12 (2H, m), 7.15-7.23 (1H, m), 7.24-7.30 (1H, m), 7.35-7.45 (1H, m).

Example 302

N-[(2S,3R,4S)-4-fluoro-2-[(2-fluoro[1,1'-biphenyl]-3-yl)methyl]-1-((2R)-oxetane-2-carbonyl)pyrrolidin-3-yl]ethanesulfonamide A) benzyl (2S,3R,4S)-3-[(ethanesulfonyl)amino]-4-fluoro-2-[(2-fluoro[1,1'-biphenyl]-3-yl)methyl]pyrrolidine-1-carboxylate A mixture of benzyl (2S,3R,4S)-2-[(3-chloro-2-fluorophenyl)methyl]-3-[(ethanesulfonyl)amino]-4-fluoropyrrolidine-1-carboxylate (129 mg), phenylboronic acid (66.5 mg), XPhos Pd G3 (23.1 mg) and 1 M aqueous potassium phosphate solution (0.818 mL) in DME (4 mL) was stirred at 80° C. under nitrogen atmosphere for 1 h. The mixture was diluted with water and extracted with EtOAc. The combined organic layers were dried over magnesium sulfate, filtered and concentrated under reduced pressure. The residue obtained was purified by column chromatography (silica gel, eluted with EtOAc/hexane) to give the title compound (92 mg).
MS: $[M+H]^+$ 515.1.

B) N-{(2S,3R,4S)-4-fluoro-2-[(2-fluoro[1,1'-biphenyl]-3-yl)methyl]pyrrolidin-3-yl}ethanesulfonamide Hydrobromide To benzyl (2S,3R,4S)-3-[(ethanesulfonyl)amino]-4-fluoro-2-[(2-fluoro[1,1'-biphenyl]-3-yl)methyl]pyrrolidine-1-carboxylate (90 mg) was added 30% HBr/acetic acid solution (1 mL) at room temperature. The mixture was stirred at room temperature for 1.5 h, and the solvent was evaporated with toluene. The solid obtained was suspended in IPE and collected by filtration to give the title compound (80.9 mg).
MS: $[M+H]^+$ 381.0.

C) N-[(2S,3R,4S)-4-fluoro-2-[(2-fluoro[1,1'-biphenyl]-3-yl)methyl]-1-((2R)-oxetane-2-carbonyl)pyrrolidin-3-yl]ethanesulfonamide To a solution of N-{(2S,3R,4S)-4-fluoro-2-[(2-fluoro[1,1'-biphenyl]-3-yl)methyl]pyrrolidin-3-yl}ethanesulfonamide hydrobromide (35 mg) and oxetane-2-carboxylic acid (23.2 mg) in DMF (2 mL) were added HATU (43.3 mg) and DIPEA (0.053 mL) at 0° C. The mixture was stirred at room temperature for 1.5 h. The mixture was quenched with water and extracted with EtOAc. The organic layer was dried over magnesium sulfate, filtered and concentrated under reduced pressure. The residue was purified by preparative HPLC (Column: YMC-Actus Triant C18, mobile phase: $H_2O$ 10 mM $NH_4HCO_3$/$CH_3CN$) to give the title compound (11.5 mg).
$^1$H NMR (300 MHz, DMSO-$d_6$) δ 1.19-1.31 (3H, m,), 2.30-2.46 (1H, m), 2.60-2.86 (2H, m), 3.02-3.20 (3H, m), 3.46-3.68 (1H, m), 3.77-4.28 (4H, m), 4.39-5.40 (3H, m), 7.09-7.61 (8H, m), 7.81 (1H, br s).

Example 304

N-{(2S,3R,4S)-4-fluoro-1-(oxetane-2-carbonyl)-2-[(2,3',5'-trifluoro[1,1'-biphenyl]-3-yl)methyl]pyrrolidin-3-yl}ethanesulfonamide with Shorter Retention Time A) benzyl (2S,3R,4S)-3-[(ethanesulfonyl)amino]-4-fluoro-2-[(2,3',5'-trifluoro[1,1'-biphenyl]-3-yl)methyl]pyrrolidine-1-carboxylate To a mixture of benzyl (2S,3R,4S)-2-[(3-chloro-2-fluorophenyl)methyl]-3-[(ethanesulfonyl)amino]-4-fluoropyrrolidine-1-carboxylate (129 mg), (3,5-difluorophenyl)boronic acid (94.6 mg), XPhos Pd G3 (21.9 mg) and DME (2.0 mL) was added 1 M aqueous potassium phosphate solution (0.60 mL) at room temperature. The mixture was stirred at 90° C. under nitrogen atmosphere for 4 h. To the mixture was added water, and the mixture was extracted with EtOAc. The organic layer was separated, washed with water and saturated brine, dried over sodium sulfate and concentrated under reduced pressure. The residue was purified by column chromatography (silica gel, eluted with EtOAc/hexane) to give the title compound (30.4 mg).
MS: $[M+H]^+$ 551.2.

B) N-{(2S,3R,4S)-4-fluoro-1-(oxetane-2-carbonyl)-2-[(2,3',5'-trifluoro[1,1'-biphenyl]-3-yl)methyl]pyrrolidin-3-yl}ethanesulfonamide with Shorter Retention Time A mixture of benzyl (2S,3R,4S)-3-[(ethanesulfonyl)amino]-4-fluoro-2-[(2,3',5'-trifluoro[1,1'-biphenyl]-3-yl)methyl]pyrrolidine-1-carboxylate (30.4 mg) and 10% Pd—C (3.0 mg) in MeOH (1.0 mL) was hydrogenated under balloon pressure overnight at room temperature. The catalyst was removed by filtration, and the filtrate was concentrated under reduced pressure. To a mixture of the obtained residue, 2-oxetanecarboxylic acid (10.2 mg), DIPEA (0.030 mL) and DMF (1.0 mL) was added HATU (36.1 mg) at room temperature. The mixture was stirred at room temperature for 1 h. To the mixture was added saturated aqueous sodium hydrogen carbonate solution, and the mixture was extracted with EtOAc. The organic layer was separated, washed with water and saturated brine, dried over sodium sulfate and concentrated under reduced pressure. The residue was purified by preparative HPLC (Column: YMC-Actus Triant C18, mobile phase: $H_2O$ 10 mM $NH_4HCO_3$/$CH_3CN$) to give the title compound (5.2 mg).

$^1$H NMR (300 MHz, DMSO-$d_6$) δ 1.17-1.33 (3H, m), 2.22-2.45 (1H, m), 2.58-3.20 (5H, m), 3.48-5.42 (8H, m), 7.13-7.51 (6H, m), 7.73-7.91 (1H, m).

Example 305

N-{(2S,3R,4S)-4-fluoro-1-(oxetane-2-carbonyl)-2-[(2,3',5'-trifluoro[1,1'-biphenyl]-3-yl)methyl]pyrrolidin-3-yl}ethanesulfonamide with Longer Retention Time A mixture of benzyl (2S,3R,4S)-3-[(ethanesulfonyl)amino]-4-fluoro-2-[(2,3',5'-trifluoro[1,1'-biphenyl]-3-yl)methyl]pyrrolidine-1-carboxylate (30.4 mg) and 10% Pd—C (3.0 mg) in MeOH (1.0 mL) was hydrogenated under balloon pressure overnight at room temperature. The catalyst was removed by filtration, and the filtrate was concentrated under reduced pressure. To a mixture of the obtained residue, 2-oxetanecarboxylic acid (10.2 mg), DIPEA (0.030 mL) and DMF (1.0 mL) was added HATU (36.1 mg) at room temperature. The mixture was stirred at room temperature for 1 h. To the mixture was added saturated aqueous sodium hydrogen carbonate solution, and the mixture was extracted with EtOAc. The organic layer was separated, washed with water and saturated brine, dried over sodium sulfate and concentrated under reduced pressure. The residue was purified by preparative HPLC (Column: YMC-Actus Triant C18, mobile phase: $H_2O$ 10 mM $NH_4HCO_3$/$CH_3CN$) to give the title compound (4.1 mg).

$^1$H NMR (300 MHz, DMSO-$d_6$) δ 1.19-1.33 (3H, m), 2.22-2.44 (1H, m), 2.61-3.22 (4H, m), 3.42-5.41 (9H, m), 7.12-7.56 (6H, m), 7.73-8.00 (1H, m).

Example 307

N-{(2S,3R,4S)-4-fluoro-1-(oxetane-2-carbonyl)-2-[(2,2',3'-trifluoro[1,1'-biphenyl]-3-yl)methyl]pyrrolidin-3-yl}ethanesulfonamide with Shorter Retention Time A) benzyl (2S,3R,4S)-3-[(ethanesulfonyl)amino]-4-fluoro-2-[(2,2',3'-trifluoro[1,1'-biphenyl]-3-yl)methyl]pyrrolidine-1-carboxylate To a mixture of benzyl (2S,3R,4S)-2-[(3-chloro-2-fluorophenyl)methyl]-3-[(ethanesulfonyl)amino]-4-fluoropyrrolidine-1-carboxylate (129 mg), (2,3-difluorophenyl)boronic acid (91.9 mg), XPhos Pd G3 (21.9 mg) and DME (2.0 mL) was added 1 M aqueous potassium phosphate solution (0.60 mL) at room temperature. After being stirred at 90° C. under nitrogen atmosphere for 4 h, the mixture was concentrated under reduced pressure. The residue was purified by column chromatography (silica gel, eluted with EtOAc/hexane) to give the title compound (32.7 mg).

MS: [M+H]$^+$ 551.2.

B) N-{(2S,3R,4S)-4-fluoro-2-[(2,2',3'-trifluoro[1,1'-biphenyl]-3-yl)methyl]pyrrolidin-3-yl}ethanesulfonamide A mixture of benzyl (2S,3R,4S)-3-[(ethanesulfonyl)amino]-4-fluoro-2-[(2,2',3'-trifluoro[1,1'-biphenyl]-3-yl)methyl]pyrrolidine-1-carboxylate (32.7 mg) and 10% Pd—C (3.0 mg) in MeOH (1.0 mL) was hydrogenated under balloon pressure overnight at room temperature. The catalyst was removed by filtration, and the filtrate was concentrated under reduced pressure to give the title compound (23.6 mg).

MS: [M+H]$^+$ 417.1.

C) N-{(2S,3R,4S)-4-fluoro-1-(oxetane-2-carbonyl)-2-[(2,2',3'-trifluoro[1,1'-biphenyl]-3-yl)methyl]pyrrolidin-3-yl}ethanesulfonamide with Shorter Retention Time To a mixture of N-{(2S,3R,4S)-4-fluoro-2-[(2,2',3'-trifluoro[1,1'-biphenyl]-3-yl)methyl]pyrrolidin-3-yl}ethanesulfonamide (23.6 mg), 2-oxetanecarboxylic acid (16.1 mg), DIPEA (0.050 mL) and DMF (1.0 mL) was added HATU (26.0 mg) at room temperature. After being stirred at room temperature for 1 h, the mixture was concentrated under reduced pressure. The residue was purified by preparative HPLC (Column: YMC-Actus Triant C18, mobile phase: $H_2O$ 10 mM $NH_4HCO_3$/$CH_3CN$) to give the title compound (8.7 mg).

$^1$H NMR (300 MHz, DMSO-$d_6$) δ 1.24 (3H, t, J=7.3 Hz), 2.23-2.45 (1H, m), 2.58-2.89 (2H, m), 3.00-3.18 (3H, m), 3.41-5.39 (8H, m), 7.07-7.59 (6H, m), 7.82 (1H, br s).

Example 346

N-[(2S,3R,4S)-2-[(3'-chloro-2-fluoro[1,1'-biphenyl]-3-yl)methyl]-4-fluoro-1-(2-hydroxy-2-methylpropanoyl)pyrrolidin-3-yl]ethanesulfonamide A) N-{(2S,3R,4S)-2-[(3-chloro-2-fluorophenyl)methyl]-4-fluoropyrrolidin-3-yl}ethanesulfonamide Hydrobromide To benzyl (2S,3R,4S)-2-[(3-chloro-2-fluorophenyl)methyl]-3-[(ethanesulfonyl)amino]-4-fluoropyrrolidine-1-carboxylate (2.18 g) was added 30% HBr/acetic acid solution (20 mL) at 0° C. After being stirred at room temperature for 30 min, the mixture was concentrated under reduced pressure with heptane, and the residue was diluted with IPE. The insoluble material was collected by filtration, and washed with IPE to give the title compound (1.83 g).

MS: [M+H]$^+$ 339.0.

B) N-[(2S,3R,4S)-2-[(3-chloro-2-fluorophenyl)methyl]-4-fluoro-1-(2-hydroxy-2-methylpropanoyl)pyrrolidin-3-yl]ethanesulfonamide To a mixture of N-{(2S,3R,4S)-2-[(3-chloro-2-fluorophenyl)methyl]-4-fluoropyrrolidin-3-yl}ethanesulfonamide hydrobromide (195 mg) and DIPEA (0.402 mL) in THF (4 mL) was added alpha-acetoxy-isobutyryl chloride (0.081 mL) at 0° C., and the mixture was stirred at same temperature for 10 min. To the mixture were added water (1 mL) and 4 M aqueous lithium hydroxide solution (1.16 mL), and the mixture was stirred overnight at room temperature. The mixture was quenched with saturated aqueous sodium hydrogen carbonate solution, and extracted with EtOAc. The extract was washed with saturated brine, dried over magnesium sulfate and concentrated under reduced pressure. The residue was purified by column chromatography (silica gel, eluted with EtOAc/hexane) to give the title compound (180 mg).

MS: [M+H]$^+$ 425.0.

C) N-[(2S,3S,4S)-2-[(3'-chloro-2-fluoro[1,1'-biphenyl]-3-yl)methyl]-4-fluoro-1-(2-hydroxy-2-methylpropanoyl)pyrrolidin-3-yl]ethanesulfonamide A mixture of N-[(2S,3R,4S)-2-[(3-chloro-2-fluorophenyl)methyl]-4-fluoro-1-(2-hydroxy-2-methylpropanoyl)pyrrolidin-3-yl]ethanesulfonamide (45 mg), (3-chlorophenyl)boronic acid (21.5 mg), XPhos Pd G3 (8.96 mg) and 1 M aqueous potassium phosphate solution (0.318 mL) in DME (2 mL) was stirred at 80° C. for 2 h. After cooling back to room temperature, the solvent was removed under reduced pressure, and the residue was purified by preparative HPLC (Column: YMC-Actus Triant C18, mobile phase: H$_2$O 10 mM NH$_4$HCO$_3$/CH$_3$CN) and then column chromatography (NH silica gel, eluted with EtOAc/hexane) to give the title compound (11.4 mg).

$^1$H NMR (400 MHz, CDCl$_3$) δ 1.10-1.22 (3H, m), 1.40 (6H, s), 2.73-3.27 (5H, m), 3.94-4.31 (3H, m), 4.76-5.33 (3H, m), 7.13-7.55 (7H, m).

Example 374

N-{(2S,3R,4S)-1-(bicyclo[1.1.1]pentane-1-carbonyl)-4-fluoro-2-[(2,3',5'-trifluoro[1,1'-biphenyl]-3-yl)methyl]pyrrolidin-3-yl}methanesulfonamide A) N-((2S,3R,4S)-1-(bicyclo[1.1.1]pentane-1-carbonyl)-2-(3-chloro-2-fluorobenzyl)-4-fluoropyrrolidin-3-yl)methanesulfonamide To a solution of N-{(2S,3R,4S)-2-[(3-chloro-2-fluorophenyl)methyl]-4-fluoropyrrolidin-3-yl}methanesulfonamide hydrobromide (100 mg) and bicyclo[1.1.1]pentane-1-carboxylic acid (0.044 mL) in DMF (3 mL) were added HATU (141 mg) and DIPEA (0.129 mL) at 0° C. The mixture was stirred at room temperature for 1.5 h, then it was quenched with a saturated aqueous sodium hydrogen carbonate solution and extracted with EtOAc. The combined organic layers were washed with saturated brine, dried over magnesium sulfate, filtered and concentrated. The residue was purified by column chromatography (silica gel, eluted with EtOAc/hexane) to give the title compound (102 mg).

MS: [M+H]$^+$ 419.0.

B) N-{(2S,3R,4S)-1-(bicyclo[1.1.1]pentane-1-carbonyl)-4-fluoro-2-[(2,3',5'-trifluoro[1,1'-biphenyl]-3-yl)methyl]pyrrolidin-3-yl}methanesulfonamide A mixture of N-((2S,3R,4S)-1-(bicyclo[1.1.1]pentane-1-carbonyl)-2-(3-chloro-2-fluorobenzyl)-4-fluoropyrrolidin-3-yl)methanesulfonamide (20 mg), (3,5-difluorophenyl)boronic acid (15.1 mg), XPhos Pd G3 (4.04 mg) and 1 M aqueous potassium phosphate solution (0.143 mL) in DME (0.8 mL) was stirred at 80° C. under nitrogen atmosphere for 2 h. The mixture was purified by column chromatography (silica gel, eluted with EtOAc/hexane) followed by preparative HPLC ((Column: L-Column 2 ODS, mobile phase: H$_2$O 5 mM NH$_4$HCO$_3$/CH$_3$CN) to give the title compound (15.5 mg).

$^1$H NMR (400 MHz, CDCl$_3$) δ 1.75-1.94 (1H, m), 2.07-2.38 (5H, m), 2.53 (3H, d, J=26.2 Hz), 2.88-3.31 (3H, m), 3.62-4.47 (3H, m), 4.65-5.35 (3H, m), 6.78-6.88 (1H, m), 7.02-7.12 (2H, m), 7.16-7.26 (2H, m), 7.46-7.55 (1H, m).

Example 375

N-{(2S,3R)-4,4-difluoro-1-((1r,3S)-3-fluorocyclobutane-1-carbonyl)-2-[(2,3',5'-trifluoro[1,1'-biphenyl]-3-yl)methyl]pyrrolidin-3-yl}ethanesulfonamide A mixture of N-{(2S,3R)-2-[(3-chloro-2-fluorophenyl)methyl]-4,4-difluoro-1-[(1r,3S)-3-fluorocyclobutane-1-carbonyl]pyrrolidin-3-yl}ethanesulfonamide (28 mg), (3,5-difluorophenyl)boronic acid (19.4 mg), XPhos Pd G3 (5.19 mg) and 1 M aqueous potassium phosphate solution (0.184 mL) in DME (2 mL) was stirred at 80° C. for 2 h. After cooling back to room temperature, the solvent was removed under reduced pressure, and the residue was purified by column chromatography (NH silica gel, eluted with EtOAc/hexane) and preparative HPLC (Column: YMC-Actus Triant C18, mobile phase: H$_2$O 10 mM NH$_4$HCO$_3$/CH$_3$CN) to give the title compound (28.3 mg).

$^1$H NMR (300 MHz, DMSO-d$_6$) δ 1.21-1.73 (4H, m), 2.00-2.42 (3H, m), 2.60-3.26 (5H, m), 3.68-5.13 (5H, m), 7.11-7.55 (6H, m), 8.09-8.40 (1H, m).

Example 376

N-{(2S,3R)-4,4-difluoro-1-((1r,3S)-3-fluorocyclobutane-1-carbonyl)-2-[(2,2',5'-trifluoro[1,1'-biphenyl]-3-yl)methyl]pyrrolidin-3-yl}ethanesulfonamide A mixture of N-{(2S,3R)-2-[(3-chloro-2-fluorophenyl)methyl]-4,4-difluoro-1-[(1r,3S)-3-fluorocyclobutane-1-carbonyl]pyrrolidin-3-yl}ethanesulfonamide (28 mg), (2,5-difluorophenyl)boronic acid (19.4 mg), XPhos Pd G3 (5.19 mg) and 1 M aqueous potassium phosphate solution (0.184 mL) in DME (2 mL) was stirred at 80° C. for 2 h. After cooling back to room temperature, the solvent was removed under reduced pressure, and the residue was purified by column chromatography (NH silica gel, eluted with EtOAc/hexane) and preparative HPLC (Column: YMC-Actus Triant C18, mobile phase: H$_2$O 10 mM NH$_4$HCO$_3$/CH$_3$CN) to give the title compound (18.2 mg).

$^1$H NMR (300 MHz, DMSO-d$_6$) δ 1.19-1.74 (4H, m), 2.01-2.42 (3H, m), 2.57-3.22 (5H, m), 3.66-5.17 (5H, m), 7.13-7.48 (6H, m), 8.11-8.37 (1H, m).

Example 378

N-[(2S,3R)-4,4-difluoro-2-[(2-fluoro[1,1'-biphenyl]-3-yl)methyl]-1-((1r,3S)-3-fluorocyclobutane-1-carbonyl)pyrrolidin-3-yl]ethanesulfonamide A mixture of N-{(2S,3R)-2-[(3-chloro-2-fluorophenyl)methyl]-4,4-difluoro-1-[(1r,3S)-3-fluorocyclobutane-1-carbonyl]pyrrolidin-3-yl}ethanesulfonamide (28 mg), phenylboronic acid (14.9 mg), XPhos Pd G3 (5.19 mg) and 1 M aqueous potassium phosphate solution (0.184 mL) in DME (2 mL) was stirred at 80° C. for 2 h. After cooling back to room temperature, the solvent was removed under reduced pressure, and the residue was purified by column chromatography (NH silica gel, eluted with EtOAc/hexane) and preparative HPLC (Column: YMC-Actus Triant C18, mobile phase: H$_2$O 10 mM NH$_4$HCO$_3$/CH$_3$CN) to give the title compound (26.9 mg).

¹H NMR (300 MHz, DMSO-d₆) δ 1.20-1.71 (4H, m), 1.99-2.43 (3H, m), 2.60-3.23 (5H, m), 3.68-5.14 (5H, m), 7.09-7.56 (8H, m), 8.11-8.38 (1H, m).

Example 380

N-{(2S,3R)-4,4-difluoro-1-((1s,3R)-3-fluorocyclobutane-1-carbonyl)-2-[(2,3',5'-trifluoro[1,1'-biphenyl]-3-yl)methyl]pyrrolidin-3-yl}ethanesulfonamide A mixture of N-{(2S,3R)-2-[(3-chloro-2-fluorophenyl)methyl]-4,4-difluoro-1-[(1s,3R)-3-fluorocyclobutane-1-carbonyl]pyrrolidin-3-yl}ethanesulfonamide (17 mg), (3,5-difluorophenyl)boronic acid (11.8 mg), XPhos Pd G3 (3.15 mg) and 1 M aqueous potassium phosphate solution (0.112 mL) in DME (1 mL) was stirred at 80° C. for 2 h. After cooling back to room temperature, the solvent was removed under reduced pressure, and the residue was purified by column chromatography (NH silica gel, eluted with EtOAc/hexane) and preparative HPLC (Column: YMC-Actus Triant C18, mobile phase: H₂O 10 mM NH₄HCO₃/CH₃CN) to give the title compound (15.8 mg).
¹H NMR (300 MHz, DMSO-d₆) δ 1.11-3.20 (12H, m), 3.73-5.00 (5H, m), 7.11-7.52 (6H, m), 8.14-8.35 (1H, m).

Example 381

N-{(2S,3R)-4,4-difluoro-1-((1s,3R)-3-fluorocyclobutane-1-carbonyl)-2-[(2,2',5'-trifluoro[1,1'-biphenyl]-3-yl)methyl]pyrrolidin-3-yl}ethanesulfonamide A mixture of N-{(2S,3R)-2-[(3-chloro-2-fluorophenyl)methyl]-4,4-difluoro-1-[(1s,3R)-3-fluorocyclobutane-1-carbonyl]pyrrolidin-3-yl}ethanesulfonamide (17 mg), (2,5-difluorophenyl)boronic acid (7.64 mg), XPhos Pd G3 (3.15 mg) and 1 M aqueous potassium phosphate solution (0.112 mL) in DME (1 mL) was stirred at 80° C. for 2 h. After cooling back to room temperature, the solvent was removed under reduced pressure, and the residue was purified by column chromatography (NH silica gel, eluted with EtOAc/hexane) and preparative HPLC (Column: YMC-Actus Triant C18, mobile phase: H₂O 10 mM NH₄HCO₃/CH₃CN) to give the title compound (12.0 mg).
¹H NMR (300 MHz, DMSO-d₆) δ 1.19-1.30 (3H, m), 1.70-2.44 (5H, m), 2.54-3.22 (4H, m), 3.70-5.12 (5H, m), 7.10-7.49 (6H, m), 8.10-8.38 (1H, m).

Example 383

N-[(2S,3R)-4,4-difluoro-2-[(2-fluoro[1,1'-biphenyl]-3-yl)methyl]-1-((1s,3R)-3-fluorocyclobutane-1-carbonyl)pyrrolidin-3-yl]ethanesulfonamide A mixture of N-{(2S,3R)-2-[(3-chloro-2-fluorophenyl)methyl]-4,4-difluoro-1-[(1s,3R)-3-fluorocyclobutane-1-carbonyl]pyrrolidin-3-yl}ethanesulfonamide (17 mg), phenylboronic acid (9.07 mg), XPhos Pd G3 (3.15 mg) and 1 M aqueous potassium phosphate solution (0.112 mL) in DME (1 mL) was stirred at 80° C. for 2 h. After cooling back to room temperature, the solvent was removed under reduced pressure, and the residue was purified by column chromatography (NH silica gel, eluted with EtOAc/hexane) and preparative HPLC (Column: YMC-Actus Triant C18, mobile phase: H₂O 10 mM NH₄HCO₃/CH₃CN) to give the title compound (8.00 mg).

¹H NMR (300 MHz, DMSO-d₆) δ 1.12-3.24 (12H, m), 3.68-5.03 (5H, m), 7.06-7.59 (8H, m), 8.10-8.40 (1H, m).

Example 388

N-[(2S,3R,4S)-2-[(3'-chloro-2-fluoro[1,1'-biphenyl]-3-yl)methyl]-4-fluoro-1-(2-hydroxy-2-methylpropanoyl)pyrrolidin-3-yl]methanesulfonamide A) benzyl (2S,3R,4S)-2-[(3-chloro-2-fluorophenyl)methyl]-4-fluoro-3-[(methanesulfonyl)amino]pyrrolidine-1-carboxylate Methanesulfonic anhydride (225 mg) was added to a stirred solution of benzyl (2S,3R,4S)-3-amino-2-[(3-chloro-2-fluorophenyl)methyl]-4-fluoropyrrolidine-1-carboxylate (328 mg) and TEA (0.360 mL) in THF (10 mL) at room temperature. After 0.5 h, the reaction mixture was concentrated under reduced pressure, and the residue was purified by column chromatography (silica gel, eluted with EtOAc/hexane) to give the title compound (336 mg).
MS: [M+H]⁺ 459.0.

B) N-{(2S,3R,4S)-2-[(3-chloro-2-fluorophenyl)methyl]-4-fluoropyrrolidin-3-yl}methanesulfonamide Hydrobromide To benzyl (2S,3R,4S)-2-[(3-chloro-2-fluorophenyl)methyl]-4-fluoro-3-[(methanesulfonyl)amino]pyrrolidine-1-carboxylate (1.17 g) was added 30% HBr/acetic acid solution (10 mL) at room temperature. The mixture was stirred at room temperature for 30 min. The mixture was evaporated with toluene, and the residue was suspended in IPE, and the insoluble substance was collected by filtration and washed with IPE to give the title compound (0.974 g).
MS, found: 325.1.

C) N-[(2S,3R,4S)-2-[(3-chloro-2-fluorophenyl)methyl]-4-fluoro-1-(2-hydroxy-2-methylpropanoyl)pyrrolidin-3-yl]methanesulfonamide To a mixture of N-{(2S,3R,4S)-2-[(3-chloro-2-fluorophenyl)methyl]-4-fluoropyrrolidin-3-yl}methanesulfonamide hydrobromide (100 mg) and DIPEA (0.299 mL) in THF (3 mL) was added alpha-acetoxy-isobutyryl chloride (0.071 mL) at 0° C., and the mixture was stirred at the same temperature for 10 min. To the mixture were added water (1 mL) and 4 M aqueous lithium hydroxide solution (1 mL), and the mixture was stirred at room temperature for 4 h. The mixture was quenched with saturated aqueous sodium hydrogen carbonate solution and extracted with EtOAc. The extract was washed with saturated brine, dried over sodium sulfate and concentrated under reduced pressure. The residue was purified by column chromatography (silica gel, eluted with EtOAc/hexane) to give the title compound (96 mg).
MS: [M+H]⁺ 411.1.

D) N-[(2S,3R,4S)-2-[(3'-chloro-2-fluoro[1,1'-biphenyl]-3-yl)methyl]-4-fluoro-1-(2-hydroxy-2-methylpropanoyl)pyrrolidin-3-yl]methanesulfonamide A mixture of N-[(2S,3R,4S)-2-[(3-chloro-2-fluorophenyl)methyl]-4-fluoro-1-(2-hydroxy-2-methylpropanoyl)pyrrolidin-3-yl]methanesulfonamide (23 mg), (3-chlorophenyl)boronic acid (17.5 mg), XPhos Pd G3 (4.74 mg) and 1 M aqueous potassium phosphate solution (0.168 mL) in DME (2 mL) was stirred at 80° C. for 2 h. After cooling back to room temperature, the solvent was removed under reduced pressure, and the residue was purified by preparative HPLC (Column: YMC-Actus Triant C18, mobile phase: H₂O 0.1% TFA/CH₃CN 0.1% TFA) and column chromatography (NH silica gel, eluted with EtOAc/hexane) to give the title compound (5.40 mg).

¹H NMR (400 MHz, CDCl₃) δ 1.42 (6H, s), 2.60 (6H, brs), 4.01-4.30 (3H, m), 4.77-5.34 (3H, m), 7.16-7.23 (1H, m), 7.27-7.55 (6H, m).

Example 392

N-[(2S,3R)-2-[(2,3'-difluoro[1,1'-biphenyl]-3-yl)methyl]-4,4-difluoro-1-(3-fluorocyclobutane-1-carbonyl)pyrrolidin-3-yl]methanesulfonamide with Longer Retention Time A) N-[(2S,3R)-2-[(3-chloro-2-fluorophenyl)methyl]-4,4-difluoro-1-(3-fluorocyclobutane-1-carbonyl)pyrrolidin-3-yl]methanesulfonamide To a solution of N-((2S,3R)-2-(3-chloro-2-fluorobenzyl)-4,4-difluoropyrrolidin-3-yl)methanesulfonamide hydrochloride (0.310 g) and 3-fluorocyclobutane-1-carboxylic acid (0.133 mL) in DMF (10 mL) were added HATU (0.466 g) and DIPEA (0.571 mL) at room temperature. The mixture was stirred overnight at room temperature. The mixture was quenched with aqueous saturated ammonium chloride solution and extracted with EtOAc. The organic layer was separated, washed with water and saturated brine, dried over sodium sulfate and concentrated under reduced pressure. The residue was purified by column chromatography (NH silica gel, eluted with EtOAc/hexane, and then silica gel, eluted with EtOAc/hexane) to give the title compound (0.196 g).

MS: [M+H]⁺ 443.0.

B) N-[(2S,3R)-2-[(2,3'-difluoro[1,1'-biphenyl]-3-yl)methyl]-4,4-difluoro-1-(3-fluorocyclobutane-1-carbonyl)pyrrolidin-3-yl]methanesulfonamide with Longer Retention Time A mixture of N-[(2S,3R)-2-[(3-chloro-2-fluorophenyl)methyl]-4,4-difluoro-1-(3-fluorocyclobutane-1-carbonyl)pyrrolidin-3-yl]methanesulfonamide (29 mg), (3-fluorophenyl)boronic acid (18.3 mg), XPhos Pd G3 (5.54 mg) and 1 M aqueous potassium phosphate solution (0.196 mL) in DME (2 mL) was stirred at 80° C. for 2 h. After cooling back to room temperature, the solvent was removed under reduced pressure, and the residue was purified by preparative HPLC (Column: YMC-Actus Triant C18, mobile phase: H₂O 0.1% TFA/CH₃CN 0.1% TFA, and then Column: CHIRALPAK IB, mobile phase: carbon dioxide/(MeOH/diethylamine=1000/3)=900/100 (v/v)) to give the title compound (11.3 mg).

¹H NMR (400 MHz, CDCl₃) δ 1.56-1.72 (1H, m), 1.95-3.14 (9H, m), 3.36-3.92 (2H, m), 4.26-4.53 (2H, m), 4.88-5.24 (2H, m), 7.26 (7H, s).

Example 393

N-[(2S,3R)-2-[(2,3'-difluoro[1,1'-biphenyl]-3-yl)methyl]-4,4-difluoro-1-(3-fluorocyclobutane-1-carbonyl)pyrrolidin-3-yl]methanesulfonamide with Shorter Retention Time A mixture of N-[(2S,3R)-2-[(3-chloro-2-fluorophenyl)methyl]-4,4-difluoro-1-(3-fluorocyclobutane-1-carbonyl)pyrrolidin-3-yl]methanesulfonamide (29 mg), (3-fluorophenyl)boronic acid (18.3 mg), XPhos Pd G3 (5.54 mg) and 1 M aqueous potassium phosphate solution (0.196 mL) in DME (2 mL) was stirred at 80° C. for 2 h. After cooling back to room temperature, the solvent was removed under reduced pressure, and the residue was purified by preparative HPLC (Column: YMC-Actus Triant C18, mobile phase: H₂O 0.1% TFA/CH₃CN 0.1% TFA, and then Column: CHIRALPAK IB, mobile phase: carbon dioxide/(MeOH/diethylamine=1000/3)=900/100 (v/v)) to give the title compound (10.2 mg).

¹H NMR (400 MHz, CDCl₃) δ 1.84-3.14 (10H, m), 3.32-3.94 (2H, m), 4.27-5.13 (4H, m), 7.03-7.46 (7H, m).

Example 431

N-{(2S,3R)-4,4-difluoro-1-((1r,3S)-3-fluorocyclobutane-1-carbonyl)-2-[(2,3',5'-trifluoro[1,1'-biphenyl]-3-yl)methyl]pyrrolidin-3-yl}methanesulfonamide A mixture of N-[(2S,3R)-2-[(3-chloro-2-fluorophenyl)methyl]-4,4-difluoro-1-(3-fluorocyclobutane-1-carbonyl)pyrrolidin-3-yl]methanesulfonamide (29 mg), (3,5-difluorophenyl)boronic acid (20.7 mg), XPhos Pd G3 (5.54 mg) and 1 M aqueous potassium phosphate solution (0.196 mL) in DME (2 mL) was stirred at 80° C. for 2 h. After cooling back to room temperature, the solvent was removed under reduced pressure, and the residue was purified by preparative HPLC (Column: YMC-Actus Triant C18, mobile phase: H₂O 0.1% TFA/CH₃CN 0.1% TFA, and then Column: CHIRALPAK IB, mobile phase: carbon dioxide/(MeOH/diethylamine=1000/3)=900/100 (v/v)) to give the title compound (9.90 mg).

¹H NMR (400 MHz, CDCl₃) δ 1.56-1.70 (1H, m), 1.98-3.14 (9H, m), 3.27-3.98 (2H, m), 4.25-4.52 (2H, m), 4.88-5.23 (2H, m), 6.78-6.88 (1H, m), 6.99-7.09 (2H, m), 7.16-7.45 (3H, m).

Example 433

N-{(2S,3R)-4,4-difluoro-1-((1s,3R)-3-fluorocyclobutane-1-carbonyl)-2-[(2,3',5'-trifluoro[1,1'-biphenyl]-3-yl)methyl]pyrrolidin-3-yl}methanesulfonamide A mixture of N-[(2S,3R)-2-[(3-chloro-2-fluorophenyl)methyl]-4,4-difluoro-1-(3-fluorocyclobutane-1-carbonyl)pyrrolidin-3-yl]methanesulfonamide (29 mg), (3,5-difluorophenyl)boronic acid (20.7 mg), XPhos Pd G3 (5.54 mg) and 1 M aqueous potassium phosphate solution (0.196 mL) in DME (2 mL) was stirred at 80° C. for 2 h. After cooling back to room temperature, the solvent was removed under reduced pressure, and the residue was purified by preparative HPLC (Column: YMC-Actus Triant C18, mobile phase: H₂O 0.1% TFA/CH₃CN 0.1% TFA, and then Column: CHIRALPAK IB, mobile phase: carbon dioxide/(MeOH/diethylamine=1000/3)=900/100 (v/v)) to give the title compound (12.3 mg).

¹H NMR (400 MHz, CDCl₃) δ 1.29-3.22 (10H, m), 3.30-5.24 (6H, m), 6.77-7.47 (6H, m).

Example 435

N-{(2S,3R)-4,4-difluoro-1-(3-fluorocyclobutane-1-carbonyl)-2-[(2,2',3'-trifluoro[1,1'-biphenyl]-3-yl)methyl]pyrrolidin-3-yl}methanesulfonamide with Longer Retention Time A mixture of N-[(2S,3R)-2-[(3-chloro-2-fluorophenyl)methyl]-4,4-difluoro-1-(3-fluorocyclobutane-1-carbonyl)

pyrrolidin-3-yl]methanesulfonamide (29 mg), (3,5-difluorophenyl)boronic acid (20.7 mg), XPhos Pd G3 (5.54 mg) and 1 M aqueous potassium phosphate solution (0.196 mL) in DME (2 mL) was stirred at 80° C. for 2 h. After cooling back to room temperature, the solvent was removed under reduced pressure, and the residue was purified by preparative HPLC (Column: YMC-Actus Triant C18, mobile phase: H$_2$O 0.1% TFA/CH$_3$CN 0.1% TFA, and then Column: CHIRALPAK IB, mobile phase: carbon dioxide/(MeOH/diethylamine=1000/3)=900/100 (v/v)) to give the title compound (9 mg).

$^1$H NMR (400 MHz, CDCl$_3$) δ 1.60-3.18 (10H, m), 3.36-3.94 (2H, m), 4.28-4.53 (2H, m), 4.92-5.24 (2H, m), 7.05-7.46 (6H, m).

Example 436

N-{(2S,3R)-4,4-difluoro-1-(3-fluorocyclobutane-1-carbonyl)-2-[(2,2',3'-trifluoro[1,1'-biphenyl]-3-yl)methyl]pyrrolidin-3-yl}methanesulfonamide with Shorter Retention Time A mixture of N-[(2S,3R)-2-[(3-chloro-2-fluorophenyl)methyl]-4,4-difluoro-1-(3-fluorocyclobutane-1-carbonyl)pyrrolidin-3-yl]methanesulfonamide (29 mg), (3,5-difluorophenyl)boronic acid (20.7 mg), XPhos Pd G3 (5.54 mg) and 1 M aqueous potassium phosphate solution (0.196 mL) in DME (2 mL) was stirred at 80° C. for 2 h. After cooling back to room temperature, the solvent was removed under reduced pressure, and the residue was purified by preparative HPLC (Column: YMC-Actus Triant C18, mobile phase: H$_2$O 0.1% TFA/CH$_3$CN 0.1% TFA, and then Column: CHIRALPAK IB, mobile phase: carbon dioxide/(MeOH/diethylamine=1000/3)=900/100 (v/v)) to give the title compound (7.6 mg).

$^1$H NMR (400 MHz, CDCl$_3$) δ 1.54-3.23 (10H, m), 3.27-5.08 (6H, m), 7.04-7.47 (6H, m).

Example 437

N-{(2S,3R)-4,4-difluoro-1-(3-fluorocyclobutane-1-carbonyl)-2-[(2,2',5'-trifluoro[1,1'-biphenyl]-3-yl)methyl]pyrrolidin-3-yl}methanesulfonamide with Longer Retention Time A mixture of N-[(2S,3R)-2-[(3-chloro-2-fluorophenyl)methyl]-4,4-difluoro-1-(3-fluorocyclobutane-1-carbonyl)pyrrolidin-3-yl]methanesulfonamide (29 mg), (2,5-difluorophenyl)boronic acid (20.7 mg), XPhos Pd G3 (5.54 mg) and 1 M aqueous potassium phosphate solution (0.196 mL) in DME (2 mL) was stirred at 80° C. for 2 h. After cooling back to room temperature, the solvent was removed under reduced pressure, and the residue was purified by preparative HPLC (Column: YMC-Actus Triant C18, mobile phase: H$_2$O 0.1% TFA/CH$_3$CN 0.1% TFA, and then Column: CHIRALPAK IA, mobile phase: carbon dioxide/(MeOH/diethylamine=1000/3)=900/100 (v/v)) to give the title compound (6.1 mg).

$^1$H NMR (400 MHz, CDCl$_3$) δ 1.54-3.36 (10H, m), 3.33-3.94 (2H, m), 4.27-4.53 (2H, m), 4.91-5.24 (2H, m), 7.02-7.46 (6H, m).

Example 438

N-{(2S,3R)-4,4-difluoro-1-(3-fluorocyclobutane-1-carbonyl)-2-[(2,2',5'-trifluoro[1,1'-biphenyl]-3-yl)methyl]pyrrolidin-3-yl}methanesulfonamide with Shorter Retention Time A mixture of N-[(2S,3R)-2-[(3-chloro-2-fluorophenyl)methyl]-4,4-difluoro-1-(3-fluorocyclobutane-1-carbonyl)pyrrolidin-3-yl]methanesulfonamide (29 mg), (2,5-difluorophenyl)boronic acid (20.7 mg), XPhos Pd G3 (5.54 mg) and 1 M aqueous potassium phosphate solution (0.196 mL) in DME (2 mL) was stirred at 80° C. for 2 h. After cooling back to room temperature, the solvent was removed under reduced pressure, and the residue was purified by preparative HPLC (Column: YMC-Actus Triant C18, mobile phase: H$_2$O 0.1% TFA/CH$_3$CN 0.1% TFA, and then Column: CHIRALPAK TA, mobile phase: carbon dioxide/(MeOH/diethylamine=1000/3)=900/100 (v/v)) to give the title compound (8.4 mg).

$^1$H NMR (400 MHz, CDCl$_3$) δ 1.30-3.21 (10H, m), 3.25-5.07 (6H, m), 6.97-7.47 (6H, m).

Example 440

N-[(2S,3R)-4,4-difluoro-2-[(2-fluoro[1,1'-biphenyl]-3-yl)methyl]-1-(3-fluorocyclobutane-1-carbonyl)pyrrolidin-3-yl]methanesulfonamide with Longer Retention Time A mixture of N-[(2S,3R)-2-[(3-chloro-2-fluorophenyl)methyl]-4,4-difluoro-1-(3-fluorocyclobutane-1-carbonyl)pyrrolidin-3-yl]methanesulfonamide (29 mg), phenylboronic acid (16.0 mg), XPhos Pd G3 (5.54 mg) and 1 M aqueous potassium phosphate solution (0.196 mL) in DME (2 mL) was stirred at 80° C. for 2 h. After cooling back to room temperature, the solvent was removed under reduced pressure, and the residue was purified by preparative HPLC (Column: YMC-Actus Triant C18, mobile phase: H$_2$O 0.1% TFA/CH$_3$CN 0.1% TFA, and then Column: CHIRALPAK OJ-H, mobile phase: carbon dioxide/(MeOH/diethylamine=1000/3)=900/100 (v/v)) to give the title compound (11.8 mg).

$^1$H NMR (400 MHz, CDCl$_3$) δ 1.54-3.15 (10H, m), 3.32-3.93 (2H, m), 4.27-4.52 (2H, m), 4.91-5.23 (2H, m), 7.09-7.53 (8H, m).

Example 441

N-[(2S,3R)-4,4-difluoro-2-[(2-fluoro[1,1'-biphenyl]-3-yl)methyl]-1-(3-fluorocyclobutane-1-carbonyl)pyrrolidin-3-yl]methanesulfonamide with Shorter Retention Time A mixture of N-[(2S,3R)-2-[(3-chloro-2-fluorophenyl)methyl]-4,4-difluoro-1-(3-fluorocyclobutane-1-carbonyl)pyrrolidin-3-yl]methanesulfonamide (29 mg), phenylboronic acid (16.0 mg), XPhos Pd G3 (5.54 mg) and 1 M aqueous potassium phosphate solution (0.196 mL) in DME (2 mL) was stirred at 80° C. for 2 h. After cooling back to room temperature, the solvent was removed under reduced pressure, and the residue was purified by HPLC (Column: YMC-Actus Triant C18, mobile phase: H$_2$O 0.1% TFA/CH$_3$CN 0.1% TFA, and then Column: CHIRALPAK OJ-H, mobile phase: carbon dioxide/(MeOH/diethylamine=1000/3)=900/100 (v/v)) to give the title compound (8 mg).

$^1$H NMR (400 MHz, CDCl$_3$) δ 1.29-3.20 (10H, m), 3.35-5.19 (6H, m), 7.10-7.53 (8H, m).

Example 442

(2S,3R)-3-[(dimethylsulfamoyl)amino]-4,4-difluoro-2-[(2-fluoro-3'-methyl[1,1'-biphenyl]-3-yl)methyl]-N,N-dimethylpyrrolidine-1-carboxamide A) tert-butyl (2S,3R)-2-[(3-chloro-2-fluorophenyl)methyl]-3-[(dimethylsulfamoyl)amino]-4,4-difluoropyrrolidine-1-carboxylate A mixture of tert-butyl (2S,3R)-3-amino-2-[(3-chloro-2-fluorophenyl)methyl]-4,4-difluoropyrrolidine-1-carboxylate (300 mg), dimethylsulfamoyl chloride (800 mg) and DMAP (201 mg) was stirred overnight under nitrogen atmosphere at 50° C. The reaction mixture was diluted with saturated aqueous sodium hydrogen carbonate solution, and extracted with EtOAc. The organic layer was separated, washed with saturated brine, dried over anhydrous magnesium sulfate, and concentrated under reduced pressure. The residue was purified by silica gel column chromatography (EtOAc/hexane) to give the title compound (225 mg).

MS: [M−H]⁻ 470.1.

B) tert-butyl (2S,3R)-3-[(dimethylsulfamoyl)amino]-4,4-difluoro-2-[(2-fluoro-3'-methyl[1,1'-biphenyl]-3-yl)methyl]pyrrolidine-1-carboxylate A mixture of tert-butyl (2S,3R)-2-[(3-chloro-2-fluorophenyl)methyl]-3-[(dimethylsulfamoyl)amino]-4,4-difluoropyrrolidine-1-carboxylate (200 mg), (3-methylphenyl)boronic acid (86 mg), XPhos Pd G3 (35.9 mg), 1M aqueous potassium phosphate solution (0.636 mL) and THF (3 ml) was irradiated with microwave at 80° C. for 1 hr. The mixture was neutralized with saturated aqueous sodium hydrogen carbonate solution at 0° C., and extracted with EtOAc. The organic layer was separated, washed with water and saturated brine, dried over anhydrous magnesium sulfate, and concentrated under reduced pressure. The residue was purified by silica gel column chromatography (NH, EtOAc/hexane) to give the title compound (150 mg).

MS: [M−H]⁻ 526.2.

C) N'-{(2S,3R)-4,4-difluoro-2-[(2-fluoro-3'-methyl[1,1'-biphenyl]-3-yl)methyl]pyrrolidin-3-yl}-N,N-dimethylsulfuric Diamide Hydrochloride A mixture of tert-butyl (2S,3R)-3-[(dimethylsulfamoyl)amino]-4,4-difluoro-2-[(2-fluoro-3'-methyl[1,1'-biphenyl]-3-yl)methyl]pyrrolidine-1-carboxylate (145 mg) and 4M hydrogen chloride/CPME solution (5 mL) was stirred at 60° C. for 4 hr. The reaction mixture was concentrated under reduced pressure to give the title compound (125 mg).

MS, found: 428.1.

D) (2S,3R)-3-[(dimethylsulfamoyl)amino]-4,4-difluoro-2-[(2-fluoro-3'-methyl[1,1'-biphenyl]-3-yl)methyl]pyrrolidine-1-carbonyl Chloride To a mixture of N'-{(2S,3R)-4,4-difluoro-2-[(2-fluoro-3'-methyl[1,1'-biphenyl]-3-yl)methyl]pyrrolidin-3-yl}-N,N-dimethylsulfuric diamide hydrochloride (50 mg), DIPEA (27.9 mg) and THF (4.7 ml) was added bis(trichloromethyl) carbonate (25.6 mg) at 0° C. The reaction mixture was stirred at 0° C. for 10 min, and then stirred at room temperature for 10 min. The mixture was neutralized with saturated aqueous sodium hydrogen carbonate solution at 0° C., and extracted with EtOAc. The organic layer was separated, washed with water and saturated brine, dried over anhydrous magnesium sulfate, and concentrated under reduced pressure to give the title compound (48 mg).

MS: [M+H]⁺ 490.1.

E) (2S,3R)-3-[(dimethylsulfamoyl)amino]-4,4-difluoro-2-[(2-fluoro-3'-methyl[1,1'-biphenyl]-3-yl)methyl]-N,N-dimethylpyrrolidine-1-carboxamide To a mixture of (2S,3R)-3-[(dimethylsulfamoyl)amino]-4,4-difluoro-2-[(2-fluoro-3'-methyl[1,1'-biphenyl]-3-yl)methyl]pyrrolidine-1-carbonyl chloride (48 mg) and THF (0.5 ml) was added 2M N-methylmethanamine/THF solution (0.5 mL) at 0° C. The mixture was stirred at room temperature for 2 hr, and purified by silica gel column chromatography (EtOAc/hexane) to give the title compound (35 mg).

¹H NMR (400 MHz, CDCl₃) δ 2.40 (3H, s), 2.60 (6H, s), 2.76-2.88 (7H, m), 2.98-3.05 (1H, m), 3.66-3.78 (1H, m), 3.88-4.00 (1H, m), 4.14-4.27 (1H, m), 4.82-4.90 (1H, m), 5.05 (1H, d, J=9.7 Hz), 7.09-7.34 (7H, m).

Example 443

N'-{(2S,3R)-1-(azetidine-1-carbonyl)-4,4-difluoro-2-[(2-fluoro-3'-methyl[1,1'-biphenyl]-3-yl)methyl]pyrrolidin-3-yl}-N,N-dimethylsulfuric Diamide To a mixture of (2S,3R)-3-[(dimethylsulfamoyl)amino]-4,4-difluoro-2-[(2-fluoro-3'-methyl[1,1'-biphenyl]-3-yl)methyl]pyrrolidine-1-carbonyl chloride (50 mg) and THF (0.5 ml) was added azetidine (17.5 mg) at 0° C. The mixture was stirred at room temperature for 2 hr, and purified by silica gel column chromatography (EtOAc/hexane) to give the title compound (20 mg).

¹H NMR (400 MHz, CDCl₃) δ 1.99-2.11 (2H, m), 2.41 (3H, s), 2.78 (6H, s), 2.83-2.93 (1H, m), 2.96-3.09 (1H, m), 3.58-3.91 (6H, m), 4.10-4.26 (1H, m), 4.69-4.87 (1H, m), 4.87-5.01 (1H, m), 7.12-7.23 (2H, m), 7.24-7.36 (5H, m).

Example 450

N-{(2S,3R,4S)-1-(azetidine-1-carbonyl)-4-fluoro-2-[(2,3',5'-trifluoro[1,1'-biphenyl]-3-yl)methyl]pyrrolidin-3-yl}ethanesulfonamide

A) N-{(2S,3R,4S)-1-(azetidine-1-carbonyl)-2-[(3-chloro-2-fluorophenyl)methyl]-4-fluoropyrrolidin-3-yl}ethanesulfonamide To a mixture of N-{(2S,3R,4S)-2-[(3-chloro-2-fluorophenyl)methyl]-4-fluoropyrrolidin-3-yl}ethanesulfonamide hydrobromide (60 mg), bis(trichloromethyl)carbonate (25.5 mg) and THF (1.4 mL) was added DIPEA (0.075 mL) at 0° C. After being stirred at 0° C. for 30 min, the mixture was poured into water and extracted with EtOAc. The combined organic layers were dried over sodium sulfate, filtered and concentrated under reduced pressure. The residue was diluted with THF (1.4 mL), and azetidine (0.029 mL) was added thereto at room temperature. After being stirred at room temperature for 2 h, the mixture was poured into aqueous saturated ammonium chloride solution and extracted with EtOAc. The combined organic layers were dried over sodium sulfate, filtered and concentrated under reduced pressure. The residue was purified by preparative HPLC (Column: L-Column 2 ODS, mobile phase: H₂O 10 mM NH₄HCO₃/CH₃CN) to give the title compound (49.0 mg).

MS: [M+H]⁺ 422.1.

B) N-{(2S,3R,4S)-1-(azetidine-1-carbonyl)-4-fluoro-2-[(2,3',5'-trifluoro[1,1'-biphenyl]-3-yl)methyl]pyrrolidin-3-yl}ethanesulfonamide A mixture of N-{(2S,3R,4S)-1-(azetidine-1-carbonyl)-2-[(3-chloro-2-fluorophenyl)methyl]-4-fluoropyrrolidin-3-yl}ethanesulfonamide (23 mg), (3,5-difluorophenyl)boronic acid (17.2 mg), XPhos Pd G3 (4.61 mg) and 1 M aqueous potassium phosphate solution (0.164 mL) in DME (0.8 mL)

was stirred at 80° C. under nitrogen atmosphere for 2 h. The mixture was directly purified by column chromatography (NH silica gel, eluted with EtOAc/hexane) to give the title compound (24.5 mg).

$^1$H NMR (400 MHz, CDCl$_3$) δ 1.28 (3H, t, J=7.4 Hz), 2.13 (2H, quin, J=8.0 Hz), 2.95 (3H, q, J=7.3 Hz), 3.04-3.14 (1H, m), 3.61-3.79 (4H, m), 3.89-4.08 (3H, m), 4.66-4.75 (1H, m), 4.86 (1H, d, J=10.3 Hz), 5.06-5.27 (1H, m), 6.82 (1H, t, J=8.9 Hz), 7.08 (2H, d, J=7.0 Hz), 7.15-7.22 (1H, m), 7.27-7.31 (1H, m), 7.36 (1H, t, J=7.1 Hz).

Example 451

N-{(2S,3R,4S)-1-(azetidine-1-carbonyl)-4-fluoro-2-[(2-fluoro-3'-methyl[1,1'-biphenyl]-3-yl)methyl]pyrrolidin-3-yl}ethanesulfonamide A mixture of N-{(2S,3R,4S)-1-(azetidine-1-carbonyl)-2-[(3-chloro-2-fluorophenyl)methyl]-4-fluoropyrrolidin-3-yl}ethanesulfonamide (23 mg), m-tolylboronic acid (14.8 mg), XPhos Pd G3 (4.61 mg) and 1 M aqueous potassium phosphate solution (0.164 mL) in DME (0.8 mL) was stirred at 80° C. under nitrogen atmosphere for 2 h. The mixture was directly purified by column chromatography (NH silica gel, eluted with EtOAc/hexane) to give the title compound (23.5 mg).

$^1$H NMR (400 MHz, CDCl$_3$) δ 1.22 (3H, t, J=7.3 Hz), 2.06-2.18 (2H, m), 2.38-2.45 (3H, m), 2.87 (2H, q, J=7.2 Hz), 2.92-3.01 (1H, m), 3.05-3.14 (1H, m), 3.60-3.82 (4H, m), 3.88-4.09 (3H, m), 4.68 (1H, q, J=7.3 Hz), 4.88 (1H, d, J=10.3 Hz), 5.04-5.27 (1H, m), 7.13-7.21 (2H, m), 7.27-7.37 (5H, m).

Example 458

N'-{(2S,3R,4S)-1-(azetidine-1-carbonyl)-4-fluoro-2-[(2,3',5'-trifluoro[1,1'-biphenyl]-3-yl)methyl]pyrrolidin-3-yl}-N,N-dimethylsulfuric Diamide A) benzyl (2S,3R,4S)-2-[(3-chloro-2-fluorophenyl)methyl]-3-[(dimethylsulfamoyl)amino]-4-fluoropyrrolidine-1-carboxylate A mixture of benzyl (2S,3R,4S)-3-amino-2-[(3-chloro-2-fluorophenyl)methyl]-4-fluoropyrrolidine-1-carboxylate (100 mg), DMAP (64.2 mg) and dimethylsulfamoyl chloride (3 mL) was stirred overnight under nitrogen atmosphere at 50° C. The reaction mixture was purified by column chromatography (NH silica gel, eluted with EtOAc/hexane) to give the title compound (114 mg).

MS: [M+H]$^+$ 488.1.

B) N'-{(2S,3R,4S)-2-[(3-chloro-2-fluorophenyl)methyl]-4-fluoropyrrolidin-3-yl}-N,N-dimethylsulfuric Diamide Hydrobromide To benzyl (2S,3R,4S)-2-[(3-chloro-2-fluorophenyl)methyl]-3-[(dimethylsulfamoyl)amino]-4-fluoropyrrolidine-1-carboxylate (225 mg) was added 30% HBr/acetic acid solution (10 mL) at room temperature. The mixture was stirred at room temperature 16 h then the solvent was evaporated with toluene. The solid obtained was suspended in IPE and collected by filtration to give the title compound (180 mg).

MS: [M+H]$^+$ 354.0.

C) (2S,3R,4S)-2-[(3-chloro-2-fluorophenyl methyl]-3-[(dimethylsulfamoyl)amino]-4-fluoropyrrolidine-1-carbonyl Chloride Bis(trichloromethyl) carbonate (76 mg) was added to a solution of N'-{(2S,3R,4S)-2-[(3-chloro-2-fluorophenyl)methyl]-4-fluoropyrrolidin-3-yl}-N,N-dimethylsulfuric diamide hydrobromide (140 mg) and DIPEA (0.112 mL) in THF (4.7 mL) at 0° C. After being stirred at 0° C. for 10 min and at room temperature for 10 min, the mixture was neutralized with saturated aqueous sodium hydrogen carbonate solution at 0° C. and extracted with EtOAc. The organic layer was separated, washed with water and saturated brine, dried over magnesium sulfate and concentrated under reduced pressure to give the title compound (120 mg).

MS: [M−H]$^−$ 414.0.

D) N'-{(2S,3S,4S)-1-(azetidine-1-carbonyl)-2-[(3-chloro-2-fluorophenyl)methyl]-4-fluoropyrrolidin-3-yl}-N,N-dimethylsulfuric Diamide Azetidine (300 µL) was added to a solution of (2S,3R,4S)-2-[(3-chloro-2-fluorophenyl)methyl]-3-[(dimethylsulfamoyl)amino]-4-fluoropyrrolidine-1-carbonyl chloride (80 mg) in THF (3 mL) at 0° C. The mixture was stirred at room temperature under a dry atmosphere for 2 h. The mixture was neutralized with 0.05 M hydrochloric acid at 0° C. and extracted with EtOAc. The organic layer was separated, washed with saturated aqueous sodium hydrogen carbonate solution, water and saturated brine, dried over magnesium sulfate and concentrated under reduced pressure to give the title compound (70.0 mg).

MS: [M+H]$^+$ 437.1.

E) N'-{(2S,3R,4S)-1-(azetidine-1-carbonyl)-4-fluoro-2-[(2,3',5'-trifluoro[1,1'-biphenyl]-3-yl)methyl]pyrrolidin-3-yl}-N,N-dimethylsulfuric diamide A mixture of N'-{(2S,3R,4S)-1-(azetidine-1-carbonyl)-2-[(3-chloro-2-fluorophenyl)methyl]-4-fluoropyrrolidin-3-yl}-N,N-dimethylsulfuric diamide (35 mg), (3,5-difluorophenyl)boronic acid (19.0 mg), XPhos Pd G3 (6.78 mg) and 1 M aqueous potassium phosphate solution (0.120 mL) in THF (3 mL) was heated at 80° C. for 1 h under microwave irradiation. The mixture was neutralized with aqueous saturated ammonium chloride solution at 0° C. and extracted with EtOAc. The organic layer was separated, washed with water and saturated brine, dried over magnesium sulfate and concentrated under reduced pressure. The crude was purified by preparative TLC (silica gel, eluted with EtOAc/hexane) to give the title compound (20.0 mg).

$^1$H NMR (400 MHz, CDCl$_3$) δ 1.99-2.21 (2H, m), 2.71 (6H, s), 2.84-3.00 (1H, m), 3.00-3.18 (1H, m), 3.63-3.80 (4H, m), 3.80-4.01 (3H, m), 4.58-4.81 (1H, m), 4.77-4.97 (1H, m), 5.05-5.37 (1H, m), 6.70-6.90 (1H, m), 7.02-7.21 (3H, m), 7.25-7.30 (1H, m), 7.32-7.45 (1H, m).

Example 459

(2S,3R,4S)-3-[(dimethylsulfamoyl)amino]-4-fluoro-2-[(2-fluoro-3'-methyl[1,1'-biphenyl]-3-yl)methyl]-N,N-dimethylpyrrolidine-1-carboxamide A) (2S,3R,4S)-2-[(3-chloro-2-fluorophenyl)methyl]-3-[(dimethylsulfamoyl)amino]-4-fluoro-N,N-dimethylpyrrolidine-1-carboxamide Dimethylamine (366 µL) was added to a solution of (2S,3R,4S)-2-[(3-chloro-2-fluorophenyl)methyl]-3-[(dimethylsulfamoyl)amino]-4-fluoropyrrolidine-1-carbonyl chloride (40 mg) in THF (2 mL) at 0° C. The mixture was stirred at room temperature under a dry atmosphere for 2 h. The mixture was neutralized with 0.05 M hydrochloric acid at 0° C. and extracted with EtOAc. The organic layer was separated, washed with water and saturated brine, dried over magnesium sulfate and concentrated under reduced pressure to give the title compound (35.0 mg).

MS: [M+H]$^+$ 425.0.

B) (2S,3R,4S)-3-[(dimethylsulfamoyl)amino]-4-fluoro-2-[(2-fluoro-3'-methyl[1,1'-biphenyl]-3-yl)methyl]-N,N-dimethylpyrrolidine-1-carboxamide A mixture of (2S,3R,4S)-2-[(3-chloro-2-fluorophenyl)methyl]-3-[(dimethylsulfamoyl)amino]-4-fluoro-N,N-dimethylpyrrolidine-1-carboxamide (35 mg), m-tolylboronic acid (16.8 mg), XPhos Pd G3 (6.97 mg) and 1 M potassium phosphate, aqueous solution (0.247 mL) in THF (3 mL) was heated at 85° C. for 3 h under microwave irradiation. The mixture was neutralized with saturated aqueous sodium hydrogen carbonate solution at 0° C. and extracted with EtOAc. The organic layer was separated, washed with water and saturated brine, dried over magnesium sulfate and concentrated under reduced pressure. The crude was purified by column chromatography (NH silica gel, eluted with EtOAc/hexane) to give the title compound (13.0 mg).

$^1$H NMR (400 MHz, CDCl$_3$) δ 2.41 (3H, s), 2.65 (6H, s), 2.80 (6H, s), 2.82-2.90 (1H, m), 3.00-3.08 (1H, m), 3.58-3.76 (1H, m), 3.78-4.04 (2H, m), 4.75-4.89 (2H, m), 5.01-5.39 (1H, m), 7.07-7.15 (1H, m), 7.15-7.23 (2H, m), 7.24-7.27 (1H, m), 7.28-7.36 (3H, m).

Example 462

N'-[(2S,3R,4S)-4-fluoro-2-[(2-fluoro-3'-methyl[1,1'-biphenyl]-3-yl)methyl]-1-(1-hydroxycyclobutane-1-carbonyl)pyrrolidin-3-yl]-N,N-dimethylsulfuric Diamide A) N'-[(2S,3R,4S)-2-[(3-chloro-2-fluorophenyl)methyl]-4-fluoro-1-(1-hydroxycyclobutane-1-carbonyl)pyrrolidin-3-yl]-N,N-dimethylsulfuric Diamide To a solution of N'-{(2S,3R,4S)-2-[(3-chloro-2-fluorophenyl)methyl]-4-fluoropyrrolidin-3-yl}-N,N-dimethylsulfuric diamide hydrobromide (40 mg) and 1-hydroxycyclobutane-1-carboxylic acid (12.8 mg) in DMF (1 mL) were added HATU (52.5 mg) and DIPEA (0.048 mL) at room temperature. The mixture was stirred overnight at room temperature. The mixture was quenched with saturated aqueous sodium hydrogen carbonate solution and extracted with EtOAc. The organic layer was separated, washed with water and saturated brine, dried over magnesium sulfate and concentrated under reduced pressure. The residue was purified by column chromatography (NH silica gel, eluted with EtOAc/hexane) to give the title compound (40.0 mg).

MS: [M+H]$^+$ 452.0.

B) N'-[(2S,3R,4S)-4-fluoro-2-[(2-fluoro-3'-methyl[1,1'-biphenyl]-3-yl)methyl]-1-(1-hydroxycyclobutane-1-carbonyl)pyrrolidin-3-yl]-N,N-dimethylsulfuric Diamide A mixture of N'-[(2S,3R,4S)-2-[(3-chloro-2-fluorophenyl)methyl]-4-fluoro-1-(1-hydroxycyclobutane-1-carbonyl)pyrrolidin-3-yl]-N,N-dimethylsulfuric diamide (40 mg), m-tolylboronic acid (18.1 mg), XPhos Pd G3 (7.49 mg) and 1 M aqueous potassium phosphate solution (0.266 mL) in THF (3 mL) was heated at 85° C. for 3 h under microwave irradiation. The mixture was neutralized with aqueous saturated ammonium chloride solution at 0° C. and extracted with EtOAc. The organic layer was separated, washed with water and saturated brine, dried over magnesium sulfate and concentrated under reduced pressure. The residue was purified by column chromatography (NH silica gel, eluted with EtOAc/hexane) to give the title compound (32.0 mg).

$^1$H NMR (400 MHz, CDCl$_3$) δ 1.59-1.70 (1H, m), 1.82-1.97 (1H, m), 1.97-2.14 (2H, m), 2.15-2.20 (1H, m), 2.41 (3H, s), 2.57 (8H, s), 2.98-3.11 (1H, m), 3.11-3.27 (1H, m), 3.74-4.30 (3H, m), 4.72-4.84 (1H, m), 4.85-5.01 (1H, m), 5.09-5.34 (1H, m), 7.10-7.23 (2H, m), 7.26-7.30 (1H, m), 7.31 (3H, s), 7.36-7.47 (1H, m).

Example 463

N'-{(2S,3R,4S)-1-(azetidine-1-carbonyl)-4-fluoro-2-[(2-fluoro-3'-methyl[1,1'-biphenyl]-3-yl)methyl]pyrrolidin-3-yl}-N,N-dimethylsulfuric Diamide A mixture of N'-{(2S,3R,4S)-1-(azetidine-1-carbonyl)-2-[(3-chloro-2-fluorophenyl)methyl]-4-fluoropyrrolidin-3-yl}-N,N-dimethylsulfuric diamide (35 mg), m-tolylboronic acid (16.3 mg), XPhos Pd G3 (6.78 mg) and 1 M aqueous potassium phosphate solution (0.240 m) in THF (3 mL) was heated at 85° C. for 3 h under microwave irradiation. The mixture was neutralized with aqueous saturated ammonium chloride solution at 0° C. and extracted with EtOAc. The organic layer was separated, washed with water and saturated brine, dried over magnesium sulfate and concentrated under reduced pressure. The residue was purified by column chromatography (NH silica gel, eluted with EtOAc/hexane) to give the title compound (13.0 mg).

$^1$H NMR (400 MHz, CDCl$_3$) δ 2.03-2.16 (2H, m), 2.41 (3H, s), 2.63-2.69 (6H, m), 2.90-2.99 (1H, m), 3.03-3.15 (1H, m), 3.59-4.01 (7H, m), 4.63-4.76 (1H, m), 4.76-4.91 (1H, m), 5.03-5.41 (1H, m), 7.10-7.21 (2H, m), 7.26-7.37 (5H, m).

Example 505

N-[(2S,3R)-2-{[3'-(difluoromethyl)-2-fluoro[1,1'-biphenyl]-3-yl]methyl}-4,4-difluoro-1-(3-fluorocyclobutane-1-carbonyl)pyrrolidin-3-yl]ethanesulfonamide with Longer Retention Time A) tert-butyl (2S,3R)-2-{[3'-(difluoromethyl)-2-fluoro[1,1'-biphenyl]-3-yl]methyl}-3-[(ethanesulfonyl)amino]-4,4-difluoropyrrolidine-1-carboxylate A mixture of tert-butyl (2S,3R)-2-(3-chloro-2-fluorobenzyl)-3-(ethylsulfonamido)-4,4-difluoropyrrolidine-1-carboxylate (270 mg), (3-(difluoromethyl)phenyl)boronic acid (203 mg), XPhos Pd G3 (50.0 mg) and 1 M aqueous potassium phosphate solution (1.77 mL) in THF (7 mL) was stirred overnight at 90° C. in sealed tube. The mixture was quenched with saturated aqueous sodium hydrogen carbonate solution and extracted with EtOAc. The organic layer was separated, washed with saturated brine, dried over sodium sulfate and concentrated under reduced pressure.

The mixture was purified by column chromatography (silica gel, eluted with EtOAc/hexane) to give the title compound (231 mg).
MS: [M–H]⁻ 547.2.

B) N-[(2S,3R)-2-{[3'-(difluoromethyl)-2-fluoro[1,1'-biphenyl]-3-yl]methyl}-4,4-difluoropyrrolidin-3-yl]ethanesulfonamide Hydrochloride The mixture of tert-butyl (2S,3R)-2-{[3'-(difluoromethyl)-2-fluoro[1,1'-biphenyl]-3-yl]methyl}-3-[(ethanesulfonyl)amino]-4,4-difluoropyrrolidine-1-carboxylate (231 mg) and 4 M HCl/CPME solution (5 mL) was stirred at room temperature for 2 h. White solid was collected by filtration to give the title compound (195 mg).
MS: [M+H]⁺ 449.1.

C) N-[(2S,3R)-2-{[3'-(difluoromethyl)-2-fluoro[1,1'-biphenyl]-3-yl]methyl}-4,4-difluoro-1-(3-fluorocyclobutane-1-carbonyl)pyrrolidin-3-yl]ethanesulfonamide with Longer Retention Time To a mixture of 3-fluorocyclobutanecarboxylic acid (29.2 mg), N-[(2S,3R)-2-{[3'-(difluoromethyl)-2-fluoro[1,1'-biphenyl]-3-yl]methyl}-4,4-difluoropyrrolidin-3-yl]ethanesulfonamide hydrochloride (60 mg), DIPEA (0.130 mL) and DMF (1 mL) was added HATU (75 mg) at room temperature. The mixture was stirred at room temperature for 3 h. The mixture was quenched with aqueous saturated ammonium chloride solution at room temperature and extracted with EtOAc. The organic layer was separated, washed with saturated aqueous sodium hydrogen carbonate solution and saturated brine, dried over sodium sulfate and concentrated under reduced pressure. The residue was purified by column chromatography (silica gel, eluted with EtOAc/hexane) and then preparative HPLC (Column: CHIRALCEL OJ-H, mobile phase: carbon dioxide/MeOH=900/100 (v/v)) to give the title compound (25.6 mg).
¹H NMR (400 MHz, CDCl₃) δ 1.25-1.48 (3H, m), 1.63-3.30 (9H, m), 3.70-5.30 (6H, m), 6.53-6.88 (1H, m), 7.14-7.71 (7H, m).

Example 542

N'-{(2S,3R)-4,4-difluoro-1-[(2R)-oxetane-2-carbonyl]-2-[(2,3',5'-trifluoro[1,1'-biphenyl]-3-yl)methyl]pyrrolidin-3-yl}-N,N-dimethylsulfuric Diamide A) (2R)-oxetane-2-carboxylic Acid Iodobenzene diacetate (8.04 g), (2,2,6,6-Tetramethylpiperidin-1-yl)oxyl (0.532 g) and (R)-oxetan-2-ylmethanol (1.00 g) were combined, and to this mixture were added CH₃CN (50 mL) and water (50.0 mL) and then the mixture was stirred for 3 h at room temperature. The mixture was neutralized with 1 M NaOH aqueous solution at 0° C. and the aqueous layer was washed with IPE. The aqueous layer was acidified with 2 M hydrochloric acid at 0° C. To the mixture was added NaCl and the mixture was extracted with THF/EtOAc). The organic layer was separated, dried over magnesium sulfate and concentrated under reduced pressure. To the residue was added toluene and the mixture was concentrated under reduced pressure to give the title compound (0.510 g).
¹H NMR (400 MHz, CDCl₃) δ 2.69-2.90 (1H, m), 3.00-3.22 (1H, m), 4.68-4.88 (2H, m), 5.07-5.33 (1H, m).

B) tert-butyl (2S,3R)-2-[(3-chloro-2-fluorophenyl)methyl]-3-[(dimethylsulfamoyl)amino]-4,4-difluoropyrrolidine-1-carboxylate A mixture of tert-butyl (2S,3R)-3-amino-2-[(3-chloro-2-fluorophenyl)methyl]-4,4-difluoropyrrolidine-1-carboxylate (500 mg) and DMAP (335 mg) in dimethylsulfamoyl chloride (4 mL) was stirred at 65° C. for 5 h under nitrogen atmosphere. The reaction mixture was cooled to room temperature and purified by column chromatography (NH silica gel, eluted with EtOAc/hexane) to give the title compound (541 mg).
MS, found: 416.0.

C) N'-{(2S,3R)-2-[(3-chloro-2-fluorophenyl)methyl]-4,4-difluoropyrrolidin-3-yl}-N,N-dimethylsulfuric Diamide Hydrochloride tert-Butyl (2S,3R)-2-[(3-chloro-2-fluorophenyl)methyl]-3-[(dimethylsulfamoyl)amino]-4,4-difluoropyrrolidine-1-carboxylate (541 mg) was stirred in 4 M HCl/CPME solution (10 mL) at 60° C. for 1 h. The mixture was concentrated under reduced pressure, triturated with IPE and collected by filtration to give the title compound (439 mg).
MS: [M+H]⁺ 372.0.

D) N'-{(2S,3R)-2-[(3-chloro-2-fluorophenyl)methyl]-4,4-difluoro-1-[(2R)-oxetane-2-carbonyl]pyrrolidin-3-yl}-N,N-dimethylsulfuric Diamide To a solution of N'-{(2S,3R)-2-[(3-chloro-2-fluorophenyl)methyl]-4,4-difluoropyrrolidin-3-yl}-N,N-dimethylsulfuric diamide hydrochloride (100 mg) and (2R)-oxetane-2-carboxylic acid (0.034 mL) in DMF (5 mL) were added HATU (140 mg) and DIPEA (0.171 mL) at room temperature. The mixture was stirred overnight at room temperature. The mixture was quenched with aqueous saturated ammonium chloride solution and extracted with EtOAc. The organic layer was separated, washed with water and saturated brine, dried over sodium sulfate and concentrated under reduced pressure. The residue was purified by column chromatography (NH silica gel, eluted with EtOAc/hexane) to give the title compound (109 mg).
MS: [M+H]⁺ 456.0.

E) N'-{(2S,3R)-4,4-difluoro-1-[(2R)-oxetane-2-carbonyl]-2-[(2,3',5'-trifluoro[1,1'-biphenyl]-3-yl)methyl]pyrrolidin-3-yl}-N,N-dimethylsulfuric Diamide A mixture of N'-{(2S,3R)-2-[(3-chloro-2-fluorophenyl)methyl]-4,4-difluoro-1-[(2R)-oxetane-2-carbonyl]pyrrolidin-3-yl}-N,N-dimethylsulfuric diamide (22 mg), (3,5-difluorophenyl)boronic acid (15.2 mg), XPhos Pd G3 (4.08 mg) and 1M aqueous potassium phosphate solution (0.145 mL) in DME (0.8 mL) was stirred at 80° C. under nitrogen atmosphere for 2 h. The mixture was purified by column chromatography (silica gel, eluted with EtOAc/hexane) to give the title compound (16.4 mg).
¹H NMR (400 MHz, CDCl₃) δ 2.71-3.06 (9H, m), 3.06-3.25 (1H, m), 3.69-3.90 (1H, m), 4.05-5.17 (7H, m), 6.77-6.87 (1H, m), 7.06 (2H, d, J=7.0 Hz), 7.21 (1H, q, J=7.3 Hz), 7.27-7.48 (2H, m).

The compounds of Examples are shown in the following tables. MS in the tables means actual measured value. The compounds of Examples 6, 9-12, 14-20, 22-24, 27-34, 36-43, 47-49, 53-55, 57-65, 69-72, 74, 75, 80, 82-86, 89, 90, 93, 95, 96, 99-105, 107-115, 117-120, 123, 125-128, 130, 132, 134-143, 148-170, 172-201, 203, 204, 206-209, 213-219, 221-224, 227-235, 237, 238, 240-244, 246, 247, 252-256, 258-266, 268-271, 273-301, 303, 306, 308-345, 347-373, 377, 379, 382, 384-387, 389-391, 394-430, 432, 434, 438, 444-449, 452-457, 460, 461, 464-504, 506-541 and 543-616 in the following tables were produced according to the methods described in the above-mentioned Examples, or methods analogous thereto.

TABLE 1-1

| EX. | IUPAC NAME | Structure | ADDITIVE | MS |
|---|---|---|---|---|
| 1 | N-[(2S,3R)-2-[(2,3'-difluoro[1,1'-biphenyl]-3-yl)methyl]-4,4-difluoro-1-((2R)-oxetane-2-carbonyl)pyrrolidin-3-yl]ethanesulfonamide | 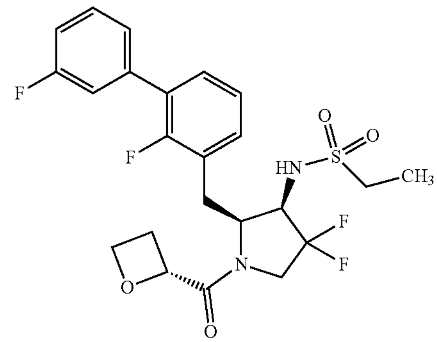 [SMILES: CCS(=O)(=O)N[C@@H]1[C@H](Cc2cccc(-c3cccc(F)c3)c2F)N(C(=O)[C@H]2CCO2)CC1(F)F] | | 501.4 |
| 2 | N-{(2S,3R)-4,4-difluoro-1-(2-hydroxy-2-methylpropanoyl)-2-[(2,3',5'-trifluoro[1,1'-biphenyl]-3-yl)methyl]pyrrolidin-3-yl}-methanesulfonamide | 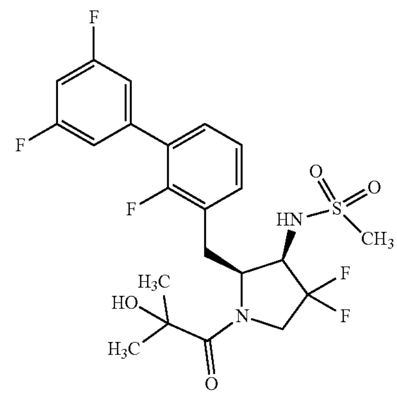 [SMILES: CC(C)(O)C(=O)N1CC(F)(F)[C@H](NS(C)(=O)=O)[C@@H]1Cc1cccc(-c2cc(F)cc(F)c2)c1F] | | 507.1 |
| 3 | N-{(2S,3R)-4,4-difluoro-1-(2-hydroxy-2-methylpropanoyl)-2-[(2,3',5'-trifluoro[1,1'-biphenyl]-3-yl)methyl]pyrrolidin-3-yl}-ethanesulfonamide | 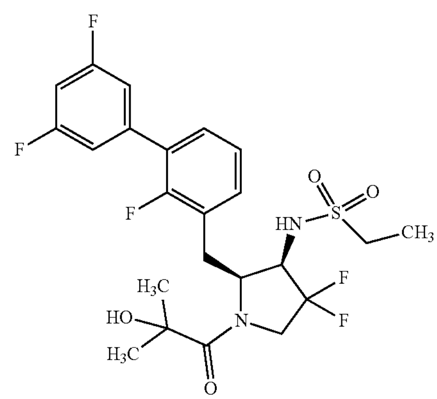 [SMILES: CCS(=O)(=O)N[C@@H]1[C@H](Cc2cccc(-c3cc(F)cc(F)c3)c2F)N(C(=O)C(C)(C)O)CC1(F)F] | | 521.1 |
| 4 | N-[(2S,3R)-4,4-difluoro-2-[(2-fluoro[1,1'-biphenyl]-3-yl)methyl]-1-(2-hydroxy-2-methylpropanoyl)pyrrolidin-3-yl]methanesulfonamide | 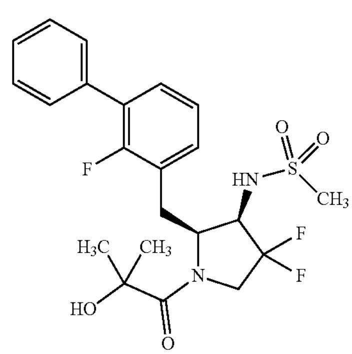 [SMILES: CC(C)(O)C(=O)N1CC(F)(F)[C@H](NS(C)(=O)=O)[C@@H]1Cc1cccc(-c2ccccc2)c1F] | | 471.2 |

TABLE 1-1-continued

| EX. | IUPAC NAME | Structure | ADDITIVE | MS |
|---|---|---|---|---|
| 5 | N-[(2S,3R)-4,4-difluoro-2-[(2-fluoro[1,1'-biphenyl]-3-yl)methyl]-1-(2-hydroxy-2-methylpropanoyl)pyrrolidin-3-yl]ethanesulfonamide | 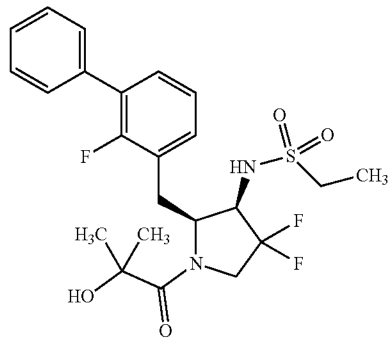 [SMILES: CCS(=O)(=O)N[C@@H]1[C@H](Cc2cccc(-c3ccccc3)c2F)N(C(=O)C(C)(C)O)CC1(F)F] | | 485.2 |
| 6 | N-{(2S,3R)-4,4-difluoro-2-[(2-fluoro[1,1'-biphenyl]-3-yl)methyl]-1-[(2R)-3,3,3-trifluoro-2-hydroxy-2-methylpropanoyl]-pyrrolidin-3-yl}methanesulfonamide | 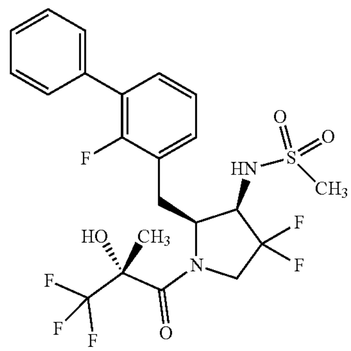 [SMILES: C[C@@](O)(C(=O)N1CC(F)(F)[C@H](NS(C)(=O)=O)[C@@H]1Cc1cccc(-c2ccccc2)c1F)C(F)(F)F] | | 523.3 |
| 7 | N-[(2S,3R)-2-[(2,3'-difluoro[1,1'-biphenyl]-3-yl)methyl]-4,4-difluoro-1-(2-hydroxy-2-methylpropanoyl)pyrrolidin-3-yl]methanesulfonamide | 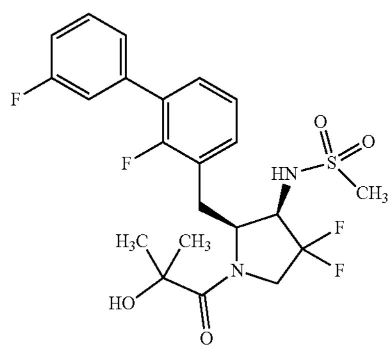 [SMILES: CC(C)(O)C(=O)N1CC(F)(F)[C@H](NS(C)(=O)=O)[C@@H]1Cc1cccc(-c2cccc(F)c2)c1F] | | 487.2 |
| 8 | N-[(2S,3R)-2-[(2,3'-difluoro[1,1'-biphenyl]-3-yl)methyl]-4,4-difluoro-1-(2-hydroxy-2-methylpropanoyl)pyrrolidin-3-yl]ethanesulfonamide | 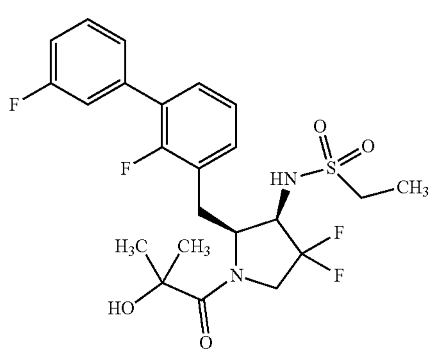 [SMILES: CCS(=O)(=O)N[C@@H]1[C@H](Cc2cccc(-c3cccc(F)c3)c2F)N(C(=O)C(C)(C)O)CC1(F)F] | | 503.1 |

TABLE 1-1-continued

| EX. | IUPAC NAME | Structure | ADDITIVE | MS |
|---|---|---|---|---|
| 9 | N-{(2S,3R)-2-[(2,3'-difluoro[1,1'-biphenyl]-3-yl)methyl]-4,4-difluoro-1-[(2R)-oxolane-2-carbonyl]pyrrolidin-3-yl}methanesulfonamide | 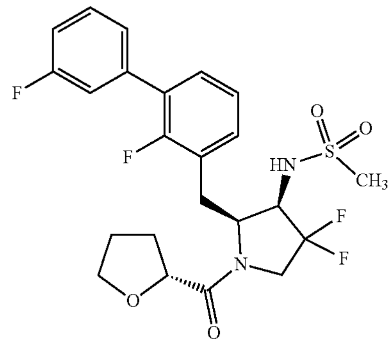 [SMILES: CS(=O)(=O)N[C@@H]1[C@H](Cc2cccc(-c3cccc(F)c3)c2F)N(C(=O)[C@H]2CCCO2)CC1(F)F] | | 501.1 |
| 10 | (2S,3R)-2-[(2,3'-difluoro[1,1'-biphenyl]-3-yl)methyl]-4,4-difluoro-3-[(methanesulfonyl)amino]-N,N-dimethylpyrrolidine-1-carboxamide | 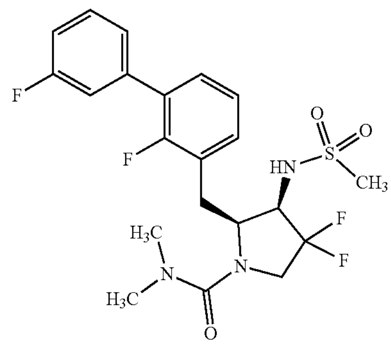 [SMILES: CN(C)C(=O)N1CC(F)(F)[C@H](NS(C)(=O)=O)[C@@H]1Cc1cccc(-c2cccc(F)c2)c1F] | | 474.1 |
| 11 | N-{(2S,3R)-1-(azetidine-1-carbonyl)-2-[(2,3'-difluoro[1,1'-biphenyl]-3-yl)methyl]-4,4-difluoropyrrolidin-3-yl}methanesulfonamide | 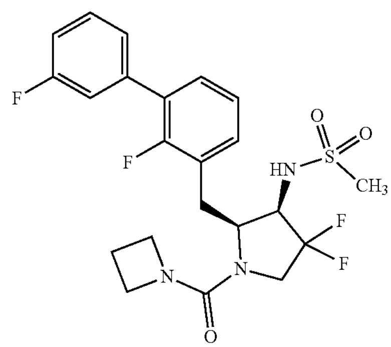 [SMILES: CS(=O)(=O)N[C@@H]1[C@H](Cc2cccc(-c3cccc(F)c3)c2F)N(C(=O)N2CCC2)CC1(F)F] | | 486.1 |
| 12 | N-[(2S,3R)-2-[(2,3'-difluoro[1,1'-biphenyl]-3-yl)methyl]-4,4-difluoro-1-(3-fluoroazetidine-1-carbonyl)pyrrolidin-3-yl]methanesulfonamide | 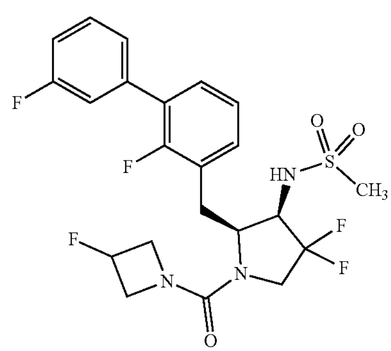 [SMILES: CS(=O)(=O)N[C@@H]1[C@H](Cc2cccc(-c3cccc(F)c3)c2F)N(C(=O)N2CC(F)C2)CC1(F)F] | | 504.1 |

TABLE 1-1-continued

| EX. | IUPAC NAME | Structure | ADDITIVE | MS |
|---|---|---|---|---|
| 13 | N-[(2S,3R)-2-[(2,3'-difluoro[1,1'-biphenyl]-3-yl)methyl]-4,4-difluoro-1-(1-hydroxy-cyclobutane-1-carbonyl)pyrrolidin-3-yl]-methanesulfonamide | 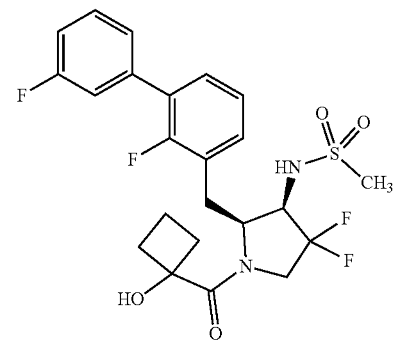 [SMILES: CS(=O)(=O)N[C@@H]1[C@H](Cc2cccc(-c3cccc(F)c3)c2F)N(C(=O)C2(O)CCC2)CC1(F)F] | | 501.1 |
| 14 | N-[(2S,3R)-2-[(3',5',-difluoro[1,1'-biphenyl]-3-yl)methyl]-4,4-difluoro-1-(2-hydroxy-2-methylpropanoyl)pyrrolidin-3-yl]ethane-sulfonamide | 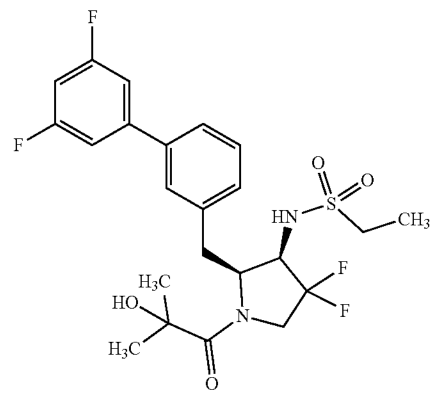 [SMILES: CCS(=O)(=O)N[C@@H]1[C@H](Cc2cccc(-c3cc(F)cc(F)c3)c2)N(C(=O)C(C)(C)O)CC1(F)F] | | 503.1 |
| 15 | rac-N-[(2S,3R,4R)-2-[(2,3'-difluoro[1,1'-biphenyl]-3-yl)methyl]-4-fluoro-1-(2-hydroxy-2-methylpropanoyl)pyrrolidin-3-yl]methanesulfonamide | 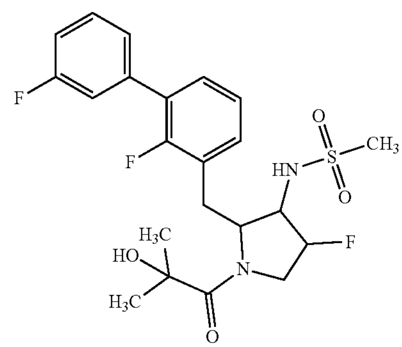 [SMILES: CC(C)(O)C(=O)N1CC(F)C(NS(C)(=O)=O)C1Cc1cccc(-c2cccc(F)c2)c1F] | | 471.2 |
| 16 | N-[(2S,3R)-2-[(2,3'-difluoro[1,1'-biphenyl]-3-yl)methyl]-4,4-difluoro-1-(2-hydroxy-2-methylbutaroyl)pyrrolidin-3-yl]methane-sulfonamide with shorter retention time | 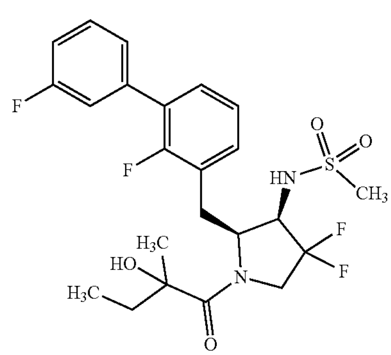 [SMILES: CCC(C)(O)C(=O)N1CC(F)(F)[C@H](NS(C)(=O)=O)[C@@H]1Cc1cccc(-c2cccc(F)c2)c1F] | | 503.2 |

TABLE 1-1-continued

| EX. | IUPAC NAME | Structure | ADDITIVE | MS |
|---|---|---|---|---|
| 17 | N-[(2S,3R)-2-[(2,3'-difluoro[1,1'-biphenyl]-3-yl)methyl]-4,4-difluoro-1-(2-hydroxy-2-methylbutanoyl)pyrrolidin-3-yl]methanesulfonamide with longer retention time | 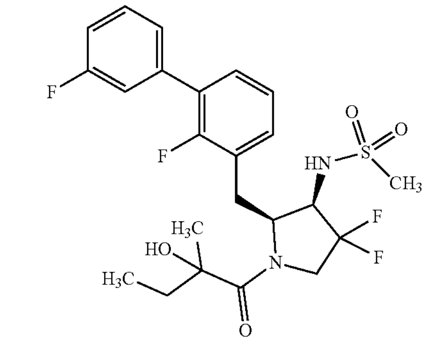 [SMILES: CCC(C)(O)C(=O)N1CC(F)(F)[C@H](NS(C)(=O)=O)[C@@H]1Cc1cccc(-c2cccc(F)c2)c1F] | | 503.2 |
| 18 | N-{(2S,3R)-4,4-difluoro-1-(2-hydroxy-2-methylpropanoyl)-2-[(3'-methyl[1,1'-biphenyl]-3-yl)methyl]pyrrolidin-3-yl}-ethanesulfonamide | 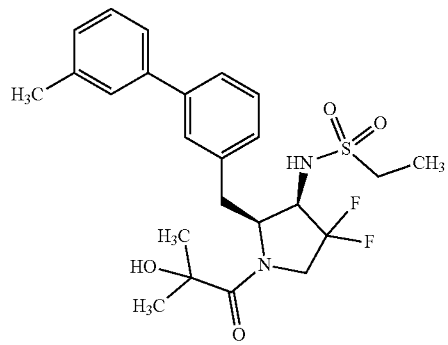 [SMILES: CCS(=O)(=O)N[C@@H]1[C@H](Cc2cccc(-c3cccc(C)c3)c2)N(C(=O)C(C)(C)O)CC1(F)F] | | 481.2 |
| 19 | N-[(2S,3R)-2-[(2',3'-difluoro[1,1'-biphenyl]-3-yl)methyl]-4,4-difluoro-1-(2-hydroxy-2-methylpropanoyl)pyrrolidin-3-yl]ethanesulfonamide | 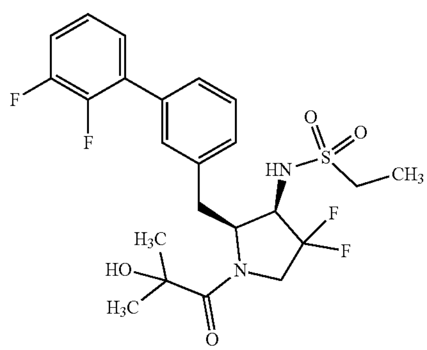 [SMILES: CCS(=O)(=O)N[C@@H]1[C@H](Cc2cccc(-c3cccc(F)c3F)c2)N(C(=O)C(C)(C)O)CC1(F)F] | | 503.2 |
| 20 | N-[(2S,3R)-4,4-difluoro-2-[(3'-fluoro[1,1'-biphenyl]-3-yl)methyl]-1-(2-hydroxy-2-methylpropanoyl)pyrrolidin-3-yl]ethanesulfonamide | 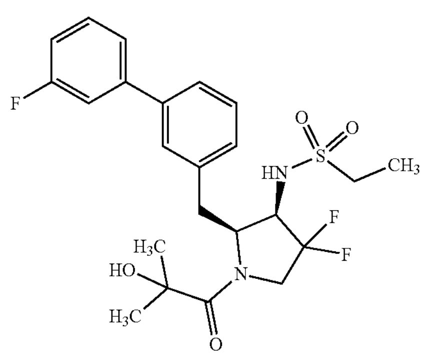 [SMILES: CCS(=O)(=O)N[C@@H]1[C@H](Cc2cccc(-c3cccc(F)c3)c2)N(C(=O)C(C)(C)O)CC1(F)F] | | 485.2 |

TABLE 1-1-continued

| EX. | IUPAC NAME | Structure | ADDITIVE | MS |
|---|---|---|---|---|
| 21 | N-{(2S,3R)-1-(bicyclo[1.1.1]pentane-1-carbonyl)-4,4-difluoro-2-[(3'-fluoro[1,1'-biphenyl]-3-yl)methyl]pyrrolidin-3-yl]-methanesulfonamide | 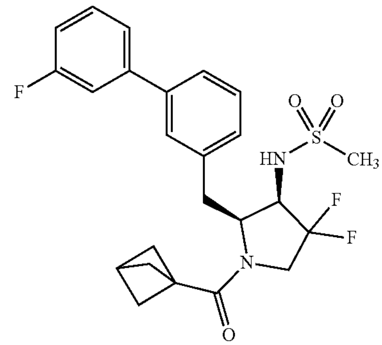 [SMILES: CS(=O)(=O)N[C@@H]1[C@H](Cc2cccc(-c3cccc(F)c3)c2)N(C(=O)C23CC(C2)C3)CC1(F)F] | | 479.2 |
| 22 | N-{(2S,3R)-1-(1-cyanocyclobutane-1-carbonyl)-4,4-difluoro-2-[(3'-fluoro[1,1'-biphenyl]-3-yl)methyl]pyrrolidin-3-yl}methanesulfonamide | 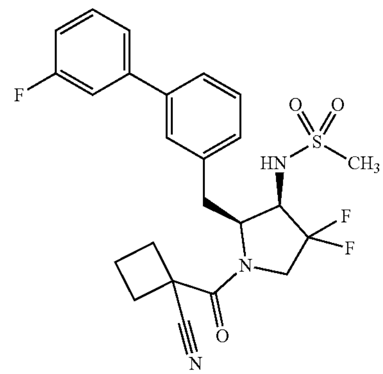 [SMILES: CS(=O)(=O)N[C@@H]1[C@H](Cc2cccc(-c3cccc(F)c3)c2)N(C(=O)C2(C#N)CCC2)CC1(F)F] | | 490.2 |
| 23 | N-[(2S,3R)-4,4-difluoro-2-[(2-fluoro[1,1'-biphenyl]-3-yl)methyl]-1-(1-hydroxy-cyclobutane-1-carbonyl)pyrrolidin-3-yl]-ethanesulfonamide | 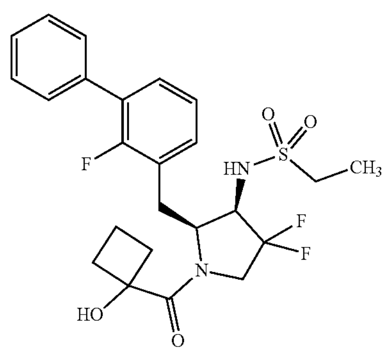 [SMILES: CCS(=O)(=O)N[C@@H]1[C@H](Cc2cccc(-c3ccccc3)c2F)N(C(=O)C2(O)CCC2)CC1(F)F] | | 497.2 |
| 24 | N-[(2S,3R)-4,4-difluoro-2-[(2-fluoro[1,1'-biphenyl]-3-yl)methyl]-1-(3-hydroxy-azetidine-1-carbonyl)pyrrolidin-3-yl]-ethanesulfonamide | 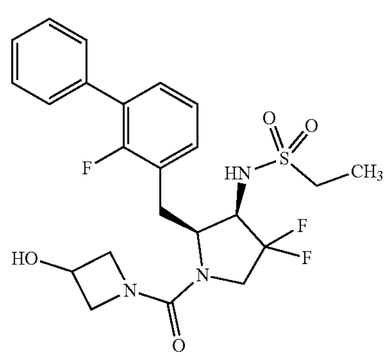 [SMILES: CCS(=O)(=O)N[C@@H]1[C@H](Cc2cccc(-c3ccccc3)c2F)N(C(=O)N2CC(O)C2)CC1(F)F] | | 498.2 |

TABLE 1-1-continued

| EX. | IUPAC NAME | Structure | ADDITIVE | MS |
|---|---|---|---|---|
| 25 | N-[(2S,3R)-4,4-difluoro-2-[(2-fluoro-3'-methyl[1,1'-biphenyl]-3-yl)methyl]-1-(2-hydroxy-2-methylpropanoyl)pyrrolidin-3-yl]methanesulfonamide | 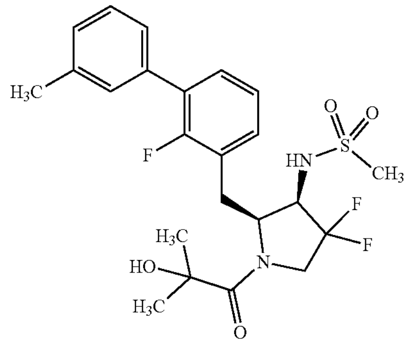 | | 485.2 |
| 26 | N-{(2S,3R)-4,4-difluoro-2-[(3'-fluoro[1,1'-biphenyl]-3-yl)methyl]-1-[(2R)-oxolane-2-carbonyl]pyrrolidin-3-yl}methanesulfonamide | 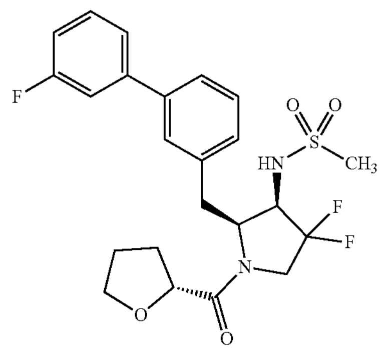 [SMILES: CS(=O)(=O)N[C@@H]1[C@H](Cc2cccc(-c3cccc(F)c3)c2)N(C(=O)[C@H]2CCCO2)CC1(F)F] | | 483.2 |
| 27 | N-[(2S,3R)-2-{[3'-(difluoromethyl)-2-fluoro[1,1'-biphenyl]-3-yl]methyl}-4,4-difluoro-1-(2-hydroxy-2-methylpropanoyl)-pyrrolidin-3-yl]methanesulfonamide | 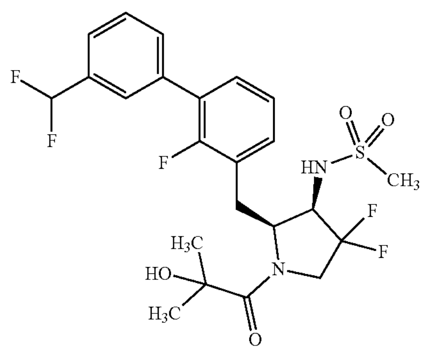 [SMILES: CC(C)(O)C(=O)N1CC(F)(F)[C@H](NS(C)(=O)=O)[C@@H]1Cc1cccc(-c2cccc(C(F)F)c2)c1F] | | 521.2 |
| 28 | N-{(2S,3R)-1-(bicyclo[1.1.1]pentane-1-carbonyl)-2-[(2,3'-difluoro[1,1'-biphenyl]-3-yl)methyl]-4,4-difluoropyrrolidin-3-yl}methanesulfonamide | 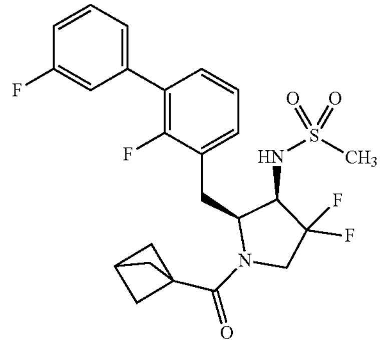 [SMILES: CS(=O)(=O)N[C@@H]1[C@H](Cc2cccc(-c3cccc(F)c3)c2F)N(C(=O)C23CC(C2)C3)CC1(F)F] | | 497.2 |

TABLE 1-1-continued

| EX. | IUPAC NAME | Structure | ADDITIVE | MS |
|---|---|---|---|---|
| 29 | N-{(2S,3R)-2-[(1,1'-biphenyl]-3-yl)-methyl]-4,4-difluoro-1-[(2R)-oxolane-2-carbonyl]pyrrolidin-3-yl)methane-sulfonamide | 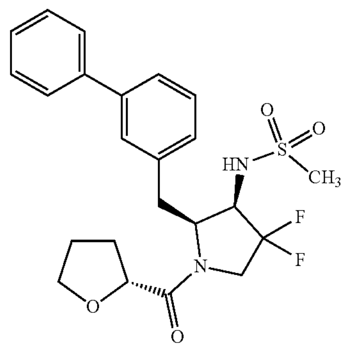 [SMILES: CS(=O)(=O)N[C@@H]1[C@H](Cc2cccc(-c3ccccc3)c2)N(C(=O)[C@H]2CCCO2)CC1(F)F] | | 465.2 |
| 30 | N-{(2S,3R)-1-(bicyclo[1.1.1]pentane-1-carbonyl)-2-[([1,1'-biphenyl]-3-yl)methyl]-4,4-difluoropyrrolidin-3-yl}methane-sulfonamide | 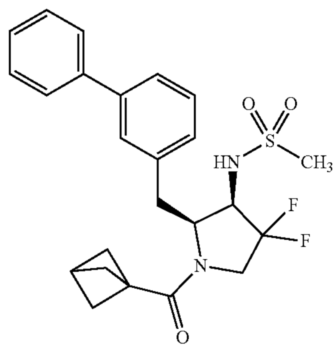 [SMILES: CS(=O)(=O)N[C@@H]1[C@H](Cc2cccc(-c3ccccc3)c2)N(C(=O)C23CC(C2)C3)CC1(F)F] | | 461.2 |
| 31 | N-[(2S,3R)-2-[(2,3'-difluoro-5'-methyl[1,1'-biphenyl]-3-yl)methyl]-4,4-difluoro-1-(2-hydroxy-2-methylpropanoyl)pyrrolidin-3-yl]methanesulfonamide | 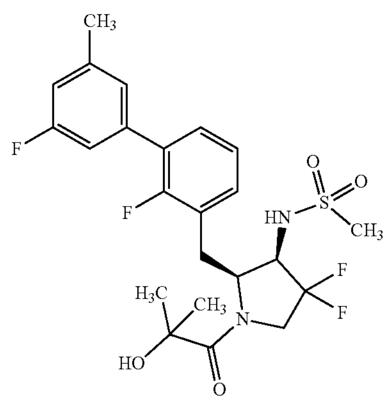 [SMILES: Cc1cc(F)cc(-c2cccc(C[C@H]3[C@@H](NS(C)(=O)=O)C(F)(F)CN3C(=O)C(C)(C)O)c2F)c1] | | 503.2 |
| 32 | N-{(2S,3R)-1-(bicyclo[1.1.1]pentane-1-carbonyl)-4,4-difluoro-2-[(3,-methyl[1,1'-biphenyl]-3-yl)methyl]pyrrolidin-3-yl}-methanesulfonamide | 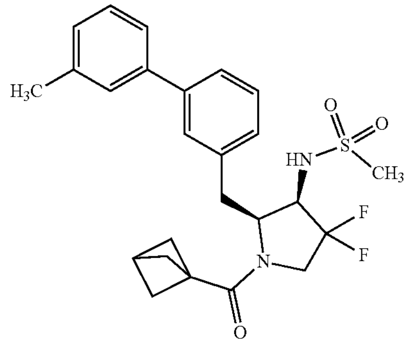 [SMILES: Cc1cccc(-c2cccc(C[C@H]3[C@@H](NS(C)(=O)=O)C(F)(F)CN3C(=O)C34CC(C3)C4)c2)c1] | | 475.2 |

TABLE 1-1-continued

| EX. | IUPAC NAME | Structure | ADDITIVE | MS |
|---|---|---|---|---|
| 33 | N-[(2S,3R)-4,4-difluoro-2-[(2-fluoro-3'-methoxy[1,1'-biphenyl]-3-yl)methyl]-1-(2-hydroxy-2-methylpropanoyl)pyrrolidin-3-yl]methanesulfonamide | 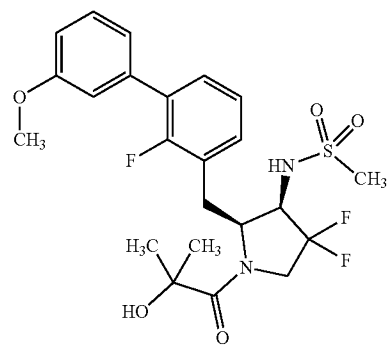 [SMILES: COc1cccc(-c2cccc(C[C@H]3[C@@H](NS(C)(=O)=O)C(F)(F)CN3C(=O)C(C)(C)O)c2F)c1] | | 501.2 |
| 34 | N-[(2S,3R)-2-[(3',5'-difluoro[1,1'-biphenyl]-3-yl)methyl]-4,4-difluoro-1-(1-methyl-cyclopropane-1-carbonyl)pyrrolidin-3-yl]-methanesulfonamide | 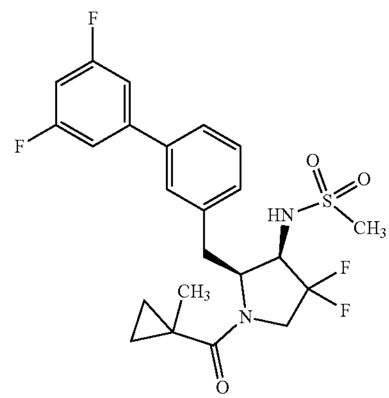 [SMILES: CC1(C(=O)N2CC(F)(F)[C@H](NS(C)(=O)=O)[C@@H]2Cc2cccc(-c3cc(F)cc(F)c3)c2)CC1] | | 483.2 |
| 35 | N-[(2S,3R)-2-[(3',5'-difluoro[1,1'-biphenyl]-3-yl)methyl]-4,4-difluoro-1-(2-methyl-propanoyl)pyrrolidin-3-yl]methane-sulfonamide | 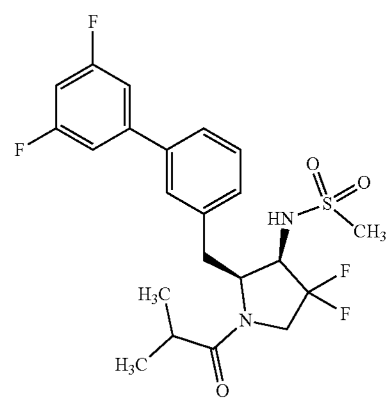 [SMILES: CC(C)C(=O)N1CC(F)(F)[C@H](NS(C)(=O)=O)[C@@H]1Cc1cccc(-c2cc(F)cc(F)c2)c1] | | 473.2 |
| 36 | N-{(2S,3R)-2-[(3',5'-difluoro[1,1'-biphenyl]-3-yl)methyl]-4,4-difluoro-1-[(2R)-oxolane-2-carbonyl]pyrrolidin-3-yl}methane-sulfonamide | 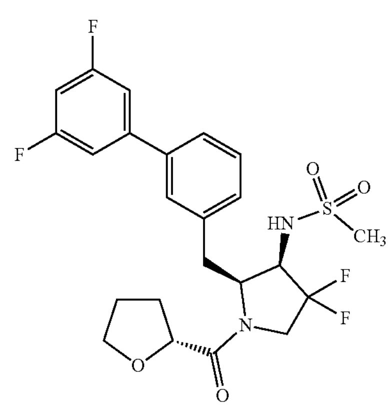 [SMILES: CS(=O)(=O)N[C@@H]1[C@H](Cc2cccc(-c3cc(F)cc(F)c3)c2)N(C(=O)[C@H]2CCCO2)CC1(F)F] | | 501.2 |

TABLE 1-1-continued

| EX. | IUPAC NAME | Structure | ADDITIVE | MS |
|---|---|---|---|---|
| 37 | N-{(2S,3R)-4,4-difluoro-1-(2-hydroxy-2-methylpropanoyl)-2-[(2,2',5'-trifluoro[1,1'-biphenyl]-3-yl)methyl]pyrrolidin-3-yl}-methanesulfonamide | 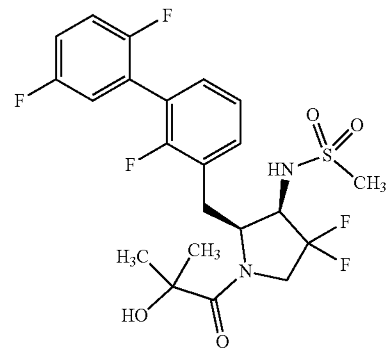 [SMILES: CC(C)(O)C(=O)N1CC(F)(F)[C@H](NS(C)(=O)=O)[C@@H]1Cc1cccc(-c2cc(F)ccc2F)c1F] | | 507.1 |
| 38 | N-{(2S,3R)-4,4-difluoro-1-(2-hydroxy-2-methylpropanoyl)-2-[(2,2',3'-trifluoro[1,1'-biphenyl]-3-yl)methyl]pyrrolidin-3-yl}-methanesulfonamide | 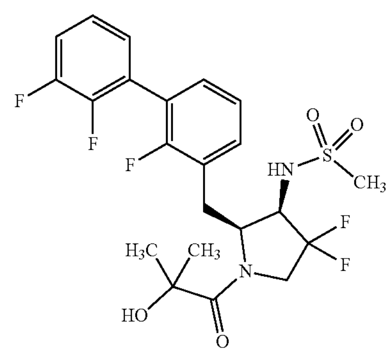 [SMILES: CC(C)(O)C(=O)N1CC(F)(F)[C@H](NS(C)(=O)=O)[C@@H]1Cc1cccc(-c2cccc(F)c2F)c1F] | | 507.2 |
| 39 | N-[(2S,3R)-2-[(2,3,-difluoro[1,1'-biphenyl]-3-yl)methyl]-4,4-difluoro-1-(2-hydroxy-2-methylpropanoyl)pyrrolidin-3-yl]cyclopropanesulfonamide | 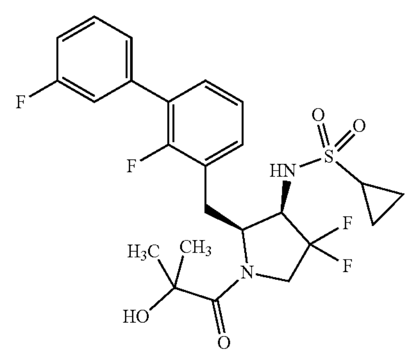 [SMILES: CC(C)(O)C(=O)N1CC(F)(F)[C@H](NS(=O)(=O)C2CC2)[C@@H]1Cc1cccc(-c2cccc(F)c2)c1F] | | 515.2 |
| 40 | N-[(2S,3R)-4,4-difluoro-2-[(2-fluoro[1,1'-biphenyl]-3-yl)methyl]-1-(2-hydroxy-2-methylpropanoyl)pyrrolidin-3-yl]cyclopropanesulfonamide | 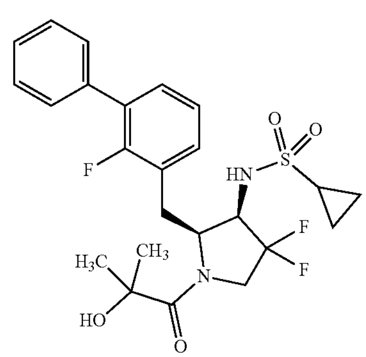 [SMILES: CC(C)(O)C(=O)N1CC(F)(F)[C@H](NS(=O)(=O)C2CC2)[C@@H]1Cc1cccc(-c2ccccc2)c1F] | | 497.2 |

TABLE 1-1-continued

| EX. | IUPAC NAME | Structure | ADDITIVE | MS |
|---|---|---|---|---|
| 41 | N-[(2S,3R)-2-{[3'-(difluoromethoxy)-2-fluoro[1,1'-biphenyl]-3-yl]methyl}-4,4-difluoro-1-(2-hydroxy-2-methyl-propanoyl)pyrrolidin-3-yl]methane-sulfonamide | 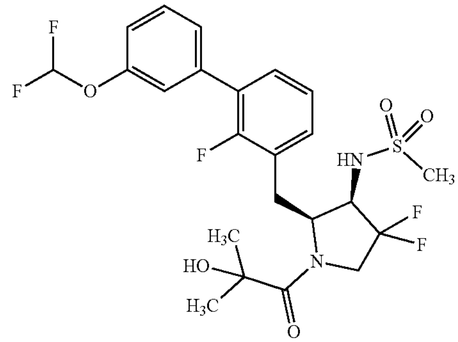 [SMILES: CC(C)(O)C(=O)N1CC(F)(F)[C@H](NS(C)(=O)=O)[C@@H]1Cc1cccc(-c2cccc(OC(F)F)c2)c1F] | | 537.1 |
| 42 | N-{(2S,3R)-1-(bicyclo[1.1.1]pentane-1-carbonyl)-2-[(3'-chloro[1,1'-biphenyl]-3-yl)methyl]-4,4-difluoropyrrolidin-3-yl}methanesulfonamide | 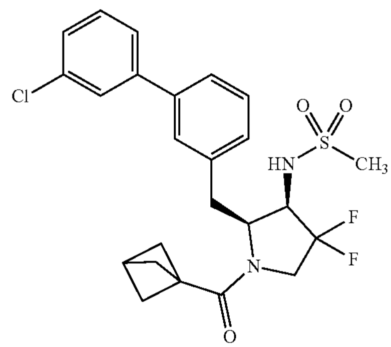 [SMILES: CS(=O)(=O)N[C@@H]1[C@H](Cc2cccc(-c3cccc(Cl)c3)c2)N(C(=O)C23CC(C2)C3)CC1(F)F] | | 495.1 |
| 43 | N-{(2S,3R)-2-[(3'-chloro[1,1'-biphenyl]-3-yl)methyl]-4,4-difluoro-1-[(2R)-oxolane-2-carbonyl]pyrrolidin-3-yl}methanesulfon-amide | 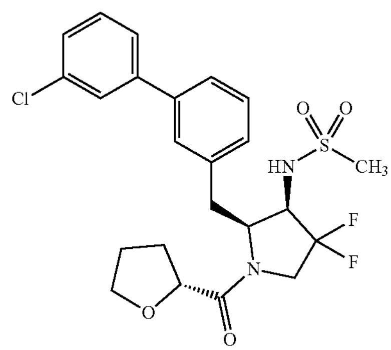 [SMILES: CS(=O)(=O)N[C@@H]1[C@H](Cc2cccc(-c3cccc(Cl)c3)c2)N(C(=O)[C@H]2CCCO2)CC1(F)F] | | 499.1 |
| 44 | N-[(2S,3R)-2-[(3'-chloro-2-fluoro[1,1'-biphenyl]-3-yl)methyl]-4,4-difluoro-1-(2-hydroxy-2-methylpropanoyl)pyrrolidin-3-yl]methanesulfonamide | 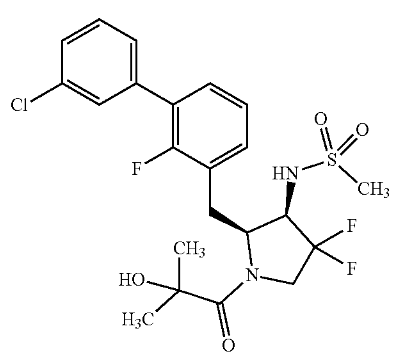 [SMILES: CC(C)(O)C(=O)N1CC(F)(F)[C@H](NS(C)(=O)=O)[C@@H]1Cc1cccc(-c2cccc(Cl)c2)c1F] | | 505.1 |

TABLE 1-1-continued

| EX. | IUPAC NAME | Structure | ADDITIVE | MS |
|---|---|---|---|---|
| 45 | N-[(2S,3R)-4,4-difluoro-2-[(2-fluoro[1,1'-biphenyl]-3-yl)methyl]-1-(oxetane-2-carbonyl)pyrrolidin-3-yl]ethanesulfonamide with shorter retention time | 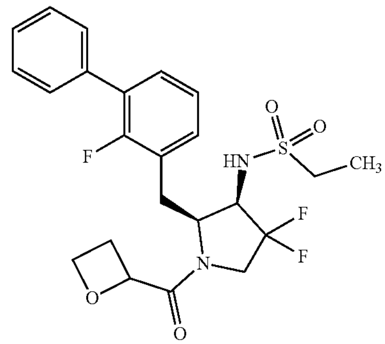 [SMILES: CCS(=O)(=O)N[C@@H]1[C@H](Cc2cccc(-c3ccccc3)c2F)N(C(=O)C2CCO2)CC1(F)F] | | 483.2 |
| 46 | N-[(2S,3R)-4,4-difluoro-2-[(2-fluoro[1,1'-biphenyl]-3-yl)methyl]-1-(oxetane-2-carbonyl)pyrrolidin-3-yl]ethanesulfonamide with longer retention time | 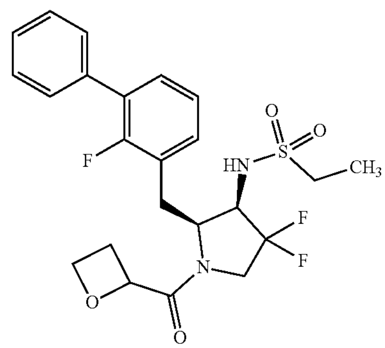 [SMILES: CCS(=O)(=O)N[C@@H]1[C@H](Cc2cccc(-c3ccccc3)c2F)N(C(=O)C2CCO2)CC1(F)F] | | 483.1 |
| 47 | N-[(2S,3R)-2-[(3',5'-difluoro[1,1'-biphenyl]-3-yl)methyl]-4,4-difluoro-1-(oxetane-2-carbonyl)pyrrolidin-3-yl]methanesulfonamide with shorter retention time | 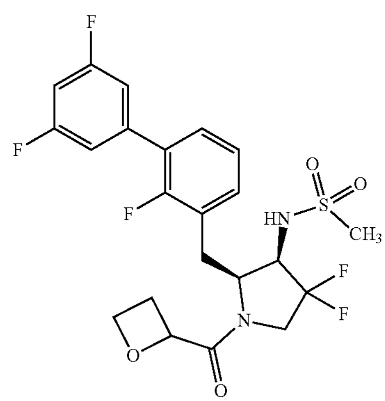 [SMILES: CS(=O)(=O)N[C@@H]1[C@H](Cc2cccc(-c3cc(F)cc(F)c3)c2F)N(C(=O)C2CCO2)CC1(F)F] | | 487.2 |
| 48 | N-[(2S,3R)-2-[(3',5'-difluoro[1,1'-biphenyl]-3-yl)methyl]-4,4-difluoro-1-(oxetane-2-carbonyl)pyrrolidin-3-yl]methanesulfonamide with longer retention time | 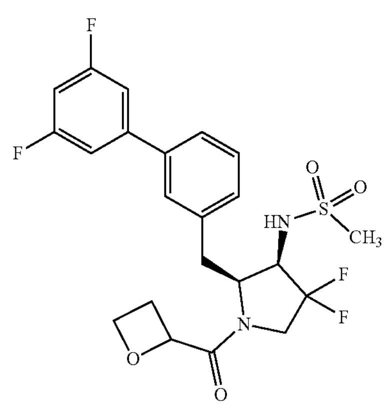 [SMILES: CS(=O)(=O)N[C@@H]1[C@H](Cc2cccc(-c3cc(F)cc(F)c3)c2)N(C(=O)C2CCO2)CC1(F)F] | | 487.1 |

TABLE 1-1-continued

| EX. | IUPAC NAME | Structure | ADDITIVE | MS |
|-----|------------|-----------|----------|-----|
| 49 | N-[(2S,3R)-2-[(2,3,-difluoro[1,1'-biphenyl]-3-yl)methyl]-4,4-difluoro-1-((2S)-oxetane-2-carbonyl)pyrrolidin-3-yl]ethanesulfonamide | 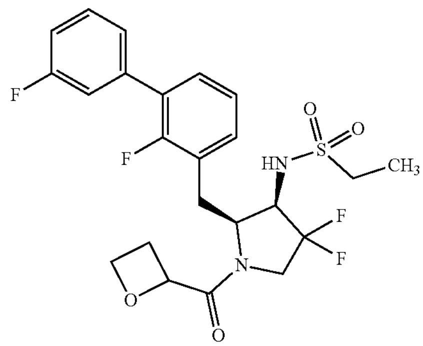 [SMILES: CCS(=O)(=O)N[C@@H]1[C@H](Cc2cccc(-c3cccc(F)c3)c2F)N(C(=O)C2CCO2)CC1(F)F] | | 501.1 |
| 50 | N-[(2S,3R)-2-[([1,1'-biphenyl]-3-yl)methyl]-4,4-difluoro-1-(oxetane-2-carbonyl)-pyrrolidin-3-yl]ethanesulfonamide with shorter retention time | 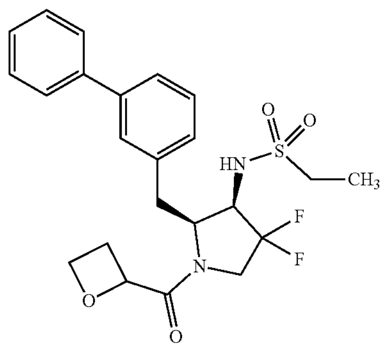 [SMILES: CCS(=O)(=O)N[C@@H]1[C@H](Cc2cccc(-c3ccccc3)c2)N(C(=O)C2CCO2)CC1(F)F] | | 465.2 |
| 51 | N-[(2S,3R)-2-[([1,1'-biphenyl]-3-yl)-methyl]-4,4-difluoro-1-(oxetane-2-carbonyl)pyrrolidin-3-yl]ethanesulfonamide with longer retention time | 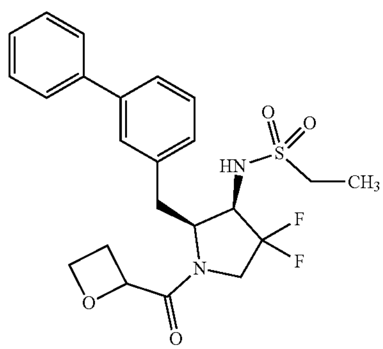 [SMILES: CCS(=O)(=O)N[C@@H]1[C@H](Cc2cccc(-c3ccccc3)c2)N(C(=O)C2CCO2)CC1(F)F] | | 465.2 |
| 52 | N-[(2S,3R)-4,4-difluoro-2-[(3'-fluoro[1,1'-biphenyl]-3-yl)methyl]-1-(oxetane-2-carbonyl)pyrrolidin-3-yl]ethanesulfonamide with shorter retention time | 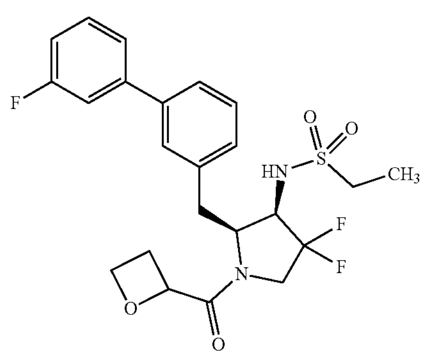 [SMILES: CCS(=O)(=O)N[C@@H]1[C@H](Cc2cccc(-c3cccc(F)c3)c2)N(C(=O)C2CCO2)CC1(F)F] | | 483.2 |

TABLE 1-1-continued

| EX. | IUPAC NAME | Structure | ADDITIVE | MS |
|---|---|---|---|---|
| 53 | N-[(2S,3R)-4,4-difluoro-2-[(3'-fluoro[1,1'-biphenyl]-3-yl)methyl]-1-(oxetane-2-carbonyl)pyrrolidin-3-yl]ethanesulfonamide with longer retention time | 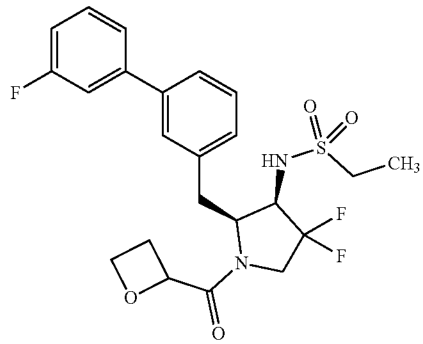 [SMILES: CCS(=O)(=O)N[C@@H]1[C@H](Cc2cccc(-c3cccc(F)c3)c2)N(C(=O)C2CCO2)CC1(F)F] | | 483.2 |
| 54 | N-[(2S,3R)-2-[(3',5'-difluoro[1,1'-biphenyl]-3-yl)methyl]-4,4-difluoro-1-(oxetane-2-carbonyl)pyrrolidin-3-yl]ethanesulfonamide with shorter retention time | 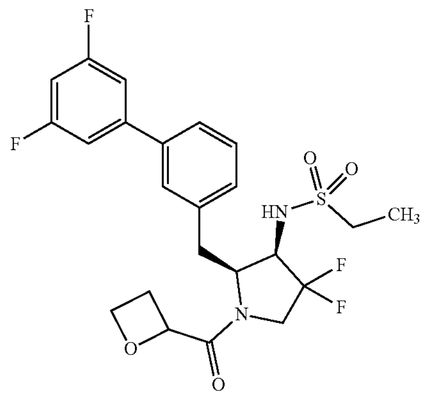 [SMILES: CCS(=O)(=O)N[C@@H]1[C@H](Cc2cccc(-c3cc(F)cc(F)c3)c2)N(C(=O)C2CCO2)CC1(F)F] | | 501.2 |
| 55 | N-[(2S,3R)-2-[(3',5'-difluoro[1,1'-biphenyl]-3-yl)methyl]-4,4-difluoro-1-(oxetane-2-carbonyl)pyrrolidin-3-yl]ethanesulfonamide with longer retention time | 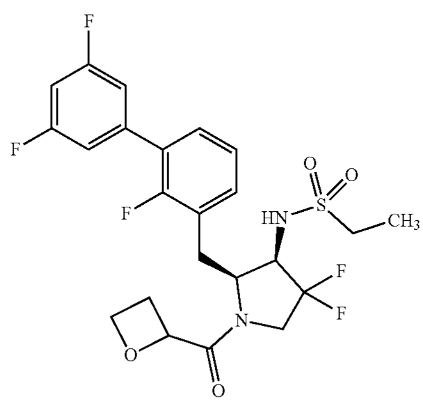 [SMILES: CCS(=O)(=O)N[C@@H]1[C@H](Cc2cccc(-c3cc(F)cc(F)c3)c2F)N(C(=O)C2CCO2)CC1(F)F] | | 501.1 |
| 56 | N-{(2S,3R)-4,4-difluoro-1-((2R)-oxetane-2-carbonyl)-2-[(2,3',5'-trifluoro[1,1'-biphenyl]-3-yl)methyl]pyrrolidin-3-yl}-ethanesulfonamide | 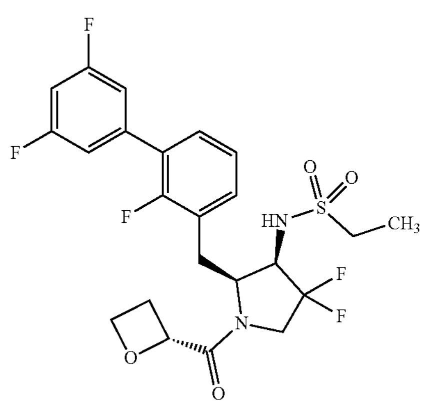 | | 519.1 |

TABLE 1-1-continued

| EX. | IUPAC NAME | Structure | ADDITIVE | MS |
|---|---|---|---|---|
| 57 | N-{(2S,3R)-4,4-difluoro-1-((2S)-oxetane-2-carbonyl)-2-[(2,3',5'-trifluoro[1,1'-biphenyl]-3-yl)methyl]pyrrolidin-3-yl}-ethanesulfonamide | 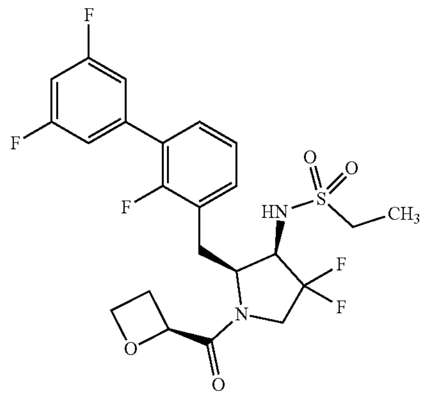 [SMILES: CCS(=O)(=O)N[C@@H]1[C@H](Cc2cccc(-c3cc(F)cc(F)c3)c2F)N(C(=O)[C@@H]2CCO2)CC1(F)F] | | 519.1 |
| 58 | N-{(2S,3R)-1-(cyclobutanecarbonyl)-4,4-difluoro-2-[(3'-fluoro[1,1'-biphenyl]-3-yl)methyl]pyrrolidin-3-yl}methanesulfonamide | 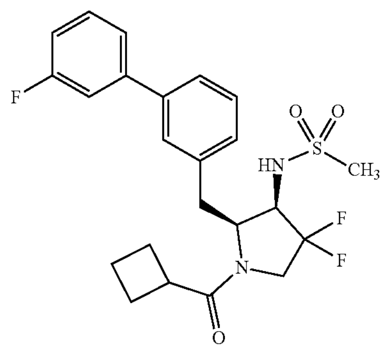 [SMILES: CS(=O)(=O)N[C@@H]1[C@H](Cc2cccc(-c3cccc(F)c3)c2)N(C(=O)C2CCC2)CC1(F)F] | | 467.2 |
| 59 | (2S,3R)-4,4-difluoro-2-[(3'-fluoro[1,1'-biphenyl]-3-yl)methyl]-3-[(methanesulfonyl)amino]-N,N-dimethylpyrrolidine-1-carboxamide | 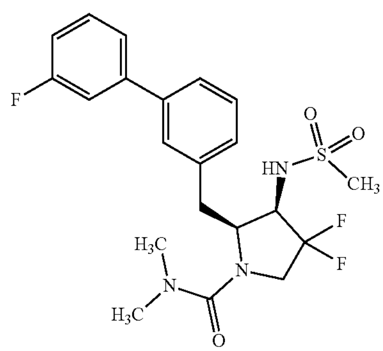 [SMILES: CN(C)C(=O)N1CC(F)(F)[C@H](NS(C)(=O)=O)[C@@H]1Cc1cccc(-c2cccc(F)c2)c1] | | 456.2 |
| 60 | N-{(2S,3R)-1-(azetidine-1-carbonyl)-4,4-difluoro-2-[(3'-fluoro[1,1'-biphenyl]-3-yl)methyl]pyrrolidin-3-yl}methanesulfonamide | 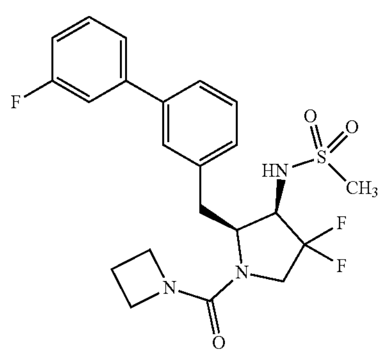 [SMILES: CS(=O)(=O)N[C@@H]1[C@H](Cc2cccc(-c3cccc(F)c3)c2)N(C(=O)N2CCC2)CC1(F)F] | | 468.2 |

TABLE 1-1-continued

| EX. | IUPAC NAME | Structure | ADDITIVE | MS |
|---|---|---|---|---|
| 61 | N-[(2S,3R)-4,4-difluoro-2-[(3'-fluoro[1,1'-biphenyl]-3-yl)methyl]-1-(oxetane-2-carbonyl)pyrrolidin-3-yl]methanesulfonamide with shorter retention time | 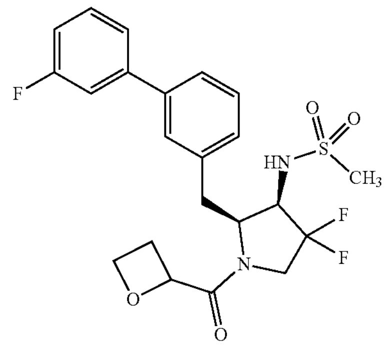 [SMILES: CS(=O)(=O)N[C@@H]1[C@H](Cc2cccc(-c3cccc(F)c3)c2)N(C(=O)C2CCO2)CC1(F)F] | | 469.2 |
| 62 | N-[(2S,3R)-4,4-difluoro-2-[(3'-fluoro[1,1'-biphenyl]-3-yl)methyl]-1-(oxetane-2-carbonyl)pyrrolidin-3-yl]methanesulfonamide with longer retention time | 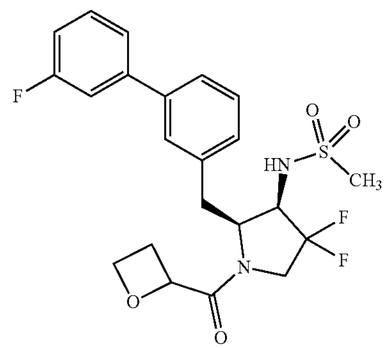 [SMILES: CS(=O)(=O)N[C@@H]1[C@H](Cc2cccc(-c3cccc(F)c3)c2)N(C(=O)C2CCO2)CC1(F)F] | | 469.2 |
| 63 | N-[(2S,3R)-2-[([1,1'-biphenyl]-3-yl)methyl]-4,4-difluoro-1-(oxetane-2-carbonyl)-pyrrolidin-3-yl]methanesulfonamide with shorter retention time | 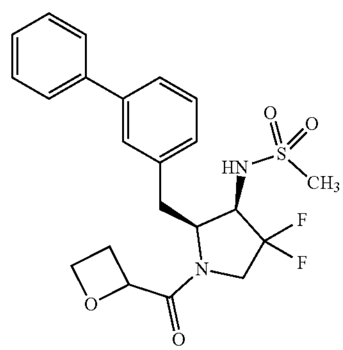 [SMILES: CS(=O)(=O)N[C@@H]1[C@H](Cc2cccc(-c3ccccc3)c2)N(C(=O)C2CCO2)CC1(F)F] | | 451.2 |
| 64 | N-[(2S,3R)-2-[([1,1'-biphenyl]-3-yl)methyl]-4,4-difluoro-1-(oxetane-2-carbonyl)-pyrrolidin-3-yl]methanesulfonamide with longer retention time | 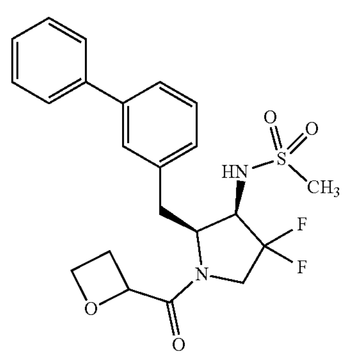 [SMILES: CS(=O)(=O)N[C@@H]1[C@H](Cc2cccc(-c3ccccc3)c2)N(C(=O)C2CCO2)CC1(F)F] | | 451.2 |

TABLE 1-1-continued

| EX. | IUPAC NAME | Structure | ADDITIVE | MS |
|---|---|---|---|---|
| 65 | N-[(2S,3R)-2-[(2,2'-difluoro-3'-methyl[1,1'-biphenyl]-3-yl)methyl]-4,4-difluoro-1-(2-hydroxy-2-methylpropanoyl)pyrrolidin-3-yl]ethanesulfonamide | 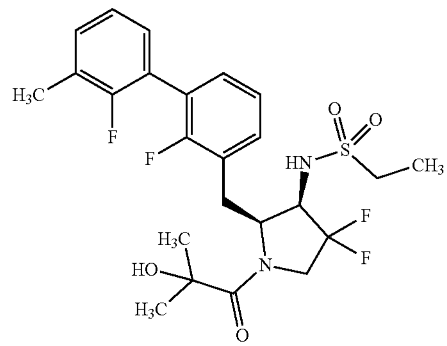 [SMILES: CCS(=O)(=O)N[C@@H]1[C@H](Cc2cccc(-c3cccc(C)c3F)c2F)N(C(=O)C(C)(C)O)CC1(F)F] | | 517.2 |
| 66 | N-{(2S,3R)-4,4-difluoro-1-(2-hydroxy-2-methylpropanoyl)-2-[(2,2',3'-trifluoro[1,1'-biphenyl]-3-yl)methyl]pyrrolidin-3-yl}ethanesulfonamide | 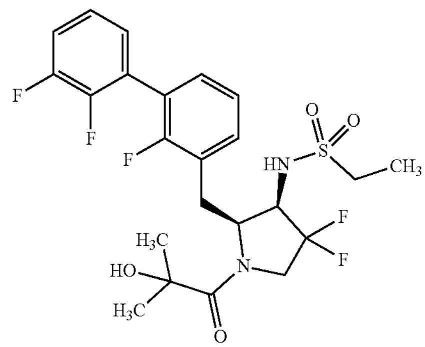 [SMILES: CCS(=O)(=O)N[C@@H]1[C@H](Cc2cccc(-c3cccc(F)c3F)c2F)N(C(=O)C(C)(C)O)CC1(F)F] | | 521.1 |
| 67 | N-{(2S,3R)-4,4-difluoro-1-(2-hydroxy-2-methylpropanoyl)-2-[(2,2',5'-trifluoro[1,1'-biphenyl]-3-yl)methyl]pyrrolidin-3-yl]-ethanesulfonamide | 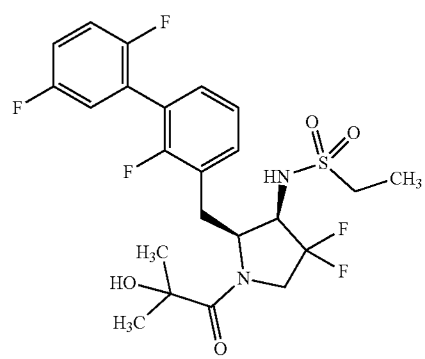 [SMILES: CCS(=O)(=O)N[C@@H]1[C@H](Cc2cccc(-c3cc(F)ccc3F)c2F)N(C(=O)C(C)(C)O)CC1(F)F] | | 521.1 |
| 68 | N-[(2S,3R)-2-[(3'-chloro-2-fluoro[1,1'-biphenyl]-3-yl)methyl]-4,4-difluoro-1-(2-hydroxy-2-methylpropanoyl)pyrrolidin-3-yl]ethanesulfonamide | 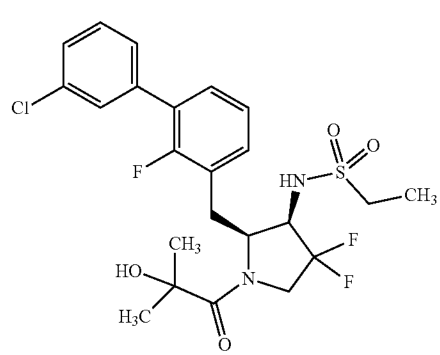 [SMILES: CCS(=O)(=O)N[C@@H]1[C@H](Cc2cccc(-c3cccc(Cl)c3)c2F)N(C(=O)C(C)(C)O)CC1(F)F] | | 519.1 |

TABLE 1-1-continued

| EX. | IUPAC NAME | Structure | ADDITIVE | MS |
|---|---|---|---|---|
| 69 | N-[(2S,3R)-4,4-difluoro-2-{[2-fluoro-3-(6-methylpyridin-2-yl)phenyl]methyl}-1-(2-hydroxy-2-methylpropanoyl)pyrrolidin-3-yl]ethanesulfonamide | 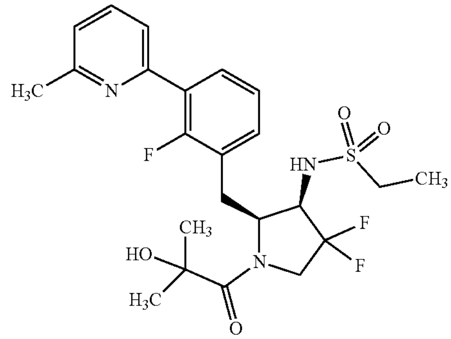 [SMILES: CCS(=O)(=O)N[C@@H]1[C@H](Cc2cccc(-c3cccc(C)n3)c2F)N(C(=O)C(C)(C)O)CC1(F)F] | | 500.2 |
| 70 | N-[(2S,3R)-4,4-difluoro-2-{[2-fluoro-3-(4-methylpyridin-2-yl)phenyl]methyl}-1-(2-hydroxy-2-methylpropanoyl)pyrrolidin-3-yl]ethanesulfonamide | 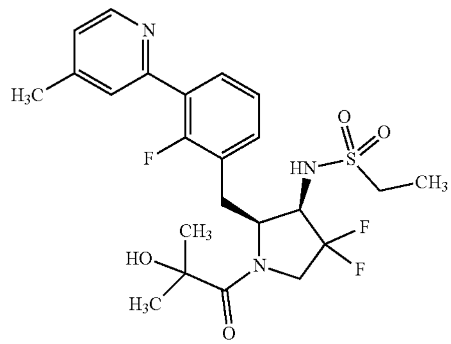 [SMILES: CCS(=O)(=O)N[C@@H]1[C@H](Cc2cccc(-c3cc(C)ccn3)c2F)N(C(=O)C(C)(C)O)CC1(F)F] | | 500.2 |
| 71 | N-[(2S,3R)-2-{[3-(4,6-dimethylpyridin-2-yl)-2-fluorophenyl]methyl}-4,4-difluoro-1-(2-hydroxy-2-methylpropanoyl)pyrrolidin-3-yl]ethanesulfonamide | 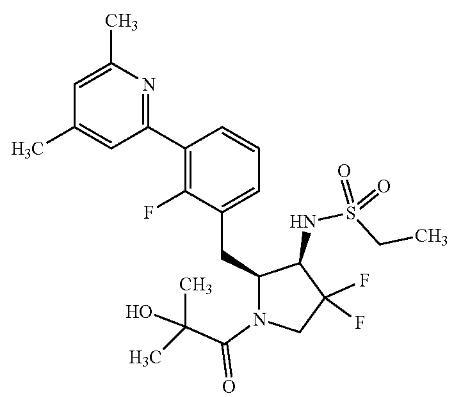 [SMILES: CCS(=O)(=O)N[C@@H]1[C@H](Cc2cccc(-c3cc(C)cc(C)n3)c2F)N(C(=O)C(C)(C)O)CC1(F)F] | | 514.2 |
| 72 | N-{(2S,3R)-4,4-difluoro-1-[(2R)-oxolane-2-carbonyl]-2-[(2,3',5'-trifluoro[1,1'-biphenyl]-3-yl)methyl]pyrrolidin-3-yl}-methanesulfonamide | 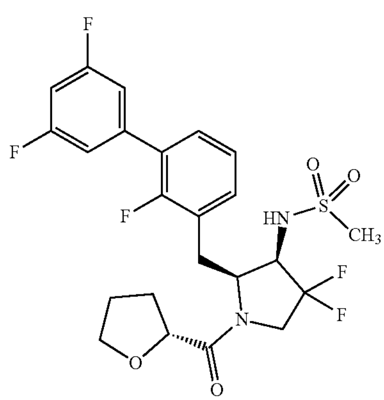 [SMILES: CS(=O)(=O)N[C@@H]1[C@H](Cc2cccc(-c3cc(F)cc(F)c3)c2F)N(C(=O)[C@H]2CCCO2)CC1(F)F] | | 519.1 |

TABLE 1-1-continued

| EX. | IUPAC NAME | Structure | ADDITIVE | MS |
|---|---|---|---|---|
| 73 | N-{(2S,3R)-4,4-difluoro-2-[(2-fluoro[1,1'-biphenyl]-3-yl)methyl]-1-[(2R)-oxolane-2-carbonyl]pyrrolidin-3-yl}methanesulfonamide | 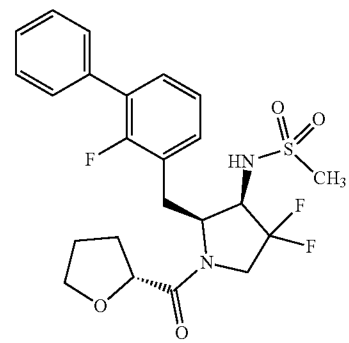 [SMILES: CS(=O)(=O)N[C@@H]1[C@H](Cc2cccc(-c3ccccc3)c2F)N(C(=O)[C@H]2CCCO2)CC1(F)F] | | 483.2 |
| 74 | N-{(2S,3R)-4,4-difluoro-1-[(2R)-oxolane-2-carbonyl]-2-[(2,2',3',-trifluoro[1,1'-biphenyl]-3-yl)methyl]pyrrolidin-3-yl}-methanesulfonamide | 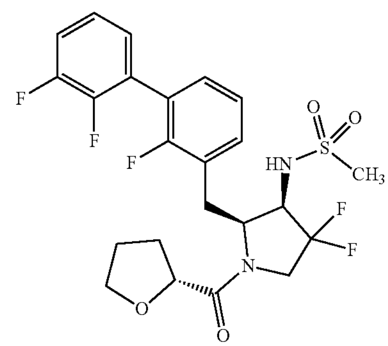 [SMILES: CS(=O)(=O)N[C@@H]1[C@H](Cc2cccc(-c3cccc(F)c3F)c2F)N(C(=O)[C@H]2CCCO2)CC1(F)F] | | 519.1 |
| 75 | N-{(2S,3R)-4,4-difluoro-1-[(2R)-oxolane-2-carbonyl]-2-[(2,2',5'-trifluoro[1,1'-biphenyl]-3-yl)methyl]pyrrolidin-3-yl]-methanesulfonamide | 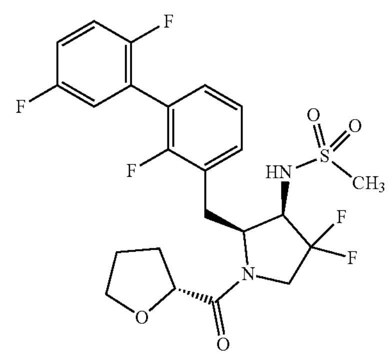 [SMILES: CS(=O)(=O)N[C@@H]1[C@H](Cc2cccc(-c3cc(F)ccc3F)c2F)N(C(=O)[C@H]2CCCO2)CC1(F)F] | | 519.1 |
| 76 | N-[(2S,3R)-4,4-difluoro-2-[(2-fluoro[1,1'-biphenyl]-3-yl)methyl]-1-(1-hydroxycyclobutane-1-carbonyl)pyrrolidin-3-yl]methanesulfonamide | 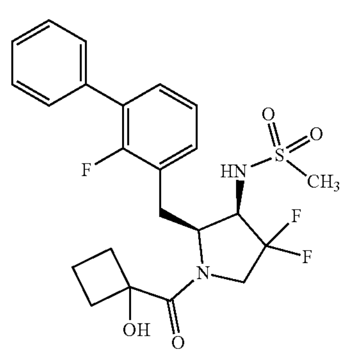 [SMILES: CS(=O)(=O)N[C@@H]1[C@H](Cc2cccc(-c3ccccc3)c2F)N(C(=O)C2(O)CCC2)CC1(F)F] | | 483.2 |

TABLE 1-1-continued

| EX. | IUPAC NAME | Structure | ADDITIVE | MS |
|---|---|---|---|---|
| 77 | N-[(2S,3R)-4,4-difluoro-2-[(2-fluoro[1,1'-biphenyl]-3-yl)methyl]-1-(2-methyl-propanoyl)pyrrolidin-3-yl]methane-sulfonamide | 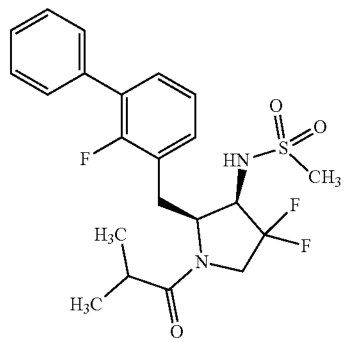 [SMILES: CC(C)C(=O)N1CC(F)(F)[C@H](NS(C)(=O)=O)[C@@H]1Cc1cccc(-c2ccccc2)c1F] | | 455.2 |
| 78 | N-((2S,3R)-1-(bicyclo[1.1.1]pentane-1-carbonyl)-4,4-difluoro-2-[(2-fluoro[1,1'-biphenyl]-3-yl)methyl]pyrrolidin-3-yl}-methanesulfonamide | 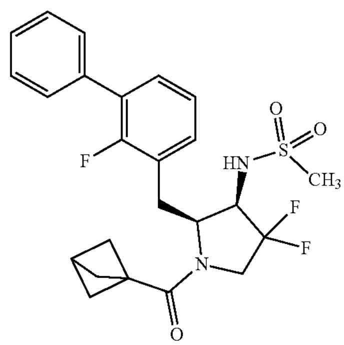 [SMILES: CS(=O)(=O)N[C@@H]1[C@H](Cc2cccc(-c3ccccc3)c2F)N(C(=O)C23CC(C2)C3)CC1(F)F] | | 479.2 |
| 79 | N-[(2S,3R)-4,4-difluoro-2-[(2-fluoro[1,1'-biphenyl]-3-yl)methyl]-1-(oxetane-2-carbonyl)pyrrolidin-3-yl]methane-sulfonamide with shorter retention time | 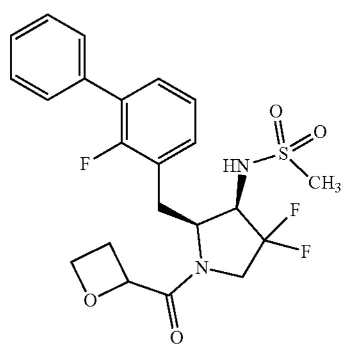 [SMILES: CS(=O)(=O)N[C@@H]1[C@H](Cc2cccc(-c3ccccc3)c2F)N(C(=O)C2CCO2)CC1(F)F] | | 469.2 |
| 80 | N-[(2S,3R)-4,4-difluoro-2-[(2-fluoro[1,1'-biphenyl]-3-yl)methyl]-1-(oxetane-2-carbonyl)pyrrolidin-3-yl]methanesulfon-amide with longer retention time | 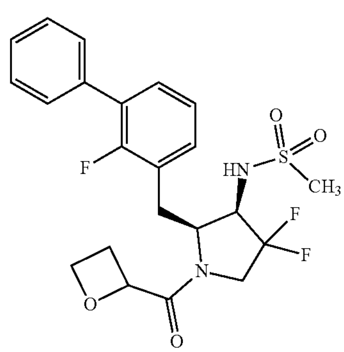 [SMILES: CS(=O)(=O)N[C@@H]1[C@H](Cc2cccc(-c3ccccc3)c2F)N(C(=O)C2CCO2)CC1(F)F] | | 469.2 |

TABLE 1-1-continued

| EX. | IUPAC NAME | Structure | ADDITIVE | MS |
|---|---|---|---|---|
| 81 | N-[(2S,3R)-2-[(2,3'-difluoro[1,1'-biphenyl]-3-yl)methyl]-4,4-difluoro-1-((2R)-oxetane-2-carbonyl)pyrrolidin-3-yl]methanesulfonamide | 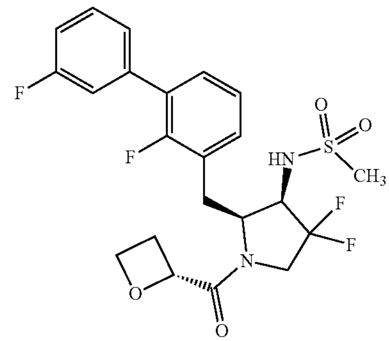 [SMILES: CS(=O)(=O)N[C@@H]1[C@H](Cc2cccc(-c3cccc(F)c3)c2F)N(C(=O)[C@H]2CCO2)CC1(F)F] | | 487.2 |
| 82 | N-[(2S,3R)-2-[(2,3'-difluoro[1,1'-biphenyl]-3-yl)methyl]-4,4-difluoro-1-((2S)-oxetane-2-carbonyl)pyrrolidin-3-yl]methanesulfonamide | 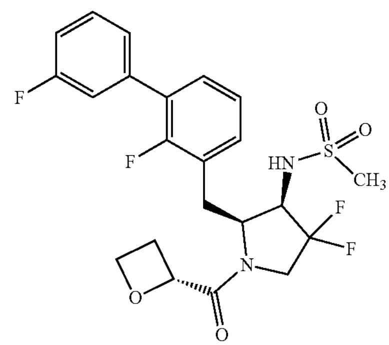 [SMILES: CS(=O)(=O)N[C@@H]1[C@H](Cc2cccc(-c3cccc(F)c3)c2F)N(C(=O)[C@H]2CCO2)CC1(F)F] | | 487.2 |
| 83 | N-{(2S,3R)-2-[([1,1'-biphenyl]-3-yl)methyl]-4,4-difluoro-1-[(2R)-oxolane-2-carbonyl]pyrrolidin-3-yl}ethanesulfonamide | 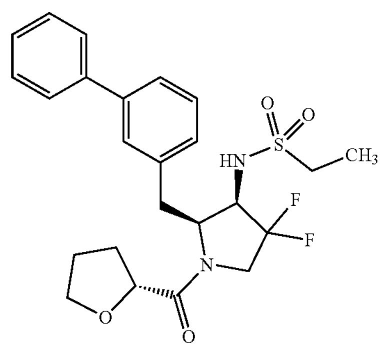 [SMILES: CCS(=O)(=O)N[C@@H]1[C@H](Cc2cccc(-c3ccccc3)c2)N(C(=O)[C@H]2CCCO2)CC1(F)F] | | 479.2 |
| 84 | N-{(2S,3R)-2-[(3',5'-difluoro[1,1'-biphenyl]-3-yl)methyl]-4,4-difluoro-1-[(2R)-oxolane-2-carbonyl]pyrrolidin-3-yl}ethanesulfonamide | 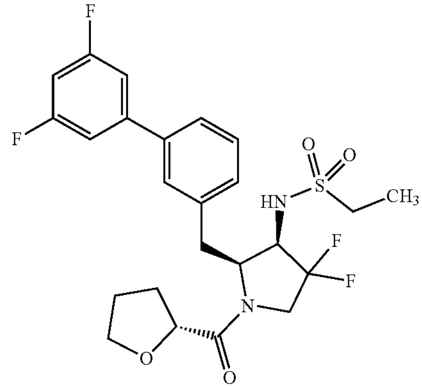 [SMILES: CCS(=O)(=O)N[C@@H]1[C@H](Cc2cccc(-c3cc(F)cc(F)c3)c2)N(C(=O)[C@H]2CCCO2)CC1(F)F] | | 515.2 |

TABLE 1-1-continued

| EX. | IUPAC NAME | Structure | ADDITIVE | MS |
|---|---|---|---|---|
| 85 | N-{(2S,3R)-2-[(2',3'-difluoro[1,1'-biphenyl]-3-yl)methyl]-4,4-difluoro-1-[(2R)-oxolane-2-carbonyl]pyrrolidin-3-yl}ethanesulfonamide | 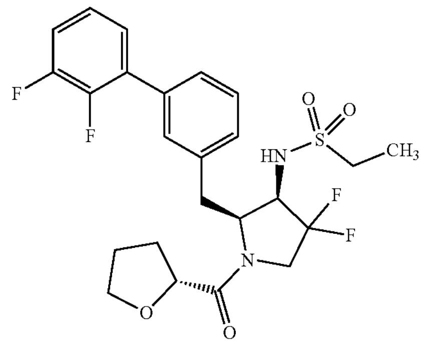 [SMILES: CCS(=O)(=O)N[C@@H]1[C@H](Cc2cccc(-c3cccc(F)c3F)c2)N(C(=O)[C@H]2CCCO2)CC1(F)F] | | 515.2 |
| 86 | N-{(2S,3R)-2-[(2',5'-difluoro[1,1'-biphenyl]-3-yl)methyl]-4,4-difluoro-1-[(2R)-oxolane-2-carbonyl]pyrrolidin-3-yl}ethanesulfonamide | 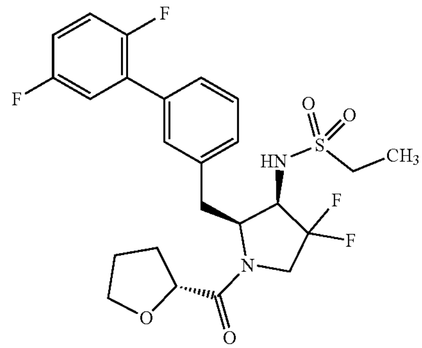 [SMILES: CCS(=O)(=O)N[C@@H]1[C@H](Cc2cccc(-c3cc(F)ccc3F)c2)N(C(=O)[C@H]2CCCO2)CC1(F)F] | | 515.2 |
| 87 | N-{(2S,3R)-1-(bicyclo[1.1.1]pentane-1-carbonyl)-4,4-difluoro-2-[(2,3',5'-trifluoro[1,1'-biphenyl]-3-yl)methyl]pyrrolidin-3-yl}methanesulfonamide | 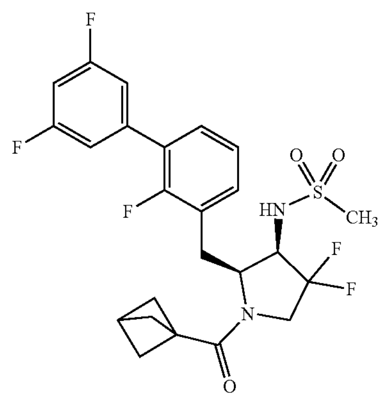 [SMILES: CS(=O)(=O)N[C@@H]1[C@H](Cc2cccc(-c3cc(F)cc(F)c3)c2F)N(C(=O)C23CC(C2)C3)CC1(F)F] | | 515.3 |
| 88 | N-{(2S,3R)-4,4-difluoro-2-[(3'-fluoro[1,1'-biphenyl]-3-yl)methyl]-1-[(2R)-oxolane-2-carbonyl]pyrrolidin-3-yl}ethanesulfonamide | 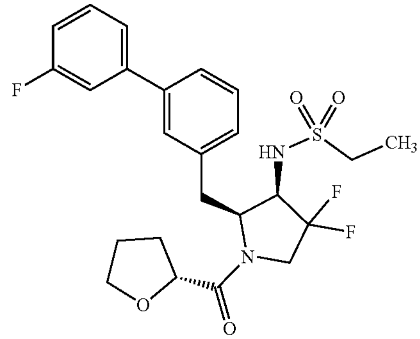 [SMILES: CCS(=O)(=O)N[C@@H]1[C@H](Cc2cccc(-c3cccc(F)c3)c2)N(C(=O)[C@H]2CCCO2)CC1(F)F] | | 497.2 |

TABLE 1-1-continued

| EX. | IUPAC NAME | Structure | ADDITIVE | MS |
|---|---|---|---|---|
| 89 | N-[(2S,3R)-4,4-difluoro-2-[(3'-fluoro[1,1'-biphenyl]-3-yl)methyl]-1-(2-methyloxolane-2-carbonyl)pyrrolidin-3-yl]ethanesulfonamide with shorter retention | 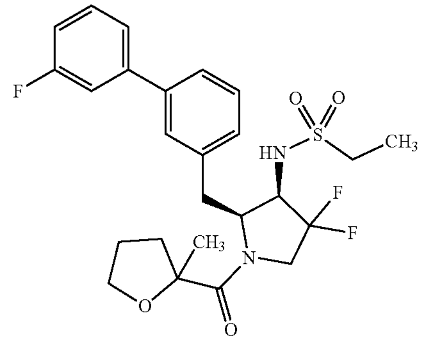 [SMILES: CCS(=O)(=O)N[C@@H]1[C@H](Cc2cccc(-c3cccc(F)c3)c2)N(C(=O)C2(C)CCCO2)CC1(F)F] | | 511.2 |
| 90 | N-[(2S,3R)-4,4-difluoro-2-[(3'-fluoro[1,1'-biphenyl]-3-yl)methyl]-1-(2-methyloxolane-2-carbonyl)pyrrolidin-3-yl]ethanesulfonamide with longer retention time | 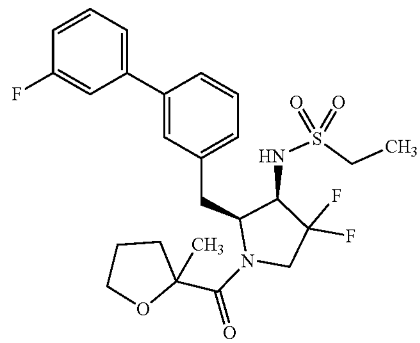 [SMILES: CCS(=O)(=O)N[C@@H]1[C@H](Cc2cccc(-c3cccc(F)c3)c2)N(C(=O)C2(C)CCCO2)CC1(F)F] | | 511.2 |
| 91 | N-{(2S,3R)-4,4-difluoro-1-((2R)-oxetane-2-carbonyl)-2-[(2,3',5'-trifluoro[1,1'-biphenyl]-3-yl)methyl]pyrrolidin-3-yl]-methanesulfonamide | 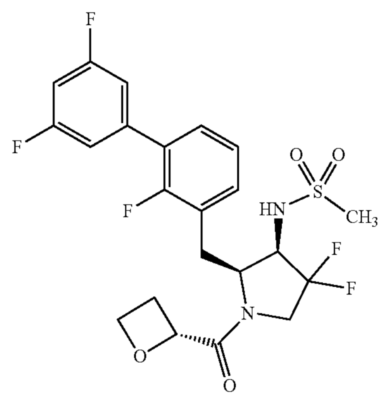 [SMILES: CS(=O)(=O)N[C@@H]1[C@H](Cc2cccc(-c3cc(F)cc(F)c3)c2F)N(C(=O)[C@H]2CCO2)CC1(F)F] | | 505.1 |
| 92 | N-{(2S,3R)-4,4-difluoro-1-((2S)-oxetane-2-carbonyl)-2-[(2,3',5'-trifluoro[1,1'-biphenyl]-3-yl)methyl]pyrrolidin-3-yl]methanesulfonamide | 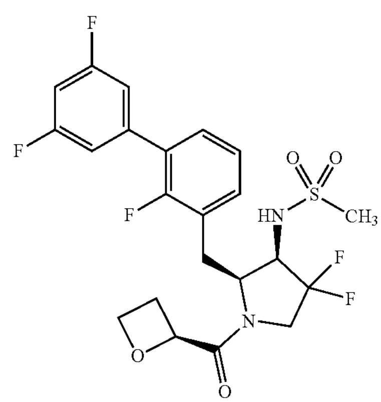 [SMILES: CS(=O)(=O)N[C@@H]1[C@H](Cc2cccc(-c3cc(F)cc(F)c3)c2F)N(C(=O)[C@@H]2CCO2)CC1(F)F] | | 505.1 |

TABLE 1-1-continued

| EX. | IUPAC NAME | Structure | ADDITIVE | MS |
|---|---|---|---|---|
| 93 | N-{(2S,3R)-1-(bicyclo[1.1.1]pentane-1-carbonyl)-2-[(2,3'-difluoro[1,1'-biphenyl]-3-yl)methyl]-4,4-difluoropyrrolidin-3-yl}ethanesulfonamide | 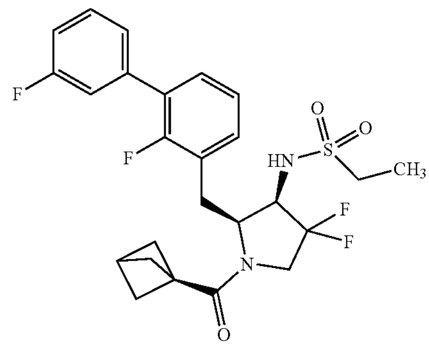 | | 511.2 |
| 94 | N-[(2S,3R)-2-[(2,3'-difluoro[1,1'-biphenyl]-3-yl)methyl]-4,4-difluoro-1-(2-methylpropanoyl)pyrrolidin-3-yl]ethanesulfonamide | 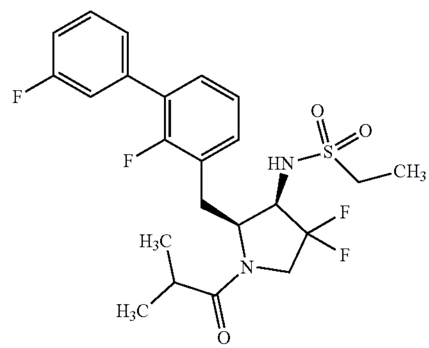 [SMILES: CCS(=O)(=O)N[C@@H]1[C@H](Cc2cccc(-c3cccc(F)c3)c2F)N(C(=O)C(C)C)CC1(F)F] | | 487.2 |
| 95 | rac-N-[(2S,3R,4S)-2-[([1,1'-biphenyl]-3-yl)methyl]-4-fluoro-1-(2-hydroxy-2-methylpropanoyl)pyrrolidin-3-yl]methanesulfonamide | 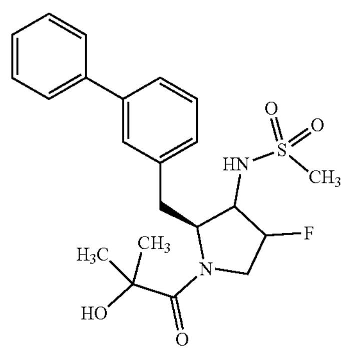 [SMILES: CC(C)(O)C(=O)N1CC(F)C(NS(C)(=O)=O)[C@@H]1Cc1cccc(-c2ccccc2)c1] | | 435.2 |
| 96 | N-{(2S,3R)-1-(bicyclo[1.1.1]pentane-1-carbonyl)-4,4-difluoro-2-[(3'-fluoro[1,1'-biphenyl]-3-yl)methyl]pyrrolidin-3-yl}ethanesulfonamide | 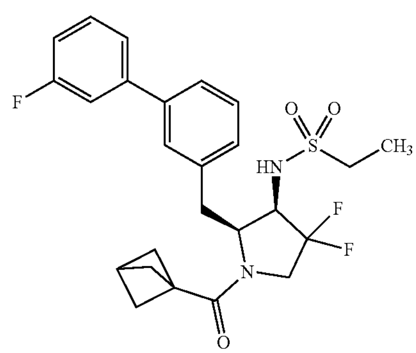 [SMILES: CCS(=O)(=O)N[C@@H]1[C@H](Cc2cccc(-c3cccc(F)c3)c2)N(C(=O)C23CC(C2)C3)CC1(F)F] | | 493.2 |

TABLE 1-1-continued

| EX. | IUPAC NAME | Structure | ADDITIVE | MS |
|---|---|---|---|---|
| 97 | N-[(2S,3R)-4,4-difluoro-2-[(3'-fluoro[1,1'-biphenyl]-3-yl)methyl]-1-(2-methyl-propanoyl)pyrrolidin-3-yl]ethanesulfon-amide | 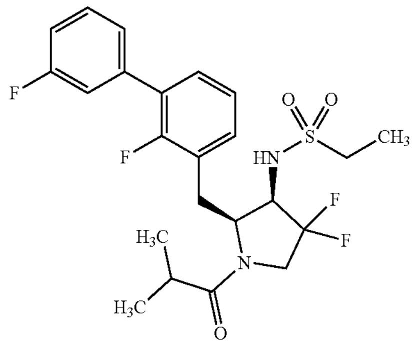 [SMILES: CCS(=O)(=O)N[C@@H]1[C@H](Cc2cccc(-c3cccc(F)c3)c2F)N(C(=O)C(C)C)CC1(F)F] | | 469.2 |
| 98 | N-[(2S,3R)-2-[(2,3'-difluoro[1,1'-biphenyl]-3-yl)methyl]-4,4-difluoro-1-(2-methyl-propanoyl)pyrrolidin-3-yl]methane-sulfonamide | 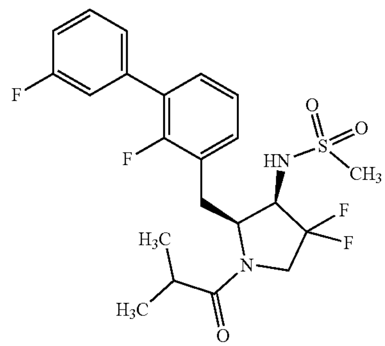 [SMILES: CC(C)C(=O)N1CC(F)(F)[C@H](NS(C)(=O)=O)[C@@H]1Cc1cccc(-c2cccc(F)c2)c1F] | | 473.2 |
| 99 | N-[(2S,3R)-1-(bicyclo[1.1.1]pentane-1-carbonyl)-4,4-difluoro-2-{[2-fluoro-3-(6-methylpyridin-2-yl)phenyl]methyl}-pyrrolidin-3-yl]methanesulfonamide | 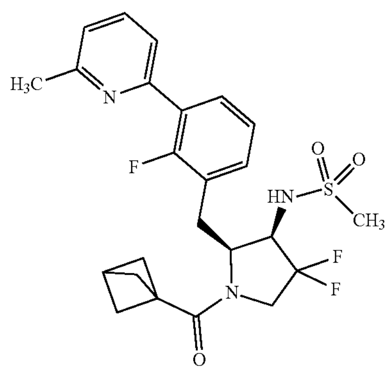 [SMILES: Cc1cccc(-c2cccc(C[C@H]3[C@@H](NS(C)(=O)=O)C(F)(F)CN3C(=O)C34CC(C3)C4)c2F)n1] | | 494.2 |
| 100 | N-[(2S,3R)-1-(bicyclo[1.1.1]pentane-1-carbonyl)-4,4-difluoro-2-{[2-fluoro-3-(4-methylpyridin-2-yl)phenyl]methyl}-pyrrolidin-3-yl]methanesulfonamide | 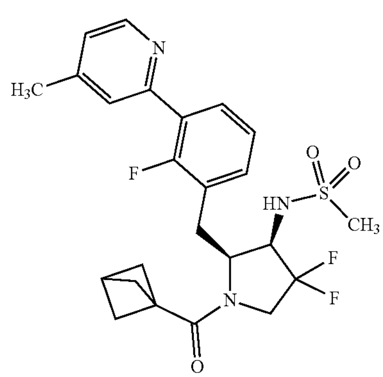 [SMILES: Cc1ccnc(-c2cccc(C[C@H]3[C@@H](NS(C)(=O)=O)C(F)(F)CN3C(=O)C34CC(C3)C4)c2F)c1] | | 494.2 |

TABLE 1-1-continued

| EX. | IUPAC NAME | Structure | ADDITIVE | MS |
|---|---|---|---|---|
| 101 | N-[(2S,3R)-1-(bicyclo[1.1.1]pentane-1-carbonyl)-2-{[3-(4,6-dimethylpyridin-2-yl)-2-fluorophenyl]methyl}-4,4-difluoro-pyrrolidin-3-yl]methanesulfonamide | 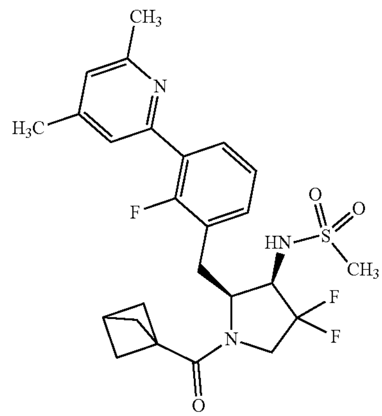 [SMILES: Cc1cc(C)nc(-c2cccc(C[C@H]3[C@@H](NS(C)(=O)=O)C(F)(F)CN3C(=O)C34CC(C3)C4)c2F)c1] | | 508.2 |
| 102 | N-[(2S,3R)-1-(bicyclo[1.1.1]pentane-1-carbonyl)-2-{[3-(2,6-dimethylpyridin-4-yl)-2-fluorophenyl]methyl}-4,4-difluoro-pyrrolidin-3-yl]methanesulfonamide | 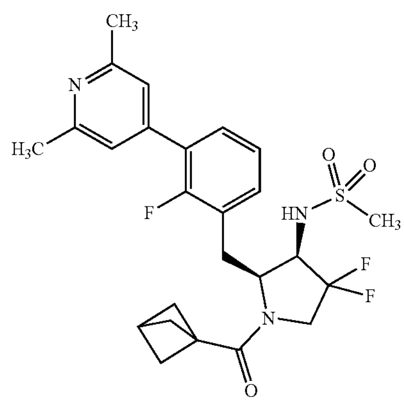 | | 508.2 |
| 103 | N-[(2S,3R)-1-(bicyclo[1.1.1]pentane-1-carbonyl)-4,4-difluoro-2-{[2-fluoro-3-(6-methoxypyridin-2-yl)phenyl]methyl}-pyrrolidin-3-yl]methanesulfonamide | 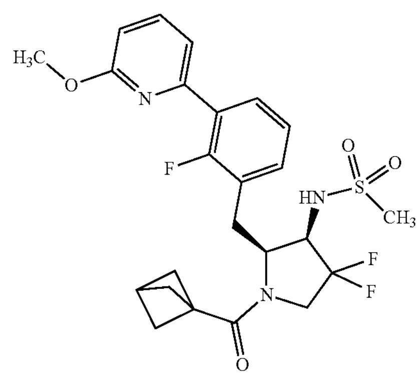 [SMILES: COc1cccc(-c2cccc(C[C@H]3[C@@H](NS(C)(=O)=O)C(F)(F)CN3C(=O)C34CC(C3)C4)c2F)n1] | | 510.2 |
| 104 | N-[(2S,3R)-1-(2,2-dimethylpropanoyl)-4,4-difluoro-2-{[3-(4-methylpyridin-2-yl)-phenyl]methyl}pyrrolidin-3-yl]ethane-sulfonamide | 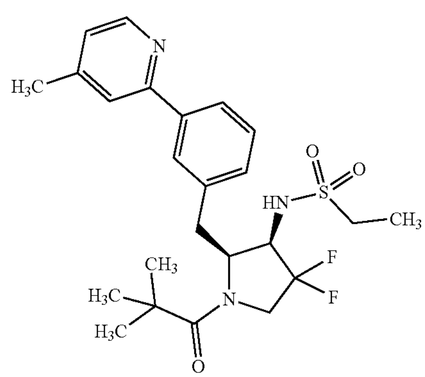 [SMILES: CCS(=O)(=O)N[C@@H]1[C@H](Cc2cccc(-c3cc(C)ccn3)c2)N(C(=O)C(C)(C)C)CC1(F)F] | | 480.2 |

TABLE 1-1-continued

| EX. | IUPAC NAME | Structure | ADDITIVE | MS |
|---|---|---|---|---|
| 105 | N-{(2S,3R)-4,4-difluoro-2-[(2-fluoro[1,1'-biphenyl]-3-yl)methyl]-1-[(2R)-oxolane-2-carbonyl]pyrrolidin-3-yl}ethanesulfonamide | 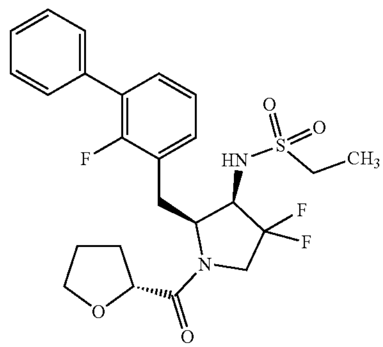 [SMILES: CCS(=O)(=O)N[C@@H]1[C@H](Cc2cccc(-c3ccccc3)c2F)N(C(=O)[C@H]2CCCO2)CC1(F)F] | | 497.1 |
| 106 | N-[(2S,3R)-4,4-difluoro-2-[(2-fluoro[1,1'-biphenyl]-3-yl)methyl]-1-(2-methylpropanoyl)pyrrolidin-3-yl]ethanesulfonamide | 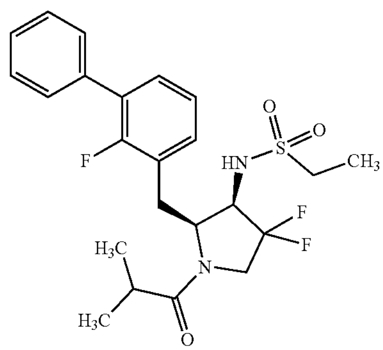 [SMILES: CCS(=O)(=O)N[C@@H]1[C@H](Cc2cccc(-c3ccccc3)c2F)N(C(=O)C(C)C)CC1(F)F] | | 469.2 |
| 107 | N-{(2S,3R)-1-(bicyclo[1.1.1]pentane-1-carbonyl)-2-[([1,1'-biphenyl]-3-yl)methyl]-4,4-difluoropyrrolidin-3-yl}ethanesulfonamide | 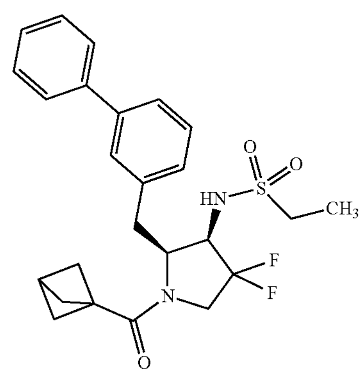 [SMILES: CCS(=O)(=O)N[C@@H]1[C@H](Cc2cccc(-c3ccccc3)c2)N(C(=O)C23CC(C2)C3)CC1(F)F] | | 475.2 |
| 108 | N-[(2S,3R)-1-(bicyclo[1.1.1]pentane-1-carbonyl)-4,4-difluoro-2-{[3-(6-methylpyridin-2-yl)phenyl]methyl}pyrrolidin-3-yl]ethanesulfonamide | 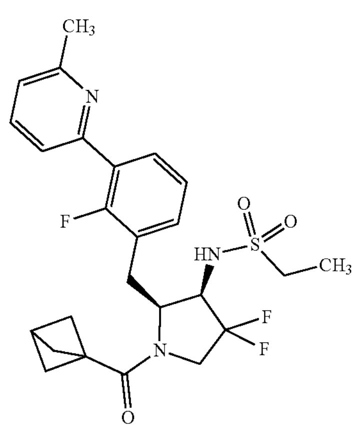 [SMILES: CCS(=O)(=O)N[C@@H]1[C@H](Cc2cccc(-c3cccc(C)n3)c2F)N(C(=O)C23CC(C2)C3)CC1(F)F] | | 490.2 |

TABLE 1-1-continued

| EX. | IUPAC NAME | Structure | ADDITIVE | MS |
|---|---|---|---|---|
| 109 | N-[(2S,3R)-1-(bicyclo[1.1.1]pentane-1-carbonyl)-2-{[3-(4,6-dimethylpyridin-2-yl)phenyl]methyl}-4,4-difluoropyrrolidin-3-yl]ethanesulfonamide | 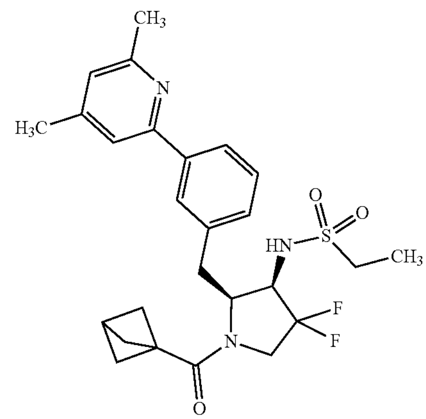 [SMILES: CCS(=O)(=O)N[C@@H]1[C@H](Cc2cccc(-c3cc(C)cc(C)n3)c2)N(C(=O)C23CC(C2)C3)CC1(F)F] | | 504.2 |
| 110 | N-[(2S,3R)-1-(bicyclo[1.1.1]pentane-1-carbonyl)-4,4-difluoro-2-{[3-(4-methylpyridin-2-yl)phenyl]methyl}pyrrolidin-3-yl]ethanesulfonamide | 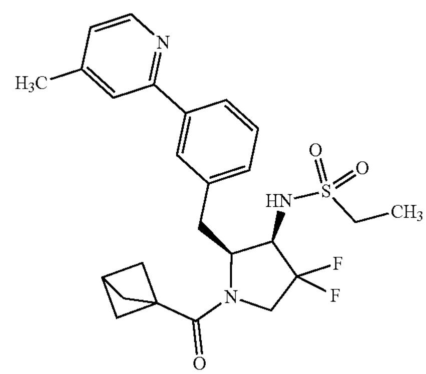 [SMILES: CCS(=O)(=O)N[C@@H]1[C@H](Cc2cccc(-c3cc(C)ccn3)c2)N(C(=O)C23CC(C2)C3)CC1(F)F] | | 490.2 |
| 111 | N-[(2S,3R)-1-(bicyclo[1.1.1]pentane-1-carbonyl)-2-{[3-(2,6-dimethylpyrimidin-4-yl)-2-fluorophenyl]methyl}-4,4-difluoropyrrolidin-3-yl]methanesulfonamide | 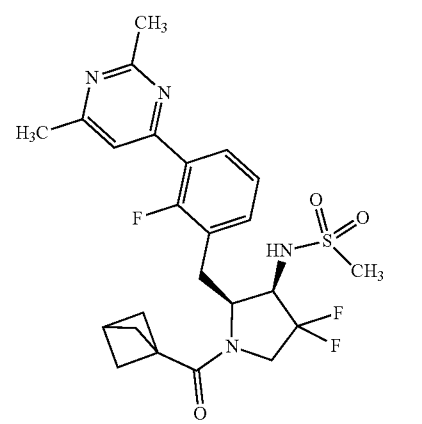 [SMILES: Cc1cc(-c2cccc(C[C@H]3[C@@H](NS(C)(=O)=O)C(F)(F)CN3C(=O)C34CC(C3)C4)c2F)nc(C)n1] | | 509.1 |
| 112 | N-[(2S,3R)-1-(bicyclo[1.1.1]pentane-1-carbonyl)-2-{[3-(4,6-dimethylpyrimidin-2-yl)phenyl]methyl}-4,4-difluoropyrrolidin-3-yl]ethanesulfonamide | 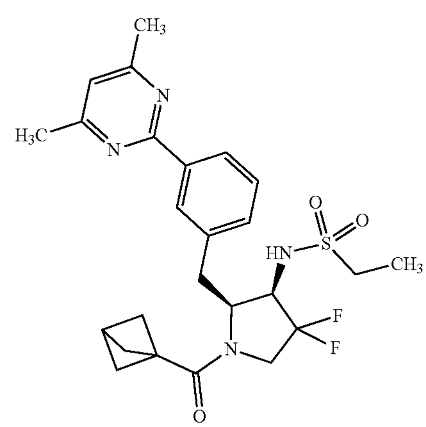 [SMILES: CCS(=O)(=O)N[C@@H]1[C@H](Cc2cccc(-c3nc(C)cc(C)n3)c2)N(C(=O)C23CC(C2)C3)CC1(F)F] | | 505.2 |

TABLE 1-1-continued

| EX. | IUPAC NAME | Structure | ADDITIVE | MS |
|---|---|---|---|---|
| 113 | N-[(2S,3R)-1-(bicyclo[1.1.1]pentane-1-carbonyl)-4,4-difluoro-2-{[3-(6-methoxy-pyridin-2-yl)phenyl]methyl}pyrrolidin-3-yl]ethanesulfonamide | 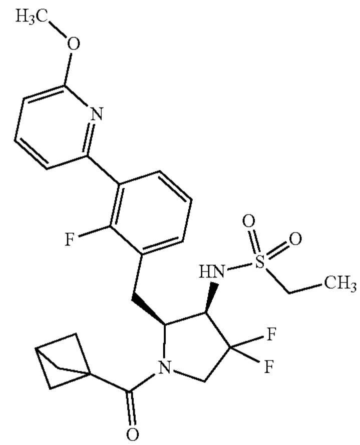 [SMILES: CCS(=O)(=O)N[C@@H]1[C@H](Cc2cccc(-c3cccc(OC)n3)c2F)N(C(=O)C23CC(C2)C3)CC1(F)F] | | 506.2 |
| 114 | N-[(2S,3R)-4,4-difluoro-1-(2-methyl-propanoyl)-2-{[3-(4-methylpyridin-2-yl)phenyl]methyl}pyrrolidin-3-yl]-ethanesulfonamide | 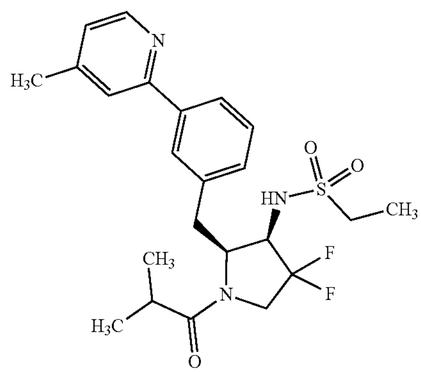 [SMILES: CCS(=O)(=O)N[C@@H]1[C@H](Cc2cccc(-c3cc(C)ccn3)c2)N(C(=O)C(C)C)CC1(F)F] | | 466.2 |
| 115 | N-[(2S,3R)-2-[([1,1'-biphenyl]-3-yl)-methyl]-4,4-difluoro-1-(2-methyl-propanoyl)pyrrolidin-3-yl]ethanesulfon-amide | 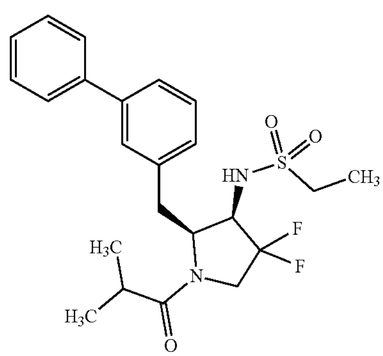 [SMILES: CCS(=O)(=O)N[C@@H]1[C@H](Cc2cccc(-c3ccccc3)c2)N(C(=O)C(C)C)CC1(F)F] | | 451.2 |
| 116 | N-[(2S,3R)-2-[(3',5'-difluoro[1,1'-biphenyl]-3-yl)methyl]-4,4-difluoro-1-(2-methylpropanoyl)pyrrolidin-3-yl]-ethanesulfonamide | 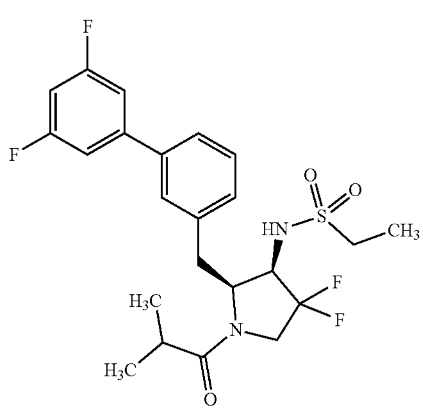 [SMILES: CCS(=O)(=O)N[C@@H]1[C@H](Cc2cccc(-c3cc(F)cc(F)c3)c2)N(C(=O)C(C)C)CC1(F)F] | | 487.2 |

TABLE 1-1-continued

| EX. | IUPAC NAME | Structure | ADDITIVE | MS |
|---|---|---|---|---|
| 117 | N-[(2S,3R)-4,4-difluoro-1-(2-methyl-propanoyl)-2-{[3-(6-methylpyridin-2-yl)phenyl]methyl}pyrrolidin-3-yl]-ethanesulfonamide | 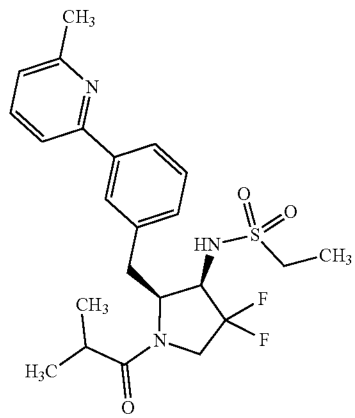 [SMILES: CCS(=O)(=O)N[C@@H]1[C@H](Cc2cccc(-c3cccc(C)n3)c2)N(C(=O)C(C)C)CC1(F)F] | | 466.2 |
| 118 | N-[(2S,3R)-2-{[3-(4,6-dimethylpyridin-2-yl)phenyl]methyl}-4,4-difluoro-1-(2-methylpropanoyl)pyrrolidin-3-yl]-ethanesulfonamide | 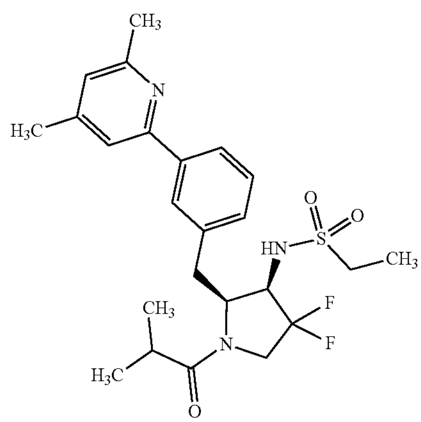 [SMILES: CCS(=O)(=O)N[C@@H]1[C@H](Cc2cccc(-c3cc(C)cc(C)n3)c2)N(C(=O)C(C)C)CC1(F)F] | | 480.2 |
| 119 | N-[(2S,3R)-2-[([1,1'-biphenyl]-3-yl)-methyl]-4,4-difluoro-1-(2-methyl-propanoyl)pyrrolidin-3-yl]methane-sulfonamide | 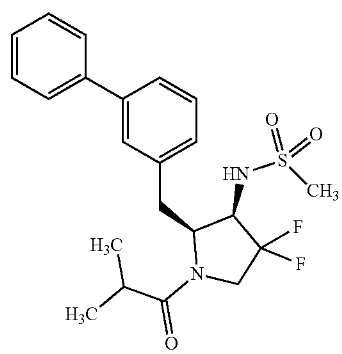 [SMILES: CC(C)C(=O)N1CC(F)(F)[C@H](NS(C)(=O)=O)[C@@H]1Cc1cccc(-c2ccccc2)c1] | | 437.2 |
| 120 | N-[(2S,3R)-4,4-difluoro-2-[(3'-fluoro[1,1'-biphenyl]-3-yl)methyl]-1-(2-methyl-propanoyl)pyrrolidin-3-yl]methane-sulfonamide | 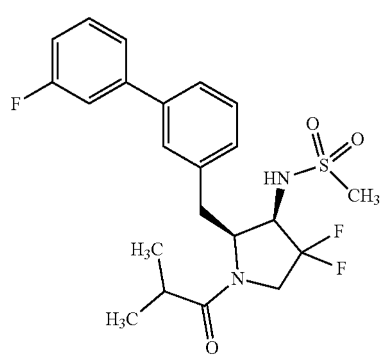 [SMILES: CC(C)C(=O)N1CC(F)(F)[C@H](NS(C)(=O)=O)[C@@H]1Cc1cccc(-c2cccc(F)c2)c1] | | 453.2 |

TABLE 1-1-continued

| EX. | IUPAC NAME | ADDITIVE | MS |
|---|---|---|---|
| 121 | N-{(2S,3R)-4,4-difluoro-1-((2R)-oxetane-2-carbonyl)-2-[{2,2',3'-trifluoro[1,1'-biphenyl]-3-yl)methyl]pyrrolidin-3-yl]methanesulfonamide | | 505.1 |
| 122 | N-[(2S,3R)-M-difluoro-1-((2R)-oxetane-2-carbonyl)-2-[(2,2',5'-trifluoro[1,1'-biphenyl]-3-yl)methyl]pyrrolidin-3-yl]-methanesulfonamide | | 505.1 |
| 123 | N-{(2S,3R)-1-(bicyclo[1.1.1]pentane-1-carbonyl)-4,4-difluoro-2-[(2-fluoro[1,1'-biphenyl]-3-yl)methyl]pyrrolidin-3-yl}ethanesulfonamide | | 493.3 |
| 124 | N-[(2S,3R)-4,4-difluoro-2-[(2-fluoro[1,1'-biphenyl]-3-yl)methyl]-1-(oxetane-2-carbonyl)pyrrolidin-3-yl]cyclopropane-sulfonamide with shorter retention time | | 495.2 |

TABLE 1-1-continued

| EX. | IUPAC NAME | Structure | ADDITIVE | MS |
|---|---|---|---|---|
| 125 | N-[(2S,3R)-4,4-difluoro-2-[(2-fluoro[1,1'-biphenyl]-3-yl)methyl]-1-(oxetane-2-carbonyl)pyrrolidin-3-yl]cyclopropane-sulfonamide with longer retention time | 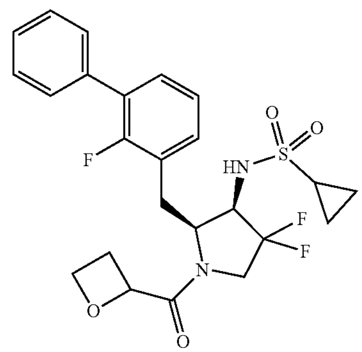 [SMILES: O=C(C1CCO1)N1CC(F)(F)[C@H](NS(=O)(=O)C2CC2)[C@@H]1Cc1cccc(-c2ccccc2)c1F] | | 495.2 |
| 126 | N-{(2S,3R)-4,4-difluoro-2-[(2-fluoro[1,1'-biphenyl]-3-yl)methyl]-2-[(2R)-oxolane-2-carbonyl]pyrrolidin-3-yl}cyclopropane-sulfonamide | 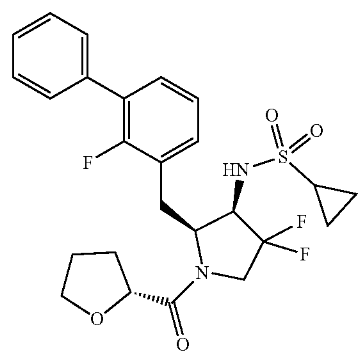 [SMILES: O=C([C@H]1CCCO1)N1CC(F)(F)[C@H](NS(=O)(=O)C2CC2)[C@@H]1Cc1cccc(-c2ccccc2)c1F] | | 509.2 |
| 127 | N-[(2S,3R)-4,4-difluoro-2-[(2-fluoro[1,1'-biphenyl]-3-yl)methyl]-1-(2-methyl-oxetane-2-carbonyl)pyrrolidin-3-yl]-methanesulfonamide with shorter retention time by HPLC (column: CHIRALPAK IC (4.6 mmI · D. × 250 mmL, 5 μm), mobile phase: hexane/EtOH/diethylamine = 550/450/1 (v/v/v)) | 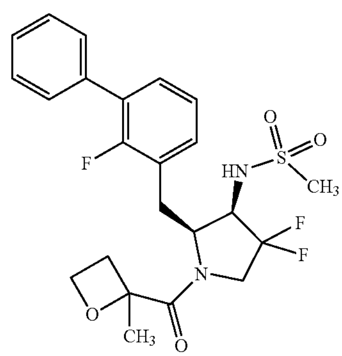 [SMILES: CC1(C(=O)N2CC(F)(F)[C@H](NS(C)(=O)=O)[C@@H]2Cc2cccc(-c3ccccc3)c2F)CCO1] | | 483.2 |
| 128 | N-[(2S,3R)-4,4-difluoro-2-[(2-fluoro[1,1'-biphenyl]-3-yl)methyl]-1-(2-methyl-oxetane-2-carbonyl)pyrrolidin-3-yl]-methanesulfonamide with longer retention time by HPLC (column: CHIRALPAK IC (4.6 mmI · D. × 250 mmL, 5 μm), mobile phase: hexane/EtOH/diethylamine = 550/450/1 (v/v/v)) | 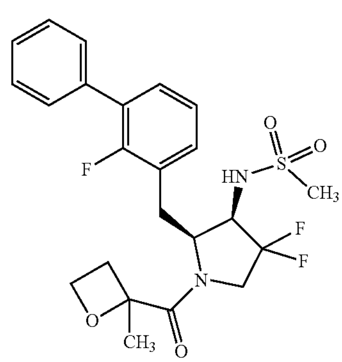 [SMILES: CC1(C(=O)N2CC(F)(F)[C@H](NS(C)(=O)=O)[C@@H]2Cc2cccc(-c3ccccc3)c2F)CCO1] | | 483.2 |

TABLE 1-1-continued

| EX. | IUPAC NAME | Structure | ADDITIVE | MS |
|---|---|---|---|---|
| 129 | N-[(2S,3R)-2-[(2,3'-difluoro[1,1'-biphenyl]-3-yl)methyl]-4,4-difluoro-1-(oxetane-2-carbonyl)pyrrolidin-3-yl]cyclopropane-sulfonamide with shorter retention time | 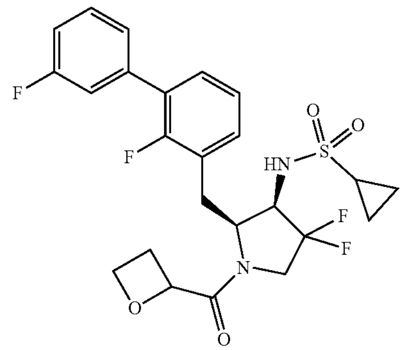 [SMILES: O=C(C1CCO1)N1CC(F)(F)[C@H](NS(=O)(=O)C2CC2)[C@@H]1Cc1cccc(-c2cccc(F)c2)c1F] | | 513.2 |
| 130 | N-[(2S,3R)-2-[(2,3'-difluoro[1,1'-biphenyl]-3-yl)methyl]-4,4-difluoro-1-(oxetane-2-carbonyl)pyrrolidin-3-yl]cyclopropane-sulfonamide with longer retention time | 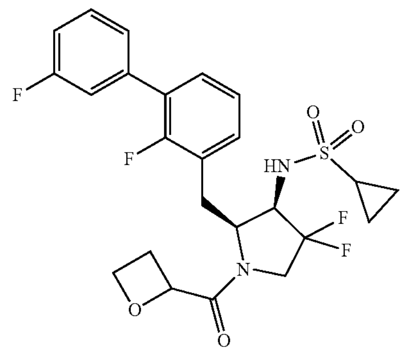 [SMILES: O=C(C1CCO1)N1CC(F)(F)[C@H](NS(=O)(=O)C2CC2)[C@@H]1Cc1cccc(-c2cccc(F)c2)c1F] | | 513.1 |
| 131 | N-[(2S,3R)-2-[(2',3'-difluoro[1,1'-biphenyl]-3-yl)methyl]-4,4-difluoro-1-(2-methylpropanoyl)pyrrolidin-3-yl]methanesulfonamide | 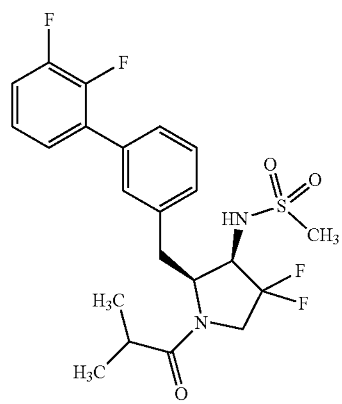 [SMILES: CC(C)C(=O)N1CC(F)(F)[C@H](NS(C)(=O)=O)[C@@H]1Cc1cccc(-c2cccc(F)c2F)c1] | | 473.2 |
| 132 | N-[(2S,3R)-2-[(2',5'-difluoro[1,1'-biphenyl]-3-yl)methyl]-4,4-difluoro-1-(2-methylpropanoyl)pyrrolidin-3-yl]-methanesulfonamide | 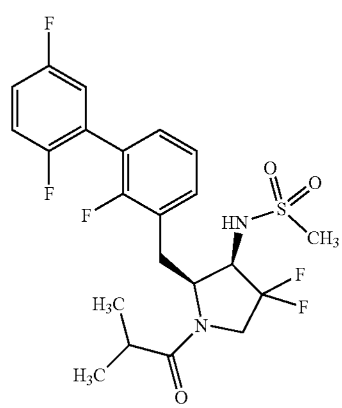 [SMILES: CC(C)C(=O)N1CC(F)(F)[C@H](NS(C)(=O)=O)[C@@H]1Cc1cccc(-c2cc(F)ccc2F)c1F] | | 473.2 |

TABLE 1-1-continued

| EX. | IUPAC NAME | Structure | ADDITIVE | MS |
|---|---|---|---|---|
| 133 | N-{(2S,3R)-4,4-difluoro-1-({2S}-oxetane-2-carbonyl)-2-[(2,2',3'-trifluoro[1,1'-biphenyl]-3-yl)methyl]pyrrolidin-3-yl]-methanesulfonamide | 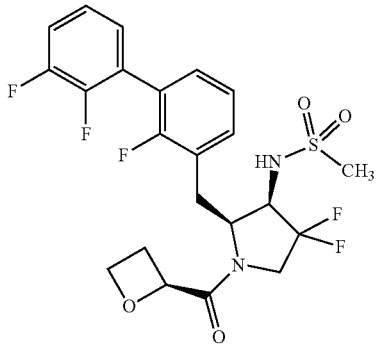 [SMILES: CS(=O)(=O)N[C@@H]1[C@H](Cc2cccc(-c3cccc(F)c3F)c2F)N(C(=O)[C@@H]2CCO2)CC1(F)F] | | 505.1 |
| 134 | N-{(2S,3R)-4,4-difluoro-1-({2S}-oxetane-2-carbonyl)-2-[(2,2',5'-trifluoro[1,1'-biphenyl]-3-yl)methyl]pyrrolidin-3-yl]-methanesulfonamide | 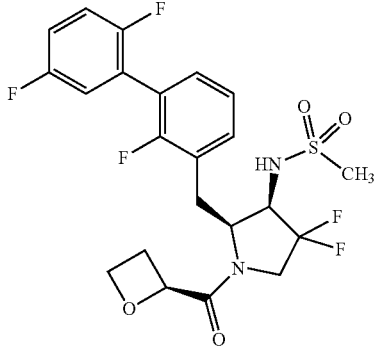 [SMILES: CS(=O)(=O)N[C@@H]1[C@H](Cc2cccc(-c3cc(F)ccc3F)c2F)N(C(=O)[C@@H]2CCO2)CC1(F)F] | | 505.1 |
| 135 | N'-[(2S,3R)-4,4-difluoro-2-[(2-fluoro[1,1'-biphenyl]-3-yl)methyl]-1-(oxetane-2-carbonyl)pyrrolidin-3-yl]-N,N-dimethyl-sulfuric diamide with shorter retention time | 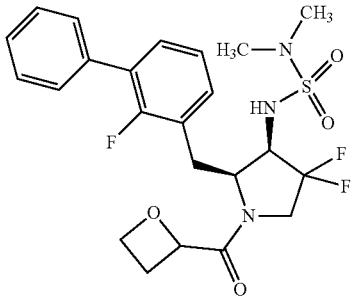 [SMILES: CN(C)S(=O)(=O)N[C@@H]1[C@H](Cc2cccc(-c3ccccc3)c2F)N(C(=O)C2CCO2)CC1(F)F] | | 498.1 |
| 136 | rac-N-[(2S,3R)-2-{[2-(3,5-difluorophenyl)-1,3-thiazol-4-yl]methyl}-4,4-difluoro-1-(1-hydroxycyclobutane-1-carbonyl)-pyrrolidin-3-yl]methanesulfonamide | 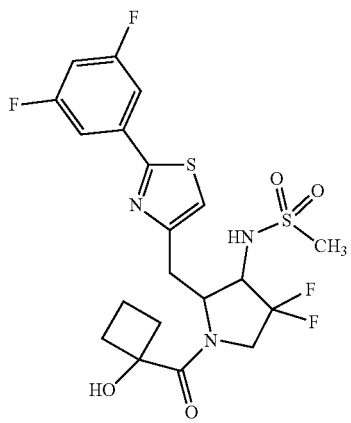 [SMILES: CS(=O)(=O)NC1C(Cc2csc(-c3cc(F)cc(F)c3)n2)N(C(=O)C2(O)CCC2)CC1(F)F] | | 508.1 |

TABLE 1-1-continued

| EX. | IUPAC NAME | Structure | ADDITIVE | MS |
|---|---|---|---|---|
| 137 | N'-[(2S,3R)-4,4-difluoro-2-[(2-fluoro[1,1'-biphenyl]-3-yl)methyl]-1-(oxetane-2-carbonyl)pyrrolidin-3-yl]-N,N-dimethyl-sulfuric diamide with longer retention time | 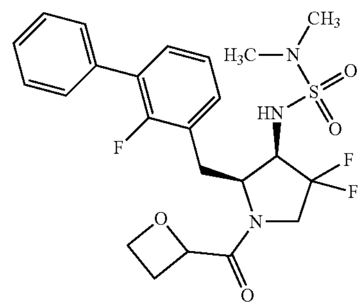 [SMILES: CN(C)S(=O)(=O)N[C@@H]1[C@H](Cc2cccc(-c3ccccc3)c2F)N(C(=O)C2CCO2)CC1(F)F] | | 498.1 |
| 138 | (2S,3R)-3-[(dimethylsulfamoyl)amino]-4,4-difluoro-2-[(2-fluoro[1,1'-biphenyl]-3-yl)methyl]-N,N-dimethylpyrrolidine-1-carboxamide | 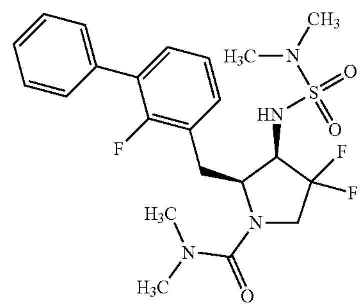 [SMILES: CN(C)C(=O)N1CC(F)(F)[C@H](NS(=O)(=O)N(C)C)[C@@H]1Cc1cccc(-c2ccccc2)c1F] | | 485.2 |
| 139 | N'-{(2S,3R)-1-(azetidine-1-carbonyl)-4,4-difluoro-2-[(2-fluoro[1,1'-biphenyl]-3-yl)methyl]pyrrolidin-3-yl}-N,N-dimethyl-sulfuric diamide | 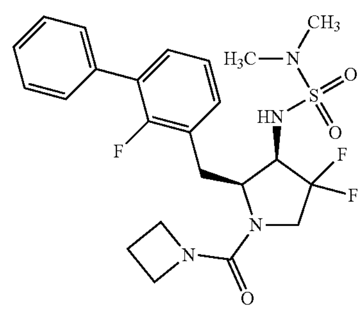 [SMILES: CN(C)S(=O)(=O)N[C@@H]1[C@H](Cc2cccc(-c3ccccc3)c2F)N(C(=O)N2CCC2)CC1(F)F] | | 497.2 |
| 140 | N'-[(2S,3R)-4,4-difluoro-2-[(2-fluoro[1,1'-biphenyl]-3-yl)methyl]-1-(2-hydroxy-2-methylpropanoyl)pyrrolidin-3-yl]-N,N-dimethylsulfuric diamide | 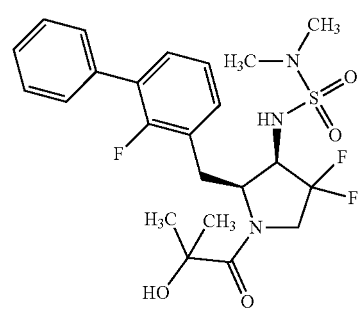 [SMILES: CN(C)S(=O)(=O)N[C@@H]1[C@H](Cc2cccc(-c3ccccc3)c2F)N(C(=O)C(C)(C)O)CC1(F)F] | | 500.3 |
| 141 | N'-{(2S,3R)-1-(cyclobutanecarbonyl)-4,4-difluoro-2-[(2-fluoro[1,1'-biphenyl]-3-yl)methyl]pyrrolidin-3-yl}-N,N-dimethyl-sulfuric diamide | 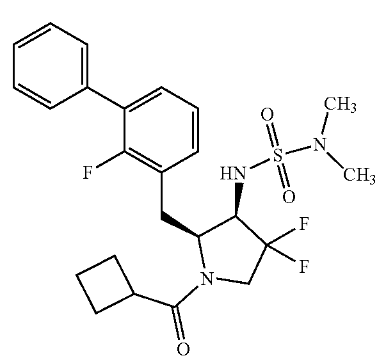 [SMILES: CN(C)S(=O)(=O)N[C@@H]1[C@H](Cc2cccc(-c3ccccc3)c2F)N(C(=O)C2CCC2)CC1(F)F] | | 496.2 |

TABLE 1-1-continued

| EX. | IUPAC NAME | Structure | ADDITIVE | MS |
|---|---|---|---|---|
| 142 | (2S,3R)-3-[(dimethylsulfamoyl)amino]-4,4-difluoro-2-[(2-fluoro[1,1'-biphenyl]-3-yl)-methyl]-N-methoxy-N-methylpyrrolidine-1-carboxamide | 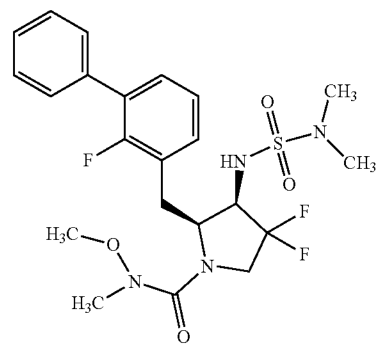 [SMILES: CON(C)C(=O)N1CC(F)(F)[C@H](NS(=O)(=O)N(C)C)[C@@H]1Cc1cccc(-c2ccccc2)c1F] | | 501.2 |
| 143 | N'-{(2S,3R)-1-(bicyclo[1.1.1]pentane-1-carbonyl)-4,4-difluoro-2-[(2-fluoro[1,1'-biphenyl]-3-yl)methyl]pyrrolidin-3-yl}-N,N-dimethylsulfuric diamide | 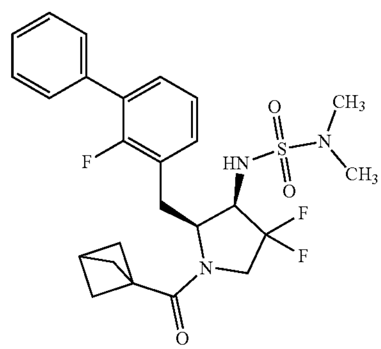 | | 508.2 |
| 144 | N-{(2S,3R)-1-(cyclopropanecarbonyl)-4,4-difluoro-2-[(2,3',5'-trifluoro[1,1'-biphenyl]-3-yl)methyl]pyrrolidin-3-yl}ethanesulfonamide | 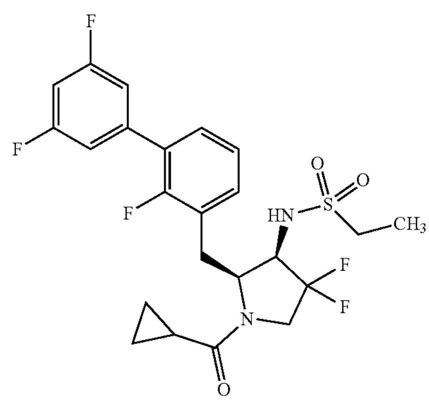 [SMILES: CCS(=O)(=O)N[C@@H]1[C@H](Cc2cccc(-c3cc(F)cc(F)c3)c2F)N(C(=O)C2CC2)CC1(F)F] | | 500.8 |
| 145 | N'-[(2S,3R)-4,4-difluoro-2-[(2-fluoro[1,1'-biphenyl]-3-yl)methyl]-1-(1-hydroxycyclobutane-1-carbonyl)pyrrolidin-3-yl]-N,N-dimethylsulfuric diamide | 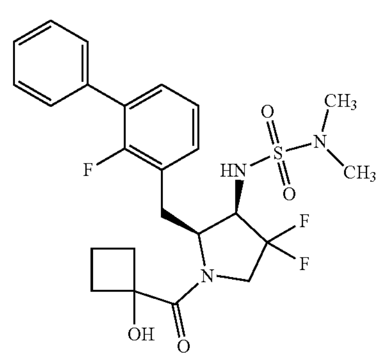 [SMILES: CN(C)S(=O)(=O)N[C@@H]1[C@H](Cc2cccc(-c3ccccc3)c2F)N(C(=O)C2(O)CCC2)CC1(F)F] | | 512.2 |

TABLE 1-1-continued

| EX. | IUPAC NAME | Structure | ADDITIVE | MS |
|---|---|---|---|---|
| 146 | N-{(2S,3R)-4,4-difluoro-1-(2-methyl-propanoyl)-2-[(2,3',5',-trifluoro[1,1'-biphenyl]-3-yl)methyl]pyrrolidin-3-yl}-ethanesulfonamide | 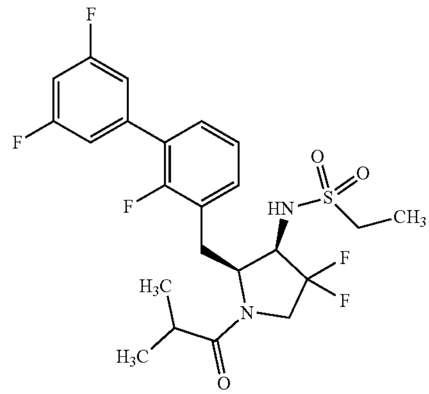 [SMILES: CCS(=O)(=O)N[C@@H]1[C@H](Cc2cccc(-c3cc(F)cc(F)c3)c2F)N(C(=O)C(C)C)CC1(F)F] | | 505.2 |
| 147 | N-{(2S,3R)-4,4-difluoro-1-(2-methyl-propanoyl)-2-[(2,2',5'-trifluoro[1,1'-biphenyl]-3-yl)methyl]pyrrolidin-3-yl)-ethanesulfonamide | 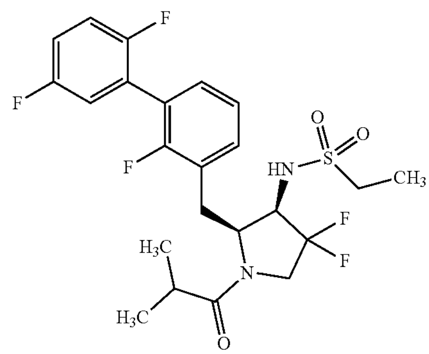 [SMILES: CCS(=O)(=O)N[C@@H]1[C@H](Cc2cccc(-c3cc(F)ccc3F)c2F)N(C(=O)C(C)C)CC1(F)F] | | 505.2 |
| 148 | N-{(2S,3R)-4,4-difluoro-1-(2-methyl-propanoyl)-2-[(2,2',3'-trifluoro[1,1'-biphenyl]-3-yl)methyl]pyrrolidin-3-yl}-ethanesulfonamide | 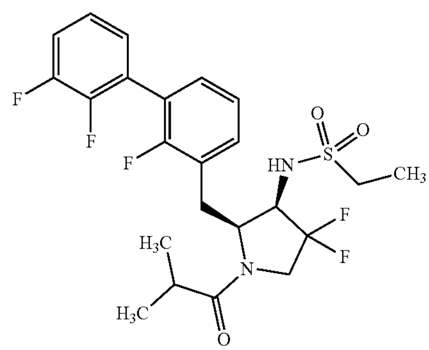 [SMILES: CCS(=O)(=O)N[C@@H]1[C@H](Cc2cccc(-c3cccc(F)c3F)c2F)N(C(=O)C(C)C)CC1(F)F] | | 505.2 |
| 149 | N'-[(2S,3R)-4,4-difluoro-2-[(2-fluoro-[1,1'-biphenyl]-3-yl)methyl]-1-(2-methylpropanoyl)pyrrolidin-3-yl]-N,N-dimethylsulfuric diamide | 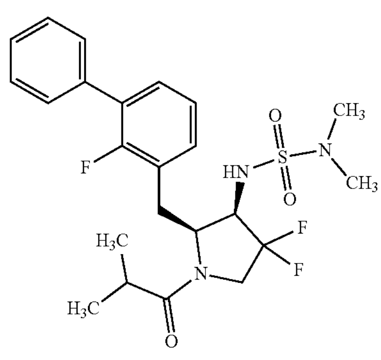 [SMILES: CC(C)C(=O)N1CC(F)(F)[C@H](NS(=O)(=O)N(C)C)[C@@H]1Cc1cccc(-c2ccccc2)c1F] | | 484.2 |

| EX. | IUPAC NAME | Structure | ADDITIVE | MS |
|---|---|---|---|---|
| 150 | N-[(2S,3R)-1-(2,2-dimethylpropanoyl)-4,4-difluoro-2-{[2-fluoro-3-(4-methyl-pyridin-2-yl)phenyl]methyl}pyrrolidin-3-yl]methanesulfonamide | 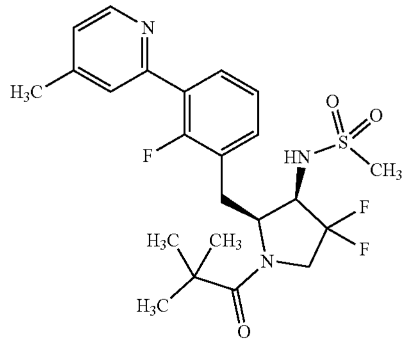 [SMILES: Cc1ccnc(-c2cccc(C[C@H]3[C@@H](NS(C)(=O)=O)C(F)(F)CN3C(=O)C(C)(C)C)c2F)c1] | | 484.2 |
| 151 | N-[(2S,3R)-1-(2,2-dimethylpropanoyl)-2-{[3-(4,6-dimethylpyrimidin-2-yl)-2-fluorophenyl]methyl}-4,4-difluoro-pyrrolidin-3-yl]methanesulfonamide | 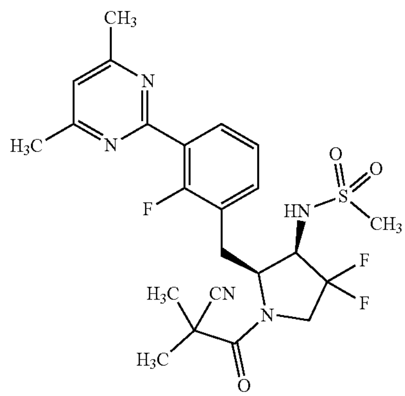 [SMILES: Cc1cc(C)nc(-c2cccc(C[C@H]3[C@@H](NS(C)(=O)=O)C(F)(F)CN3C(=O)C(C)(C)C#N)c2F)n1] | | 499.3 |
| 152 | N-[(2S,3R)-4,4-difluoro-2-[(2-fluoro[1,1'-biphenyl]-3-yl)methyl]-1-(2-methyloxetane-2-carbonyl)pyrrolidin-3-yl]ethanesulfon-amide with shorter retention time by SFC (column: CHIRALPAK IC (4.6 mml · D. × 150 mmL, 5 μm), mobile phase: carbon dioxide/(MeOH/diethylamine) = 1000/1) = 750/250 (v/v)) | 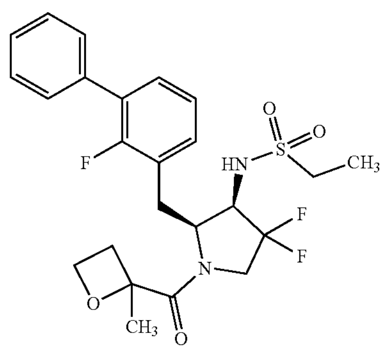 [SMILES: CCS(=O)(=O)N[C@@H]1[C@H](Cc2cccc(-c3ccccc3)c2F)N(C(=O)C2(C)CCO2)CC1(F)F] | | 497.2 |
| 153 | N-{(2S,3R)-4,4-difluoro-1-(oxetane-2-carbonyl)-2-[(2,3',5'-trifluoro[1,1'-biphenyl]-3-yl)methyl]pyrrolidin-3-yl}cyclopropanesulfonamide with longer retention time | 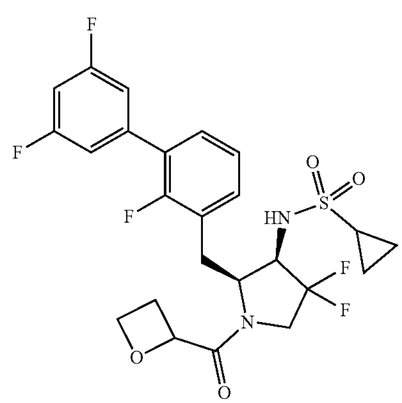 [SMILES: O=C(C1CCO1)N1CC(F)(F)[C@H](NS(=O)(=O)C2CC2)[C@@H]1Cc1cccc(-c2cc(F)cc(F)c2)c1F] | | 531.1 |

TABLE 1-1-continued

| EX. | IUPAC NAME | Structure | ADDITIVE | MS |
|---|---|---|---|---|
| 154 | N-[(2S,3R)-1-(2,2-dimethylpropanoyl)-2-{[3-(4,6-dimethylpyridin-2-yl)-2-fluorophenyl]imethyl}-4,4-difluoroopyrrolidin-3-yl]methanesulfonamide | 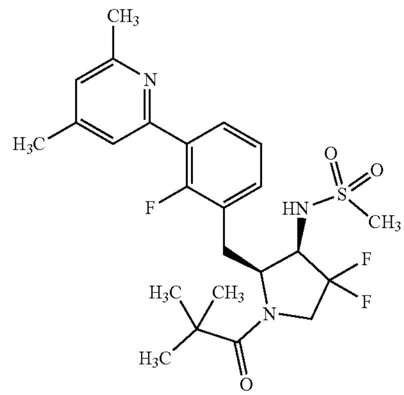 [SMILES: Cc1cc(C)nc(-c2cccc(C[C@H]3[C@@H](NS(C)(=O)=O)C(F)(F)CN3C(=O)C(C)(C)C)c2F)c1] | | 498.2 |
| 155 | N-[(2S,3R)-1-(2,2-dimethylpropanoyl)-4,4-difluoro-2-{[2-fluoro-3-(6-methylpyridin-2-yl)phenyl]methyl}pyrrolidin-3-yl]methanesulfonamide | 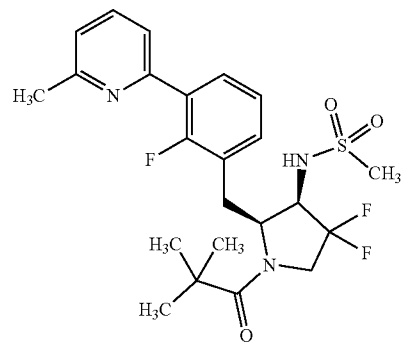 [SMILES: Cc1cccc(-c2cccc(C[C@H]3[C@@H](NS(C)(=O)=O)C(F)(F)CN3C(=O)C(C)(C)C)c2F)n1] | | 484.2 |
| 156 | N-{(2S,3R)-4,4-difluoro-1-(oxetane-2-carbonyl)-2-[(2,2',5'-trifluoro[1,1'-biphenyl]-3-yl)methyl]pyrrolidin-3-yl}cyclopropanesulfonamide with longer retention time | 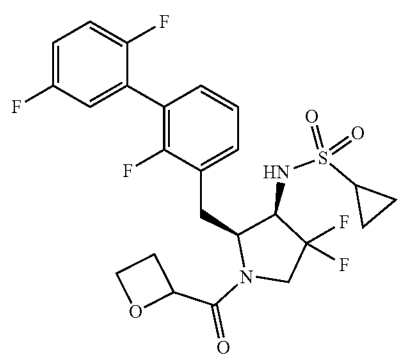 [SMILES: O=C(C1CCO1)N1CC(F)(F)[C@H](NS(=O)(=O)C2CC2)[C@@H]1Cc1cccc(-c2cc(F)ccc2F)c1F] | | 531.1 |
| 157 | N-{(2S,3R)-4,4-difluoro-1-(oxetane-2-carbonyl)-2-[(2,2',5'-trifluoro[1,1'-biphenyl]-3-yl)methyl]pyrrolidin-3-yl}cyclopropanesulfonamide with shorter retention time | 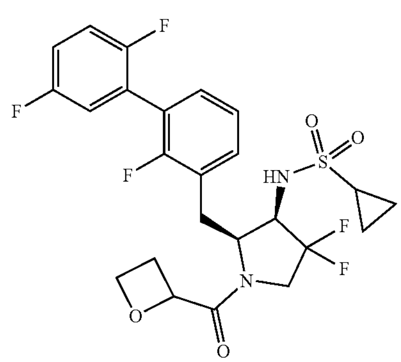 [SMILES: O=C(C1CCO1)N1CC(F)(F)[C@H](NS(=O)(=O)C2CC2)[C@@H]1Cc1cccc(-c2cc(F)ccc2F)c1F] | | 531.1 |

TABLE 1-1-continued

| EX. | IUPAC NAME | Structure | ADDITIVE | MS |
|---|---|---|---|---|
| 158 | N-[(2S,3R)-2-[(2,3'-difluoro[1,1'-biphenyl]-3-yl)methyl]-4,4-difluoro-1-(2-methyloxetane-2-carbonyl)pyrrolidin-3-yl]-methanesulfonamide with longer retention time | 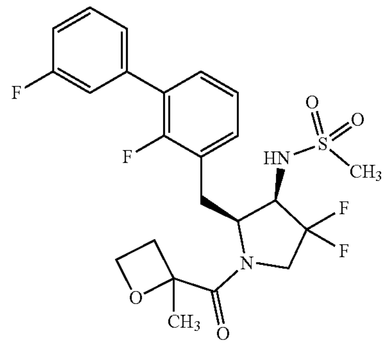 [SMILES: CC1(C(=O)N2CC(F)(F)[C@H](NS(C)(=O)=O)[C@@H]2Cc2cccc(-c3cccc(F)c3)c2F)CCO1] | | 501.2 |
| 159 | N-{(2S,3R)-4,4-difluoro-1-(oxetane-2-carbonyl)-2-[(2,2',3'-trifluoro[1,1'-biphenyl]-3-yl)methyl]pyrrolidin-3-yl}cyclopropanesulfonamide with longer retention time | 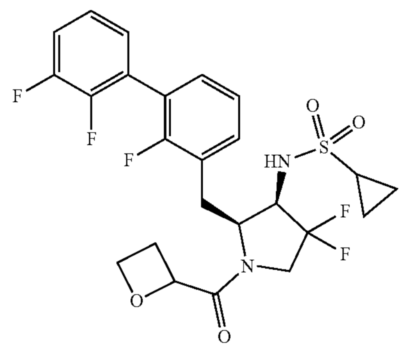 [SMILES: O=C(C1CCO1)N1CC(F)(F)[C@H](NS(=O)(=O)C2CC2)[C@@H]1Cc1cccc(-c2cccc(F)c2F)c1F] | | 531.2 |
| 160 | N-[(2S,3R)-2-[(3',4'-difluoro[1,1'-biphenyl]-3-yl)methyl]-4,4-difluoro-1-(2-methylpropanoyl)pyrrolidin-3-yl]-methanesulfonamide | 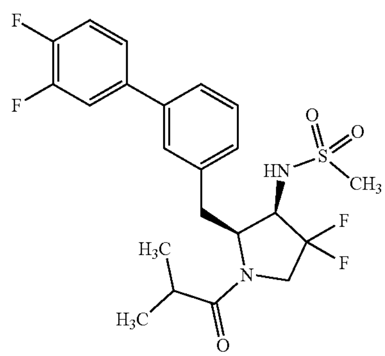 [SMILES: CC(C)C(=O)N1CC(F)(F)[C@H](NS(C)(=O)=O)[C@@H]1Cc1cccc(-c2ccc(F)c(F)c2)c1] | | 471.2 |
| 161 | N-[(2S,3R)-4,4-difluoro-2-[(2-fluoro[1,1'-biphenyl]-3-yl)methyl]-1-(2-methyloxetane-2-carbonyl)pyrrolidin-3-yl]ethanesulfonamide with longer retention time by SFC (column: CHIRALPAK IC (4.6 mml · D. × 150 mmL, 5 μm), mobile phase: carbon dioxide/(MeOH/diethylamine) = 1000/1) = 750/250 (v/v)) | 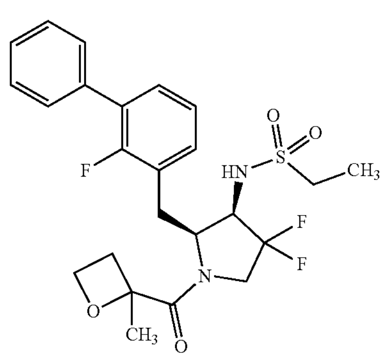 [SMILES: CCS(=O)(=O)N[C@@H]1[C@H](Cc2cccc(-c3ccccc3)c2F)N(C(=O)C2(C)CCO2)CC1(F)F] | | 497.2 |

TABLE 1-1-continued

| EX. | IUPAC NAME | Structure | ADDITIVE | MS |
|---|---|---|---|---|
| 162 | N-{(2S,3R)-4,4-difluoro-1-(oxetane-2-carbonyl)-2-[(2,3',5'-trifluoro[1,1'-biphenyl]-3-yl)methyl]pyrrolidin-3-yl)-cyclopropanesulfonamide with shorter retention time | 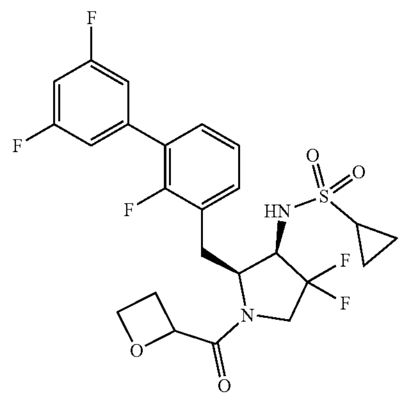 [SMILES: O=C(C1CCO1)N1CC(F)(F)[C@H](NS(=O)(=O)C2CC2)[C@@H]1Cc1cccc(-c2cc(F)cc(F)c2)c1F] | | 531.2 |
| 163 | N-[(2S,3R)-2-[(2,3'-difluoro[1,1'-biphenyl]-3-yl)methyl]-4,4-difluoro-1-(2-methyl-propanoyl)pyrrolidin-3-yl]cyclopropane-sulfonamide | 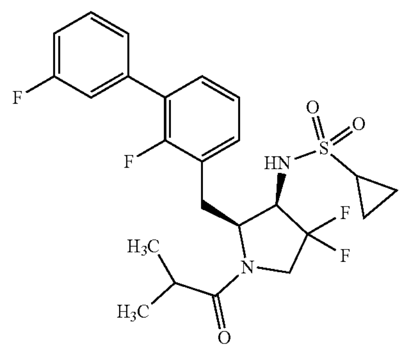 [SMILES: CC(C)C(=O)N1CC(F)(F)[C@H](NS(=O)(=O)C2CC2)[C@@H]1Cc1cccc(-c2cccc(F)c2)c1F] | | 499.2 |
| 164 | N-[(2S,3R)-2-[(2,3'-dlfluoro[1.1'-biphenyl]-3-yl)methyl]-4,4-difluoro-1-(2-methyl-oxetane-2-carbonyl)pyrrolidin-3-yl]-methanesulfonamide with shorter retention time | 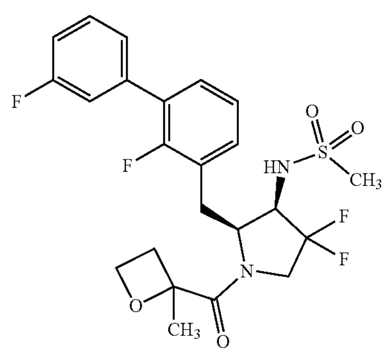 [SMILES: CC1(C(=O)N2CC(F)(F)[C@H](NS(C)(=O)=O)[C@@H]2Cc2cccc(-c3cccc(F)c3)c2F)CCO1] | | 501.1 |
| 165 | N-{(2S,3R)-4,4-difluoro-1-(oxetane-2-carbonyl)-2-[(2,2',3'-trifluoro[1,1'-biphenyl]-3-yl)methyl]pyrrolidin-3-yl}-cyclopropanesulfonamide with shorter retention time | 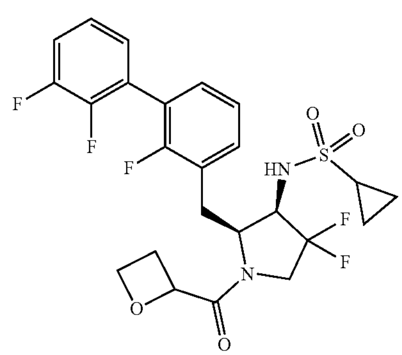 [SMILES: O=C(C1CCO1)N1CC(F)(F)[C@H](NS(=O)(=O)C2CC2)[C@@H]1Cc1cccc(-c2cccc(F)c2F)c1F] | | 531.1 |

TABLE 1-1-continued

| EX. | IUPAC NAME | Structure | ADDITIVE | MS |
|---|---|---|---|---|
| 166 | N-{(2S,3R)-4,4-difluoro-1-(2-methyl-propanoyl)-2-[(2,3',5'-trifluoro[1,1'-biphenyl]-3-yl)methyl]pyrrolidin-3-yl]-cyclopropanesulfonamide | 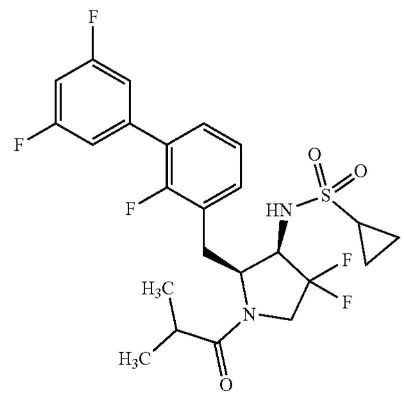 [SMILES: CC(C)C(=O)N1CC(F)(F)[C@H](NS(=O)(=O)C2CC2)[C@@H]1Cc1cccc(-c2cc(F)cc(F)c2)c1F] | | 517.2 |
| 167 | N-{(2S,3R)-4,4-difluoro-1-(2-methyl-propanoyl)-2-[(2,2',5'-trifluoro[1,1'-biphenyl]-3-yl)methyl]pyrrolidin-3-yl}-cyclopropanesulfonamide | 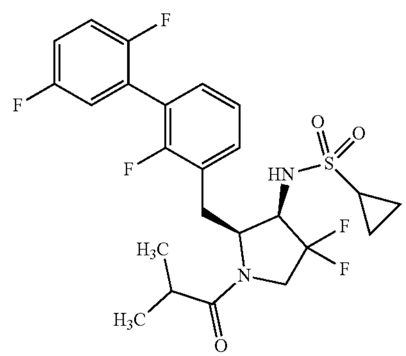 [SMILES: CC(C)C(=O)N1CC(F)(F)[C@H](NS(=O)(=O)C2CC2)[C@@H]1Cc1cccc(-c2cc(F)ccc2F)c1F] | | 517.1 |
| 168 | N-{(2S,3R)-4,4-difluoro-1-(2-methyl-propanoyl)-2-[(2,2',3'-trifluoro[1,1'-biphenyl]-3-yl)methyl]pyrrolidin-3-yl}-cyclopropanesulfonamide | 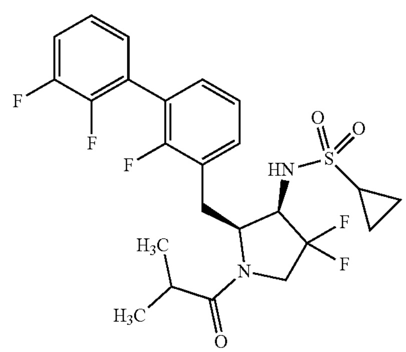 [SMILES: CC(C)C(=O)N1CC(F)(F)[C@H](NS(=O)(=O)C2CC2)[C@@H]1Cc1cccc(-c2cccc(F)c2F)c1F] | | 517.2 |
| 169 | N-[(2S,3R)-2-[(3',5'-difluoro[1,1'-biphenyl]-3-yl)methyl]-4,4-difluoro-1-(oxetane-2-carbonyl)pyrrolidin-3-yl]-cyclopropanesulfonamide with shorter retention time | 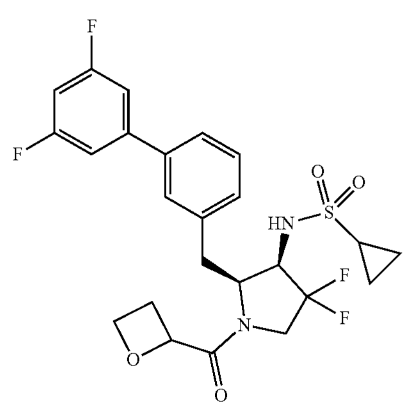 [SMILES: O=C(C1CCO1)N1CC(F)(F)[C@H](NS(=O)(=O)C2CC2)[C@@H]1Cc1cccc(-c2cc(F)cc(F)c2)c1] | | 513.1 |

TABLE 1-1-continued

| EX. | IUPAC NAME | ADDITIVE | MS |
|---|---|---|---|
| 170 | N-[(2S,3R)-2-[(3',5'-difluoro[1,1'-biphenyl]-3-yl)methyl]-4,4-difluoro-1-(oxetane-2-carbonyl)pyrrolidin-3-yl]-cyclopropanesulfonamide with longer retention time | | 513.2 |
| 171 | N-[(2S,3R)-4,4-difluoro-2-[(2-fluoro[1,1'-biphenyl]-3-yl)methyl]-1-(2-methyl-propanoyl)pyrrolidin-3-yl]cyclopropane-sulfonamide | | 481.2 |
| 172 | N-[(2S,3R)-2-[(2',5',-difluoro[1,1'-biphenyl]-3-yl)methyl]-4,4-difluoro-1-(oxetane-2-carbonyl)pyrrolidin-3-yl]-ethanesulfonamide with shorter retention | | 501.1 |
| 173 | N-[(2S,3R)-2-[(2',5',-difluoro[1,1'-biphenyl]-3-yl)methyl]-4,4-difluoro-1-(oxetane-2-carbonyl)pyrrolidin-3-yl]-ethanesulfonamide with longer retention time | | 501.1 |

TABLE 1-1-continued

| EX. | IUPAC NAME | Structure | ADDITIVE | MS |
|---|---|---|---|---|
| 174 | N-[(2S,3R)-2-[(2',3'-difluoro[1,1'-biphenyl]-3-yl)methyl]-4,4-difluoro-1-(oxetane-2-carbonyl)pyrrolidin-3-yl]-ethanesulfonamide with shorter retention time | 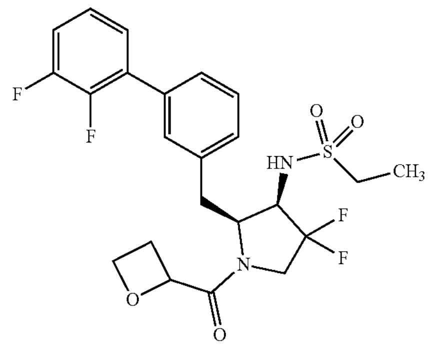 [SMILES: CCS(=O)(=O)N[C@@H]1[C@H](Cc2cccc(-c3cccc(F)c3F)c2)N(C(=O)C2CCO2)CC1(F)F] | | 501.2 |
| 175 | N-[(2S,3R)-2-[(2',3'-difluoro[1,1'-biphenyl]-3-yl)methyl]-4,4-difluoro-1-(oxetane-2-carbonyl)pyrrolidin-3-yl]-ethanesulfonamide with longer retention time | 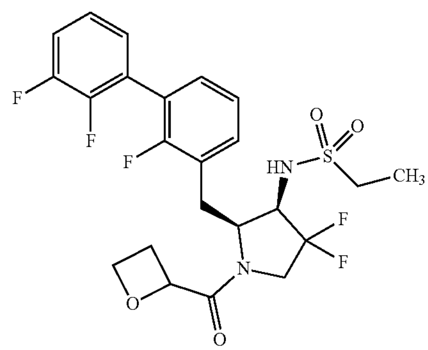 [SMILES: CCS(=O)(=O)N[C@@H]1[C@H](Cc2cccc(-c3cccc(F)c3F)c2F)N(C(=O)C2CCO2)CC1(F)F] | | 501.2 |
| 176 | N-[(2S,3R)-1-(2,2-dimethylpropanoyl)-4,4-difluoro-2-{[2-fluoro-3-(4-methyl-pyridin-2-yl)phenyl]methyl}pyrrolidin-3-yl]ethanesulfonamide | 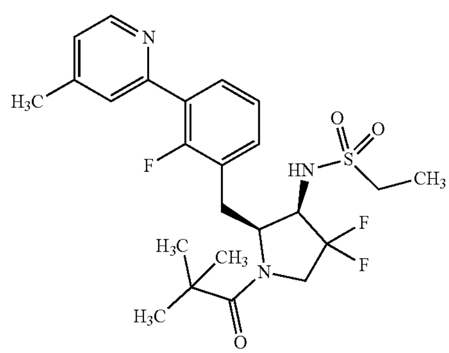 [SMILES: CCS(=O)(=O)N[C@@H]1[C@H](Cc2cccc(-c3cc(C)ccn3)c2F)N(C(=O)C(C)(C)C)CC1(F)F] | | 498.2 |
| 177 | N-[(2S,3R)-1-(2,2-dimethylpropanoyl)-4,4-difluoro-2-{[2-fluoro-3-(6-methyl-pyridin-2-yl)phenyl]methyl}pyrrolidin-3-yl]ethanesulfonamide | 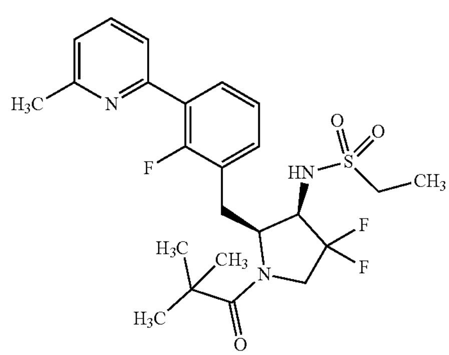 [SMILES: CCS(=O)(=O)N[C@@H]1[C@H](Cc2cccc(-c3cccc(C)n3)c2F)N(C(=O)C(C)(C)C)CC1(F)F] | | 498.2 |

TABLE 1-1-continued

| EX. | IUPAC NAME | Structure | ADDITIVE | MS |
|---|---|---|---|---|
| 178 | N-[(2S,3R)-1-(2,2-dimethylpropanoyl)-2-{[3-(4,6-dimethylpyridin-2-yl)-2-fluorophenyl]methyl}-4,4-difluoropyrrolidin-3-yl]ethanesulfonamide | 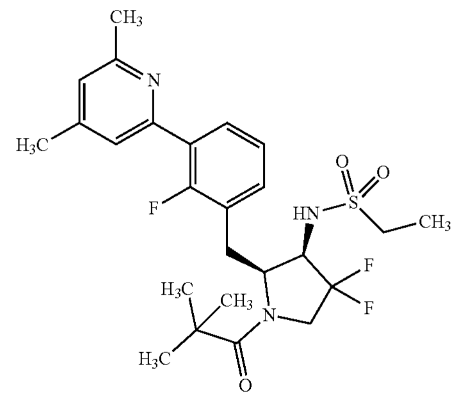 [SMILES: CCS(=O)(=O)N[C@@H]1[C@H](Cc2cccc(-c3cc(C)cc(C)n3)c2F)N(C(=O)C(C)(C)C)CC1(F)F] | | 512.2 |
| 179 | N-[(2S,3R)-1-(2,2-dimethylpropanoyl)-2-{[3-(4,6-dimethylpyrimidin-2-yl)-2-fluorophenyl]methyl}-4,4-difluoropyrrolidin-3-yl]ethanesulfonamide | 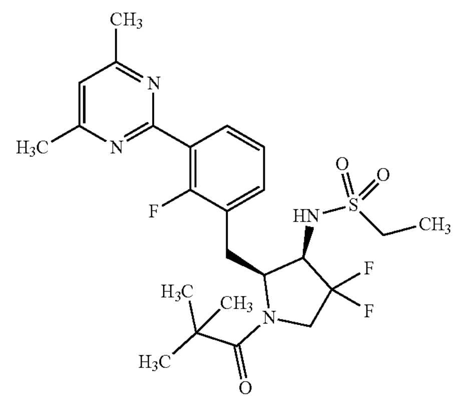 | | 513.3 |
| 180 | N-[(2S,3R)-2-[([1,1'-biphenyl]-3-yl)methyl]-4,4-difluoro-1-(oxetane-carbonyl)pyrrolidin-3-yl]cyclopropanesulfonamide with retention time | 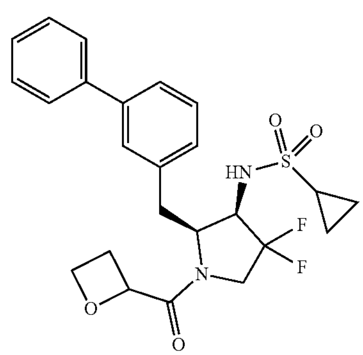 [SMILES: O=C(C1CCO1)N1CC(F)(F)[C@H](NS(=O)(=O)C2CC2)[C@@H]1Cc1cccc(-c2ccccc2)c1] | | 477.2 |
| 181 | N-[(2S,3R)-2-[([1,1-biphenyl]-3-yl)methyl]-4,4-difluoro-1-(oxetane-2-carbonyl)pyrrolidin-3-yl]cyclopropanesulfonamide with longer retention time | 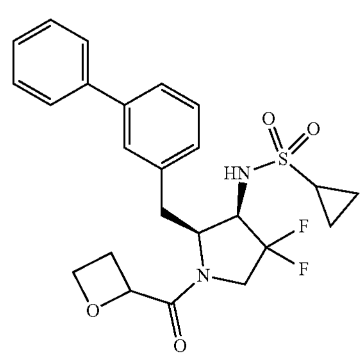 [SMILES: O=C(C1CCO1)N1CC(F)(F)[C@H](NS(=O)(=O)C2CC2)[C@@H]1Cc1cccc(-c2ccccc2)c1] | | 477.2 |

TABLE 1-1-continued

| EX. | IUPAC NAME | Structure | ADDITIVE | MS |
|---|---|---|---|---|
| 182 | N-{(2S,3R)-4,4-difluoro-1-(2-methyl-propanoyl)-2-[(2,3',5'-trifluoro[1,1'-biphenyl]-3-yl)methyl]pyrrolidin-3-yl}methanesulfonamide | 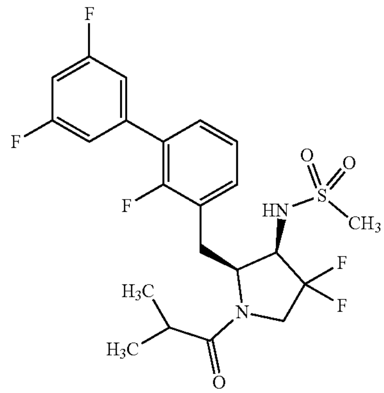 [SMILES: CC(C)C(=O)N1CC(F)(F)[C@H](NS(C)(=O)=O)[C@@H]1Cc1cccc(-c2cc(F)cc(F)c2)c1F] | | 489.2 |
| 183 | N-{(2S,3R)-4,4-difluoro-1-(2-methyl-propanoyl)-2-[(2,2',3'-trifluoro[1,1'-biphenyl]-3-yl)methyl]pyrrolidin-3-yl}-methanesulfonamide | 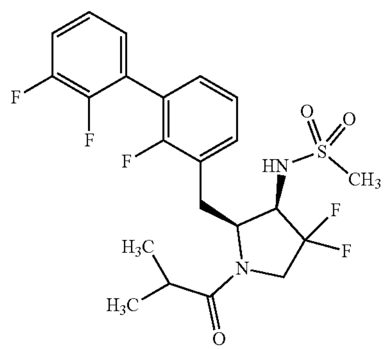 [SMILES: CC(C)C(=O)N1CC(F)(F)[C@H](NS(C)(=O)=O)[C@@H]1Cc1cccc(-c2cccc(F)c2F)c1F] | | 491.1 |
| 184 | N-{(2S,3R)-4,4-difluoro-1-(2-methyl-propanoyl)-2-[(2,2',5'-trifluoro[1,1'-biphenyl]-3-yl)methyl]pyrrolidin-3-yl}-methanesulfonamide | 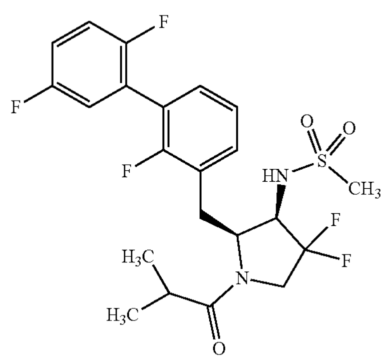 [SMILES: CC(C)C(=O)N1CC(F)(F)[C@H](NS(C)(=O)=O)[C@@H]1Cc1cccc(-c2cc(F)ccc2F)c1F] | | 491.2 |
| 185 | N-((2S,3R)-2-[(2,2,-difluoro[1,1'-biphenyl]-3-yl)methyl]-4,4-difluoro-1-[(2R)-oxolane-2-carbonyl]pyrrolidin-3-yl}ethanesulfon-amide | 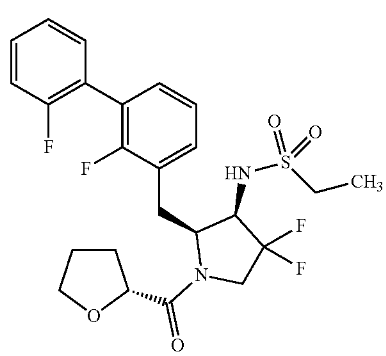 [SMILES: CCS(=O)(=O)N[C@@H]1[C@H](Cc2cccc(-c3ccccc3F)c2F)N(C(=O)[C@H]2CCCO2)CC1(F)F] | | 515.2 |

TABLE 1-1-continued

| EX. | IUPAC NAME | Structure | ADDITIVE | MS |
|---|---|---|---|---|
| 186 | N-[(2S,3R)-2-[(2,2'-difluoro[1,1'-biphenyl]-3-yl)methyl]-4,4-difluoro-1-(2-methyl-propanoyl)pyrrolidin-3-yl]ethanesulfon-amide | 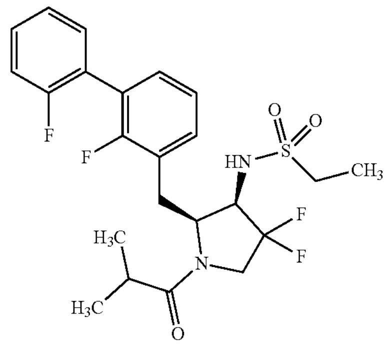 [SMILES: CCS(=O)(=O)N[C@@H]1[C@H](Cc2cccc(-c3ccccc3F)c2F)N(C(=O)C(C)C)CC1(F)F] | | 487.2 |
| 187 | N-[(2S,3R)-2-[(2,2'-difluoro[1,1'-biphenyl]-3-yl)methyl]-4,4-difluoro-1-(oxetane-2-carbonyl)pyrrolidin-3-yl]ethanesulfonamide with shorter retention time | 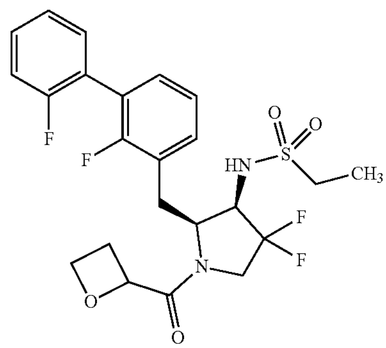 [SMILES: CCS(=O)(=O)N[C@@H]1[C@H](Cc2cccc(-c3ccccc3F)c2F)N(C(=O)C2CCO2)CC1(F)F] | | 501.2 |
| 188 | N-[(2S,3R)-2-[(2,2'-difluoro[1,1'-biphenyl]-3-yl)methyl]-4,4-difluoro-1-(oxetane-2-carbonyl)pyrrolidin-3-yl]ethanesulfonamide with longer retention time | 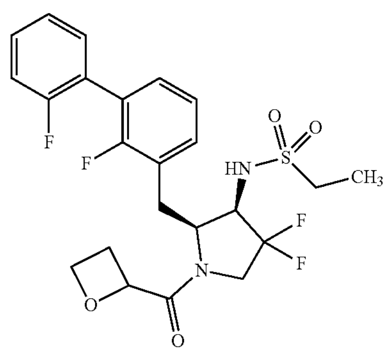 [SMILES: CCS(=O)(=O)N[C@@H]1[C@H](Cc2cccc(-c3ccccc3F)c2F)N(C(=O)C2CCO2)CC1(F)F] | | 501.1 |
| 189 | N-[(2S,3R)-2-[(2,3'-difluoro[1,1'-biphenyl]-3-yl)methyl]-4,4-difluoro-1-(2-methyl-oxetane-2-carbonyl)pyrrolidin-3-yl]-ethanesulfonamide with longer retention time | 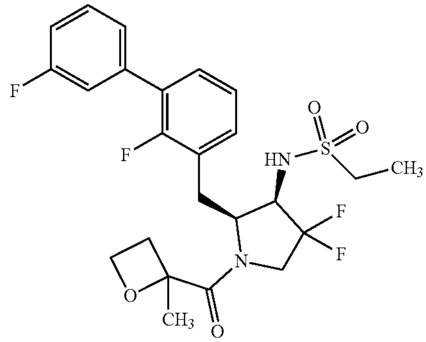 [SMILES: CCS(=O)(=O)N[C@@H]1[C@H](Cc2cccc(-c3cccc(F)c3)c2F)N(C(=O)C2(C)CCO2)CC1(F)F] | | 515.2 |

TABLE 1-1-continued

| EX. | IUPAC NAME | Structure | ADDITIVE | MS |
|---|---|---|---|---|
| 190 | N-[(2S,3R)-2-[(2,2'-difluoro[1,1'-biphenyl]-3-yl)methyl]-4,4-difluoro-1-(2-methyl-propanoyl)pyrrolidin-3-yl]cyclopropane-sulfonamide | 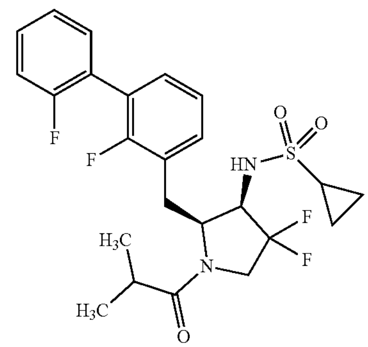 [SMILES: CC(C)C(=O)N1CC(F)(F)[C@H](NS(=O)(=O)C2CC2)[C@@H]1Cc1cccc(-c2ccccc2F)c1F] | | 499.2 |
| 191 | N-[(2S,3R)-2-[(2,2'-difluoro[1,1'-biphenyl]-3-yl)methyl]-4,4-difluoro-1-(oxetane-2-carbonyl)pyrrolidin-3-yl]cyclopropane-sulfonamide with longer retention time | 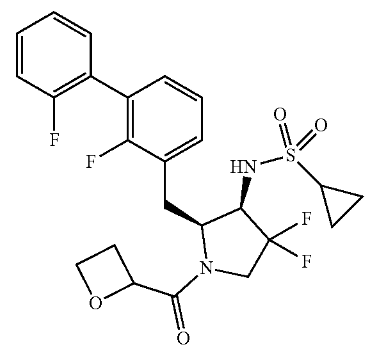 [SMILES: O=C(C1CCO1)N1CC(F)(F)[C@H](NS(=O)(=O)C2CC2)[C@@H]1Cc1cccc(-c2ccccc2F)c1F] | | 513.2 |
| 192 | N-[(2S,3R)-2-[(2,2'-difluoro[1,1'-biphenyl]-3-yl)methyl]-4,4-difluoro-1-(oxetane-2-carbonyl)pyrrolidin-3-yl]cyclopropane-sulfonamide with shorter retention time | 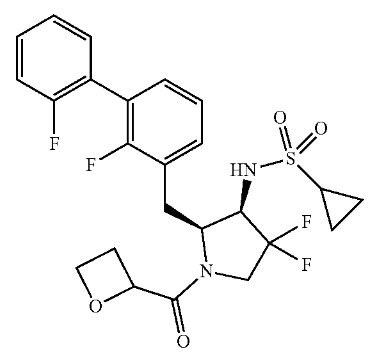 [SMILES: O=C(C1CCO1)N1CC(F)(F)[C@H](NS(=O)(=O)C2CC2)[C@@H]1Cc1cccc(-c2ccccc2F)c1F] | | 513.2 |
| 193 | N-{(2S,3R)-4,4-difluoro-2-[(2-fluoro[1,1'-biphenyl]-3-yl)methyl]-1-[(2S)-oxolane-2-carbonyl]pyrrolidin-3-yl}methanesulfon-amide | 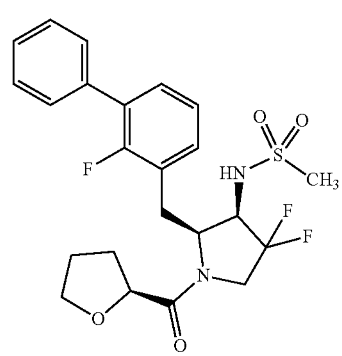 [SMILES: CS(=O)(=O)N[C@@H]1[C@H](Cc2cccc(-c3ccccc3)c2F)N(C(=O)[C@@H]2CCCO2)CC1(F)F] | | 483.2 |

TABLE 1-1-continued

| EX. | IUPAC NAME | Structure | ADDITIVE | MS |
|---|---|---|---|---|
| 194 | N-[(2S,3R)-2-[(2,3,-difluoro[1,1'-biphenyl]-3-yl)methyl]-4,4-difluoro-1-(2-methyl-oxetane-2-carbonyl)pyrrolidin-3-yl]-ethanesulfonamide with shorter retention time | 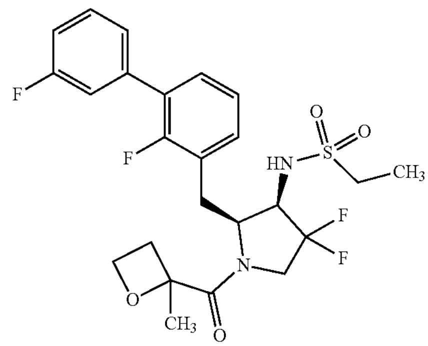 [SMILES: CCS(=O)(=O)N[C@@H]1[C@H](Cc2cccc(-c3cccc(F)c3)c2F)N(C(=O)C2(C)CCO2)CC1(F)F] | | 515.1 |
| 195 | rac-N-{(2S,3R,4R)-4-fluoro-1-(2-hydroxy-2-methylpropanoyl)-4-methyl-2-[(2,3',5'-trifluoro[1,1'-biphenyl]-3-yl)methyl]-pyrrolidin-3-yl}methanesulfonamide | 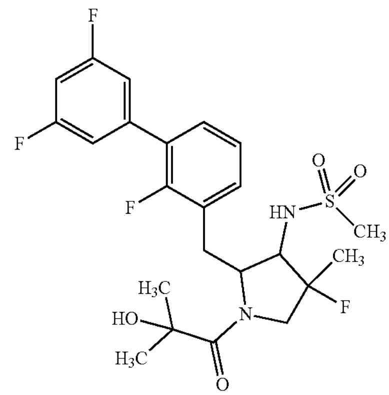 [SMILES: CC(C)(O)C(=O)N1CC(C)(F)C(NS(C)(=O)=O)C1Cc1cccc(-c2cc(F)cc(F)c2)c1F] | | 503.2 |
| 196 | N-[(2S,3R)-2-[(3'-chloro-2-fluoro[1,1'-biphenyl]-3-yl)methyl]-4,4-difluoro-1-(2-methylpropanoyl)pyrrolidin-3-yl]methane-sulfonamide | 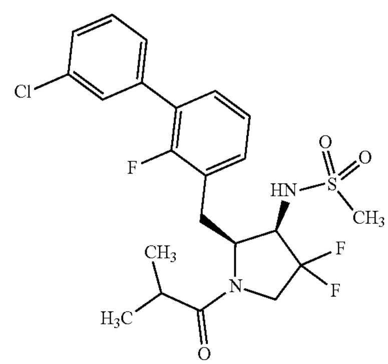 [SMILES: CC(C)C(=O)N1CC(F)(F)[C@H](NS(C)(=O)=O)[C@@H]1Cc1cccc(-c2cccc(Cl)c2)c1F] | | 489.2 |
| 197 | N-{(2S,3R)-1-(bicyclo[1.1.1]pentane-1-carbonyl)-4,4-difluoro-2-[(2,2',3'-trifluoro-[1,1'-biphenyl]-3-yl)methyl]pyrrolidin-3-yl]methanesulfonamide | 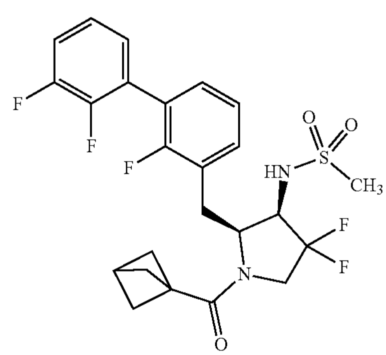 [SMILES: CS(=O)(=O)N[C@@H]1[C@H](Cc2cccc(-c3cccc(F)c3F)c2F)N(C(=O)C23CC(C2)C3)CC1(F)F] | | 515.2 |

TABLE 1-1-continued

| EX. | IUPAC NAME | Structure | ADDITIVE | MS |
|---|---|---|---|---|
| 198 | N-{(2S,3R)-1-(bicyclo[1.1.1]pentane-1-carbonyl)-4,4-difluoro-2-[(2,2',5'-trifluoro-[1,1'-biphenyl]-3-yl)methyl]pyrrolidin-3-yl}methanesulfonamide | 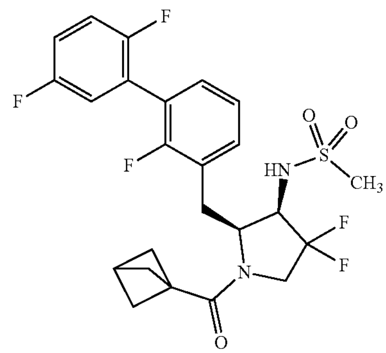 [SMILES: CS(=O)(=O)N[C@@H]1[C@H](Cc2cccc(-c3cc(F)ccc3F)c2F)N(C(=O)C23CC(C2)C3)CC1(F)F] | | 515.2 |
| 199 | N-{(2S,3R)-1-(bicyclo[1.1.1]pentane-1-carbonyl)-2-[(2,2'-difluoro[1,1'-biphenyl]-3-yl)methyl]-4,4-difluoropyrrolidin-3-yl}ethanesulfonamide | 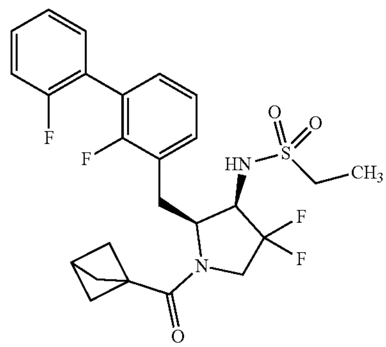 [SMILES: CCS(=O)(=O)N[C@@H]1[C@H](Cc2cccc(-c3ccccc3F)c2F)N(C(=O)C23CC(C2)C3)CC1(F)F] | | 511.2 |
| 200 | N-{(2S,3R)-1-(bicyclo[1.1.1]pentane-1-carbonyl)-4,4-difluoro-2-[(2,2',5'-trifluoro-[1,1-biphenyl]-3-yl)methyl]pyrrolidin-3-yl)ethanesulfonamide | 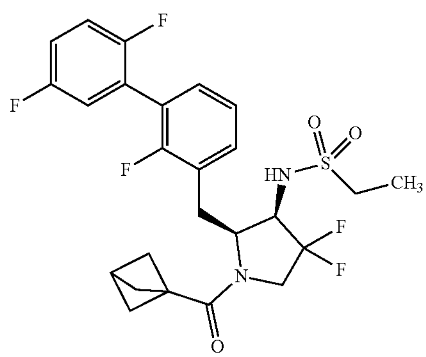 [SMILES: CCS(=O)(=O)N[C@@H]1[C@H](Cc2cccc(-c3cc(F)ccc3F)c2F)N(C(=O)C23CC(C2)C3)CC1(F)F] | | 529.0 |
| 201 | N-{(2S,3R)-1-(cyclopropanecarbonyl)-4,4-difluoro-2-[(2,2',5'-trifluoro[1,1'-biphenyl]-3-yl)methyl]pyrrolidin-3-yl)ethanesulfonamide | 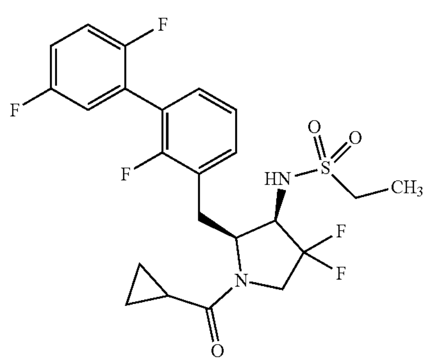 [SMILES: CCS(=O)(=O)N[C@@H]1[C@H](Cc2cccc(-c3cc(F)ccc3F)c2F)N(C(=O)C2CC2)CC1(F)F] | | 503.1 |

TABLE 1-1-continued

| EX. | IUPAC NAME | Structure | ADDITIVE | MS |
|---|---|---|---|---|
| 202 | N-{(2S,3R)-1-(cyclopropanecarbonyl)-2-[(2,3'-difluoro[1,1'-biphenyl]-3-yl)methyl]-4,4-difluoropyrrolidin-3-yl}ethanesulfonamide | 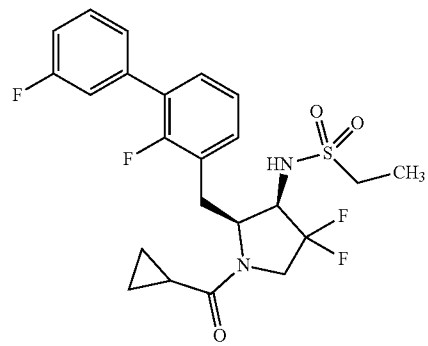 [SMILES: CCS(=O)(=O)N[C@@H]1[C@H](Cc2cccc(-c3cccc(F)c3)c2F)N(C(=O)C2CC2)CC1(F)F] | | 485.1 |
| 203 | N-{(2S,3R)-1-(bicyclo[1.1.1]pentane-1-carbonyl)-4,4-difluoro-2-[(2,2',3'-trifluoro-[1,1'-biphenyl]-3-yl)methyl]pyrrolidin-3-yl}ethanesulfonamide | 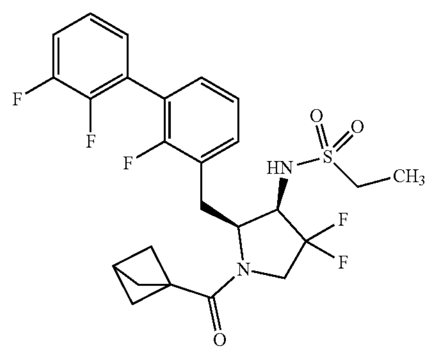 [SMILES: CCS(=O)(=O)N[C@@H]1[C@H](Cc2cccc(-c3cccc(F)c3F)c2F)N(C(=O)C23CC(C2)C3)CC1(F)F] | | 529.1 |
| 204 | N-{(2S,3R)-1-(cyclopropanecarbonyl)-4,4-difluoro-2-[(2,2',3'-trifluoro[1,1'-biphenyl]-3-yl)methyl]pyrrolidin-3-yl}ethanesulfonamide | 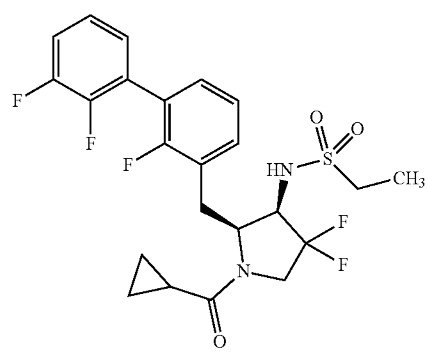 [SMILES: CCS(=O)(=O)N[C@@H]1[C@H](Cc2cccc(-c3cccc(F)c3F)c2F)N(C(=O)C2CC2)CC1(F)F] | | 503.2 |
| 205 | N-{(2S,3R)-1-(cyclopropanecarbonyl)-4,4-difluoro-2-[(2-fluoro[1,1'-biphenyl]-3-yl)methylpyrrolidin-3-yl}ethanesulfonamide | 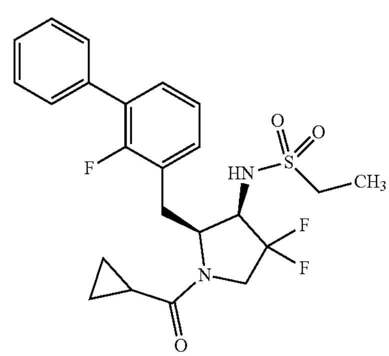 [SMILES: CCS(=O)(=O)N[C@@H]1[C@H](Cc2cccc(-c3ccccc3)c2F)N(C(=O)C2CC2)CC1(F)F] | | 467.2 |

TABLE 1-1-continued

| EX. | IUPAC NAME | Structure | ADDITIVE | MS |
|---|---|---|---|---|
| 206 | N'-[(2S,3R)-4,4-difluoro-2-[(2-fluoro[1,1'-biphenyl]-3-yl)methyl]-1-(3-hydroxy-2,2-dimethylpropanoyl)pyrrolidin-3-yl]-N,N-dimethylsulfuric diamide | 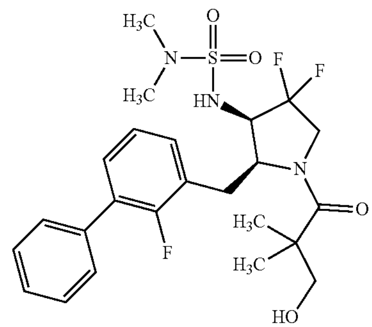 [SMILES: CN(C)S(=O)(=O)N[C@@H]1[C@H](Cc2cccc(-c3ccccc3)c2F)N(C(=O)C(C)(C)CO)CC1(F)F] | | 514.2 |
| 207 | N-[(2S,3R,4S)-2-[(2,3'-difluoro[1,1'-biphenyl]-3-yl)methyl]-4-fluoro-1-(2-hydroxy-2-methylpropanoyl)pyrrolidin-3-yl]ethanesulfonamide | 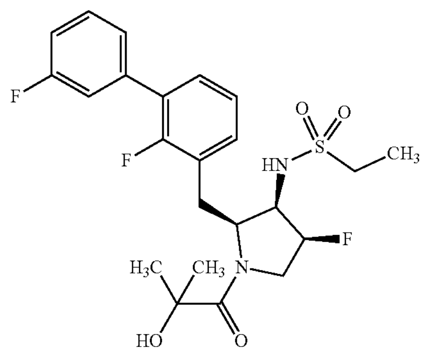 [SMILES: CCS(=O)(=O)N[C@H]1[C@@H](F)CN(C(=O)C(C)(C)O)[C@H]1Cc1cccc(-c2cccc(F)c2)c1F] | | 485.2 |
| 208 | N-[(2S,3R,4S)-2-[(2,3'-difluoro[1,1'-biphenyl]-3-yl)methyl]-4-fluoro-1-(1-hydroxycyclobutane-1-carbonyl)pyrrolidin-3-yl]ethanesulfonamide | 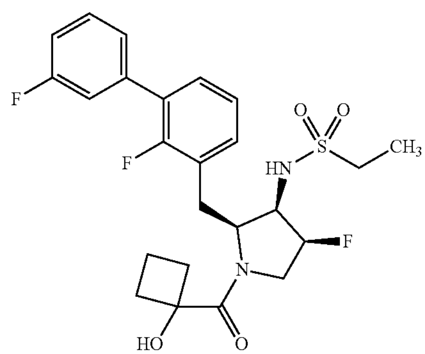 [SMILES: CCS(=O)(=O)N[C@H]1[C@@H](F)CN(C(=O)C2(O)CCC2)[C@H]1Cc1cccc(-c2cccc(F)c2)c1F] | | 497.1 |
| 209 | N-[(2S,3R,4S)-2-[(2,3'-difluoro[1,1'-biphenyl]-3-yl)methyl]-4-fluoro-1-(2-methylpropanoyl)pyrrolidin-3-yl]-ethanesulfonamide | 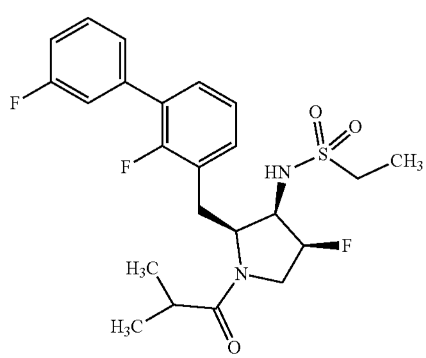 [SMILES: CCS(=O)(=O)N[C@H]1[C@@H](F)CN(C(=O)C(C)C)[C@H]1Cc1cccc(-c2cccc(F)c2)c1F] | | 469.2 |

TABLE 1-1-continued

| EX. | IUPAC NAME | Structure | ADDITIVE | MS |
|---|---|---|---|---|
| 210 | (2S,3R,4S)-2-[(2,3'-difluoro[1,1'-biphenyl]-3-yl)methyl]-3-[(ethanesulfonyl)amino]-4-fluoro-N,N-dimethylpyrrolidine-1-carboxamide | 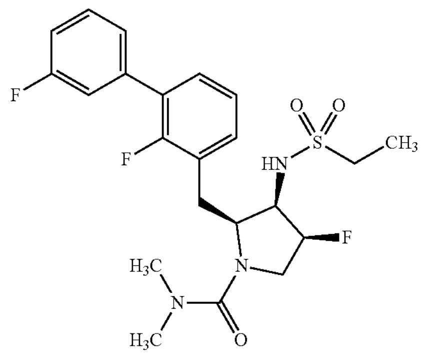 [SMILES: CCS(=O)(=O)N[C@H]1[C@@H](F)CN(C(=O)N(C)C)[C@H]1Cc1cccc(-c2cccc(F)c2)c1F] | | 470.2 |
| 211 | N-{(2S,3R,4S)-1-(azetidine-1-carbonyl)-2-[(2,3'-difluoro[1,1'-biphenyl]-3-yl)methyl]-4-fluoropyrrolidin-3-yl}ethanesulfonamide | 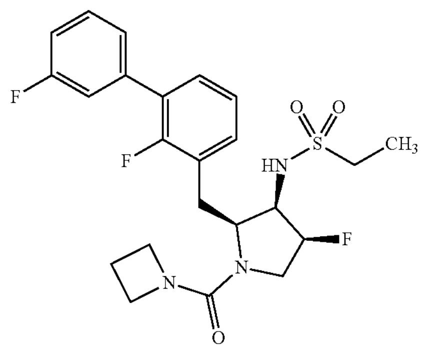 [SMILES: CCS(=O)(=O)N[C@H]1[C@@H](F)CN(C(=O)N2CCC2)[C@H]1Cc1cccc(-c2cccc(F)c2)c1F] | | 482.2 |
| 212 | N-{(2S,3R,4S)-1-(cyclopropanecarbonyl)-2-[(2,3'-difluoro[1,1'-biphenyl]-3-yl)methyl]-4-fluoropyrrolidin-3-yl}ethanesulfonamide | 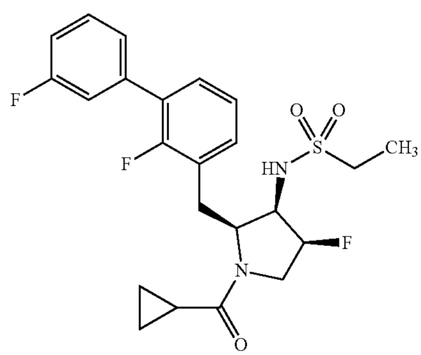 [SMILES: CCS(=O)(=O)N[C@H]1[C@@H](F)CN(C(=O)C2CC2)[C@H]1Cc1cccc(-c2cccc(F)c2)c1F] | | 467.2 |
| 213 | N-{(2S,3R,4S)-1-(bicyclo[1.1.1]pentane-1-carbonyl)-2-[(2,3'-difluoro[1,1'-biphenyl]-3-yl)methyl]-4-fluoropyrrolidin-3-yl}-ethanesulfonamide | 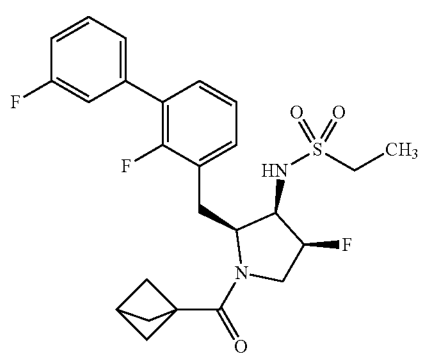 [SMILES: CCS(=O)(=O)N[C@H]1[C@@H](F)CN(C(=O)C23CC(C2)C3)[C@H]1Cc1cccc(-c2cccc(F)c2)c1F] | | 493.2 |

TABLE 1-1-continued

| EX. | IUPAC NAME | Structure | ADDITIVE | MS |
|---|---|---|---|---|
| 214 | N-{(2S,3R,4S)-2-[(2,3'-difluoro(1,1'-biphenyl]-3-yl)methyl]-4-fluoro-1-[(2R)-oxolane-2-carbonyl]pyrrolidin-3-yl}-ethanesulfonamide | 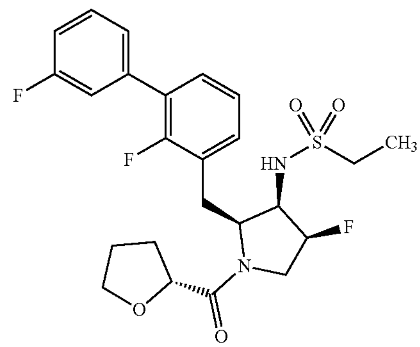 [SMILES: CCS(=O)(=O)N[C@H]1[C@@H](F)CN(C(=O)[C@H]2CCCO2)[C@H]1Cc1cccc(-c2cccc(F)c2)c1F] | | 497.3 |
| 215 | N-{(2S,3R,4S)-2-[(2,3,-difluoro[1,1'-biphenyl]-3-yl)methyl]-4-fluoro-1-[(2S)-oxolane-2-carbonyl]pyrrolidin-3-yl}-ethanesulfonamide | 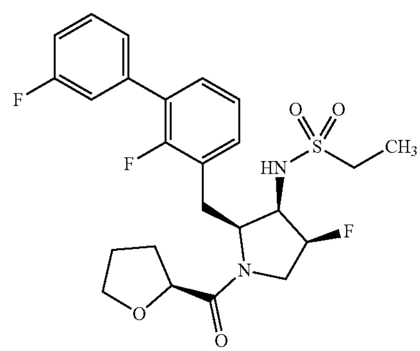 [SMILES: CCS(=O)(=O)N[C@H]1[C@@H](F)CN(C(=O)[C@@H]2CCCO2)[C@H]1Cc1cccc(-c2cccc(F)c2)c1F] | | 497.3 |
| 216 | N-[(2S,3R,4S)-2-[(2,3'-difluoro[1,1'-biphenyl]-3-yl)methyl]-4-fluoro-1-(oxetane-2-carbonyl)pyrrolidin-3-yl]-ethanesulfonamide with shorter retention time | 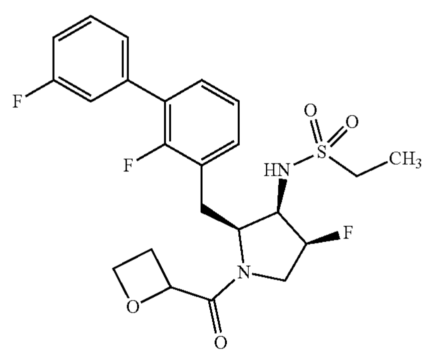 [SMILES: CCS(=O)(=O)N[C@H]1[C@@H](F)CN(C(=O)C2CCO2)[C@H]1Cc1cccc(-c2cccc(F)c2)c1F] | | 483.2 |
| 217 | N-[(2S,3R,4S)-2-[(2,3'-difluoro[1,1'-biphenyl]-3-yl)methyl]-4-fluoro-1-(oxetane-2-carbonyl)pyrrolidin-3-yl]-ethanesulfonamide with longer retention time | 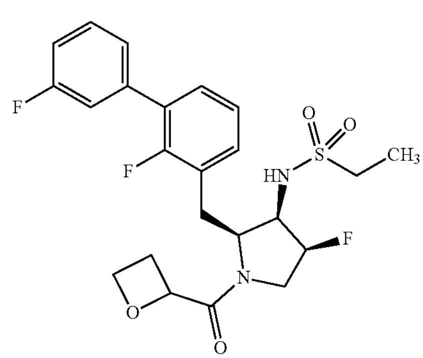 [SMILES: CCS(=O)(=O)N[C@H]1[C@@H](F)CN(C(=O)C2CCO2)[C@H]1Cc1cccc(-c2cccc(F)c2)c1F] | | 483.2 |

TABLE 1-1-continued

| EX. | IUPAC NAME | Structure | ADDITIVE | MS |
|---|---|---|---|---|
| 218 | N-[(2S,3R)-2-[(2,3'-difluoro[1,1'-biphenyl]-3-yl)methyl]-1-(3,3-difluorocyclobutane-1-carbonyl)-4,4-difluoropyrrolidin-3-yl]-ethanesulfonamide | 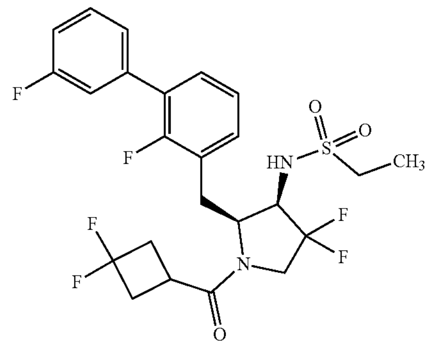 [SMILES: CCS(=O)(=O)N[C@@H]1[C@H](Cc2cccc(-c3cccc(F)c3)c2F)N(C(=O)C2CC(F)(F)C2)CC1(F)F] | | 533.3 |
| 219 | N-{(2S,3R)-1-(3,3-difluoroazetidine-1-carbonyl)-2-[(2,3'-difluoro[1,1'-biphenyl]-3-yl)methyl]-4,4-difluoropyrrolidin-3-yl}ethanesulfonamide | 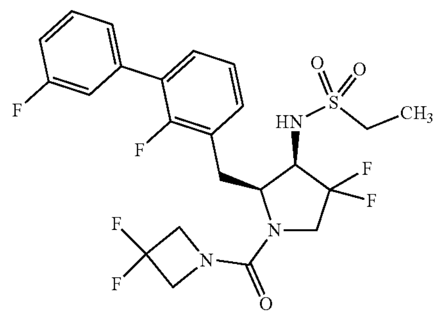 [SMILES: CCS(=O)(=O)N[C@@H]1[C@H](Cc2cccc(-c3cccc(F)c3)c2F)N(C(=O)N2CC(F)(F)C2)CC1(F)F] | | 536.4 |
| 220 | N-{(2S,3R,4S)-4-fluoro-1-(2-hydroxy-2-methylpropanoyl)-2-[(2,3',5'-trifluoro[1,1'-biphenyl]-3-yl)methyl]pyrrolidin-3-yl}-ethanesulfonamide | 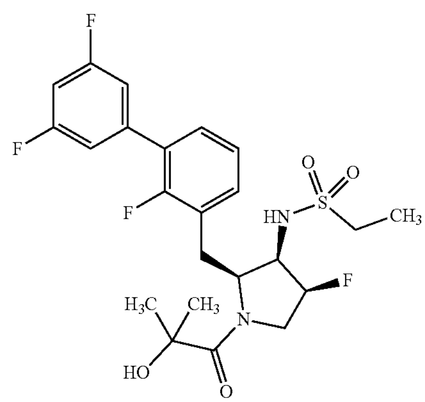 [SMILES: CCS(=O)(=O)N[C@H]1[C@@H](F)CN(C(=O)C(C)(C)O)[C@H]1Cc1cccc(-c2cc(F)cc(F)c2)c1F] | | 503.4 |
| 221 | N-{(2S,3R,4S)-4-fluoro-1-{2-hydroxy-2-methylpropanoyl)-2-[(2,2',5'-trifluoro[1,1'-biphenyl]-3-yl)methyl]pyrrolidin-3-yl}-ethanesulfonamide | 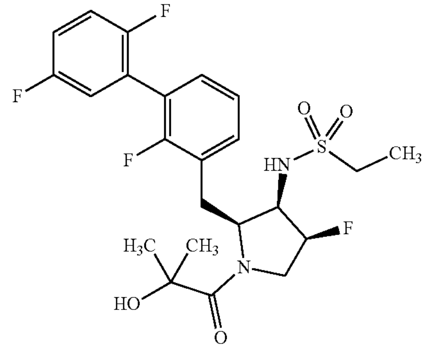 [SMILES: CCS(=O)(=O)N[C@H]1[C@@H](F)CN(C(=O)C(C)(C)O)[C@H]1Cc1cccc(-c2cc(F)ccc2F)c1F] | | 503.4 |

TABLE 1-1-continued

| EX. | IUPAC NAME | Structure | ADDITIVE | MS |
|---|---|---|---|---|
| 222 | N-{(2S,3R,4S)-4-fluoro-1-(2-hydroxy-2-methylpropanoyl)-2-[{2,2',3'-trifluoro[1,1'-biphenyl]-3-yl}methyl]pyrrolidin-3-yl}-ethanesulfonamide | 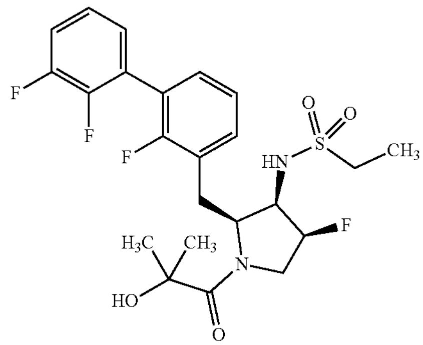 [SMILES: CCS(=O)(=O)N[C@H]1[C@@H](F)CN(C(=O)C(C)(C)O)[C@H]1Cc1cccc(-c2cccc(F)c2F)c1F] | | 503.4 |
| 223 | N-{(2S,3R)-1-(cyclobutanecarbonyl)-4,4-difluoro-2-[(2-fluoro[1,1'-biphenyl]-3-yl)methyl]pyrrolidin-3-yl}ethanesulfonamide | 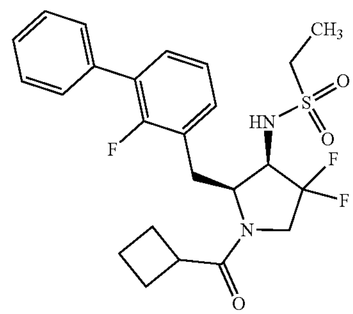 [SMILES: CCS(=O)(=O)N[C@@H]1[C@H](Cc2cccc(-c3ccccc3)c2F)N(C(=O)C2CCC2)CC1(F)F] | | 481.4 |
| 224 | rac-N-{(2S,3R,4S)-4-fluoro-1-(2-hydroxy-2-methylpropanoyl)-4-methyl-2-[(2,3',5'-trifluoro[1,1'-biphenyl]-3-yl)methyl]-pyrrolidin-3-yl}methanesulfonamide | 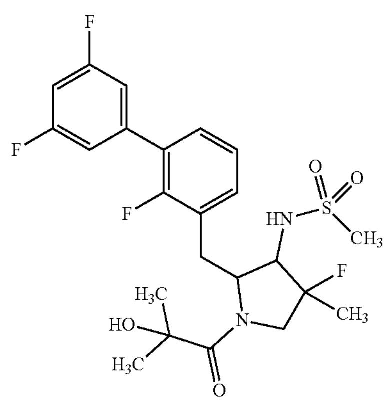 [SMILES: CC(C)(O)C(=O)N1CC(C)(F)C(NS(C)(=O)=O)C1Cc1cccc(-c2cc(F)cc(F)c2)c1F] | | 503.4 |
| 225 | N-[(2S,3R)-2-[(2,3'-difluoro[1,1'-biphenyl]-3-yl)methyl]-4,4-difluoro-1-((1r,3S)-3-fluorocyclobutane-1-carbonyl)pyrrolidin-3-yl]ethanesulfonamide | 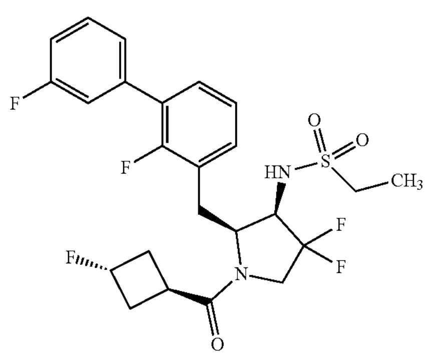 [SMILES: CCS(=O)(=O)N[C@@H]1[C@H](Cc2cccc(-c3cccc(F)c3)c2F)N(C(=O)[C@H]2C[C@H](F)C2)CC1(F)F] | | 515.2 |

TABLE 1-1-continued

| EX. | IUPAC NAME | Structure | ADDITIVE | MS |
|---|---|---|---|---|
| 226 | N-[(2S,3R)-2-[(2,3'-difluoro[1,1'-biphenyl]-3-yl)methyl]-4,4-difluoro-1-((1s,3R)-3-fluorocyclobutane-1-carbonyl)pyrrolidin-3-yl]ethanesulfonamide | 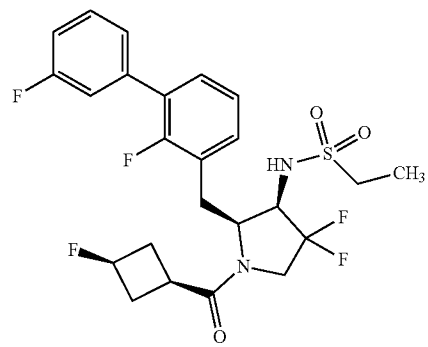 [SMILES: CCS(=O)(=O)N[C@@H]1[C@H](Cc2cccc(-c3cccc(F)c3)c2F)N(C(=O)[C@H]2C[C@@H](F)C2)CC1(F)F] | | 515.2 |
| 227 | (2S,3R)-3-[(ethanesulfonyl)amino]-4,4-difluoro-2-[(2-fluoro[1,1'-biphenyl]-3-yl)methyl]-N,N-dimethylpyrrolidine-1-carboxamide | 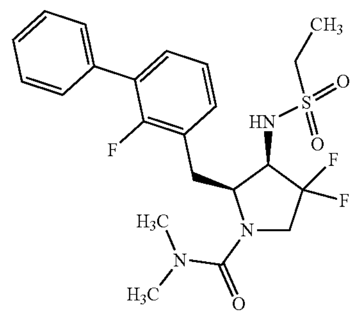 [SMILES: CCS(=O)(=O)N[C@@H]1[C@H](Cc2cccc(-c3ccccc3)c2F)N(C(=O)N(C)C)CC1(F)F] | | 470.4 |
| 228 | N-{(2S,3R)-1-(azetidine-1-carbonyl)-4,4-difluoro-2-[(2-fluoro[1,1'-biphenyl]-3-yl)methyl]pyrrolidin-3-yl}ethanesulfonamide | 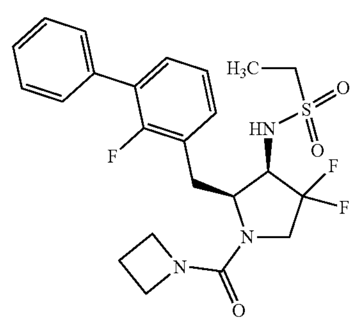 [SMILES: CCS(=O)(=O)N[C@@H]1[C@H](Cc2cccc(-c3ccccc3)c2F)N(C(=O)N2CCC2)CC1(F)F] | | 482.4 |
| 229 | N-[(2S,3R,4S)-4-fluoro-2-[(2-fluoro[1,1'-biphenyl]-3-yl)methyl]-1-(2-hydroxy-2-methylpropanoyl)pyrrolidin-3-yl]ethanesulfonamide | 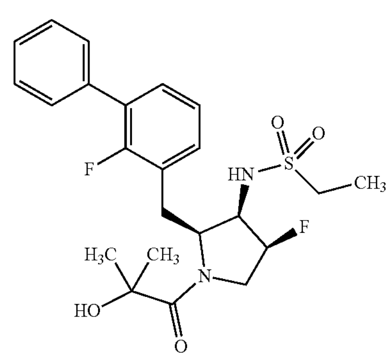 [SMILES: CCS(=O)(=O)N[C@H]1[C@@H](F)CN(C(=O)C(C)(C)O)[C@H]1Cc1cccc(-c2ccccc2)c1F] | | 467.4 |

TABLE 1-1-continued

| EX. | IUPAC NAME | Structure | ADDITIVE | MS |
|---|---|---|---|---|
| 230 | N-[(2S,3R,4S)-2-[(2,2'-difluoro[1,1'-biphenyl]-3-yl)methyl]-4-fluoro-1-(2-hydroxy-2-methylpropanoyl)pyrrolidin-3-yl]ethanesulfonamide | 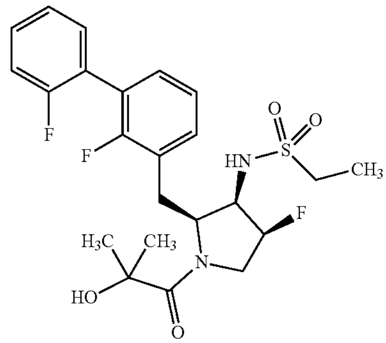 [SMILES: CCS(=O)(=O)N[C@H]1[C@@H](F)CN(C(=O)C(C)(C)O)[C@H]1Cc1cccc(-c2ccccc2F)c1F] | | 485.5 |
| 231 | N-{(2S,3R,4S)-1-(bicyclo[1.1.1]pentane-1-carbonyl)-2-[(2,3'-difluoro[1,1'-biphenyl]-3-yl)methyl]-4-fluoropyrrolidin-3-yl}-methanesulfonamide | 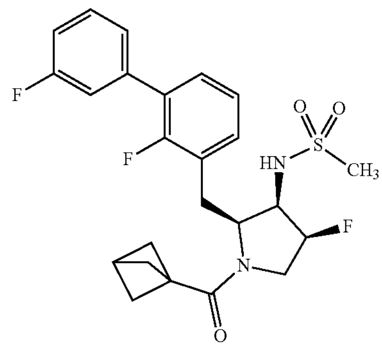 [SMILES: CS(=O)(=O)N[C@H]1[C@@H](F)CN(C(=O)C23CC(C2)C3)[C@H]1Cc1cccc(-c2cccc(F)c2)c1F] | | 479.4 |
| 232 | N-[(2S,3R,4S)-2-[(2,3'-difluoro[1,1'-biphenyl]-3-yl)methyl]-4-fluoro-1-(2-methylpropanoyl)pyrrolidin-3-yl]-methanesulfonamide | 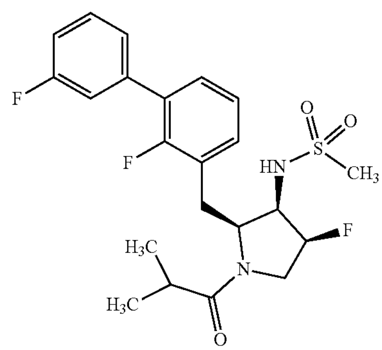 [SMILES: CC(C)C(=O)N1C[C@H](F)[C@H](NS(C)(=O)=O)[C@@H]1Cc1cccc(-c2cccc(F)c2)c1F] | | 455.4 |
| 233 | N-{(2S,3R,4S)-1-(cyclopropanecarbonyl)-2-[(2,3'-difluoro[1,1'-biphenyl]-3-yl)-methyl]-4-fluoropyrrolidin-3-yl}methane-sulfonamide | 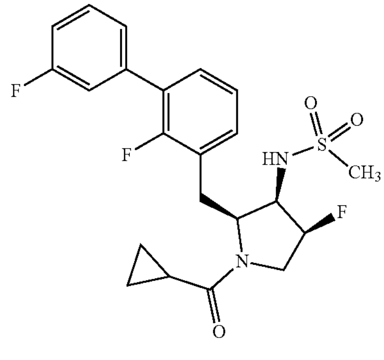 [SMILES: CS(=O)(=O)N[C@H]1[C@@H](F)CN(C(=O)C2CC2)[C@H]1Cc1cccc(-c2cccc(F)c2)c1F] | | 453.4 |

TABLE 1-1-continued

| EX. | IUPAC NAME | Structure | ADDITIVE | MS |
|---|---|---|---|---|
| 234 | (2S,3R)-3-[(ethanesulfonyl)amino]-4,4-difluoro-2-[(2-fluoro[1,1'-biphenyl]-3-yl)methyl]-N-methoxy-N-methylpyrrolidin-1-carboxamide | 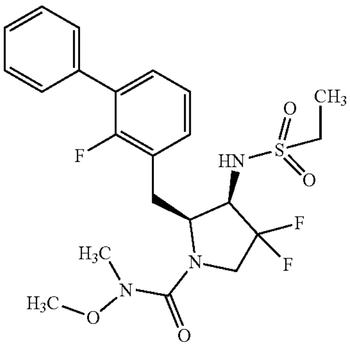 [SMILES: CCS(=O)(=O)N[C@@H]1[C@H](Cc2cccc(-c3ccccc3)c2F)N(C(=O)N(C)OC)CC1(F)F] | | 486.4 |
| 235 | N-[(2S,3R,4S)-2-[(2,3',-difluoro[1,1'-biphenyl]-3-yl)methyl]-4-fluoro-1-(2-hydroxy-2-methylpropanoyl)pyrrolidin-3-yl]methanesulfonamide | 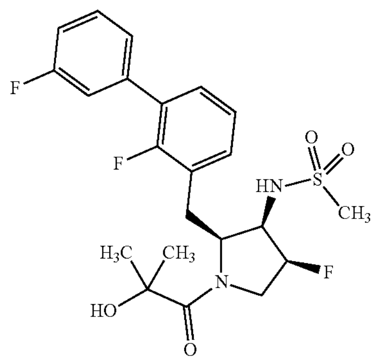 [SMILES: CC(C)(O)C(=O)N1C[C@H](F)[C@H](NS(C)(=O)=O)[C@@H]1Cc1cccc(-c2cccc(F)c2)c1F] | | 471.4 |
| 236 | N-{(2S,3R,4S)-1-(cyclopropanecarbonyl)-4-fluoro-2-[(2,3',5'-trifluoro[1,1'-biphenyl]-3-yl)methyl]pyrrolidin-3-yl}ethanesulfonamide | 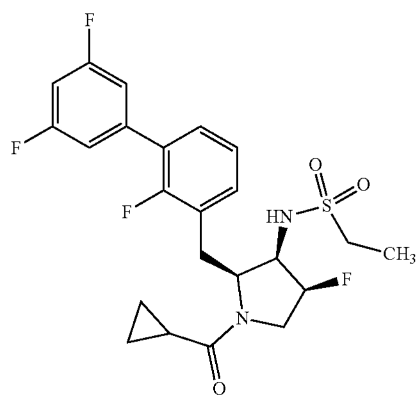 [SMILES: CCS(=O)(=O)N[C@H]1[C@@H](F)CN(C(=O)C2CC2)[C@H]1Cc1cccc(-c2cc(F)cc(F)c2)c1F] | | 485.4 |
| 237 | N-{(2S,3R,4S)-1-(cyclopropanecarbonyl)-4-fluoro-2-[(2,2',3'-trifluoro[1,1'-biphenyl]-3-yl)methyl]pyrrolidin-3-yl}ethanesulfonamide | 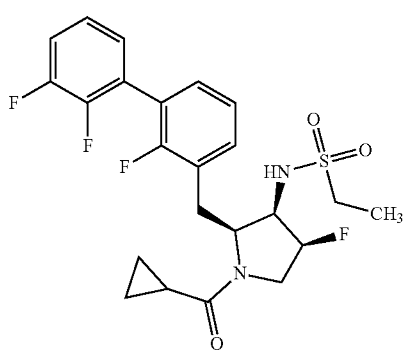 [SMILES: CCS(=O)(=O)N[C@H]1[C@@H](F)CN(C(=O)C2CC2)[C@H]1Cc1cccc(-c2cccc(F)c2F)c1F] | | 485.4 |

TABLE 1-1-continued

| EX. | IUPAC NAME | Structure | ADDITIVE | MS |
|---|---|---|---|---|
| 238 | N-{(2S,3R,4S)-1-(cyclopropanecarbonyl)-4-fluoro-2-[(2,2',5'-trifluoro[1,1'-biphenyl]-3-yl)methyl]pyrrolidin-3-yl}ethanesulfonamide | 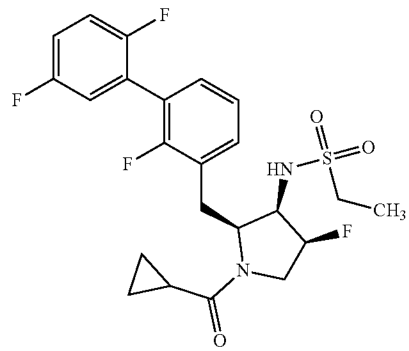 [SMILES: CCS(=O)(=O)N[C@H]1[C@@H](F)CN(C(=O)C2CC2)[C@H]1Cc1cccc(-c2cc(F)ccc2F)c1F] | | 485.4 |
| 239 | N-{(2S,3R,4S)-1-(cyclopropanecarbonyl)-4-fluoro-2-[(2-fluoro[1,1'-biphenyl]-3-yl)methyl]pyrrolidin-3-yl}ethanesulfonamide | 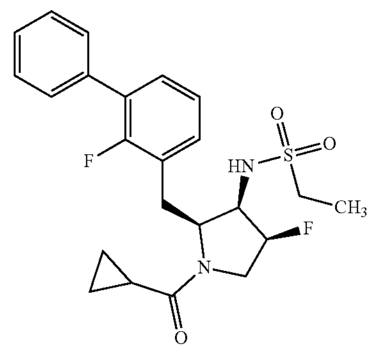 [SMILES: CCS(=O)(=O)N[C@H]1[C@@H](F)CN(C(=O)C2CC2)[C@H]1Cc1cccc(-c2ccccc2)c1F] | | 449.4 |
| 240 | N-{(2S,3R,4S)-4-fluoro-1-(2-hydroxy-2-methylpropanoyl)-2-[(2,3',5'-trifluoro[1,1'-biphenyl]-3-yl)methyl]pyrrolidin-3-yl}-methanesulfonamide | 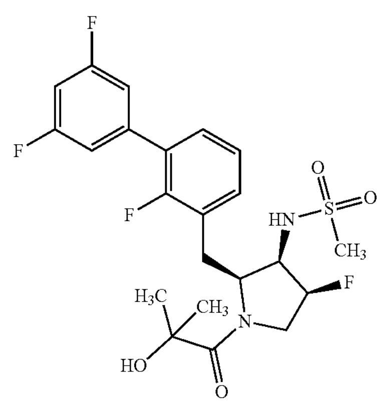 [SMILES: CC(C)(O)C(=O)N1C[C@H](F)[C@H](NS(C)(=O)=O)[C@@H]1Cc1cccc(-c2cc(F)cc(F)c2)c1F] | | 489.3 |
| 241 | N-{(2S,3R,4S)-4-fluoro-1-(2-hydroxy-2-methylpropanoyl)-2-[(2,2',3',-trifluoro[1,1'-biphenyl]-3-yl)methyl]pyrrolidin-3-yl}-methanesulfonamide | 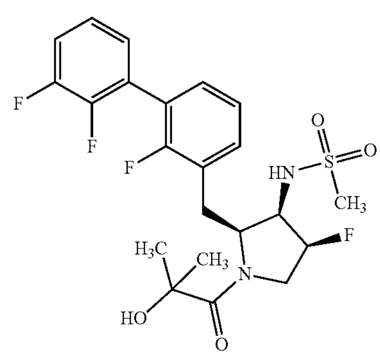 [SMILES: CC(C)(O)C(=O)N1C[C@H](F)[C@H](NS(C)(=O)=O)[C@@H]1Cc1cccc(-c2cccc(F)c2F)c1F] | | 489.4 |

TABLE 1-1-continued

| EX. | IUPAC NAME | Structure | ADDITIVE | MS |
|---|---|---|---|---|
| 242 | N-{(2S,3R,4S)-4-fluoro-1-(2-hydroxy-2-methylpropanoyl)-2-[(2,2',5'-trifluoro[1,1'-biphenyl]-3-yl)methyl]pyrrolidin-3-yl}-methanesulfonamide | 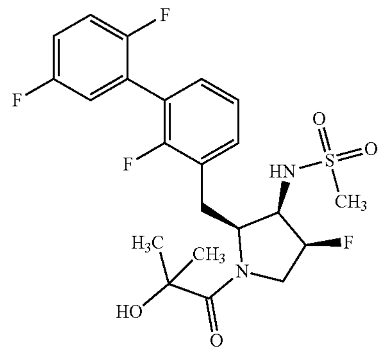 [SMILES: CC(C)(O)C(=O)N1C[C@H](F)[C@H](NS(C)(=O)=O)[C@@H]1Cc1cccc(-c2cc(F)ccc2F)c1F] | | 489.4 |
| 243 | N-[(2S,3R,4S)-4-fluoro-2-[(2-fluoro[1,1'-biphenyl]-3-yl)methyl]-1-(2-hydroxy-2-methylpropanoyl)pyrrolidin-3-yl]-methanesulfonamide | 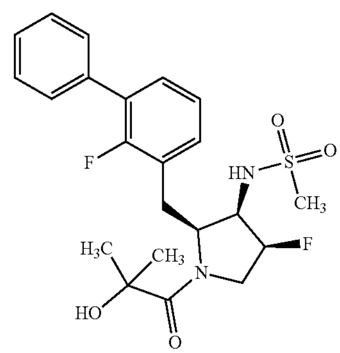 [SMILES: CC(C)(O)C(=O)N1C[C@H](F)[C@H](NS(C)(=O)=O)[C@@H]1Cc1cccc(-c2ccccc2)c1F] | | 453.4 |
| 244 | N-[(2S,3R,4S)-2-[(2,2,-difluoro[1,1'-biphenyl]-3-yl)methyl]-4-fluoro-1-(2-hydroxy-2-methylpropanoyl)pyrrolidin-3-yl]methanesulfonamide | 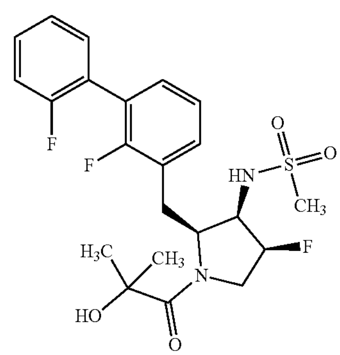 [SMILES: CC(C)(O)C(=O)N1C[C@H](F)[C@H](NS(C)(=O)=O)[C@@H]1Cc1cccc(-c2ccccc2F)c1F] | | 471.4 |
| 245 | N-[(2S,3R)-2-[(3'-chloro-2,5'-difluoro[1,1'-biphenyl]-3-yl)methyl]-1-(cyclopropane-carbonyl)-4,4-difluoropyrrolidin-3-yl]-methanesulfonamide | 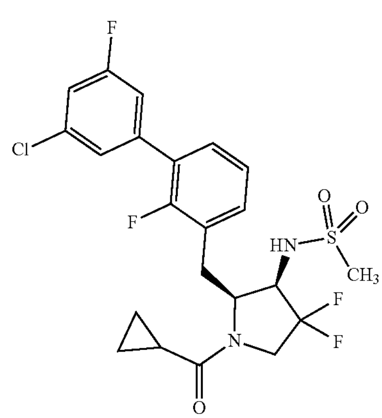 [SMILES: CS(=O)(=O)N[C@@H]1[C@H](Cc2cccc(-c3cc(F)cc(Cl)c3)c2F)N(C(=O)C2CC2)CC1(F)F] | | 503.1 |

TABLE 1-1-continued

| EX. | IUPAC NAME | Structure | ADDITIVE | MS |
|---|---|---|---|---|
| 246 | N-[(2S,3R)-4,4-difluoro-2-{[2-fluoro-3-{6-methylpyridin-2-yl)phenyl]methyl}-1-(1-methylcyclopropane-1-carbonyl)pyrrolidin-3-yl]ethanesulfonamide | 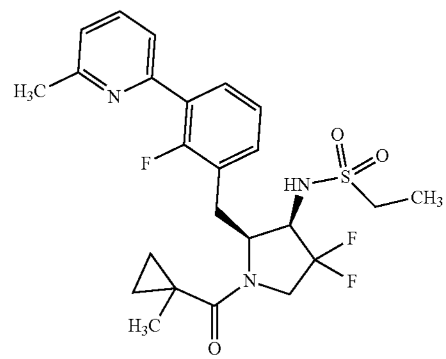 | | 496.2 |
| 247 | N-[(2S,3R)-4,4-difluoro-2-{[2-fluoro-3-(4-methylpyridin-2-yl)phenyl]methyl}-1-(1-methylcyclopropane-1-carbonyl)pyrrolidin-3-yl]ethanesulfonamide | 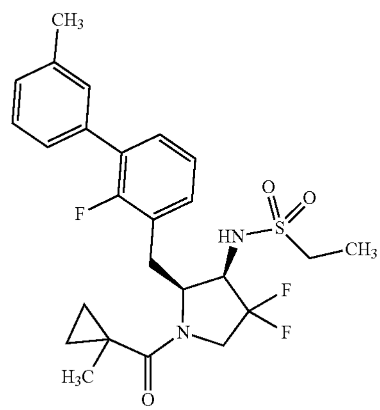 [SMILES: CCS(=O)(=O)N[C@@H]1[C@H](Cc2cccc(-c3cccc(C)c3)c2F)N(C(=O)C2(C)CC2)CC1(F)F] | | 496.1 |
| 248 | N-[(2S,3R)-2-[(3'-chloro-2,5'-difluoro[1,1'-biphenyl]-3-yl)methyl]-1-(cyclopropane-carbonyl)-4,4-difluoropyrrolidin-3-yl]-ethanesulfonamide | 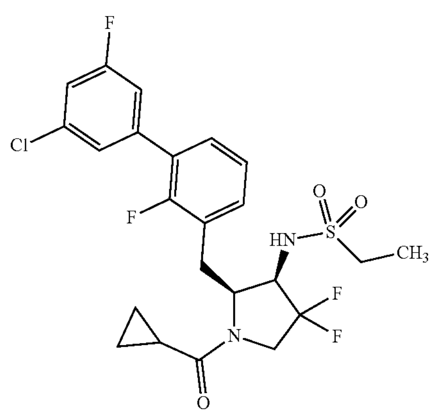 [SMILES: CCS(=O)(=O)N[C@@H]1[C@H](Cc2cccc(-c3cc(F)cc(Cl)c3)c2F)N(C(=O)C2CC2)CC1(F)F] | | 519.1 |
| 249 | N-[(2S,3R)-2-[(3'-chloro-2,2'-difluoro[1,1'-biphenyl]-3-yl)methyl]-1-(cyclopropane-carbonyl-4,4-difluoropyrrolidin-3-yl]-ethanesulfonamide | 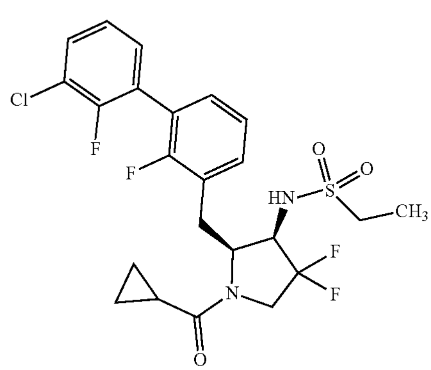 [SMILES: CCS(=O)(=O)N[C@@H]1[C@H](Cc2cccc(-c3cccc(Cl)c3F)c2F)N(C(=O)C2CC2)CC1(F)F] | | 519.1 |

TABLE 1-1-continued

| EX. | IUPAC NAME | Structure | ADDITIVE | MS |
|---|---|---|---|---|
| 250 | N-[(2S,3R)-2-[(3'-chloro-2-fluoro[1,1'-biphenyl]-3-yl)methyl]-1-(cyclopropane-carbonyl)-4,4-difluoropyrrolidin-3-yl]-methanesulfonamide | 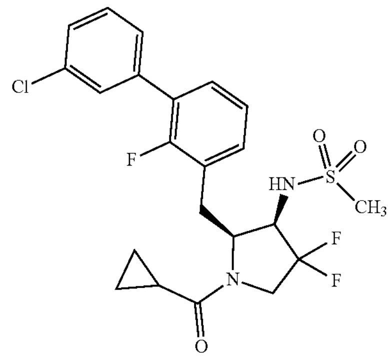 [SMILES: CS(=O)(=O)N[C@@H]1[C@H](Cc2cccc(-c3cccc(Cl)c3)c2F)N(C(=O)C2CC2)CC1(F)F] | | 487.1 |
| 251 | N-[(2S,3R)-2-[(5,-chloro-2,2'-difluoro[1,1'-biphenyl]-3-yl)methyl]-1-(cyclopropane-carbonyl)-4,4-difluoropyrrolidin-3-yl]-ethanesulfonamide | 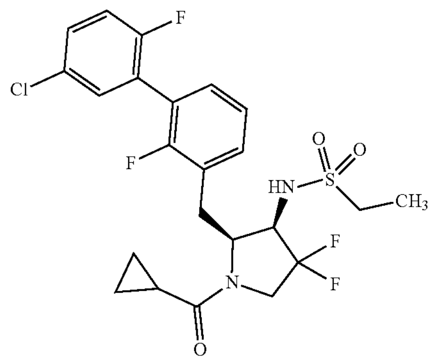 [SMILES: CCS(=O)(=O)N[C@@H]1[C@H](Cc2cccc(-c3cc(Cl)ccc3F)c2F)N(C(=O)C2CC2)CC1(F)F] | | 519.1 |
| 252 | N-[(2S,3R)-2-[(5'-chloro-2,2'-difluoro[1,1'-biphenyl]-3-yl)methyl]-1-(cyclopropane-carbonyl)-4,4-difluoropyrrolidin-3-yl]-methanesulfonamide | 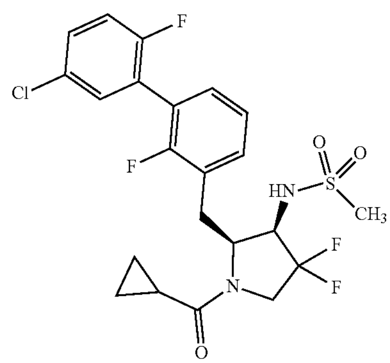 [SMILES: CS(=O)(=O)N[C@@H]1[C@H](Cc2cccc(-c3cc(Cl)ccc3F)c2F)N(C(=O)C2CC2)CC1(F)F] | | 505.1 |
| 253 | N-[(2S,3R)-2-[(3'-chloro-2,2'-difluoro[1,1'-biphenyl]-3-yl)methyl]-1-(cyclopropane-carbonyl)-4,4-difluoropyrrolidin-3-yl]-methanesulfonamide | 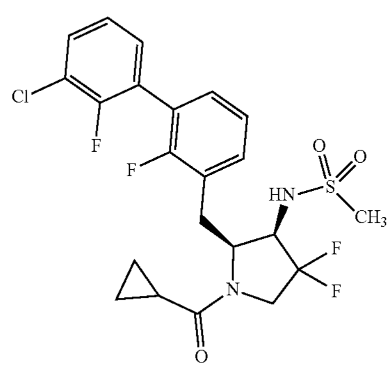 [SMILES: CS(=O)(=O)N[C@@H]1[C@H](Cc2cccc(-c3cccc(Cl)c3F)c2F)N(C(=O)C2CC2)CC1(F)F] | | 505.1 |

TABLE 1-1-continued

| EX. | IUPAC NAME | Structure | ADDITIVE | MS |
|---|---|---|---|---|
| 254 | N-[(2S,3R)-2-[(3'-chloro-2-fluoro[1,1'-biphenyl]-3-yl)methyl]-1-(cyclopropane-carbonyl)-4,4-difluoropyrrolidin-3-yl]-ethanesulfonamide | 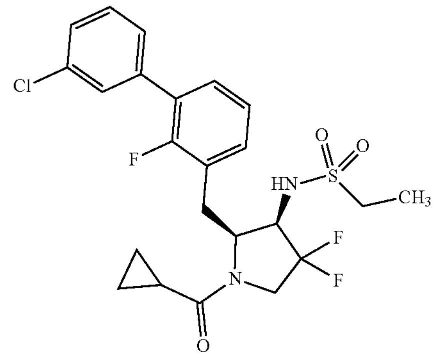 [SMILES: CCS(=O)(=O)N[C@@H]1[C@H](Cc2cccc(-c3cccc(Cl)c3)c2F)N(C(=O)C2CC2)CC1(F)F] | | 501.1 |
| 255 | N-[(2S,3R)-2-{[3-(4,6-dimethylpyrimidin-2-yl)-2-fluorophenyl]methyl}-4,4-difluoro-1-(1-methylcyclopropane-1-carbonyl)-pyrrolidin-3-yl]ethanesulfonamide | 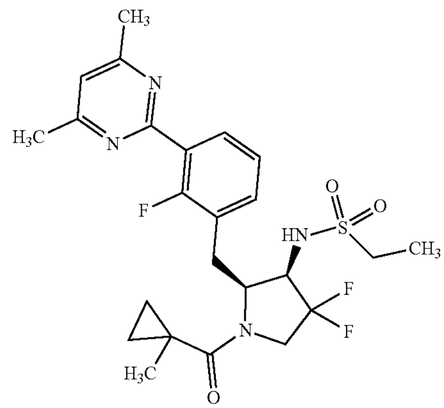 [SMILES: CCS(=O)(=O)N[C@@H]1[C@H](Cc2cccc(-c3nc(C)cc(C)n3)c2F)N(C(=O)C2(C)CC2)CC1(F)F] | | 511.2 |
| 256 | ethyl(2S,3R)-2-[(2,3'-difluoro[1,1'-biphenyl]-3-yl)methyl]-3-[(ethanesulfonyl)-amino]-4,4-difluoropyrrolidine-1-carboxylate | 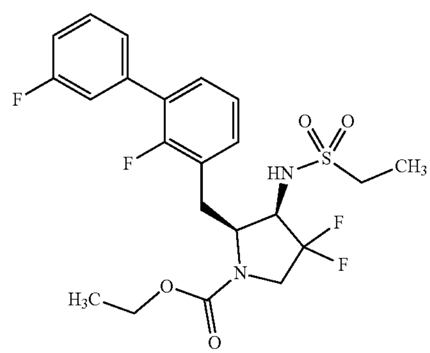 [SMILES: CCOC(=O)N1CC(F)(F)[C@H](NS(=O)(=O)CC)[C@@H]1Cc1cccc(-c2cccc(F)c2)c1F] | | 487.2 |
| 257 | N-{(2S,3R)-1-butanoyl-2-[(2,3'-difluoro-[1,1'-biphenyl]-3-yl)methyl]-4,4-difluoro-pyrrolidin-3-yl}ethanesulfonamide | 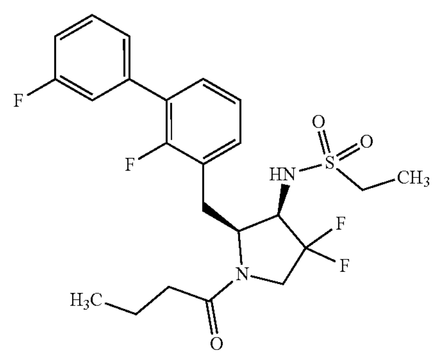 [SMILES: CCCC(=O)N1CC(F)(F)[C@H](NS(=O)(=O)CC)[C@@H]1Cc1cccc(-c2cccc(F)c2)c1F] | | 487.4 |

TABLE 1-1-continued

| EX. | IUPAC NAME | Structure | ADDITIVE | MS |
|---|---|---|---|---|
| 258 | N-{(2S,3R)-1-(2-cyano-2-methylpropanoyl)-2-[(2,3'-difluoro[1,1'-biphenyl]-3-yl)methyl]-4,4-difluoropyrrolidin-3-yl}ethanesulfonamide | 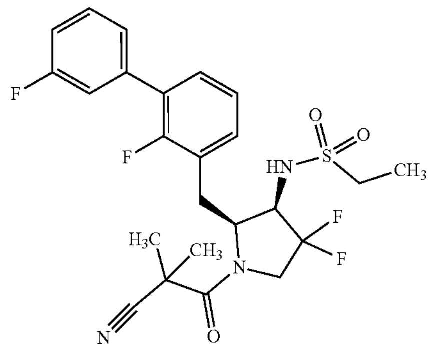 [SMILES: CCS(=O)(=O)N[C@@H]1[C@H](Cc2cccc(-c3cccc(F)c3)c2F)N(C(=O)C(C)(C)C#N)CC1(F)F] | | 510.2 |
| 259 | N-[(2S,3R)-2-[(3'-chloro-2-fluoro[1,1'-biphenyl]-3-yl)methyl]-4,4-difluoro-1-(oxetane-2-carbonyl)pyrrolidin-3-yl]methanesulfonamide with shorter retention time | 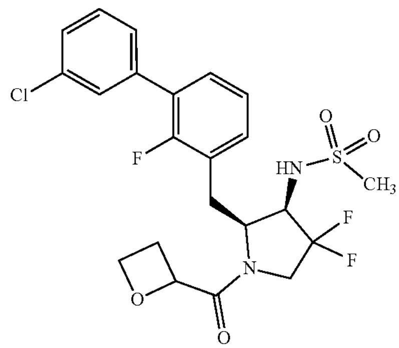 [SMILES: CS(=O)(=O)N[C@@H]1[C@H](Cc2cccc(-c3cccc(Cl)c3)c2F)N(C(=O)C2CCO2)CC1(F)F] | | 503.4 |
| 260 | N-[(2S,3R)-2-[(3'-chloro-2-fluoro[1,1'-biphenyl]-3-yl)methyl]-4,4-difluoro-1-(oxetane-2-carbonyl)pyrrolidin-3-yl]methanesulfonamide with longer retention time | 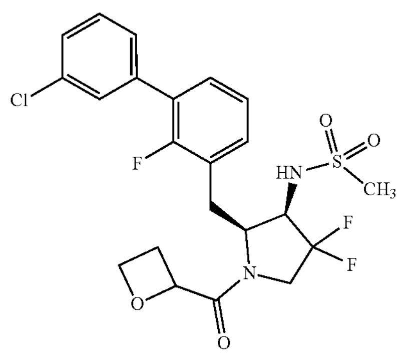 [SMILES: CS(=O)(=O)N[C@@H]1[C@H](Cc2cccc(-c3cccc(Cl)c3)c2F)N(C(=O)C2CCO2)CC1(F)F] | | 503.4 |
| 261 | N-[(2S,3R)-2-[(5'-chloro-2,2'-difluoro[1,1'-biphenyl]-3-yl)methyl]-4,4-difluoro-1-(oxetane-2-carbonyl)pyrrolidin-3-yl]methanesulfonamide with shorter retention time | 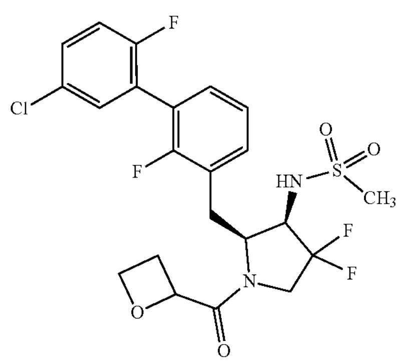 [SMILES: CS(=O)(=O)N[C@@H]1[C@H](Cc2cccc(-c3cc(Cl)ccc3F)c2F)N(C(=O)C2CCO2)CC1(F)F] | | 521.3 |

TABLE 1-1-continued

| EX. | IUPAC NAME | Structure | ADDITIVE | MS |
|---|---|---|---|---|
| 262 | N-[(2S,3R)-2-[(5'-chloro-2,2'-difluoro[1,1'-biphenyl]-3-yl)methyl]-4,4-difluoro-1-(oxetane-2-carbonyl)pyrrolidin-3-yl]-methanesulfonamide with longer retention time | 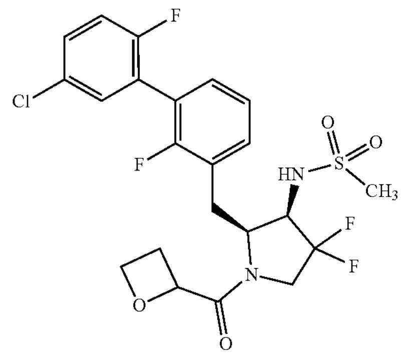 [SMILES: CS(=O)(=O)N[C@@H]1[C@H](Cc2cccc(-c3cc(Cl)ccc3F)c2F)N(C(=O)C2CCO2)CC1(F)F] | | 521.3 |
| 263 | N-[(2S,3R)-2-[(3'-chloro-2,2'-difluoro[1,1'-biphenyl]-3-yl)methyl]-4,4-difluoro-1-(oxetane-2-carbonyl)pyrrolidin-3-yl]-methanesulfonamide with shorter retention time | 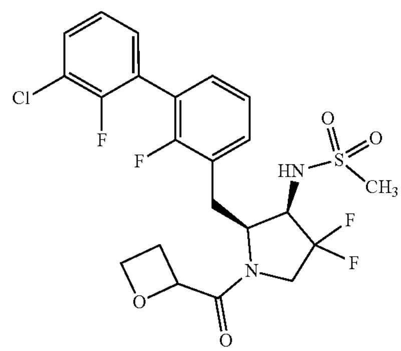 [SMILES: CS(=O)(=O)N[C@@H]1[C@H](Cc2cccc(-c3cccc(Cl)c3F)c2F)N(C(=O)C2CCO2)CC1(F)F] | | 521.3 |
| 264 | N-[(2S,3R)-2-[(3'-chloro-2,2,-difluoro[1,1'-biphenyl]-3-yl)methyl]-4,4-difluoro-1-(oxetane-2-carbonyl)pyrrolidin-3-yl]-methanesulfonamide with longer retention time | 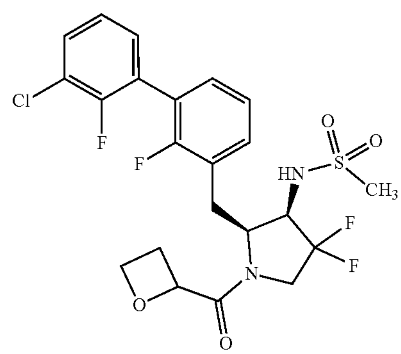 [SMILES: CS(=O)(=O)N[C@@H]1[C@H](Cc2cccc(-c3cccc(Cl)c3F)c2F)N(C(=O)C2CCO2)CC1(F)F] | | 521.3 |
| 265 | N-[(2S,3R)-2-[(3'-chloro-2,5'-difluoro[1,1'-biphenyl]-3-yl)methyl]-4,4-difluoro-1-(oxetane-2-carbonyl)pyrrolidin-3-yl]-methanesulfonamide with shorter retention time | 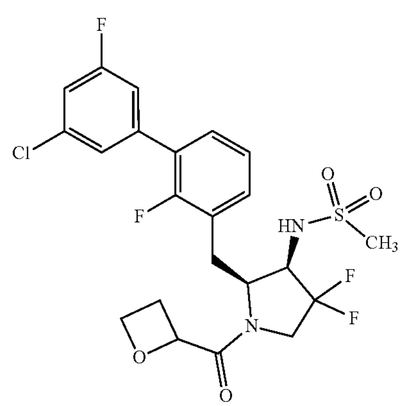 [SMILES: CS(=O)(=O)N[C@@H]1[C@H](Cc2cccc(-c3cc(F)cc(Cl)c3)c2F)N(C(=O)C2CCO2)CC1(F)F] | | 521.3 |

TABLE 1-1-continued

| EX. | IUPAC NAME | Structure | ADDITIVE | MS |
|---|---|---|---|---|
| 266 | N-[(2S,3R)-2-[(3'-chloro-2,5'-difluoro[1,1'-biphenyl]-3-yl)methyl]-4,4-difluoro-1-(oxetane-2-carbonyl)pyrrolidin-3-yl]-methanesulfonamide with longer retention time | 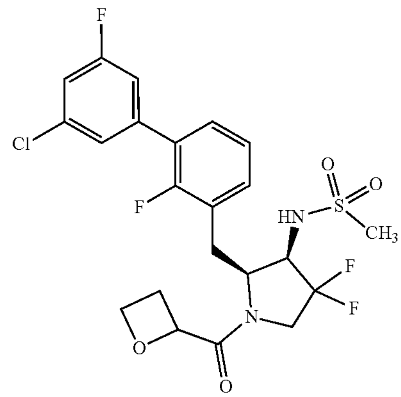 [SMILES: CS(=O)(=O)N[C@@H]1[C@H](Cc2cccc(-c3cc(F)cc(Cl)c3)c2F)N(C(=O)C2CCO2)CC1(F)F] | | 521.3 |
| 267 | N-[(2S,3R)-2-[(3'-chloro-2-fluoro[1,1'-biphenyl]-3-yl)methyl]-4,4-difluoro-1-(oxetane-2-carbonyl)pyrrolidin-3-yl]-ethanesulfonamide with shorter retention time | 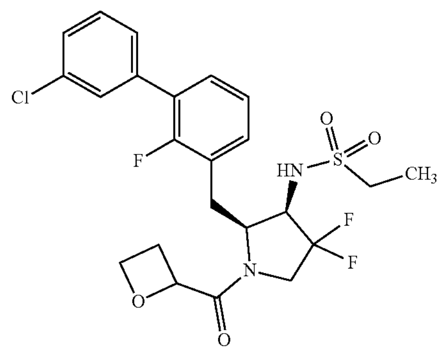 [SMILES: CCS(=O)(=O)N[C@@H]1[C@H](Cc2cccc(-c3cccc(Cl)c3)c2F)N(C(=O)C2CCO2)CC1(F)F] | | 517.4 |
| 268 | N-[(2S,3R)-2-[(3'-chloro-2-fluoro[1,1'-biphenyl]-3-yl)methyl]-4,4-difluoro-1-(oxetane-2-carbonyl)pyrrolidin-3-yl]-ethanesulfonamide with longer retention time | 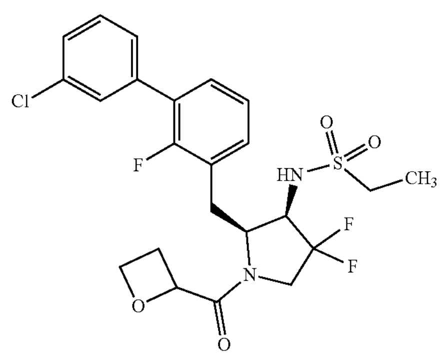 [SMILES: CCS(=O)(=O)N[C@@H]1[C@H](Cc2cccc(-c3cccc(Cl)c3)c2F)N(C(=O)C2CCO2)CC1(F)F] | | 517.4 |
| 269 | rac-N-[(2S,3R)-2-{[2-(3,5-difluorophenyl)-1,3-thiazol-4-yl]methyl}-4,4-difluoro-1-(2-hydroxy-2-methylpropanoyl)pyrrolidin-3-yl]ethanesulfonamide | 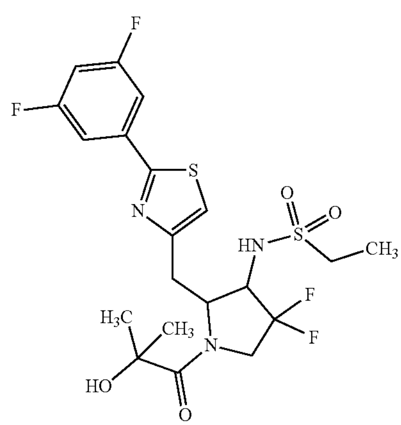 [SMILES: CCS(=O)(=O)NC1C(Cc2csc(-c3cc(F)cc(F)c3)n2)N(C(=O)C(C)(C)O)CC1(F)F] | | 510.2 |

TABLE 1-1-continued

| EX. | IUPAC NAME | Structure | ADDITIVE | MS |
|---|---|---|---|---|
| 270 | rac-N-[(2S,3R)-2-{[2-(3,5-difluorophenyl)-1,3-thiazol-4-yl]methyl}-4,4-difluoro-1-{1-hydroxycyclobutane-1-carbonyl)pyrrolidin-3-yl]ethanesulfonamide | 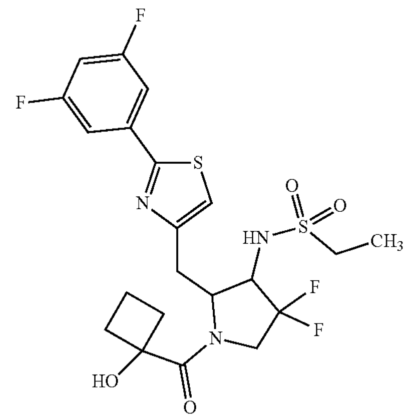 [SMILES: CCS(=O)(=O)NC1C(Cc2csc(-c3cc(F)cc(F)c3)n2)N(C(=O)C2(O)CCC2)CC1(F)F] | | 522.1 |
| 271 | rac-N-{(2S,3R,4R)-4-fluoro-1-(2-hydroxy-2-methylpropanoyl)-4-methyl-2-[(2,3',5'-trifluoro[1,1'-biphenyl]-3-yl)methyl]-pyrrolidin-3-yl}ethanesulfonamide | 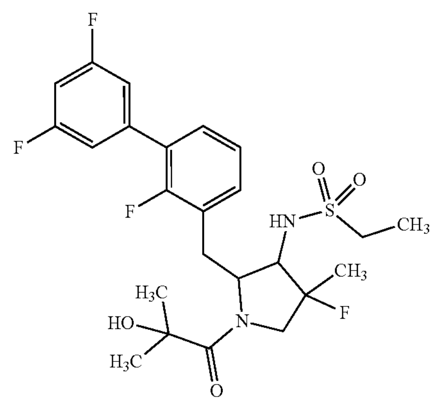 [SMILES: CCS(=O)(=O)NC1C(Cc2cccc(-c3cc(F)cc(F)c3)c2F)N(C(=O)C(C)(C)O)CC1(C)F] | | 517.2 |
| 272 | N-{(2S,3R)-4,4-difluoro-1-(1-hydroxy-cyclobutane-1-carbonyl)-2-[(2,3',5'-trifluoro[1,1'-biphenyl]-3-yl)methyl]-pyrrolidin-3-yl}ethanesulfonamide | 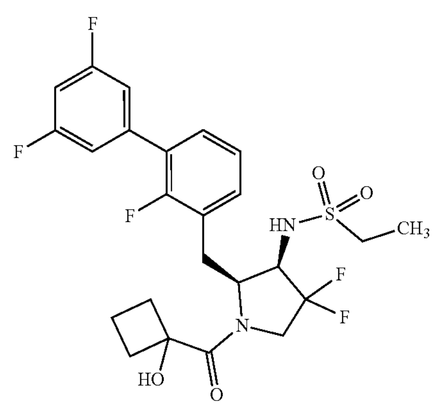 [SMILES: CCS(=O)(=O)N[C@@H]1[C@H](Cc2cccc(-c3cc(F)cc(F)c3)c2F)N(C(=O)C2(O)CCC2)CC1(F)F] | | 531.2 |
| 273 | N-[(2S,3R)-2-[(2,3'-difluoro[1,1'-biphenyl]-3-yl)methyl]-4,4-difluoro-1-(1-hydroxy-cyclobutane-1-carbonyl)pyrrolidin-3-yl]-ethanesulfonamide | 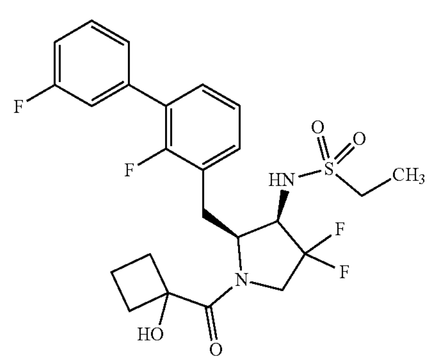 [SMILES: CCS(=O)(=O)N[C@@H]1[C@H](Cc2cccc(-c3cccc(F)c3)c2F)N(C(=O)C2(O)CCC2)CC1(F)F] | | 515.2 |

TABLE 1-1-continued

| EX. | IUPAC NAME | Structure | ADDITIVE | MS |
|---|---|---|---|---|
| 274 | N-{(2S,3R)-4,4-difluoro-1-(1-hydroxy-cyclobutane-1-carbonyl)-2-[(2,2',3'-trifluoro[1,1'-biphenyl]-3-yl)methyl]-pyrrolidin-3-yl]ethanesulfonamide | 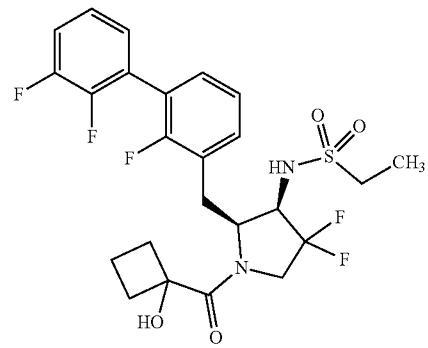 [SMILES: CCS(=O)(=O)N[C@@H]1[C@H](Cc2cccc(-c3cccc(F)c3F)c2F)N(C(=O)C2(O)CCC2)CC1(F)F] | | 533.2 |
| 275 | N-((2S,3R)-4,4-difluoro-2-[(2-fluoro-3'-methyl[1,1'-biphenyl]-3-yl)methyl]-1-(1-hydroxycyclobutane-1-carbonyl)pyrrolidin-3-yl]ethanesulfonamide | 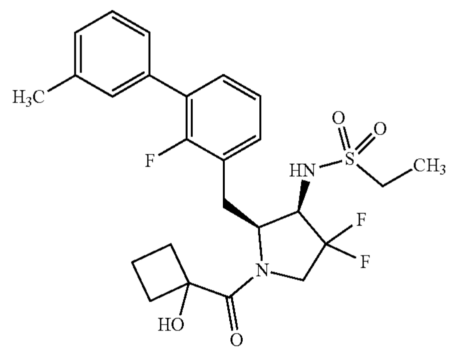 [SMILES: CCS(=O)(=O)N[C@@H]1[C@H](Cc2cccc(-c3cccc(C)c3)c2F)N(C(=O)C2(O)CCC2)CC1(F)F] | | 511.2 |
| 276 | N-[(2S,3R)-2-[(2,2'-difluoro-3'-methyl[1,1'-biphenyl]-3-yl)methyl]-4,4-difluoro-1-(1-hydroxycyclobutane-1-carbonyl)pyrrolidin-3-yl]ethanesulfonamide | 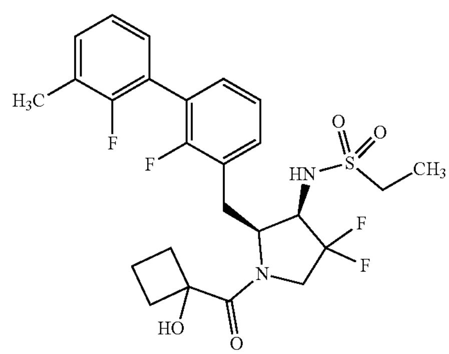 [SMILES: CCS(=O)(=O)N[C@@H]1[C@H](Cc2cccc(-c3cccc(C)c3F)c2F)N(C(=O)C2(O)CCC2)CC1(F)F] | | 529.2 |
| 277 | N-[(2S,3R)-4,4-difluoro-2-[(2-fluoro-3'-methyl[1,1'-biphenyl]-3-yl)methyl]-1-(oxetane-2-carbonyl)pyrrolidin-3-yl]-ethanesulfonamide with shorter retention time | 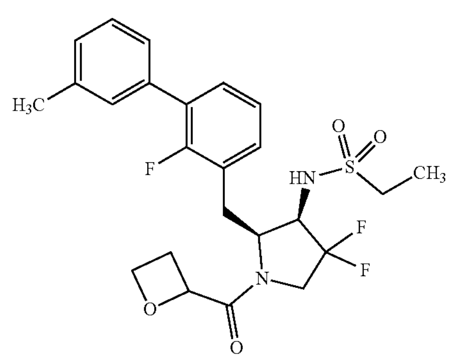 [SMILES: CCS(=O)(=O)N[C@@H]1[C@H](Cc2cccc(-c3cccc(C)c3)c2F)N(C(=O)C2CCO2)CC1(F)F] | | 497.2 |

TABLE 1-1-continued

| EX. | IUPAC NAME | Structure | ADDITIVE | MS |
|---|---|---|---|---|
| 278 | N-[(2S,3R)-2-[(2,2'-difluoro-3'-methyl[1,1'-biphenyl]-3-yl)methyl]-4,4-difluoro-1-(oxetane-2-carbonyl)pyrrolidin-3-yl]-ethanesulfonamide with shorter retention time | 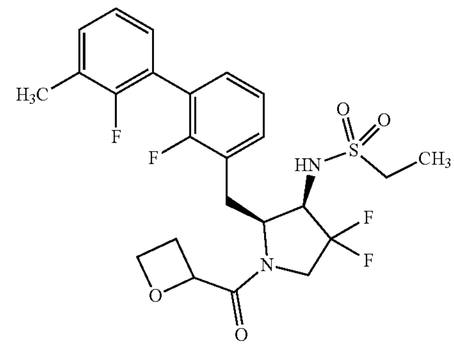 [SMILES: CCS(=O)(=O)N[C@@H]1[C@H](Cc2cccc(-c3cccc(C)c3F)c2F)N(C(=O)C2CCO2)CC1(F)F] | | 515.2 |
| 279 | N-[(2S,3R)-4,4-difluoro-2-[(2-fluoro-3'-methyl[1,1'-biphenyl]-3-yl)methyl]-1-(oxetane-2-carbonyl)pyrrolidin-3-yl]-ethanesulfonamide with longer retention time | 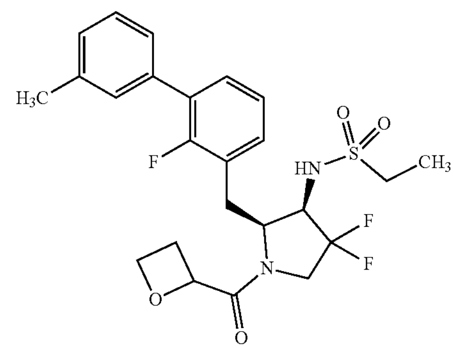 [SMILES: CCS(=O)(=O)N[C@@H]1[C@H](Cc2cccc(-c3cccc(C)c3)c2F)N(C(=O)C2CCO2)CC1(F)F] | | 497.2 |
| 280 | N-[(2S,3R)-2-[(2,2'-difluoro-3'-methyl[1,1'-biphenyl]-3-yl)methyl]-4,4-difluoro-1-(oxetane-2-carbonyl)pyrrolidin-3-yl]-ethanesulfonamide with longer retention time | 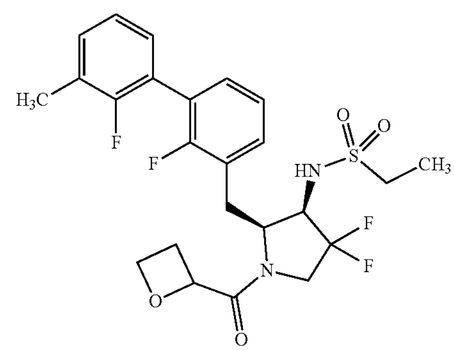 [SMILES: CCS(=O)(=O)N[C@@H]1[C@H](Cc2cccc(-c3cccc(C)c3F)c2F)N(C(=O)C2CCO2)CC1(F)F] | | 515.2 |
| 281 | N-[(2S,3R)-2-{[3-(4,6-dimethylpyridin-2-yl)-2-fluorophenyl]methyl}-4,4-difluoro-1-(1-methylcyclopropane-1-carbonyl)-pyrrolidin-3-yl]ethanesulfonamide | 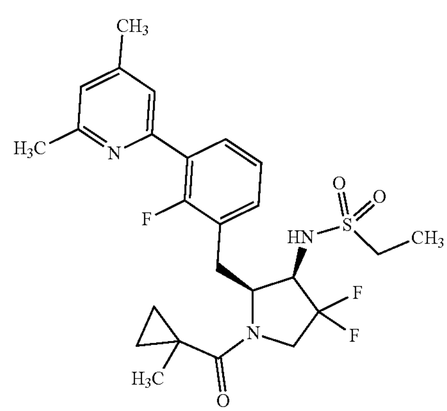 [SMILES: CCS(=O)(=O)N[C@@H]1[C@H](Cc2cccc(-c3cc(C)cc(C)n3)c2F)N(C(=O)C2(C)CC2)CC1(F)F] | | 510.2 |

TABLE 1-1-continued

| EX. | IUPAC NAME | Structure | ADDITIVE | MS |
|---|---|---|---|---|
| 282 | (2S,3R)-3-[(ethanesulfonyl)amino]-4,4-difluoro-N,N-dimethyl-2-[(2,3',5'-trifluoro[1,1'-biphenyl]-3-yl)methyl]-pyrrolidine-1-carboxamide | 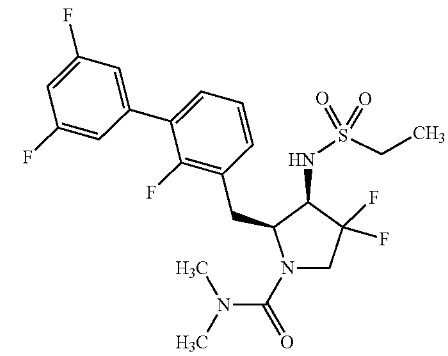 [SMILES: CCS(=O)(=O)N[C@@H]1[C@H](Cc2cccc(-c3cc(F)cc(F)c3)c2F)N(C(=O)N(C)C)CC1(F)F] | | 506.2 |
| 283 | N-{(2S,3R)-1-(azetidine-1-carbonyl)-4,4-difluoro-2-[(2,3',5'-trifluoro[1,1'-biphenyl]-3-yl)methyl]pyrrolidin-3-yl}ethanesulfonamide | 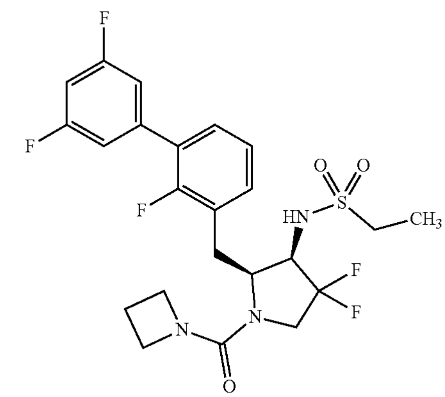 [SMILES: CCS(=O)(=O)N[C@@H]1[C@H](Cc2cccc(-c3cc(F)cc(F)c3)c2F)N(C(=O)N2CCC2)CC1(F)F] | | 518.2 |
| 284 | (2S,3R)-3-[(ethanesulfony)amino]-4,4-difluoro-2-[(2-fluoro-3'-methyl[1,1'-biphenyl]-3-yl)methyl]-N,N-dimethyl-pyrrolidine-1-carboxamide | 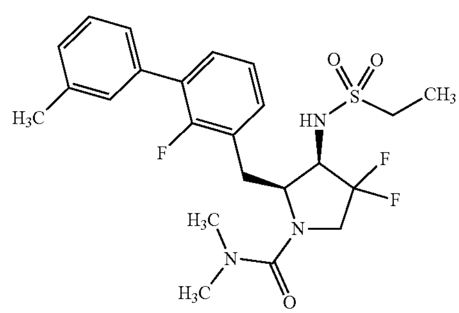 [SMILES: CCS(=O)(=O)N[C@@H]1[C@H](Cc2cccc(-c3cccc(C)c3)c2F)N(C(=O)N(C)C)CC1(F)F] | | 484.2 |
| 285 | N-{(2S,3R)-1-(azetidine-1-carbonyl)-4,4-difluoro-2-[(2-fluoro-3'-methyl[1,1'-biphenyl]-3-yl)methyl]pyrrolidin-3-yl}-ethanesulfonamide | 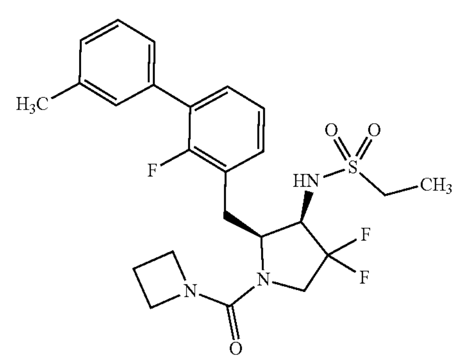 [SMILES: CCS(=O)(=O)N[C@@H]1[C@H](Cc2cccc(-c3cccc(C)c3)c2F)N(C(=O)N2CCC2)CC1(F)F] | | 496.2 |

TABLE 1-1-continued

| EX. | IUPAC NAME | Structure | ADDITIVE | MS |
|---|---|---|---|---|
| 286 | (2S,3R)-2-[(2,3'-difluoro[1,1'-biphenyl]-3-yl)methyl]-3-[(ethanesulfonyl)amino]-4,4-difluoro-N,N-dimethylpyrrolidine-1-carboxamide | 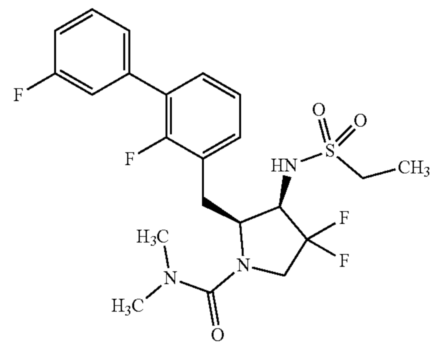 [SMILES: CCS(=O)(=O)N[C@@H]1[C@H](Cc2cccc(-c3cccc(F)c3)c2F)N(C(=O)N(C)C)CC1(F)F] | | 488.2 |
| 287 | N-{(2S,3R)-1-(azetidine-1-carbonyl)-2-[(2,3'-difluoro[1,1'-biphenyl]-3-yl)methyl]-4,4-difluoropyrrolidin-3-yl}ethanesulfonamide | 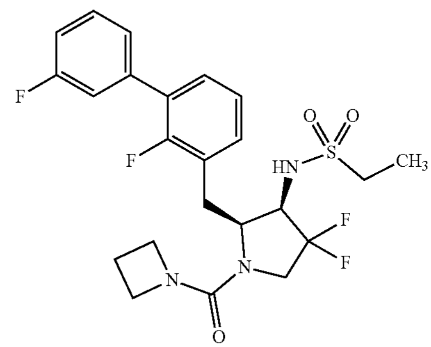 [SMILES: CCS(=O)(=O)N[C@@H]1[C@H](Cc2cccc(-c3cccc(F)c3)c2F)N(C(=O)N2CCC2)CC1(F)F] | | 500.2 |
| 288 | (2S,3R)-3-[(ethanesulfonyl)amino]-4,4-difluoro-N,N-dimethyl-2-[(2,2',3'-trifluoro-[1,1'-biphenyl]-3-yl)methyl]pyrrolidine-1-carboxamide | 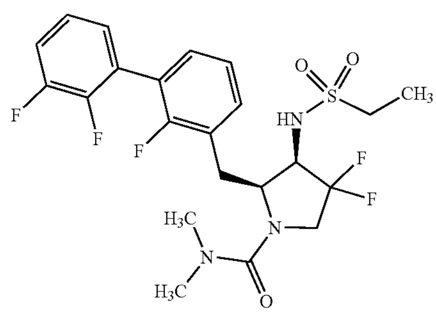 [SMILES: CCS(=O)(=O)N[C@@H]1[C@H](Cc2cccc(-c3cccc(F)c3F)c2F)N(C(=O)N(C)C)CC1(F)F] | | 506.2 |
| 289 | N-{(2S,3R)-1-(azetidine-1-carbonyl)-4,4-difluoro-2-[(2,2',3'-trifluoro[1,1'-biphenyl]-3-yl)methyl]pyrrolidin-3-yl)ethanesulfonamide | 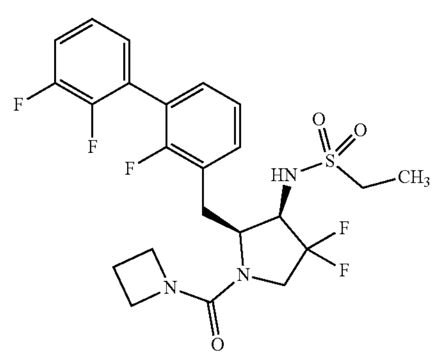 [SMILES: CCS(=O)(=O)N[C@@H]1[C@H](Cc2cccc(-c3cccc(F)c3F)c2F)N(C(=O)N2CCC2)CC1(F)F] | | 518.1 |

TABLE 1-1-continued

| EX. | IUPAC NAME | Structure | ADDITIVE | MS |
|---|---|---|---|---|
| 290 | (2S,3R)-2-[(2,2'-difluoro-3'-methyl[1,1'-biphenyl]-3-yl)methyl]-3-[(ethanesulfonyl)-amino]-4,4-difluoro-N,N-dimethyl-pyrrolidine-1-carboxamide | 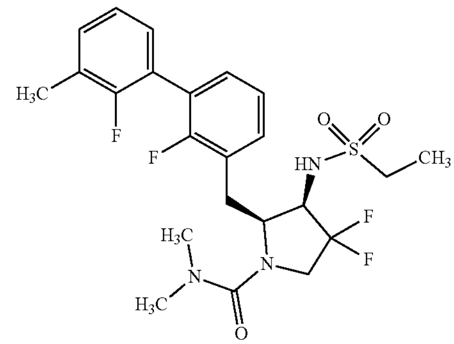 [SMILES: CCS(=O)(=O)N[C@@H]1[C@H](Cc2cccc(-c3cccc(C)c3F)c2F)N(C(=O)N(C)C)CC1(F)F] | | 502.2 |
| 291 | N-{(2S,3R)-1-(azetidine-1-carbonyl)-2-[(2,2'-difluoro-3'-methyl[1,1'-biphenyl]-3-yl)methyl]-4,4-difluoropyrrolidin-3-yl}-ethanesulfonamide | 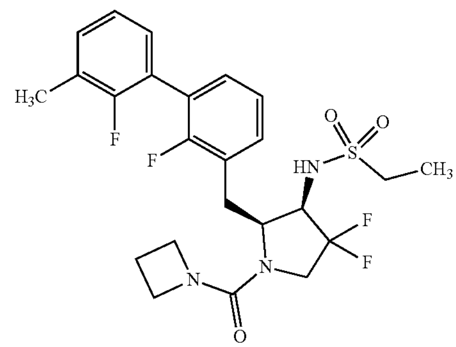 [SMILES: CCS(=O)(=O)N[C@@H]1[C@H](Cc2cccc(-c3cccc(C)c3F)c2F)N(C(=O)N2CCC2)CC1(F)F] | | 514.1 |
| 292 | N-{(2S,3R,4S)-4-fluoro-1-(2-methyl-propanoyl)-2-[(2,2',5'-trifluoro[1,1'-biphenyl]-3-yl)methyl]pyrrolidin-3-yl}-ethanesufonamide | 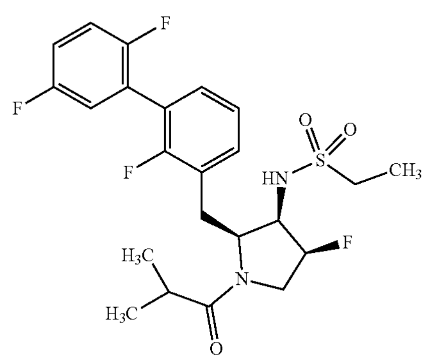 [SMILES: CCS(=O)(=O)N[C@H]1[C@@H](F)CN(C(=O)C(C)C)[C@H]1Cc1cccc(-c2cc(F)ccc2F)c1F] | | 487.2 |
| 293 | N-[(2S,3R,4S)-4-fluoro-2-[(2-fluoro[1,1'-biphenyl]-3-yl)methyl]-1-(2-methyl-propanoyl)pyrrolidin-3-yl]ethanesulfon-amide | 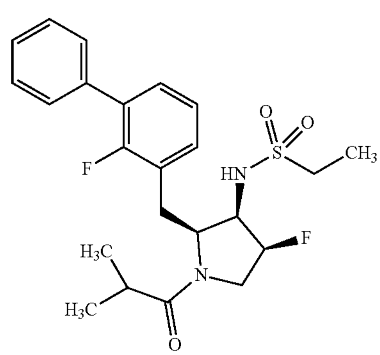 [SMILES: CCS(=O)(=O)N[C@H]1[C@@H](F)CN(C(=O)C(C)C)[C@H]1Cc1cccc(-c2ccccc2)c1F] | | 451.3 |

TABLE 1-1-continued

| EX. | IUPAC NAME | Structure | ADDITIVE | MS |
|---|---|---|---|---|
| 294 | (2S,3R,4S)-3-[(ethanesulfonyl)amino]-4-fluoro-N,N-dimethyl-2-[(2,2',5'-trifluoro-[1,1'-biphenyl]-3-yl)methyl]pyrrolidine-1-carboxamide | 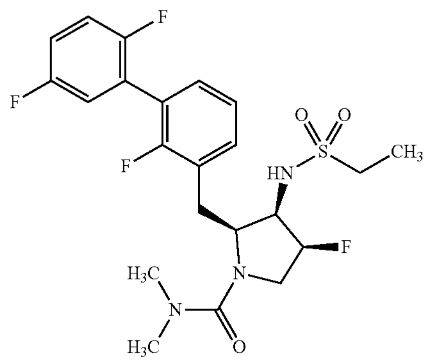 [SMILES: CCS(=O)(=O)N[C@H]1[C@@H](F)CN(C(=O)N(C)C)[C@H]1Cc1cccc(-c2cc(F)ccc2F)c1F] | | 488.2 |
| 295 | (2S,3R,4S)-3-[(ethanesulfonyl)amino}-4-fluoro-2-[(2-fluoro[1,1'-biphenyl]-3-yl)methyl]-N,N-dimethylpyrrolidine-1-carboxamide | 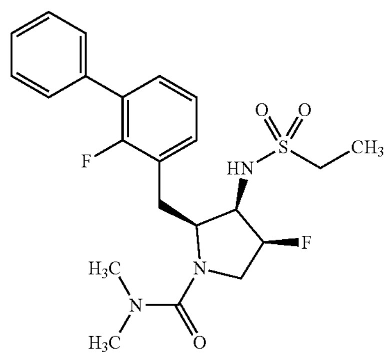 [SMILES: CCS(=O)(=O)N[C@H]1[C@@H](F)CN(C(=O)N(C)C)[C@H]1Cc1cccc(-c2ccccc2)c1F] | | 452.2 |
| 296 | N-{(2S,3R,4S)-4-fluoro-1-(2-methyl-propanoyl)-2-[(2,3',5'-trifluoro[1,1'-biphenyl]-3-yl)methyl]pyrrolidin-3-yl}-ethanesulfonamide | 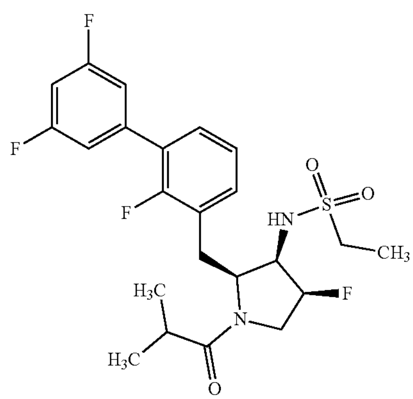 [SMILES: CCS(=O)(=O)N[C@H]1[C@@H](F)CN(C(=O)C(C)C)[C@H]1Cc1cccc(-c2cc(F)cc(F)c2)c1F] | | 487.2 |
| 297 | N-{(2S,3R,4S)-4-fluoro-1-(2-methyl-propanoyl)-2-[(2,2',3'-trifluoro[1,1'-biphenyl]-3-yl)methyl]pyrrolidin-3-yl)-ethanesulfonamide | 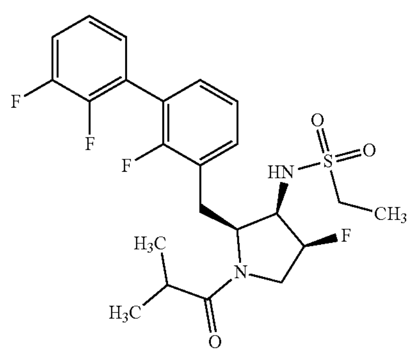 [SMILES: CCS(=O)(=O)N[C@H]1[C@@H](F)CN(C(=O)C(C)C)[C@H]1Cc1cccc(-c2cccc(F)c2F)c1F] | | 487.2 |

TABLE 1-1-continued

| EX. | IUPAC NAME | Structure | ADDITIVE | MS |
|---|---|---|---|---|
| 298 | N-[(2S,3R,4S)-2-[(3'-chloro-2-fluoro[1,1'-biphenyl]-3-yl)methyl]-4-fluoro-1-(2-methylpropanoyl)pyrrolidin-3-yl]ethanesulfonamide | 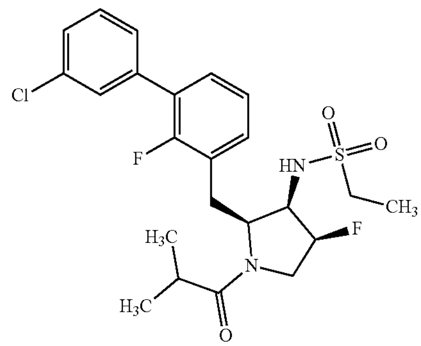 [SMILES: CCS(=O)(=O)N[C@H]1[C@@H](F)CN(C(=O)C(C)C)[C@H]1Cc1cccc(-c2cccc(Cl)c2)c1F] | | 485.2 |
| 299 | N-[(2S,3R,4S)-4-fluoro-2-[(3'-fluoro[1,1'-biphenyl]-3-yl)methyl]-1-(2-hydroxy-2-methylpropanoyl)pyrrolidin-3-yl]ethanesulfonamide | 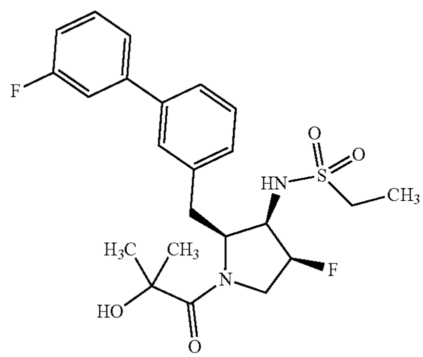 [SMILES: CCS(=O)(=O)N[C@H]1[C@@H](F)CN(C(=O)C(C)(C)O)[C@H]1Cc1cccc(-c2cccc(F)c2)c1] | | 467.2 |
| 300 | N-{(2S,3R,4S)-4-fluoro-1-(oxetane-2-carbonyl)-2-[(2,2',5'-trifluoro[1,1'-biphenyl]-3-yl)methyl]pyrrolidin-3-yl}-ethanesulfonamide with shorter retention time | 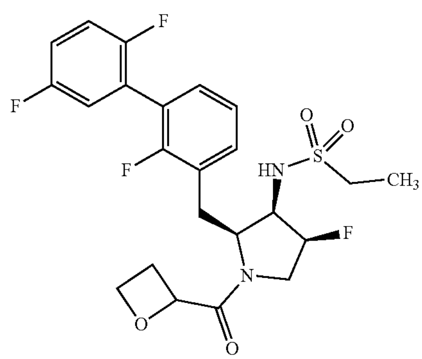 [SMILES: CCS(=O)(=O)N[C@H]1[C@@H](F)CN(C(=O)C2CCO2)[C@H]1Cc1cccc(-c2cc(F)ccc2F)c1F] | | 501.2 |
| 301 | N-{(2S,3R,4S)-4-fluoro-1-(oxetane-2-carbonyl)-2-[(2,2',5'-trifluoro[1,1'-biphenyl]-3-yl)methyl]pyrrolidin-3-yl}ethanesulfonamide with longer retention time | 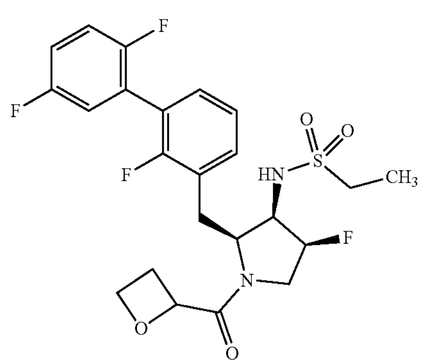 [SMILES: CCS(=O)(=O)N[C@H]1[C@@H](F)CN(C(=O)C2CCO2)[C@H]1Cc1cccc(-c2cc(F)ccc2F)c1F] | | 501.1 |

TABLE 1-1-continued

| EX. | IUPAC NAME | Structure | ADDITIVE | MS |
|---|---|---|---|---|
| 302 | N-[(2S,3R,4S)-4-fluoro-2-[(2-fluoro[1,1'-biphenyl]-3-yl)methyl]-1-((2R)-oxetane-2-carbonyl)pyrrolidin-3-yl]ethanesulfonamide | 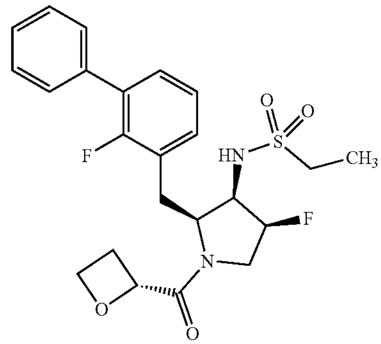 [SMILES: CCS(=O)(=O)N[C@H]1[C@@H](F)CN(C(=O)[C@H]2CCO2)[C@H]1Cc1cccc(-c2ccccc2)c1F] | | 465.2 |
| 303 | N-[(2S,3R,4S)-4-fluoro-2-[(2-fluoro[1,1'-biphenyl]-3-yl)methyl]-1-({2S)-oxetane-2-carbonyl)pyrrolidin-3-yl]ethanesulfonamide | 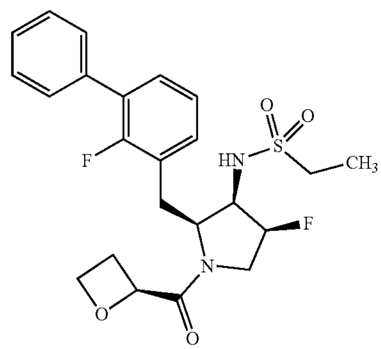 [SMILES: CCS(=O)(=O)N[C@H]1[C@@H](F)CN(C(=O)[C@@H]2CCO2)[C@H]1Cc1cccc(-c2ccccc2)c1F] | | 465.2 |
| 304 | N-{(2S,3R,4S)-4-fluoro-1-(oxetane-2-carbonyl)-2-[(2,3',5'-trifluoro[1,1'-biphenyl]-3-yl)methyl]pyrrolidin-3-yl}-ethanesulfonamide with shorter retention time | 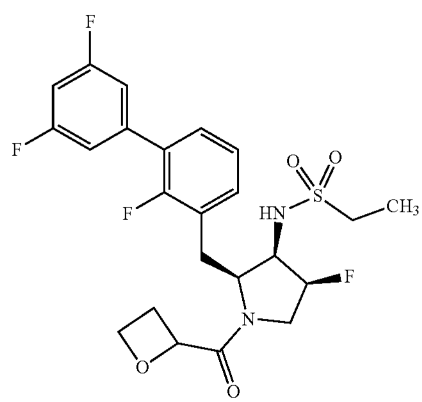 [SMILES: CCS(=O)(=O)N[C@H]1[C@@H](F)CN(C(=O)C2CCO2)[C@H]1Cc1cccc(-c2cc(F)cc(F)c2)c1F] | | 501.2 |
| 305 | N-{(2S,3R,4S)-4-fluoro-1-(oxetane-2-carbonyl)-2-[(2,3',5'-trifluoro[1,1'-biphenyl]-3-yl)methyl]pyrrolidin-3-yl}-ethanesulfonamide with longer retention time | 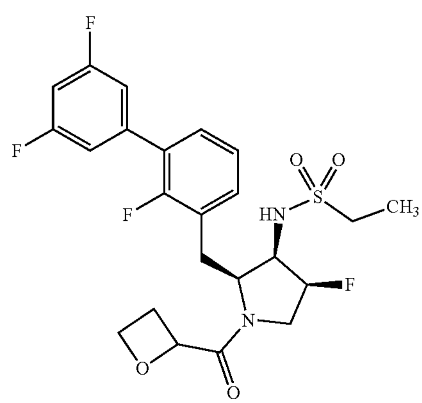 [SMILES: CCS(=O)(=O)N[C@H]1[C@@H](F)CN(C(=O)C2CCO2)[C@H]1Cc1cccc(-c2cc(F)cc(F)c2)c1F] | | 501.1 |

TABLE 1-1-continued

| EX. | IUPAC NAME | Structure | ADDITIVE | MS |
|---|---|---|---|---|
| 306 | N-{(2S,3R,4S)-1-(bicyclo[1.1.1]pentane-1-carbonyl)-4-fluoro-2-[(2,2',5'-trifluoro[1,1'-biphenyl]-3-yl)methyl]pyrrolidin-3-yl}-ethanesulfonamide | 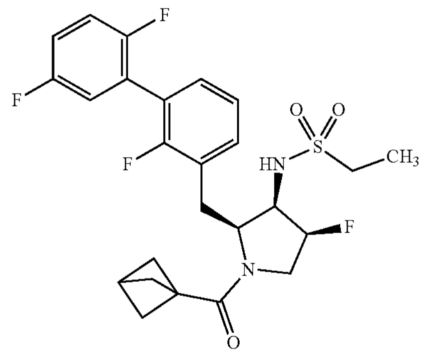 [SMILES: CCS(=O)(=O)N[C@H]1[C@@H](F)CN(C(=O)C23CC(C2)C3)[C@H]1Cc1cccc(-c2cc(F)ccc2F)c1F] | | 511.2 |
| 307 | N-{(2S,3R,4S)-4-fluoro-1-(oxetane-2-carbonyl)-2-[(2,2',3'-trifluoro[1,1'-biphenyl]-3-yl)methyl]pyrrolidin-3-yl}-ethanesulfonamide with shorter retention time | 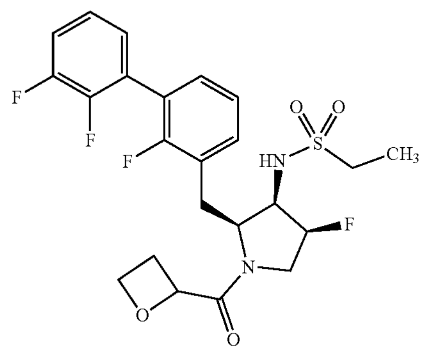 [SMILES: CCS(=O)(=O)N[C@H]1[C@@H](F)CN(C(=O)C2CCO2)[C@H]1Cc1cccc(-c2cccc(F)c2F)c1F] | | 501.1 |
| 308 | N-{(2S,3R,4S)-1-(bicyclo[1.1.1]pentane-1-carbonyl)-4-fluoro-2-[(2-fluoro[1,1'-biphenyl]-3-yl)methyl]pyrrolidin-3-yl}-ethanesulfonamide | 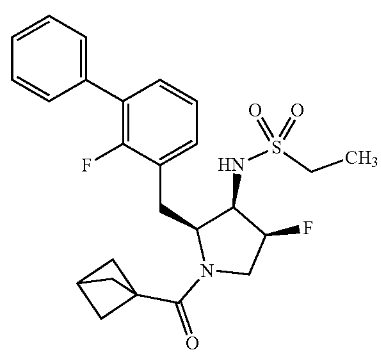 [SMILES: CCS(=O)(=O)N[C@H]1[C@@H](F)CN(C(=O)C23CC(C2)C3)[C@H]1Cc1cccc(-c2ccccc2)c1F] | | 475.3 |
| 309 | N-{(2S,3R,4S)-4-fluoro-1-(oxetane-2-carbonyl)-2-[(2,2',3'-trifluoro[1,1'-biphenyl]-3-yl)methyl]pyrrolidin-3-yl}-ethanesulfonamide with longer retention time | 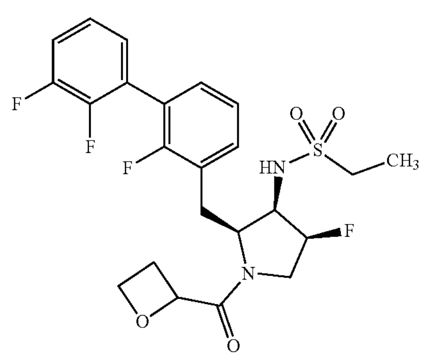 [SMILES: CCS(=O)(=O)N[C@H]1[C@@H](F)CN(C(=O)C2CCO2)[C@H]1Cc1cccc(-c2cccc(F)c2F)c1F] | | 501.1 |

TABLE 1-1-continued

| EX. | IUPAC NAME | Structure | ADDITIVE | MS |
|---|---|---|---|---|
| 310 | N-{(2S,3R,4S)-1-(cyclopropanecarbonyl)-4-fluoro-2-[(3'-fluoro[1,1'-biphenyl]-3-yl)methyl]pyrrolidin-3-yl}ethanesulfonamide | 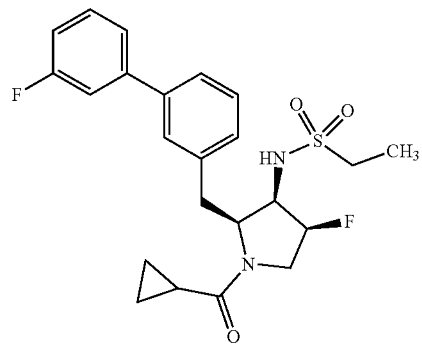 [SMILES: CCS(=O)(=O)N[C@H]1[C@@H](F)CN(C(=O)C2CC2)[C@H]1Cc1cccc(-c2cccc(F)c2)c1] | | 449.0 |
| 311 | N-{(2S,3R,4S)-1-(cyclopropanecarbonyl)-4-fluoro-2-[(2,3',5'-trifluoro[1,1'-biphenyl]-3-yl)methyl]pyrrolidin-3-yl}methanesulfonamide | 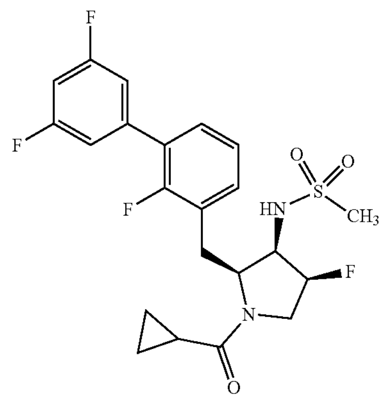 [SMILES: CS(=O)(=O)N[C@H]1[C@@H](F)CN(C(=O)C2CC2)[C@H]1Cc1cccc(-c2cc(F)cc(F)c2)c1F] | | 468.9 |
| 312 | N-{(2S,3R,4S)-1-(cyclopropanecarbonyl)-4-fluoro-2-[(2,2',3'-trifluoro[1,1'-biphenyl]-3-yl)methyl]pyrrolidin-3-yl}methanesulfonamide | 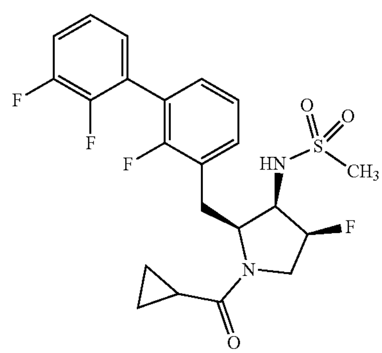 [SMILES: CS(=O)(=O)N[C@H]1[C@@H](F)CN(C(=O)C2CC2)[C@H]1Cc1cccc(-c2cccc(F)c2F)c1F] | | 471.0 |
| 313 | N-{(2S,3R,4S)-1-(cyclopropanecarbonyl)-4-fluoro-2-[(2,2',5'-trifluoro[1,1'-biphenyl]-3-yl)methyl]pyrrolidin-3-yl}methanesulfonamide | 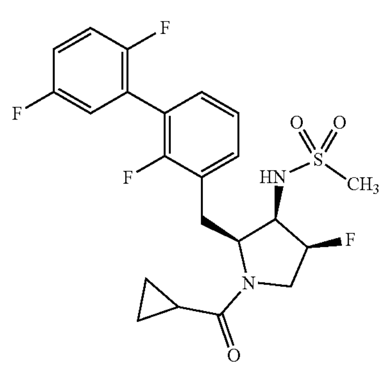 [SMILES: CS(=O)(=O)N[C@H]1[C@@H](F)CN(C(=O)C2CC2)[C@H]1Cc1cccc(-c2cc(F)ccc2F)c1F] | | 471.0 |

TABLE 1-1-continued

| EX. | IUPAC NAME | Structure | ADDITIVE | MS |
|---|---|---|---|---|
| 314 | N-{(2S,3R,4S)-4-fluoro-1-(2-methyl-propanoyl)-2-[(2,2',3'-trifluoro[1,1'-biphenyl]-3-yl)methyl]pyrrolidin-3-yl}-methanesulfonamide | 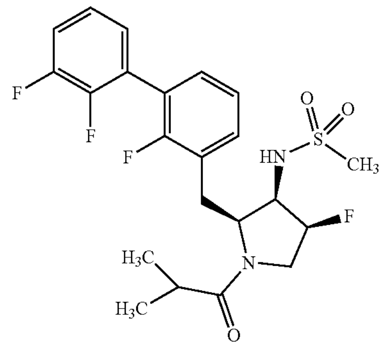 [SMILES: CC(C)C(=O)N1C[C@H](F)[C@H](NS(C)(=O)=O)[C@@H]1Cc1cccc(-c2cccc(F)c2F)c1F] | | 473.0 |
| 315 | N-{(2S,3R,4S)-4-fluoro-1-(2-methyl-propanoyl)-2-[(2,2',5'-trifluoro[1,1'-biphenyl]-3-yl)methyl]pyrrolidin-3-yl}-methanesulfonamide | 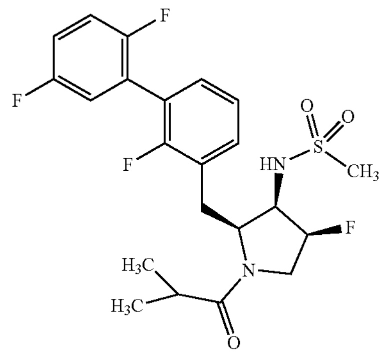 [SMILES: CC(C)C(=O)N1C[C@H](F)[C@H](NS(C)(=O)=O)[C@@H]1Cc1cccc(-c2cc(F)ccc2F)c1F] | | 473.0 |
| 316 | N-{(2S,3R,4S)-4-fluoro-1-(2-methyl-propanoyl)-2-[(2,3',5'-trifluoro[1,1'-biphenyl]-3-yl)methyl]pyrrolidin-3-yl}-methanesulfonamide | 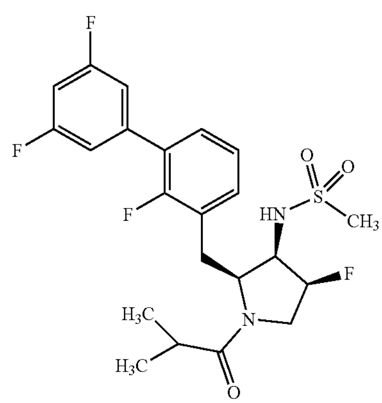 [SMILES: CC(C)C(=O)N1C[C@H](F)[C@H](NS(C)(=O)=O)[C@@H]1Cc1cccc(-c2cc(F)cc(F)c2)c1F] | | 473.0 |
| 317 | N-[(2S,3R,4S)-4-fluoro-2-[(2-fluoro[1,1'-biphenyl]-3-yl)methyl]-1-(2-methyl-propanoyl)pyrrolidin-3-yl]methane-sulfonamide | 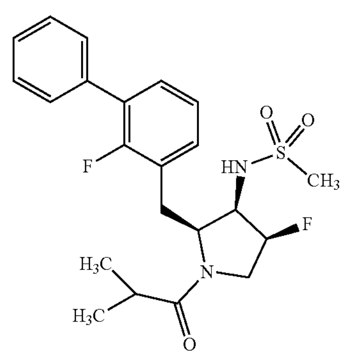 [SMILES: CC(C)C(=O)N1C[C@H](F)[C@H](NS(C)(=O)=O)[C@@H]1Cc1cccc(-c2ccccc2)c1F] | | 437.1 |

TABLE 1-1-continued

| EX. | IUPAC NAME | Structure | ADDITIVE | MS |
|---|---|---|---|---|
| 318 | N-[(2S,3R,4S)-2-[(2,3'-difluoro[1,1'-biphenyl]-3-yl)methyl]-4-fluoro-1-(oxetane-2-carbonyl)pyrrolidin-3-yl]-methanesulfonamide with longer retention time | 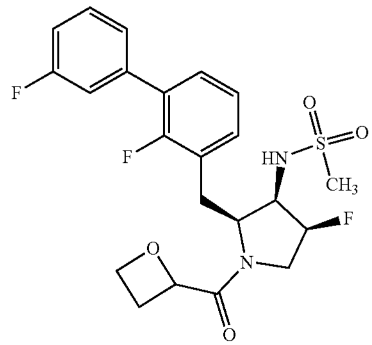 [SMILES: CS(=O)(=O)N[C@H]1[C@@H](F)CN(C(=O)C2CCO2)[C@H]1Cc1cccc(-c2cccc(F)c2)c1F] | | 469.0 |
| 319 | N-{(2S,3R,4S)-4-fluoro-1-(oxetane-2-carbonyl)-2-[(2,3',5'-trifluoro[1,1'-biphenyl]-3-yl)methyl]pyrrolidin-3-yl}-methanesulfonamide with longer retention time | 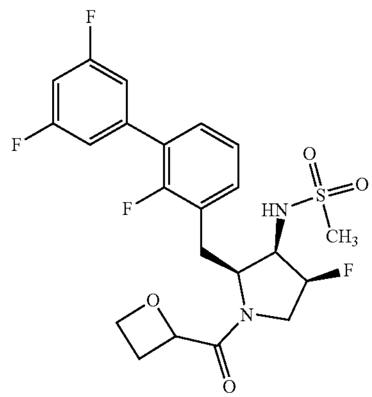 [SMILES: CS(=O)(=O)N[C@H]1[C@@H](F)CN(C(=O)C2CCO2)[C@H]1Cc1cccc(-c2cc(F)cc(F)c2)c1F] | | 484.8 |
| 320 | N-{(2S,3R,4S)-4-fluoro-1-(oxetane-2-carbonyl)-2-[(2,2',3'-trifluoro[1,1'-biphenyl]-3-yl)methyl]pyrrolidin-3-yl}-methanesulfonamide with longer retention time | 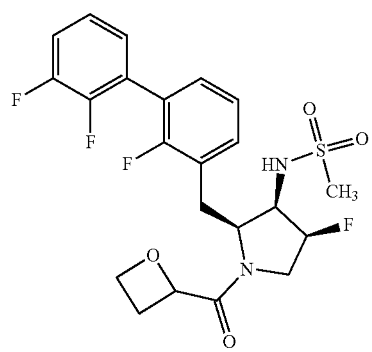 [SMILES: CS(=O)(=O)N[C@H]1[C@@H](F)CN(C(=O)C2CCO2)[C@H]1Cc1cccc(-c2cccc(F)c2F)c1F] | | 486.9 |
| 321 | N-{(2S,3R,4S)-4-fluoro-1-(oxetane-2-carbonyl)-2-[(2,2',5'-trifluoro[1,1-biphenyl]-3-yl)methyl]pyrrolidin-3-yl}-methanesulfonamide with longer retention time | 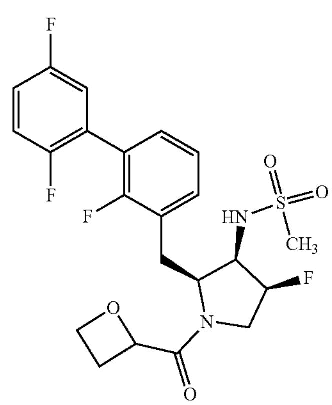 [SMILES: CS(=O)(=O)N[C@H]1[C@@H](F)CN(C(=O)C2CCO2)[C@H]1Cc1cccc(-c2cc(F)ccc2F)c1F] | | 486.9 |

TABLE 1-1-continued

| EX. | IUPAC NAME | Structure | ADDITIVE | MS |
|---|---|---|---|---|
| 322 | N-[(2S,3R,4S)-2-[(3'-chloro-2-fluoro[1,1'-biphenyl]-3-yl)methyl]-4-fluoro-1-(oxetane-2-carbonyl)pyrrolidin-3-yl]-methanesulfonamide with longer retention time | 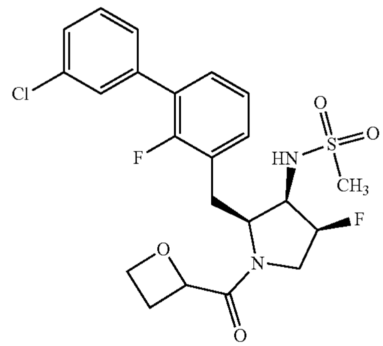 [SMILES: CS(=O)(=O)N[C@H]1[C@@H](F)CN(C(=O)C2CCO2)[C@H]1Cc1cccc(-c2cccc(Cl)c2)c1F] | | 484.9 |
| 323 | N-[(2S,3R,4S)-2-[(2,3'-difluoro[1,1'-biphenyl]-3-yl)methyl]-4-fluoro-1-(oxetane-2-carbonyl)pyrrolidin-3-yl]-methanesulfonamide with shorter retention time | 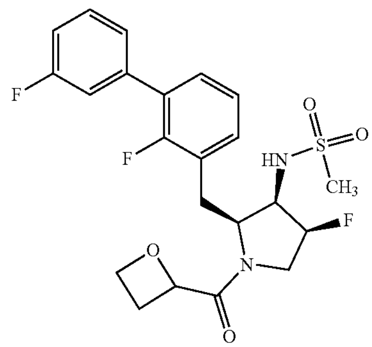 [SMILES: CS(=O)(=O)N[C@H]1[C@@H](F)CN(C(=O)C2CCO2)[C@H]1Cc1cccc(-c2cccc(F)c2)c1F] | | 469.0 |
| 324 | N-{(2S,3R,4S)-4-fluoro-1-(oxetane-2-carbonyl)-2-[(2,3',5'-trifluoro[1,1'-biphenyl]-3-yl)methyl]pyrrolidin-3-yl}-methanesulfonamide with shorter retention time | 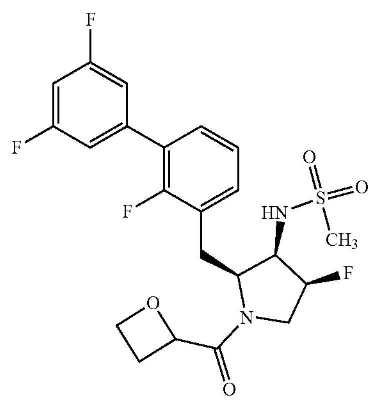 [SMILES: CS(=O)(=O)N[C@H]1[C@@H](F)CN(C(=O)C2CCO2)[C@H]1Cc1cccc(-c2cc(F)cc(F)c2)c1F] | | 486.9 |
| 325 | N-{(2S,3R,4S)-4-fluoro-1-(oxetane-2-carbonyl)-2-[(2,2',3',-trifluoro[1,1'-biphenyl]-3-yl)methyl]pyrrolidin-3-yl}-methanesulfonamide with shorter retention time | 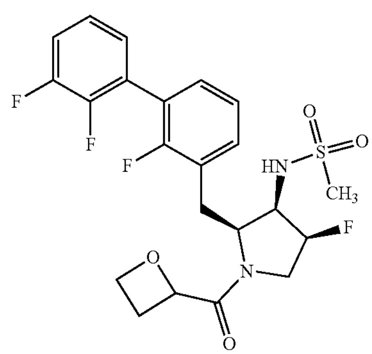 [SMILES: CS(=O)(=O)N[C@H]1[C@@H](F)CN(C(=O)C2CCO2)[C@H]1Cc1cccc(-c2cccc(F)c2F)c1F] | | 486.9 |

TABLE 1-1-continued

| EX. | IUPAC NAME | Structure | ADDITIVE | MS |
|---|---|---|---|---|
| 326 | N-{(2S,3R,4S)-4-fluoro-1-(oxetane-2-carbonyl)-2-[(2,2',5'-trifluoro[1,1'-biphenyl]-3-yl)methyl]pyrrolidin-3-yl}-methanesulfonamide with shorter retention time | 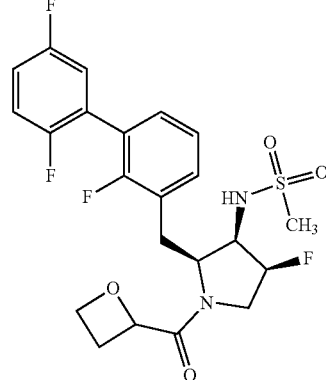 | | 486.9 |
| 327 | N-[(2S,3R,4S)-4-fluoro-2-[(2-fluoro[1,1'-biphenyl]-3-yl)methyl]-1-(oxetane-2-carbonyl)pyrrolidin-3-yl]methanesulfonamide derived from N-[(2S,3R,4S)-2-[(3-chloro-2-fluorophenyl)methyl]-4-fluoro-1-(oxetane-2-carbonyl)pyrrolidin-3-yl]-methanesulfonamide with shorter retention time by HPLC (column: L-Column2 ODS (3.0 mmI · D. × 50 mmL, 3 μm), mobile phase: water/acetonitrile (including 0.05% TFA) | 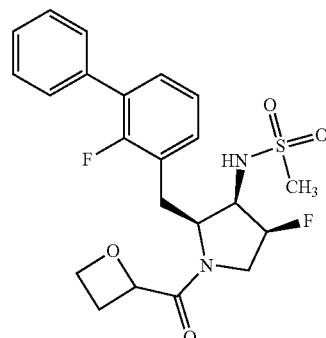 | | 451.0 |
| 328 | N-[(2S,3R,4S)-2-[(3'-chloro-2-fluoro-[1,1'-biphenyl]-3-yl)methyl]-4-fluoro-1-(oxetane-2-carbonyl)pyrrolidin-3-yl]-methanesulfonamide with shorter retention time | 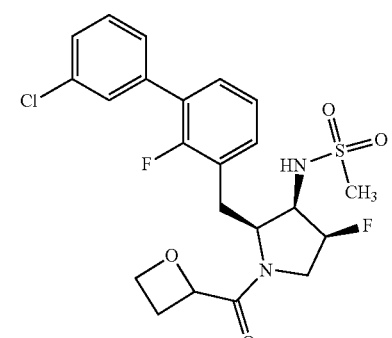 | | 484.9 |
| 329 | (2S,3R,4S)-3-[(ethanesulfonyl)amino]-fluoro-N,N-dimethyl-2-[(2,3',5'-trifluoro[1,1'-biphenyl]-3-yl)methyl]-pyrrolidine-1-carboxamide | 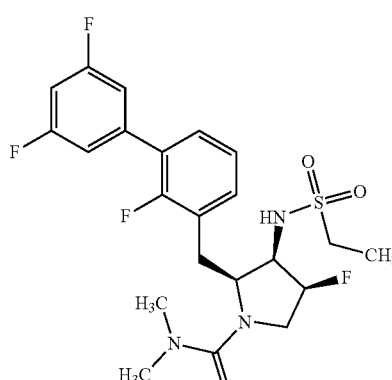 | | 488.0 |

TABLE 1-1-continued

| EX. | IUPAC NAME | Structure | ADDITIVE | MS |
|---|---|---|---|---|
| 330 | (2S,3R,4S)-3-[(ethanesulfonyl)amino]-fluoro-N,N-dimethyl-2-[(2,2',3'-trifluoro-[1,1'-biphenyl]-3-yl)methyl]pyrrolidine-1-carboxamide | 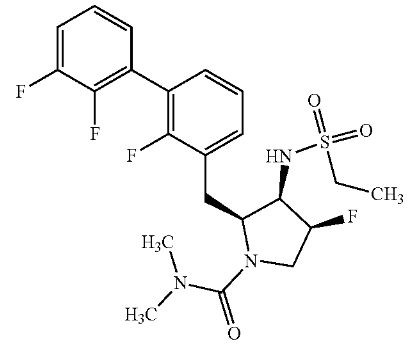 [SMILES: CCS(=O)(=O)N[C@H]1[C@@H](F)CN(C(=O)N(C)C)[C@H]1Cc1cccc(-c2cccc(F)c2F)c1F] | | 488.0 |
| 331 | (2S,3R,4S)-2-[(2,2'-difluoro[1,1'-biphenyl]-3-yl)methyl]-3-[(ethanesulfonyl)amino]-4-fluoro-N,N-dimethylpyrrolidine-1-carboxamide | 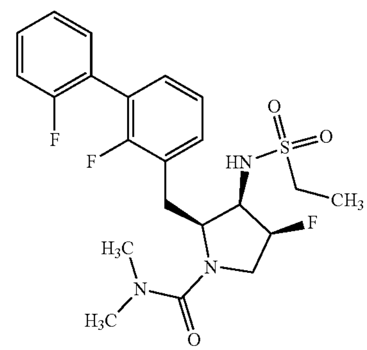 [SMILES: CCS(=O)(=O)N[C@H]1[C@@H](F)CN(C(=O)N(C)C)[C@H]1Cc1cccc(-c2ccccc2F)c1F] | | 470.0 |
| 332 | (2S,3R,4S)-2-[(3'-chloro-2-fluoro[1,1'-biphenyl]-3-yl)methyl]-3-[(ethanesulfonyl)amino]-4-fluoro-N,N-dimethylpyrrolidine-1-carboxamide | 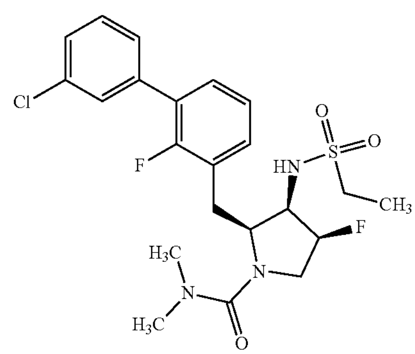 [SMILES: CCS(=O)(=O)N[C@H]1[C@@H](F)CN(C(=O)N(C)C)[C@H]1Cc1cccc(-c2cccc(Cl)c2)c1F] | | 485.9 |
| 333 | (2S,3R,4S)-3-[(ethanesulfonyl)amino]-4-fluoro-2-[(2-fluoro-3'-methyl[1,1'-biphenyl]-3-yl)methyl]-N,N-dimethyl-pyrrolidine-1-carboxamide | 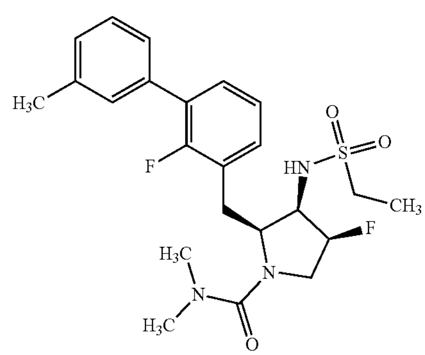 [SMILES: CCS(=O)(=O)N[C@H]1[C@@H](F)CN(C(=O)N(C)C)[C@H]1Cc1cccc(-c2cccc(C)c2)c1F] | | 466.0 |

TABLE 1-1-continued

| EX. | IUPAC NAME | Structure | ADDITIVE | MS |
|---|---|---|---|---|
| 334 | (2S,3R,4S)-4-fluoro-2-[2-fluoro[1,1'-biphenyl]-3-yl)methyl]-3-[(methanesulfonyl)amino]-N,N-dimethyl-pyrrolidine-1-carboxamide | 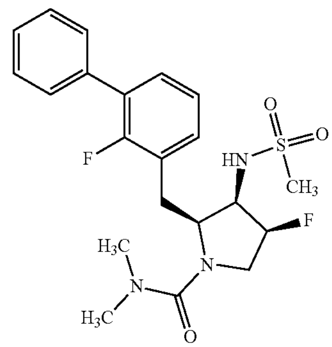 [SMILES: CN(C)C(=O)N1C[C@H](F)[C@H](NS(C)(=O)=O)[C@@H]1Cc1cccc(-c2ccccc2)c1F] | | 438.1 |
| 335 | (2S,3R,4S)-2-[(2,3'-difluoro[1,1'-biphenyl]-3-yl)methyl]-4-fluoro-3-[(methanesulfonyl)amino]-N,N-dimethylpyrrolidine-1-carboxamide | 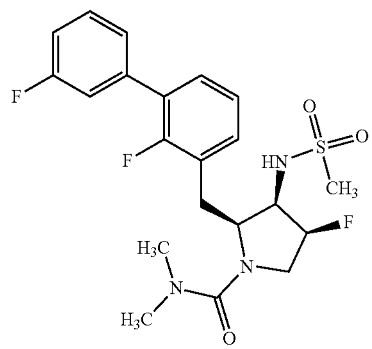 [SMILES: CN(C)C(=O)N1C[C@H](F)[C@H](NS(C)(=O)=O)[C@@H]1Cc1cccc(-c2cccc(F)c2)c1F] | | 456.0 |
| 336 | (2S,3R,4S)-4-fluoro-3-[(methanesulfonyl)amino]-N,N-dimethyl-2-[(2,3',5'-trifluoro-[1,1'-biphenyl]-3-yl)methyl]pyrrolidine-1-carboxamide | 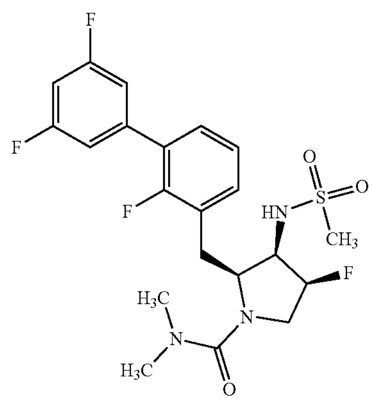 [SMILES: CN(C)C(=O)N1C[C@H](F)[C@H](NS(C)(=O)=O)[C@@H]1Cc1cccc(-c2cc(F)cc(F)c2)c1F] | | 474.0 |
| 337 | (2S,3R,4S)-4-fluoro-3-[(methanesulfonyl)amino]-N,N-dimethyl-2-[(2,2',3'-trifluoro-[1,1'-biphenyl]-3-yl)methyl]pyrrolidine-1-carboxamide | 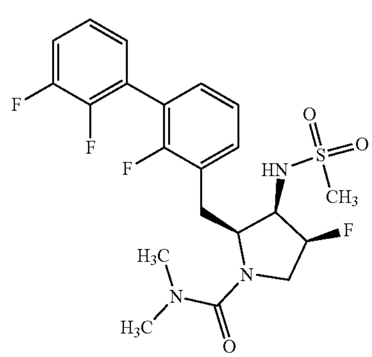 [SMILES: CN(C)C(=O)N1C[C@H](F)[C@H](NS(C)(=O)=O)[C@@H]1Cc1cccc(-c2cccc(F)c2F)c1F] | | 474.0 |

TABLE 1-1-continued

| EX. | IUPAC NAME | Structure | ADDITIVE | MS |
|---|---|---|---|---|
| 338 | (2S,3R,4S)-4-fluoro-3-[(methanesulfonyl)-amino]-N,N-dimethyl-2-[(2,2',5'-trifluoro[1,1'-biphenyl]-3-yl)methyl]-pyrrolidine-1-carboxamide | 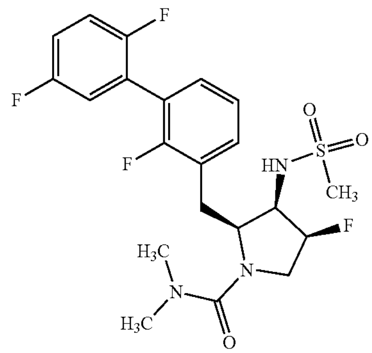 [SMILES: CN(C)C(=O)N1C[C@H](F)[C@H](NS(C)(=O)=O)[C@@H]1Cc1cccc(-c2cc(F)ccc2F)c1F] | | 474.0 |
| 339 | (2S,3R,4S)-2-[(2,2'-difluoro[1,1'-biphenyl]-3-yl)methyl]-4-fluoro-3-[(methanesulfonyl)-amino]-N,N-dimethylpyrrolidine-1-carboxamide | 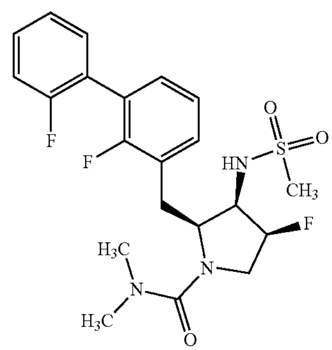 [SMILES: CN(C)C(=O)N1C[C@H](F)[C@H](NS(C)(=O)=O)[C@@H]1Cc1cccc(-c2ccccc2F)c1F] | | 456.0 |
| 340 | (2S,3R,4S)-4-fluoro-2-[(2-fluoro-3'-methyl[1,1'-biphenyl]-3-yl)methyl]-3-[(methanesulfonyl)amino]-N,N-dimethylpyrrolidine-1-carboxamide | 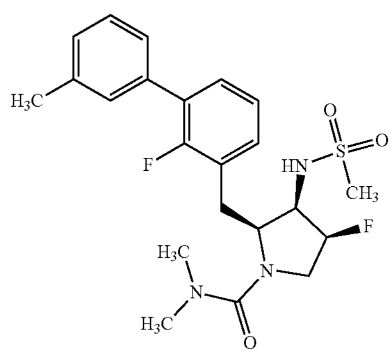 [SMILES: Cc1cccc(-c2cccc(C[C@H]3[C@@H](NS(C)(=O)=O)[C@@H](F)CN3C(=O)N(C)C)c2F)c1] | | 452.0 |
| 341 | (2S,3R,4S)-2-[(3'-chloro-2-fluoro[1,1'-biphenyl]-3-yl)methyl]-4-fluoro-3-[(methanesulfonyl)amino]-N,N-dimethyl-pyrrolidine-1-carboxamide | 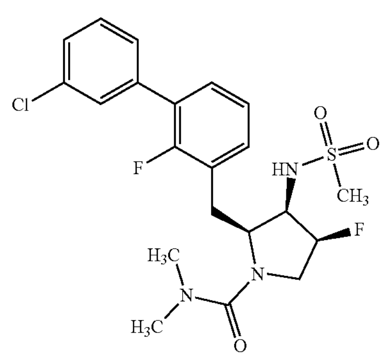 [SMILES: CN(C)C(=O)N1C[C@H](F)[C@H](NS(C)(=O)=O)[C@@H]1Cc1cccc(-c2cccc(Cl)c2)c1F] | | 471.9 |

TABLE 1-1-continued

| EX. | IUPAC NAME | Structure | ADDITIVE | MS |
|-----|------------|-----------|----------|-----|
| 342 | N-{(2S,3R,4S)-1-(cyclopropanecarbonyl)-2-[(2,2'-difluoro[1,1'-biphenyl]-3-yl)-methyl]4-fluoropyrrolidin-3-yl}methane-sulfonamide | 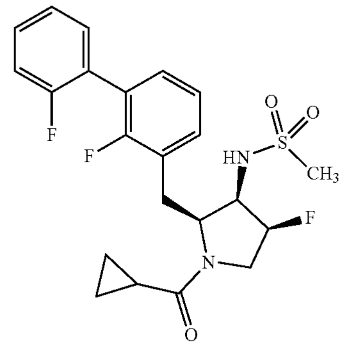 [SMILES: CS(=O)(=O)N[C@H]1[C@@H](F)CN(C(=O)C2CC2)[C@H]1Cc1cccc(-c2ccccc2F)c1F] | | 452.9 |
| 343 | N-{(2S,3R,4S)-1-(cyclopropanecarbonyl)-4-fluoro-2-[(2-fluoro[1,1'-biphenyl]-3-yl)methyl]pyrrolidin-3-yl}methane-sulfonamide | 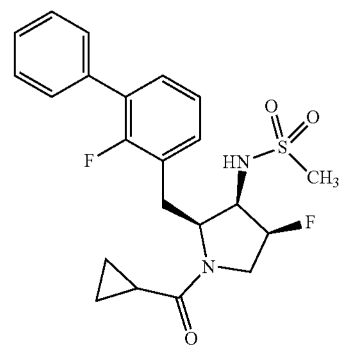 [SMILES: CS(=O)(=O)N[C@H]1[C@@H](F)CN(C(=O)C2CC2)[C@H]1Cc1cccc(-c2ccccc2)c1F] | | 435.1 |
| 344 | (2S,3R,4S)-2-[(2,3'-difluoro[1,1'-biphenyl]-3-yl)methyl]-3-[(dimethylsulfamoyl)-amino]-4-fluoro-N,N-dimethylpyrrolidine-1-carboxamide | 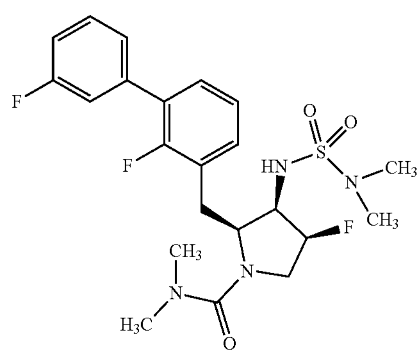 [SMILES: CN(C)C(=O)N1C[C@H](F)[C@H](NS(=O)(=O)N(C)C)[C@@H]1Cc1cccc(-c2cccc(F)c2)c1F] | | 485.0 |
| 345 | N-[(2S,3R,4S)-2-[(3'-chloro-2,5'-difluoro-[1,1'-biphenyl]-3-yl)methyl]-4-fluoro-1-(2-hydroxy-2-methylpropanoyl)pyrrolidin-3-yl]ethanesulfonamide | 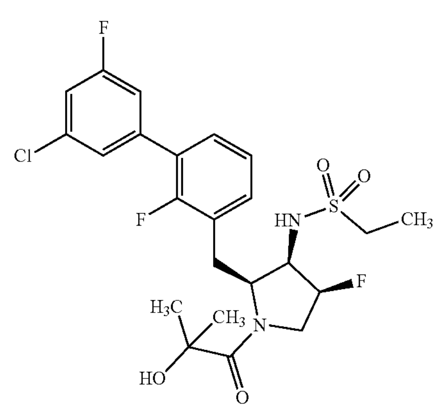 [SMILES: CCS(=O)(=O)N[C@H]1[C@@H](F)CN(C(=O)C(C)(C)O)[C@H]1Cc1cccc(-c2cc(F)cc(Cl)c2)c1F] | | 516.8 |

TABLE 1-1-continued

| EX. | IUPAC NAME | Structure | ADDITIVE | MS |
|---|---|---|---|---|
| 346 | N-[(2S,3R,4S)-2-[(3'-chloro-2-fluoro[1,1'-biphenyl]-3-yl)methyl]-4-fluoro-1-(2-hydroxy-2-methylpropanoyl)pyrrolidin-3-yl]ethanesulfonamide | 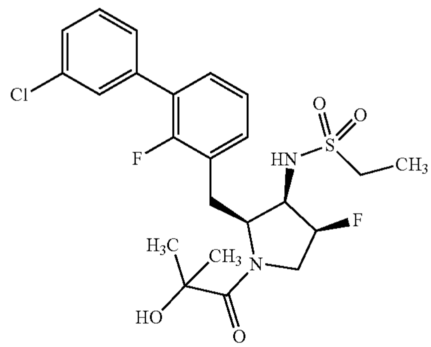 [SMILES: CCS(=O)(=O)N[C@H]1[C@@H](F)CN(C(=O)C(C)(C)O)[C@H]1Cc1cccc(-c2cccc(Cl)c2)c1F] | | 501.0 |
| 347 | N-[(2S,3R,4S)-2-[(3'-chloro-2,2'-difluoro-[1,1'-biphenyl]-3-yl)methyl]-4-fluoro-1-(2-hydroxy-2-methylpropanoyl)pyrrolidin-3-yl]ethanesulfonamide | 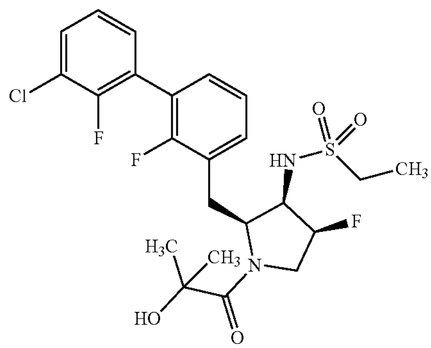 [SMILES: CCS(=O)(=O)N[C@H]1[C@@H](F)CN(C(=O)C(C)(C)O)[C@H]1Cc1cccc(-c2cccc(Cl)c2F)c1F] | | 518.9 |
| 348 | N-[(2S,3R,S)-2-[(5,-chloro-2,2'-difluoro-[1,1'-biphenyl]-3-yl)methyl]-4-fluoro-2-(2-hydroxy-2-methylpropanoyl)pyrrolidin-3-yl]ethanesulfonamide | 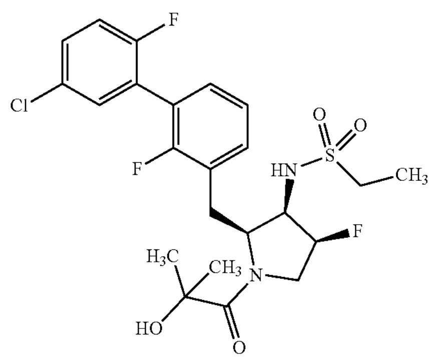 [SMILES: CCS(=O)(=O)N[C@H]1[C@@H](F)CN(C(=O)C(C)(C)O)[C@H]1Cc1cccc(-c2cc(Cl)ccc2F)c1F] | | 518.9 |
| 349 | N-{(2S,3R)-4,4-difluoro-1-(3-fluoro-cyclobutane-1-carbonyl)-2-[(2,2',3'-trifluro[1,1'-biphenyl]-3-yl)methyl]-pyrrolidin-3-yl}ethanesulfonamide with longer retention time | 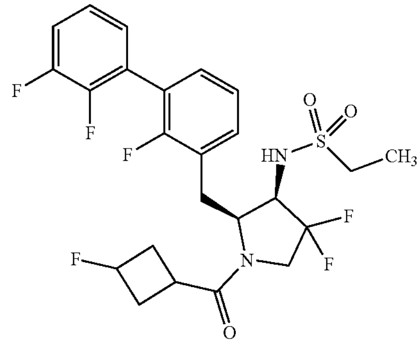 [SMILES: CCS(=O)(=O)N[C@@H]1[C@H](Cc2cccc(-c3cccc(F)c3F)c2F)N(C(=O)C2CC(F)C2)CC1(F)F] | | 532.9 |

TABLE 1-1-continued

| EX. | IUPAC NAME | Structure | ADDITIVE | MS |
|---|---|---|---|---|
| 350 | N-{(2S,3R,4S)-1-(cyclobutanecarbonyl)-4-fluoro-2-[(3'-fluoro[1,1'-biphenyl]-3-yl)methyl]pyrrolidin-3-yl}ethanesulfonamide | 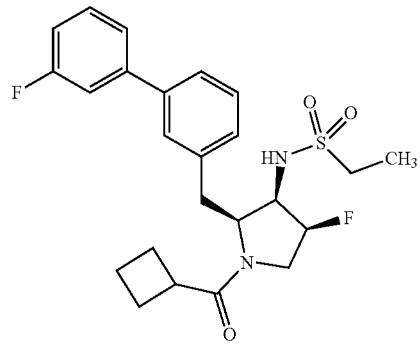 [SMILES: CCS(=O)(=O)N[C@H]1[C@@H](F)CN(C(=O)C2CCC2)[C@H]1Cc1cccc(-c2cccc(F)c2)c1] | | 463.0 |
| 351 | N-{(2S,3R)-4,4-difluoro-1-(3-fluorocyclobutane-1-carbonyl)-2-[(2,2',3'-trifluoro[1,1'-biphenyl]-3-yl)methyl]-pyrrolidin-3-yl}ethanesulfonamide with shorter retention time | 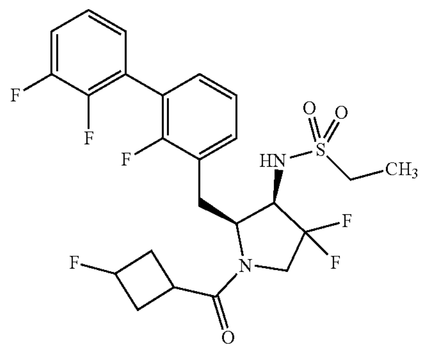 [SMILES: CCS(=O)(=O)N[C@@H]1[C@H](Cc2cccc(-c3cccc(F)c3F)c2F)N(C(=O)C2CC(F)C2)CC1(F)F] | | 532.9 |
| 352 | N-{(2S,3R)-2-[(2',5'-difluoro[1,1'-biphenyl]-3-yl)methyl]-4,4-difluoro-1-[(2R)-oxolane-2-carbonyl]pyrrolidin-3-yl}methanesulfonamide | 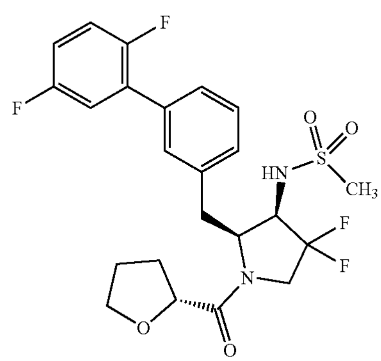 [SMILES: CS(=O)(=O)N[C@@H]1[C@H](Cc2cccc(-c3cc(F)ccc3F)c2)N(C(=O)[C@H]2CCCO2)CC1(F)F] | | 501.2 |
| 353 | rac-N-[(2S,3R)-2-{[2-(3,5-difluorophenyl)-1,3-thiazol-4-yl]methyl}-4,4-difluoro-1-(2-hydroxy-2-methylpropanoyl)pyrrolidin-3-yl]methanesulfonamide | 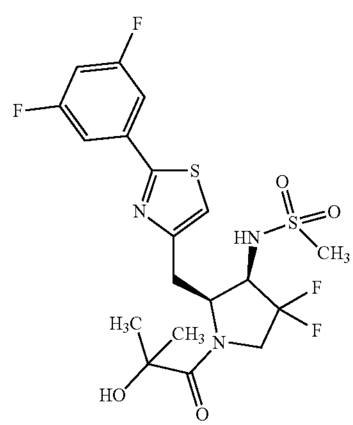 [SMILES: CC(C)(O)C(=O)N1CC(F)(F)[C@H](NS(C)(=O)=O)[C@@H]1Cc1csc(-c2cc(F)cc(F)c2)n1] | | 496.1 |

TABLE 1-1-continued

| EX. | IUPAC NAME | Structure | ADDITIVE | MS |
|---|---|---|---|---|
| 354 | N-{(2S,3R)-2-[(2',3'-difluoro[1,1'-biphenyl]-3-yl)methyl]-4,4-difluoro-1-[(2R)-oxolane-2-carbonyl]pyrrolidin-3-yl}methanesulfonamide | 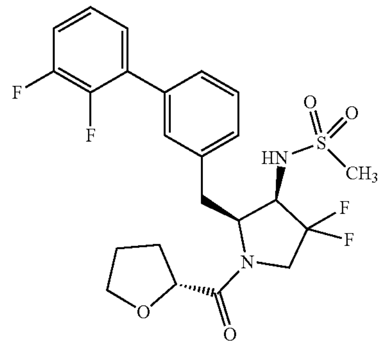 [SMILES: CS(=O)(=O)N[C@@H]1[C@H](Cc2cccc(-c3cccc(F)c3F)c2)N(C(=O)[C@H]2CCCO2)CC1(F)F] | | 501.2 |
| 355 | N-{(2S,3R)-4,4-difluoro-1-(oxetane-2-carbonyl)-2-[(2,2',3'-trifliioro[1,1'-biphenyl]-3-yl)methyl]pyrrolidin-3-yl}-ethanesulfonamide derived from N-[(2S,3R)-2-[(3-chloro-2-fluorophenyl)-methyl]-4,4-difluoro-1-(oxetane-2-carbonyl)pyrrolidin-3-yl]ethanesulfon-amide with shorter retention time by HPLC (column: L-Column2 ODS (3.0 mml · D. × 50 mmL,3μm), mobile phase: water/acetonitrile (including 0.05% TFA) | 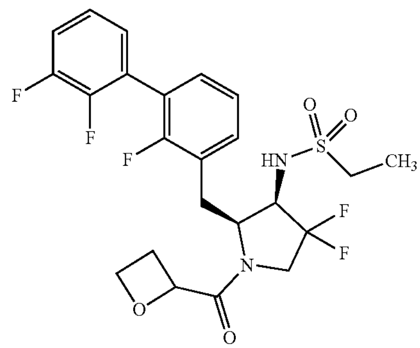 [SMILES: CCS(=O)(=O)N[C@@H]1[C@H](Cc2cccc(-c3cccc(F)c3F)c2F)N(C(=O)C2CCO2)CC1(F)F] | | 519.1 |
| 356 | N-{(2S,3R)-4,4-difluoro-1-(oxetane-2-carbonyl)-2-[(2,2',5'-trifluoro[1,1'-biphenyl]-3-yl)methyl]pyrrolidin-3-yl}ethanesulfonamide derived from N-[(2S,3R)-2-[(3-chloro-2-fluorophenyl)-methyl]-4,4-difluoro-1-(oxetane-2-carbonyl)pyrrolidin-3-yl]ethanesulfon-amide with shorter retention time by HPLC (column: L-Column2 ODS (3.0 mml · D. × 50 mmL, 3 μm), mobile phase: water/acetonitrile (including 0.05% TFA) | 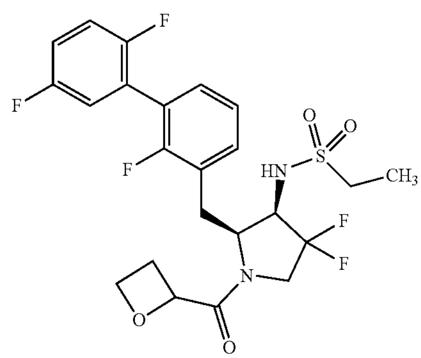 [SMILES: CCS(=O)(=O)N[C@@H]1[C@H](Cc2cccc(-c3cc(F)ccc3F)c2F)N(C(=O)C2CCO2)CC1(F)F] | | 519.2 |
| 357 | N-[(2S,3R)-4,4-difluoro-2-[(3'-fluoro[1,1'-biphenyl]-3-yl)methyl]-1-(oxetane-2-carbonyl)pyrrolidin-3-yl]cyclopropane-sulfonamide with shorter retention time | 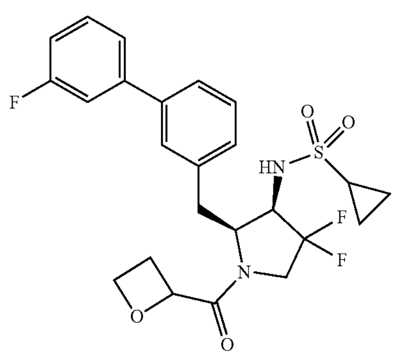 [SMILES: O=C(C1CCO1)N1CC(F)(F)[C@H](NS(=O)(=O)C2CC2)[C@@H]1Cc1cccc(-c2cccc(F)c2)c1] | | 495.2 |

TABLE 1-1-continued

| EX. | IUPAC NAME | Structure | ADDITIVE | MS |
|---|---|---|---|---|
| 358 | N-[(2S,3R)-4,4-difluoro-2-[(3'-fluoro[1,1'-biphenyl]-3-yl)methyl]-1-(oxetane-2-carbonyl)pyrrolidin-3-yl]cyclopropane-sulfonamide with longer retention time | 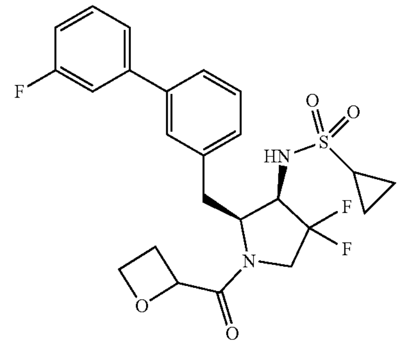 [SMILES: O=C(C1CCO1)N1CC(F)(F)[C@H](NS(=O)(=O)C2CC2)[C@@H]1Cc1cccc(-c2cccc(F)c2)c1] | | 495.2 |
| 359 | rac-N-{(2S,3R,4S)-4-fluoro-1-(2-hydroxy-2-methylpropanoyl)-4-methyl-2-[(2,3',5'-trifluoro[1,1'-biphenyl]-3-yl)methyl]-pyrrolidin-3-yl}ethanesulfonamide | 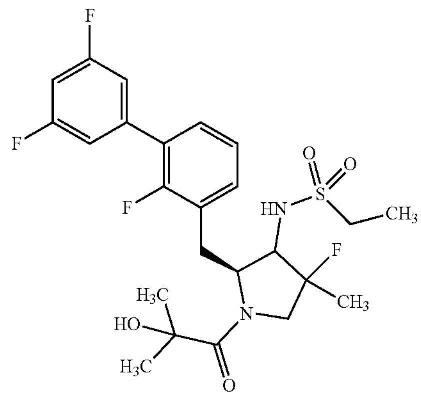 [SMILES: CCS(=O)(=O)NC1[C@H](Cc2cccc(-c3cc(F)cc(F)c3)c2F)N(C(=O)C(C)(C)O)CC1(C)F] | | 517.3 |
| 360 | N-[(2S,3R,4S)-2-[(2,2'-difluoro[1,1'-biphenyl]-3-yl)methyl]-4-fluoro-1-(2-methylpropanoyl)pyrrolidin-3-yl]-methanesulfonamide | 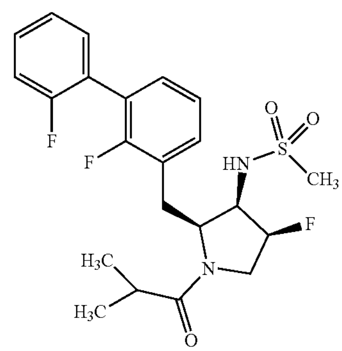 [SMILES: CC(C)C(=O)N1C[C@H](F)[C@H](NS(C)(=O)=O)[C@@H]1Cc1cccc(-c2ccccc2F)c1F] | | 455.2 |
| 361 | N-{(2S,3R,4S)-1-(bicyclo[1.1.1]pentane-1-carbonyl-4-fluoro-2-[(2,2',3'-trifluoro[1,1'-biphenyl]-3-yl)methyl]pyrrolidin-3-yl}-methanesulfonamide | 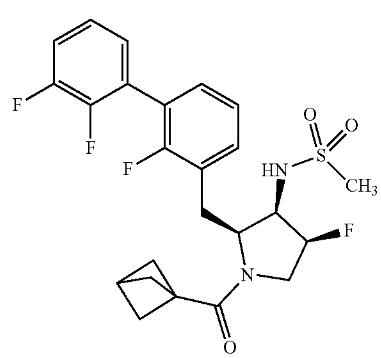 [SMILES: CS(=O)(=O)N[C@H]1[C@@H](F)CN(C(=O)C23CC(C2)C3)[C@H]1Cc1cccc(-c2cccc(F)c2F)c1F] | | 497.2 |

TABLE 1-1-continued

| EX. | IUPAC NAME | Structure | ADDITIVE | MS |
|---|---|---|---|---|
| 362 | N-{(2S,3R,4S)-1-(bicyclo[1.1.1]pentane-1-carbonyl)-4-fluoro-2-[(2-fluoro[1,1'-biphenyl]-3-yl)methyl]pyrrolidin-3-yl}methanesulfonamide | 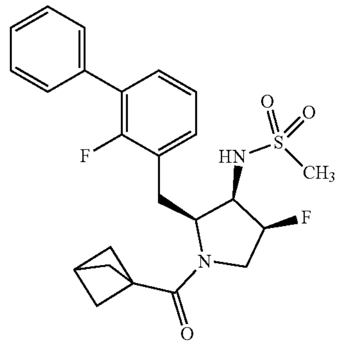 [SMILES: CS(=O)(=O)N[C@H]1[C@@H](F)CN(C(=O)C23CC(C2)C3)[C@H]1Cc1cccc(-c2ccccc2)c1F] | | 461.2 |
| 363 | N-{(2S,3R,4S)-1-(bicyclo[1.1.1]pentane-1-carbonyl)-4-fluoro-2-[(2,2',5'-trifluoro[1,1'-biphenyl]-3-yl)methyl]pyrrolidin-3-yl}-methanesulfonamide | 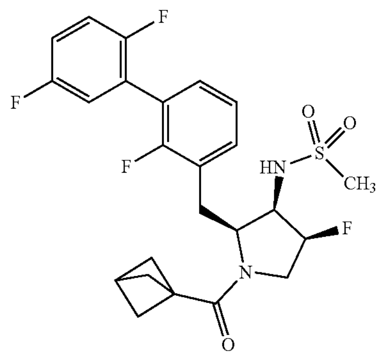 [SMILES: CS(=O)(=O)N[C@H]1[C@@H](F)CN(C(=O)C23CC(C2)C3)[C@H]1Cc1cccc(-c2cc(F)ccc2F)c1F] | | 497.2 |
| 364 | N-[{2S,3R,4S)-4-fluoro-2-[(3'-fluoro[1,1'-biphenyl]-3-yl)methyl]-1-(1-hydroxy-cyclobutane-1-carbonyl)pyrrolidin-3-yl]-ethanesulfonamide | 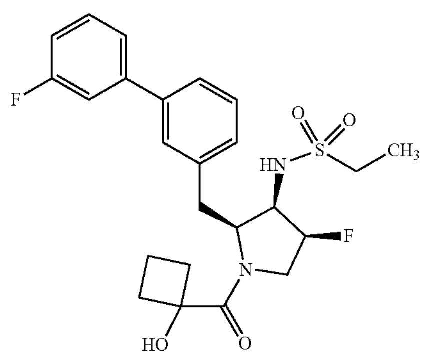 [SMILES: CCS(=O)(=O)N[C@H]1[C@@H](F)CN(C(=O)C2(O)CCC2)[C@H]1Cc1cccc(-c2cccc(F)c2)c1] | | 479.2 |
| 365 | N-{(2S,3R,4S)-1-(bicyclo[1.1.1]pentane-1-carbonyl)-4-fluoro-2-[(2,3',5'-trifluoro[1,1'-biphenyl]-3-yl)methyl]pyrrolidin-3-yl}-ethanesulfonamide | 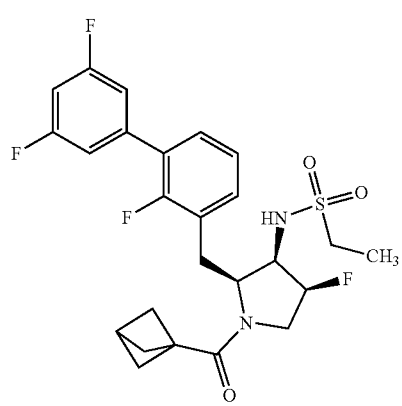 [SMILES: CCS(=O)(=O)N[C@H]1[C@@H](F)CN(C(=O)C23CC(C2)C3)[C@H]1Cc1cccc(-c2cc(F)cc(F)c2)c1F] | | 511.2 |

TABLE 1-1-continued

| EX. | IUPAC NAME | Structure | ADDITIVE | MS |
|---|---|---|---|---|
| 366 | N-{(2S,3R,4S)-1-(bicyclo[1.1.1]pentane-1-carbonyl)-4-fluoro-2-[(2,2',3'-trifluoro[1,1'-biphenyl]-3-yl)methyl]pyrrolidin-3-yl}-ethanesulfonamide | 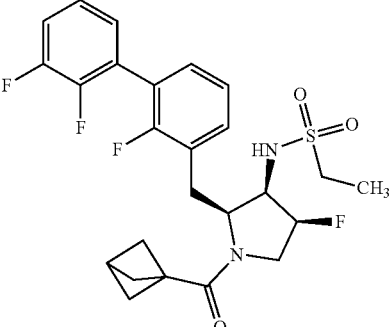 | | 511.1 |
| 367 | N-[(2S,3R,4S)-2-[(2,2'-difluoro(1,1'-biphenyl]-3-yl)methyl]-4-fluoro-1-(oxetane-2-carbonyl)pyrrolidin-3-yl]-ethanesulfonamide with longer retention time | 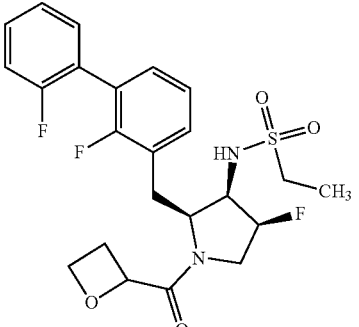 | | 483.2 |
| 368 | N-[(2S,3R,4S)-2-[(3'-chloro-2-fluoro[1,1'-biphenyl]-3-yl)methyl]-4-fluoro-1-(oxetane-2-carbonyl)pyrrolidin-3-yl]-ethanesulfonamide with longer retention time | 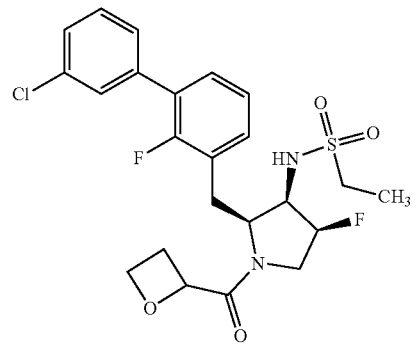 [SMILES: CCS(=O)(=O)N[C@H]1[C@@H](F)CN(C(=O)C2CCO2)[C@H]1Cc1cccc(-c2cccc(Cl)c2)c1F] | | 499.2 |
| 369 | N-[(2S,3R,4S)-2-[(2,3'-difluoro[1,1'-biphenyl]-3-yl)methyl]-4-fluoro-1-(2-hydroxy-2-methylpropanoyl)pyrrolidin-3-yl]cyclopropanesulfonamide | 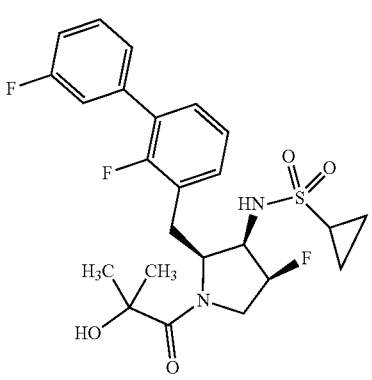 [SMILES: CC(C)(O)C(=O)N1C[C@H](F)[C@H](NS(=O)(=O)C2CC2)[C@@H]1Cc1cccc(-c2cccc(F)c2)c1F] | | 497.2 |

TABLE 1-1-continued

| EX. | IUPAC NAME | Structure | ADDITIVE | MS |
|---|---|---|---|---|
| 370 | N-{(2S,3R,4S)-4-fluoro-1-(2-hydroxy-2-methylpropanoyl)-2-[(2,3',5',-trifluoro[1,1'-biphenyl]-3-yl)methyl]pyrrolidin-3-yl}-cyclopropanesulfonamide | 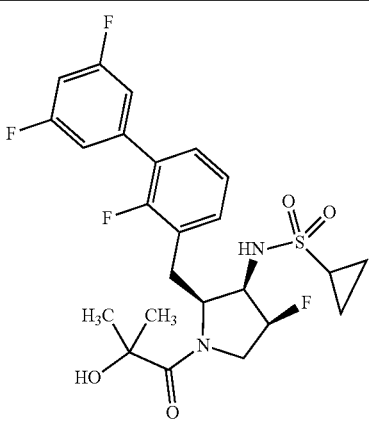 | | 515.2 |
| 371 | N-{(2S,3R,4S)-4-fluoro-1-(2-hydroxy-2-methylpropanoyl)-2-[(2,2',3'-trifluoro[1,1'-biphenyl]-3-yl)methyl]pyrrolidin-3-yl}-cyclopropanesulfonamide | 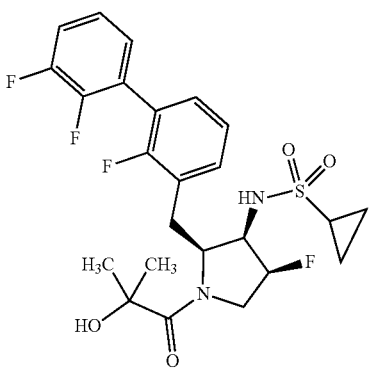 [SMILES: CC(C)(O)C(=O)N1C[C@H](F)[C@H](NS(=O)(=O)C2CC2)[C@@H]1Cc1cccc(-c2cccc(F)c2F)c1F] | | 515.1 |
| 372 | N-{(2S,3R,4S)-1-(cyclopropanecarbonyl)-2-[(2,3'-difluoro[1,1'-biphenyl]-3-yl)methyl]-4-fluoropyrrolidin-3-yl}cyclopropane-sulfonamide | 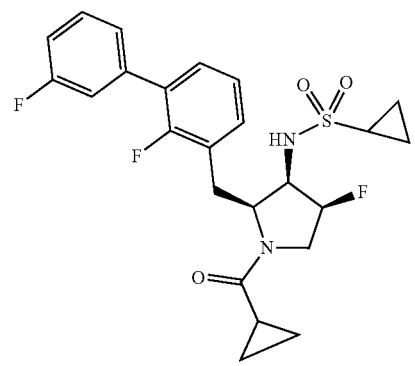 [SMILES: O=C(C1CC1)N1C[C@H](F)[C@H](NS(=O)(=O)C2CC2)[C@@H]1Cc1cccc(-c2cccc(F)c2)c1F] | | 479.2 |
| 373 | N-{(2S,3R,4S)-1-(cyclopropanecarbonyl)-4-fluoro-2-[(2,3',5'-trifluoro[1,1'-biphenyl]-3-yl)methyl]pyrrolidin-3-yl}cyclopropane-sulfonamide | 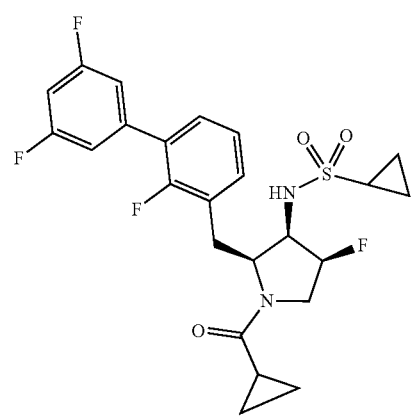 [SMILES: O=C(C1CC1)N1C[C@H](F)[C@H](NS(=O)(=O)C2CC2)[C@@H]1Cc1cccc(-c2cc(F)cc(F)c2)c1F] | | 497.2 |

TABLE 1-1-continued

| EX. | IUPAC NAME | Structure | ADDITIVE | MS |
|---|---|---|---|---|
| 374 | N-{(2S,3R,4S)-1-(bicyclo[1.1.1]pentane-1-carbonyl)-4-fluoro-2-[(2,3',5'-trifluoro[1,1'-biphenyl]-3-yl)methyl]pyrrolidin-3-yl}-methanesulfonamide | 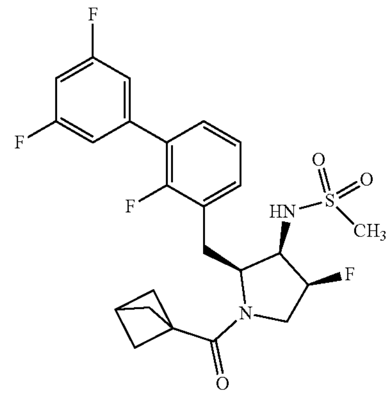 [SMILES: CS(=O)(=O)N[C@H]1[C@@H](F)CN(C(=O)C23CC(C2)C3)[C@H]1Cc1cccc(-c2cc(F)cc(F)c2)c1F] | | 497.2 |
| 375 | N-{(2S,3R)-4,4-difluoro-1-((1r,3S)-3-fluorocyclobutane-1-carbonyl)-2-[(2,3',5'-trifluoro[1,1'-biphenyl]-3-yl)methyl]-pyrrolidin-3-yl}ethanesulfonamide | 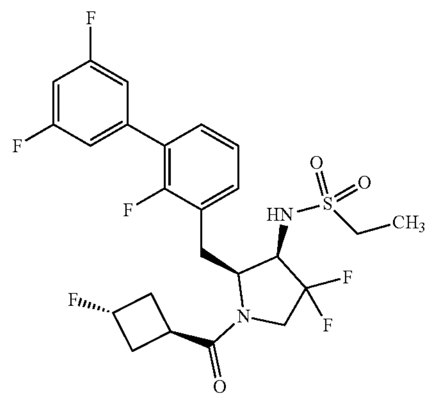 [SMILES: CCS(=O)(=O)N[C@@H]1[C@H](Cc2cccc(-c3cc(F)cc(F)c3)c2F)N(C(=O)[C@H]2C[C@H](F)C2)CC1(F)F] | | 533.2 |
| 376 | N-{(2S,3R)-4,4-difluoro-1-((1r,3S)-3-fluorocyclobutane-1-carbonyl)-2-[(2,2',5'-trifluoro[1,1'-biphenyl]-3-yl)methyl]-pyrrolidin-3-yl}ethanesulfonamide | 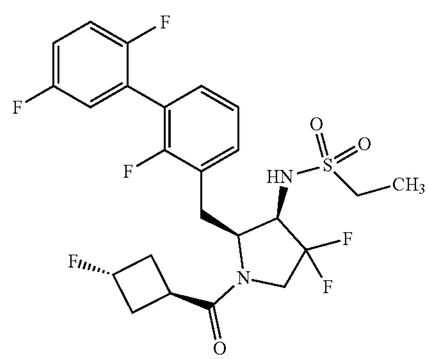 [SMILES: CCS(=O)(=O)N[C@@H]1[C@H](Cc2cccc(-c3cc(F)ccc3F)c2F)N(C(=O)[C@H]2C[C@H](F)C2)CC1(F)F] | | 533.2 |
| 377 | N-{(2S,3R,4S)-1-(cyclopropanecarbonyl)-4-fluoro-2-[(2,2',3'-trifluoro[1,1'-biphenyl]-3-yl)methyl]pyrrolidin-3-yl}cyclopropane-sulfonamide | 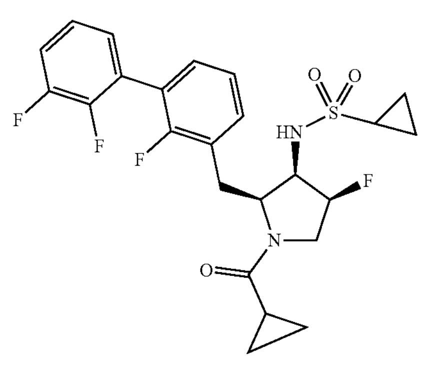 [SMILES: O=C(C1CC1)N1C[C@H](F)[C@H](NS(=O)(=O)C2CC2)[C@@H]1Cc1cccc(-c2cccc(F)c2F)c1F] | | 497.2 |

TABLE 1-1-continued

| EX. | IUPAC NAME | Structure | ADDITIVE | MS |
|---|---|---|---|---|
| 378 | N-[(2S,3R)-4,4-difluoro-2-[(2-fluoro[1,1'-biphenyl]-3-yl)methyl]-1-((1r,3S)-3-fluorocyclobutane-1-carbonyl)pyrrolidin-3-yl]ethanesulfonamide | 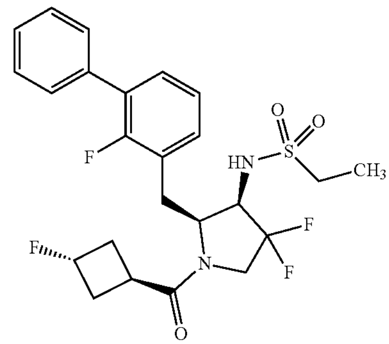 [SMILES: CCS(=O)(=O)N[C@@H]1[C@H](Cc2cccc(-c3ccccc3)c2F)N(C(=O)[C@H]2C[C@H](F)C2)CC1(F)F] | | 497.2 |
| 379 | N-{(2S,3R,4S)-1-(cyclopropanecarbonyl)-4-fluoro-2-[(2,2',5'-trifluoro[1,1'-biphenyl]-3-yl)methyl]pyrrolidin-3-yl}cyclopropane-sulfonamide | 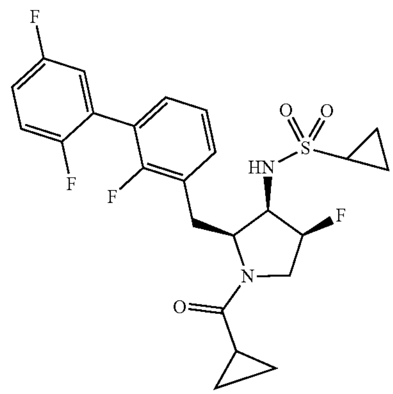 [SMILES: O=C(C1CC1)N1C[C@H](F)[C@H](NS(=O)(=O)C2CC2)[C@@H]1Cc1cccc(-c2cc(F)ccc2F)c1F] | | 497.2 |
| 380 | N-{(2S,3R)-4,4-difluoro-1-((1s,3R)-3-fluorocyclobutane-1-carbonyl)-2-[(2,3',5'-trifluoro[1,1'-biphenyl]-3-yl)methyl]-pyrrolidin-3-yl}ethanesulfonamide | 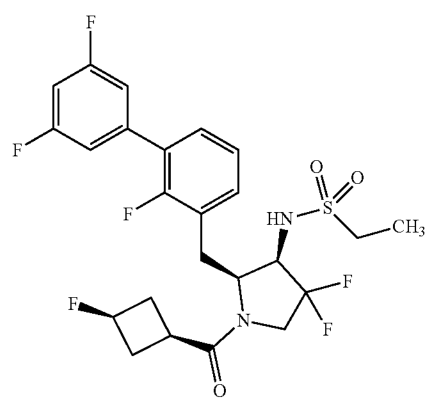 [SMILES: CCS(=O)(=O)N[C@@H]1[C@H](Cc2cccc(-c3cc(F)cc(F)c3)c2F)N(C(=O)[C@H]2C[C@@H](F)C2)CC1(F)F] | | 533.2 |
| 381 | N-{(2S,3R)-4,4-difluoro-1-((1s,3R)-3-fluorocyclobutane-1-carbonyl)-2-[(2,2',5'-trifluoro[1,1'-biphenyl]-3-yl)methyl]-pyrrolidin-3-yl}ethanesulfonamide | 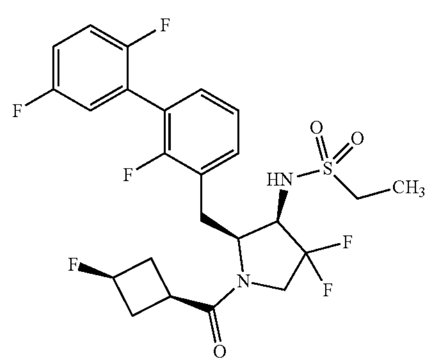 [SMILES: CCS(=O)(=O)N[C@@H]1[C@H](Cc2cccc(-c3cc(F)ccc3F)c2F)N(C(=O)[C@H]2C[C@@H](F)C2)CC1(F)F] | | 533.2 |

TABLE 1-1-continued

| EX. | IUPAC NAME | Structure | ADDITIVE | MS |
|---|---|---|---|---|
| 382 | N-[(2S,3R,4S)-2-[(2,3'-difluoro[1,1'-biphenyl]-3-yl)methyl]-4-fluoro-1-(2-methylpropanoyl)pyrrolidin-3-yl]-cyclopropanesulfonamide | 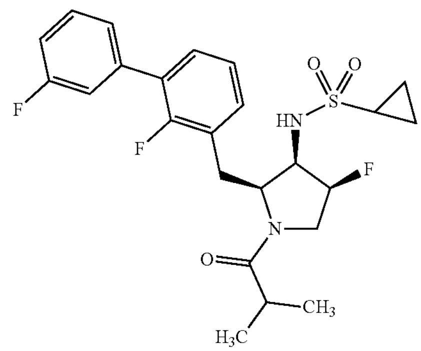 [SMILES: CC(C)C(=O)N1C[C@H](F)[C@H](NS(=O)(=O)C2CC2)[C@@H]1Cc1cccc(-c2cccc(F)c2)c1F] | | 481.2 |
| 383 | N-[(2S,3R)-4,4-difluoro-2-[(2-fluoro[1,1'-biphenyl]-3-yl)methyl]-1-((1s,3R)-3-fluorocyclobutane-1-carbonyl)pyrrolidin-3-yl]ethanesulfonamide | 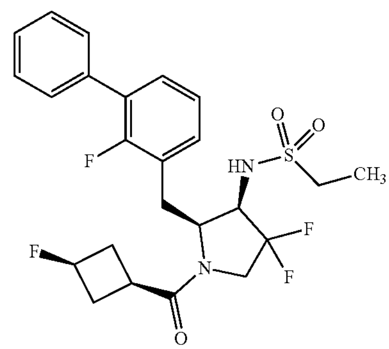 [SMILES: CCS(=O)(=O)N[C@@H]1[C@H](Cc2cccc(-c3ccccc3)c2F)N(C(=O)[C@H]2C[C@@H](F)C2)CC1(F)F] | | 499.2 |
| 384 | N-{(2S,3R,4S)-1-(bicyclo[1.1.1]pentane-1-carbonyl)-2-[(2,3'-difluoro[1,r-biphenyl]-3-yl)methyl]-4-fluoropyrrolidin-3-yl}cyclopropanesulfonamide | 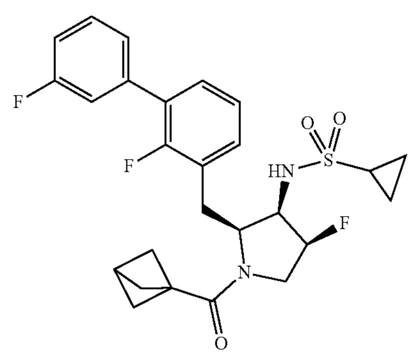 [SMILES: O=C(N1C[C@H](F)[C@H](NS(=O)(=O)C2CC2)[C@@H]1Cc1cccc(-c2cccc(F)c2)c1F)C12CC(C1)C2] | | 505.2 |
| 385 | N-[(2S,3R,4S)-2-[(2,3'-difluoro[1,1'-biphenyl]-3-yl)methyl]-4-fluoro-1-(oxetane-2-carbonyl)pyrrolidin-3-yl]-cyclopropanesulfonamide with shorter retention time | 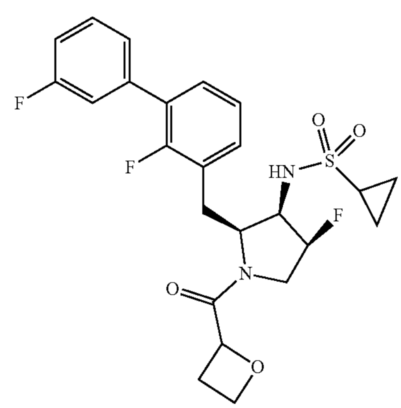 [SMILES: O=C(C1CCO1)N1C[C@H](F)[C@H](NS(=O)(=O)C2CC2)[C@@H]1Cc1cccc(-c2cccc(F)c2)c1F] | | 495.1 |

TABLE 1-1-continued

| EX. | IUPAC NAME | Structure | ADDITIVE | MS |
|---|---|---|---|---|
| 386 | N-[{2S,3R,4S)-2-[(2,3'-difluoro[1,1'-biphenyl]-3-yl)methyl]-4-fluoro-1-(oxetane-2-carbonyl)pyrrolidin-3-yl]-cyclopropanesulfonamide with longer retention time | 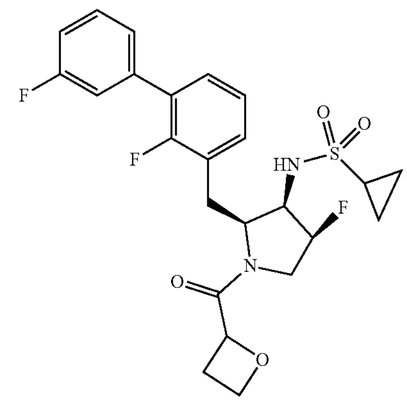 [SMILES: O=C(C1CCO1)N1C[C@H](F)[C@H](NS(=O)(=O)C2CC2)[C@@H]1Cc1cccc(-c2cccc(F)c2)c1F] | | 495.2 |
| 387 | (2S,3R,4S)-3-[(cyclopropanesulfonyl)-amino]-2-[(2,3'-difluoro[1,1'-biphenyl]-3-yl)methyl]-4-fluoro-N,N-dimethyl-pyrrolidine-1-carboxamide | 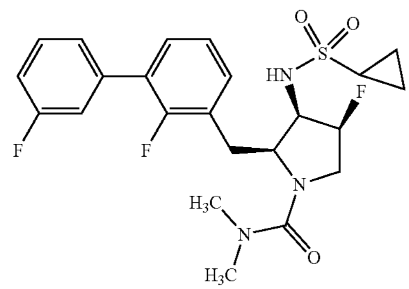 [SMILES: CN(C)C(=O)N1C[C@H](F)[C@H](NS(=O)(=O)C2CC2)[C@@H]1Cc1cccc(-c2cccc(F)c2)c1F] | | 482.2 |
| 388 | N-[(2S,3R,4S)-2-[(3'-chloro-2-fluoro[1,1'-biphenyl]-3-yl)methyl]-4-fluoro-1-(2-hydroxy-2-methylpropanoyl)pyrrolidin-3-yl]methanesulfonamide | 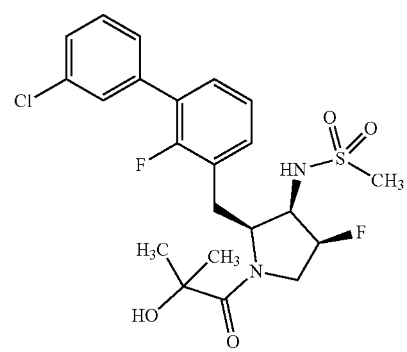 [SMILES: CC(C)(O)C(=O)N1C[C@H](F)[C@H](NS(C)(=O)=O)[C@@H]1Cc1cccc(-c2cccc(Cl)c2)c1F] | | 487.1 |
| 389 | N-[(2S,3R,4S)-2-[(3'-chloro-2,2'-difluoro-[1,1'-biphenyl]-3-yl)methyl]-4-fluoro-1-(2-hydroxy-2-methylpropanoyl)pyrrolidin-3-yl]methanesulfonamide | 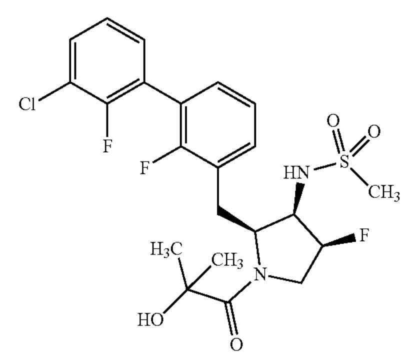 [SMILES: CC(C)(O)C(=O)N1C[C@H](F)[C@H](NS(C)(=O)=O)[C@@H]1Cc1cccc(-c2cccc(Cl)c2F)c1F] | | 505.1 |

TABLE 1-1-continued

| EX. | IUPAC NAME | Structure | ADDITIVE | MS |
|---|---|---|---|---|
| 390 | N-[(2S,3R,4S)-2-[(5'-chloro-2,2'-difluoro-[1,1'-biphenyl]-3-yl)methyl]-4-fluoro-1-(2-hydroxy-2-methylpropanoyl)pyrrolidin-3-yl]methanesulfonamide | 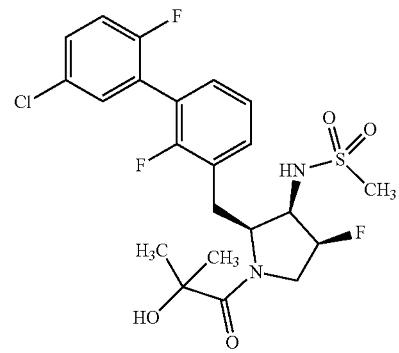 [SMILES: CC(C)(O)C(=O)N1C[C@H](F)[C@H](NS(C)(=O)=O)[C@@H]1Cc1cccc(-c2cc(Cl)ccc2F)c1F] | | 505.1 |
| 391 | N-[(2S,3R,4S)-2-[(3'-chloro-2,5'-difluoro-[1,1'-biphenyl]-3-yl)methyl]-4-fluoro-1-(2-hydroxy-2-methylpropanoyl)pyrrolidin-3-yl]methanesulfonamide | 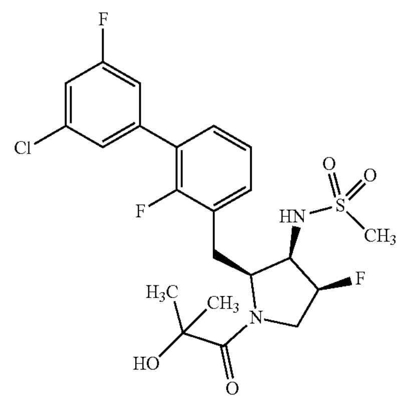 [SMILES: CC(C)(O)C(=O)N1C[C@H](F)[C@H](NS(C)(=O)=O)[C@@H]1Cc1cccc(-c2cc(F)cc(Cl)c2)c1F] | | 505.1 |
| 392 | N-[(2S,3R)-2-[(2,3'-difluoro[1,1'-biphenyl]-3-yl)methyl]-4,4-difluoro-1-(3-fluoro-cyclobutane-1-carbonyl)pyrrolidin-3-yl]-methanesulfonamide with longer retention time | 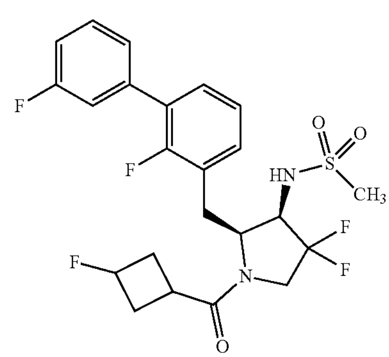 [SMILES: CS(=O)(=O)N[C@@H]1[C@H](Cc2cccc(-c3cccc(F)c3)c2F)N(C(=O)C2CC(F)C2)CC1(F)F] | | 501.2 |
| 393 | N-[(2S,3R)-2-[(2,3'-difluoro[1,1'-biphenyl]-3-yl)methyl]-4,4-difluoro-1-(3-fluoro-cyclobutane-1-carbonyl)pyrrolidin-3-yl]-methanesulfonamide with shorter retention time | 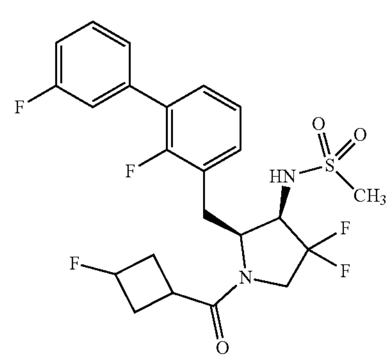 [SMILES: CS(=O)(=O)N[C@@H]1[C@H](Cc2cccc(-c3cccc(F)c3)c2F)N(C(=O)C2CC(F)C2)CC1(F)F] | | 501.2 |

| EX. | IUPAC NAME | ADDITIVE | MS |
|---|---|---|---|
| 394 | N-[(2S,3R)-2-[(2,3'-difluoro-5'-methyl[1,1'-biphenyl]-3-yl)methyl]-4,4-difluoro-1-(1-hydroxycyclobutane-1-carbonyl)pyrrolidin-3-yl]ethanesulfonamide | | 529.1 |
| 395 | N-[(2S,3R,4S)-2-[([1,1'-biphenyl]-3-yl)-methyl]-1-(cyclopropanecarbonyl)-4-fluoropyrrolidin-3-yl]ethanesulfonamide | | 431.1 |
| 396 | N-{(2S,3R,4S)-1-(cyclopropanecarbonyl)-2-[(3',5'-difluoro[1,1'-biphenyl]-3-yl)-methyl]-4-fluoropyrrolidin-3-yl}-ethanesulfonamide | | 467.0 |
| 397 | N-{(2S,3R,4S)-1-(cyclopropanecarbonyl)-2-[(2',3'-difluoro[1,1'-biphenyl]-3-yl)-methyl]-4-fluoropyrrolidin-3-yl}-ethanesulfonamide | | 467.0 |

TABLE 1-1-continued

| EX. | IUPAC NAME | Structure | ADDITIVE | MS |
|---|---|---|---|---|
| 398 | N-{(2S,3R,4S)-1-(cyclopropanecarbonyl)-2-[(2',5'-difluoro[1,1'-biphenyl]-3-yl)-methyl]-4-fluoropyrrolidin-3-yl}ethane-sulfonamide | 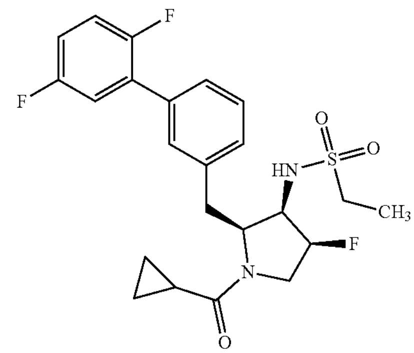 [SMILES: CCS(=O)(=O)N[C@H]1[C@@H](F)CN(C(=O)C2CC2)[C@H]1Cc1cccc(-c2cc(F)ccc2F)c1] | | 467.0 |
| 399 | N-{(2S,3R,4S)-1-(cyclopropanecarbonyl)-4-fluoro-2-[(2'-fluoro[1,1'-biphenyl]-3-yl)methyl]pyrrolidin-3-yl}ethane-sulfonamide | 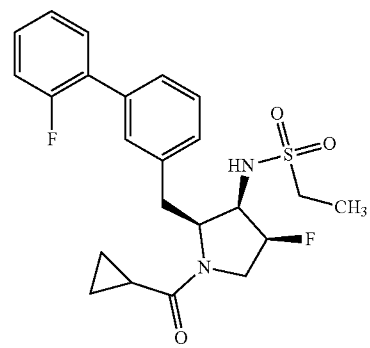 [SMILES: CCS(=O)(=O)N[C@H]1[C@@H](F)CN(C(=O)C2CC2)[C@H]1Cc1cccc(-c2ccccc2F)c1] | | 449.1 |
| 400 | N-[(2S,3R,4S)-4-fluoro-2-[(3'-fluoro[1,1'-biphenyl]-3-yl)methyl]-1-(2-methyl-propanoyl)pyrrolidin-3-yl]ethane-sulfonamide | 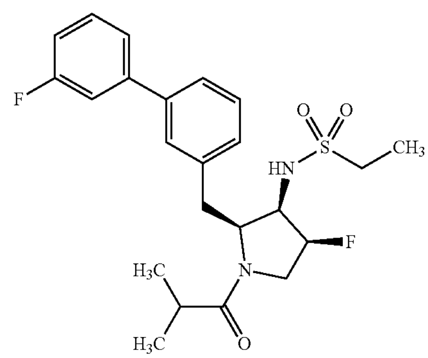 | | 451.1 |
| 401 | N-{(2S,3R,4S)-1-(bicyclo[1.1.1]pentane-1-carbonyl)-4-fluoro-2-[(3'-fluoro[1,1'-biphenyl]-3-yl)methyl]pyrrolidin-3-yl}-ethanesulfonamide | 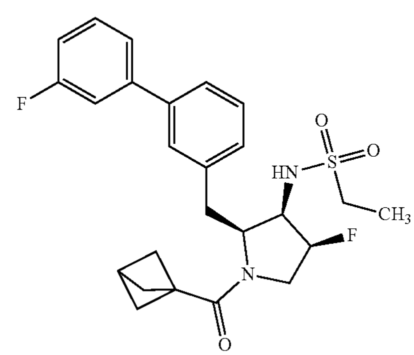 [SMILES: CCS(=O)(=O)N[C@H]1[C@@H](F)CN(C(=O)C23CC(C2)C3)[C@H]1Cc1cccc(-c2cccc(F)c2)c1] | | 475.0 |

TABLE 1-1-continued

| EX. | IUPAC NAME | Structure | ADDITIVE | MS |
|---|---|---|---|---|
| 402 | N-{(2S,3R,4S)-4-fluoro-2-[(3'-fluoro[1,1'-biphenyl]-3-yl)methyl]-1-[(2S)-oxolane-2-carbonyl]pyrrolidin-3-yl}ethanesulfonamide | 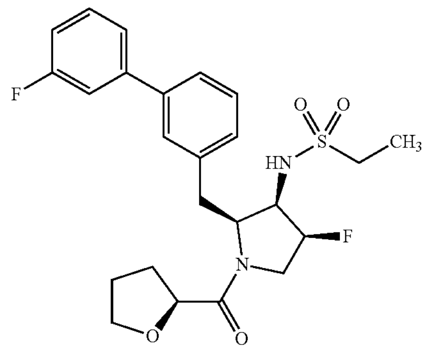 [SMILES: CCS(=O)(=O)N[C@H]1[C@@H](F)CN(C(=O)[C@@H]2CCCO2)[C@H]1Cc1cccc(-c2cccc(F)c2)c1] | | 479.0 |
| 403 | N-{(2S,3R,4S)-4-fluoro-2-[(3'-fluoro[1,1'-biphenyl]-3-yl)methyl]-1-[(2R)-oxolane-2-carbonyl]pyrrolidin-3-yl}ethanesulfonamide | 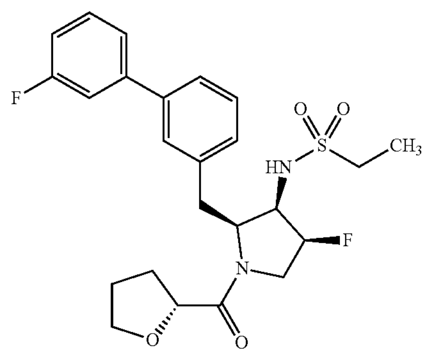 [SMILES: CCS(=O)(=O)N[C@H]1[C@@H](F)CN(C(=O)[C@H]2CCCO2)[C@H]1Cc1cccc(-c2cccc(F)c2)c1] | | 479.0 |
| 404 | (2S,3R,4S)-3-[(ethanesulfonyl)amino]-4-fluoro-2-[(3'-fluoro[1,1'-biphenyl]-3-yl)methyl]-N,N-dimethylpyrrolidine-1-carboxamide | 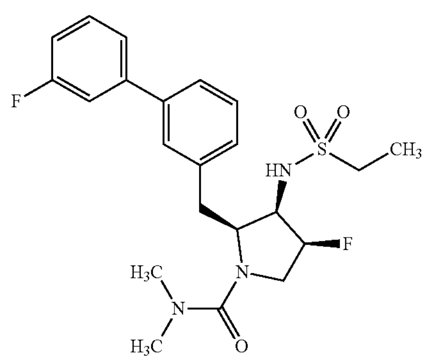 [SMILES: CCS(=O)(=O)N[C@H]1[C@@H](F)CN(C(=O)N(C)C)[C@H]1Cc1cccc(-c2cccc(F)c2)c1] | | 452.0 |
| 405 | N-{(2S,3R,4S)-1-(azetidine-1-carbonyl)-4-fluoro-2-[(3'-fluoro[1,1'-biphenyl]-3-yl)-methyl]pyrrolidin-3-yl}ethanesulfonamide | 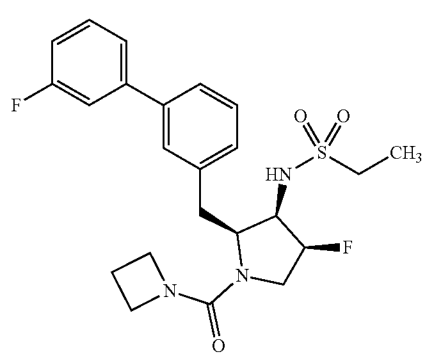 [SMILES: CCS(=O)(=O)N[C@H]1[C@@H](F)CN(C(=O)N2CCC2)[C@H]1Cc1cccc(-c2cccc(F)c2)c1] | | 464.0 |

TABLE 1-1-continued

| EX. | IUPAC NAME | Structure | ADDITIVE | MS |
|---|---|---|---|---|
| 406 | N-[(2S,3R,4S)-4-fluoro-2-[(3'-fluoro[1,1'-biphenyl]-3-yl)methyl]-1-(oxetane-2-carbonyl)pyrrolidin-3-yl]ethanesulfonamide with longer retention time | 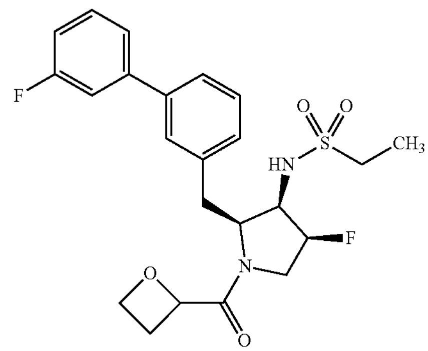 [SMILES: CCS(=O)(=O)N[C@H]1[C@@H](F)CN(C(=O)C2CCO2)[C@H]1Cc1cccc(-c2cccc(F)c2)c1] | | 465.0 |
| 407 | N-[(2S,3R,4S)-4-fluoro-2-[(3'-fluoro[1,1'-biphenyl]-3-yl)methyl]-1-(oxetane-2-carbonyl)pyrrolidin-3-yl]ethanesulfonamide with shorter retention time | 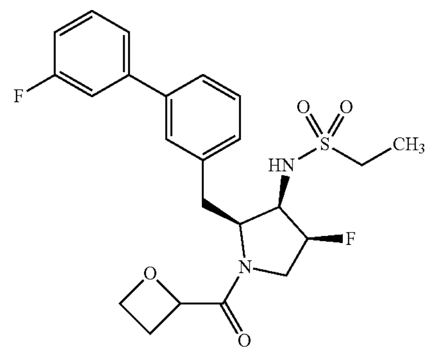 [SMILES: CCS(=O)(=O)N[C@H]1[C@@H](F)CN(C(=O)C2CCO2)[C@H]1Cc1cccc(-c2cccc(F)c2)c1] | | 465.0 |
| 408 | (2S,3R,4S)-2-[(2,2'-difluoro-3'-methyl[1,1'-biphenyl]-3-yl)methyl]-3-[(ethanesulfonyl)-amino]-4-fluoro-N,N-dimethylpyrrolidine-1-carboxamide | 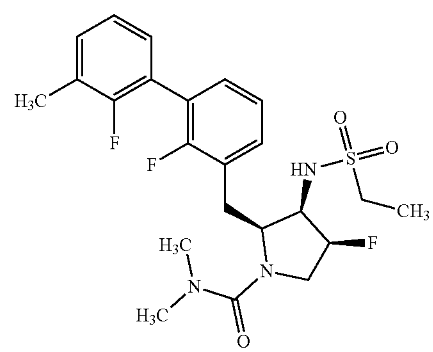 [SMILES: CCS(=O)(=O)N[C@H]1[C@@H](F)CN(C(=O)N(C)C)[C@H]1Cc1cccc(-c2cccc(C)c2F)c1F] | | 484.0 |
| 409 | (2S,3R,4S)-2-[(2,4'-difluoro-3'-methyl[1,1'-biphenyl]-3-yl)methyl]-3-[(ethanesulfonyl)-amino]-4-fluoro-N,N-dimethylpyrrolidine-1-carboxamide | 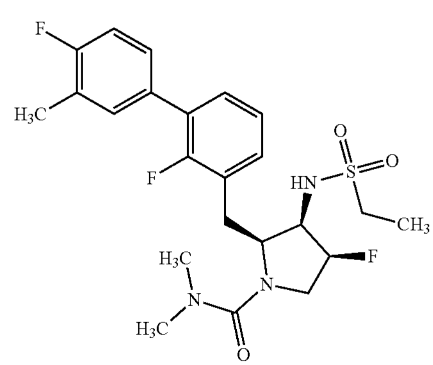 [SMILES: CCS(=O)(=O)N[C@H]1[C@@H](F)CN(C(=O)N(C)C)[C@H]1Cc1cccc(-c2ccc(F)c(C)c2)c1F] | | 484.0 |

TABLE 1-1-continued

| EX. | IUPAC NAME | Structure | ADDITIVE | MS |
|---|---|---|---|---|
| 410 | (2S,3R,4S)-2-[(2,3'-difluoro-5'-methyl[1,1'-biphenyl]-3-yl)methy)]-3-[(ethanesulfonyl)-amino]-4-fluoro-N,N-dimethylpyrrolidine-1-carboxamide | 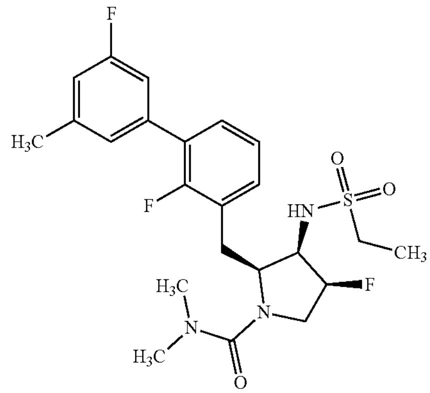 [SMILES: CCS(=O)(=O)N[C@H]1[C@@H](F)CN(C(=O)N(C)C)[C@H]1Cc1cccc(-c2cc(C)cc(F)c2)c1F] | | 484.0 |
| 411 | (2S,3R,4S)-2-[(2,2'-difluoro-5,-methyl[1,1'-biphenyl]-3-yl)methyl]-3-[(ethanesulfonyl)-amino]-4-fluoro-N,N-dimethylpyrrolidine-1-carboxamide | 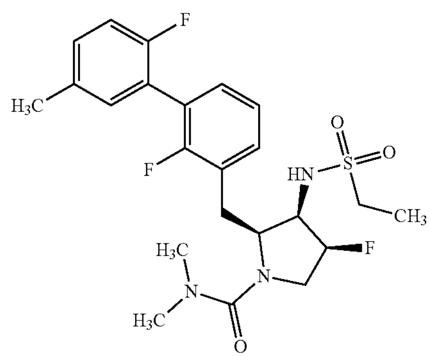 [SMILES: CCS(=O)(=O)N[C@H]1[C@@H](F)CN(C(=O)N(C)C)[C@H]1Cc1cccc(-c2cc(C)ccc2F)c1F] | | 484.0 |
| 412 | (2S,3R,4S)-2-[(2,4'-difluoro[1,1'-biphenyl]-3-yl)methyl]-3-[(ethanesulfonyl)amino]-4-fluoro-N,N-dimethylpyrrolidine-1-carboxamide | 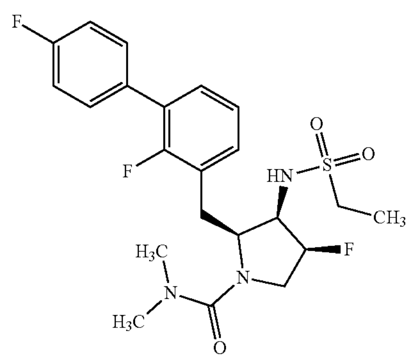 [SMILES: CCS(=O)(=O)N[C@H]1[C@@H](F)CN(C(=O)N(C)C)[C@H]1Cc1cccc(-c2ccc(F)cc2)c1F] | | 470.0 |
| 413 | N-{(2S,3R,4S)-4-fluoro-2-[(2-fluoro[1,1'-biphenyl]-3-yl)methyl]-1-[(2R)-oxolane-2-carbonyl]pyrrolidin-3-1}ethanesulfonamide | 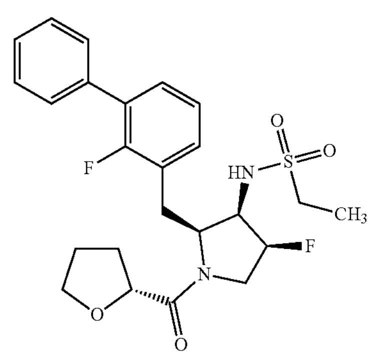 [SMILES: CCS(=O)(=O)N[C@H]1[C@@H](F)CN(C(=O)[C@H]2CCCO2)[C@H]1Cc1cccc(-c2ccccc2)c1F] | | 479.0 |

TABLE 1-1-continued

| EX. | IUPAC NAME | Structure | ADDITIVE | MS |
|---|---|---|---|---|
| 414 | N-{(2S,3R,4S)-4-fluoro-1-[(2R)-oxolane-2-carbonyl]-2-[(2,3',5'-trifluoro[1,1'-biphenyl]-3-yl)methyl]pyrrolidin-3-yl}-ethanesulfonamide | 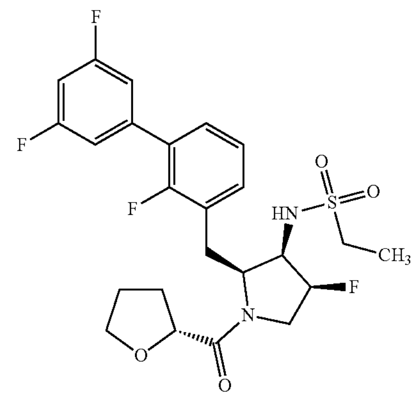 [SMILES: CCS(=O)(=O)N[C@H]1[C@@H](F)CN(C(=O)[C@H]2CCCO2)[C@H]1Cc1cccc(-c2cc(F)cc(F)c2)c1F] | | 515.0 |
| 415 | N-{(2S,3R,4S)-4-fluoro-1-[(2R)-oxolane-2-carbonyl]-2-[(2,2',3'-trifluoro[1,1'-biphenyl]-3-yl)methyl]pyrrolidin-3-yl}-ethanesulfonamide | 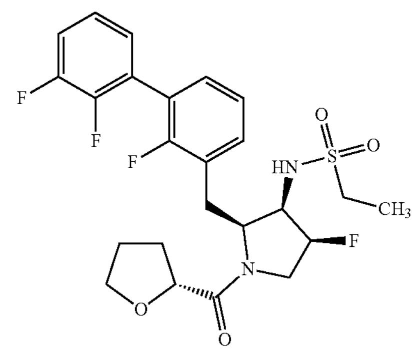 [SMILES: CCS(=O)(=O)N[C@H]1[C@@H](F)CN(C(=O)[C@H]2CCCO2)[C@H]1Cc1cccc(-c2cccc(F)c2F)c1F] | | 515.0 |
| 416 | N-[(2S,3R,4S)-4-fluoro-1-[(2R)-oxolane-2-carbonyl]-2-[(2,2',5'-trifluoro[1,1'-biphenyl]-3-yl)methyl]pyrrolidin-3-yl}-ethanesulfonamide | 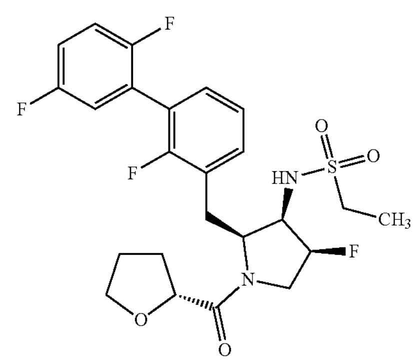 [SMILES: CCS(=O)(=O)N[C@H]1[C@@H](F)CN(C(=O)[C@H]2CCCO2)[C@H]1Cc1cccc(-c2cc(F)ccc2F)c1F] | | 515.0 |
| 417 | N-{(2S,3R,4S)-4-fluoro-2-[(2-fluoro-3'-methyl[1,1'-biphenyl]-3-yl)methyl]-1-[(2R)-oxolane-2-carbonyl]pyrrolidin-3-yl}ethanesulfonamide | 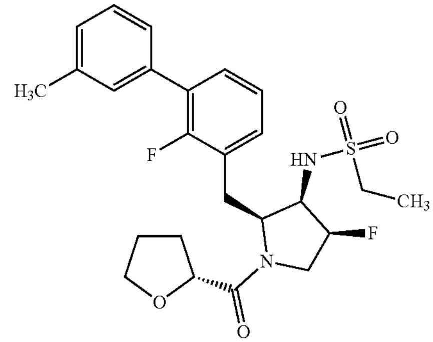 [SMILES: CCS(=O)(=O)N[C@H]1[C@@H](F)CN(C(=O)[C@H]2CCCO2)[C@H]1Cc1cccc(-c2cccc(C)c2)c1F] | | 493.0 |

TABLE 1-1-continued

| EX. | IUPAC NAME | Structure | ADDITIVE | MS |
|---|---|---|---|---|
| 418 | N-((2S,3R,4S)-2-[(2,2'-difluoro-3'-methyl-[1,1'-biphenyl]-3-yl)methyl]-4-fluoro-1-[(2R)-oxolane-2-carbonyl]pyrrolidin-3-yl}ethanesulfonamide | 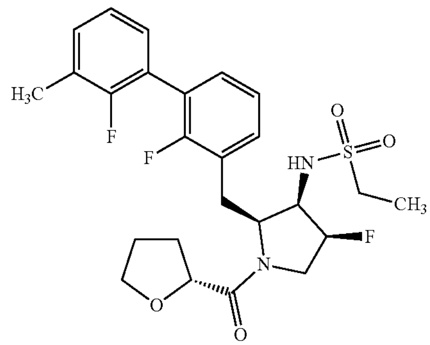 [SMILES: CCS(=O)(=O)N[C@H]1[C@@H](F)CN(C(=O)[C@H]2CCCO2)[C@H]1Cc1cccc(-c2cccc(C)c2F)c1F] | | 511.0 |
| 419 | N-((2S,3R,4S)-2-[(2,3'-difluoro-5'-methyl-[1,1'-biphenyl]-3-yl)methyl]-4-fluoro-1-[(2R)-oxolane-2-carbonyl]pyrrolidin-3-yl}ethanesulfonamide | 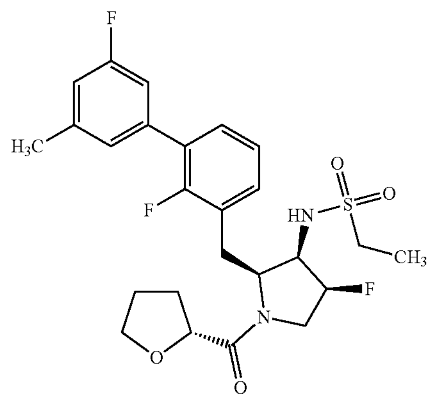 [SMILES: CCS(=O)(=O)N[C@H]1[C@@H](F)CN(C(=O)[C@H]2CCCO2)[C@H]1Cc1cccc(-c2cc(C)cc(F)c2)c1F] | | 511.0 |
| 420 | N-{(2S,3R,4S)-2-[(2,2'-difluoro-5'-methyl[1,1'-biphenyl]-3-yl)methyl]-4-fluoro-1-[(2R)-oxolane-2-carbonyl]pyrrolidin-3-yl}ethanesulfonamide | 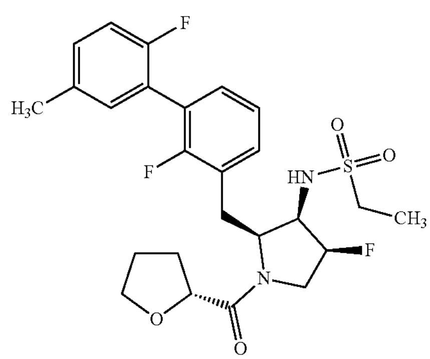 [SMILES: CCS(=O)(=O)N[C@H]1[C@@H](F)CN(C(=O)[C@H]2CCCO2)[C@H]1Cc1cccc(-c2cc(C)ccc2F)c1F] | | 511.0 |
| 421 | N-[2S,3R,4S)-2-[(2,2'-difluoro[1,1'-biphenyl]-3-yl)methyl]-4-fluoro-1-(oxetane-2-carbonyl)pyrrolidin-3-yl]-ethanesulfonamide with shorter retention time | 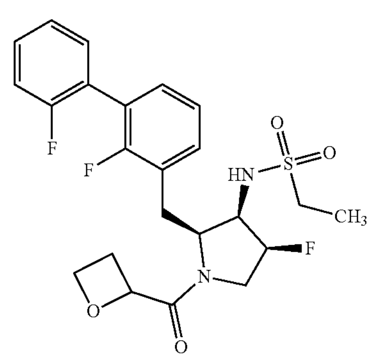 [SMILES: CCS(=O)(=O)N[C@H]1[C@@H](F)CN(C(=O)C2CCO2)[C@H]1Cc1cccc(-c2ccccc2F)c1F] | | 483.0 |

TABLE 1-1-continued

| EX. | IUPAC NAME | Structure | ADDITIVE | MS |
|---|---|---|---|---|
| 422 | N-[(2S,3R,4S)-2-[(3'-chloro-2-fluoro[1,1'-biphenyl]-3-yl)methyl]-4-fluoro-1-(oxetane-2-carbonyl)pyrrolidin-3-yl]-ethanesulfonamide with shorter retention time | 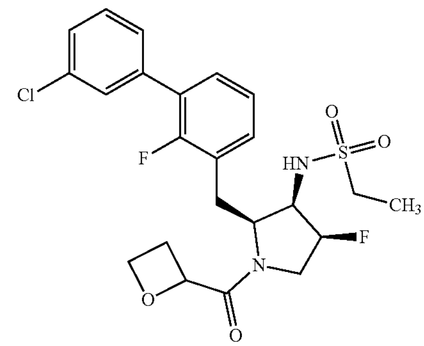 [SMILES: CCS(=O)(=O)N[C@H]1[C@@H](F)CN(C(=O)C2CCO2)[C@H]1Cc1cccc(-c2cccc(Cl)c2)c1F] | | 498.9 |
| 423 | N-[(2S,3R,4S)-2-[(3'-chloro-2,2'-difluoro-[1,1'-biphenyl]-3-yl)methyl]-4-fluoro-1-(oxetane-2-carbonyl)pyrrolidin-3-yl]-ethanesulfonamide derived from N-[(2S,3R,4S)-2-[(3-chloro-2-fluorophenyl)-methyl]-4-fluoro-1-(oxetane-2-carbonyl)-pyrrolidin-3-yl]ethanesulfonamide with shorter retention time by HPLC (column: L-Column2 ODS (3.0 mml · D. × 50mmL, 3 μm) mobile phase: water/acetonitrile (including 0.05% TFA) | 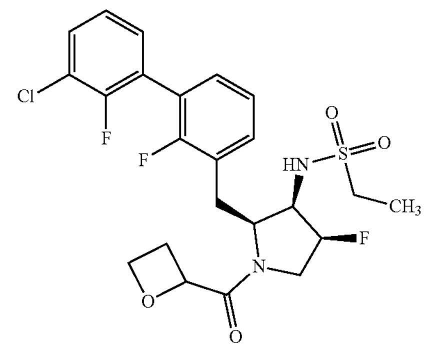 [SMILES: CCS(=O)(=O)N[C@H]1[C@@H](F)CN(C(=O)C2CCO2)[C@H]1Cc1cccc(-c2cccc(Cl)c2F)c1F] | | 516.9 |
| 424 | N-{(2S,3R)-4,4-difluoro-1-(1-hydroxy-cyclobutane-1-carbonyl)-2-[(2,2',3'-trifluoro[1,1'-biphenyl]-3-yl)methyl]-pyrrolidin-3-yl}cyclopropanesulfonamide | 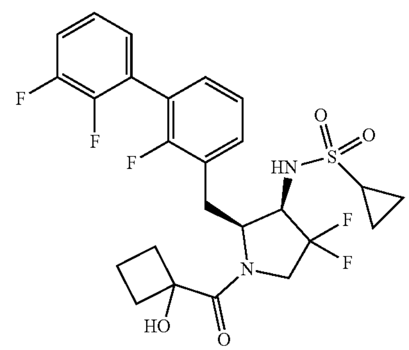 [SMILES: O=C(N1CC(F)(F)[C@H](NS(=O)(=O)C2CC2)[C@@H]1Cc1cccc(-c2cccc(F)c2F)c1F)C1(O)CCC1] | | 544.9 |
| 425 | (2S,3R)-3-[(cyclopropanesulfonyl)amino]-4,4-difluoro-2-[(2-fluoro-3'-methyl[1,1'-biphenyl]-3-yl)methyl]-N,N-dimethyl-pyrrolidine-1-carboxamide | 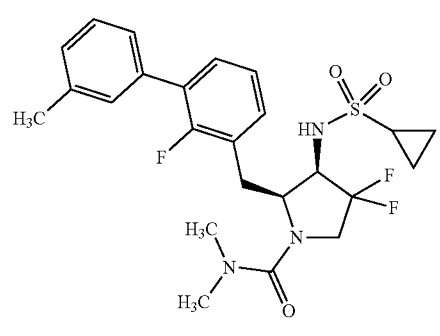 [SMILES: Cc1cccc(-c2cccc(C[C@H]3[C@@H](NS(=O)(=O)C4CC4)C(F)(F)CN3C(=O)N(C)C)c2F)c1] | | 496.0 |

TABLE 1-1-continued

| EX. | IUPAC NAME | Structure | ADDITIVE | MS |
|---|---|---|---|---|
| 426 | N-{(2S,3R)-1-(azetidine-1-carbonyl)-4,4-difluoro-2-[(2-fluoro-3'-methyl[1,1'-biphenyl]-3-yl)methyl]pyrrolidin-3-yl}-cyclopropanesulfonamide | 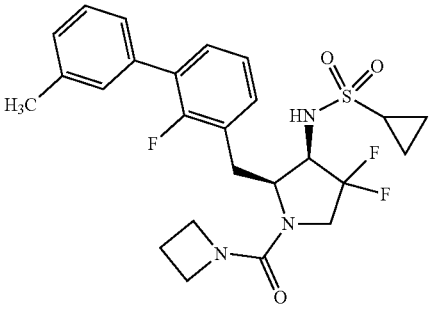 [SMILES: Cc1cccc(-c2cccc(C[C@H]3[C@@H](NS(=O)(=O)C4CC4)C(F)(F)CN3C(=O)N3CCC3)c2F)c1] | | 508.0 |
| 427 | N'-[(2S,3R)-4,4-difluoro-2-[(2-fluoro-3'-methyl[1,1'-biphenyl]-3-yl)methyl]-1-(1-hydroxycyclobutane-1-carbonyl)pyrrolidin-3-yl]-N,N-dimethylsulfuric diamide | 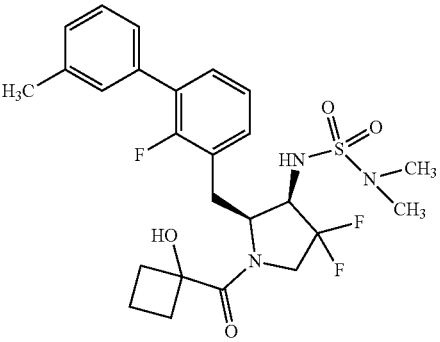 | | 526.0 |
| 428 | N-[(2S,3R)-4,4-difluoro-2-[(2-fluoro-3'-methyl[1,1'-biphenyl]-3-yl)methyl]-1-(oxetane-2-carbonyl)pyrrolidin-3-yl]-cyclopropanesulfonamide with shorter retention time | 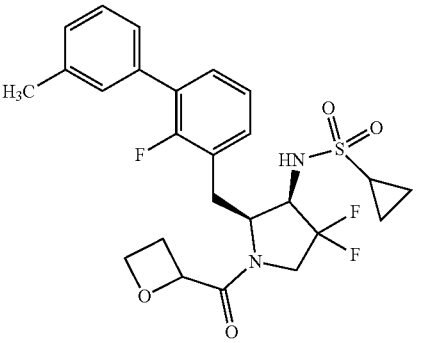 [SMILES: Cc1cccc(-c2cccc(C[C@H]3[C@@H](NS(=O)(=O)C4CC4)C(F)(F)CN3C(=O)C3CCO3)c2F)c1] | | 509.0 |
| 429 | N-[(2S,3R)-4,4-difluoro-2-[(2-fluoro-3'-methyl[1,1'-biphenyl]-3-yl)methyl]-1-(oxetane-2-carbonyl)pyrrolidin-3-yl]-cyclopropanesulfonamide with longer retention time | 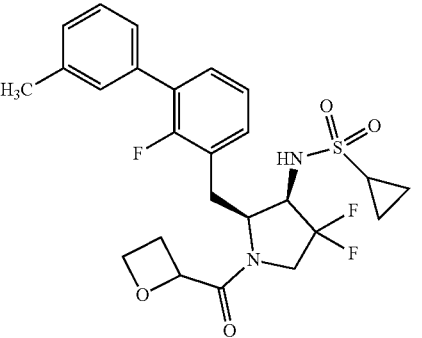 [SMILES: Cc1cccc(-c2cccc(C[C@H]3[C@@H](NS(=O)(=O)C4CC4)C(F)(F)CN3C(=O)C3CCO3)c2F)c1] | | 509.0 |

TABLE 1-1-continued

| EX. | IUPAC NAME | Structure | ADDITIVE | MS |
|---|---|---|---|---|
| 430 | N-[(2S,3R)-4,4-difluoro-2-[(2-fluoro-3'-methyl[1,1'-biphenyl]-3-yl)methyl]-1-(1-hydroxycyclobutane-1-carbonyl)pyrrolidin-3-yl]cyclopropanesulfonamide | 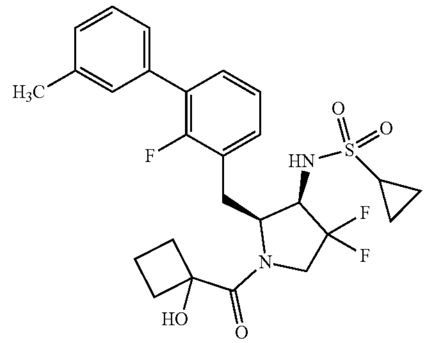 [SMILES: Cc1cccc(-c2cccc(C[C@H]3[C@@H](NS(=O)(=O)C4CC4)C(F)(F)CN3C(=O)C3(O)CCC3)c2F)c1] | | 523.0 |
| 431 | N-{(2S,3R)-4,4-difluoro-1-((1r,3S)-3-fluorocyclobutane-1-carbonyl)-2-[(2,3',5'-trifluoro[1,1'-biphenyl]-3-yl)methyl]-pyrrolidin-3-yl}methanesulfonamide | 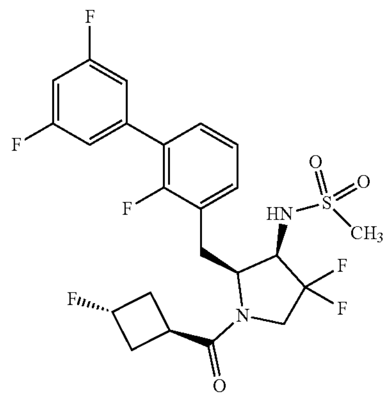 [SMILES: CS(=O)(=O)N[C@@H]1[C@H](Cc2cccc(-c3cc(F)cc(F)c3)c2F)N(C(=O)[C@H]2C[C@H](F)C2)CC1(F)F] | | 518.8 |
| 432 | N'-[(2S,3R)-4,4-difluoro-2-[(2-fluoro-3'-methyl[1,1'-biphenyl]-3-yl)methyl]-1-(oxetane-2-carbonyl)pyrrolidin-3-yl]-N,N-dimethylsulfuric diamide with shorter retention time | 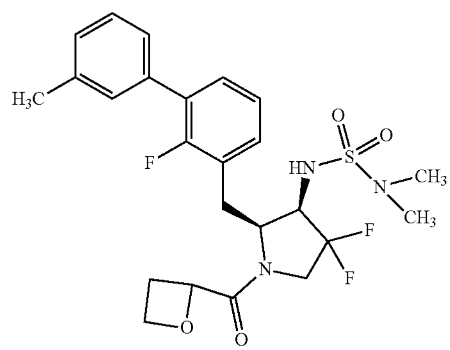 | | 512.0 |
| 433 | N-{{2S,3R)-4,4-difluoro-1-((1s,3R)-3-fluorocyclobutane-1-carbonyl)-2-[(2,3',5'-trifluoro[1,1'-biphenyl]-3-yl)methyl]-pyrrolidin-3-yl}methanesulfonamide | 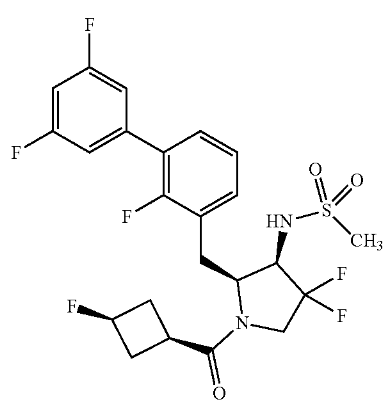 [SMILES: CS(=O)(=O)N[C@@H]1[C@H](Cc2cccc(-c3cc(F)cc(F)c3)c2F)N(C(=O)[C@H]2C[C@@H](F)C2)CC1(F)F] | | 518.9 |

TABLE 1-1-continued

| EX. | IUPAC NAME | Structure | ADDITIVE | MS |
|---|---|---|---|---|
| 434 | N'-[(2S,3R)-4,4-difluoro-2-[(2-fluoro-3'-methyl[1,1'-biphenyl]-3-yl)methyl]-1-(oxetane-2-carbonyl)pyrrolidin-3-yl]-N,N-dimethylsulfuric diamide with longer retention time | 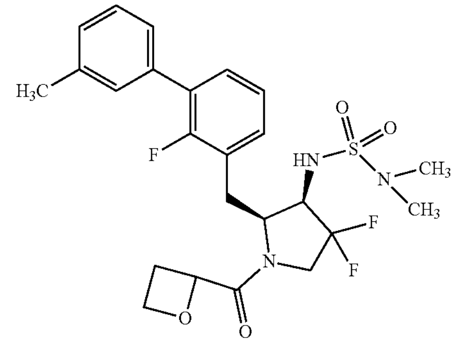 | | 512.0 |
| 435 | N-{(2S,3R)-4,4-difluoro-1-(3-fluoro-cyclobutane-1-carbonyl)-2-[(2,2',3'-trifluoro[1,1'-biphenyl]-3-yl)methyl]-pyrrolidin-3-yl)methanesulfonamide with longer retention time | 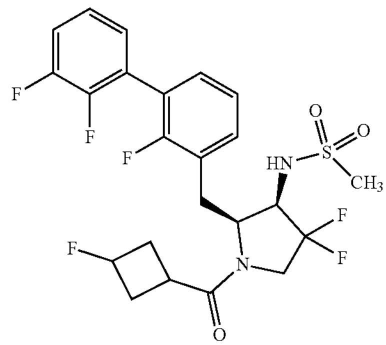 [SMILES: CS(=O)(=O)N[C@@H]1[C@H](Cc2cccc(-c3cccc(F)c3F)c2F)N(C(=O)C2CC(F)C2)CC1(F)F] | | 518.8 |
| 436 | N-{(2S,3R)-4,4-difluoro-1-(3-fluoro-cyclobutane-1-carbonyl)-2-[(2,2',3'-trifluoro[1,1'-biphenyl]-3-yl)methyl]-pyrrolidin-3-yl}methanesulfonamide with shorter retention time | 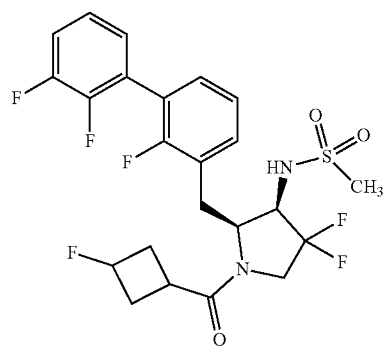 [SMILES: CS(=O)(=O)N[C@@H]1[C@H](Cc2cccc(-c3cccc(F)c3F)c2F)N(C(=O)C2CC(F)C2)CC1(F)F] | | 518.9 |
| 437 | N-{(2S,3R)-4,4-difluoro-1-(3-fluoro-cyclobutane-1-carbonyl)-2-[(2,2',5'-trifluoro[1,1'-biphenyl]-3-yl)methyl]-pyrrolidin-3-yl}methanesulfonamide with longer retention time | 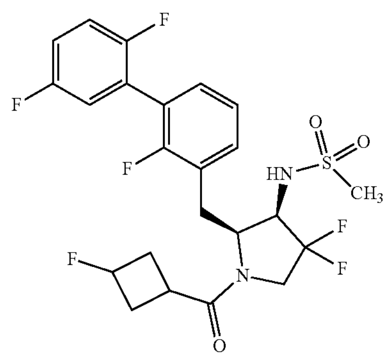 [SMILES: CS(=O)(=O)N[C@@H]1[C@H](Cc2cccc(-c3cc(F)ccc3F)c2F)N(C(=O)C2CC(F)C2)CC1(F)F] | | 518.8 |

TABLE 1-1-continued

| EX. | IUPAC NAME | Structure | ADDITIVE | MS |
|---|---|---|---|---|
| 438 | N'-{(2S,3R)-4,4-difluoro-1-(1-hydroxy-cyclobutane-1-carbonyl)-2-[(2,2',3'-trifluoro[1,1'-biphenyl]-3-yl)methyl]-pyrrolidin-3-yl}-N,N-dimethylsulfuric diamide | 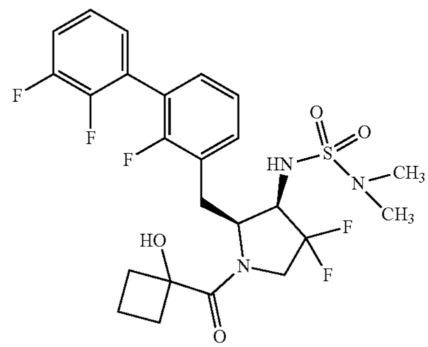 [SMILES: CN(C)S(=O)(=O)N[C@@H]1[C@H](Cc2cccc(-c3cccc(F)c3F)c2F)N(C(=O)C2(O)CCC2)CC1(F)F] | | 547.9 |
| 439 | N-{(2S,3R)-4,4-difluoro-1-(3-fluoro-cyclobutane-1-carbonyl)-2-[(2,2',5'-trifluoro[1,1'-biphenyl]-3-yl)methyl]-pyrrolidin-3-yl}methanesulfonamide with shorter retention time | 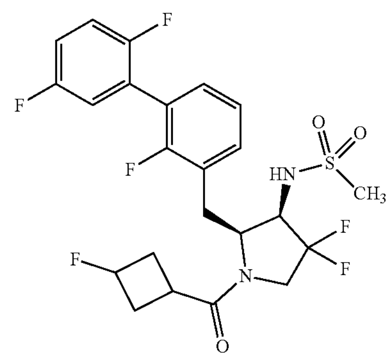 [SMILES: CS(=O)(=O)N[C@@H]1[C@H](Cc2cccc(-c3cc(F)ccc3F)c2F)N(C(=O)C2CC(F)C2)CC1(F)F] | | 518.9 |
| 440 | N-[(2S,3R)-4,4-difluoro-2-[(2-fluoro[1,1'-biphenyl]-3-yl)methyl]-1-(3-fluoro-cyclobutane-1-carbonyl)pyrrolidin-3-yl]-methanesulfonamide with longer retention time | 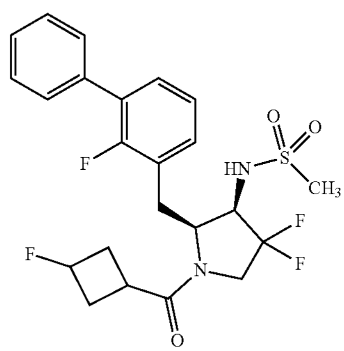 [SMILES: CS(=O)(=O)N[C@@H]1[C@H](Cc2cccc(-c3ccccc3)c2F)N(C(=O)C2CC(F)C2)CC1(F)F] | | 482.9 |
| 441 | N-[(2S,3R)-4,4-difluoro-2-[(2-fluoro[1,1'-biphenyl]-3-yl)methyl]-1-(3-fluoro-cyclobutane-1-carbonyl)pyrrolidin-3-yl]-methanesulfonamide with shorter retention time | 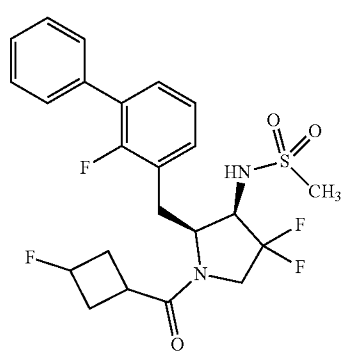 [SMILES: CS(=O)(=O)N[C@@H]1[C@H](Cc2cccc(-c3ccccc3)c2F)N(C(=O)C2CC(F)C2)CC1(F)F] | | 482.9 |

TABLE 1-1-continued

| EX. | IUPAC NAME | Structure | ADDITIVE | MS |
|---|---|---|---|---|
| 442 | (2S,3R)-3-[(dimethylsulfamoyl)amino]-4,4-difluoro-2-[(2-fluoro-3'-methyl[1,1'-biphenyl]-3-yl)methyl]-N,N-dimethyl-pyrrolidine-1-carboxamide | 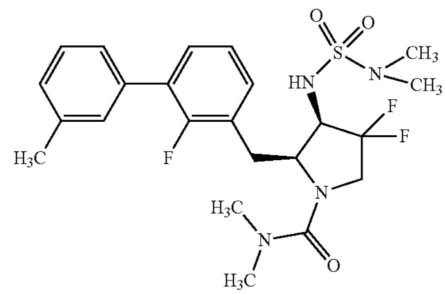 [SMILES: Cc1cccc(-c2cccc(C[C@H]3[C@@H](NS(=O)(=O)N(C)C)C(F)(F)CN3C(=O)N(C)C)c2F)c1] | | 499.0 |
| 443 | N'-{(2S,3R)-1-(azetidine-1-carbonyl)-4,4-difluoro-2-[(2-fluoro-3'-methyl[1,1'-biphenyl]-3-yl)methyl]pyrrolidin-3-yl}-N,N-dimethylsulfuric diamide | 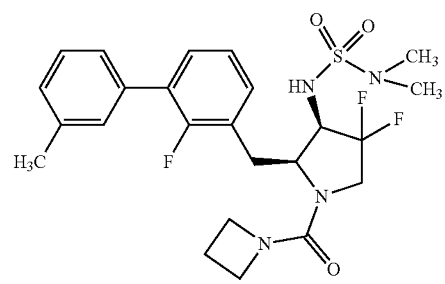 [SMILES: Cc1cccc(-c2cccc(C[C@H]3[C@@H](NS(=O)(=O)N(C)C)C(F)(F)CN3C(=O)N3CCC3)c2F)c1] | | 511.0 |
| 444 | N-{(2S,3R)-1-(azetidine-1-carbonyl)-2-[(2,3'-difluoro-5'-methyl[1,1'-biphenyl]-3-yl)methyl]-4,4-difluoropyrrolidin-3-yl}-ethanesulfonamide | 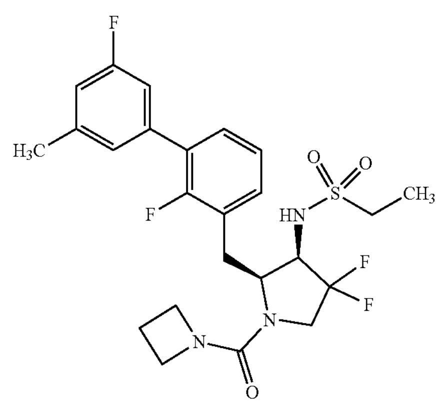 [SMILES: CCS(=O)(=O)N[C@@H]1[C@H](Cc2cccc(-c3cc(C)cc(F)c3)c2F)N(C(=O)N2CCC2)CC1(F)F] | | 514.0 |
| 445 | N-[(2S,3R)-2-[(2,3'-difluoro-5'-methyl[1,1'-biphenyl]-3-yl)methyl]-4,4-difluoro-1-(oxetane-2-carbonyl)pyrrolidin-3-yl]-ethanesulfonamide with longer retention time | 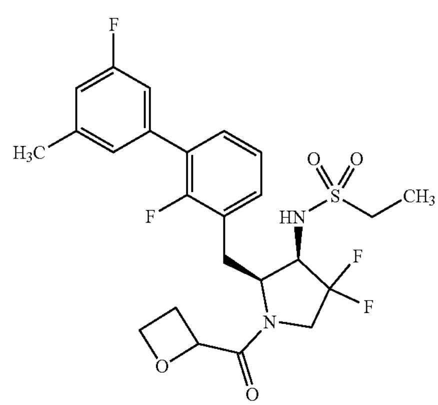 [SMILES: CCS(=O)(=O)N[C@@H]1[C@H](Cc2cccc(-c3cc(C)cc(F)c3)c2F)N(C(=O)C2CCO2)CC1(F)F] | | 515.0 |

TABLE 1-1-continued

| EX. | IUPAC NAME | Structure | ADDITIVE | MS |
|---|---|---|---|---|
| 446 | N-[(2S,3R)-2-[(2,3'-difluoro-5'-methyl[1,1'-biphenyl]-3-yl)methyl]-4,4-difluoro-1-(oxetane-2-carbonyl)pyrrolidin-3-yl]-ethanesulfonamide with shorter retention time | 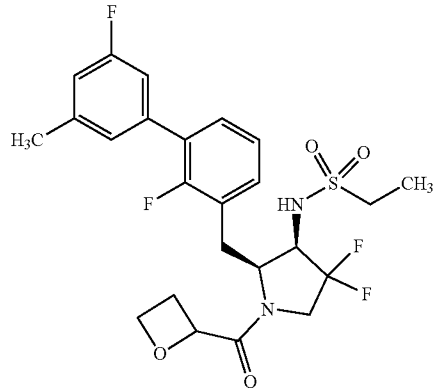 [SMILES: CCS(=O)(=O)N[C@@H]1[C@H](Cc2cccc(-c3cc(C)cc(F)c3)c2F)N(C(=O)C2CCO2)CC1(F)F] | | 515.0 |
| 447 | (2S,3R)-2-[(2,3'-difluoro-5'-methyl[1,1'-biphenyl]-3-yl)methyl]-3-[(ethanesulfonyl)-amino]-4,4-difluoro-N,N-dimethyl-pyrrolidine-1-carboxamide | 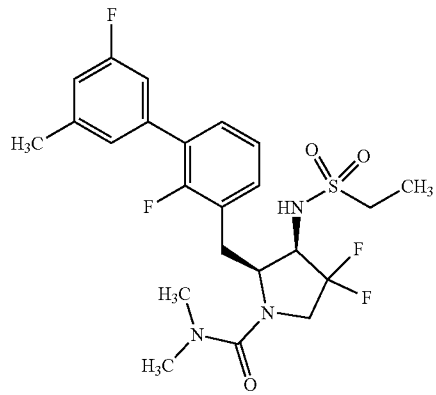 [SMILES: CCS(=O)(=O)N[C@@H]1[C@H](Cc2cccc(-c3cc(C)cc(F)c3)c2F)N(C(=O)N(C)C)CC1(F)F] | | 501.9 |
| 448 | N-[(2S,3R)-4,4-difluoro-2-[(2-fluoro-3',5'-dimethyl[1,1'-biphenyl]-3-yl)methyl]-1-(1-hydroxycyclobutane-1-carbonyl)pyrrolidin-3-yl]ethanesulfonamide | 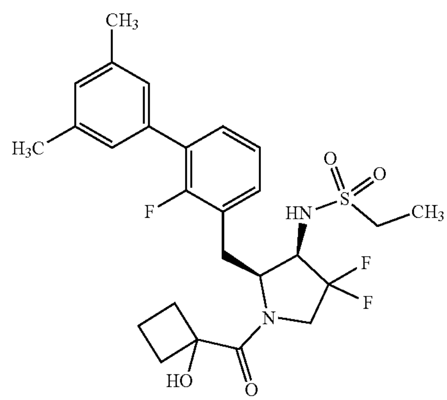 [SMILES: CCS(=O)(=O)N[C@@H]1[C@H](Cc2cccc(-c3cc(C)cc(C)c3)c2F)N(C(=O)C2(O)CCC2)CC1(F)F] | | 525.0 |
| 449 | N-[(2S,3R,4S)-2-[(3'-chloro-2,5'-difluoro-[1,1'-biphenyl]-3-yl)methyl]-4-fluoro-1-(oxetane-2-carbonyl)pyrrolidin-3-yl]-ethanesulfonamide derived from N-[(2S,3R,4S)-2-[(3-chloro-2-fluorophenyl)-methyl]-4-fluoro-1-(oxetane-2-carbonyl)-pyrrolidin-3-yl]ethanesulfonamide with shorter retention time by HPLC (column: L-Column2 ODS (3.0 mmI · D. × 50 mmL, 3 μm), mobile phase: water/acetonitrile (including 0.05% TFA) | 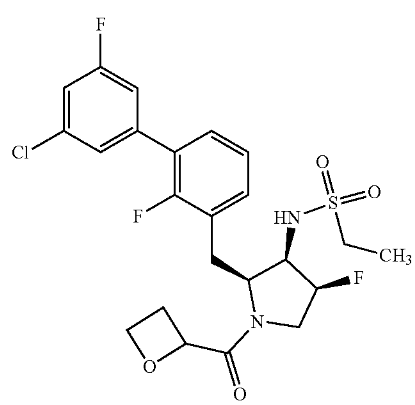 [SMILES: CCS(=O)(=O)N[C@H]1[C@@H](F)CN(C(=O)C2CCO2)[C@H]1Cc1cccc(-c2cc(F)cc(Cl)c2)c1F] | | 517.0 |

TABLE 1-1-continued

| EX. | IUPAC NAME | Structure | ADDITIVE | MS |
|---|---|---|---|---|
| 450 | N-{(2S,3R,4S)-1-(azetidine-1-carbonyl)-4-fluoro-2-[(2,3',5'-trifluoro[1,1'-biphenyl]-3-yl)methyl]pyrrolidin-3-yl}ethanesulfonamide | 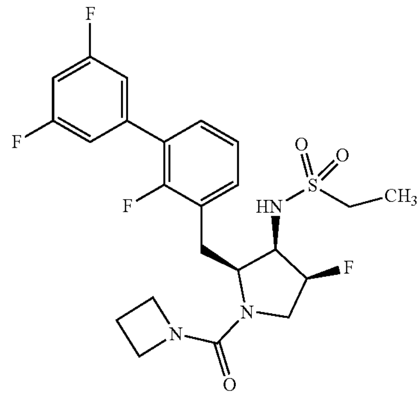 [SMILES: CCS(=O)(=O)N[C@H]1[C@@H](F)CN(C(=O)N2CCC2)[C@H]1Cc1cccc(-c2cc(F)cc(F)c2)c1F] | | 500.2 |
| 451 | N-{(2S,3R,4S)-1-(azetidine-1-carbonyl)-4-fluoro-2-[(2-fluoro-3'-methyl[1,1'-biphenyl]-3-yl)methyl]pyrrolidin-3-yl}-ethanesulfonamide | 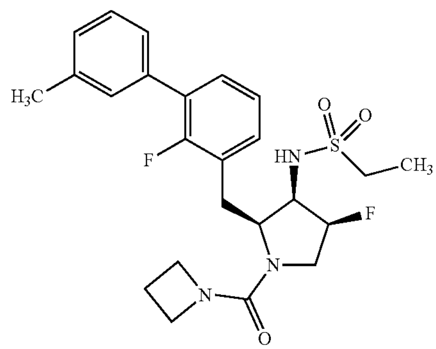 [SMILES: CCS(=O)(=O)N[C@H]1[C@@H](F)CN(C(=O)N2CCC2)[C@H]1Cc1cccc(-c2cccc(C)c2)c1F] | | 478.3 |
| 452 | N-[(2S,3R,4S)-4-fluoro-2-[(2-fluoro-3'-methyl[1,1'-biphenyl]-3-yl)methyl]-1-(oxetane-2-carbonyl)pyrrolidin-3-yl]-ethanesulfonamide with shorter retention time | 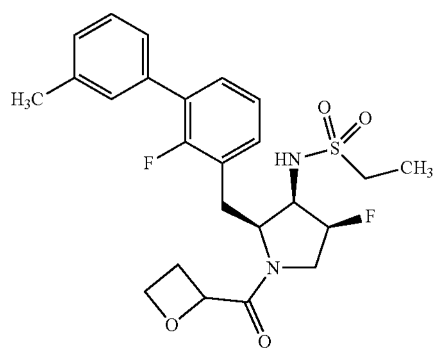 | | 479.2 |
| 453 | N-{(2S,3R)-2-[(2,3'-difluoro[1,1'-biphenyl]-3-yl)methyl]-4,4-difluoro-1-[(2R)-oxolane-2-carbonyl]pyrrolidin-3-yl}ethane-sulfonamide | 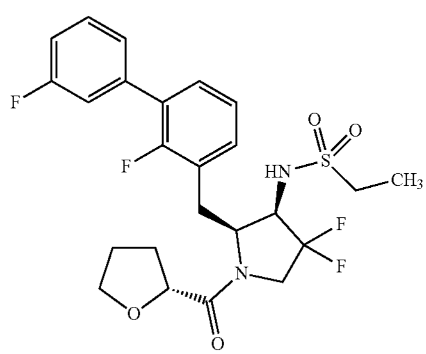 [SMILES: CCS(=O)(=O)N[C@@H]1[C@H](Cc2cccc(-c3cccc(F)c3)c2F)N(C(=O)[C@H]2CCCO2)CC1(F)F] | | 515.2 |

TABLE 1-1-continued

| EX. | IUPAC NAME | Structure | ADDITIVE | MS |
|---|---|---|---|---|
| 454 | N-{(2S,3R)-4,4-difluoro-1-[(2R)-oxolane-2-carbonyl]-2-[(2,3',5'-trifluoro[1,1'-biphenyl]-3-yl)methyl]pyrrolidin-3-yl}-ethanesulfonamide | 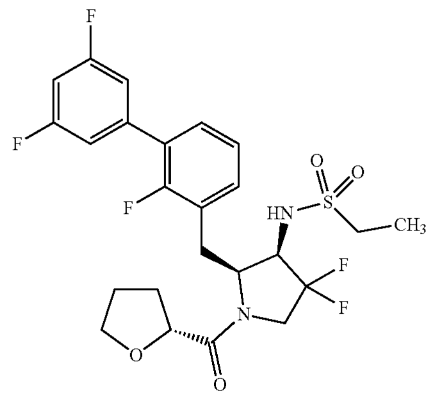 [SMILES: CCS(=O)(=O)N[C@@H]1[C@H](Cc2cccc(-c3cc(F)cc(F)c3)c2F)N(C(=O)[C@H]2CCCO2)CC1(F)F] | | 533.2 |
| 455 | N-{(2S,3R)-4,4-difluoro-1-[(2R)-oxolane-2-carbonyl]-2-[(2,2',3'-trifluoro[1,1'-biphenyl]-3-yl)methyl]pyrrolidin-3-yl}-ethanesulfonamide | 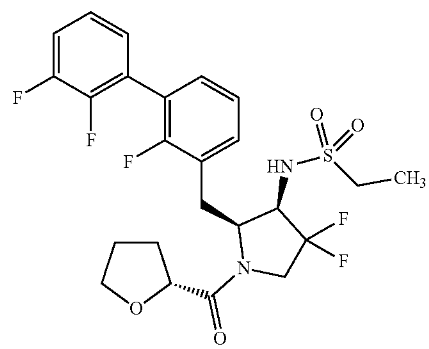 [SMILES: CCS(=O)(=O)N[C@@H]1[C@H](Cc2cccc(-c3cccc(F)c3F)c2F)N(C(=O)[C@H]2CCCO2)CC1(F)F] | | 533.2 |
| 456 | N-{(2S,3R)-4,4-difluoro-1-[(2R)-oxolane-2-carbonyl]-2-[(2,2',5'-trifluoro[1,1'-biphenyl]-3-yl)methyl]pyrrolidin-3-yl}-ethanesulfonamide | 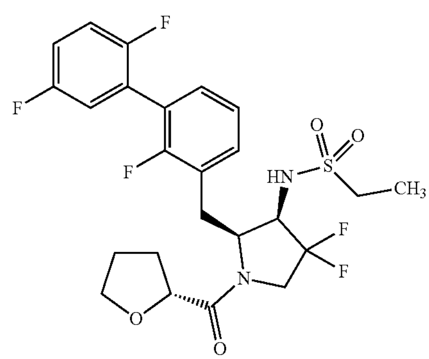 [SMILES: CCS(=O)(=O)N[C@@H]1[C@H](Cc2cccc(-c3cc(F)ccc3F)c2F)N(C(=O)[C@H]2CCCO2)CC1(F)F] | | 533.2 |
| 457 | N-{(2S,3R)-2-{[3'-(difluoromethyl)-2-fluoro[1,1'-biphenyl]-3-yl]methyl}-4,4-difluoro-1-[(2R)-oxolane-2-carbonyl]-pyrrolidin-3-yl}ethanesulfonamide | 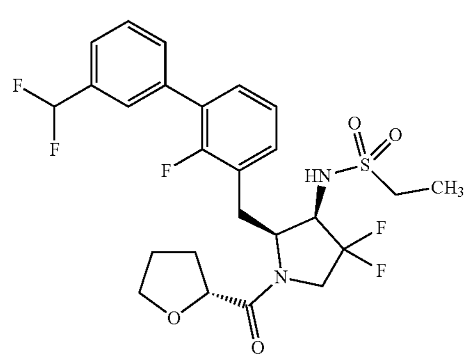 [SMILES: CCS(=O)(=O)N[C@@H]1[C@H](Cc2cccc(-c3cccc(C(F)F)c3)c2F)N(C(=O)[C@H]2CCCO2)CC1(F)F] | | 547.2 |

TABLE 1-1-continued

| EX. | IUPAC NAME | Structure | ADDITIVE | MS |
|---|---|---|---|---|
| 458 | N'-{(2S,3R,4S)-1-(azetidine-1-carbonyl)-4-fluoro-2-[(2,3',5'-trifluoro[1,1'-biphenyl]-3-yl)methyl]pyrrolidin-3-yl}-N,N-dimethyl-sulfuric diamide | 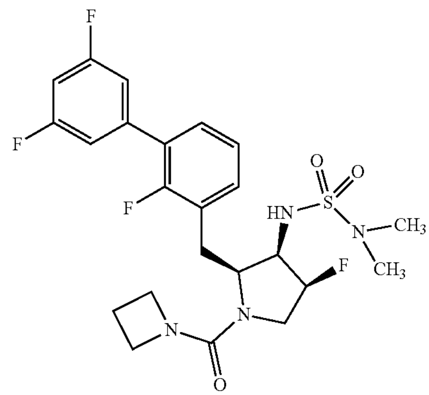 [SMILES: CN(C)S(=O)(=O)N[C@H]1[C@@H](F)CN(C(=O)N2CCC2)[C@H]1Cc1cccc(-c2cc(F)cc(F)c2)c1F] | | 515.2 |
| 459 | (2S,3R,4S)-3-[(dimethylsulfamoyl)amino]-4-fluoro-2-[(2-fluoro-3'-methyl[1,1'-biphenyl]-3-yl)methyl]-N,N-dimethyl-pyrrolidine-1-carboxamide | 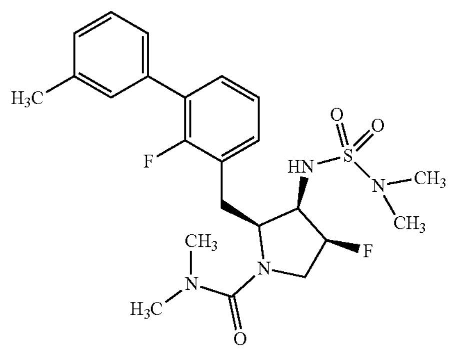 | | 481.3 |
| 460 | N-[(2S,3R,4S)-2-[(2,2'-difluoro-3'-methyl-[1,1'-biphenyl]-3-yl)methyl]-4-fluoro-1-(oxetane-2-carbonyl)pyrrolidin-3-yl]-ethanesulfonamide with shorter retention time | 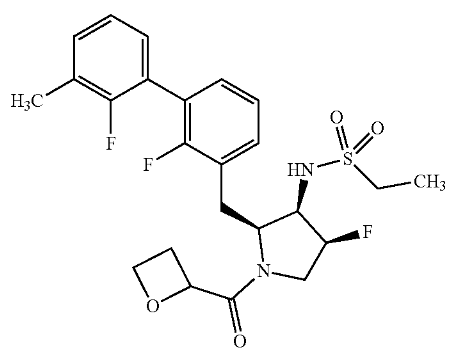 [SMILES: CCS(=O)(=O)N[C@H]1[C@@H](F)CN(C(=O)C2CCO2)[C@H]1Cc1cccc(-c2cccc(C)c2F)c1F] | | 497.2 |
| 461 | N-[(2S,3R,4S)-2-[(2,3'-difluoro-5'-methyl-[1,1'-biphenyl]-3-yl)methyl]-4-fluoro-1-(oxetane-2-carbonyl)pyrrolidin-3-yl]-ethanesulfonamide with shorter retention time | 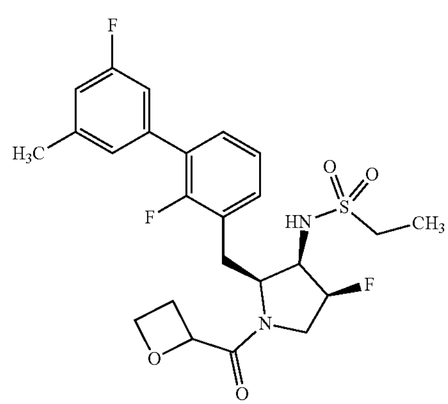 [SMILES: CCS(=O)(=O)N[C@H]1[C@@H](F)CN(C(=O)C2CCO2)[C@H]1Cc1cccc(-c2cc(C)cc(F)c2)c1F] | | 497.2 |

TABLE 1-1-continued

| EX. | IUPAC NAME | Structure | ADDITIVE | MS |
|---|---|---|---|---|
| 462 | N'-[(2S,3R,4S)-4-fluoro-2-[(2-fluoro-3'-methyl[1,1'-biphenyl]-3-yl)methyl]-1-(1-hydroxycyclobutane-1-carbonyl)pyrrolidin-3-yl]-N,N-dimethylsulfuric diamide | 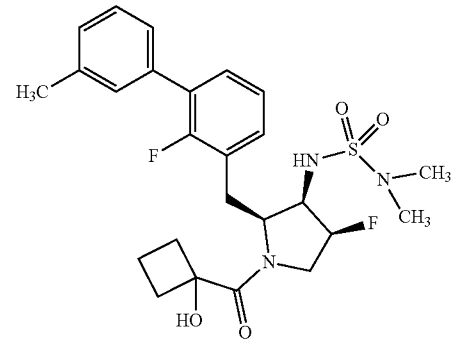 | | 508.2 |
| 463 | N'-{(2S,3R,4S)-1-(azetidine-1-carbonyl)-4-fluoro-2-[(2-fluoro-3'-methyl[1,1'-biphenyl]-3-yl)methyl]pyrrolidin-3-yl}-N,N-dimethylsulfuric diamide | 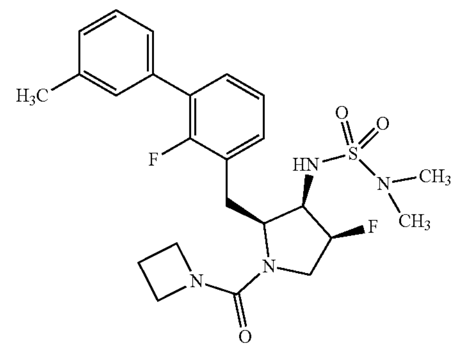 | | 493.3 |
| 464 | N-[(2S,3R,4S)-2-[(2,2'-difluoro-5'-methyl-[1,1'-biphenyl]-3-yl)methyl]-4-fluoro-1-(oxetane-2-carbonyl)pyrrolidin-3-yl]-ethanesulfonamide with shorter retention time | 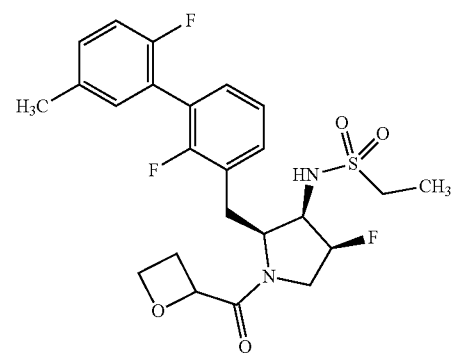 [SMILES: CCS(=O)(=O)N[C@H]1[C@@H](F)CN(C(=O)C2CCO2)[C@H]1Cc1cccc(-c2cc(C)ccc2F)c1F] | | 497.2 |
| 465 | N-[(2S,3R)-4,4-difluoro-2-[(2-fluoro-3'-methyl[1,1'-biphenyl]-3-yl)methyl]-1-(2-hydroxy-2-methylpropanoyl)pyrrolidin-3-yl]ethanesulfonamide | 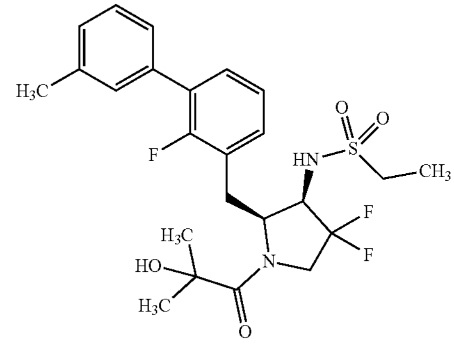 [SMILES: CCS(=O)(=O)N[C@@H]1[C@H](Cc2cccc(-c3cccc(C)c3)c2F)N(C(=O)C(C)(C)O)CC1(F)F] | | 499.2 |

TABLE 1-1-continued

| EX. | IUPAC NAME | Structure | ADDITIVE | MS |
|---|---|---|---|---|
| 466 | N-[(2S,3R)-2-[(2,4'-difluoro-3'-methyl[1,1'-biphenyl]-3-yl)methyl]-4,4-difluoro-1-(2-hydroxy-2-methylpropanoyl)pyrrolidin-3-yl]ethanesulfonamide | 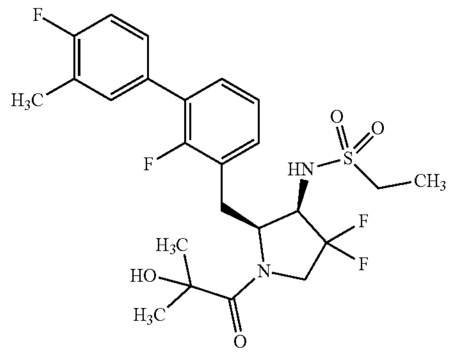 [SMILES: CCS(=O)(=O)N[C@@H]1[C@H](Cc2cccc(-c3ccc(F)c(C)c3)c2F)N(C(=O)C(C)(C)O)CC1(F)F] | | 517.1 |
| 467 | N-{(2S,3R)-4,4-difluoro-1-(oxetane-2-carbonyl)-2-[(2,3',4'-trifluoro[1,1'-biphenyl]-3-yl)methyl]pyrrolidin-3-yl}ethanesulfonamide with longer retention time | 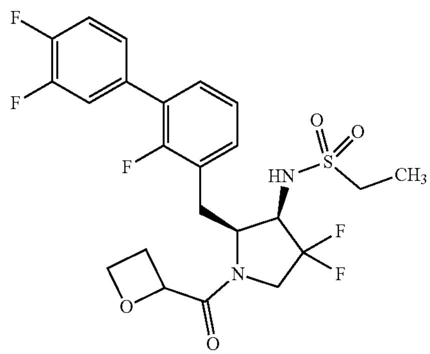 [SMILES: CCS(=O)(=O)N[C@@H]1[C@H](Cc2cccc(-c3ccc(F)c(F)c3)c2F)N(C(=O)C2CCO2)CC1(F)F] | | 517.2 |
| 468 | N-{(2S,3R)-4,4-difluoro-1-(oxetane-2-carbonyl)-2-[(2,3',4'-trifluoro[1,1'-biphenyl]-3-yl)methyl]pyrrolidin-3-yl}-ethanesulfonamide with shorter retention time | 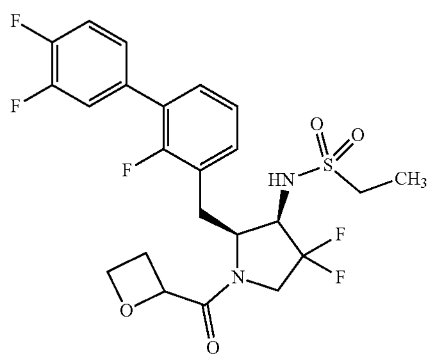 [SMILES: CCS(=O)(=O)N[C@@H]1[C@H](Cc2cccc(-c3ccc(F)c(F)c3)c2F)N(C(=O)C2CCO2)CC1(F)F] | | 519.2 |
| 469 | N-{(2S,3R)-4,4-difluoro-1-(oxetane-2-carbonyl)-2-[(2,2',4',5'-tetrafluoro[1,1'-biphenyl]-3-yl)methyl]pyrrolidin-3-yl}-ethanesulfonamide with longer retention time | 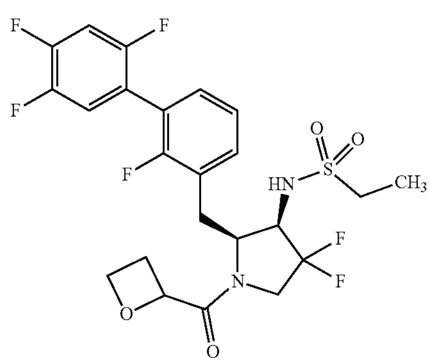 [SMILES: CCS(=O)(=O)N[C@@H]1[C@H](Cc2cccc(-c3cc(F)c(F)cc3F)c2F)N(C(=O)C2CCO2)CC1(F)F] | | 535.1 |

TABLE 1-1-continued

| EX. | IUPAC NAME | Structure | ADDITIVE | MS |
|---|---|---|---|---|
| 470 | N-{(2S,3R)-4,4-difluoro-1-(oxetane-2-carbonyl)-2-[(2,2',3',4-tetrafluoro[1,1'-biphenyl]-3-yl)methyl]pyrrolidin-3-yl}-ethanesulfonamide with shorter retention | 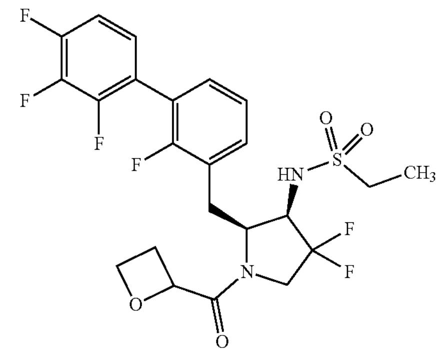 [SMILES: CCS(=O)(=O)N[C@@H]1[C@H](Cc2cccc(-c3ccc(F)c(F)c3F)c2F)N(C(=O)C2CCO2)CC1(F)F] | | 537.1 |
| 471 | N-{(2S,3R)-4,4-difluoro-1-(oxetane-2-carbonyl)-2-[(2,2',3',4'-tetrafluoro[1,1'-biphenyl]-3-yl)methyl]pyrrolidin-3-yl}-ethanesulfonamide with longer retention time | 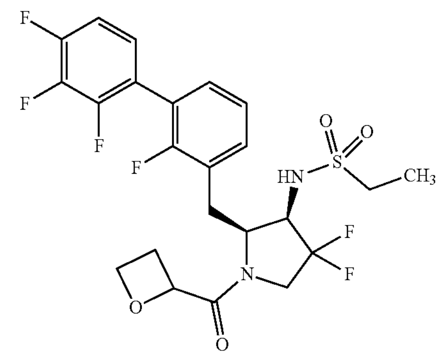 [SMILES: CCS(=O)(=O)N[C@@H]1[C@H](Cc2cccc(-c3ccc(F)c(F)c3F)c2F)N(C(=O)C2CCO2)CC1(F)F] | | 537.1 |
| 472 | N-[(2S,3R)-2-[(2,4'-difluoro-3'-methyl[1,1'-biphenyl]-3-yl)methyl]-4,4-difluoro-1-(oxetane-2-carbonyl)pyrrolidin-3-yl]-ethanesulfonamide with longer retention time | 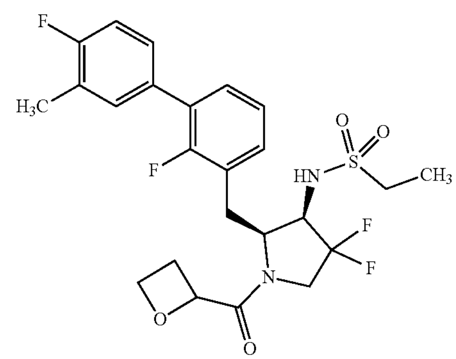 [SMILES: CCS(=O)(=O)N[C@@H]1[C@H](Cc2cccc(-c3ccc(F)c(C)c3)c2F)N(C(=O)C2CCO2)CC1(F)F] | | 515.2 |
| 473 | N-{(2S,3R)-4,4-difluoro-1-(oxetane-2-carbonyl)-2-[(2,3',4',5'-tetrafluoro[1,1'-biphenyl]-3-yl)methyl]pyrrolidin-3-yl}-ethanesulfonamide with longer retention time | 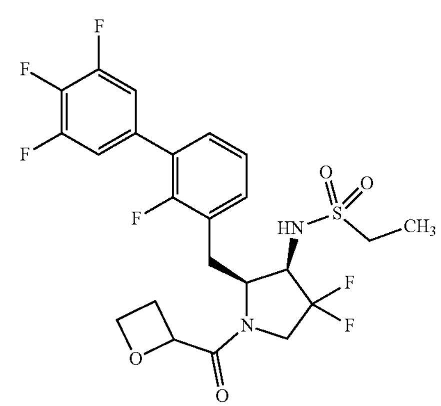 [SMILES: CCS(=O)(=O)N[C@@H]1[C@H](Cc2cccc(-c3cc(F)c(F)c(F)c3)c2F)N(C(=O)C2CCO2)CC1(F)F] | | 535.1 |

TABLE 1-1-continued

| EX. | IUPAC NAME | Structure | ADDITIVE | MS |
|---|---|---|---|---|
| 474 | N-{(2S,3R)-4,4-difluoro-1-(oxetane-2-carbonyl)-2-[(2,2',4'-trifluoro-3'-methyl-[1,1'-biphenyl]-3-yl)methyl]pyrrolidin-3-yl}ethanesulfonamide with longer retention time | 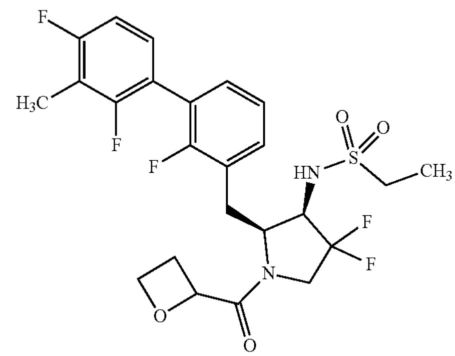 [SMILES: CCS(=O)(=O)N[C@@H]1[C@H](Cc2cccc(-c3ccc(F)c(C)c3F)c2F)N(C(=O)C2CCO2)CC1(F)F] | | 533.2 |
| 475 | N-{(2S,3R)-4,4-difluoro-1-(oxetane-2-carbonyl)-2-[(2,3',4',5'-tetrafluoro[1,1'-biphenyl]-3-yl)methyl]pyrrolidin-3-yl}-ethanesulfonamide with shorter retention time | 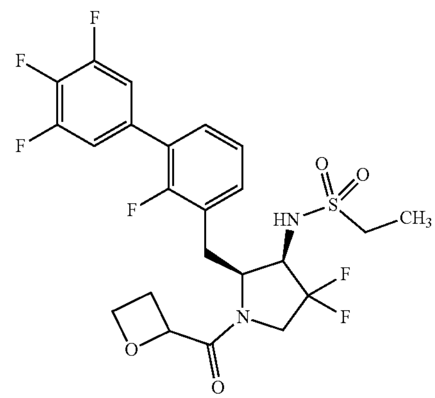 [SMILES: CCS(=O)(=O)N[C@@H]1[C@H](Cc2cccc(-c3cc(F)c(F)c(F)c3)c2F)N(C(=O)C2CCO2)CC1(F)F] | | 535.2 |
| 476 | N-[(2S,3R)-2-[(2,4'-difluoro-3'-methyl-[1,1'-biphenyl]-3-yl)methyl]-4,4-difluoro-1-(oxetane-2-carbonyl)pyrrolidin-3-yl]-ethanesulfonamide with shorter retention time | 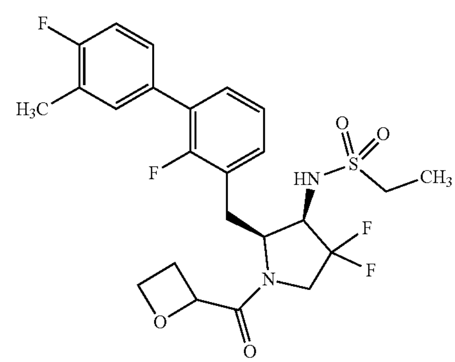 [SMILES: CCS(=O)(=O)N[C@@H]1[C@H](Cc2cccc(-c3ccc(F)c(C)c3)c2F)N(C(=O)C2CCO2)CC1(F)F] | | 515.2 |
| 477 | N-{(2S,3R)-4,4-difluoro-1-(oxetane-2-carbonyl)-2-[(2,2',4',5'-tetrafluoro[1,1'-biphenyl]-3-yl)methyl]pyrrolidin-3-yl}-ethanesulfonamide with shorter retention time | 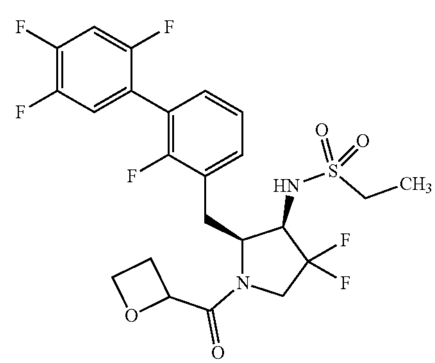 [SMILES: CCS(=O)(=O)N[C@@H]1[C@H](Cc2cccc(-c3cc(F)c(F)cc3F)c2F)N(C(=O)C2CCO2)CC1(F)F] | | 537.2 |

TABLE 1-1-continued

| EX. | IUPAC NAME | Structure | ADDITIVE | MS |
|---|---|---|---|---|
| 478 | N-{(2S,3R)-4,4-difluoro-1-(oxetane-2-carbonyl)-2-[(2,2',4'-trifluoro-3'-methyl-[1,1'-biphenyl]-3-yl)methyl]pyrrolidin-3-yl}ethanesulfonamide with shorter retention time | 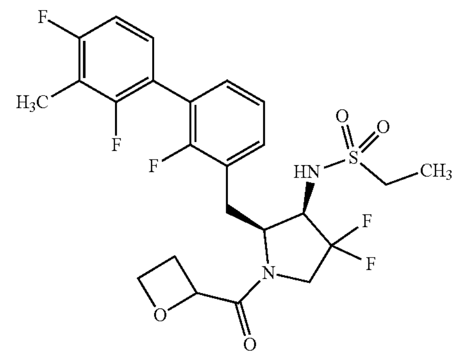 [SMILES: CCS(=O)(=O)N[C@@H]1[C@H](Cc2cccc(-c3ccc(F)c(C)c3F)c2F)N(C(=O)C2CCO2)CC1(F)F] | | 533.2 |
| 479 | N-{(2S,3R,4S)-4-fluoro-1-(oxetane-2-carbonyl)-2-[(2,3',5'-trifluoro[1,1'-biphenyl]-3-yl)methyl]pyrrolidin-3-yl}-cyclopropanesulfonamide with shorter retention time | 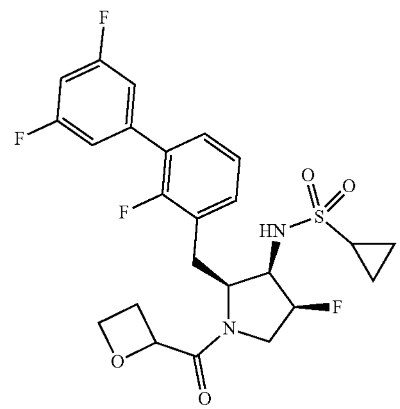 [SMILES: O=C(C1CCO1)N1C[C@H](F)[C@H](NS(=O)(=O)C2CC2)[C@@H]1Cc1cccc(-c2cc(F)cc(F)c2)c1F] | | 513.2 |
| 480 | N-{(2S,3R,4S)-4-fluoro-1-(oxetane-2-carbonyl)-2-[(2,2',3'-trifluoro[1,1'-biphenyl]-3-yl)methyl]pyrrolidin-3-yl}-cyclopropanesulfonamide with shorter retention time | 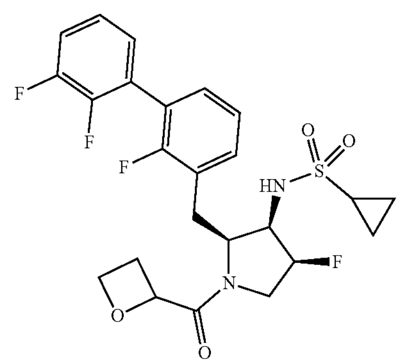 [SMILES: O=C(C1CCO1)N1C[C@H](F)[C@H](NS(=O)(=O)C2CC2)[C@@H]1Cc1cccc(-c2cccc(F)c2F)c1F] | | 513.2 |
| 481 | N-{(2S,3R,4S)-4-fluoro-1-(oxetane-2-carbonyl)-2-[(2,2',5'-trifluoro[1,1'-biphenyl]-3-yl)methyl]pyrrolidin-3-yl}-cyclopropanesulfonamide with shorter retention time | 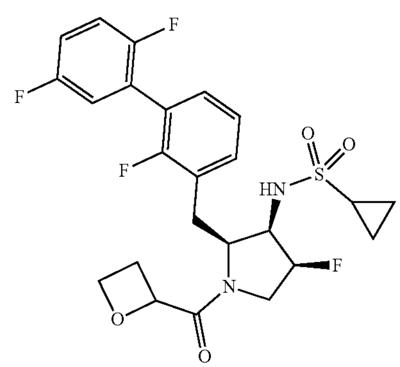 [SMILES: O=C(C1CCO1)N1C[C@H](F)[C@H](NS(=O)(=O)C2CC2)[C@@H]1Cc1cccc(-c2cc(F)ccc2F)c1F] | | 513.2 |

TABLE 1-1-continued

| EX. | IUPAC NAME | Structure | ADDITIVE | MS |
|---|---|---|---|---|
| 482 | N-[(2S,3R,4S)-4-fluoro-2-[(2-fluoro[1,1'-biphenyl]-3-yl)methyl]-1-(oxetane-2-carbonyl)pyrrolidin-3-yl]cyclopropane-sulfonamide with shorter retention time | 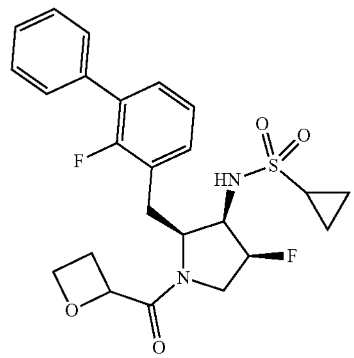 [SMILES: O=C(C1CCO1)N1C[C@H](F)[C@H](NS(=O)(=O)C2CC2)[C@@H]1Cc1cccc(-c2ccccc2)c1F] | | 477.2 |
| 483 | N-[(2S,3R,4S)-2-[(2,2'-difluoro[1,1'-biphenyl]-3-yl)methyl]-4-fluoro-1-(oxetane-2-carbonyl)pyrrolidin-3-yl]-cyclopropanesulfonamide derived from N-[(2S,3R,4S)-2-[(3-chloro-2-fluoro-phenyl)methyl]-4-fluoro-1-(oxetane-2-carbonyl)pyrrolidin-3-yl]cyclopropane-sulfonamide with shorter retention time by HPLC (column: L-Column2 ODS (3.0 mmI · D. × 50 mmL, 3 μm), mobile phase: water/acetonitrile (including 0.05% TFA) | 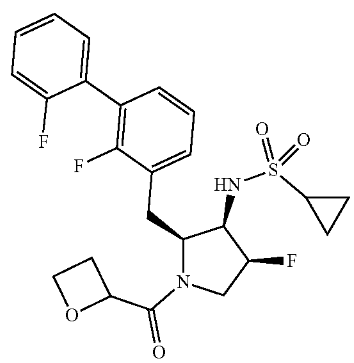 [SMILES: O=C(C1CCO1)N1C[C@H](F)[C@H](NS(=O)(=O)C2CC2)[C@@H]1Cc1cccc(-c2ccccc2F)c1F] | | 495.2 |
| 484 | N-[(2S,3R,4S)-4-fluoro-2-[(2-fluoro-3'-methyl[1,1'-biphenyl]-3-yl)methyl]-1-(oxetane-2-carbonyl)pyrrolidin-3-yl]-cyclopropanesulfonamide with shorter retention time | 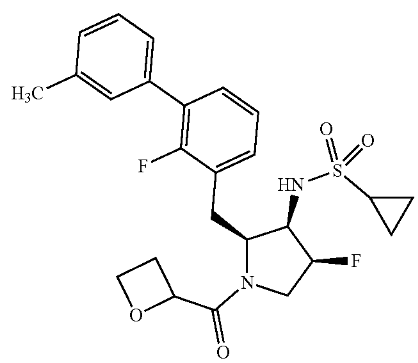 [SMILES: Cc1cccc(-c2cccc(C[C@H]3[C@@H](NS(=O)(=O)C4CC4)[C@@H](F)CN3C(=O)C3CCO3)c2F)c1] | | 491.2 |
| 492 | N-[(2S,3R,4S)-2-[(2,2'-difluoro-5'-methyl-[1,1'-biphenyl]-3-yl)methyl]-4-fluoro-1-(oxetane-2-carbonyl)pyrrolidin-3-yl]-cyclopropanesulfonamide with longer retention time | 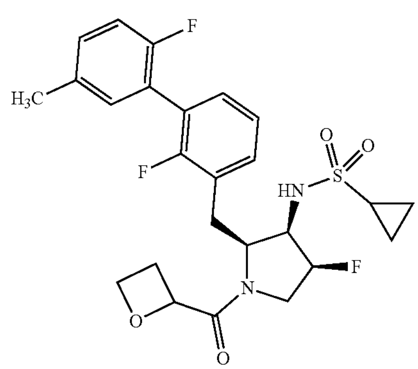 [SMILES: Cc1ccc(F)c(-c2cccc(C[C@H]3[C@@H](NS(=O)(=O)C4CC4)[C@@H](F)CN3C(=O)C3CCO3)c2F)c1] | | 509.1 |

TABLE 1-1-continued

| EX. | IUPAC NAME | Structure | ADDITIVE | MS |
|---|---|---|---|---|
| 493 | N-{(2S,3R,4S)-4-fluoro-1-(oxetane-2-carbonyl)-2-[(2,3',5'-trifluoro[1,1'-biphenyl]-3-yl)methyl]pyrrolidin-3-yl}cyclopropanesulfonamide with longer retention time | 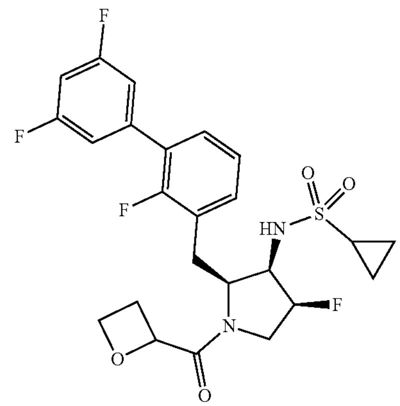 [SMILES: O=C(C1CCO1)N1C[C@H](F)[C@H](NS(=O)(=O)C2CC2)[C@@H]1Cc1cccc(-c2cc(F)cc(F)c2)c1F] | | 513.1 |
| 494 | N-{(2S,3R,4S)-4-fluoro-1-(oxetane-2-carbonyl)-2-[(2,2',3',-trifluoro[1,1'-biphenyl]-3-yl)methyl]pyrrolidin-3-yl}-cyclopropanesulfonamide with longer retention time | 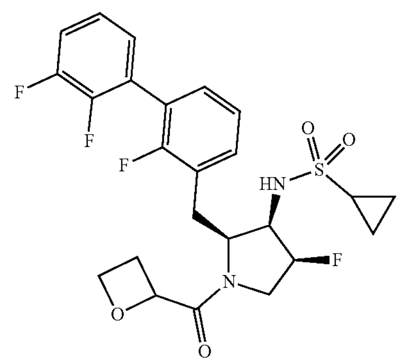 [SMILES: O=C(C1CCO1)N1C[C@H](F)[C@H](NS(=O)(=O)C2CC2)[C@@H]1Cc1cccc(-c2cccc(F)c2F)c1F] | | 513.1 |
| 495 | N-{(2S,3R,4S)-4-fluoro-1-(oxetane-2-carbonyl)-2-[(2,2',5'-trifluoro[1,1'-biphenyl]-3-yl)methyl]pyrrolidin-3-yl}-cyclopropanesulfonamide with longer retention time | 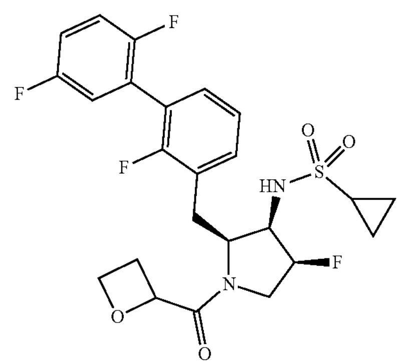 [SMILES: O=C(C1CCO1)N1C[C@H](F)[C@H](NS(=O)(=O)C2CC2)[C@@H]1Cc1cccc(-c2cc(F)ccc2F)c1F] | | 513.2 |
| 496 | N-[(2S,3R,4S)-4-fluoro-2-[(2-fluoro[1,1'-biphenyl]-3-yl)methyl]-1-(oxetane-2-carbonyl)pyrrolidin-3-yl]cyclopropane-sulfonamide with longer retention time | 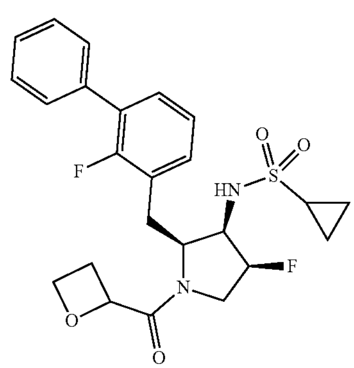 [SMILES: O=C(C1CCO1)N1C[C@H](F)[C@H](NS(=O)(=O)C2CC2)[C@@H]1Cc1cccc(-c2ccccc2)c1F] | | 477.2 |

TABLE 1-1-continued

| EX. | IUPAC NAME | Structure | ADDITIVE | MS |
|---|---|---|---|---|
| 497 | N-[(2S,3R,4S)-2-[(3,-chloro-2-fluoro[1,1'-biphenyl]-3-yl)methyl]-4-fluoro-1-(oxetane-2-carbonyl)pyrrolidin-3-yl]-cyclopropanesulfonamide with longer retention time | 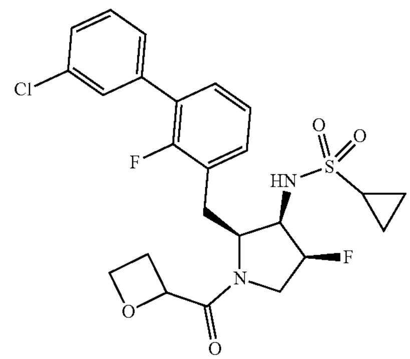 [SMILES: O=C(C1CCO1)N1C[C@H](F)[C@H](NS(=O)(=O)C2CC2)[C@@H]1Cc1cccc(-c2cccc(Cl)c2)c1F] | | 511.1 |
| 498 | N-[(2S,3R,4S)-4-fluoro-2-[(2-fluoro-3'-methyl[1,1'-biphenyl]-3-yl)methyl]-1-(oxetane-2-carbonyl)pyrrolidin-3-yl]-ethanesulfonamide with longer retention time | 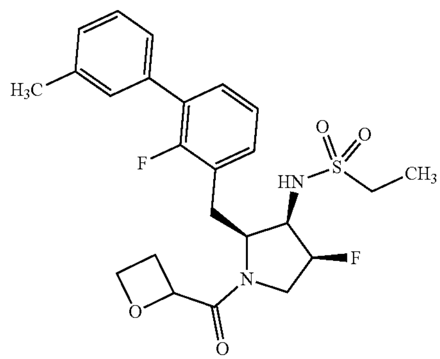 [SMILES: CCS(=O)(=O)N[C@H]1[C@@H](F)CN(C(=O)C2CCO2)[C@H]1Cc1cccc(-c2cccc(C)c2)c1F] | | 479.2 |
| 499 | N-[(2S,3R,4S)-2-[(2,2'-difluoro-3'-methyl-[1,1'-biphenyl]-3-yl)methyl]-4-fluoro-1-(oxetane-2-carbonyl)pyrrolidin-3-yl]ethane-sulfonamide with longer retention time | 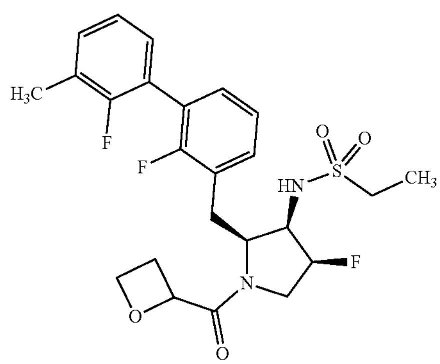 [SMILES: CCS(=O)(=O)N[C@H]1[C@@H](F)CN(C(=O)C2CCO2)[C@H]1Cc1cccc(-c2cccc(C)c2F)c1F] | | 497.2 |
| 500 | N-[(2S,3R,4S)-2-[(2,4'-difluoro-3'-methyl-[1,1'-biphenyl]-3-yl)methyl]-4-fluoro-1-(oxetane-2-carbonyl)pyrrolidin-3-yl]-ethanesulfonamide derived from N-[(2S,3R,4S)-2-[3-chloro-2-fluorophenyl)-methyl]-4-fluoro-1-(oxetane-2-carbonyl)-pyrrolidin-3-yl]ethanesulfonamide with longer retention time by HPLC (column: L-Column2 ODS (3.0 mml · D. × 50 mmL, 3 μm), mobile phase: water/acetonitrile (including 0.05% TFA) | 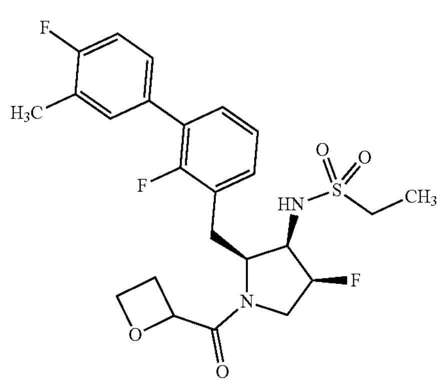 [SMILES: CCS(=O)(=O)N[C@H]1[C@@H](F)CN(C(=O)C2CCO2)[C@H]1Cc1cccc(-c2ccc(F)c(C)c2)c1F] | | 497.2 |

TABLE 1-1-continued

| EX. | IUPAC NAME | Structure | ADDITIVE | MS |
|---|---|---|---|---|
| 501 | N-[(2S,3R,4S)-2-[(2,3'-difluoro-5'-methyl-[1,1'-biphenyl]-3-yl)methyl]-4-fluoro-1-(oxetane-2-carbonyl)pyrrolidin-3-yl]-ethanesulfonamide with longer retention time | 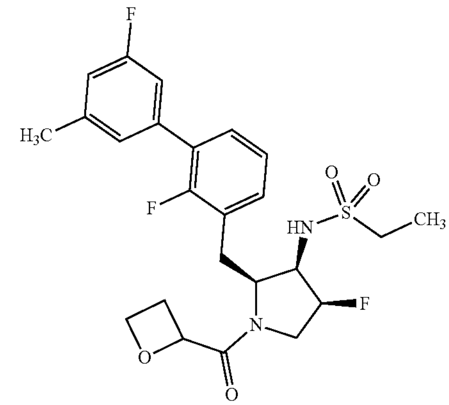 [SMILES: CCS(=O)(=O)N[C@H]1[C@@H](F)CN(C(=O)C2CCO2)[C@H]1Cc1cccc(-c2cc(C)cc(F)c2)c1F] | | 497.2 |
| 502 | N-[(2S,3R,4S)-2-[(2,2'-difluoro-5'-methyl-[1,1'-biphenyl]-3-yl)methyl]-4-fluoro-1-(oxetane-2-carbonyl)pyrrolidin-3-yl]ethane-sulfonamide with longer retention time | 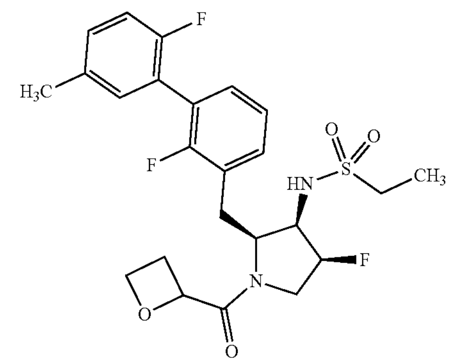 [SMILES: CCS(=O)(=O)N[C@H]1[C@@H](F)CN(C(=O)C2CCO2)[C@H]1Cc1cccc(-c2cc(C)ccc2F)c1F] | | 497.2 |
| 503 | N-[(2S,3R)-2-{[3'-(difluoromethyl)-2-fluoro[1,1'-biphenyl]-3-yl]methyl}-4,4-difluoro-1-(oxetane-2-carbonyl)pyrrolidin-3-yl]ethanesulfonamide with longer retention time | 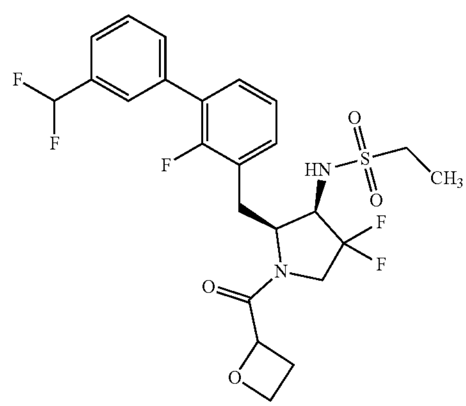 [SMILES: CCS(=O)(=O)N[C@@H]1[C@H](Cc2cccc(-c3cccc(C(F)F)c3)c2F)N(C(=O)C2CCO2)CC1(F)F] | | 533.1 |
| 504 | N-[(2S,3R)-2-{[3'-(difluoromethyl)-2-fluoro[1,1'-biphenyl]-3-yl]methyl}-4,4-difluoro-1-(oxetane-2-carbonyl)pyrrolidin-3-yl]ethanesulfonamide with shorter retention time | 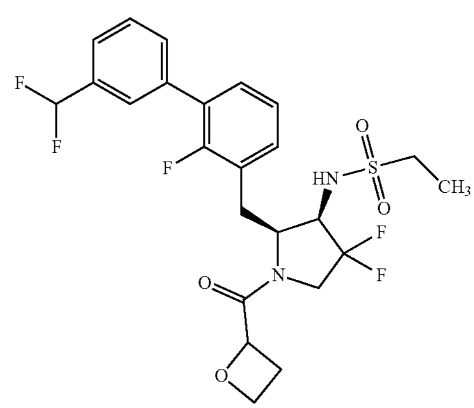 [SMILES: CCS(=O)(=O)N[C@@H]1[C@H](Cc2cccc(-c3cccc(C(F)F)c3)c2F)N(C(=O)C2CCO2)CC1(F)F] | | 533.2 |

TABLE 1-1-continued

| EX. | IUPAC NAME | Structure | ADDITIVE | MS |
|---|---|---|---|---|
| 505 | N-[(2S,3R)-2-{[3-(difluoromethyl)-2-fluoro[1,1'-biphenyl]-3-yl]methyl}-4,4-difluoro-1-(3-fluorocyclobutane-1-carbonyl)pyrrolidin-3-yl]ethanesulfonamide | 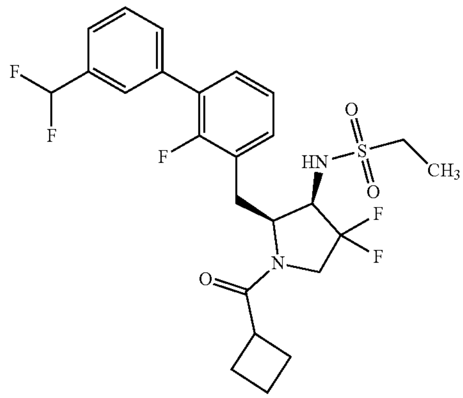 [SMILES: CCS(=O)(=O)N[C@@H]1[C@H](Cc2cccc(-c3cccc(C(F)F)c3)c2F)N(C(=O)C2CCC2)CC1(F)F] | | 547.2 |
| 506 | N-[(2S,3R)-2-{[3'-(difluoromethyl)-2-fluoro[1,1'-biphenyl]-3-yl]methyl}-4,4-difluoro-1-(3-fluorocyclobutane-1-carbonyl)pyrrolidin-3-yl]ethanesulfonamide | 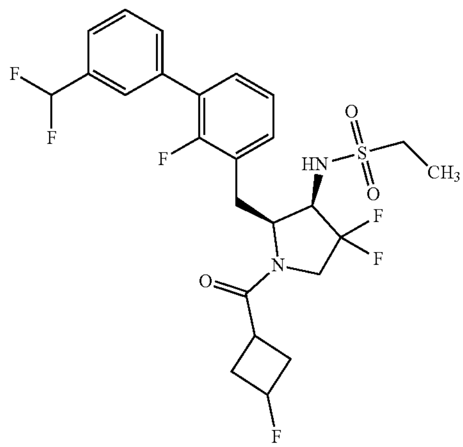 [SMILES: CCS(=O)(=O)N[C@@H]1[C@H](Cc2cccc(-c3cccc(C(F)F)c3)c2F)N(C(=O)C2CC(F)C2)CC1(F)F] | | 547.2 |
| 507 | N-[(2S,3R)-2-{[3'-(difluoromethyl)-2-fluoro(1,1'-biphenyl]-3-yl]methyl}-4,4-difluoro-1-(2-methylpropanoyl)pyrrolidin-3-yl]ethanesulfonamide | 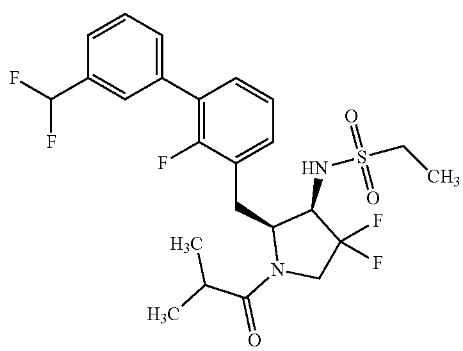 [SMILES: CCS(=O)(=O)N[C@@H]1[C@H](Cc2cccc(-c3cccc(C(F)F)c3)c2F)N(C(=O)C(C)C)CC1(F)F] | | 519.2 |
| 508 | N-[(2S,3R)-1-(cyclopropanecarbonyl)-2-{[3'-(difluoromethyl)-2-fluoro[1,1'-biphenyl]-3-yl]methyl}-4,4-difluoropyrrolidin-3-yl]ethanesulfonamide | 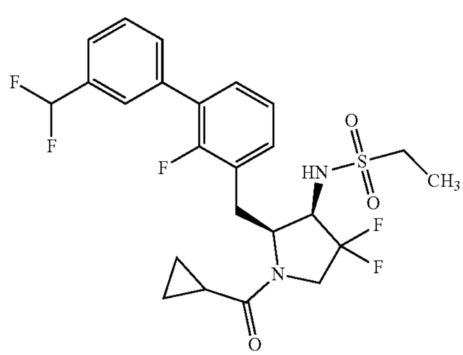 [SMILES: CCS(=O)(=O)N[C@@H]1[C@H](Cc2cccc(-c3cccc(C(F)F)c3)c2F)N(C(=O)C2CC2)CC1(F)F] | | 517.1 |

TABLE 1-1-continued

| EX. | IUPAC NAME | Structure | ADDITIVE | MS |
|---|---|---|---|---|
| 509 | N-[(2S,3R)-1-(bicyclo[1.1.1]pentane-1-carbonyl)-2-{[3'-(difluoromethyl)-2-fluoro[1,1'-biphenyl]-3-yl]methyl}-4,4-difluoropyrrolidin-3-yl]ethanesulfonamide | 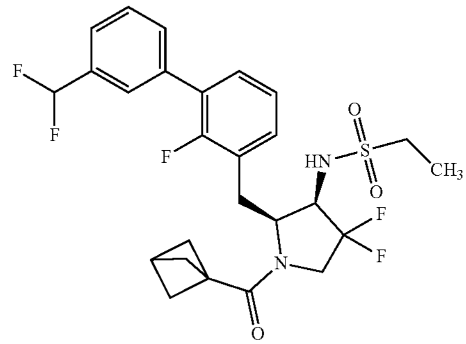 [SMILES: CCS(=O)(=O)N[C@@H]1[C@H](Cc2cccc(-c3cccc(C(F)F)c3)c2F)N(C(=O)C23CC(C2)C3)CC1(F)F] | | 543.2 |
| 510 | N-{(2S,3R)-1-(bicyclo[1.1.1]pentane-1-carbonyl)-4,4-difluoro-2-[(2-fluoro-3'-methoxy[1,1'-biphenyl]-3-yl)methyl]-pyrrolidin-3-yl}ethanesulfonamide | 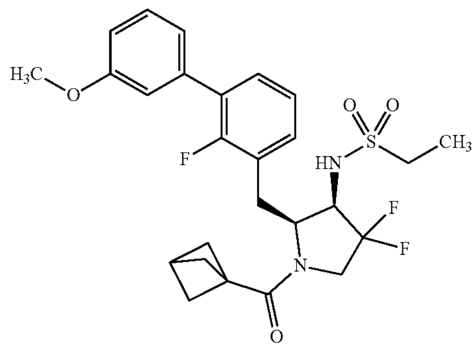 [SMILES: CCS(=O)(=O)N[C@@H]1[C@H](Cc2cccc(-c3cccc(OC)c3)c2F)N(C(=O)C23CC(C2)C3)CC1(F)F] | | 523.2 |
| 511 | N-[(2S,3R)-4,4-difluoro-2-[(2-fluoro-3'-methoxy[1,1'-biphenyl]-3-yl)methyl]-1-(2-methylpropanoyl)pyrrolidin-3-yl]-ethanesulfonamide | 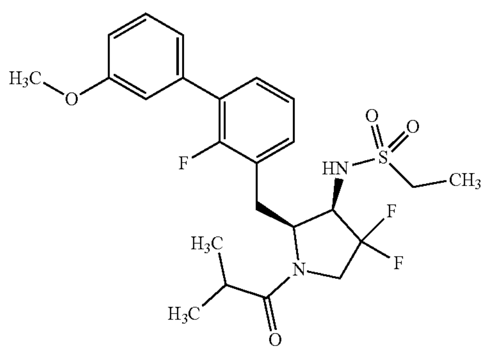 [SMILES: CCS(=O)(=O)N[C@@H]1[C@H](Cc2cccc(-c3cccc(OC)c3)c2F)N(C(=O)C(C)C)CC1(F)F] | | 499.1 |
| 512 | N-{(2S,3R)-1-(cyclopropanecarbonyl)-4,4-difluoro-2-[{2-fluoro-3'-methoxy[1,1'-biphenyl]-3-yl)methyl]pyrrolidin-3-yl}-ethanesulfonamide | 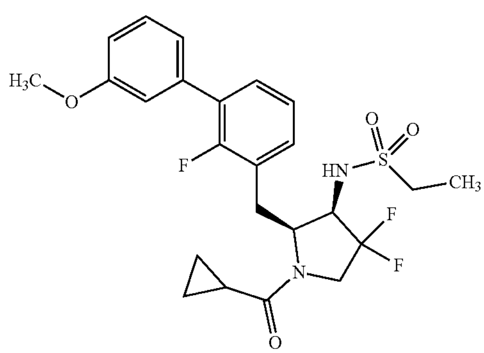 [SMILES: CCS(=O)(=O)N[C@@H]1[C@H](Cc2cccc(-c3cccc(OC)c3)c2F)N(C(=O)C2CC2)CC1(F)F] | | 497.2 |

TABLE 1-1-continued

| EX. | IUPAC NAME | Structure | ADDITIVE | MS |
|---|---|---|---|---|
| 513 | N-[(2S,3R)-4,4-difluoro-2-[(2-fluoro-3'-methoxy[1,1'-biphenyl]-3-yl)methyl]-1-(1-hydroxycyclobutane-1-carbonyl)-pyrrolidin-3-yl]ethanesulfonamide | 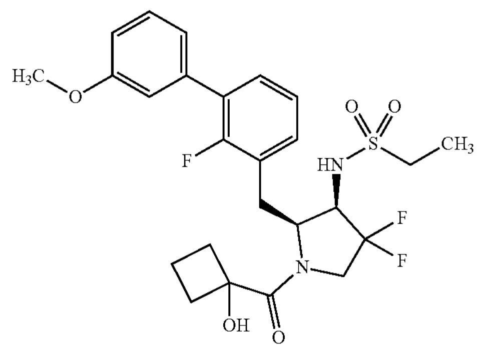 [SMILES: CCS(=O)(=O)N[C@@H]1[C@H](Cc2cccc(-c3cccc(OC)c3)c2F)N(C(=O)C2(O)CCC2)CC1(F)F] | | 527.2 |
| 514 | N-{(2S,3R,4S)-1-(cyclopropanecarbonyl)-4-fluoro-2-[(2-fluoro-3'-methyl[1,1'-biphenyl]-3-yl)methyl]pyrrolidin-3-yl}-ethanesulfonamide | 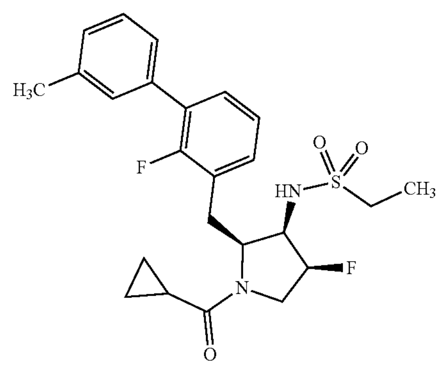 [SMILES: CCS(=O)(=O)N[C@H]1[C@@H](F)CN(C(=O)C2CC2)[C@H]1Cc1cccc(-c2cccc(C)c2)c1F] | | 463.2 |
| 515 | N-{(2S,3R,4S)-1-(cyclopropanecarbonyl)-2-[(2,3'-difluoro-5'-methyl[1,1'-biphenyl]-3-yl)methyl]-4-fluoropyrrolidin-3-yl}-ethanesulfonamide | 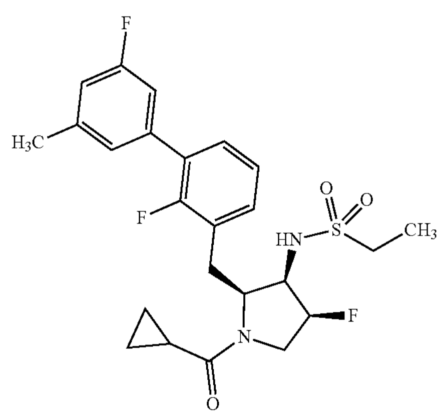 [SMILES: CCS(=O)(=O)N[C@H]1[C@@H](F)CN(C(=O)C2CC2)[C@H]1Cc1cccc(-c2cc(C)cc(F)c2)c1F] | | 481.2 |
| 516 | N-[(2S,3R,4S)-2-[(3'-chloro-2-fluoro[1,1'-biphenyl]-3-yl)methyl]-1-(cyclopropanecarbonyl)-4-fluoropyrrolidin-3-yl]ethanesulfonamide | 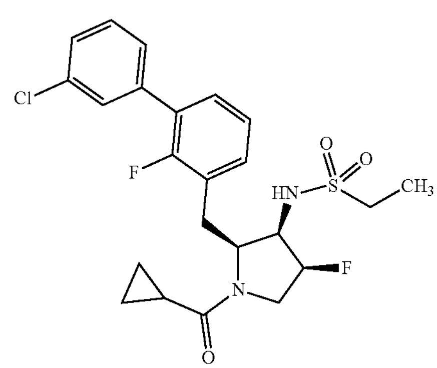 [SMILES: CCS(=O)(=O)N[C@H]1[C@@H](F)CN(C(=O)C2CC2)[C@H]1Cc1cccc(-c2cccc(Cl)c2)c1F] | | 483.2 |

TABLE 1-1-continued

| EX. | IUPAC NAME | Structure | ADDITIVE | MS |
|---|---|---|---|---|
| 517 | N-[(2S,3R,4S)-2-[(3'-chloro-2,5'-difluoro-[1,1'-biphenyl]-3-yl)methyl]-1-(cyclopropanecarbonyl)-4-fluoropyrrolidin-3-yl]ethanesulfonamide | 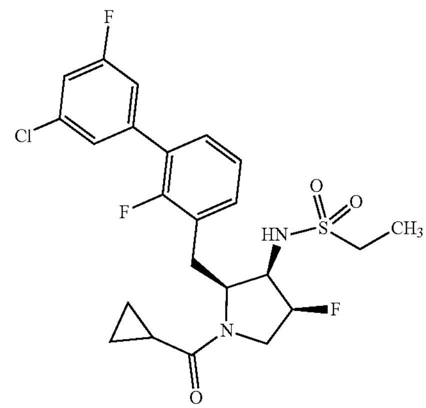 [SMILES: CCS(=O)(=O)N[C@H]1[C@@H](F)CN(C(=O)C2CC2)[C@H]1Cc1cccc(-c2cc(F)cc(Cl)c2)c1F] | | 501.1 |
| 518 | N-{(2S,3R,4S)-1-(cyclopropanecarbonyl)-2-[(2,2'-difluoro[1,1'-biphenyl]-3-yl)methyl]-4-fluoropyrrolidin-3-yl}-ethanesulfonamide | 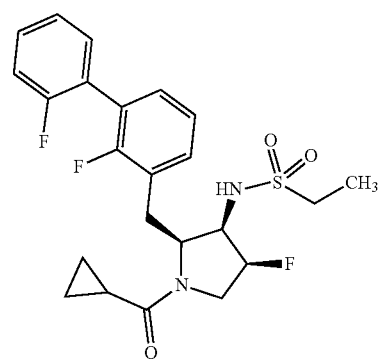 [SMILES: CCS(=O)(=O)N[C@H]1[C@@H](F)CN(C(=O)C2CC2)[C@H]1Cc1cccc(-c2ccccc2F)c1F] | | 467.1 |
| 519 | N-{(2S,3R,4S)-1-(cyclopropanecarbonyl)-2-[(2,2'-difluoro-3'-methyl[1,1'-biphenyl]-3-yl)methyl]-4-fluoropyrrolidin-3-yl}-ethanesulfonamide | 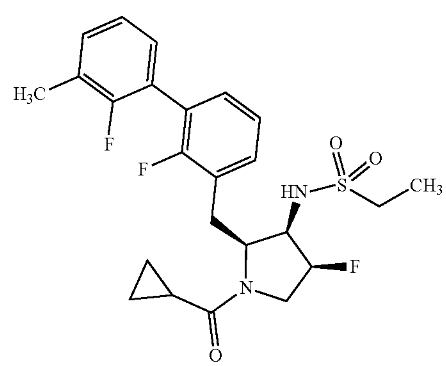 [SMILES: CCS(=O)(=O)N[C@H]1[C@@H](F)CN(C(=O)C2CC2)[C@H]1Cc1cccc(-c2cccc(C)c2F)c1F] | | 481.1 |
| 520 | N-[(2S,3R,4S)-2-[(3'-chloro-2,2'-difluoro-[1,1'-biphenyl]-3-yl)methyl]-1-(cyclopropanecarbonyl)-4-fluoropyrrolidin-3-yl]ethanesulfonamide | 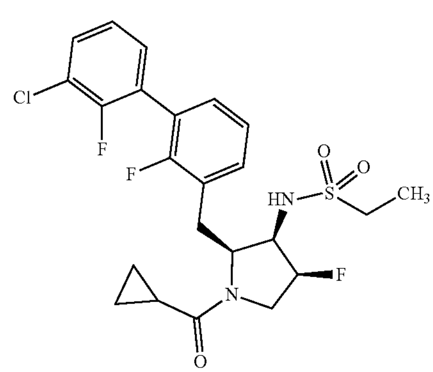 [SMILES: CCS(=O)(=O)N[C@H]1[C@@H](F)CN(C(=O)C2CC2)[C@H]1Cc1cccc(-c2cccc(Cl)c2F)c1F] | | 501.1 |

TABLE 1-1-continued

| EX. | IUPAC NAME | Structure | ADDITIVE | MS |
|---|---|---|---|---|
| 521 | (2S,3R)-3-[(cyclopropanesulfonyl)amino]-2-[(2,2'-difluoro-3'-methyl[1,1'-biphenyl]-3-yl)methyl]-4,4-difluoro-N,N-dimethylpyrrolidine-1-carboxamide | 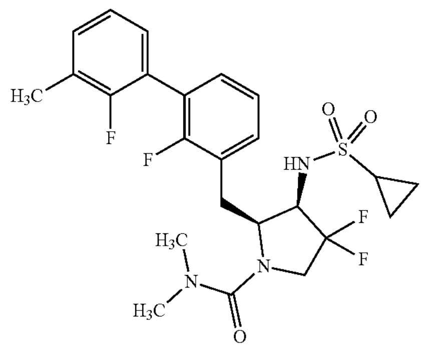 [SMILES: Cc1cccc(-c2cccc(C[C@H]3[C@@H](NS(=O)(=O)C4CC4)C(F)(F)CN3C(=O)N(C)C)c2F)c1F] | | 514.2 |
| 522 | (2S,3R)-3-[(cyclopropanesulfonyl)amino]-2-[(2,3'-difluoro-5'-methyl[1,1'-biphenyl]-3-yl)methyl]-4,4-difluoro-N,N-dimethylpyrrolidine-1-carboxamide | 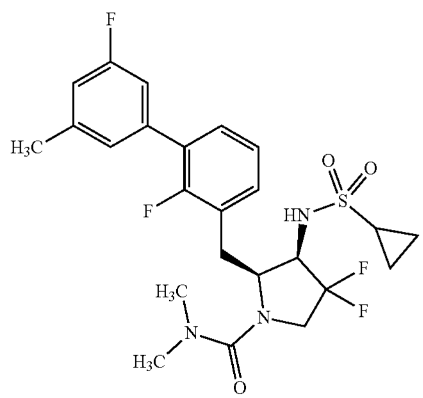 [SMILES: Cc1cc(F)cc(-c2cccc(C[C@H]3[C@@H](NS(=O)(=O)C4CC4)C(F)(F)CN3C(=O)N(C)C)c2F)c1] | | 514.2 |
| 523 | (2S,3R)-3-[(cyclopropanesulfonyl)amino]-2-[(2,3'-difluoro[1,1'-biphenyl]-3-yl)methyl]-4,4-difluoro-N,N-dimethylpyrrolidine-1-carboxamide | 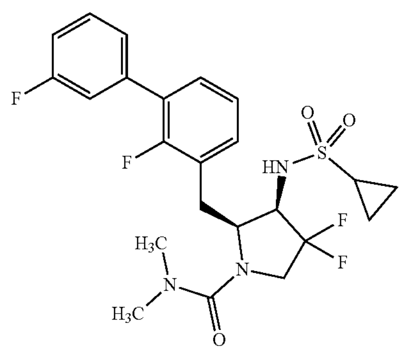 [SMILES: CN(C)C(=O)N1CC(F)(F)[C@H](NS(=O)(=O)C2CC2)[C@@H]1Cc1cccc(-c2cccc(F)c2)c1F] | | 500.2 |
| 524 | (2S,3R)-3-[(cyclopropanesulfonyl)amino]-4,4-difluoro-N,N-dimethyl-2-[(2,3',5'-trifluoro[1,1'-biphenyl]-3-yl)methyl]pyrrolidine-1-carboxamide | 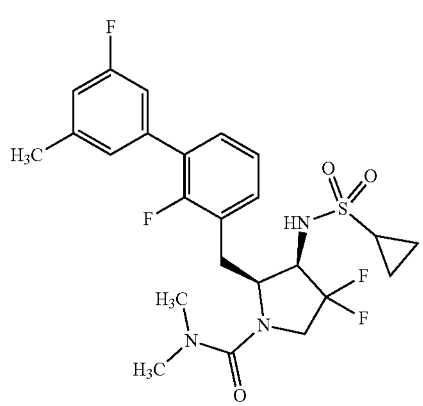 [SMILES: Cc1cc(F)cc(-c2cccc(C[C@H]3[C@@H](NS(=O)(=O)C4CC4)C(F)(F)CN3C(=O)N(C)C)c2F)c1] | | 518.2 |

TABLE 1-1-continued

| EX. | IUPAC NAME | Structure | ADDITIVE | MS |
|---|---|---|---|---|
| 525 | N-{(2S,3R)-1-(azetidine-1-carbonyl)-4,4-difluoro-2-[(2,3',5'-trifluoro[1,1'-biphenyl]-3-yl)methyl]pyrrolidin-3-yl}cyclopropane-sulfonamide | 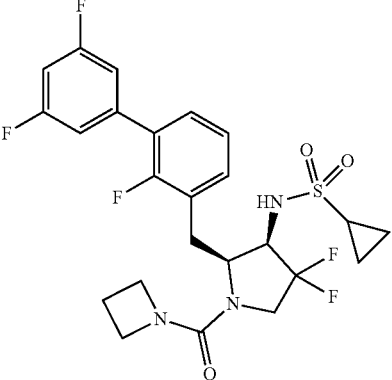 [SMILES: O=C(N1CCC1)N1CC(F)(F)[C@H](NS(=O)(=O)C2CC2)[C@@H]1Cc1cccc(-c2cc(F)cc(F)c2)c1F] | | 530.1 |
| 526 | (2S,3R)-2-[(2,3'-difluoro-5'-methyl[1,1'-biphenyl]-3-yl)methyl]-3-[(dimethyl-sulfamoyl)amino]-4,4-difluoro-N,N-dimethylpyrrolidine-1-carboxamide | 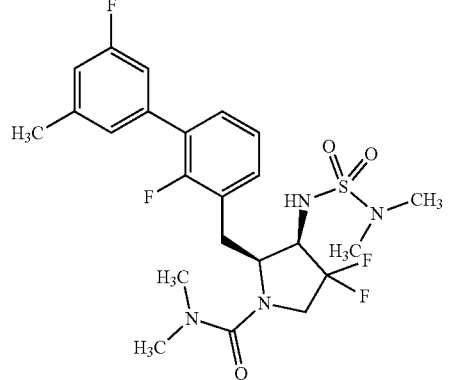 | | 517.2 |
| 527 | N-{(2S,3R)-1-(azetidine-1-carbonyl)-2-[(2,2'-difluoro-3'-methyl[1,1'-biphenyl]-3-yl)methyl]-4,4-difluoropyrrolidin-3-yl}-cyclopropanesulfonamide | 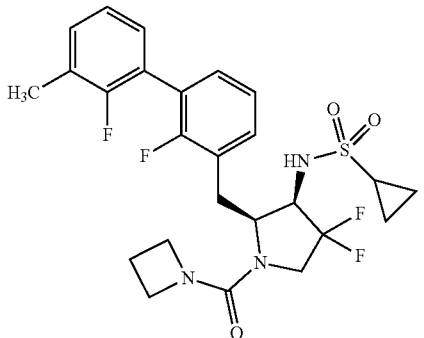 [SMILES: Cc1cccc(-c2cccc(C[C@H]3[C@@H](NS(=O)(=O)C4CC4)C(F)(F)CN3C(=O)N3CCC3)c2F)c1F] | | 526.1 |
| 528 | (2S,3R)-2-[(2,3'-difluoro[1,1'-biphenyl]-3-yl)methyl]-3-[(dimethylsulfamoyl)amino]-4,4-difluoro-N,N-dimethylpyrrolidine-1-carboxamide | 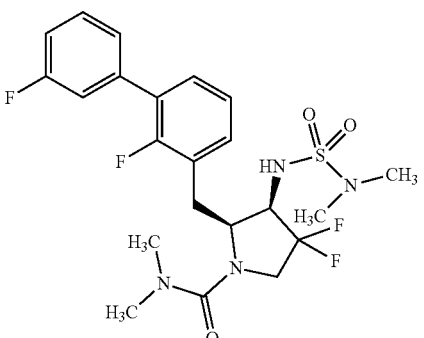 | | 503.2 |

TABLE 1-1-continued

| EX. | IUPAC NAME | Structure | ADDITIVE | MS |
|---|---|---|---|---|
| 529 | N-{(2S,3R)-1-(azetidine-1-carbonyl)-2-[(2,3'-difluoro-5'-methyl[1,1'-biphenyl]-3-yl)methyl]-4,4-difluoropyrrolidin-3-yl}-cyclopropanesulfonamide | 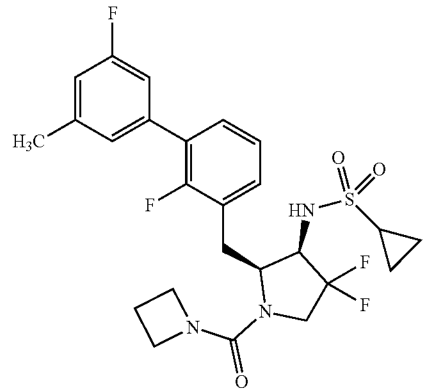 | | 526.2 |
| 530 | N-{(2S,3R)-2-[(2,2'-difluoro-3'-methyl[1,1'-biphenyl]-3-yl)methyl]-4,4-difluoro-1-[(2R)-oxetane-2-carbonyl]pyrrolidin-3-yl}cyclopropanesulfonamide | 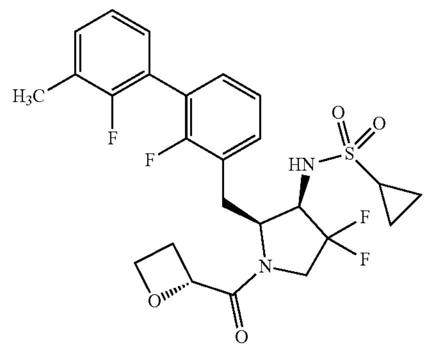 [SMILES: Cc1cccc(-c2cccc(C[C@H]3[C@@H](NS(=O)(=O)C4CC4)C(F)(F)CN3C(=O)[C@H]3CCO3)c2F)c1F] | | 527.2 |
| 531 | (2S,3R)-2-[(2,2'-difluoro-3'-methyl[1,1'-biphenyl]-3-yl)methyl]-3-[(dimethyl-sulfamoyl)amino]-4,4-difluoro-N,N-dimethylpyrrolidine-1-carboxamide | 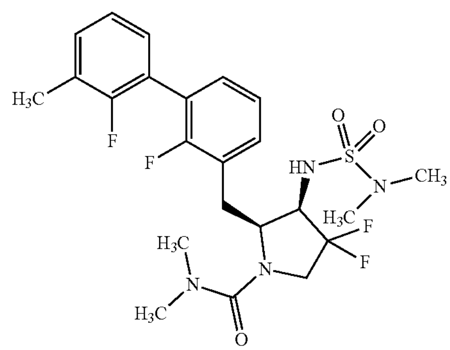 | | 517.2 |
| 532 | (2S,3R)-3-[(dimethylsulfamoyl)amino]-4,4-difluoro-N,N-dimethyl-2-[(2,3',5'-trifluoro-[1,1'-biphenyl]-3-yl)methyl]pyrrolidine-1-carboxamide | 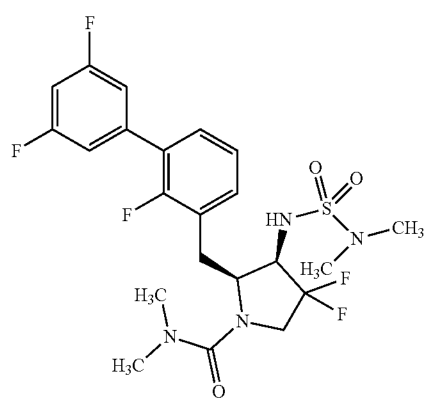 [SMILES: CN(C)C(=O)N1CC(F)(F)[C@H](NS(=O)(=O)N(C)C)[C@@H]1Cc1cccc(-c2cc(F)cc(F)c2)c1F] | | 521.2 |

TABLE 1-1-continued

| EX. | IUPAC NAME | Structure | ADDITIVE | MS |
|---|---|---|---|---|
| 533 | N-{(2S,3R)-2-[(2,3,-difluoro-5'-methyl[1,1'-biphenyl]-3-yl)methyl]-4,4-difluoro-1-[(2R)-oxetane-2-carbonyl]pyrrolidln-3-yl}cyclopropanesulfonamide | 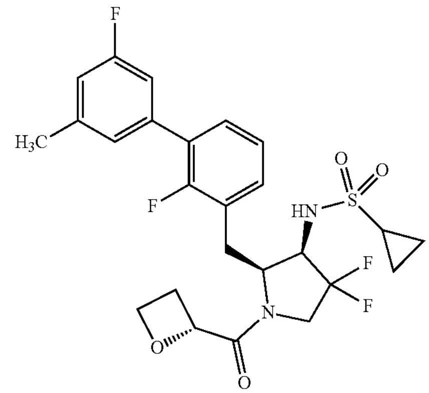 [SMILES: Cc1cc(F)cc(-c2cccc(C[C@H]3[C@@H](NS(=O)(=O)C4CC4)C(F)(F)CN3C(=O)[C@H]3CCO3)c2F)c1] | | 527.1 |
| 534 | N-{(2S,3R)-1-(azetidine-1-carbonyl)-2-[(2,3'-difluoro[1,1'-biphenyl]-3-yl)methyl]-4,4-difluoropyrrolidin-3-yl}cyclopropane-sulfonamide | 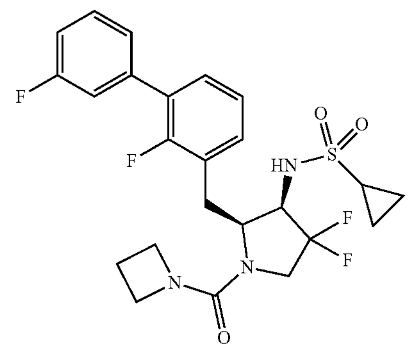 [SMILES: O=C(N1CCC1)N1CC(F)(F)[C@H](NS(=O)(=O)C2CC2)[C@@H]1Cc1cccc(-c2cccc(F)c2)c1F] | | 512.2 |
| 535 | N-[(2S,3R,4S)-2-{[3'-(difluoromethyl)-2-fluoro[1,1'-biphenyl]-3-yl]methyl}-4-fluoro-1-(oxetane-2-carbonyl)pyrrolidin-3-yl]ethanesulfonamide derived from N-[(2S,3R,4S)-2-[(3-chloro-2-fluorophenyl)-methyl]-4-fluoro-1-(oxetane-2-carbonyl)-pyrrolidin-3-yl]ethanesulfonamide with shorter retention time by HPLC (column: L-Column2 ODS (3.0 mml · D. × 50 mmL, 3 µm), mobile phase: water/acetonitrile (including 0.05% TFA) | 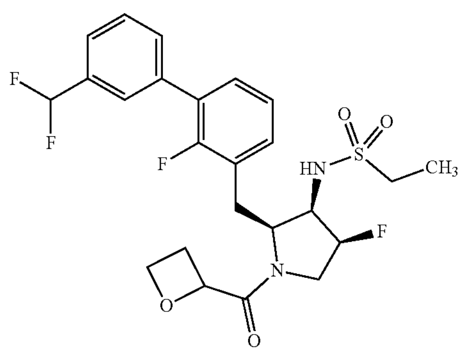 [SMILES: CCS(=O)(=O)N[C@H]1[C@@H](F)CN(C(=O)C2CCO2)[C@H]1Cc1cccc(-c2cccc(C(F)F)c2)c1F] | | 515.1 |
| 536 | N-[(2S,3R,4S)-4-fluoro-2-[(2-fluoro-3'-methyl[1,r-biphenyl]-3-yl)methyl]-1-(1-hydroxycyclobutane-1-carbonyl)-pyrrolidin-3-yl]ethanesulfonamide | 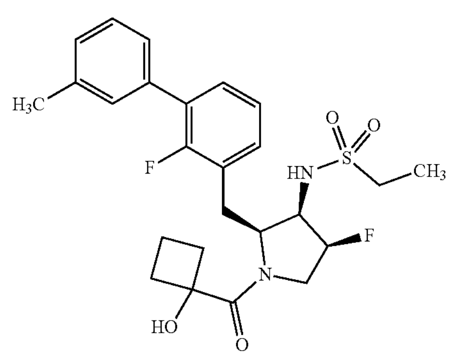 [SMILES: CCS(=O)(=O)N[C@H]1[C@@H](F)CN(C(=O)C2(O)CCC2)[C@H]1Cc1cccc(-c2cccc(C)c2)c1F] | | 493.2 |

TABLE 1-1-continued

| EX. | IUPAC NAME | Structure | ADDITIVE | MS |
|---|---|---|---|---|
| 537 | N-[(2S,3R,4S)-4-fluoro-2-[(2-fluoro-3'-methyl[1,1'-biphenyl]-3-yl)methyl]-1-(1-hydroxycyclobutane-1-carbonyl)pyrrolidin-3-yl]cyclopropanesulfonamide | 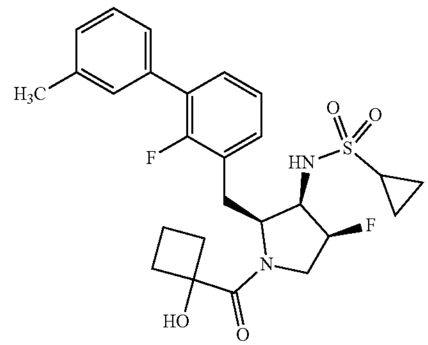 [SMILES: Cc1cccc(-c2cccc(C[C@H]3[C@@H](NS(=O)(=O)C4CC4)[C@@H](F)CN3C(=O)C3(O)CCC3)c2F)c1] | | 505.3 |
| 538 | (2S,3R,4S)-3-[(cyclopropanesulfonyl)-amino]-4-fluoro-2-[(2-fluoro-3'-methyl-[1,1'-biphenyl]-3-yl)methyl]-N,N-dimethyl-pyrrolidine-1-carboxamide | 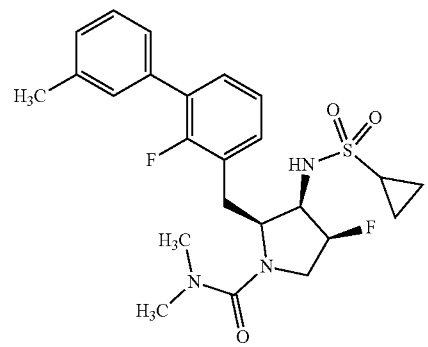 [SMILES: Cc1cccc(-c2cccc(C[C@H]3[C@@H](NS(=O)(=O)C4CC4)[C@@H](F)CN3C(=O)N(C)C)c2F)c1] | | 478.2 |
| 539 | N'-{(2S,3R)-2-[(2,2'-difluoro-3'-methyl-[1,1'-biphenyl]-3-yl)methyl]-4,4-difluoro-1-[(2R)-oxetane-2-carbonyl]pyrrolidin-3-yl}-N,N-dimethylsulfuric diamide | 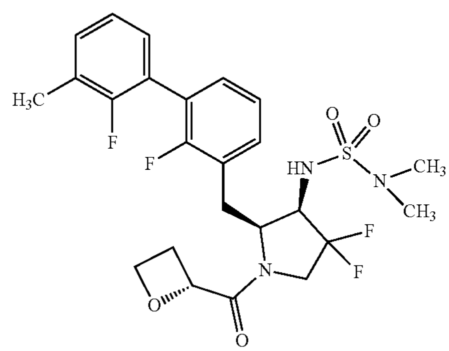 | | 530.2 |
| 540 | N'-{(2S,3R)-2-[(2,3'-difluoro-5'-methyl-[1,1'-biphenyl]-3-yl)methyl]-4,4-difluoro-1-[(2R)-oxetane-2-carbonyl]pyrrolidin-3-yl}-N,N-dimethylsulfuric diamide | 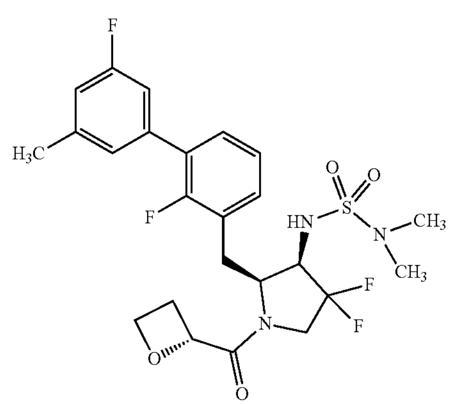 | | 530.2 |

TABLE 1-1-continued

| EX. | IUPAC NAME | Structure | ADDITIVE | MS |
|---|---|---|---|---|
| 541 | N'-{(2S,3R)-2-[(2,3'-difluoro[1,1'-biphenyl]-3-yl)methyl]-4,4-difluoro-1-[(2R)-oxetane-2-carbonyl]pyrrolidin-3-yl}-N,N-dimethylsulfuric diamide | 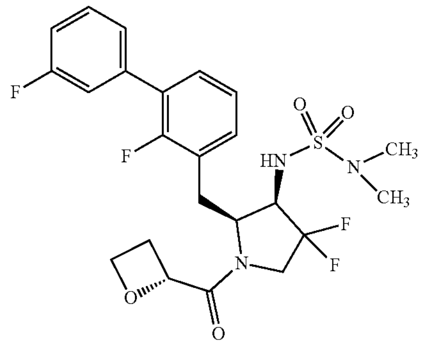 [SMILES: CN(C)S(=O)(=O)N[C@@H]1[C@H](Cc2cccc(-c3cccc(F)c3)c2F)N(C(=O)[C@H]2CCO2)CC1(F)F] | | 516.2 |
| 542 | N'-{(2S,3R)-4,4-difluoro-1-[(2R)-oxetane-2-carbonyl]-2-[(2,3',5'-trifluoro[1,1'-biphenyl]-3-yl)methyl]pyrrolidin-3-yl)-N,N-dimethylsulfuric diamide | 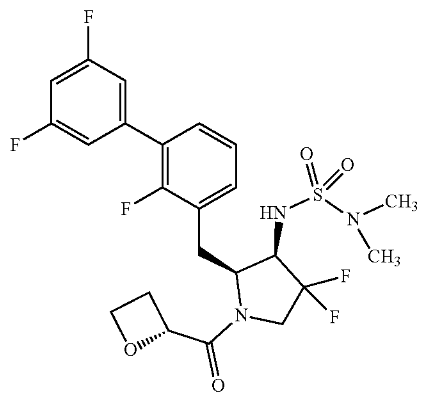 [SMILES: CN(C)S(=O)(=O)N[C@@H]1[C@H](Cc2cccc(-c3cc(F)cc(F)c3)c2F)N(C(=O)[C@H]2CCO2)CC1(F)F] | | 534.1 |
| 543 | N-{(2S,3R,4S)-1-(azetidine-1-carbonyl)-4-fluoro-2-[(2-fluoro-3'-methyl[1,1'-biphenyl]-3-yl)methyl]pyrrolidin-3-yl}-cyclopropanesulfonamide | 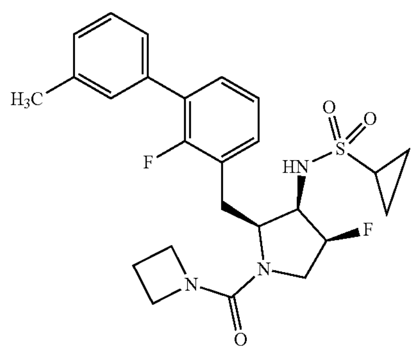 [SMILES: Cc1cccc(-c2cccc(C[C@H]3[C@@H](NS(=O)(=O)C4CC4)[C@@H](F)CN3C(=O)N3CCC3)c2F)c1] | | 490.1 |
| 544 | N-{(2S,3R,4S)-1-(azetidine-1-carbonyl)-4-fluoro-2-[(2,3',5'-trifluoro[1,1'-biphenyl]-3-yl)methyl]pyrrolidin-3-yl}cyclopropane-sulfonamide | 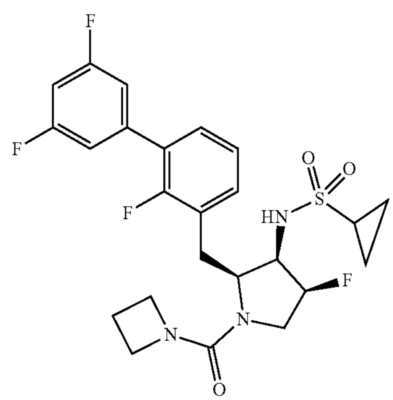 [SMILES: O=C(N1CCC1)N1C[C@H](F)[C@H](NS(=O)(=O)C2CC2)[C@@H]1Cc1cccc(-c2cc(F)cc(F)c2)c1F] | | 512.2 |

TABLE 1-1-continued

| EX. | IUPAC NAME | Structure | ADDITIVE | MS |
|---|---|---|---|---|
| 545 | N'-{(2S,3R)-1-(azetidine-1-carbonyl)-2-[(2,2'-difluoro-3'-methyl[1,1'-biphenyl]-3-yl)methyl]-4,4-difluoropyrrolidin-3-yl}-N,N-dimethylsulfuric diamide | 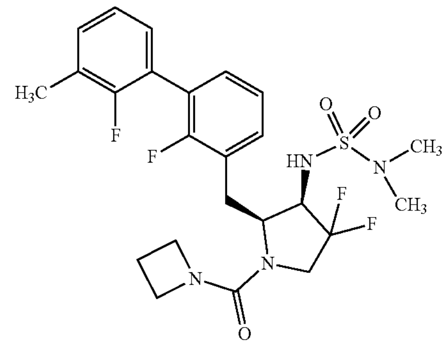 | | 529.2 |
| 546 | N'-{(2S,3R)-1-(azetidine-1-carbonyl)-2-[(2,3'-difluoro-5'-methyl[1,1'-biphenyl]-3-yl)methyl]-4,4-difluoropyrrolidin-3-yl}-N,N-dimethylsulfuric diamide | 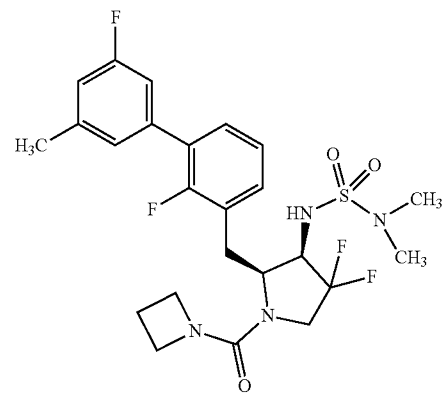 | | 529.2 |
| 547 | N'-{(2S,3R)-1-(azetidine-1-carbonyl)-2-[(2,3'-difluoro[1,1'-biphenyl]-3-yl)methyl]-4,4-difluoropyrrolidin-3-yl}-N,N-dimethyl-sulfuric diamide | 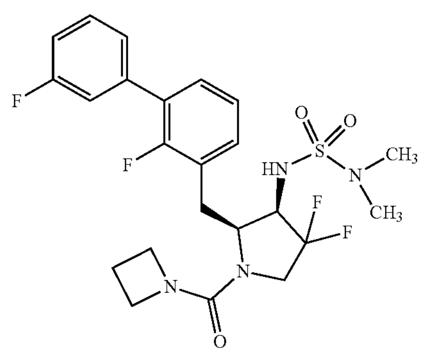 [SMILES: CN(C)S(=O)(=O)N[C@@H]1[C@H](Cc2cccc(-c3cccc(F)c3)c2F)N(C(=O)N2CCC2)CC1(F)F] | | 515.2 |
| 548 | N'-{(2S,3R)-1-(azetidine-1-carbonyl)-4,4-difluoro-2-[(2,3',5'-trifluoro[1,1'-biphenyl]-3-yl)methyl]pyrrolidin-3-yl}-N,N-dimethyl-sulfuric diamide | 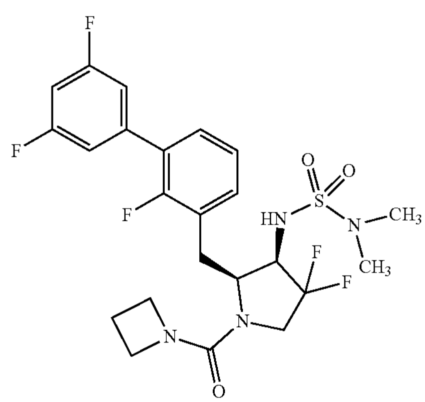 [SMILES: CN(C)S(=O)(=O)N[C@@H]1[C@H](Cc2cccc(-c3cc(F)cc(F)c3)c2F)N(C(=O)N2CCC2)CC1(F)F] | | 533.2 |

TABLE 1-1-continued

| EX. | IUPAC NAME | Structure | ADDITIVE | MS |
|---|---|---|---|---|
| 549 | N-[(2S,3R)-2-{[3'-(difluoromethoxy)-2-fluoro[1,1'-bjphenyl]-3-yl]methyl}-4,4-difluoro-1-(2-methylpropanoyl)pyrrolidin-3-yl]ethanesulfonamide | 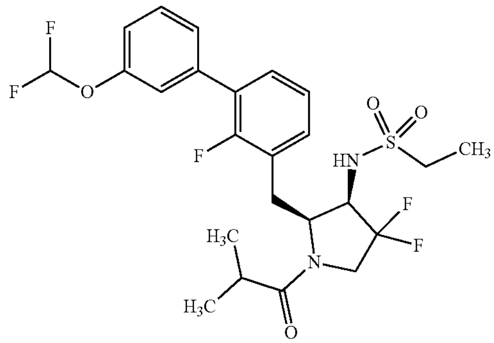 [SMILES: CCS(=O)(=O)N[C@@H]1[C@H](Cc2cccc(-c3cccc(OC(F)F)c3)c2F)N(C(=O)C(C)C)CC1(F)F] | | 535.1 |
| 550 | N-[(2S,3R)-1-(cyclopropanecarbonyl)-2-{[3'-(difluoromethoxy)-2-fluoro[1,1'-biphenyl]-3-yl]methyl}-4,4-difluoro-pyrrolidin-3-yl]ethanesulfonamide | 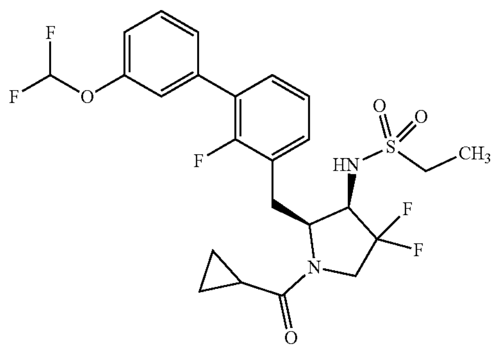 [SMILES: CCS(=O)(=O)N[C@@H]1[C@H](Cc2cccc(-c3cccc(OC(F)F)c3)c2F)N(C(=O)C2CC2)CC1(F)F] | | 533.2 |
| 551 | N-[(2S,3R)-1-(bicyclo[1.1.1]pentane-1-carbonyl)-2-{[3'-(difluoromethoxy)-2-fluoro[1,1'-biphenyl]-3-yl]methyl}-4,4-difluoropyrrolidin-3-yl]ethanesulfonamide | 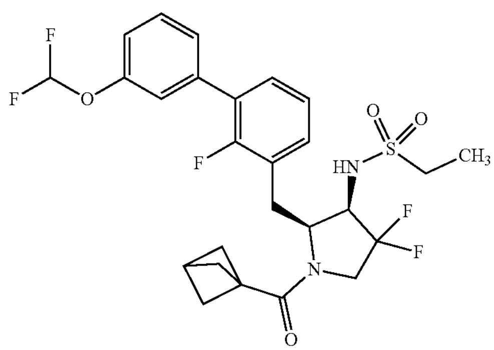 [SMILES: CCS(=O)(=O)N[C@@H]1[C@H](Cc2cccc(-c3cccc(OC(F)F)c3)c2F)N(C(=O)C23CC(C2)C3)CC1(F)F] | | 559.2 |
| 552 | N-[(2S,3R)-2-{[3'-(difluoromethoxy)-2-fluoro[1,1'-biphenyl]-3-yl]methyl}-4,4-difluoro-1-(1-hydroxycyclobutane-1-carbonyl)pyrrolidin-3-yl]ethanesulfonamide | 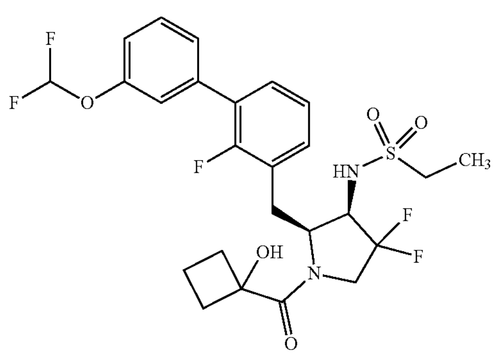 [SMILES: CCS(=O)(=O)N[C@@H]1[C@H](Cc2cccc(-c3cccc(OC(F)F)c3)c2F)N(C(=O)C2(O)CCC2)CC1(F)F] | | 563.1 |

TABLE 1-1-continued

| EX. | IUPAC NAME | Structure | ADDITIVE | MS |
|---|---|---|---|---|
| 553 | N-[(2S,3R)-2-[(3'-chloro-2,4'-difluoro-[1,1'-biphenyl]-3-yl)methyl]-4,4-difluoro-1-((2S)-oxetane-2-carbonyl)pyrrolidin-3-yl]ethanesulfonamide | 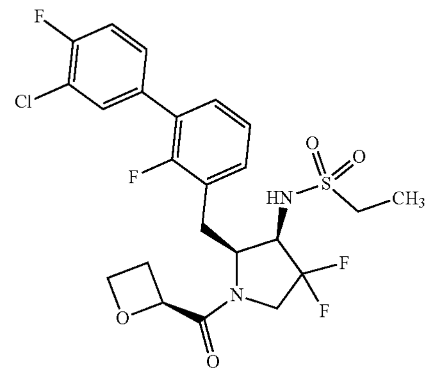 [SMILES: CCS(=O)(=O)N[C@@H]1[C@H](Cc2cccc(-c3ccc(F)c(Cl)c3)c2F)N(C(=O)[C@@H]2CCO2)CC1(F)F] | | 535.0 |
| 554 | N-{(2S,3R)-2-[(3'-chloro-2,4'-difluoro[1,1'-biphenyl]-3-yl)methyl]-4,4-difluoro-1-[(2R)-oxetane-2-carbonyl]pyrrolidin-3-yl}ethanesulfonamide | 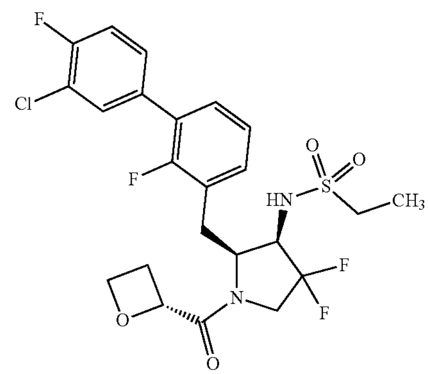 [SMILES: CCS(=O)(=O)N[C@@H]1[C@H](Cc2cccc(-c3ccc(F)c(Cl)c3)c2F)N(C(=O)[C@H]2CCO2)CC1(F)F] | | 535.1 |
| 555 | N-{(2S,3R)-4,4-difluoro-1-(oxetane-2-carbonyl)-2-[(2,2',4'-trifluoro-5'-methyl-[1,1'-biphenyl]-3-yl)methyl]pyrrolidin-3-yl}ethanesulfonamide with longer retention time | 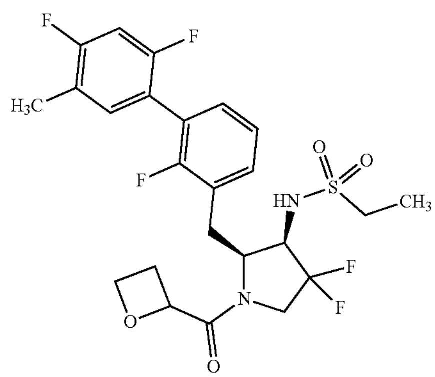 [SMILES: CCS(=O)(=O)N[C@@H]1[C@H](Cc2cccc(-c3cc(C)c(F)cc3F)c2F)N(C(=O)C2CCO2)CC1(F)F] | | 533.1 |
| 556 | N-{(2S,3R)-4,4-difluoro-1-(oxetane-2-carbonyl)-2-[(2,2',4'-trifluoro-5'-methyl-[1,1'-biphenyl]-3-yl)methyl]pyrrolidin-3-yl}ethanesulfonamide with shorter retention time | 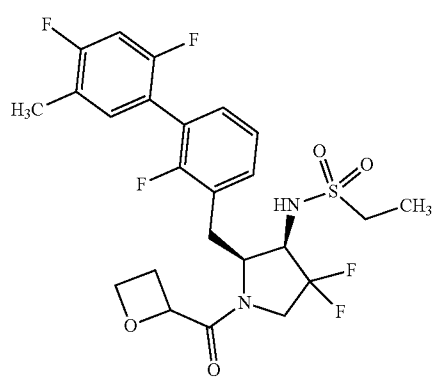 [SMILES: CCS(=O)(=O)N[C@@H]1[C@H](Cc2cccc(-c3cc(C)c(F)cc3F)c2F)N(C(=O)C2CCO2)CC1(F)F] | | 533.1 |

TABLE 1-1-continued

| EX. | IUPAC NAME | Structure | ADDITIVE | MS |
|---|---|---|---|---|
| 557 | N-{(2S,3R)-1-(azetidine-1-carbonyl)-2-[(4'-bromo-2,3'-difluoro[1,1'-biphenyl]-3-yl)methyl]-4,4-difluoropyrrolidin-3-yl}methanesulfonamide | 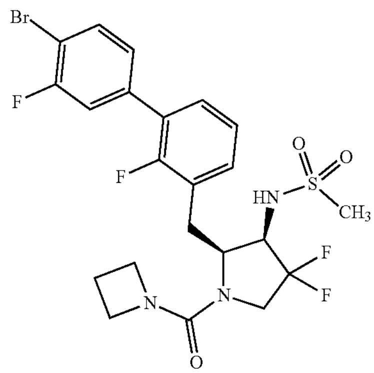 [SMILES: CS(=O)(=O)N[C@@H]1[C@H](Cc2cccc(-c3ccc(Br)c(F)c3)c2F)N(C(=O)N2CCC2)CC1(F)F] | | 564.0 |
| 558 | N-{(2S,3R)-4,4-difluoro-1-(3-fluorocyclobutane-1-carbonyl)-2-[(2-fluoro-3'-methoxy-[1,1'-biphenyl]-3-yl)methyl]-pyrrolidin-3-yl}ethanesulfonamide with longer retention time | 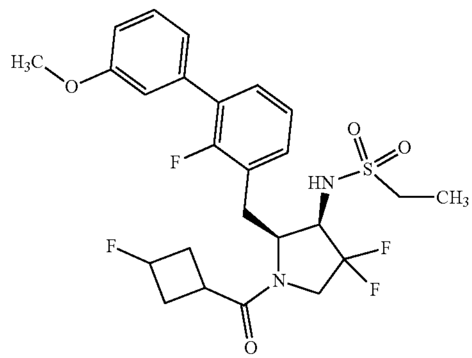 [SMILES: CCS(=O)(=O)N[C@@H]1[C@H](Cc2cccc(-c3cccc(OC)c3)c2F)N(C(=O)C2CC(F)C2)CC1(F)F] | | 529.1 |
| 559 | N-{(2S,3R)-4,4-difluoro-1-{3-fluoro-cyclobutane-1-carbonyl)-2-[(2-fluoro-3'-methoxy[1,1'-biphenyl]-3-yl)methyl]-pyrrolidin-3-yl}ethanesulfonamide with shorter retention time | 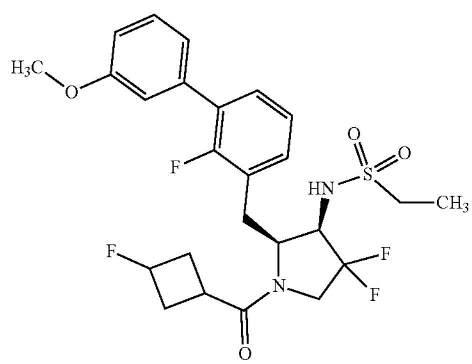 [SMILES: CCS(=O)(=O)N[C@@H]1[C@H](Cc2cccc(-c3cccc(OC)c3)c2F)N(C(=O)C2CC(F)C2)CC1(F)F] | | 529.1 |
| 560 | N'-((2S,3R)-1-(azetidine-1-carbonyl)-2-[(3-chloro-2-fluorophenyl)methyl]-4,4-difluoropyrrolidin-3-yl]-N,N-dimethyl-sulfuric diamide | 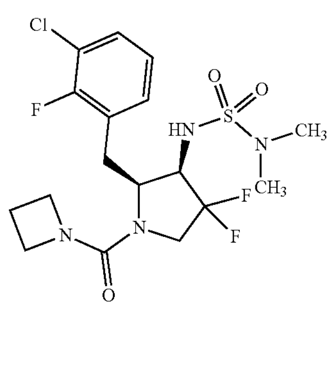 [SMILES: CN(C)S(=O)(=O)N[C@@H]1[C@H](Cc2cccc(Cl)c2F)N(C(=O)N2CCC2)CC1(F)F] | | 455.1 |

TABLE 1-1-continued

| EX. | IUPAC NAME | Structure | ADDITIVE | MS |
|---|---|---|---|---|
| 561 | rac-N-[(2S,3R)-2-{[6-(3,5-difluorophenyl)-pyridin-2-yl]methyl}-4,4-difluoro-1-(2-hydroxy-2-methylpropanoyl)pyrrolidin-3-yl]methanesulfonamide | 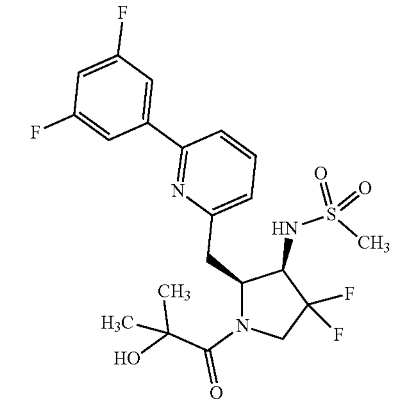 [SMILES: CC(C)(O)C(=O)N1CC(F)(F)[C@H](NS(C)(=O)=O)[C@@H]1Cc1cccc(-c2cc(F)cc(F)c2)n1] | | 490.1 |
| 562 | rac-N-[(2S,3R)-2-{[6-(3,5-difluorophenyl)-pyridin-2-yl]methyl}-4,4-difluoro-1-(1-hydroxycyclobutane-1-carbonyl)pyrrolidin-3-yl]methanesulfonamide | 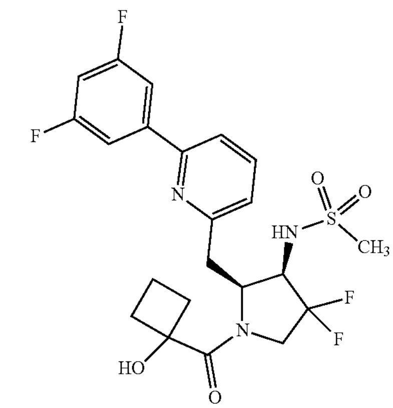 [SMILES: CS(=O)(=O)N[C@@H]1[C@H](Cc2cccc(-c3cc(F)cc(F)c3)n2)N(C(=O)C2(O)CCC2)CC1(F)F] | | 502.1 |
| 563 | N-{(2S,3R)-2-[(2,2'-difluoro-3,-methyl-[1,1'-biphenyl]-3-yl)methyl]-4,4-difluoro-1-{(2S)-oxetane-2-carbonyl]pyrrolidin-3-yl}-cyclopropanesulfonamide | 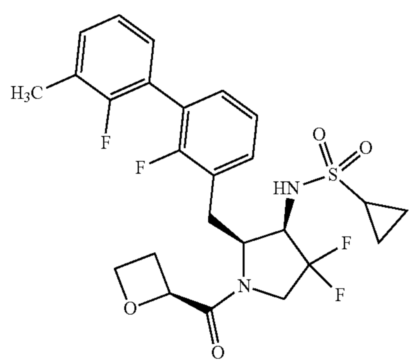 [SMILES: Cc1cccc(-c2cccc(C[C@H]3[C@@H](NS(=O)(=O)C4CC4)C(F)(F)CN3C(=O)[C@@H]3CCO3)c2F)c1F] | | 527.1 |
| 564 | N-{(2S,3R)-2-[(2,3'-difluoro-5'-methyl-[1,1'-biphenyl]-3-yl)methyl]-4,4-difluoro-1-[(2S)-oxetane-2-carbonyl]pyrrolidin-3-y}cyclopropanesulfonamide | 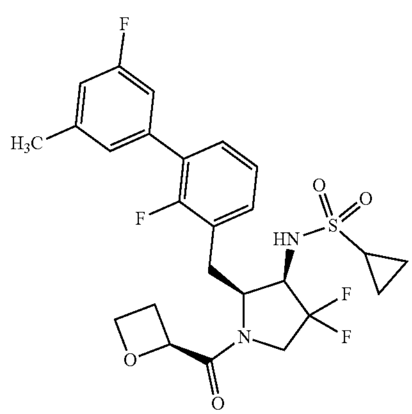 [SMILES: Cc1cc(F)cc(-c2cccc(C[C@H]3[C@@H](NS(=O)(=O)C4CC4)C(F)(F)CN3C(=O)[C@@H]3CCO3)c2F)c1] | | 527.1 |

TABLE 1-1-continued

| EX. | IUPAC NAME | Structure | ADDITIVE | MS |
|---|---|---|---|---|
| 565 | N'-[(2S,3R)-2-[(2,3'-difluoro[1,1'-biphenyl]-3-yl)methyl]-4,4-difluoro-1-(1-hydroxy-cyclobutane-1-carbonyl)pyrrolidin-3-yl]-N,N-dimethylsulfuric diamide | 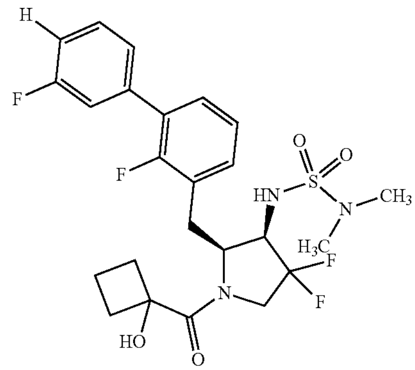 [SMILES: CN(C)S(=O)(=O)N[C@@H]1[C@H](Cc2cccc(-c3cccc(F)c3)c2F)N(C(=O)C2(O)CCC2)CC1(F)F] | | 530.1 |
| 566 | N'-[(2S,3R)-2-[(4'-bromo-2,3'-difluoro-[1,1'-biphenyl]-3-yl)methyl]-4,4-difluoro-1-(1-hydroxycyclobutane-1-carbonyl)-pyrrolidin-3-yl]-N,N-dimethylsulfuric diamide | 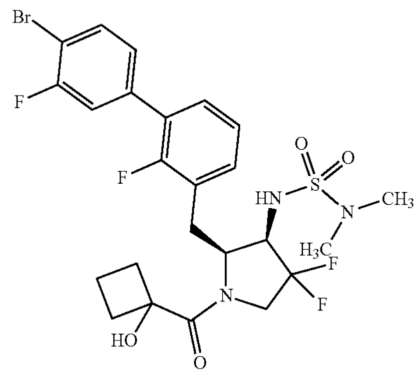 [SMILES: CN(C)S(=O)(=O)N[C@@H]1[C@H](Cc2cccc(-c3ccc(Br)c(F)c3)c2F)N(C(=O)C2(O)CCC2)CC1(F)F] | | 608.0 |
| 567 | N-[(2SR,3RS)-2-{[6-(3,5-difluorophenyl)-pyridin-2-yl]methyl}-4,4-difluoro-1-(oxetane-2-carbonyl)pyrrolidin-3-yl]-methanesulfonamide | 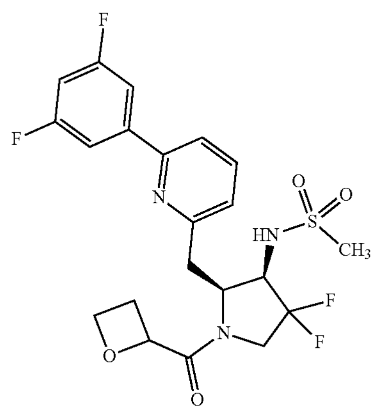 [SMILES: CS(=O)(=O)N[C@@H]1[C@H](Cc2cccc(-c3cc(F)cc(F)c3)n2)N(C(=O)C2CCO2)CC1(F)F] | | 488.1 |
| 568 | rac-N-[(2S,3R)-1-(bicyclo[1.1.1]pentane-1-carbonyl)-2-{[6-(3,5-difluorophenyl)-pyridin-2-yl]methyl}-4,4-difluoro-pyrrolidin-3-yl]methanesulfonamide | 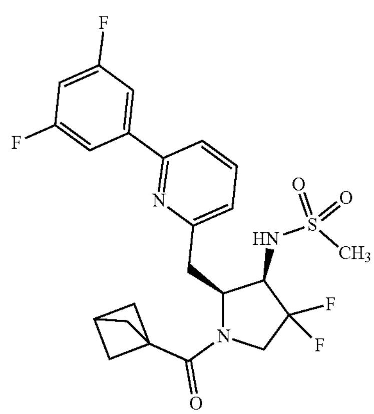 [SMILES: CS(=O)(=O)N[C@@H]1[C@H](Cc2cccc(-c3cc(F)cc(F)c3)n2)N(C(=O)C23CC(C2)C3)CC1(F)F] | | 498.2 |

TABLE 1-1-continued

| EX. | IUPAC NAME | Structure | ADDITIVE | MS |
|---|---|---|---|---|
| 569 | [(2SR,3RS)-2-{[6-(3,5-difluorophenyl)-pyridin-2-yl]methyl}-4,4-difluoro-1-(oxetane-2-carbonyl)pyrrolidin-3-yl]-methanesulfonamide | 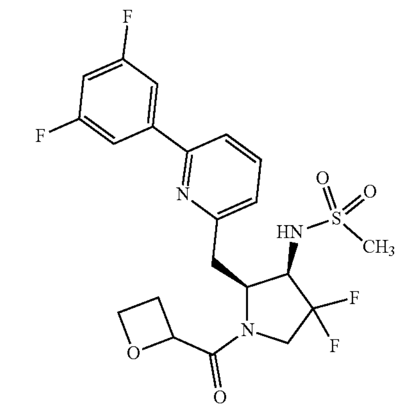 [SMILES: CS(=O)(=O)N[C@@H]1[C@H](Cc2cccc(-c3cc(F)cc(F)c3)n2)N(C(=O)C2CCO2)CC1(F)F] | | 488.1 |
| 570 | N-{(2S,3R)-2-[(5'-chloro-2,2',4'-trifluoro-[1,1'-biphenyl]-3-yl)methyl]-4,4-difluoro-1-[(2R)-oxetane-2-carbonyl]pyrrolidin-3-yl}ethanesulfonamide | 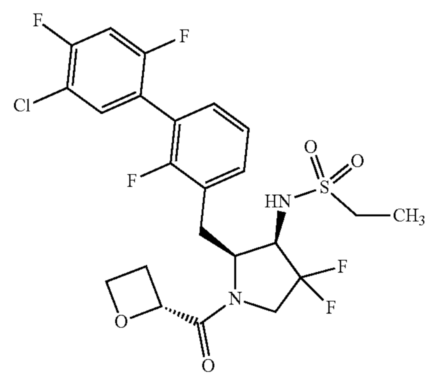 [SMILES: CCS(=O)(=O)N[C@@H]1[C@H](Cc2cccc(-c3cc(Cl)c(F)cc3F)c2F)N(C(=O)[C@H]2CCO2)CC1(F)F] | | 553.1 |
| 571 | N-{(2S,3R)-2-[(3'-chloro-2,2',4'-trifluoro-[1,1'-biphenyl]-3-yl)methyl]-4,4-difluoro-1-[(2R)-oxetane-2-carbonyl]pyrrolidin-3-yl}ethanesulfonamide | 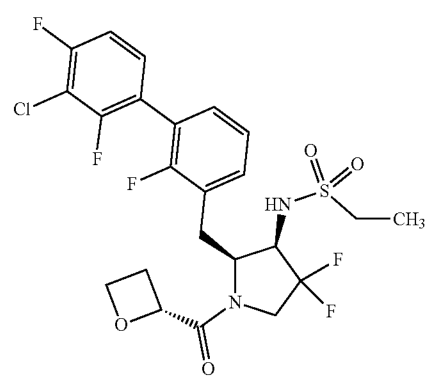 [SMILES: CCS(=O)(=O)N[C@@H]1[C@H](Cc2cccc(-c3ccc(F)c(Cl)c3F)c2F)N(C(=O)[C@H]2CCO2)CC1(F)F] | | 553.0 |
| 572 | rac-N-[(2S,3R)-2-{[6-(3,5-difluorophenyl)-pyridin-2-yl]methyl}-4,4-difluoro-1-(2-hydroxy-2-methylpropanoyl)pyrrolidin-3-yl]ethanesulfonamide | 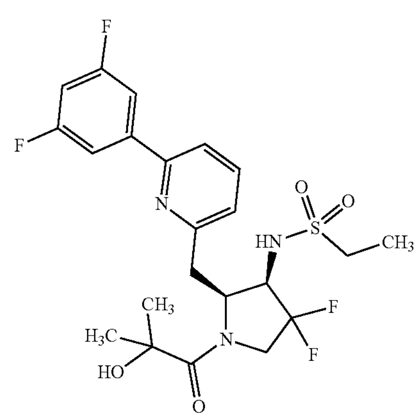 [SMILES: CCS(=O)(=O)N[C@@H]1[C@H](Cc2cccc(-c3cc(F)cc(F)c3)n2)N(C(=O)C(C)(C)O)CC1(F)F] | | 504.1 |

TABLE 1-1-continued

| EX. | IUPAC NAME | Structure | ADDITIVE | MS |
|---|---|---|---|---|
| 573 | rac-N-[(2S,3R)-2-{[6-(3,5-difluorophenyl)-pyridin-2-yl]methyl}-4,4-difluoro-1-(2-methylpropanoyl)pyrrolidin-3-yl]ethanesulfonamide | 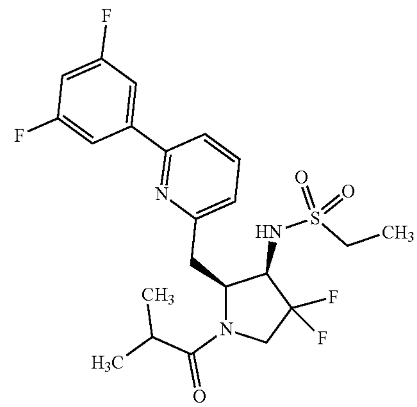 [SMILES: CCS(=O)(=O)N[C@@H]1[C@H](Cc2cccc(-c3cc(F)cc(F)c3)n2)N(C(=O)C(C)C)CC1(F)F] | | 488.1 |
| 574 | rac-N-[(2S,3R)-1-(bicyclo[1.1.1]pentane-1-carbonyl)-2-{[6-(3,5-difluorophenyl)-pyridin-2-yl]methyl}-4,4-difluoro-pyrrolidin-3-yl]ethanesulfonamide | 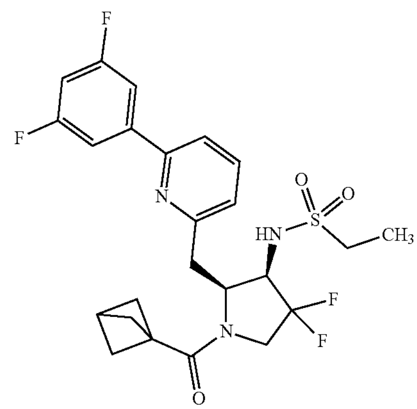 [SMILES: CCS(=O)(=O)N[C@@H]1[C@H](Cc2cccc(-c3cc(F)cc(F)c3)n2)N(C(=O)C23CC(C2)C3)CC1(F)F] | | 512.1 |
| 575 | N'-{(2S,3R)-2-[(2,2'-difluoro-3'-methyl-[1,1'-biphenyl]-3-yl)methyl]-4,4-difluoro-1-[(2S)-oxetane-2-carbonyl]pyrrolidin-3-yl}-N,N-dimethylsulfuric diamide | 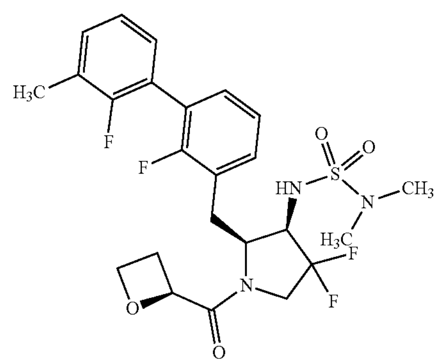 | | 530.2 |
| 576 | N'-{(2S,3R)-2-[(2,3,-difluoro-5,-methyl-[1,1'-biphenyl]-3-yl)methyl]-4,4-difluoro-1-[(2S)-oxetane-2-carbonyl]pyrrolidin-3-yl}-N,N-dimethylsulfuric diamide | 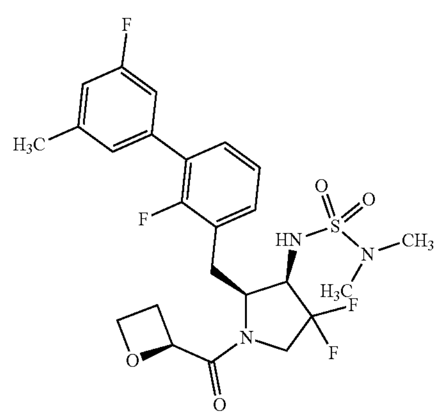 | | 530.1 |

TABLE 1-1-continued

| EX. | IUPAC NAME | Structure | ADDITIVE | MS |
|---|---|---|---|---|
| 577 | N'-{(2S,3R)-2-[(2,3'-difluoro[1,1'-biphenyl]-3-yl)methyl]-4,4-difluoro-1-[(2S)-oxetane-2-carbonyl]pyrrolidin-3-yl}-N,N-dimethylsulfuric diamide | 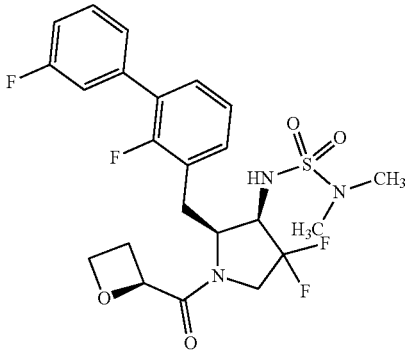 [SMILES: CN(C)S(=O)(=O)N[C@@H]1[C@H](Cc2cccc(-c3cccc(F)c3)c2F)N(C(=O)[C@@H]2CCO2)CC1(F)F] | | 516.1 |
| 578 | N'-{(2S,3R)-4,4-difluoro-1-[(2S)-oxetane-2-carbonyl]-2-[(2,3',5'-trifluoro[1,1'-biphenyl]-3-yl)methyl]pyrrolidin-3-yl}-N,N-dimethylsulfuric diamide | 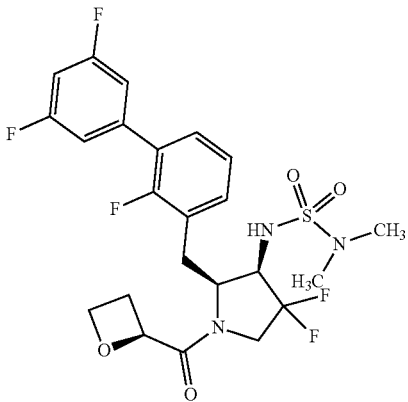 [SMILES: CN(C)S(=O)(=O)N[C@@H]1[C@H](Cc2cccc(-c3cc(F)cc(F)c3)c2F)N(C(=O)[C@@H]2CCO2)CC1(F)F] | | 534.1 |
| 579 | N-{(2S,3R)-4,4-difluoro-1-(2-hydroxy-2-methylpropanoyl)-2-[(2,2',4'-trifluoro-3'-methyl[1,1'-biphenyl]-3-yl)methyl]pyrrolidin-3-yl}ethanesulfonamide | 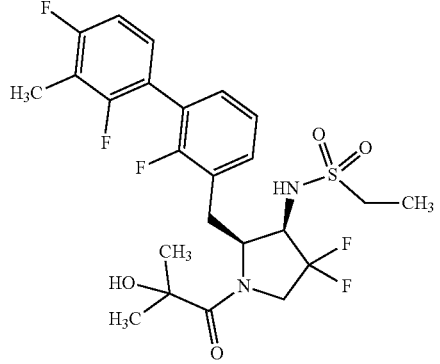 [SMILES: CCS(=O)(=O)N[C@@H]1[C@H](Cc2cccc(-c3ccc(F)c(C)c3F)c2F)N(C(=O)C(C)(C)O)CC1(F)F] | | 535.1 |
| 580 | rac-N-[(2S,3R)-2-{[6-(3,5-difluorophenyl)-pyridin-2-yl]methyl}-4,4-difluoro-1-(1-hydroxycyclobutane-1-carbonyl)pyrrolidin-3-yl]ethanesulfonamide | 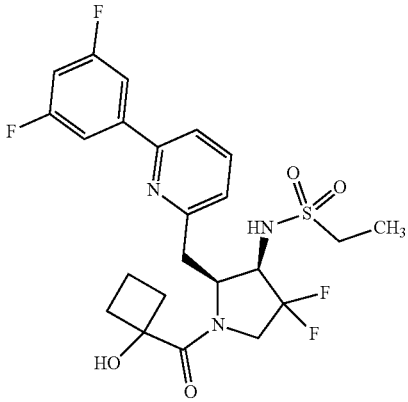 [SMILES: CCS(=O)(=O)N[C@@H]1[C@H](Cc2cccc(-c3cc(F)cc(F)c3)n2)N(C(=O)C2(O)CCC2)CC1(F)F] | | 516.1 |

TABLE 1-1-continued

| EX. | IUPAC NAME | Structure | ADDITIVE | MS |
|---|---|---|---|---|
| 581 | N-[(2SR,3RS)-2-{[6-(3,5-difluorophenyl)-pyridin-2-yl]methyl}-4,4-difluoro-1-(oxetane-2-carbonyl)pyrrolidin-3-yl]-ethanesulfonamide | 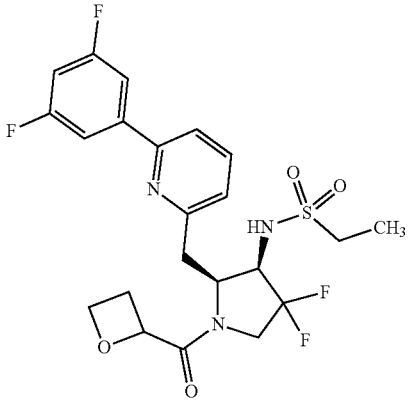 [SMILES: CCS(=O)(=O)N[C@@H]1[C@H](Cc2cccc(-c3cc(F)cc(F)c3)n2)N(C(=O)C2CCO2)CC1(F)F] | | 502.1 |
| 582 | N-[(2SR,3RS)-2-{[6-(3,5-difluorophenyl)-pyridin-2-yl]methyl}-4,4-difluoro-1-(oxetane-2-carbonyl)pyrrolidin-3-yl]-ethanesulfonamide | 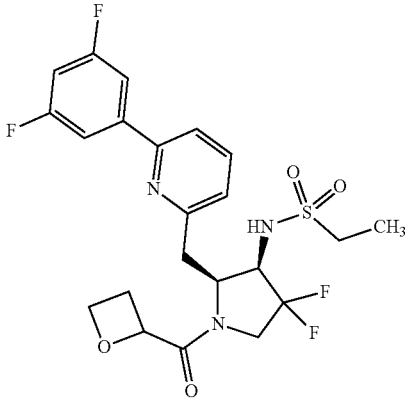 [SMILES: CCS(=O)(=O)N[C@@H]1[C@H](Cc2cccc(-c3cc(F)cc(F)c3)n2)N(C(=O)C2CCO2)CC1(F)F] | | 502.1 |
| 583 | N'-[(2S,3R)-2-[(4'-bromo-2-fluoro-3'-methyl[1,1'-biphenyl]-3-yl)methyl]-4,4-difluoro-1-(1-hydroxycyclobutane-1-carbonyl)pyrrolidin-3-yl]-N,N-dimethyl-sulfuric diamide | 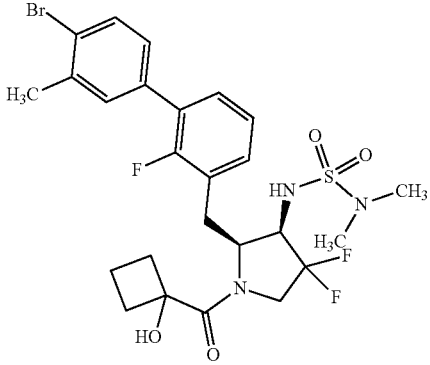 | | 602.1 |
| 584 | rac-N-[(2S,3R,4S)-2-{[2-(3,5-difluoro-phenyl)-1,3-thiazol-4-yl]methyl}-4-fluoro-1-(2-hydroxy-2-methylpropanoyl)-pyrrolidin-3-yl]methanesulfonamide | 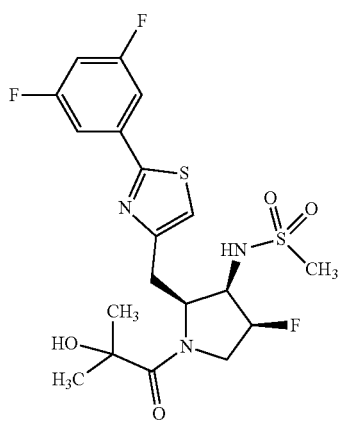 [SMILES: CC(C)(O)C(=O)N1C[C@H](F)[C@H](NS(C)(=O)=O)[C@@H]1Cc1csc(-c2cc(F)cc(F)c2)n1] | | 478.1 |

TABLE 1-1-continued

| EX. | IUPAC NAME | Structure | ADDITIVE | MS |
|---|---|---|---|---|
| 585 | rac-N-[(2S,3R,4S)-1-(cyclobutanecarbonyl)-2-{[2-(3,5-difluorophenyl)-1,3-thiazol-4-yl]methyl}-4-fluoropyrrolidin-3-yl]-methanesulfonamide | 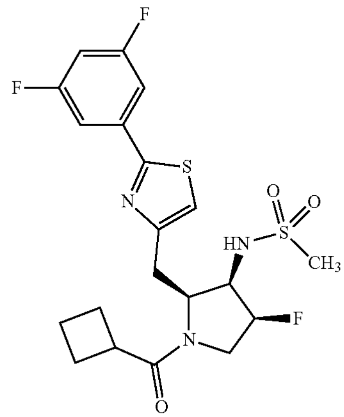 [SMILES: CS(=O)(=O)N[C@H]1[C@@H](F)CN(C(=O)C2CCC2)[C@H]1Cc1csc(-c2cc(F)cc(F)c2)n1] | | 474.1 |
| 586 | rac-(2S,3R,4S)-2-{[2-(3,5-difluorophenyl)-1,3-thiazol-4-yl]methyl}-4-fluoro-3-[(methanesulfonyl)amino]-N,N-dimethyl-pyrrolidine-1-carboxamide | 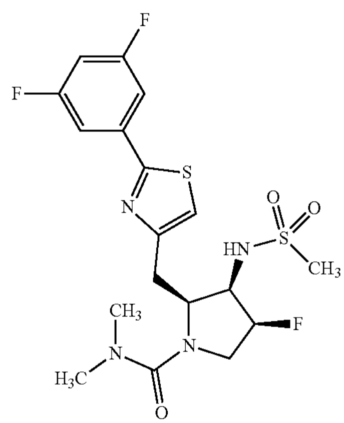 [SMILES: CN(C)C(=O)N1C[C@H](F)[C@H](NS(C)(=O)=O)[C@@H]1Cc1csc(-c2cc(F)cc(F)c2)n1] | | 463.1 |
| 587 | rac-N-((2S,3R,4S)-2-{[2-(3,5-difluoro-phenyl)-1,3-thiazol-4-yl]methyl}-4-fluoro-1-(1-hydroxycyclobutane-1-carbonyl)pyrrolidin-3-yl]methane-sulfonamide | 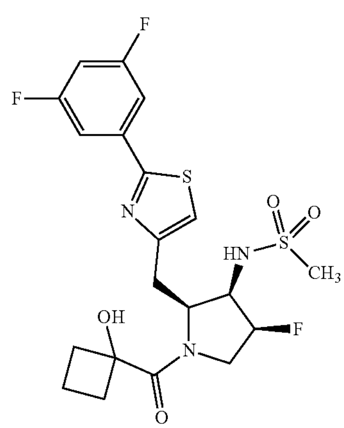 [SMILES: CS(=O)(=O)N[C@H]1[C@@H](F)CN(C(=O)C2(O)CCC2)[C@H]1Cc1csc(-c2cc(F)cc(F)c2)n1] | | 490.0 |

TABLE 1-1-continued

| EX. | IUPAC NAME | Structure | ADDITIVE | MS |
|---|---|---|---|---|
| 588 | N-[(2S,3R)-2-[(2,3'-difluoro[1,1'-biphenyl]-3-yl)methyl]-4,4-difluoro-1-(trimethyl-hydrazinecarbonyl)pyrrolidin-3-yl]-ethanesulfonamide | 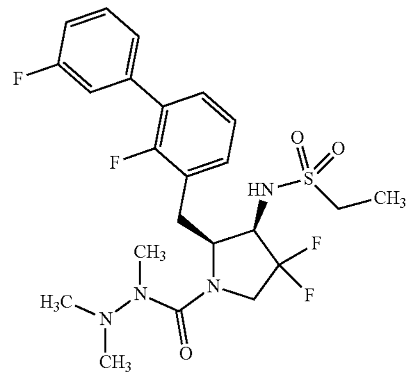 [SMILES: CCS(=O)(=O)N[C@@H]1[C@H](Cc2cccc(-c3cccc(F)c3)c2F)N(C(=O)N(C)N(C)C)CC1(F)F] | | 517.0 |
| 589 | N'-[(2S,3R)-1-(azetidine-1-carbonyl)-4,4-difluoro-2-{[2-fluoro-3-(6-methylpyridin-2-yl)phenyl]methyl}pyrrolidin-3-yl]-N,N-dimethylsulfuric diamide | 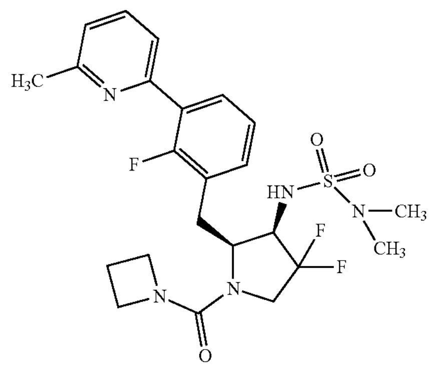 | | 512.0 |
| 590 | (2S,3R)-3-[(dimethylsulfamoyl)amino]-4,4-difluoro-2-{[2-fluoro-3-(6-methylpyridin-2-yl)phenyl]methyl}-N,N-dimethyl-pyrrolidine-1-carboxamide | 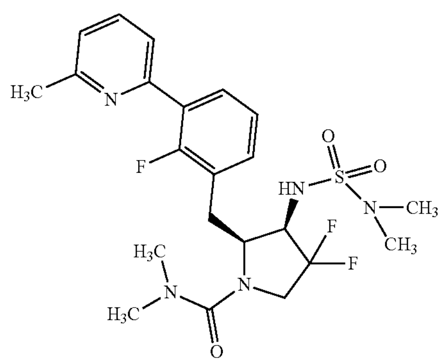 | | 500.0 |
| 591 | N'-[(2S,3R)-4,4-difluoro-2-{[2-fluoro-3-(6-methylpyridin-2-yl)phenyl]methyl}-1-(1-hydroxycyclobutane-1-carbonyl)pyrrolidin-3-yl]-N,N-dimethylsulfuric diamide | 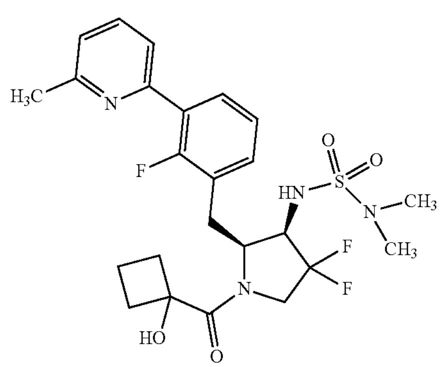 | | 527.0 |

TABLE 1-1-continued

| EX. | IUPAC NAME | Structure | ADDITIVE | MS |
|---|---|---|---|---|
| 592 | N-[(2S,3R)-4,4-difluoro-2-{[2-fluoro-3-(6-methylpyridin-2-yl)phenyl]methyl)-2-(1-hydroxycyclobutane-1-carbonyl)pyrrolidin-3-yl]cyclopropanesulfonamide | 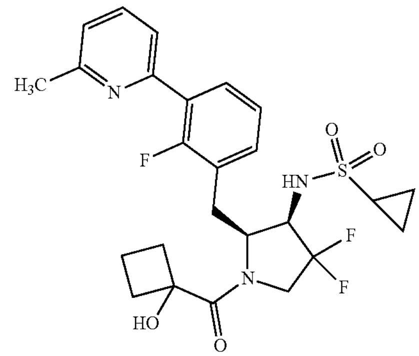 [SMILES: Cc1cccc(-c2cccc(C[C@H]3[C@@H](NS(=O)(=O)C4CC4)C(F)(F)CN3C(=O)C3(O)CCC3)c2F)n1] | | 523.9 |
| 593 | N-[(2S,3R)-1-(azetidine-1-carbonyl)-4,4-difluoro-2-{[2-fluoro-3-(6-methylpyridin-2-yl)phenyl]methyl}pyrrolidin-3-yl]-cyclopropanesulfonamide | 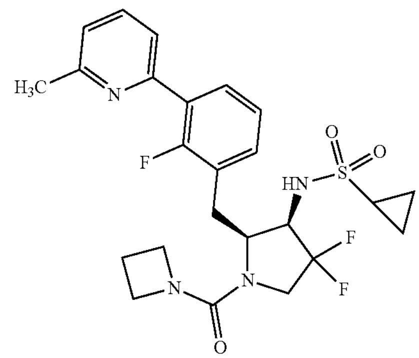 [SMILES: Cc1cccc(-c2cccc(C[C@H]3[C@@H](NS(=O)(=O)C4CC4)C(F)(F)CN3C(=O)N3CCC3)c2F)n1] | | 509.0 |
| 594 | (2S,3R)-3-[(cyclopropanesulfonyl)amino]-4,4-difluoro-2-{[2-fluoro-3-(6-methyl-pyridin-2-yl)phenyl]methyl}-N,N-dimethylpyrrolidine-1-carboxamide | 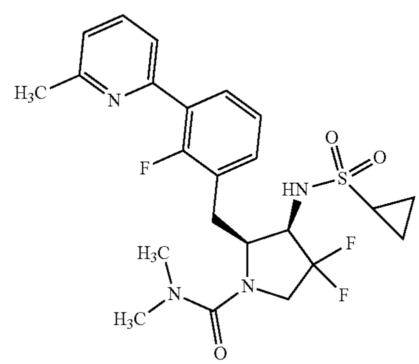 [SMILES: Cc1cccc(-c2cccc(C[C@H]3[C@@H](NS(=O)(=O)C4CC4)C(F)(F)CN3C(=O)N(C)C)c2F)n1] | | 497.0 |
| 595 | (2S,3R)-3-[(dimethylsulfamoyl)amino]-4,4-difluoro-2-{[2-fluoro-3-(6-methylpyridin-2-yl)phenyl]methyl}-N,N-dimethyl-pyrrolidine-1-carboxamide | 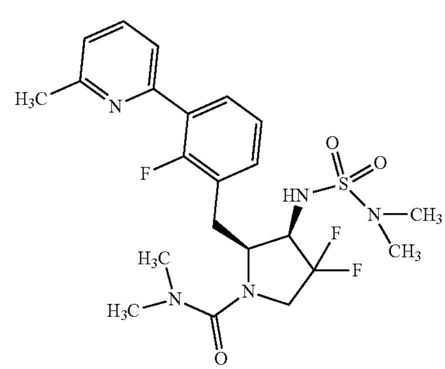 | | 500.2 |

TABLE 1-1-continued

| EX. | IUPAC NAME | Structure | ADDITIVE | MS |
|---|---|---|---|---|
| 596 | (2S,3R)-3-[(dimethylsulfamoyl)amino]-4,4-difluoro-2-{[2-fluoro-3-(5-methylpyridazin-3-yl)phenyl]methyl}-N,N-dimethyl-pyrrolidine-1-carboxamide | 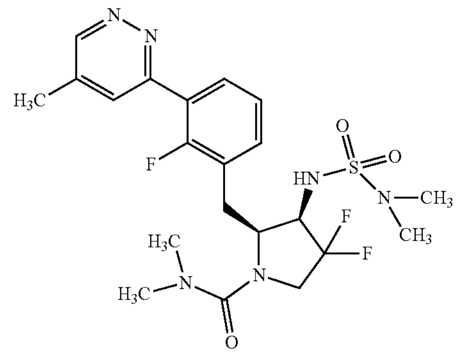 | | 501.2 |
| 597 | N'-(2S,3R)-1-(acetidine-1-carbonyl)-4,4-difluoro-2-{[2-fluoro-3-(5-methylpyridazin-3-yl)phenyl]methyl}pyrrolidin-3-yl]-N,N-dimethylsulfuric diamide | 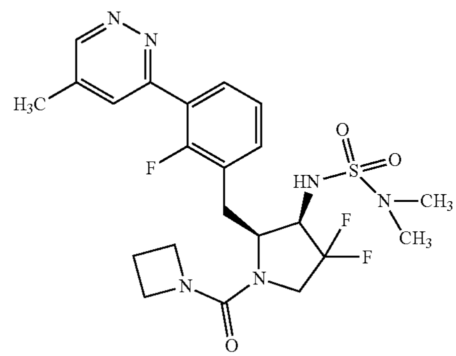 | | 513.2 |
| 598 | N'-[(2S,3R)-4,4-difluoro-2-{[2-fluoro-3-(5-methylpyridazin-3-yl)phenyl]methyl}-1-(1-hydroxycyclobutane-1-carbonyl)pyrrolidin-3-yl]-N,N-dimethylsulfuric diamide | 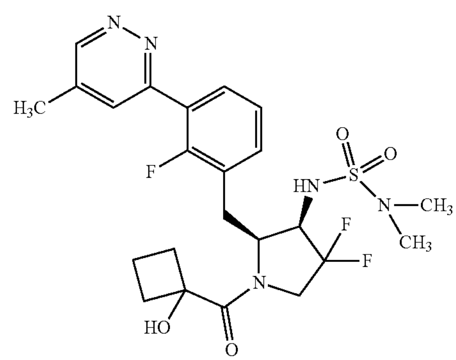 | | 528.2 |
| 599 | N-((2S,3R)-2-[(2,3'-difluoro[1,1'-biphenyl]-3-yl)methyl]-4,4-difluoro-1-(trimethyl-hydrazinecarbonyl) pyrrolidin-3-yl]-ethanesulfonamide | 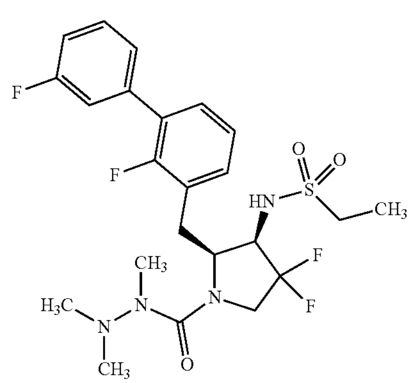 [SMILES: CCS(=O)(=O)N[C@@H]1[C@H](Cc2cccc(-c3cccc(F)c3)c2F)N(C(=O)N(C)N(C)C)CC1(F)F] | | 517.2 |

TABLE 1-1-continued

| EX. | IUPAC NAME | Structure | ADDITIVE | MS |
|---|---|---|---|---|
| 600 | N'-[(2S,3R)-2-{[3-(6-ethylpyridin-2-yl)-2-fluorophenyl]methyl}-4,4-difluoro-1-(1-hydroxycyclobutane-1-carbonyl)pyrrolidin-3-yl]-N,N-dimethylsulfuric diamide | 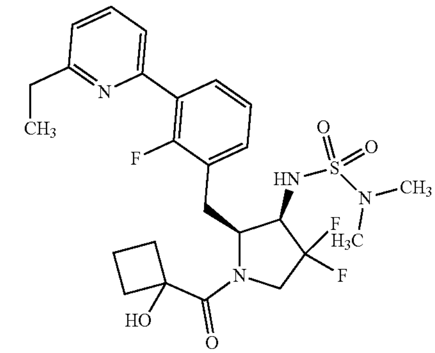 [SMILES: CCc1cccc(-c2cccc(C[C@H]3[C@@H](NS(=O)(=O)N(C)C)C(F)(F)CN3C(=O)C3(O)CCC3)c2F)n1] | | 540.9 |
| 601 | N'-[(2S,3R)-4,4-difluoro-2-{[2-fluoro-3-(5-fluoro-6-methylpyridin-2-yl)phenyl]methyl}-1-(1-hydroxycyclobutane-1-carbonyl)pyrrolidin-3-yl]-N,N-dimethyl-sulfuric diamide | 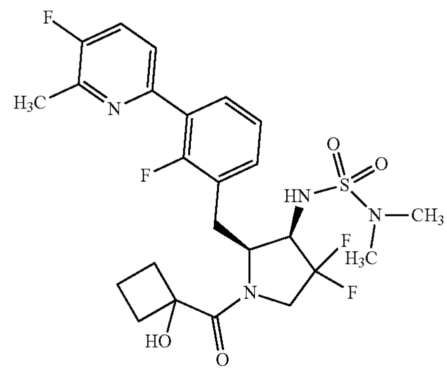 | | 544.9 |
| 602 | N'-[(2S,3R)-4,4-difluoro-2-{[2-fluoro-3-(3-fluoro-6-methylpyridin-2-yl)phenyl]methyl}-1-(1-hydroxycyclobutane-1-carbonyl)pyrrolidin-3-yl]-N,N-dimethyl-sulfuric diamide | 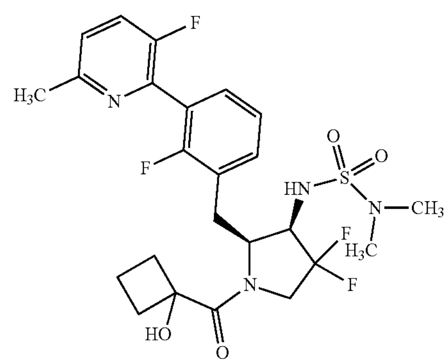 | | 544.9 |
| 603 | N'-[(2S,3R)-4,4-difluoro-2-{[2-fluoro-3-(2-methyl-1,3-thiazol-4-yl)phenyl]methyl}-1-(1-hydroxycyclobutane-1-carbonyl)-pyrrolidin-3-yl]-N,N-dimethylsulfuric diamide | 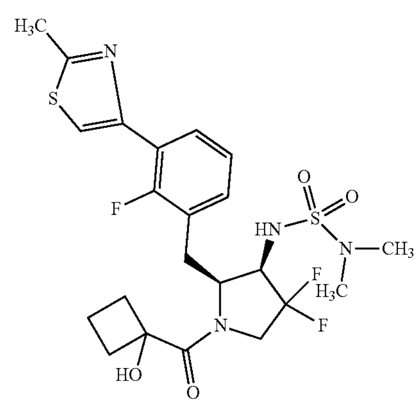 | | 532.9 |

TABLE 1-1-continued

| EX. | IUPAC NAME | Structure | ADDITIVE | MS |
|---|---|---|---|---|
| 604 | N'-[(2S,3R)-4,4-difluoro-2-({2-fluoro-3-[6-(trifluoromethyl)pyridin-2-yl]phenyl}-methyl)-1-(1-hydroxycyclobutane-1-carbonyl)pyrrolidin-3-yl]-N,N-dimethyl-sulfuric diamide | 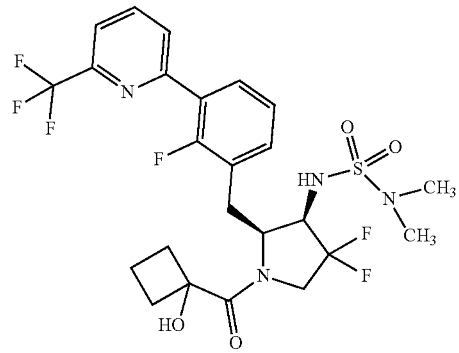 | | 580.9 |
| 605 | N'-[(2S,3R)-2-({3-[6-(difluoromethyl)-pyridin-2-yl]-2-fluorophenyl}methyl)-4,4-difluoro-1-(1-hydroxycyclobutane-1-carbonyl)pyrrolidin-3-yl]-N,N-dimethyl-sulfuric diamide | 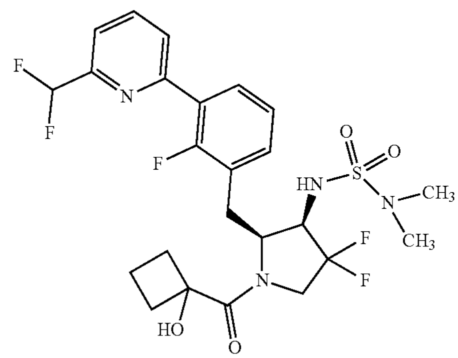 [SMILES: CN(C)S(=O)(=O)N[C@@H]1[C@H](Cc2cccc(-c3cccc(C(F)F)n3)c2F)N(C(=O)C2(O)CCC2)CC1(F)F] | | 562.9 |
| 606 | N'-[(2S,3R)-2-{[3-(4,6-dimethylpyridin-2-yl)-2-fluorophenyl]methyl}-4,4-difluoro-1-(1-hydroxycyclobutane-1-carbonyl)-pyrrolidin-3-yl]-N,N-dimethylsulfuric diamide | 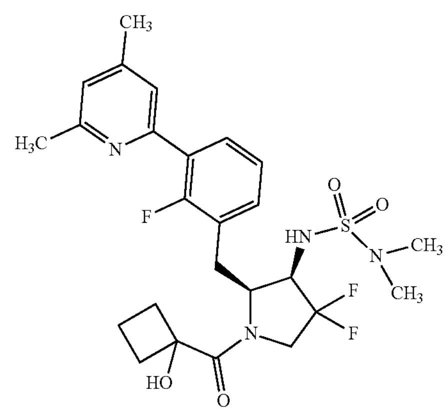 | | 540.9 |
| 607 | ethyl 2-[3-({(2S,3R)-1-(tert-butoxy-carbonyl)-3-[(dimethylsulfamoyl)amino]-4,4-difluoropyrrolidin-2-yl}methyl)-2-fluorophenyl]-1,3-oxazole-4-carboxylate | 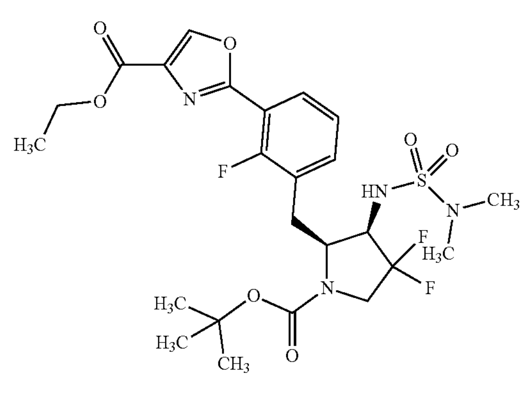 [SMILES: CCOC(=O)c1coc(-c2cccc(C[C@H]3[C@@H](NS(=O)(=O)N(C)C)C(F)(F)CN3C(=O)OC(C)(C)C)c2F)n1] | | 577.2 |

TABLE 1-1-continued

| EX. | IUPAC NAME | Structure | ADDITIVE | MS |
|---|---|---|---|---|
| 608 | N'-[(2S,3R)-2-[(3-chloro-2-fluorophenyl)-methyl]-4,4-difluoro-2-(2-hydroxycyclo-butane-2-carbonyl)pyrrolidin3-yl]-N,N-dimethylsulfuric diamide | 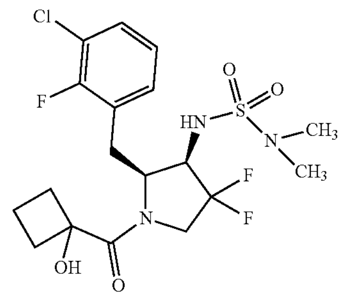 [SMILES: CN(C)S(=O)(=O)N[C@@H]1[C@H](Cc2cccc(Cl)c2F)N(C(=O)C2(O)CCC2)CC1(F)F] | | 468.1 |
| 609 | N'-[(2S,3R)-4,4-difluoro-2-({2-fluoro-3-[4-(hydroxymethyl)-1,3-oxazol-2-yl]-phenyl}methyl)-1-(1-hydroxycyclobutane-1-carbonyl)pyrrolidin-3-yl]-N,N-dimethyl-sulfuric diamide | 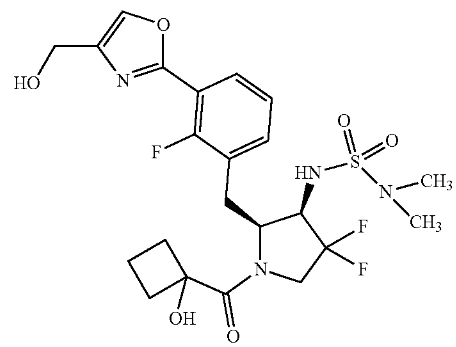 [SMILES: CN(C)S(=O)(=O)N[C@@H]1[C@H](Cc2cccc(-c3nc(CO)co3)c2F)N(C(=O)C2(O)CCC2)CC1(F)F] | | 532.9 |
| 610 | N'-[(2S,3R)-4,4-difluoro-2-{[2-fluoro-3-(4-methyl-1,3-oxazol-2-yl)phenyl]methyl}-1-(1-hydroxycyclobutane-1-carbonyl)-pyrrolidin-3-yl]-N,N-dimethylsulfuric diamide | 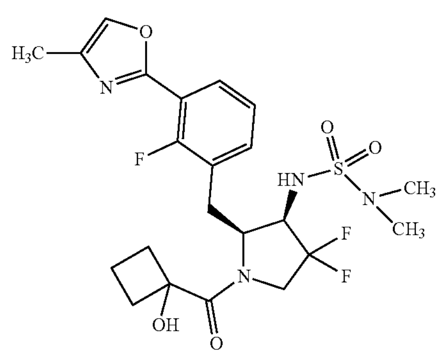 | | 517.2 |
| 611 | N'-[(2S,3R)-2-{[3-(5-chloro-2-methyl-1,3-thiazol-4-yl)-2-fluorophenyl]methyl}-4,4-difluoro-1-(1-hydroxycyclobutane-1-carbonyl)-pyrrolidin-3-yl]-N,N-dimethyl-sulfuric diamide | 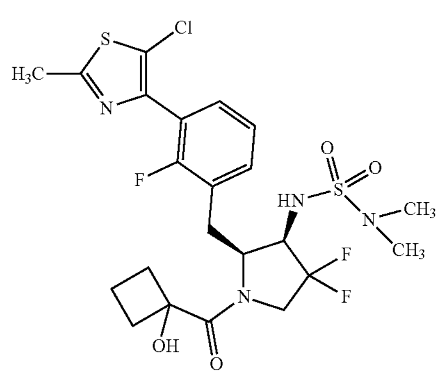 | | 567.1 |

TABLE 1-1-continued

| EX. | IUPAC NAME | Structure | ADDITIVE | MS |
|---|---|---|---|---|
| 612 | N'-[(2S,3R)-4,4-difluoro-2-{[2-fluoro-3-(2-methyl-1,3-oxazol-4-yl)phenyl]methyl}-1-(1-hydroxycyclobutane-1-carbonyl)-pyrrolidin-3-yl]-N,N-dimethylsulfuric diamide | 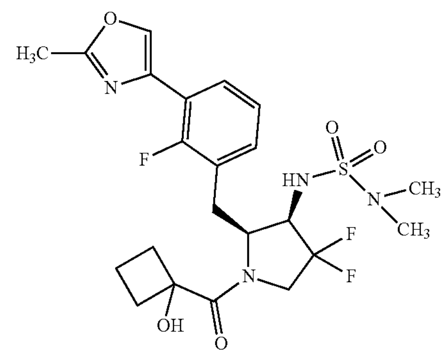 | | 517.2 |
| 613 | N'-[(2S,3R)-2-{[3-(5-chloro-2-methyl-1,3-oxazol-4-yl)-2-fluorophenyl]methyl}-4,4-difluoro-1-(1-hydroxycyclobutane-1-carbonyl)pyrrolidin-3-yl]-N,N-dimethyl-sulfuric diamide | 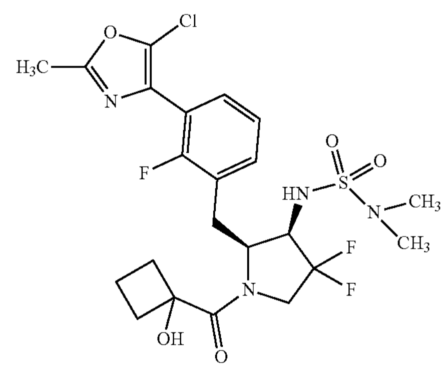 | | 551.1 |
| 614 | N'-[(2S,3R)-2-{[3-(4-ethyl-6-methyl-pyridin-2-yl)-2-fluorophenyl]methyl}-4,4-difluoro-1-(1-hydroxycyclobutane-1-carbonyl)pyrrolidin-3-yl]-N,N-dimethyl-sulfuric diamide | 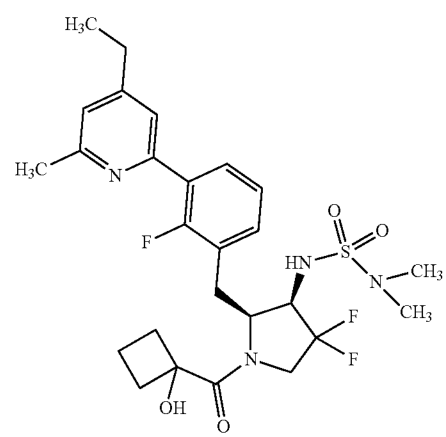 | | 555.1 |
| 615 | N-{(2S,3R)-2-[(3'-chloro-2,4',5'-trifluoro-[1,1'-biphenyl]-3-yl)methyl]-4,4-difluoro-1-[(2R)-oxetane-2-carbonyl]pyrrolidin-3-yl}ethanesulfonamide | 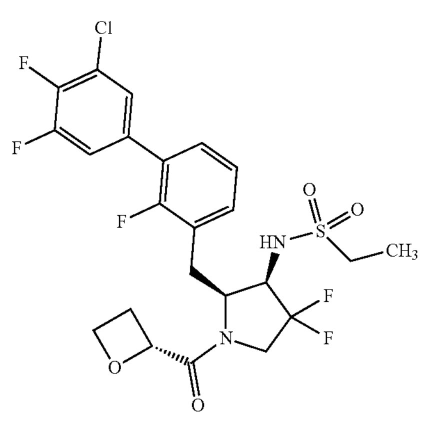 [SMILES: CCS(=O)(=O)N[C@@H]1[C@H](Cc2cccc(-c3cc(F)c(F)c(Cl)c3)c2F)N(C(=O)[C@H]2CCO2)CC1(F)F] | | 553.0 |

TABLE 1-1-continued

| EX. | IUPAC NAME | Structure | ADDITIVE | MS |
|---|---|---|---|---|
| 616 | [3-({(2S,3R)-3-[(N,N-dimethylsulfamoyl)-amino]-4,4-difluoro-1-(1-hydroxycyclo-butane-1-carbonyl)pyrrolidin-2-yl}-methyl)-2-fluorophenyl]boronic acid | 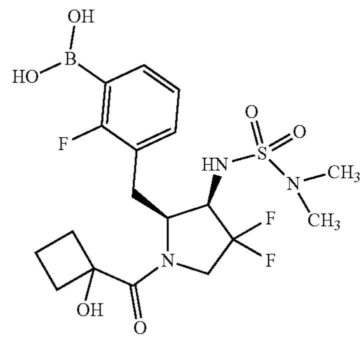 [SMILES: CN(C)S(=O)(=O)N[C@@H]1[C@H](Cc2cccc(B(O)O)c2F)N(C(=O)C2(O)CCC2)CC1(F)F] | | 480.16 |

Experimental Example 1: Obtainment of Cell Stably Expressing Human Orexin Type 2 Receptor (hOX2R)

To obtain a cell clone stably expressing human orexin type 2 receptor, human orexin type 2 receptor cDNA was inserted into pcDNA3.1(+) plasmid vector (Invitrogen), and a plasmid DNA for expression of human orexin type 2 receptor (pcDNA3.1(+)/hOX2R) was cloned. The plasmid DNA was introduced into CHO-dhfr cell by an electroporation method, and human orexin type 2 receptor expressing clone cells were obtained by limiting dilution method by using G418 drug resistance as a selection marker.

Experimental Example 2: Measurement of Orexin Type 2 Receptor Agonist Activity CHO cells forcibly expressing human OX2 receptor were seeded in each well of 384 well black transparent bottom plate (BD Falcon) at 7,500 cells/well, and cultured for one day in a 5% $CO_2$ incubator at 37° C. After removal of the medium in the cell plate, assay buffer A containing a calcium indicator (HBSS (Thermo Fisher Scientific), 20 mM HEPES (Thermo Fisher Scientific), 0.1% BSA (Sigma-Aldrich), 2.5 μg/mL Fluo-4 AM (DOJINDO Chemical), 0.08% Pluronic F127 (DOJINDO Chemical), 1.25 mM probenecid (DOJINDO Chemical)) was added at 30 μL/well. The plate was stood for 30 min in a 5% $CO_2$ incubator at 37° C., and further stood at room temperature for 30 min. A test compound prepared by diluting with assay buffer B (HBSS, 20 mM HEPES, 0.1% BSA) was added at 10 μL/well, and the fluorescence value was measured by FDSSμCELL (Hamamatsu Photonics K. K.) every one sec for 1 min, and thereafter every two sec for 1 min 40 sec. The activity (%) of the test compound was calculated assuming that variation in the fluorescence value when DMSO was added instead of the test compound was 0%, and variation in the fluorescence value when orexin A (human) (PEPTIDE INSTITUTE, INC.) was added at the final concentration of 10 nM was 100%. The activity of each compound at the concentration of 3 μM was shown in Table 2. As is clear from the results, the compound of the present invention was shown to have an agonist activity on human orexin type 2 receptor.

TABLE 2

| Test compound | OX2R agonist activity (3 μM, %) |
|---|---|
| 1 | 100 |
| 2 | 106 |
| 3 | 106 |
| 4 | 101 |
| 5 | 117 |
| 7 | 101 |
| 8 | 99 |
| 11 | 85 |
| 13 | 93 |
| 21 | 102 |
| 23 | 100 |
| 25 | 108 |
| 26 | 100 |
| 35 | 96 |
| 44 | 98 |
| 45 | 98 |
| 46 | 102 |
| 50 | 99 |
| 51 | 99 |
| 52 | 100 |
| 56 | 95 |
| 65 | 100 |
| 66 | 104 |
| 67 | 111 |
| 68 | 106 |
| 73 | 104 |
| 76 | 98 |
| 77 | 95 |
| 78 | 93 |
| 79 | 102 |
| 81 | 95 |
| 87 | 93 |
| 88 | 98 |
| 91 | 94 |
| 92 | 99 |
| 93 | 98 |
| 94 | 99 |
| 97 | 90 |
| 98 | 91 |
| 105 | 99 |
| 106 | 97 |
| 116 | 86 |
| 121 | 94 |
| 122 | 89 |
| 124 | 89 |
| 129 | 92 |
| 131 | 94 |
| 133 | 96 |
| 136 | 87 |
| 138 | 97 |
| 139 | 93 |
| 144 | 88 |
| 145 | 99 |
| 146 | 92 |
| 147 | 91 |
| 162 | 92 |

TABLE 2-continued

| Test compound | OX2R agonist activity (3 μM, %) |
|---|---|
| 163 | 105 |
| 166 | 98 |
| 171 | 99 |
| 174 | 90 |
| 175 | 95 |
| 202 | 94 |
| 204 | 89 |
| 205 | 91 |
| 207 | 88 |
| 210 | 95 |
| 211 | 94 |
| 212 | 96 |
| 216 | 95 |
| 217 | 96 |
| 220 | 90 |
| 222 | 97 |
| 225 | 96 |
| 226 | 100 |
| 228 | 99 |
| 231 | 95 |
| 236 | 100 |
| 238 | 98 |
| 239 | 102 |
| 245 | 94 |
| 248 | 90 |
| 249 | 90 |
| 250 | 96 |
| 251 | 91 |
| 257 | 96 |
| 259 | 96 |
| 263 | 103 |
| 264 | 98 |
| 265 | 96 |
| 266 | 83 |
| 267 | 92 |
| 268 | 94 |
| 272 | 88 |
| 273 | 83 |
| 274 | 93 |
| 275 | 85 |
| 276 | 88 |
| 277 | 94 |
| 282 | 96 |
| 283 | 93 |
| 284 | 92 |
| 285 | 98 |
| 287 | 94 |
| 289 | 80 |
| 291 | 90 |
| 292 | 87 |
| 293 | 83 |
| 294 | 96 |
| 295 | 95 |
| 296 | 96 |
| 297 | 95 |
| 298 | 96 |
| 302 | 85 |
| 304 | 99 |
| 305 | 103 |
| 306 | 89 |
| 307 | 100 |
| 308 | 94 |
| 314 | 109 |
| 316 | 101 |
| 323 | 92 |
| 324 | 91 |
| 328 | 86 |
| 329 | 88 |
| 330 | 98 |
| 332 | 95 |
| 333 | 78 |
| 344 | 102 |
| 345 | 92 |
| 346 | 93 |
| 347 | 102 |
| 348 | 103 |
| 349 | 98 |
| 356 | 97 |
| 365 | 93 |
| 366 | 96 |
| 368 | 95 |
| 369 | 85 |
| 370 | 91 |
| 371 | 94 |
| 372 | 89 |
| 373 | 88 |
| 374 | 93 |
| 375 | 91 |
| 376 | 99 |
| 377 | 95 |
| 378 | 106 |
| 379 | 93 |
| 380 | 93 |
| 381 | 95 |
| 382 | 102 |
| 383 | 94 |
| 384 | 98 |
| 385 | 95 |
| 387 | 85 |
| 388 | 89 |
| 389 | 89 |
| 391 | 92 |
| 392 | 97 |
| 393 | 94 |
| 394 | 86 |
| 408 | 88 |
| 409 | 92 |
| 413 | 99 |
| 414 | 95 |
| 415 | 107 |
| 416 | 101 |
| 422 | 102 |
| 423 | 90 |
| 424 | 95 |
| 425 | 95 |
| 426 | 90 |
| 427 | 99 |
| 428 | 100 |
| 430 | 96 |
| 431 | 106 |
| 432 | 95 |
| 433 | 101 |
| 434 | 101 |
| 435 | 88 |
| 436 | 92 |
| 437 | 84 |
| 438 | 95 |
| 439 | 93 |
| 440 | 94 |
| 441 | 93 |
| 442 | 96 |
| 443 | 90 |
| 444 | 98 |
| 447 | 95 |
| 450 | 86 |
| 451 | 82 |
| 453 | 85 |
| 454 | 84 |
| 455 | 85 |
| 456 | 77 |
| 457 | 80 |
| 458 | 84 |
| 459 | 78 |
| 462 | 78 |
| 463 | 79 |
| 465 | 106 |
| 466 | 103 |
| 467 | 105 |
| 468 | 102 |
| 469 | 91 |
| 470 | 103 |
| 471 | 94 |
| 472 | 95 |
| 473 | 97 |
| 474 | 96 |
| 475 | 100 |

TABLE 2-continued

| Test compound | OX2R agonist activity (3 μM, %) |
|---|---|
| 476 | 100 |
| 477 | 96 |
| 478 | 103 |
| 479 | 93 |
| 480 | 101 |
| 481 | 104 |
| 482 | 100 |
| 483 | 108 |
| 484 | 90 |
| 485 | 93 |
| 486 | 88 |
| 487 | 95 |
| 488 | 95 |
| 489 | 92 |
| 490 | 93 |
| 491 | 93 |
| 492 | 90 |
| 493 | 95 |
| 494 | 96 |
| 495 | 92 |
| 496 | 95 |
| 497 | 91 |
| 498 | 99 |
| 499 | 96 |
| 500 | 98 |
| 501 | 96 |
| 502 | 96 |
| 503 | 89 |
| 504 | 90 |
| 505 | 88 |
| 506 | 100 |
| 507 | 97 |
| 508 | 96 |
| 509 | 85 |
| 510 | 97 |
| 511 | 98 |
| 512 | 95 |
| 513 | 97 |
| 514 | 95 |
| 515 | 98 |
| 516 | 102 |
| 517 | 100 |
| 518 | 98 |
| 519 | 98 |
| 520 | 94 |
| 521 | 97 |
| 522 | 97 |
| 523 | 86 |
| 524 | 87 |
| 525 | 85 |
| 526 | 83 |
| 527 | 95 |
| 528 | 83 |
| 529 | 95 |
| 530 | 94 |
| 531 | 95 |
| 532 | 96 |
| 533 | 101 |
| 534 | 98 |
| 535 | 102 |
| 536 | 98 |
| 537 | 100 |
| 538 | 106 |
| 539 | 101 |
| 540 | 100 |
| 541 | 100 |
| 542 | 100 |
| 543 | 99 |
| 544 | 90 |
| 545 | 93 |
| 546 | 96 |
| 547 | 98 |
| 548 | 94 |
| 549 | 94 |
| 550 | 93 |
| 551 | 93 |
| 552 | 94 |

Experimental Example 3: Evaluation of Microsome Stability in Human

Human liver microsomes were purchased from Xenotech, LLC (Lenexa, KS). An incubation mixture consisted of microsomes in 50 mmol/L $KH_2PO_4$—$K_2HPO_4$ phosphate buffer (pH 7.4) and 1 μmol/L test compound. The concentration of microsomal protein was 0.2 mg/mL. An NADPH-generating system (5 mmol/L $MgCl_2$, 5 mmol/L glucose-6-phosphate, 0.5 mmol/L beta-NADP+ and 1.5 unit/mL glucose-6-phosphate dehydrogenase) was added to the incubation mixture with a half volume of the reaction mixture to initiate the enzyme reaction. The reaction was terminated 15 and 30 minutes after the initiation of the reaction by mixing the reaction mixture with acetonitrile, followed by centrifugation at 2500 rpm for 10 min. The supernatant was subjected to LC/MS/MS analysis. The metabolic rate constant was calculated as the slope of the remaining rate-time plot. The in vitro intrinsic metabolic clearance was calculated by dividing initial metabolic rate constant by microsomal protein in the incubation mixture. The results were shown in Table 3.

TABLE 3

| Test compound | Clearance (μL/min/mg) |
|---|---|
| 1 | 75 |
| 2 | 40 |
| 3 | −3 |
| 5 | 12 |
| 56 | 135 |
| 66 | 61 |
| 67 | 4 |
| 87 | 9 |
| 91 | 65 |
| 94 | 44 |
| 144 | 13 |
| 146 | 83 |
| 225 | 60 |
| 236 | 67 |
| 302 | 3 |
| 375 | 35 |
| 380 | 39 |
| 433 | 16 |

Experimental Example 4: Evaluation of Wake-Promoting Effects in Cynomolgus Monkeys The wake-promoting effects were evaluated by measuring the electroencephalogram (EEG) and electromyogram (EMG) in cynomolgus monkeys. Under isoflurane anesthesia (1-5%, Pfizer Japan Inc., Tokyo, Japan), male cynomolgus monkeys (3-5 years old, Hamri Co., Ltd., Ibaraki, Japan) were surgically implanted with radio-telemetry transmitters (TL10M3-D70-EEE, Data Sciences International Inc., MN, USA). EEG electrodes were screwed into the skull at the parietal area. EMG electrodes were implanted on the cervical muscles. After the surgery, each monkey was given penicillin (100,000 units/head, i.m., Meiji Seika Pharma Co., Ltd., Tokyo, Japan), buprenorphine (0.02 mg/kg, i.m., Otsuka Pharmaceutical Co., Ltd., Tokyo, Japan) and prednisolone (1 mg/kg, s.c., Kyoritsu Seiyaku Co., Ltd., Tokyo, Japan) daily for one week. After at least a 1-month recovery period in home cages, the monkeys were habituated to the recording chamber placed in a soundproof room. EEG and EMG signals were recorded using the telemetry system (Dataquest ART software, Data Sciences International Inc., MN, USA) and the signals were analyzed using SleepSign software (Kissei Comtec Co., Ltd., Nagano, Japan). After confirming long sleep in dark phase in the experimental room, we used animals to examine the wake-promoting effect of compounds.

Oral test compounds (3 or 10 mg/kg) suspended in 0.5% methylcellulose aqueous solution, or vehicle (i.e., 0.5% methylcellulose aqueous solution) was administered orally (p.o.) to monkeys at zeitgeber time 12 (ZT12) in a volume of 5 mL/kg body weight in cross-over design or pre-post design (n=1-4). EEG and EMG recordings were performed for 4 h after the compound administration. The time spent in wakefulness for 4 h after administration (% of vehicle treatment) was calculated by using SleepSign. The results are shown in Table 4.

Parenteral test compounds (0.1 or 0.3 mg/kg) dissolved in a mixed solution comprising 5% DMSO, 5% Cremophor EL, 20% PEG400 and 70% soluplus (1% (w/v)), or vehicle (i.e., a mixed solution comprising 5% DMSO, 5% Cremophor EL, 20% PEG400 and 70% soluplus (1% (w/v))) was administered subcutaneously (s.c.) to monkeys at ZT12 in a volume of 0.5 mL/kg body weight in a pre-post design (n=1-2). EEG and EMG recordings were performed for 4 h after the compound administration. The time 5 spent in wakefulness for 4 h after administration (% of vehicle treatment) was calculated by using SleepSign. The results are shown in Table 5.

TABLE 4

| Example No | Dose (mg/kg) | Wakefulness time (% of vehicle treatment) (Mean) |
|---|---|---|
| 1 | 3 | 233.91 |
| 2 | 3 | 599.68 |
| 3 | 3 | 612.62 |
| 5 | 10 | 411.70 |
| 56 | 3 | 417.22 |
| 66 | 3 | 463.00 |
| 67 | 3 | 355.56 |
| 87 | 3 | 832.34 |
| 91 | 10 | 548.00 |
| 94 | 3 | 441.88 |
| 144 | 3 | 649.41 |
| 146 | 3 | 426.26 |
| 225 | 3 | 317.65 |
| 236 | 10 | 716.00 |
| 302 | 10 | 287.88 |
| 375 | 3 | 396.49 |
| 380 | 3 | 483.53 |
| 433 | 3 | 727.27 |

TABLE 5

| Example No | Dose (mg/kg) | Wakefulness time (% of vehicle treatment) (Mean) |
|---|---|---|
| 443 | 0.1 | 532.00 |
| 450 | 0.3 | 813.51 |
| 451 | 0.1 | 225.10 |
| 459 | 0.3 | 431.39 |
| 462 | 0.3 | 365.46 |
| 463 | 0.1 | 483.15 |
| 542 | 0.3 | 505.45 |

As is clear from Table 4 and Table 5, the test compounds of the present invention increased the wakefulness time compared to the vehicle treatment group in cynomolgus monkeys. That is, these compounds were suggested to be potential therapeutics for narcolepsy.

Formulation Example 1 (Production of Capsule)

| | |
|---|---|
| 1) compound of Example 1 | 30 mg |
| 2) crystalline cellulose | 10 mg |
| 3) lactose | 19 mg |
| 4) magnesium stearate | 1 mg |
| total | 60 mg |

1), 2), 3) and 4) are mixed and filled in a gelatin capsule.

Formulation Example 2 (Production of Tablet)

| | |
|---|---|
| 1) compound of Example 1 | 30 g |
| 2) lactose | 50 g |
| 3) cornstarch | 15 g |
| 4) calcium carboxymethylcellulose | 44 g |
| 5) magnesium stearate | 1 g |
| 1000 tablets | 140 g in total |

The total amount of 1), 2), 3) and 30 g of 4) are kneaded with water, vacuum dried and sieved. The sieved powder is mixed with 14 g of 4) and 1 g of 5), and the mixture is punched by a tableting machine. In this way, 1000 tablets containing 30 mg of the compound of Example 1 per tablet are obtained.

INDUSTRIAL APPLICABILITY

The compound of the present invention has an orexin type 2 receptor agonist activity, and is useful as an agent for the prophylaxis or treatment of narcolepsy.

This application is based on patent application No. 2019-015488 filed on Jan. 31, 2019 in Japan, the contents of which are encompassed in full herein.

The invention claimed is:

1. A method of treating excessive sleepiness, cataplexy, or a combination thereof, in a patient in need thereof, the method comprising administering to the patient a compound selected from the group consisting of:
N'-{(2S,3R,4S)-1-(azetidine-1-carbonyl)-4-fluoro-2-[(2-fluoro-3'-methyl[1,1'-biphenyl]-3-yl)methyl]pyrrolidin-3-yl}-N,N-dimethylsulfuric diamide;
N-[(2S,3R)-2-[(2,3'-difluoro[1,1'-biphenyl]-3-yl)methyl]-4,4-difluoro-1-(2-methylpropanoyl)pyrrolidin-3-yl]ethanesulfonamide;
N-{(2S,3R)-4,4-difluoro-1-(2-hydroxy-2-methylpropanoyl)-2-[(2,3',5'-trifluoro[1,1'-biphenyl]-3-yl)methyl]pyrrolidin-3-yl}ethanesulfonamide;
N-{(2S,3R)-4,4-difluoro-1-(2-hydroxy-2-methylpropanoyl)-2-[(2,3',5'-trifluoro[1,1'-biphenyl]-3-yl)methyl]pyrrolidin-3-yl}methanesulfonamide;
N-{(2S,3R)-1-(bicyclo[1.1.1]pentane-1-carbonyl)-4,4-difluoro-2-[(2,3',5'-trifluoro[1,1'-biphenyl]-3-yl)methyl]pyrrolidin-3-yl}methanesulfonamide;
N-{(2S,3R)-1-(cyclopropanecarbonyl)-4,4-difluoro-2-[(2,3',5'-trifluoro[1,1'-biphenyl]-3-yl)methyl]pyrrolidin-3-yl}ethanesulfonamide;
N-{(2S,3R)-4,4-difluoro-1-((1s,3R)-3-fluorocyclobutane-1-carbonyl)-2-[(2,3',5'-trifluoro[1, 1'-biphenyl]-3-yl)methyl]pyrrolidin-3-yl}ethanesulfonamide;
N-{(2S,3R)-4,4-difluoro-1-((1s,3R)-3-fluorocyclobutane-1-carbonyl)-2-[(2,3',5'-trifluoro[1, 1'-biphenyl]-3-yl)methyl]pyrrolidin-3-yl}methanesulfonamide; and N'-{(2S,3R)-1-(azetidine-1-carbonyl)-4,4-difluoro-2-[(2-fluoro-3'-methyl[1,1'-biphenyl]-3-yl)methyl]pyrrolidin-3-yl}-N,N-dimethylsulfuric diamide;
or a salt thereof.

2. The method of claim 1, wherein the compound is N'-{(2S,3R,4S)-1-(azetidine-1-carbonyl)-4-fluoro-2-[(2-fluoro-3'-methyl[1,1'-biphenyl]-3-yl)methyl]pyrrolidin-3-yl}-N,N-dimethylsulfuric diamide or a salt thereof.

3. The method of claim 1, wherein the compound is N-[(2S,3R)-2-[(2,3'-difluoro[1,1'-biphenyl]-3-yl)methyl]-4,4-difluoro-1-(2-methylpropanoyl)pyrrolidin-3-yl]ethanesulfonamide or a salt thereof.

4. The method of claim 1, wherein the compound is N-{(2S,3R)-4,4-difluoro-1-(2-hydroxy-2-methylpropanoyl)-2-[(2,3',5'-trifluoro[1,1'-biphenyl]-3-yl)methyl]pyrrolidin-3-yl}ethanesulfonamide or a salt thereof.

5. The method of claim 1, wherein the compound is N-{(2S,3R)-4,4-difluoro-1-(2-hydroxy-2-methylpropanoyl)-2-[(2,3',5'-trifluoro[1,1'-biphenyl]-3-yl)methyl]pyrrolidin-3-yl}methanesulfonamide or a salt thereof.

6. The method of claim 1, wherein the compound is N-{(2S,3R)-1-(bicyclo[1.1.1]pentane-1-carbonyl)-4,4-difluoro-2-[(2,3',5'-trifluoro[1,1'-biphenyl]-3-yl)methyl]pyrrolidin-3-yl}methanesulfonamide or a salt thereof.

7. The method of claim 1, wherein the compound is N-{(2S,3R)-1-(cyclopropanecarbonyl)-4,4-difluoro-2-[(2,3',5'-trifluoro[1,1'-biphenyl]-3-yl)methyl]pyrrolidin-3-yl}ethanesulfonamide or a salt thereof.

8. The method of claim 1, wherein the compound is N-{(2S,3R)-4,4-difluoro-1-((1s,3R)-3-fluorocyclobutane-1-carbonyl)-2-[(2,3',5'-trifluoro[1,1'-biphenyl]-3-yl)methyl]pyrrolidin-3-yl}ethanesulfonamide or a salt thereof.

9. The method of claim 1, wherein the compound is N-{(2S,3R)-4,4-difluoro-1-((1s,3R)-3-fluorocyclobutane-1-carbonyl)-2-[(2,3',5'-trifluoro[1,1'-biphenyl]-3-yl)methyl]pyrrolidin-3-yl}methanesulfonamide or a salt thereof.

10. The method of claim 1, wherein the compound is N'-{(2S,3R)-1-(azetidine-1-carbonyl)-4,4-difluoro-2-[(2-fluoro-3'-methyl[1,1'-biphenyl]-3-yl)methyl]pyrrolidin-3-yl}-N,N-dimethylsulfuric diamide or a salt thereof.

11. The method of claim 1, wherein the compound is N'-{(2S,3R,4S)-1-(azetidine-1-carbonyl)-4-fluoro-2-[(2-fluoro-3'-methyl[1,1'-biphenyl]-3-yl)methyl]pyrrolidin-3-yl}-N,N-dimethylsulfuric diamide.

12. The method of claim 1, wherein the compound is N-[(2S,3R)-2-[(2,3'-difluoro[1,1'-biphenyl]-3-yl)methyl]-4,4-difluoro-1-(2-methylpropanoyl)pyrrolidin-3-yl]ethanesulfonamide.

13. The method of claim 1, wherein the compound is N-{(2S,3R)-4,4-difluoro-1-(2-hydroxy-2-methylpropanoyl)-2-[(2,3',5'-trifluoro[1,1'-biphenyl]-3-yl)methyl]pyrrolidin-3-yl}ethanesulfonamide.

14. The method of claim 1, wherein the compound is N-{(2S,3R)-4,4-difluoro-1-(2-hydroxy-2-methylpropanoyl)-2-[(2,3',5'-trifluoro[1,1'-biphenyl]-3-yl)methyl]pyrrolidin-3-yl}methanesulfonamide.

15. The method of claim 1, wherein the compound is N-{(2S,3R)-1-(bicyclo[1.1.1]pentane-1-carbonyl)-4,4-difluoro-2-[(2,3',5'-trifluoro[1,1'-biphenyl]-3-yl)methyl]pyrrolidin-3-yl}methanesulfonamide.

16. The method of claim 1, wherein the compound is N-{(2S,3R)-1-(cyclopropanecarbonyl)-4,4-difluoro-2-[(2,3',5'-trifluoro[1,1'-biphenyl]-3-yl)methyl]pyrrolidin-3-yl}ethanesulfonamide.

17. The method of claim 1, wherein the compound is N-{(2S,3R)-4,4-difluoro-1-((1s,3R)-3-fluorocyclobutane-1-carbonyl)-2-[(2,3',5'-trifluoro[1,1'-biphenyl]-3-yl)methyl]pyrrolidin-3-yl}ethanesulfonamide.

18. The method of claim 1, wherein the compound is N-{(2S,3R)-4,4-difluoro-1-((1s,3R)-3-fluorocyclobutane-1-carbonyl)-2-[(2,3',5'-trifluoro[1,1'-biphenyl]-3-yl)methyl]pyrrolidin-3-yl}methanesulfonamide.

19. The method of claim 1, wherein the compound is N'-{(2S,3R)-1-(azetidine-1-carbonyl)-4,4-difluoro-2-[(2-fluoro-3'-methyl[1,1'-biphenyl]-3-yl)methyl]pyrrolidin-3-yl}-N,N-dimethylsulfuric diamide.

\* \* \* \* \*